US012116343B2

(12) United States Patent
Dakin et al.

(10) Patent No.: US 12,116,343 B2
(45) Date of Patent: Oct. 15, 2024

(54) INHIBITORS OF APOL1 AND METHODS OF USING SAME

(71) Applicant: Vertex Pharmaceuticals Incorporated, Boston, MA (US)

(72) Inventors: Leslie A. Dakin, Framingham, MA (US); Timothy J. Senter, Arlington, MA (US); Jingrong Cao, Newton, MA (US); Jon H. Come, Cambridge, MA (US); Francois Denis, St-Lazare (CA); Warren A. Dorsch, Waltham, MA (US); Anne Fortier, Jamaica Plain, MA (US); Martine Hamel, Laval (CA); Elaine B. Krueger, Milton, MA (US); Brian Ledford, Norton, MA (US); Francois Maltais, Stoneham, MA (US); Suganthini S. Nanthakumar, Newton, MA (US); Olivier Nicolas, Montreal (CA); Camil E. Sayegh, Belmont, MA (US); Tiansheng Wang, Concord, MA (US); Stephane Dorich, Ponte-Claire (CA); Lee Fader, Hawkesbury (CA); Claudio Sturino, Ile Bizard (CA); Janek Szychowski, Montreal (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 17/161,474

(22) Filed: Jan. 28, 2021

(65) Prior Publication Data

US 2022/0340523 A1 Oct. 27, 2022

Related U.S. Application Data

(60) Provisional application No. 63/040,166, filed on Jun. 17, 2020, provisional application No. 63/038,278, filed on Jun. 12, 2020, provisional application No. 62/967,276, filed on Jan. 29, 2020.

(51) Int. Cl.

| | |
|---|---|
| *C07D 209/18* | (2006.01) |
| *C07D 401/12* | (2006.01) |
| *C07D 403/04* | (2006.01) |
| *C07D 403/12* | (2006.01) |
| *C07D 403/14* | (2006.01) |
| *C07D 405/12* | (2006.01) |
| *C07D 413/12* | (2006.01) |
| *C07D 451/02* | (2006.01) |
| *C07D 491/107* | (2006.01) |

(52) U.S. Cl.

CPC ......... *C07D 209/18* (2013.01); *C07D 401/12* (2013.01); *C07D 403/04* (2013.01); *C07D 403/12* (2013.01); *C07D 403/14* (2013.01); *C07D 405/12* (2013.01); *C07D 413/12* (2013.01); *C07D 451/02* (2013.01); *C07D 491/107* (2013.01)

(58) Field of Classification Search

None

See application file for complete search history.

(56) References Cited

U.S. PATENT DOCUMENTS

| | | | |
|---|---|---|---|
| 6,518,273 | B1 | 2/2003 | Chapman et al. |
| 6,605,633 | B1 | 8/2003 | Paquet et al. |
| 11,618,746 | B2 | 4/2023 | Cao et al. |
| 11,801,234 | B2 | 10/2023 | Mallalieu et al. |
| 11,866,446 | B2 | 1/2024 | Ahn et al. |
| 2001/0039286 | A1 | 11/2001 | Dinnell et al. |
| 2004/0006237 | A1 | 1/2004 | Dolitzky et al. |
| 2004/0138287 | A1 | 7/2004 | Barth et al. |

(Continued)

FOREIGN PATENT DOCUMENTS

| | | | |
|---|---|---|---|
| EP | 0924209 | A1 | 6/1999 |
| WO | WO 2001/017965 | A2 | 3/2001 |

(Continued)

OTHER PUBLICATIONS

Database Registry Chemical Abstracts Service, Columbus, Ohio, Accession No. RN 930014-44-1, Entered STN: Apr. 13, 2007.*

(Continued)

*Primary Examiner* — Samantha L Shterengarts

(74) *Attorney, Agent, or Firm* — Finnegan, Henderson, Farabow, Garrett & Dunner, LLP

(57) ABSTRACT

The disclosure provides at least one entity chosen from compounds of Formula (I)

(I)

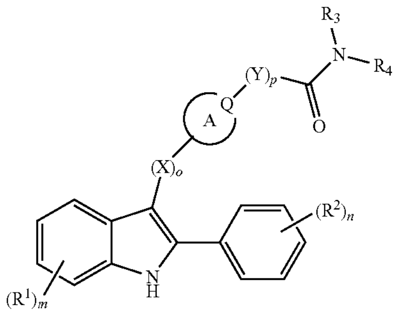

pharmaceutically acceptable salts thereof, solvates of any of the foregoing, and deuterated derivatives of any of the foregoing, compositions comprising the same, and methods of using the same, including use in treating APOL1 mediated kidney disease.

33 Claims, 1 Drawing Sheet

(56) References Cited

U.S. PATENT DOCUMENTS

| | | | |
|---|---|---|---|
| 2005/0100902 | A1 | 5/2005 | Barth et al. |
| 2013/0237532 | A1 | 9/2013 | Kim et al. |
| 2018/0118681 | A1 | 5/2018 | Ross et al. |
| 2020/0377479 | A1 | 12/2020 | Cao et al. |
| 2021/0246121 | A1 | 8/2021 | Lai et al. |
| 2021/0275496 | A1 | 9/2021 | Mallalieu et al. |
| 2022/0106327 | A1 | 10/2022 | Ahn et al. |
| 2022/0340523 | A1 | 10/2022 | Dakin et al. |
| 2023/0011118 | A1 | 1/2023 | Dakin et al. |
| 2023/0014907 | A1 | 1/2023 | Dakin et al. |
| 2023/0119114 | A1 | 4/2023 | Daniel et al. |
| 2023/0201201 | A1 | 6/2023 | Skorecki et al. |
| 2023/0203000 | A1 | 6/2023 | Dakin et al. |
| 2023/0250087 | A1 | 8/2023 | Gagnon et al. |
| 2023/0271945 | A1 | 8/2023 | Cao et al. |

FOREIGN PATENT DOCUMENTS

| | | | |
|---|---|---|---|
| WO | WO 2001/038305 | A2 | 5/2001 |
| WO | WO 2002/028831 | A1 | 4/2002 |
| WO | WO 2002/092568 | A1 | 11/2002 |
| WO | WO 2003/104180 | A1 | 12/2003 |
| WO | WO 2004/058717 | A1 | 7/2004 |
| WO | WO 2005/021505 | A1 | 3/2005 |
| WO | WO 2005/092854 | A1 | 10/2005 |
| WO | WO 2007/061763 | A2 | 5/2007 |
| WO | WO 2008/092231 | A1 | 8/2008 |
| WO | WO 2010/137351 | A1 | 12/2010 |
| WO | WO 2012/025155 | A1 | 3/2012 |
| WO | WO 2014/085154 | A1 | 6/2014 |
| WO | WO 2015/048301 | A1 | 4/2015 |
| WO | WO 2015/147639 | A1 | 10/2015 |
| WO | WO 2016/055517 | A1 | 4/2016 |
| WO | WO 2017/033093 | A1 | 3/2017 |
| WO | WO 2019/213148 | A1 | 11/2019 |
| WO | WO 2019/226611 | A1 | 11/2019 |
| WO | WO 2020/131807 | A1 | 6/2020 |
| WO | WO 2021/154997 | A1 | 8/2021 |
| WO | WO 2021/158666 | A1 | 8/2021 |
| WO | WO 2021/178768 | A1 | 9/2021 |
| WO | WO 2021/224927 | A1 | 9/2021 |
| WO | WO 2021/252849 | A1 | 12/2021 |
| WO | WO 2021/252859 | A1 | 12/2021 |
| WO | WO 2021/252863 | A1 | 12/2021 |
| WO | WO 2022/047031 | A1 | 3/2022 |
| WO | WO 2023/028237 | A1 | 3/2023 |
| WO | WO 2023/101981 | A1 | 6/2023 |
| WO | WO 2023/154309 | A1 | 8/2023 |
| WO | WO 2023/154310 | A1 | 8/2023 |
| WO | WO 2023/154314 | A1 | 8/2023 |
| WO | WO 2023/154344 | A1 | 8/2023 |

OTHER PUBLICATIONS

Database Registry Chemical Abstracts Service, Columbus, Ohio, Accession No. RN 1391756-29-8, Entered STN: Aug. 16, 2012.*

Database Registry Chemical Abstracts Service, Columbus, Ohio, Accession No. RN 1391756-83-4, Entered STN: Aug. 16, 2012.*

Database Registry Chemical Abstracts Service, Columbus, Ohio, Accession No. RN 847480-40-4, Entered STN: Mar. 29, 2005.*

Dummer, P.D. et al. (2015), "APOL1 kidney disease risk variants—an evolving landscape," *Semin Nephrol.* 35(3):22-236. HHS Public Access Author Manuscript; available in PMC May 1, 2016 (25 pages).

International Search Report and Written Opinion for International Application No. PCT/US2021/015495, dated May 11, 2021 (10 pages).

International Search Report and Written Opinion for International Application No. PCT/US2021/036954, dated Sep. 23, 2021 (10 pages).

International Search Report and Written Opinion for International Application No. PCT/US2021/047754, dated Oct. 25, 2021 (11 pages).

Lin, J. et al. (2021), "Oncogene APOL1 promotes proliferation and inhibits apoptosis via activating NOTCH1 signaling pathway in pancreatic cancer," *Cell Death and Disease* 12:760 (11 pages).

Turnu, F. et al. (2019) "Catalytic Tandem Friedel-Crafts Alkylation/C4-C3 Ring-Contraction Reaction: An Efficient Route for the Synthesis of Indolyl Cyclopropanecarbaldehydes and Ketones," *Org. Lett.* 21:7329-7332, (4 pages).

Vajgel, G. et al. (2020), "A single APOL1 nephropathy variant increases risk of advanced lupus nephritis in Brazilians," *J Rheumatol.* 47(8):1209-1217. HHS Public Access Author Manuscript; available in PMC Aug. 1, 2021 (18 pages).

*Vertex Announces Positive Results From Phase 2 Study of VX-147 in APOL1-Mediated Focal Segmental Glomerulosclerosis,* Vertex (Dec. 1, 2021), https://news.vrtx.com/press-release/vertex-announces-positive-results-phase-2-study-vx-147-apol1-mediated-focal-segmental (6 pages).

U.S. Appl. No. 17/161,474, filed Jan. 28, 2021, by Dakin et al.

U.S. Appl. No. 17/345,256, filed Jun. 11, 2021, by Dakin et al.

U.S. Appl. No. 17/345,268, filed Jun. 11, 2021, by Dakin et al.

U.S. Appl. No. 17/446,135, filed Aug. 26, 2021, by Ahn et al.

Takasawa, R. et al., "Discovery of a new type inhibitor of human glyoxalase I by myricetin-based 4-point pharmacophore," *Biorganic & Medicinal Chemistry Letters,* Pergamon, Amsterdam, NL, vol. 21, No. 14, May 16, 2011, pp. 4337-4342.

Balasubramanian, M. et al. (1970) "Studies on Conformation: Part X -Addition of Grignard Reagents to 4-Piperidones." *Indian J. Chem.,* vol. 8, May 1, 1970, pp. 420-422.

Bartolucci, S. et al. (2015), "Iridium-Catalyzed Direct Synthesis of Tryptamine Derivatives from Indoles: Exploiting N-Protected Amino Alcohols as Alkylating Agents," *J. Org. Chem,* 2015, 80, 3217-3222.

Casy, A.F. et al. (1976), "Reversed ester analogues of pethidine: isomeric 4-acetoxy-1,2,6-trimethyl-4-phenyrpiperidines." *JPP,* vol. 28, No. 2, pp. 106-110.

Database Registry (2002), Chembridge Corporation: 4-Piperidinol, 4-(2-methoxyphenyl)-1-methyl-2,6-diphenyl-II XP093022694, Database accession No. 471293-86-4 compound with Registry No. 471293-86-4.

Database Registry (2016), Aurora Fine Chemicals: "Piperidine, 4-[(I,3-diethyl-IH-pyrazol-5-yl)methyl]-2, 6-dimethyl," XP093022702, Database accession No. 1993174-76-7 compounds with Registry Nos. 1993174-76-7, 1993166-16-7 and 1993166-02-1.

Database Registry (2018), Aurora Fine Chemicals: "4-Piperidinol, 1,2,6-trimethyl-4-(2-methylphenyl)-", XP093022693, Database accession No. 2182802-01-1 compound with Registry No. 2182802-01-1.

Database Registry (2021), "2'-Cyclopropyl-7,8-dihydro-6'-methylspiro [I,6-naphthyridine-5(6H),4'-piperidine]," XP093024331, retrieved from STN Database accession No. 2645191-67-7 abstract.

Database Registry (2021), "2'-Cyclopropyl-6,7-dihydro-6,6'-dimethyls piro[I,7-naphthyridine-8(5H), 4'-piperidine]," XP093024335, retrieved from STN Database accession No. 2644543-73-5 abstract.

Database Registry (2021), Anonymous: "Name not yet assigned", XP093024338, retrieved from STN Database accession No. 2642534-36-7 abstract.

Database Registry (2021), Anonymous: "2'-Cyclopropyl-3,4-dihydro-6'-methylspiro [isoquinoline-1 (2H), 4'-piperidin]- 7-ol," XP093024340, retrieved from STN Database accession No. 2631256-91-0 abstract.

Database Registry (2021), Anonymous: "2-Cyclopropyl-7',8'-dihydro-2', 6-dimethyl spiro[piperidine-4,5' (3'H)-pyrido[4,3-d]py rimidin]-4' (6 'H) -one", XP093024343, retrieved from STN Database accession No. 2631119-41-8 abstract.

Database Registry (2021), Anonymous: "Name not yet assigned", XP093024344, retrieved from STN Database accession No. 2630494-88-9 abstract.

Database Registry (2021), Anonymous: "2'-Cyclopropyl-6,7-dihydro-6'-methylspiro [I,7-naphthyridine-8(5H),4' piperidine]-6-methanol," XP093024346, retrieved from STN Database accession No. 2626788-69-8 abstract.

Database Registry (2021), Anonymous: "rel-(2'R,6'R)-3,4-Dihydro-7-methoxy-2',6'-dimethylspiro[2,6-naphthyridine1(2H), 4'-p iperidine], "XP093024348, retrieved from STN Database accession No. 2625380-27-8 abstract.

(56) References Cited

OTHER PUBLICATIONS

Database Registry (2021), Anonymous: "2'-Cyclopropyl-3,4-dihydro-3,6'-dimethyls piro[2,6-naphthyridine-1(2H),4'piperidine]," XP093024352, retrieved from STN Database accession No. 2620609-98-3 abstract.
Database Registry (2021), Anonymous: "2'-Cyclopropyl-6,7-dihydro-6'-methylspiro [1,7-naphthyridine-8(5H),4' piperidine]-5-methanol," XP093024350, retrieved from STN Database accession No. 2617381-98-1 abstract.
Harish, B. et al. (2017) "N-Heterocyclic carbene (NHC)-catalysed atom economical construction of 2,3-disubstituted indoles," *Chem. Commun,* 2017, 53, 3338-3341.
Harper N.J. et al. (1960) "Some isomeric hydroxypiperidines." *J. Am. Chem. Soc.,* Jan. 1, 1960, pp. 2704-2711.
Jones, A.J. et al. (1973), "Carbon-13 Magnetic Resonance: the Stereochemistry of 1,2- and 1,3-Dimethyl-4-phenylpiperidine Derivatives." *Can. J. Chem.,* vol. 41, No. 11, pp. 1782-1789.
Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.
Kozikowski, A.P. et al. (1993), "Chemistry, binding affinities, and behavioral properties of a new class of "antineophobic" mitochondrial DBI receptor complex (mDRC) ligands," *J. Med. Chem.* 36(20):2908-2920.
Manimekalai, A. et al. (2007), "Benzyl group conformation in 4-benzyl-4-hydroxypiperidines," *J. Struct. Chem.,* vol. 48, No. 6, pp. 1036-1045.
Meyers, A.L. et al. (1985), ".alpha.-Amino carbanions. Preparation, metalation, and alkylation of enamidines. Synthesis of piperidine and pyrrolidine natural products and homologation of carbonyl compounds," *J. Org. Chem.,* vol. 50, No. 7, pp. 1019-1026.
Notice of Allowance and Fee(s) Due for U.S. Appl. No. 16/717,099, dated Nov. 7, 2022.
Prostakov, N.S. et al. (1975) "Synthesis of 3-Alkyl-2, 4, 6-Triphenylpyridines and 1, 3-Diphenyl-4- and -2-Azafluorenes." Chem Heterocycl Compd, vol. 11, pp. 971-975.
Trotter, B.W. et al. (2001) "2-Arylindole-3-acetamides: FPP-Competitive Inhibitors of Farnesyl Protein Transferase," Bioorg. Med. Chem. Lett. 11(2001) 865-869.
U.S. Appl. No. 17/895,582, filed Aug. 25, 2022, by Daniel et al.
U.S. Appl. No. 17/923,508, filed Nov. 11, 2022 by Skorecki, et al.
U.S. Appl. No. 18/001,371, filed Dec. 9, 2022 by Gagnon, et al.
U.S. Appl. No. 18/071,153, filed Nov. 29, 2022, by Dakin et al.
Valles, D.A. et al. (2021), "[alpha], [alpha] '-C—H Bond Difunctionalization of Unprotected Alicyclic Amines," *Org. Lett.,* vol. 23, No. 16, pp. 6367-6371.
Winters, M.P. et al. (2008), "Carboxylic acid bioisosteres acylsulfonamides, acylsulfamides, and sulfonylureas as novel antagonists of the CXCR2 receptor," *Bioorganic Med. Chem. Lett.* 18:1926-1930.
Johansson, H. et al. (2013), "3-Substituted 2-phenyl-indoles: privileged structures for medicinal chemistry" RSC Adv, 3, 945-960.
Brittain H. G. et al., (2001) "X-Ray Diffraction III: Pharmaceutical Applications of X-ray Powder Diffraction," Spectroscopy, 16(7), pp. 14-18.
Horner, et al. DE 1266763 (abstract) retrieved from STN Accession No. 1968:506703, CAPLUS, Apr. 25, 1968.
Joshi, K.C. et al. (1978), "Synthesis and CNS Activity of Some Fluorine Containing 3-Indolylglyoxamides and Tryptamines" Agric. Biol. Chem., 42(9), pp. 1723-1726.
Kang H. et al. (2018), "Potent aromatase inhibitors and molecular mechanism of inhibitory action," European Journal of Medicinal Chemistry, 143, 426-437.
Naik M. et al. (2014), "2-Phenylindole and arylsulfonamide: novel scaffolds bactericidal against Mycobacterium tuberculosis"ACS Med. Chem. Lett. 2014, 5, 9, 1005-1009.
Notice of Allowance and Fee(s) Due for U.S. Appl. No. 18/106,569, mailed Mar. 18, 2024, Examiner Deepak R Rao.
Shaw D. et al. (2001), "2-Aryl Indole NK1 Antagonists: Optimisation of the Amide Substituent," Bioorg. Med. Chem. Lett., 11, 3031-3034.
The United States Pharmacopeia, Jan. 1, 1995, 23rd Revision, USP 23/NF 18, General Chapter on X-ray diffraction, pp. 1843-1844.
U.S. Appl. No. 18/476,131, filed Sep. 27, 2023.
U.S. Appl. No. 18/504,559, filed Nov. 8, 2023.
Zhang, G.-N. et al. (2019), "An Efficient Synthesis of N-Aryl-2-(Indol-3-yl)-Acetamides via Multi-Component Reactions," Heterocycles, 98(4), 535-543.

* cited by examiner

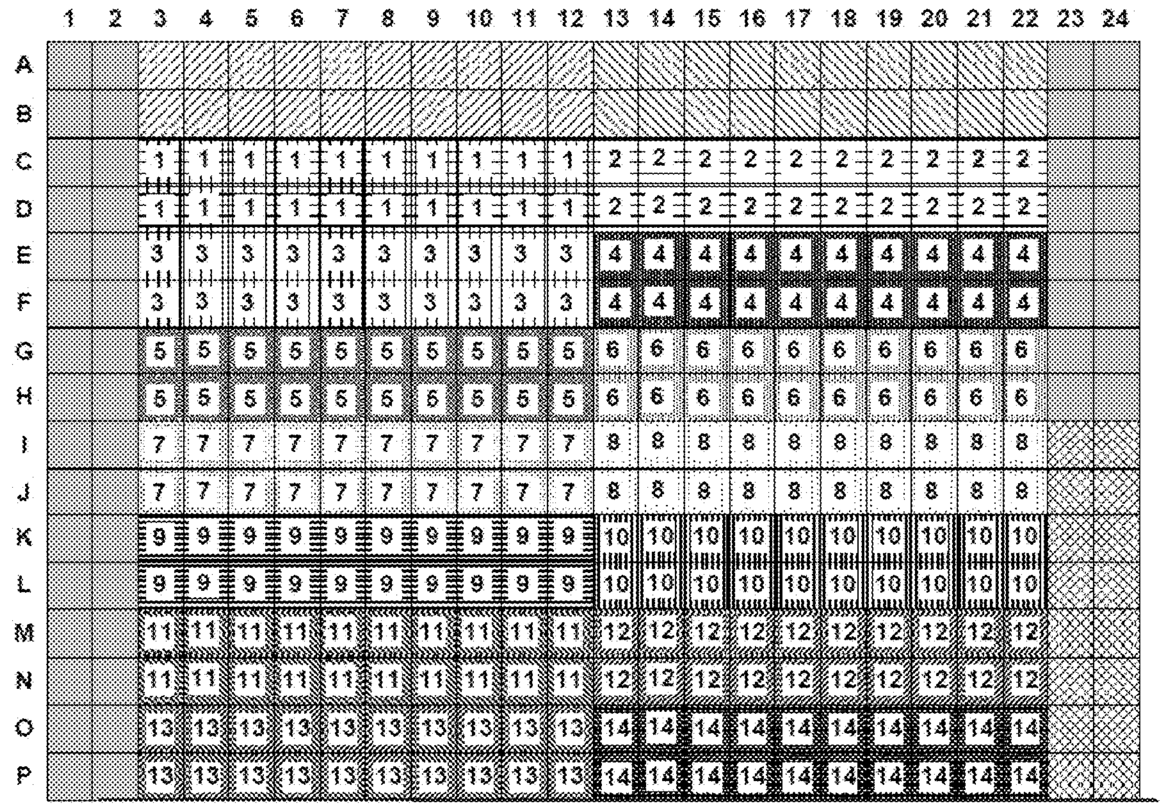
- 10 point Dose Response
- 100 uM Highest Final Assay Concentration in 20uL
- 2.5-Fold Serial Dilution
- Total DMSO Volume 200 nL
- Right to Left
- 1 Copies of each plate
- Barcodes East and South sides
- Final Plate Type: Corning 384 Polypropylene 3656
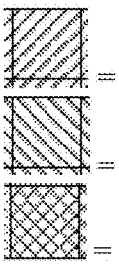
= control
= control
= control

INHIBITORS OF APOL1 AND METHODS OF USING SAME

This disclosure provides compounds that inhibit apolipoprotein L1 (APOL1) and methods of using those compounds to treat APOL1 mediated kidney disease, including focal segmental glomerulosclerosis (FSGS) and/or non-diabetic kidney disease (NDKD). In some embodiments, the FSGS and/or NDKD is associated with common APOL1 genetic variants (G1: S342G:I384M and G2: N388del:Y389del).

FSGS is a disease of the podocyte (glomerular visceral epithelial cells) responsible for proteinuria and progressive decline in kidney function. NDKD is a disease characterized by hypertension and progressive decline in kidney function. Human genetics support a causal role for the G1 and G2 APOL1 variants in inducing kidney disease. Individuals with two APOL1 risk alleles are at increased risk of developing end-stage kidney disease (ESKD), including FSGS, human immunodeficiency virus (HIV)-associated nephropathy, NDKD, arterionephrosclerosis, lupus nephritis, microalbuminuria, and chronic kidney disease. See, P. Dummer et al., *Semin Nephrol.* 35(3): 222-236 (2015).

APOL1 is a 44 kDa protein that is only expressed in humans, gorillas, and baboons. APOL1 is produced mainly by the liver and contains a signal peptide that allows for secretion into the bloodstream, where it circulates bound to a subset of high density lipoproteins. APOL1 is responsible for protection against the invasive parasite, *Trypanosoma brucei brucei* (*T. b. brucei*). APOL1 G1 and G2 variants confer additional protection against *trypanosoma* species that cause sleeping sickness. Although normal plasma concentrations of APOL1 are relatively high and can vary at least 20-fold in humans, circulating APOL1 is not causally associated with kidney disease.

However, APOL1 in the kidney is thought to be responsible for the development kidney diseases, including FSGS and NDKD. Under certain circumstances, APOL1 protein synthesis can be increased by approximately 200-fold by pro-inflammatory cytokines such as interferons or tumor necrosis factor-α. In addition, several studies have shown that APOL1 protein can form pH-gated $Na^+/K^+$ pores in the cell membrane, resulting in a net efflux of intracellular $K^+$, ultimately resulting in activation of local and systemic inflammatory responses, cell swelling, and death.

The risk of ESKD is substantially higher in people of recent sub-Saharan African ancestry as compared to those of European ancestry and in the U.S., ESKD is responsible for nearly as many lost years of life in women as from breast cancer and more lost years of life in men than from colorectal cancer. Currently, FSGS and NDKD are managed with symptomatic treatment (including blood pressure control using blockers of the renin angiotensin system), and patients with FSGS and heavy proteinuria may be offered high dose steroids. Corticosteroids induce remission in a minority of patients and are associated with numerous and at times, severe, side effects, and are often poorly tolerated. These patients, and particularly individuals of recent sub-Saharan African ancestry with two APOL1 risk alleles, experience faster disease progression leading to ESKD.

Thus, there is an unmet medical need for treatment for APOL1 mediated kidney diseases, including FSGS, NDKD, and ESKD. In view of evidence that APOL1 plays a causative role in inducing and accelerating the progression of kidney disease, inhibition of APOL1 should have a positive impact on patients with APOL1 mediated kidney disease, particularly those who carry two APOL1 risk alleles (i.e., are homozygous or compound heterozygous for the G1 or G2 alleles).

One aspect of the disclosure provides at least one entity chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing, which can be employed in the treatment of diseases mediated by APOL1, such as FSGS and NDKD.

Thus, a first aspect of the invention provides compounds chosen from compounds of Formula (I):

(I)

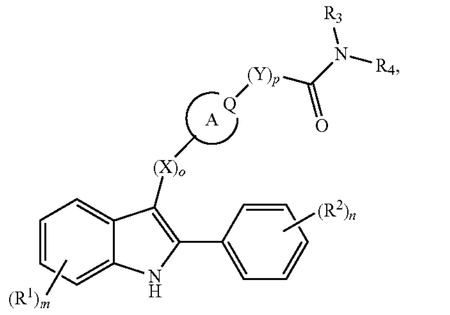

pharmaceutically acceptable salts thereof, solvates of any of the foregoing, and deuterated derivatives of any of the foregoing, wherein:

(i) Ring A is a 3- to 7-membered ring, wherein the ring is a cyclic alkyl or a heterocycle;

(ii) Q is N or $CR^5$;

(iii) each $R_1$ is independently chosen from halogen groups, hydroxy, thiol, amino, cyano, —$OC(O)C_1$-$C_6$ linear, branched, and cyclic alkyl groups, —$C(O)OC_1$-$C_6$ linear, branched, and cyclic alkyl groups, —$NHC(O)C_1$-$C_6$ linear, branched, and cyclic alkyl groups, —$C(O)NHC_1$-$C_6$ linear, branched, and cyclic alkyl groups, —NHC(O)aryl groups, —C(O)NHaryl groups, —NHC(O)heteroaryl groups, —C(O)NHheteroaryl groups, —$NHS(O)_2C_1$-$C_6$ linear, branched, and cyclic alkyl groups, —$S(O)_2NHC_1$-$C_6$ linear, branched, and cyclic alkyl groups, —$NHS(O)_2$aryl groups, —$S(O)_2$NHaryl groups, —$NHS(O)_2$heteroaryl groups, —$S(O)_2$NHheteroaryl groups, —$NHC(O)NHC_1$-$C_6$ linear, branched, and cyclic alkyl groups, —NHC(O)NHaryl groups, —NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3- to 6-membered heterocycloalkenyl groups,
3- to 6-membered heterocycloalkyl groups, and
5- and 6-membered heteroaryl groups; or two $R_1$ groups, together with the carbon atoms to which they are attached, form a $C_4$-$C_8$ cycloalkyl group, an aryl group, or a heteroaryl group;

(iv) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(v) m is chosen from 0, 1, 2, 3, and 4;

(vi) n is chosen from 0, 1, 2, 3, 4, and 5;

(vii) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with one to four groups independently chosen from:
$C_1$-$C_6$ alkyl groups,
aryl groups,
heteroaryl groups,
halogen groups,
hydroxy, and
amino;

(viii) Y is chosen from divalent amino, divalent oxygen, divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with one to three groups independently chosen from
$C_1$-$C_6$ alkyl groups optionally substituted with hydroxy,
$C_3$-$C_6$ cyclic alkyl,
aryl groups,
heteroaryl groups,
halogen groups,
hydroxy, and
amino, or wherein the divalent alkyl groups, divalent alkoxy groups, divalent aminoalkyl groups, and divalent thioalkyl groups are optionally fused to a $C_3$-$C_6$ cyclic alkyl;

(ix) o is chosen from 0, 1, 2, 3, and 4;

(x) p is chosen from 0, 1, 2, 3, and 4;

(xi) $R_3$ and $R_4$ are independently chosen from:
hydrogen,
$C_1$-$C_6$ linear and branched alkylsulfonyl groups,
$C_1$-$C_6$ linear and branched alkoxy groups optionally substituted with a $C_3$-$C_6$ cyclic alkyl group or a 3- to 6-membered heterocycle;
$C_1$-$C_6$ cyclic alkyl groups optionally substituted with one to four groups independently chosen from:
halogen groups,
hydroxy,
oxo,
$C_1$-$C_6$ linear and branched alkoxy groups,
$C_1$-$C_6$ linear and branched alkyl groups optionally substituted with one or two groups independently chosen from hydroxy and $C_1$-$C_6$ linear and branched alkoxy groups, and
amido groups,
heterocyclic groups optionally substituted with one to four groups independently chosen from:
halogen groups,
oxo,
hydroxy, and
$C_1$-$C_6$ linear and branched alkyl groups optionally substituted with one or two groups independently chosen from hydroxy and $C_1$-$C_6$ linear and branched alkoxy groups,
aryl groups optionally substituted with one to four groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups,
heteroaryl groups optionally substituted with one to four groups independently chosen from hydroxy and $C_1$-$C_6$ linear alkyl groups, and
$C_1$-$C_7$ linear and branched alkyl groups, wherein the alkyl groups are optionally substituted with one to five groups independently chosen from:
amino groups,
hydroxy,
oxo, cyano, carboxylic acid, halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, $C_1$-$C_6$ linear and branched alkylsulfonyl groups, aryl groups optionally substituted with one or two groups independently chosen from halogen groups, hydroxy, $C_1$-$C_6$ linear and branched alkyl groups optionally substituted with one or two groups independently chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups, or $R_3$ and $R_4$, together with the nitrogen atom to which they are attached, form a 4- to 10-membered heterocyclyl group optionally substituted with one to four groups independently chosen from hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups; and (xii) $R_5$ is absent or is chosen from:

hydrogen, halogen groups, hydroxy, thiol, amino, and $C_1$-$C_6$ linear and branched alkyl groups, wherein when $R_5$ is absent, Q is a bridgehead atom.

In one aspect of the disclosure, the compounds of Formulae (I), (Ia), (II), (IIIa), (IIIb), (IV), (Va), and (Vb), are chosen from Compounds 1 to 286 and Compounds 287 to 465, pharmaceutically acceptable salts of any of those compounds, solvates of any of the foregoing, and deuterated derivatives of any of the foregoing.

In some embodiments, the disclosure provides pharmaceutical compositions comprising at least one entity chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing. In some embodiments, the pharmaceutical compositions may comprise at least one compound chosen from Compounds 1 to 286 and Compounds 287 to 465, pharmaceutically acceptable salts of any of those compounds, solvates of any of the foregoing, and deuterated derivatives of any of the foregoing. These compositions may further include at least one additional active pharmaceutical ingredient and/or at least one carrier.

Another aspect of the disclosure provides methods of treating FSGS and/or NDKD comprising administering to a subject in need thereof, at least one entity chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing or a pharmaceutical composition comprising the at least one entity. In some embodiments, the methods comprise administering at least one entity chosen from Compounds 1 to 286 and Compounds 287 to 465, pharmaceutically acceptable salts of any of those compounds, solvates of any of the foregoing, and deuterated derivatives of any of the foregoing.

In some embodiments, the methods of treatment include administration of at least one additional active agent to the subject in need thereof, either in the same pharmaceutical composition as the at least one entity chosen from compounds of Formulae (I), (Ia), (II), (IIIa), (IIIb), (IV) (Va), and (Vb), pharmaceutically acceptable salts of any of those compounds, solvates of any of the foregoing, and deuterated derivatives of any of the foregoing, or as separate compositions. In some embodiments, the methods comprise administering at least one entity chosen from Compounds 1 to 286 and Compounds 287 to 465, pharmaceutically acceptable salts of any of those compounds, solvates of any of the foregoing, and deuterated derivatives of any of the foregoing with at least one additional active agent either in the same pharmaceutical composition or in a separate pharmaceutical composition.

Also provided are methods of inhibiting APOL1, comprising administering to a subject in need thereof, at least one entity chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing or a pharmaceutical composition comprising the at least one entity. In some embodiments, the methods of inhibiting APOL1 comprise administering at least one entity chosen from Compounds 1 to 286 and Compounds 287 to 465, pharmaceutically acceptable salts of any of those compounds, solvates of any of the foregoing, and deuterated derivatives of any of the foregoing or a pharmaceutical composition comprising the at least one entity.

BRIEF DESCRIPTION OF THE DRAWINGS

FIG. 1 depicts the plate map for dose response for the compounds plated in assay ready plates (ARP).

DEFINITIONS

The term "APOL1" as used herein means apolipoprotein L1 protein and the term "APOL1" means apolipoprotein L1 gene.

The term "APOL1 mediated kidney disease" refers to a disease or condition that impairs kidney function and can be attributed to APOL1. In some embodiments APOL1 mediated kidney disease is associated with patients having two APOL1 risk alleles, e.g., are homozygous or compound heterozygous for the G1 or G2 alleles. In some embodiments, the APOL1 mediated kidney disease is chosen from ESKD, NDKD, FSGS, HIV-associated nephropathy, arterionephrosclerosis, lupus nephritis, microalbuminuria, and chronic kidney disease.

The term "FSGS" as used herein means focal segmental glomerulosclerosis, which is a disease of the podocyte (glomerular visceral epithelial cells) responsible for proteinuria and progressive decline in kidney function. In some embodiments FSGS is associated with two APOL1 risk alleles.

The term "NDKD" as used herein means non-diabetic kidney disease, which is characterized by severe hypertension and progressive decline in kidney function. In some embodiments, NDKD is associated with two APOL1 risk alleles.

The terms "ESKD" and "ESRD" are used interchangeably to refer to end stage kidney disease or end stage renal disease. ESKD/ESRD is the last stage of kidney disease, i.e., kidney failure, and means that the kidneys have stopped working well enough for the patient to survive without dialysis or a kidney transplant. In some embodiments, ESKD/ESRD is associated with two APOL1 risk alleles.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted", whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$ are within the scope of this disclosure.

Unless otherwise indicated, structures depicted herein are also meant to include all isomeric forms of the structure, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of compound that exist together in equilibrium, and are readily interchanged by migration of an atom, e.g., a hydrogen atom, or group within the molecule.

"Stereoisomer" as used herein refers to enantiomers and diastereomers.

As used herein, "deuterated derivative" refers to a compound having the same chemical structure as a reference compound, but with one or more hydrogen atoms replaced by a deuterium atom ("D" or "$^2H$"). It will be recognized that some variation of natural isotopic abundance occurs in a synthesized compound depending on the origin of chemical materials used in the synthesis. The concentration of naturally abundant stable hydrogen isotopes, notwithstanding this variation is small and immaterial as compared to the degree of stable isotopic substitution of deuterated derivatives described herein. Thus, unless otherwise stated, when a reference is made to a "deuterated derivative" of compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium) at least 4500, (67.5% deuterium incorporation), at least 5000 (75% deuterium incorporation) at least 5500 (82.5% deuterium incorporation), at least 6000 (90% deuterium incorporation), at least 6333.3 (95% deuterium incorporation, at least 6466.7 (97% deuterium incorporation, or at least 6600 (99% deuterium incorporation).

The term "isotopic enrichment factor" as used herein means the ratio between the isotopic abundance and the natural abundance of a specified isotope.

The term "alkyl" or "aliphatic" as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic that has a single point of attachment to the rest of the molecule. Unless otherwise specified, alkyl groups contain 1 to 20 alkyl carbon atoms. In some embodiments, alkyl groups contain 1 to 10 aliphatic carbon atoms. In some embodiments, alkyl groups contain 1 to 8 aliphatic carbon atoms. In some embodiments, alkyl groups contain 1 to 6 alkyl carbon atoms, and in some embodiments, alkyl groups contain 1 to 4 alkyl carbon atoms, and in yet other embodiments alkyl groups contain 1 to 3 alkyl carbon atoms. Nonlimiting examples of alkyl groups include, but are not limited to, linear or branched, and substituted or unsubstituted alkyl. In some embodiments, alkyl groups are substituted. In some embodiments, alkyl groups are unsubstituted. In some embodiments, alkyl groups are straight-chain. In some embodiments, alkyl groups are branched.

The terms "cycloalkyl," "carbocycle," or "cyclic alkyl" refer to a fused, spirocyclic, or monocyclic $C_{3-8}$ hydrocarbon or a spirocyclic, bicyclic, bridged bicyclic, tricyclic, or bridged tricyclic $C_{4-14}$ hydrocarbon that is completely saturated or that contains one or more units of unsaturation, but which is not aromatic, wherein any individual ring in said bicyclic ring system has 3 to 7 members. Suitable cycloalkyl groups include cycloalkyl, bicyclic cycloalkyl (e.g., decalin), bridged bicycloalkyl such as norbornyl, [1.1.1]bicyclopentyl, or [2.2.2]bicyclo-octyl, or bridged tricyclic such as adamantyl. In some embodiments, cyclogroups are substituted. In some embodiments, cyclogroups are unsubstituted.

The term "heteroalkyl," as used herein, means aliphatic groups wherein one, two, or three carbon atoms are independently replaced by one or more of oxygen, sulfur, and/or nitrogen. In some embodiments, one or two carbon atoms may be replaced by phosphorus and/or silicon. Heteroalkyl groups may be substituted or unsubstituted, branched or unbranched, cyclic or acyclic, and include "heterocycle", "heterocyclyl", or "heterocyclic" groups. In some embodiments, the heteroalkyl is an aminoalkyl. In some embodiments, the heteroalkyl is a thioalkyl. In some embodiments, the heteroalkyl is an alkoxy. In some embodiments, the heteroalkyl has a combination of two or more heteroatoms independently selected from oxygen, nitrogen, phosphorus, and sulfur.

The term "alkenyl" as used herein, means a straight-chain (i.e., unbranched), branched, substituted or unsubstituted hydrocarbon chain that contains one or more units of saturation, or a monocyclic hydrocarbon or bicyclic hydrocarbon that contains one or more units of unsaturation, but which is not aromatic (referred to herein as, "cyclic alkenyl"). In some embodiments, alkenyl groups are substituted. In some embodiments, alkenyl groups are unsubstituted. In some embodiments, alkenyl groups are straight-chain. In some embodiments, alkenyl groups are branched.

The term "heterocycle", "heterocyclyl", or "heterocyclic" as used herein means non-aromatic, monocyclic, bicyclic, or tricyclic ring systems in which one or more ring members is an independently chosen heteroatom. In some embodiments, the "heterocycle", "heterocyclyl", or "heterocyclic" group has 3 to 14 ring members in which one or more ring members is a heteroatom independently chosen from oxygen, sulfur, nitrogen, phosphorus, boron, and silicon. In some embodiments, each ring in a bicyclic or tricyclic ring system contains 3 to 7 ring members. In some embodiments the heterocycle has at least one unsaturated carbon-carbon bond. In some embodiments, the heterocycle has at least one unsaturated carbon-nitrogen bond. In some embodiments, the heterocycle has one to three heteroatoms independently chosen from oxygen, sulfur, nitrogen, and phosphorus. In some embodiments, the heterocycle has one to three heteroatoms that are nitrogen. In some embodiments, the heterocycle has one heteroatom that is an oxygen atom. In some embodiments, the heterocycle has one heteroatom that is a sulfur atom. In some embodiments, the heterocycle has two heteroatoms that are each independently selected from nitrogen, sulfur, and oxygen. In some embodiments, the heterocycle has three heteroatoms that are each independently selected from nitrogen and oxygen. In some embodiments, heterocycles are substituted. In some embodiments, heterocycles are unsubstituted.

The term "heteroatom" means one or more non-carbon atoms selected from oxygen, sulfur, nitrogen, phosphorus, boron, and silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units or degrees of unsaturation. Unsaturation is the state in which not all of the available valance bonds in a compound are satisfied by substituents and thus the compound contains double or triple bonds.

The term "alkoxy", or "thioalkyl", as used herein, refers to an alkyl group, as previously defined, wherein one carbon of the alkyl group is replaced by an oxygen ("alkoxy") or sulfur ("thioalkyl") atom, respectively, provided that the oxygen and sulfur atoms are linked between two carbon atoms. A "cyclic alkoxy" refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl. In some embodiments, "alkoxy" and/or "thioalkyl" groups are substituted. In some embodiments, "alkoxy" and/or "thioalkyl" groups are unsubstituted.

The terms "haloalkyl" and "haloalkoxy," as used herein, means a linear or branched alkyl or alkoxy, as the case may be, which is substituted with one or more halogen atoms. Non-limiting examples of haloalkyl groups include $-CHF_2$, $-CH_2F$, $-CF_3$, $-CF_2-$, and perhaloalkyls, such as $-CF_2CF_3$. Non-limiting examples of haloalkoxy groups include $-OCHF_2$, $-OCH_2F$, $-OCF_3$, $-OCF_2-$.

The term "halogen" includes F, Cl, Br, and I, i.e., fluoro, chloro, bromo, and iodo, respectively.

The term "aminoalkyl" means an alkyl group which is substituted with or contains an amino group.

As used herein, the term "alkylsulfonyl" refers to an alkyl group, as previously defined, wherein one carbon atom of the alkyl group, and the carbon atom's substituents, are replaced by a sulfur atom, and wherein the sulfur atom is further substituted with two oxo groups. An alkylsulfonyl group may be linear or branched. In some embodiments, alkylsulfonyl groups are substituted at the alkyl portion of the alkylsulfonyl group. In some embodiments, alkylsulfonyl groups are unsubstituted at the alkyl portion of the alkylsulfonyl group.

As used herein, an "amino" refers to a group which is a primary, secondary, or tertiary amine.

As used herein, a "carbonyl" group refers to C═O.

As used herein, a "cyano" or "nitrile" group refer to —C≡N.

As used herein, a "hydroxy" group refers to —OH.

As used herein, a "thiol" group refers to —SH.

As used herein, "tert" and "t-" each refer to tertiary.

As used herein, "Me" refers to a methyl group.

As used herein, an "amido" group refers to a carbonyl group, as previously defined, wherein the carbon of the carbonyl is bonded to an amino group, as previously defined. When a chemical group is said to be substituted by an amido group, that chemical group may be bonded to the carbonyl carbon or to the amino nitrogen of the amido group.

As used herein, a "carbamate" group refers to a carbonyl group, as previously defined, wherein the carbon of the carbonyl group is bonded to an amino group, as previously defined, and a divalent oxygen. When a chemical group is said to be substituted by a carbamate group, that chemical group may be bonded to the divalent oxygen or to the amino nitrogen of the carbamate group.

As used herein, "aromatic groups" or "aromatic rings" refer to chemical groups that contain conjugated, planar ring systems with delocalized pi electron orbitals comprised of [4n+2]p orbital electrons, wherein n is an integer ranging from 0 to 6. Nonlimiting examples of aromatic groups include aryl and heteroaryl groups.

The term "aryl" used alone or as part of a larger moiety as in "arylalkyl", "arylalkoxy", or "aryloxyalkyl", refers to monocyclic, bicyclic, and tricyclic ring systems having a total of five to fourteen ring members, wherein at least one ring in the system is aromatic and wherein each ring in a bicyclic or tricyclic ring system contains 3 to 7 ring members. The term "aryl" also refers to heteroaryl ring systems as defined herein below. Nonlimiting examples of aryl groups include phenyl rings. In some embodiments, aryl groups are substituted. In some embodiments, aryl groups are unsubstituted.

The term "heteroaryl", used alone or as part of a larger moiety as in "heteroarylalkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in a bicyclic or tricyclic ring system contains 3 to 7 ring members. In some embodiments, heteroaryl groups are substituted. In some embodiments, heteroaryl groups have one or more heteroatoms chosen from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, heteroaryl groups are unsubstituted.

Non-limiting examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc), benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999) and $4^{th}$ Edition (John Wiley & Sons, New Jersey, 2014).

Non-limiting examples of suitable solvents that may be used in this disclosure include, but are not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in this disclosure include, but are not limited to, 1,8-diazabicyclo[5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

The disclosure includes pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J. Pharmaceutical Sciences,* 1977, 66, 1 to 19.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The terms "patient" and "subject" are used interchangeably and refer to an animal including a human.

The terms "effective dose" and "effective amount" are used interchangeably herein and refer to that amount of compound that produces the desired effect for which it is administered (e.g., improvement in symptoms of FSGS and/or NDKD, lessening the severity of FSGS and/NDKD or a symptom of FSGS and/or NDKD, and/or reducing progression of FSGS and/or NDKD or a symptom of FSGS and/or NDKD). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treatment" and its cognates refer to slowing or stopping disease progression. "Treatment" and its cognates as used herein, include, but are not limited to the following: complete or partial remission, lower risk of kidney failure (e.g. ESRD), and disease-related complications (e.g. edema, susceptibility to infections, or thrombo-embolic events). Improvements in or lessening the severity of any of these symptoms can be readily assessed according to methods and techniques known in the art or subsequently developed.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

As used herein, the term "ambient conditions" means room temperature, open air condition and uncontrolled humidity condition.

The at least one entity chosen from compounds of Formulae (I), (Ia), (II), (IIIa), (IIIb), (IV), (Va), and (Vb), pharmaceutically acceptable salts of any of those compounds, solvates of any of the foregoing, and/or deuterated derivatives of any of the foregoing may be administered once daily, twice daily, or three times daily, for example, for the treatment of FSGS. In some embodiments, the compounds of Formulae (I), (Ia), (II), (IIIa), (IIIb), (IV), (Va), and (Vb), are chosen from Compounds 1 to 286 and Compounds 287 to 465, pharmaceutically acceptable salts of any of those compounds, solvates of any of the foregoing, and deuterated derivatives of any of the foregoing. In some embodiments, at least one entity chosen from compounds of Formulae (I), (Ia), (II), (IIIa), (IIIb), (IV), (Va), and (Vb), pharmaceutically acceptable salts of any of those compounds, solvates of any of the foregoing, and/or deuterated derivatives of any of the foregoing is administered once daily. In some embodiments, at least one entity chosen from Compounds 1 to 286, pharmaceutically acceptable salts of any of those compounds, solvates of any of the foregoing, and deuterated derivatives of any of the foregoing is administered once daily. In some embodiments, at least one entity chosen from compounds of Formulae (I), (Ia), (II), (IIIa), (IIIb), (IV), (Va), and (Vb), pharmaceutically acceptable salts of any of those compounds, solvates of any of the foregoing, and/or deuterated derivatives of any of the foregoing is administered twice daily. In some embodiments, at least one entity chosen from Compounds 1 to 286 and Compounds 287 to 465, pharmaceutically acceptable salts of any of those compounds, solvates of any of the foregoing, and/or deuterated derivatives of any of the foregoing is administered twice daily. In some embodiments, at least one entity chosen from compounds of Formulae (I), (Ia), (II), (IIIa), (IIIb), (IV), (Va), and (Vb), pharmaceutically acceptable salts of any of those compounds, solvates of any of the foregoing, and/or deuterated derivatives of any of the foregoing are administered three times daily. In some embodiments, at least one entity chosen from Compounds 1 to 286 and Compounds 287 to 465, pharmaceutically acceptable salts of any of those compounds, solvates of any of the foregoing, and/or deuterated derivatives of any of the foregoing is administered three times daily.

In some embodiments, 2 mg to 1500 mg, 5 mg to 1000 mg, 10 mg to 500 mg, 20 mg to 300 mg, 20 mg to 200 mg, 30 mg to 150 mg, 50 mg to 150 mg, 60 mg to 125 mg, or 70 mg to 120 mg, 80 mg to 115 mg, 90 mg to 110 mg, 95 mg to 110 mg, or 100 mg to 105 mg of at least one entity chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing are administered once daily, twice daily, or three times daily. In some embodiments, 2 mg to 1500 mg, 5 mg to 1000 mg, 10 mg to 500 mg, 20 mg to 300 mg, 20 mg to 200 mg, 30 mg to 150 mg, 50 mg to 150 mg, 60 mg to 125 mg, or 70 mg to 120 mg, 80 mg to 115 mg, 90 mg to 110 mg, 95 mg to 110 mg, or 100 mg to 105 mg of at least one entity chosen from Compounds 1 to 286 and Compounds 287 to 465, pharmaceutically acceptable salts of any of those compounds, solvates of any of the foregoing, and deuterated derivatives of any of the foregoing are administered once daily, twice daily, or three times daily.

One of ordinary skill in the art would recognize that, when an amount of compound is disclosed, the relevant amount of a pharmaceutically acceptable salt form of the compound is an amount equivalent to the concentration of the free base of the compound. The amounts of the compounds, pharmaceutically acceptable salts, solvates, and deuterated derivatives disclosed herein are based upon the free base form of the reference compound. For example, "10 mg of at least one compound chosen from compounds of Formulae (I), (Ia), (II), (IIIa), (IIIb), (IV), (Va), and (Vb), and pharmaceutically acceptable salts thereof" includes 10 mg of compound of Formulae (I), (Ia), (II), (IIIa), (IIIb), (IV), (Va), and (Vb), and a concentration of a pharmaceutically acceptable salt of compounds of Formulae (I), (Ia), (II), (IIIa), (IIIb), (IV), (Va), and (Vb), equivalent to 10 mg of compounds of Formulae (I), (Ia), (II), (IIIa), (IIIb), (IV), (Va), and (Vb), Compounds and Compositions In addition to compounds, deuterated derivatives, solvates, and pharmaceutically salts of compounds of Formula (I), in some embodiments, at least one entity of the disclosure is chosen from compounds of Formula (Ia):

(Ia)

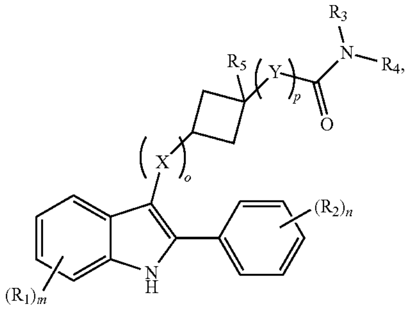

pharmaceutically acceptable salts thereof, solvates of any of the foregoing, and deuterated derivatives of any of the foregoing, wherein:

(i) each $R_1$ is independently chosen from
- halogen groups,
- hydroxy,
- thiol,
- amino,
- cyano,
- —$OC(O)C_1$-$C_6$ linear, branched, and cyclic alkyl groups,
- —$C(O)OC_1$-$C_6$ linear, branched, and cyclic alkyl groups,
- —$NHC(O)C_1$-$C_6$ linear, branched, and cyclic alkyl groups,
- —$C(O)NHC_1$-$C_6$ linear, branched, and cyclic alkyl groups,
- —NHC(O)aryl groups,
- —C(O)NHaryl groups,
- —NHC(O)heteroaryl groups,
- —C(O)NHheteroaryl groups,
- —$NHS(O)_2C_1$-$C_6$ linear, branched, and cyclic alkyl groups,
- —$S(O)_2NHC_1$-$C_6$ linear, branched, and cyclic alkyl groups,
- —$NHS(O)_2$aryl groups,
- —$S(O)_2$NHaryl groups,
- —$NHS(O)_2$heteroaryl groups,
- —$S(O)_2$NHheteroaryl groups,
- —$NHC(O)NHC_1$-$C_6$ linear, branched, and cyclic alkyl groups,
- —NHC(O)NHaryl groups,
- —NHC(O)NHheteroaryl groups,
- $C_1$-$C_6$ linear, branched, and cyclic alkyl groups,
- $C_2$-$C_6$ linear, branched, and cyclic alkenyl groups,
- $C_1$-$C_6$ linear, branched, and cyclic hydroxyalkyl groups,
- $C_1$-$C_6$ linear, branched, and cyclic alkoxy groups,
- $C_1$-$C_6$ linear, branched, and cyclic thioalkyl groups,
- $C_1$-$C_6$ linear, branched, and cyclic haloalkyl groups,
- $C_1$-$C_6$ linear, branched, and cyclic haloaminoalkyl groups,
- $C_1$-$C_6$ linear, branched, and cyclic halothioalkyl groups,
- $C_1$-$C_6$ linear, branched, and cyclic haloalkoxy groups,
- benzyloxy, benzylamino, or benzylthio groups,
- 3- to 6-membered heterocycloalkenyl groups,
- 3- to 6-membered heterocycloalkyl groups, and
- 5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from
- halogen groups,
- hydroxy,
- thiol,
- amino,
- cyano,
- —$NHC(O)C_1$-$C_6$ linear, branched, and cyclic alkyl groups,
- —$C(O)NHC_1$-$C_6$ linear, branched, and cyclic alkyl groups,
- —NHC(O)aryl groups,
- —C(O)NHaryl groups,
- —NHC(O)heteroaryl groups,
- —C(O)NHheteroaryl groups,
- —$NHS(O)_2C_1$-$C_6$ linear, branched, and cyclic alkyl groups,
- —$S(O)_2NHC_1$-$C_6$ linear, branched, and cyclic alkyl groups,
- —$NHS(O)_2$aryl groups,
- —$S(O)_2$NHaryl groups,
- —$NHS(O)_2$heteroaryl groups,
- —$S(O)_2$NHheteroaryl groups,
- —$NHC(O)NHC_1$-$C_4$ linear, branched, and cyclic alkyl groups,
- —NHC(O)NHaryl groups,
- —NHC(O)NHheteroaryl groups,
- $C_1$-$C_4$ linear, branched, and cyclic alkyl groups,
- $C_2$-$C_4$ linear, branched, and cyclic alkenyl groups,
- $C_1$-$C_4$ linear, branched, and cyclic hydroxyalkyl groups,
- $C_1$-$C_4$ linear, branched, and cyclic alkoxy groups,
- $C_1$-$C_4$ linear, branched, and cyclic thioalkyl groups,
- $C_1$-$C_4$ linear, branched, and cyclic haloalkyl groups,
- $C_1$-$C_4$ linear, branched, and cyclic haloaminoalkyl groups,
- $C_1$-$C_4$ linear, branched, and cyclic halothioalkyl groups, and
- $C_1$-$C_4$ linear, branched, and cyclic haloalkoxy groups;

(iii) m is chosen from 0, 1, 2, 3, and 4;

(iv) n is chosen from 0, 1, 2, 3 4, and 5;

(v) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with at least one group chosen from
- $C_1$-$C_6$ alkyl groups,
- aryl groups,
- heteroaryl groups,
- halogen groups,
- hydroxy, and
- amino;

(vi) Y is chosen from divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with at least one group chosen from $C_1$-$C_6$ alkyl groups, aryl groups, heteroaryl groups, halogen groups, hydroxy, and amino;

(vii) o is chosen from 0, 1, 2, 3, and 4;

(viii) p is chosen from 0, 1, 2, 3, and 4;

(ix) $R_3$ and $R_4$ are independently chosen from hydrogen, $C_1$-$C_6$ linear and branched alkylsulfonyl groups, $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each R is independently chosen from hydrogen, halogen groups, hydroxy, thiol, amino, and $C_1$-$C_6$ linear and branched alkyl groups.

In some embodiments, $R_3$ is hydrogen or methyl.

In some embodiments, wherein $R_3$ is hydrogen.

In some embodiments, each $R_1$ is independently chosen from halogen groups.

In some embodiments, each $R_1$ is fluoro.

In some embodiments, each $R_2$ is independently chosen from halogen groups and methyl.

In some embodiments, each $R_2$ is independently chosen from halogen groups.

In some embodiments, each $R_2$ is fluoro.

In some embodiments, m is 1 or 2.

In some embodiments, m is 2.

In some embodiments, n is 1 or 2.

In some embodiments, o is 1.

In some embodiments, p is 1.

In some embodiments, o is 0.

In some embodiments, p is 0.

In some embodiments, R is hydrogen.

In some embodiments, the at least one entity is chosen from compounds of Formula (II):

(II)

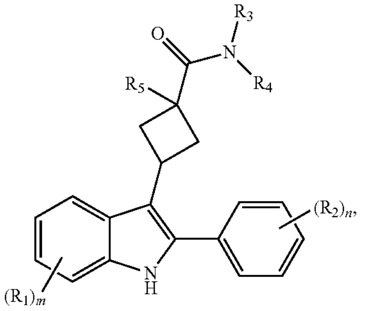

pharmaceutically acceptable salts thereof, solvates of any of the foregoing, and deuterated derivatives of any of the foregoing, wherein:

(i) each $R_1$ is independently chosen from:
- halogen groups,
- hydroxy,
- thiol,
- amino,
- cyano,
- —$OC(O)C_1$-$C_6$ linear, branched, and cyclic alkyl groups,
- —$C(O)OC_1$-$C_6$ linear, branched, and cyclic alkyl groups,
- —$NHC(O)C_1$-$C_6$ linear, branched, and cyclic alkyl groups,
- —$C(O)NHC_1$-$C_6$ linear, branched, and cyclic alkyl groups,
- —NHC(O)aryl groups,
- —C(O)NHaryl groups,
- —NHC(O)heteroaryl groups,
- —C(O)NHheteroaryl groups,
- —$NHS(O)_2C_1$-$C_6$ linear, branched, and cyclic alkyl groups,
- —$S(O)_2NHC_1$-$C_6$ linear, branched, and cyclic alkyl groups,
- —$NHS(O)_2$aryl groups,
- —$S(O)_2$NHaryl groups,
- —$NHS(O)_2$heteroaryl groups,
- —$S(O)_2$NHheteroaryl groups,
- —$NHC(O)NHC_1$-$C_6$ linear, branched, and cyclic alkyl groups,
- —NHC(O)NHaryl groups,
- —NHC(O)NHheteroaryl groups,
- $C_1$-$C_6$ linear, branched, and cyclic alkyl groups,
- $C_2$-$C_6$ linear, branched, and cyclic alkenyl groups,
- $C_1$-$C_6$ linear, branched, and cyclic hydroxyalkyl groups,
- $C_1$-$C_6$ linear, branched, and cyclic alkoxy groups,
- $C_1$-$C_6$ linear, branched, and cyclic thioalkyl groups,
- $C_1$-$C_6$ linear, branched, and cyclic haloalkyl groups,
- $C_1$-$C_6$ linear, branched, and cyclic haloaminoalkyl groups,
- $C_1$-$C_6$ linear, branched, and cyclic halothioalkyl groups,
- $C_1$-$C_6$ linear, branched, and cyclic haloalkoxy groups,
- benzyloxy, benzylamino, or benzylthio groups,
- 3- to 6-membered heterocycloalkenyl groups,
- 3- to 6-membered heterocycloalkyl groups, and
- 5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from
- halogen groups,
- hydroxy,
- thiol,
- amino,
- cyano,
- —$NHC(O)C_1$-$C_6$ linear, branched, and cyclic alkyl groups,
- —$C(O)NHC_1$-$C_6$ linear, branched, and cyclic alkyl groups,
- —NHC(O)aryl groups,
- —C(O)NHaryl groups,
- —NHC(O)heteroaryl groups,
- —C(O)NHheteroaryl groups,
- —$NHS(O)_2C_1$-$C_6$ linear, branched, and cyclic alkyl groups,
- —$S(O)_2NHC_1$-$C_6$ linear, branched, and cyclic alkyl groups,
- —$NHS(O)_2$aryl groups,
- —$S(O)_2$NHaryl groups,
- —$NHS(O)_2$heteroaryl groups,
- —$S(O)_2$NHheteroaryl groups,
- —$NHC(O)NHC_1$-$C_4$ linear, branched, and cyclic alkyl groups,
- —NHC(O)NHaryl groups,
- —NHC(O)NHheteroaryl groups,
- $C_1$-$C_4$ linear, branched, and cyclic alkyl groups,
- $C_2$-$C_4$ linear, branched, and cyclic alkenyl groups,
- $C_1$-$C_4$ linear, branched, and cyclic hydroxyalkyl groups,
- $C_1$-$C_4$ linear, branched, and cyclic alkoxy groups,
- $C_1$-$C_4$ linear, branched, and cyclic thioalkyl groups,
- $C_1$-$C_4$ linear, branched, and cyclic haloalkyl groups,
- $C_1$-$C_4$ linear, branched, and cyclic haloaminoalkyl groups,
- $C_1$-$C_4$ linear, branched, and cyclic halothioalkyl groups, and
- $C_1$-$C_4$ linear, branched, and cyclic haloalkoxy groups;

(iii) m is chosen from 0, 1, 2, 3, and 4;

(iv) n is chosen from 0, 1, 2, 3, 4, and 5;

(v) $R_3$ and $R_4$ are independently chosen from
- hydrogen,
- $C_1$-$C_6$ linear and branched alkylsulfonyl groups,
- $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups,
- heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
- aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
- heteroaryl groups optionally substituted with at least one group chosen from $C_1$-$C_6$ linear alkyl groups, and
- $C_1$-$C_6$ linear and branched alkyl groups, wherein the alkyl groups are optionally substituted with at least one group chosen from:

amino groups,
hydroxy,
cyano,
carboxylic acid,
halogen groups,
amido groups optionally substituted with one or two groups chosen from $C_1$-$C_6$ linear, branched, and cyclic alkyl groups and $C_1$-$C_6$ linear, branched, and cyclic hydroxyalkyl groups,
$C_3$-$C_6$ cyclic alkyl groups optionally substituted with one or two groups chosen from halogen groups and hydroxy,
$C_1$-$C_6$ linear and branched alkynyl groups,
$C_1$-$C_6$ linear and branched alkoxy groups optionally substituted with at least one hydroxy,
$C_1$-$C_6$ linear and branched alkylsulfonyl groups,
aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups,
carbonyl-(4-methylpiperazin-1-yl),
carbonyl-(N-morpholino),
4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and
4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from:
hydroxy,
oxo,
$C_1$-$C_6$ linear, branched, and cyclic alkyl groups optionally substituted with at least one groups chosen from hydroxy, amino groups, $C_1$-$C_6$ linear, branched, and cyclic alkoxy groups,
amide groups optionally substituted with at least one group chosen from $C_1$-$C_6$ linear, branched, and cyclic alkyl groups,
carboxamide groups optionally substituted with at least one group chosen from $C_1$-$C_6$ linear, branched, and cyclic alkyl groups,
$C_1$-$C_6$ linear, branched, and cyclic alkoxy groups optionally substituted with at least one group chosen from $C_1$-$C_6$ linear, branched, and cyclic alkyl groups and heterocyclic groups,
4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and
4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each $R_5$ is independently chosen from
hydrogen,
halogen groups,
hydroxy,
thiol,
amino, and
$C_1$-$C_6$ linear and branched alkyl groups.

In some embodiments, each $R_1$ is independently chosen from halogen groups, and $C_1$-$C_6$ linear and branched alkyl groups; each $R_2$ is independently chosen from halogen groups, and $C_1$-$C_6$ linear and branched alkyl groups; m is chosen from 0, 1, 2, and 3; and n is 1 or 2.

In some embodiments, each $R_1$ is independently chosen from halogen groups, and methyl; each $R_2$ is independently chosen from halogen groups, and methyl; m is 0, 1 or 2; and n is 1 or 2.

In some embodiments, each $R_1$ is fluoro.

In some embodiments, each $R_2$ is fluoro.

In some embodiments, m is 0, 1 or 2.

In some embodiments, m is 2.

In some embodiments, m is 0.

In some embodiments, n is 1 or 2.

In some embodiments, n is 1.

In some embodiments, $R_5$ is chosen from hydrogen, amino, alkyl, and halo.

In some embodiments, R is chosen from hydrogen and $C_1$-$C_6$ linear alkyl groups.

In some embodiments, R is hydrogen.

In some embodiments, $R_3$ is chosen from hydrogen and $C_1$-$C_6$ linear and branched alkyl groups.

In some embodiments, $R_3$ is chosen from hydrogen and methyl.

In some embodiments, $R_4$ is chosen from:

$C_1$-$C_6$ linear and branched alkyl groups optionally substituted with at least one group chosen from:
amino groups,
hydroxy,
cyano,
amido groups optionally substituted with one or two groups chosen from $C_1$-$C_6$ linear, branched, and cyclic alkyl groups and $C_1$-$C_6$ linear, branched, and cyclic hydroxyalkyl groups,
4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and
4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups.

In some embodiments, $R_4$ is chosen from:

$C_1$-$C_6$ linear and branched alkyl groups optionally substituted with at least one group chosen from:
hydroxy,
amido groups optionally substituted with one or two groups chosen from $C_1$-$C_6$ linear, branched, and cyclic alkyl groups and $C_1$-$C_6$ linear, branched, and cyclic hydroxyalkyl groups, and
5- or 6-membered heteroaryl groups optionally substituted with one or two groups chosen from $C_1$-$C_6$ linear and branched alkyl groups optionally substituted with one or two groups chosen from hydroxy and $C_1$-$C_6$ linear and branched alkoxy groups.

In some embodiments, $R_4$ is chosen from $C_1$-$C_6$ linear and branched alkyl groups optionally substituted with at least one group chosen from:

hydroxy, amido groups optionally substituted with one or two groups chosen from $C_1$-$C_6$ linear alkyl groups, and 5- or 6-membered heteroaryl groups optionally substituted with one or two groups chosen from $C_1$-$C_6$ linear alkyl groups.

In some embodiments, $R_3$ and $R_4$, together with the nitrogen atom to which they are attached, form a 4- to 10-membered heterocyclyl group optionally substituted with at least one group chosen from:

hydroxy, $C_1$-$C_6$ linear alkyl groups, and amide groups optionally substituted with at least one group chosen from $C_1$-$C_6$ linear, branched, and cyclic alkyl groups.

In some embodiments, the at least one entity of the disclosure is chosen from compounds of Formula (IIIa)

(IIIa)

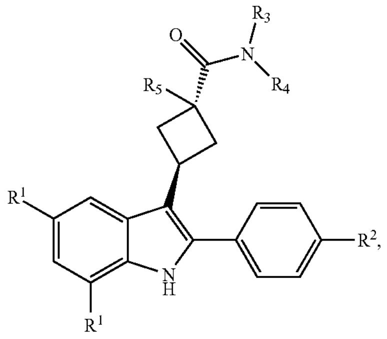

compounds of Formula (IIIb):

(IIIb)

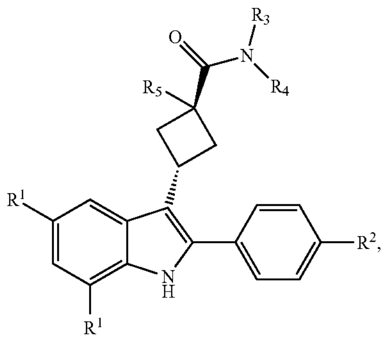

pharmaceutically acceptable salts of any of the foregoing, solvates of any of the foregoing, and deuterated derivatives of any of the foregoing, wherein:

(i) each $R_1$ is independently chosen from:

halogen groups, hydroxy, thiol, amino, cyano,

—$OC(O)C_1$-$C_6$ linear, branched, and cyclic alkyl groups,

—$C(O)OC_1$-$C_6$ linear, branched, and cyclic alkyl groups,

—$NHC(O)C_1$-$C_6$ linear, branched, and cyclic alkyl groups,

—$C(O)NHC_1$-$C_6$ linear, branched, and cyclic alkyl groups,

—NHC(O)aryl groups,

—C(O)NHaryl groups,

—NHC(O)heteroaryl groups,

—C(O)NHheteroaryl groups,

—$NHS(O)_2C_1$-$C_6$ linear, branched, and cyclic alkyl groups,

—$S(O)_2NHC_1$-$C_6$ linear, branched, and cyclic alkyl groups,

—$NHS(O)_2$aryl groups,

—$S(O)_2$NHaryl groups,

—$NHS(O)_2$heteroaryl groups,

—$S(O)_2$NHheteroaryl groups,

—$NHC(O)NHC_1$-$C_6$ linear, branched, and cyclic alkyl groups,

—NHC(O)NHaryl groups,

—NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups, $C_1$-$C_6$ linear, branched, and cyclic halothioalkyl groups, $C_1$-$C_6$ linear, branched, and cyclic haloalkoxy groups, benzyloxy, benzylamino, or benzylthio groups, 3- to 6-membered heterocycloalkenyl groups, 3- to 6-membered heterocycloalkyl groups, and 5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from:

halogen groups, hydroxy, thiol, amino, cyano,

—$NHC(O)C_1$-$C_6$ linear, branched, and cyclic alkyl groups,

—$C(O)NHC_1$-$C_6$ linear, branched, and cyclic alkyl groups,

—NHC(O)aryl groups,

—C(O)NHaryl groups,

—NHC(O)heteroaryl groups,

—C(O)NHheteroaryl groups,

—$NHS(O)_2C_1$-$C_6$ linear, branched, and cyclic alkyl groups,

—$S(O)_2NHC_1$-$C_6$ linear, branched, and cyclic alkyl groups,

—$NHS(O)_2$aryl groups,

—$S(O)_2$NHaryl groups,

—$NHS(O)_2$heteroaryl groups,

—$S(O)_2$NHheteroaryl groups,

—$NHC(O)NHC_1$-$C_4$ linear, branched, and cyclic alkyl groups,

—NHC(O)NHaryl groups,

—NHC(O)NHheteroaryl groups, $C_1$-$C_4$ linear, branched, and cyclic alkyl groups, $C_2$-$C_4$ linear, branched, and cyclic alkenyl groups, $C_1$-$C_4$ linear, branched, and cyclic hydroxyalkyl groups, $C_1$-$C_4$ linear, branched, and cyclic alkoxy groups, $C_1$-$C_4$ linear, branched, and cyclic thioalkyl groups, $C_1$-$C_4$ linear, branched, and cyclic haloalkyl groups, $C_1$-$C_4$ linear, branched, and cyclic haloaminoalkyl groups, $C_1$-$C_4$ linear, branched, and cyclic halothioalkyl groups, and $C_1$-$C_4$ linear, branched, and cyclic haloalkoxy groups;

(iii) m is chosen from 0, 1, 2, 3, and 4;

(iv) n is chosen from 0, 1, 2, 3, 4, and 5;

(v) $R_3$ and $R_4$ are independently chosen from:

hydrogen, $C_1$-$C_6$ linear and branched alkylsulfonyl groups, $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from:

hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each $R_5$ is independently chosen from hydrogen, halogen groups, hydroxy, thiol, amino, and $C_1$-$C_6$ linear and branched alkyl groups.

In some embodiments, each $R_1$ is independently chosen from halogen groups, and $C_1$-$C_6$ linear and branched alkyl groups; each $R_2$ is independently chosen from halogen groups, and $C_1$-$C_6$ linear and branched alkyl groups; m is chosen from 0, 1, 2, and 3; and n is 1 or 2.

In some embodiments, each $R_1$ is independently chosen from halogen groups, and methyl; each $R_2$ is independently chosen from halogen groups, and methyl; m is 0, 1 or 2; and n is 1 or 2.

In some embodiments, each $R_1$ is fluoro.

In some embodiments, each $R_2$ is fluoro.

In some embodiments, m is 0, 1 or 2.

In some embodiments, m is 2.

In some embodiments, m is 0.

In some embodiments, n is 1 or 2.

In some embodiments, n is 1.

In some embodiments, R is chosen from hydrogen, amino, alkyl, and halo.

In some embodiments, R is chosen from hydrogen and $C_1$-$C_6$ linear alkyl groups.

In some embodiments, R is hydrogen.

In some embodiments, $R_3$ is chosen from hydrogen and $C_1$-$C_6$ linear and branched alkyl groups.

In some embodiments, $R_3$ is chosen from hydrogen and methyl.

In some embodiments, R is chosen from $C_1$-$C_6$ linear and branched alkyl groups optionally substituted with at least one group chosen from:

amino groups, hydroxy, cyano, amido groups optionally substituted with one or two groups chosen from $C_1$-$C_6$ linear, branched, and cyclic alkyl groups and $C_1$-$C_6$ linear, branched, and cyclic hydroxyalkyl groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups.

In some embodiments, $R_4$ is chosen from $C_1$-$C_6$ linear and branched alkyl groups optionally substituted with at least one group chosen from:

hydroxy, amido groups optionally substituted with one or two groups chosen from $C_1$-$C_6$ linear, branched, and cyclic alkyl groups and $C_1$-$C_6$ linear, branched, and cyclic hydroxyalkyl groups, and 5- or 6-membered heteroaryl groups optionally substituted with one or two groups chosen from $C_1$-$C_6$ linear and branched alkyl groups optionally substituted with one or two groups chosen from hydroxy and $C_1$-$C_6$ linear and branched alkoxy groups.

In some embodiments, $R_4$ is chosen from $C_1$-$C_6$ linear and branched alkyl groups optionally substituted with at least one group chosen from:

hydroxy, amido groups optionally substituted with one or two groups chosen from $C_1$-$C_6$ linear alkyl groups, and 5- or 6-membered heteroaryl groups optionally substituted with one or two groups chosen from $C_1$-$C_6$ linear alkyl groups.

In some embodiments, $R_3$ and $R_4$, together with the nitrogen atom to which they are attached, form a 4- to 10-membered heterocyclyl group optionally substituted with at least one group chosen from:

hydroxy, $C_1$-$C_6$ linear alkyl groups, and amide groups optionally substituted with at least one group chosen from $C_1$-$C_6$ linear, branched, and cyclic alkyl groups.

In some embodiments, the at least one entity of the disclosure is chosen from compounds of Formula (IV):

(IV)

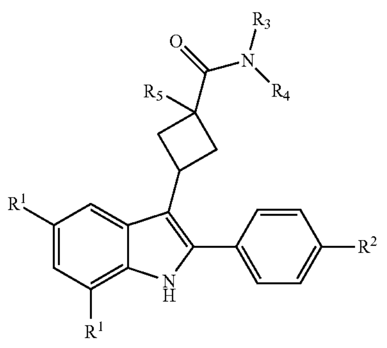

pharmaceutically acceptable salts thereof, solvates of any of the foregoing, and deuterated derivatives of any of the foregoing, wherein:

(i) each $R_1$ and $R_2$ is independently chosen from:
fluoro,
chloro,
bromo,
cyano,
methyl,
cyclopropyl,
ethyl,
hydroxypropyl,
isopropyl,
propen-2-yl,
dihydrofuran,
furan, and
methoxy;

(ii) $R_3$ and $R_4$ are independently chosen from:
hydrogen,
$C_1$-$C_6$ linear and branched alkylsulfonyl groups,
$C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups,
heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
heteroaryl groups optionally substituted with at least one group chosen from $C_1$-$C_6$ linear alkyl groups, and
$C_1$-$C_6$ linear and branched alkyl groups, wherein the alkyl groups are optionally substituted with at least one group chosen from:
amino groups,
hydroxy,
cyano,
carboxylic acid,
halogen groups,
amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (iii) each R is independently chosen from:

hydrogen, halogen groups, hydroxy, thiol, amino, and $C_1$-$C_6$ linear and branched alkyl groups.

In some embodiments, $R_3$ is hydrogen and $R_4$ is independently chosen from:

$C_1$-$C_6$ linear and branched alkylsulfonyl groups, $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups.

In some embodiments, $R_4$ is independently chosen from $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups; and $R_3$ is independently chosen from:

$C_1$-$C_6$ linear and branched alkylsulfonyl groups, $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups.

In some embodiments, $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups.

In some embodiments, in the at least one entity chosen from compounds of Formulae (I), (II), (IIIa), (IIIb), (IV), (Va), and (Vb), pharmaceutically acceptable salts of any of those compounds, solvates of any of the foregoing, and deuterated derivatives of any of the foregoing, each $R_1$ and $R_2$ is independently chosen from fluoro, chloro, bromo, cyano, and methyl.

In some embodiments, the at least one entity of the disclosure is chosen from Compounds 1 to 286 depicted in Table 1and pharmaceutically acceptable salts of any of those compounds, solvates of any of the foregoing, and deuterated derivatives of any of the foregoing. A wavy line in a compound in Table 1 (i.e., ) depicts a bond between two atoms and indicates a position of mixed stereochemistry for a collection of molecules, such as a racemic mixture, cis/trans isomers, or (E)/(Z) isomers.

TABLE 1

| Compounds 1 to 286 |
|---|
| 1 |
| 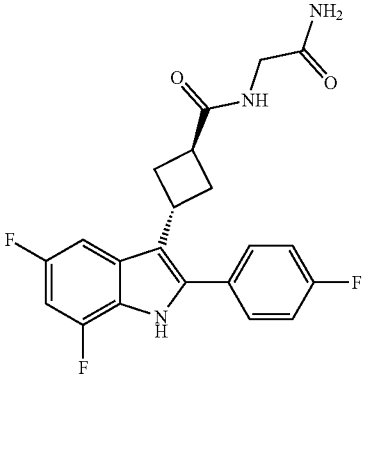 [SMILES: NC(=O)CNC(=O)[C@H]1C[C@H](c2c(-c3ccc(F)cc3)[nH]c3c(F)cc(F)cc32)C1] |

TABLE 1-continued
| Compounds 1 to 286 |
| --- |
| 2 |
| 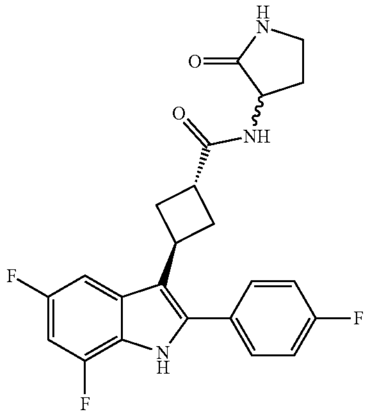 [SMILES: O=C1NCCC1NC(=O)[C@H]1C[C@H](c2c(-c3ccc(F)cc3)[nH]c3c(F)cc(F)cc32)C1] |
| 3 |
| 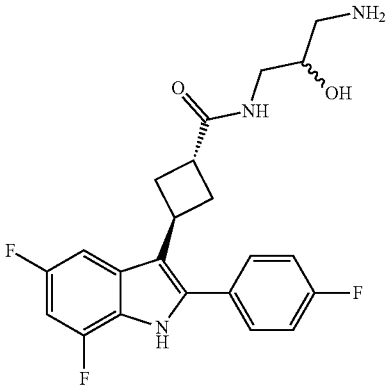 [SMILES: NCC(O)CNC(=O)[C@H]1C[C@H](c2c(-c3ccc(F)cc3)[nH]c3c(F)cc(F)cc32)C1] |
| 4 |
| 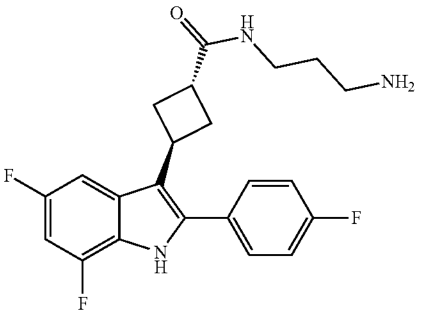 [SMILES: NCCCNC(=O)[C@H]1C[C@H](c2c(-c3ccc(F)cc3)[nH]c3c(F)cc(F)cc32)C1] |
TABLE 1-continued
| Compounds 1 to 286 |
| --- |
| 5 |
| 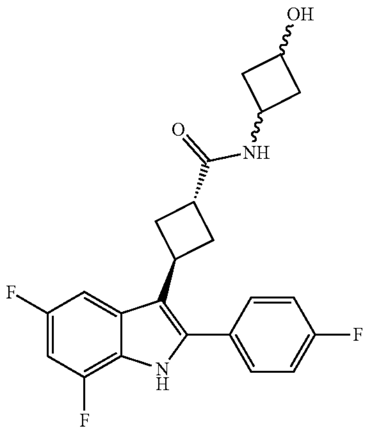 [SMILES: O=C(NC1CC(O)C1)[C@H]1C[C@H](c2c(-c3ccc(F)cc3)[nH]c3c(F)cc(F)cc32)C1] |
| 6 |
| 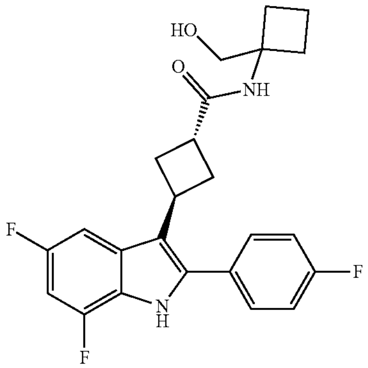 [SMILES: O=C(NC1(CO)CCC1)[C@H]1C[C@H](c2c(-c3ccc(F)cc3)[nH]c3c(F)cc(F)cc32)C1] |
| 7 |
| 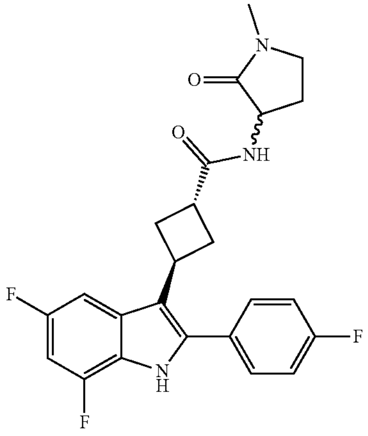 [SMILES: CN1CCC(NC(=O)[C@H]2C[C@H](c3c(-c4ccc(F)cc4)[nH]c4c(F)cc(F)cc43)C2)C1=O] |

TABLE 1-continued
| Compounds 1 to 286 |
| --- |
| 8 |
| 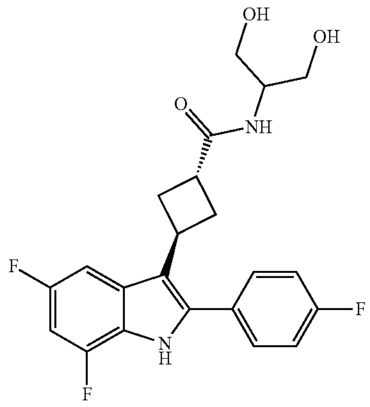 [SMILES: O=C(NC(CO)CO)[C@H]1C[C@H](c2c(-c3ccc(F)cc3)[nH]c3c(F)cc(F)cc32)C1] |
| 9 |
| 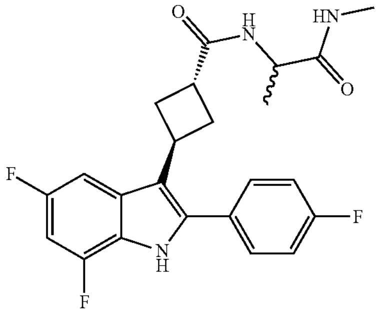 [SMILES: CNC(=O)C(C)NC(=O)[C@H]1C[C@H](c2c(-c3ccc(F)cc3)[nH]c3c(F)cc(F)cc32)C1] |
| 10 |
| 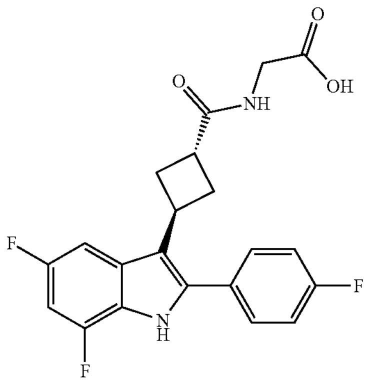 [SMILES: O=C(O)CNC(=O)[C@H]1C[C@H](c2c(-c3ccc(F)cc3)[nH]c3c(F)cc(F)cc32)C1] |
TABLE 1-continued
| Compounds 1 to 286 |
| --- |
| 11 |
| 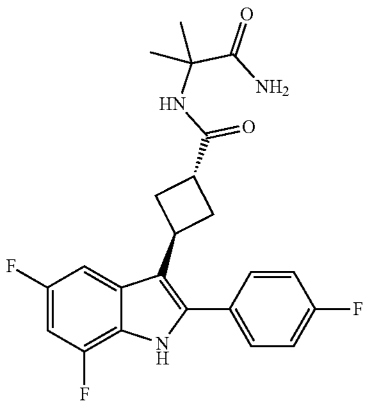 [SMILES: CC(C)(NC(=O)[C@H]1C[C@H](c2c(-c3ccc(F)cc3)[nH]c3c(F)cc(F)cc32)C1)C(N)=O] |
| 12 |
| 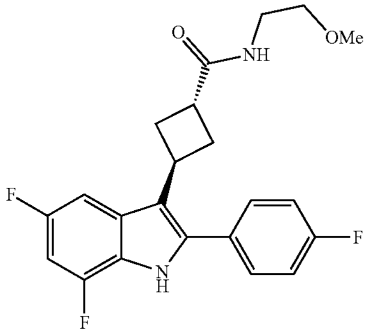 [SMILES: COCCNC(=O)[C@H]1C[C@H](c2c(-c3ccc(F)cc3)[nH]c3c(F)cc(F)cc32)C1] |
| 13 |
| 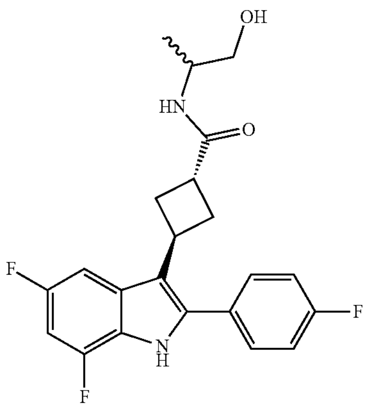 [SMILES: CC(CO)NC(=O)[C@H]1C[C@H](c2c(-c3ccc(F)cc3)[nH]c3c(F)cc(F)cc32)C1] |

TABLE 1-continued
| Compounds 1 to 286 |
|---|
14
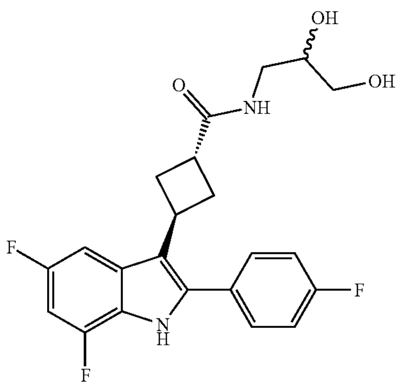 [SMILES: O=C(NCC(O)CO)[C@H]1C[C@H](c2c(-c3ccc(F)cc3)[nH]c3c(F)cc(F)cc32)C1]
15
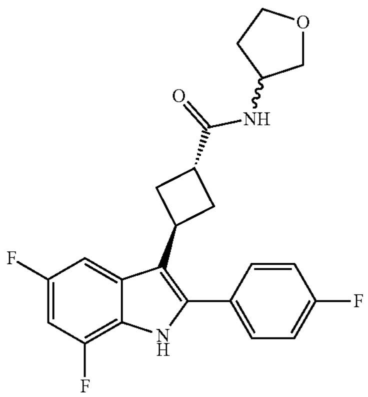 [SMILES: O=C(NC1CCOC1)[C@H]1C[C@H](c2c(-c3ccc(F)cc3)[nH]c3c(F)cc(F)cc32)C1]
16
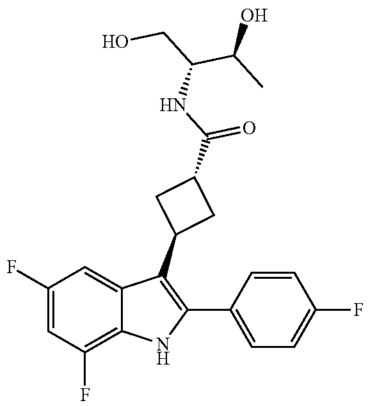 [SMILES: C[C@H](O)[C@@H](CO)NC(=O)[C@H]1C[C@H](c2c(-c3ccc(F)cc3)[nH]c3c(F)cc(F)cc32)C1]
17
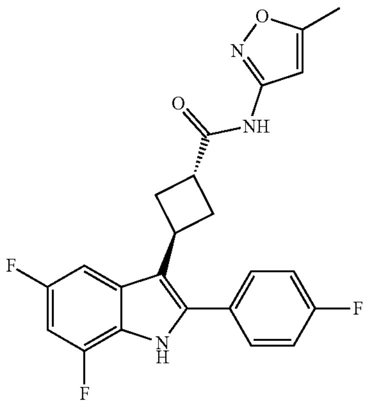 [SMILES: Cc1cc(NC(=O)[C@H]2C[C@H](c3c(-c4ccc(F)cc4)[nH]c4c(F)cc(F)cc43)C2)no1]
18
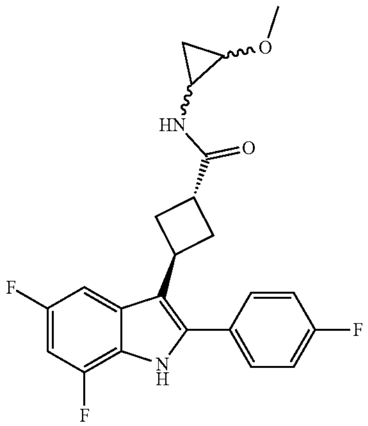 [SMILES: COC1CC1NC(=O)[C@H]1C[C@H](c2c(-c3ccc(F)cc3)[nH]c3c(F)cc(F)cc32)C1]
19
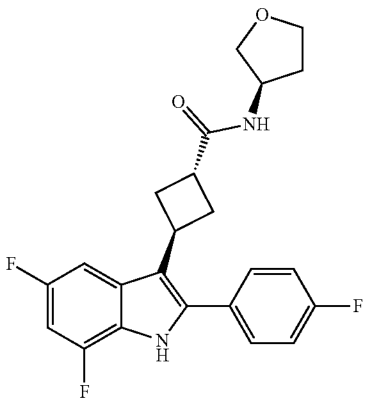 [SMILES: O=C(N[C@@H]1CCOC1)[C@H]1C[C@H](c2c(-c3ccc(F)cc3)[nH]c3c(F)cc(F)cc32)C1]

TABLE 1-continued
Compounds 1 to 286
20
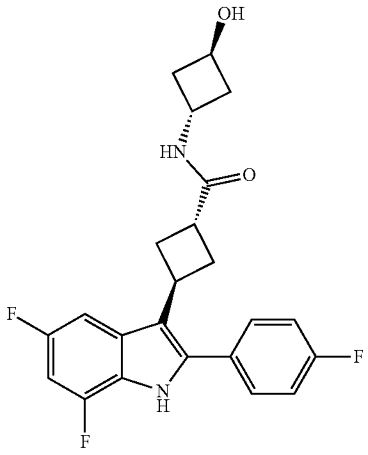 [SMILES: O=C(N[C@H]1C[C@H](O)C1)[C@H]1C[C@H](c2c(-c3ccc(F)cc3)[nH]c3c(F)cc(F)cc32)C1]
21
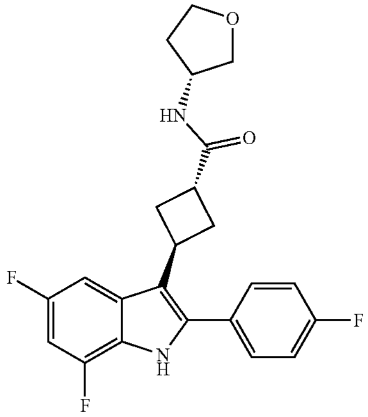 [SMILES: O=C(N[C@@H]1CCOC1)[C@H]1C[C@H](c2c(-c3ccc(F)cc3)[nH]c3c(F)cc(F)cc32)C1]
22
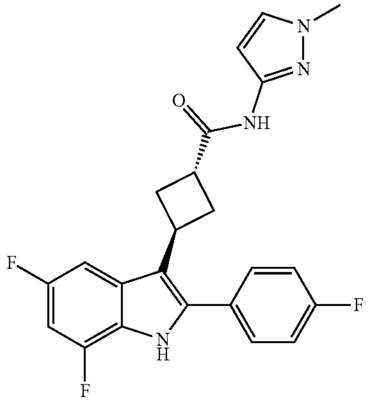 [SMILES: Cn1ccc(NC(=O)[C@H]2C[C@H](c3c(-c4ccc(F)cc4)[nH]c4c(F)cc(F)cc43)C2)n1]
23
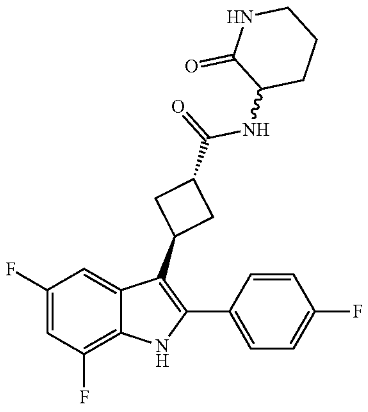 [SMILES: O=C1NCCCC1NC(=O)[C@H]1C[C@H](c2c(-c3ccc(F)cc3)[nH]c3c(F)cc(F)cc32)C1]
24
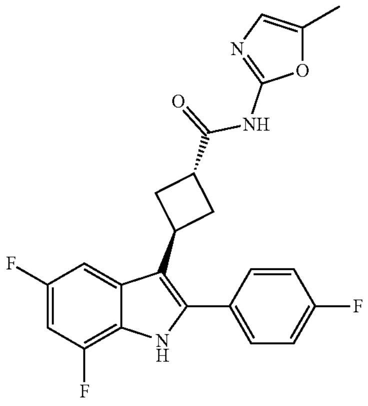 [SMILES: Cc1cnc(NC(=O)[C@H]2C[C@H](c3c(-c4ccc(F)cc4)[nH]c4c(F)cc(F)cc43)C2)o1]
25
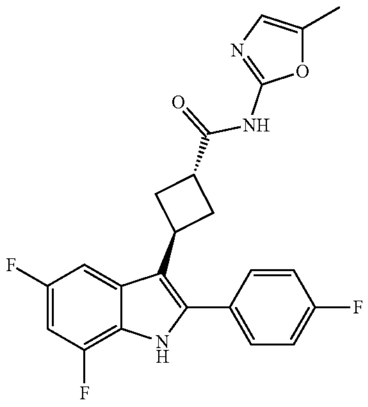 [SMILES: Cc1cnc(NC(=O)[C@H]2C[C@H](c3c(-c4ccc(F)cc4)[nH]c4c(F)cc(F)cc43)C2)o1]

TABLE 1-continued
| Compounds 1 to 286 |
|---|
| 26 |
| 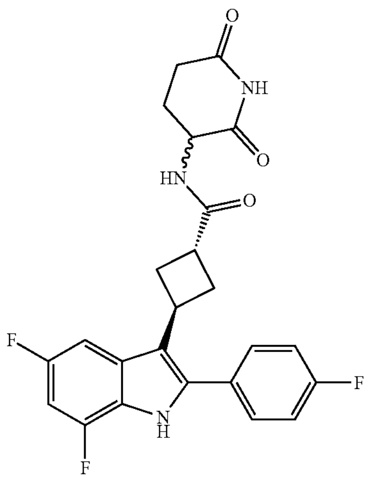 [SMILES: O=C1CCC(NC(=O)[C@H]2C[C@H](c3c(-c4ccc(F)cc4)[nH]c4c(F)cc(F)cc43)C2)C(=O)N1] |
| 27 |
| 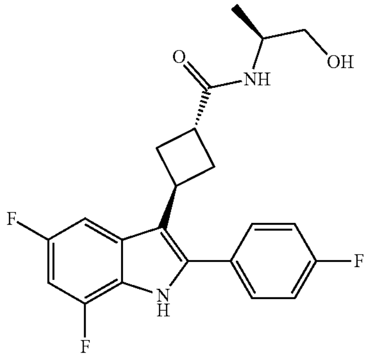 [SMILES: C[C@@H](CO)NC(=O)[C@H]1C[C@H](c2c(-c3ccc(F)cc3)[nH]c3c(F)cc(F)cc32)C1] |
| 28 |
| 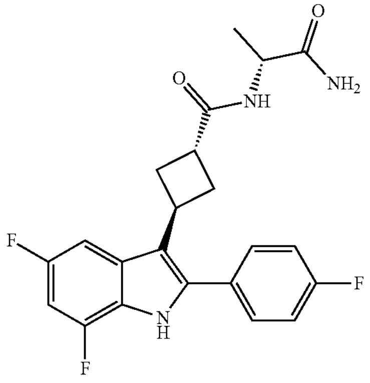 [SMILES: C[C@@H](NC(=O)[C@H]1C[C@H](c2c(-c3ccc(F)cc3)[nH]c3c(F)cc(F)cc32)C1)C(N)=O] |
TABLE 1-continued
| Compounds 1 to 286 |
|---|
| 29 |
| 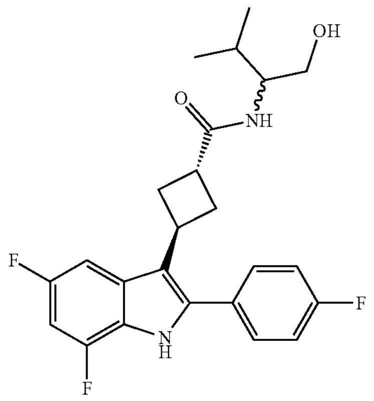 [SMILES: CC(C)C(CO)NC(=O)[C@H]1C[C@H](c2c(-c3ccc(F)cc3)[nH]c3c(F)cc(F)cc32)C1] |
| 30 |
| 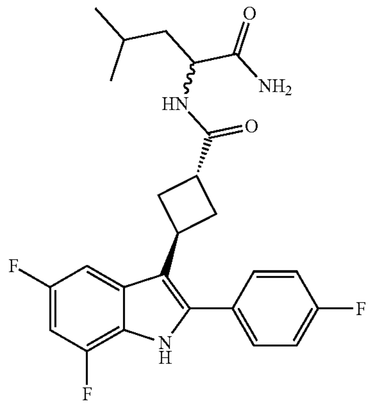 [SMILES: CC(C)CC(NC(=O)[C@H]1C[C@H](c2c(-c3ccc(F)cc3)[nH]c3c(F)cc(F)cc32)C1)C(N)=O] |
| 31 |
| 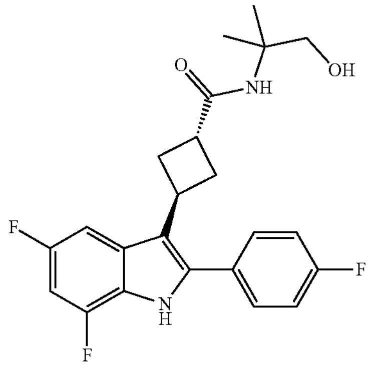 [SMILES: CC(C)(CO)NC(=O)[C@H]1C[C@H](c2c(-c3ccc(F)cc3)[nH]c3c(F)cc(F)cc32)C1] |

TABLE 1-continued
| Compounds 1 to 286 |
| --- |
| 32 |
| 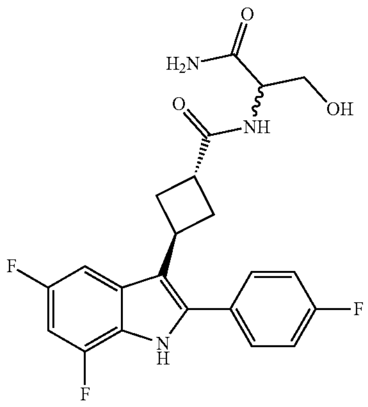 [SMILES: NC(=O)C(CO)NC(=O)[C@H]1C[C@H](c2c(-c3ccc(F)cc3)[nH]c3c(F)cc(F)cc32)C1] |
| 33 |
| 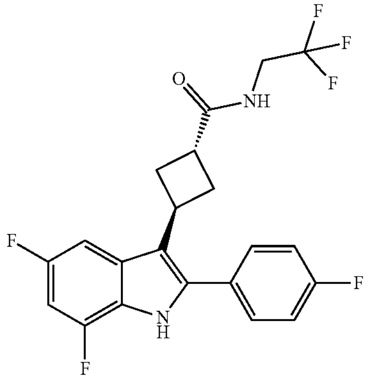 [SMILES: O=C(NCC(F)(F)F)[C@H]1C[C@H](c2c(-c3ccc(F)cc3)[nH]c3c(F)cc(F)cc32)C1] |
| 34 |
| 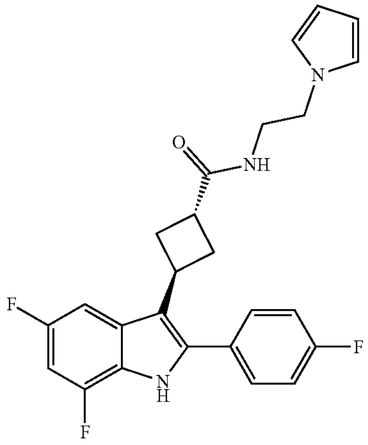 [SMILES: O=C(NCCn1cccc1)[C@H]1C[C@H](c2c(-c3ccc(F)cc3)[nH]c3c(F)cc(F)cc32)C1] |
| 35 |
| 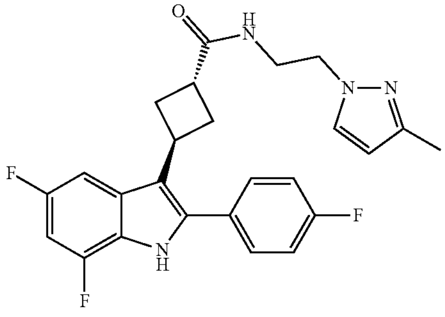 [SMILES: Cc1ccn(CCNC(=O)[C@H]2C[C@H](c3c(-c4ccc(F)cc4)[nH]c4c(F)cc(F)cc43)C2)n1] |
| 36 |
| 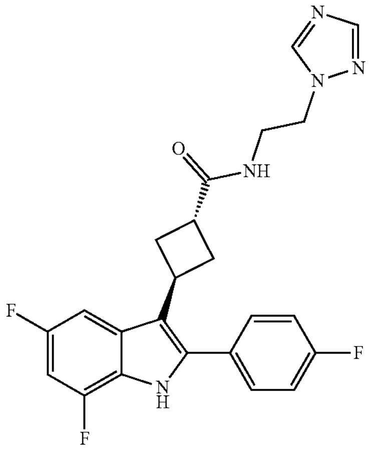 [SMILES: O=C(NCCn1cncn1)[C@H]1C[C@H](c2c(-c3ccc(F)cc3)[nH]c3c(F)cc(F)cc32)C1] |
| 37 |
| 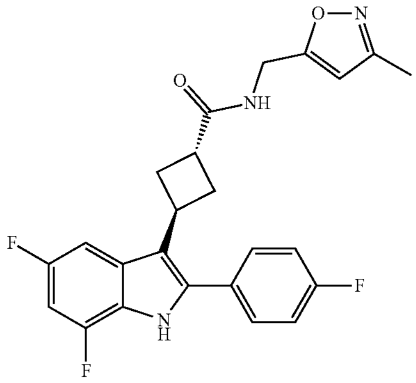 [SMILES: Cc1cc(CNC(=O)[C@H]2C[C@H](c3c(-c4ccc(F)cc4)[nH]c4c(F)cc(F)cc43)C2)on1] |

TABLE 1-continued
| Compounds 1 to 286 |
|---|
| 38 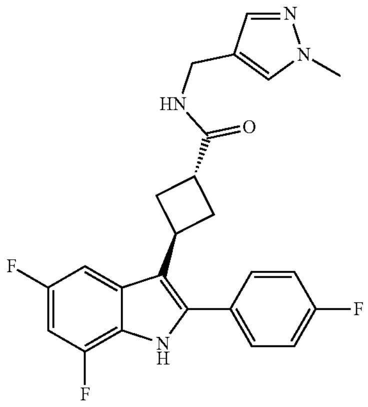 [SMILES: Cn1cc(CNC(=O)[C@H]2C[C@H](c3c(-c4ccc(F)cc4)[nH]c4c(F)cc(F)cc43)C2)cn1] |
| 39 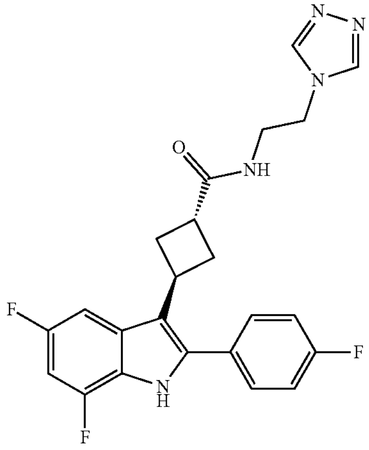 [SMILES: O=C(NCCn1cnnc1)[C@H]1C[C@H](c2c(-c3ccc(F)cc3)[nH]c3c(F)cc(F)cc32)C1] |
| 40 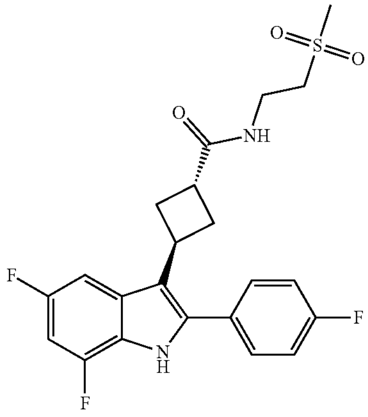 [SMILES: CS(=O)(=O)CCNC(=O)[C@H]1C[C@H](c2c(-c3ccc(F)cc3)[nH]c3c(F)cc(F)cc32)C1] |
TABLE 1-continued
| Compounds 1 to 286 |
|---|
| 41 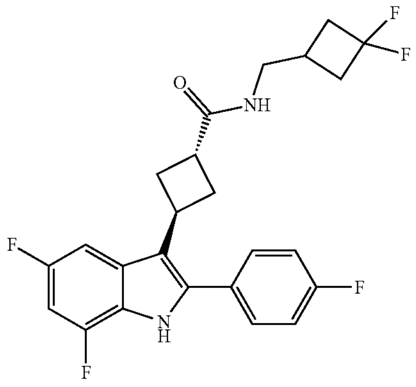 [SMILES: O=C(NCC1CC(F)(F)C1)[C@H]1C[C@H](c2c(-c3ccc(F)cc3)[nH]c3c(F)cc(F)cc32)C1] |
| 42 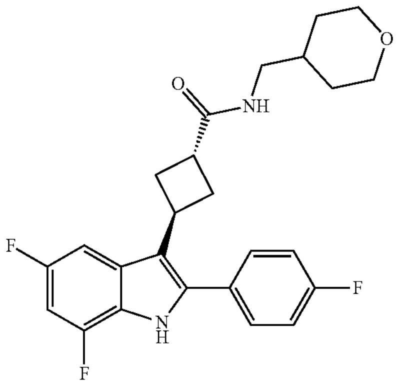 [SMILES: O=C(NCC1CCOCC1)[C@H]1C[C@H](c2c(-c3ccc(F)cc3)[nH]c3c(F)cc(F)cc32)C1] |
| 43 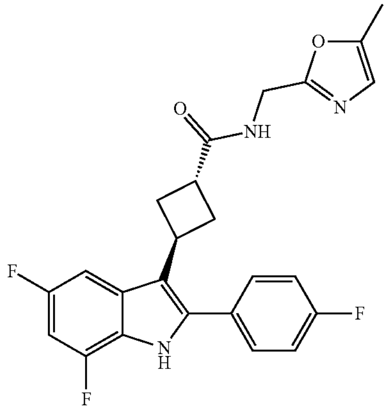 [SMILES: Cc1cnc(CNC(=O)[C@H]2C[C@H](c3c(-c4ccc(F)cc4)[nH]c4c(F)cc(F)cc43)C2)o1] |

TABLE 1-continued
Compounds 1 to 286
44
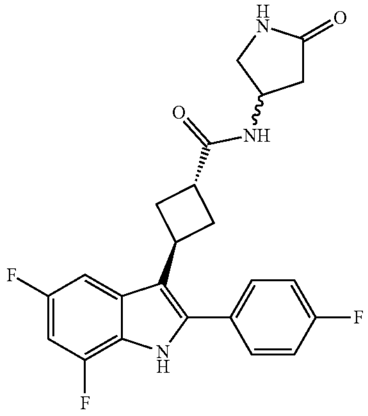 [SMILES: O=C1CC(NC(=O)[C@H]2C[C@H](c3c(-c4ccc(F)cc4)[nH]c4c(F)cc(F)cc43)C2)CN1]
45
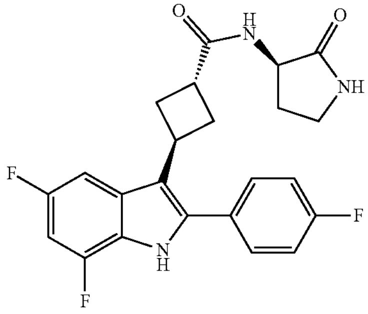 [SMILES: O=C1NCC[C@H]1NC(=O)[C@H]1C[C@H](c2c(-c3ccc(F)cc3)[nH]c3c(F)cc(F)cc32)C1]
46
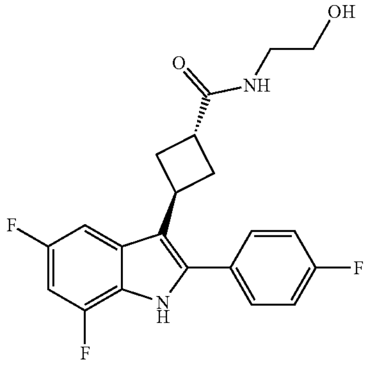 [SMILES: O=C(NCCO)[C@H]1C[C@H](c2c(-c3ccc(F)cc3)[nH]c3c(F)cc(F)cc32)C1]
47
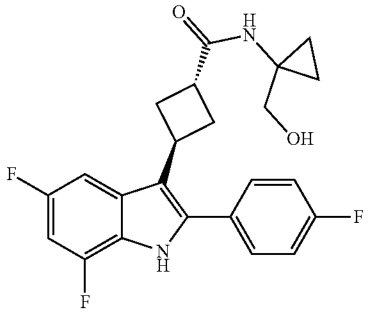 [SMILES: O=C(NC1(CO)CC1)[C@H]1C[C@H](c2c(-c3ccc(F)cc3)[nH]c3c(F)cc(F)cc32)C1]
48
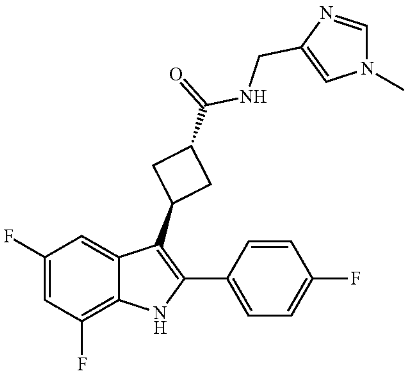 [SMILES: Cn1cnc(CNC(=O)[C@H]2C[C@H](c3c(-c4ccc(F)cc4)[nH]c4c(F)cc(F)cc43)C2)c1]
49
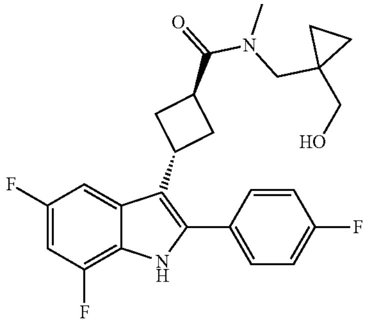 [SMILES: CN(CC1(CO)CC1)C(=O)[C@H]1C[C@H](c2c(-c3ccc(F)cc3)[nH]c3c(F)cc(F)cc32)C1]
50
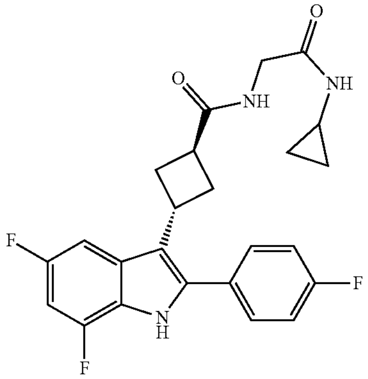 [SMILES: O=C(CNC(=O)[C@H]1C[C@H](c2c(-c3ccc(F)cc3)[nH]c3c(F)cc(F)cc32)C1)NC1CC1]
51
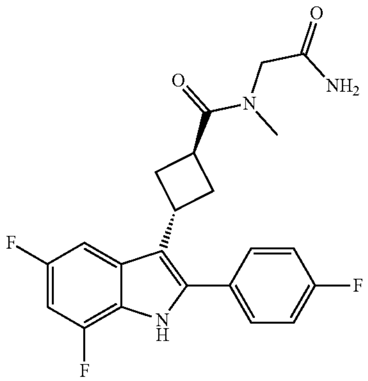 [SMILES: CN(CC(N)=O)C(=O)[C@H]1C[C@H](c2c(-c3ccc(F)cc3)[nH]c3c(F)cc(F)cc32)C1]

TABLE 1-continued
Compounds 1 to 286
52
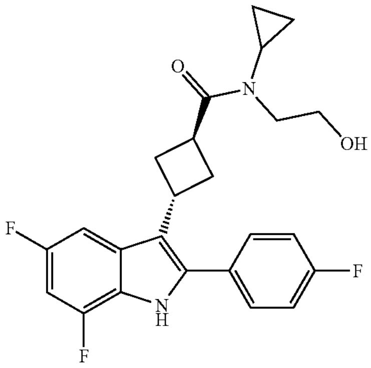 [SMILES: O=C([C@H]1C[C@H](c2c(-c3ccc(F)cc3)[nH]c3c(F)cc(F)cc32)C1)N(CCO)C1CC1]
53
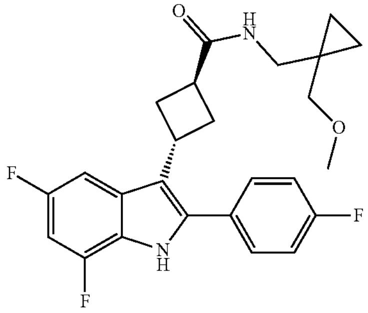 [SMILES: COCC1(CNC(=O)[C@H]2C[C@H](c3c(-c4ccc(F)cc4)[nH]c4c(F)cc(F)cc43)C2)CC1]
54
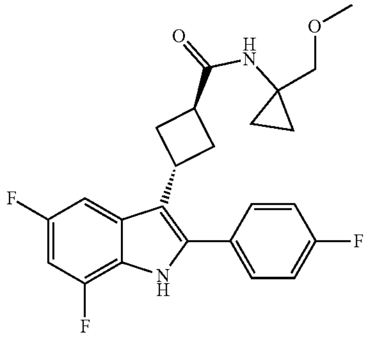 [SMILES: COCC1(NC(=O)[C@H]2C[C@H](c3c(-c4ccc(F)cc4)[nH]c4c(F)cc(F)cc43)C2)CC1]
55
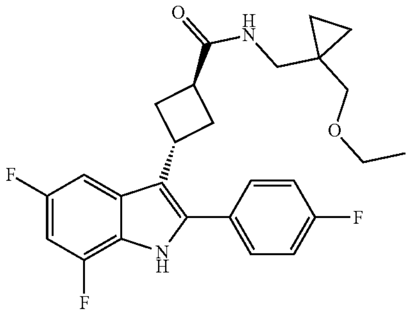 [SMILES: CCOCC1(CNC(=O)[C@H]2C[C@H](c3c(-c4ccc(F)cc4)[nH]c4c(F)cc(F)cc43)C2)CC1]
TABLE 1-continued
Compounds 1 to 286
56
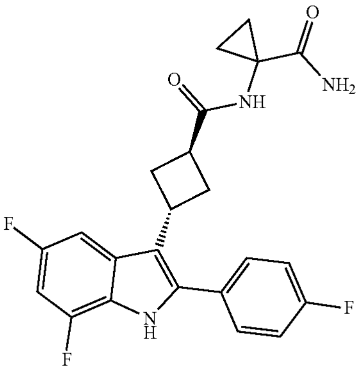 [SMILES: NC(=O)C1(NC(=O)[C@H]2C[C@H](c3c(-c4ccc(F)cc4)[nH]c4c(F)cc(F)cc43)C2)CC1]
57
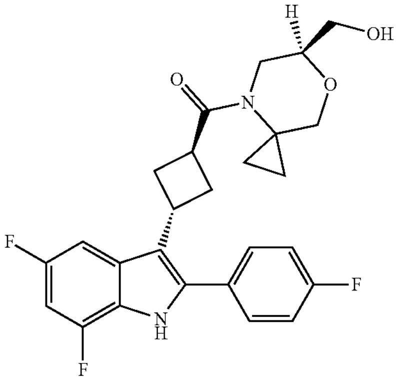 [SMILES: O=C([C@H]1C[C@H](c2c(-c3ccc(F)cc3)[nH]c3c(F)cc(F)cc32)C1)N1C[C@@H](CO)OCC12CC2]
58
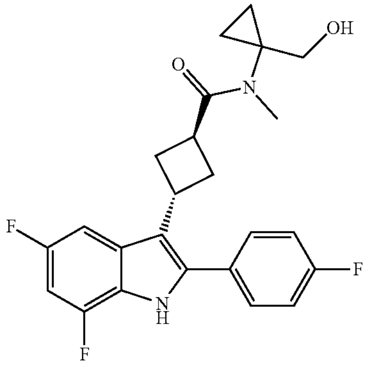 [SMILES: CN(C(=O)[C@H]1C[C@H](c2c(-c3ccc(F)cc3)[nH]c3c(F)cc(F)cc32)C1)C1(CO)CC1]

TABLE 1-continued
| Compounds 1 to 286 |
|---|
| 59 |
| 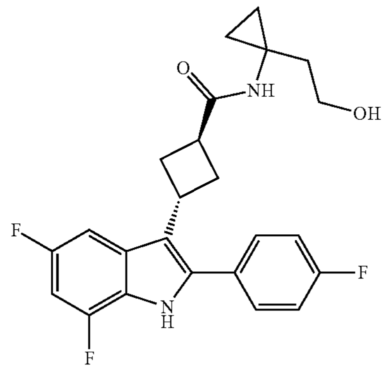 [SMILES: O=C(NC1(CCO)CC1)[C@H]1C[C@H](c2c(-c3ccc(F)cc3)[nH]c3c(F)cc(F)cc32)C1] |
| 60 |
| 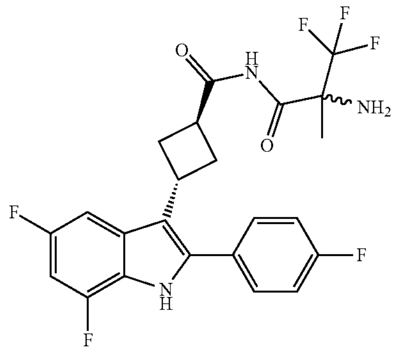 [SMILES: CC(N)(C(=O)NC(=O)[C@H]1C[C@H](c2c(-c3ccc(F)cc3)[nH]c3c(F)cc(F)cc32)C1)C(F)(F)F] |
| 61 |
| 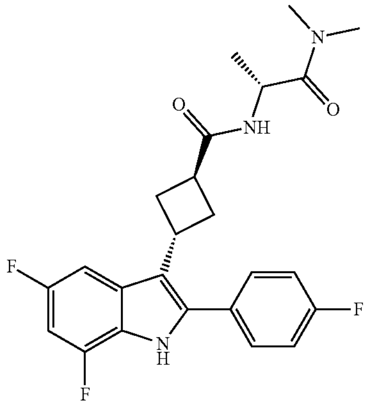 [SMILES: C[C@@H](NC(=O)[C@H]1C[C@H](c2c(-c3ccc(F)cc3)[nH]c3c(F)cc(F)cc32)C1)C(=O)N(C)C] |
TABLE 1-continued
| Compounds 1 to 286 |
|---|
| 62 |
| 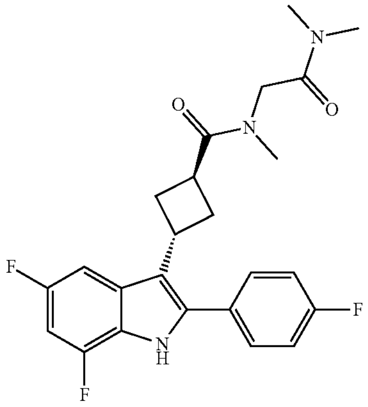 [SMILES: CN(C)C(=O)CN(C)C(=O)[C@H]1C[C@H](c2c(-c3ccc(F)cc3)[nH]c3c(F)cc(F)cc32)C1] |
| 63 |
| 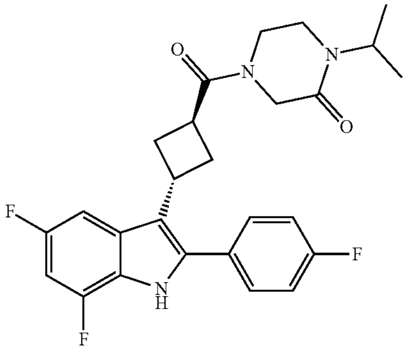 [SMILES: CC(C)N1CCN(C(=O)[C@H]2C[C@H](c3c(-c4ccc(F)cc4)[nH]c4c(F)cc(F)cc43)C2)CC1=O] |
| 64 |
| 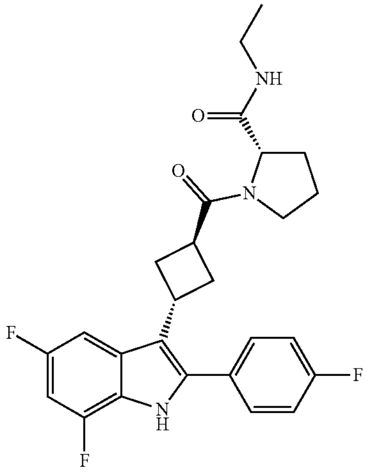 [SMILES: CCNC(=O)[C@@H]1CCCN1C(=O)[C@H]1C[C@H](c2c(-c3ccc(F)cc3)[nH]c3c(F)cc(F)cc32)C1] |

TABLE 1-continued
Compounds 1 to 286
65
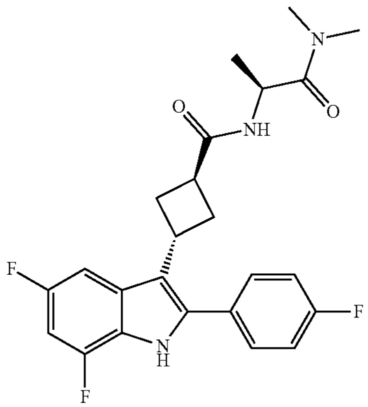 [SMILES: C[C@H](NC(=O)[C@H]1C[C@H](c2c(-c3ccc(F)cc3)[nH]c3c(F)cc(F)cc32)C1)C(=O)N(C)C]
66
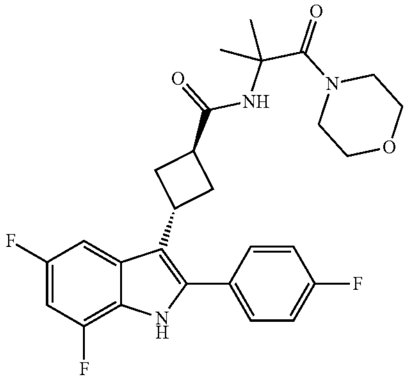 [SMILES: CC(C)(NC(=O)[C@H]1C[C@H](c2c(-c3ccc(F)cc3)[nH]c3c(F)cc(F)cc32)C1)C(=O)N1CCOCC1]
67
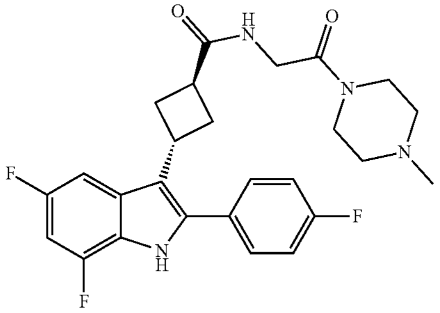 [SMILES: CN1CCN(C(=O)CNC(=O)[C@H]2C[C@H](c3c(-c4ccc(F)cc4)[nH]c4c(F)cc(F)cc43)C2)CC1]
68
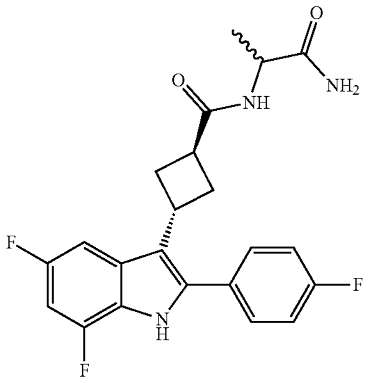 [SMILES: CC(NC(=O)[C@H]1C[C@H](c2c(-c3ccc(F)cc3)[nH]c3c(F)cc(F)cc32)C1)C(N)=O]
69
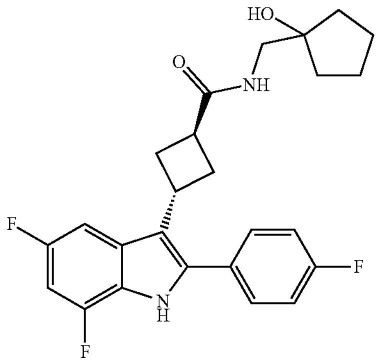 [SMILES: O=C(NCC1(O)CCCC1)[C@H]1C[C@H](c2c(-c3ccc(F)cc3)[nH]c3c(F)cc(F)cc32)C1]
70
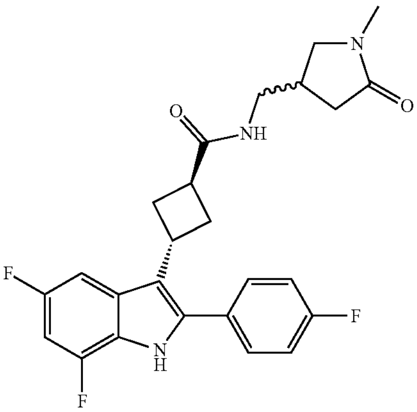 [SMILES: CN1CC(CNC(=O)[C@H]2C[C@H](c3c(-c4ccc(F)cc4)[nH]c4c(F)cc(F)cc43)C2)CC1=O]

TABLE 1-continued
| Compounds 1 to 286 |
| --- |
| 71 |
| 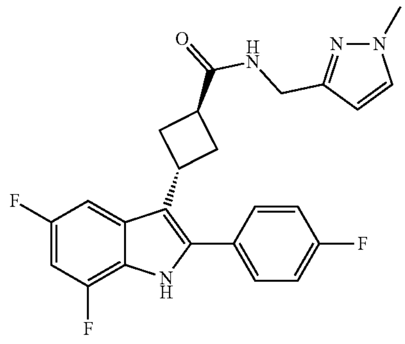 [SMILES: Cn1ccc(CNC(=O)[C@H]2C[C@H](c3c(-c4ccc(F)cc4)[nH]c4c(F)cc(F)cc43)C2)n1] |
| 72 |
| 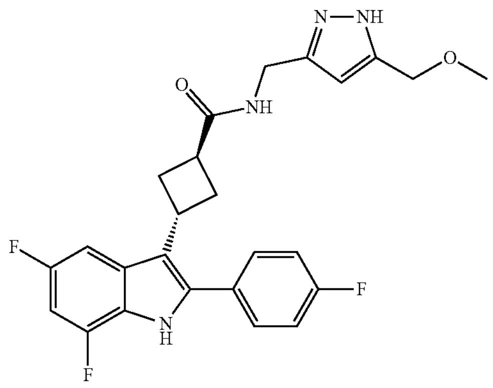 [SMILES: COCc1cc(CNC(=O)[C@H]2C[C@H](c3c(-c4ccc(F)cc4)[nH]c4c(F)cc(F)cc43)C2)n[nH]1] |
| 73 |
| 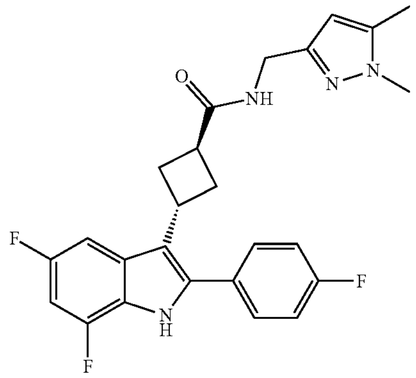 [SMILES: Cc1cc(CNC(=O)[C@H]2C[C@H](c3c(-c4ccc(F)cc4)[nH]c4c(F)cc(F)cc43)C2)nn1C] |
| 74 |
| 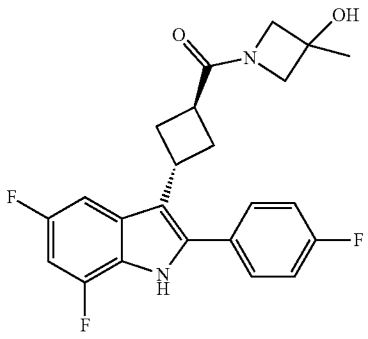 [SMILES: CC1(O)CN(C(=O)[C@H]2C[C@H](c3c(-c4ccc(F)cc4)[nH]c4c(F)cc(F)cc43)C2)C1] |
TABLE 1-continued
| Compounds 1 to 286 |
| --- |
| 75 |
| 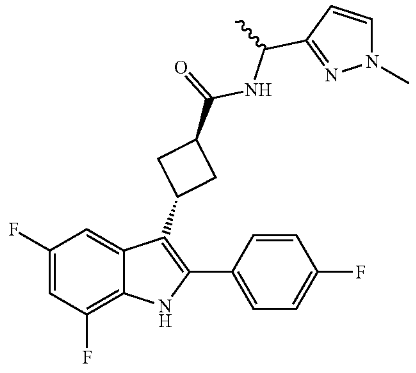 [SMILES: CC(NC(=O)[C@H]1C[C@H](c2c(-c3ccc(F)cc3)[nH]c3c(F)cc(F)cc32)C1)c1ccn(C)n1] |
| 76 |
| 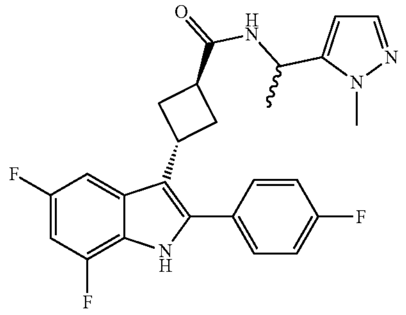 [SMILES: CC(NC(=O)[C@H]1C[C@H](c2c(-c3ccc(F)cc3)[nH]c3c(F)cc(F)cc32)C1)c1ccnn1C] |
| 77 |
| 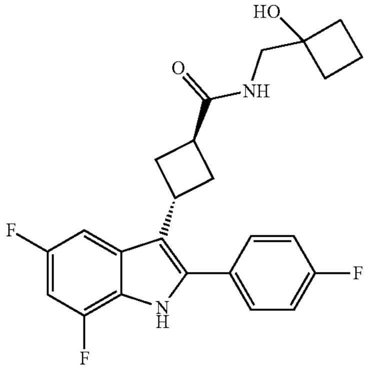 [SMILES: O=C(NCC1(O)CCC1)[C@H]1C[C@H](c2c(-c3ccc(F)cc3)[nH]c3c(F)cc(F)cc32)C1] |

TABLE 1-continued
| Compounds 1 to 286 |
|---|
| 78 |
| 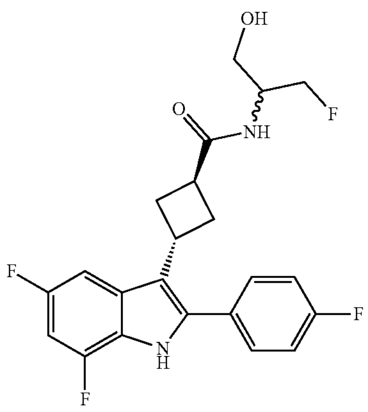 [SMILES: O=C(NC(CO)CF)[C@H]1C[C@H](c2c(-c3ccc(F)cc3)[nH]c3c(F)cc(F)cc32)C1] |
| 79 |
| 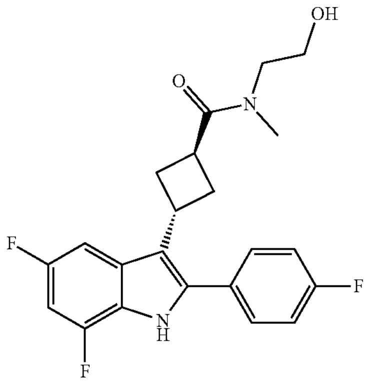 [SMILES: CN(CCO)C(=O)[C@H]1C[C@H](c2c(-c3ccc(F)cc3)[nH]c3c(F)cc(F)cc32)C1] |
| 80 |
| 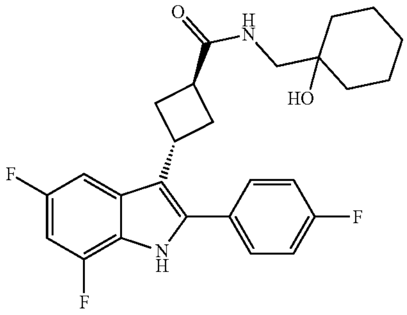 [SMILES: O=C(NCC1(O)CCCCC1)[C@H]1C[C@H](c2c(-c3ccc(F)cc3)[nH]c3c(F)cc(F)cc32)C1] |
TABLE 1-continued
| Compounds 1 to 286 |
|---|
| 81 |
| 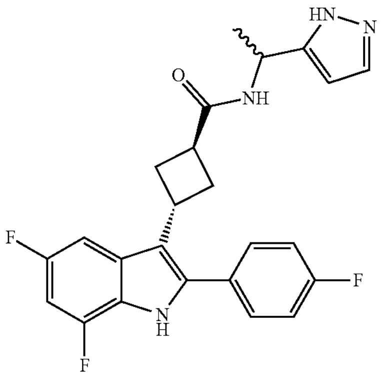 [SMILES: CC(NC(=O)[C@H]1C[C@H](c2c(-c3ccc(F)cc3)[nH]c3c(F)cc(F)cc32)C1)c1ccn[nH]1] |
| 82 |
| 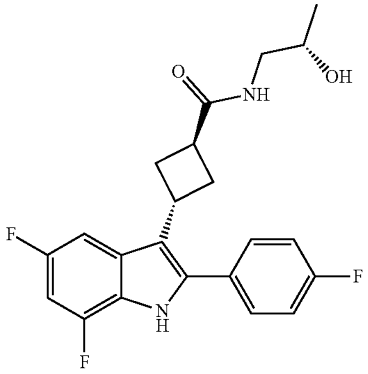 [SMILES: C[C@H](O)CNC(=O)[C@H]1C[C@H](c2c(-c3ccc(F)cc3)[nH]c3c(F)cc(F)cc32)C1] |
| 83 |
| 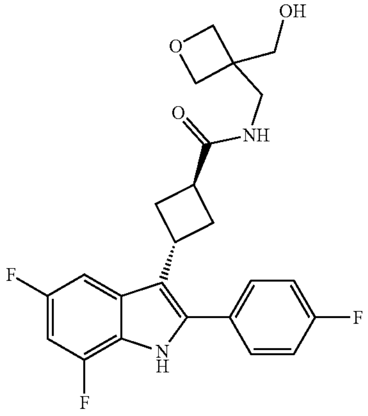 [SMILES: O=C(NCC1(CO)COC1)[C@H]1C[C@H](c2c(-c3ccc(F)cc3)[nH]c3c(F)cc(F)cc32)C1] |

TABLE 1-continued
Compounds 1 to 286
84
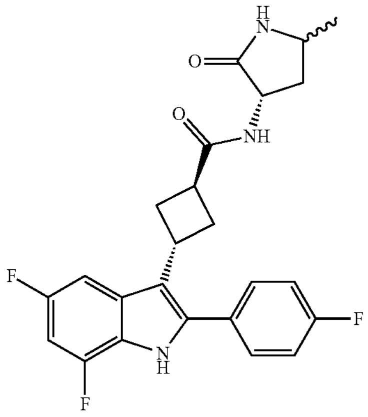 [SMILES: CC1C[C@H](NC(=O)[C@H]2C[C@H](c3c(-c4ccc(F)cc4)[nH]c4c(F)cc(F)cc43)C2)C(=O)N1]
85
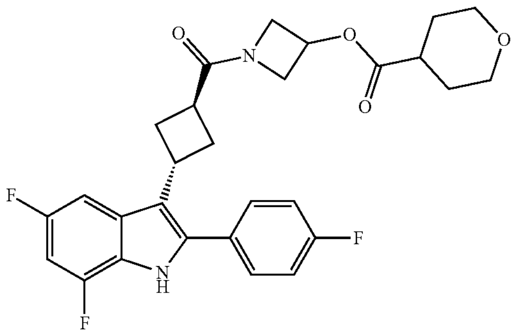
86
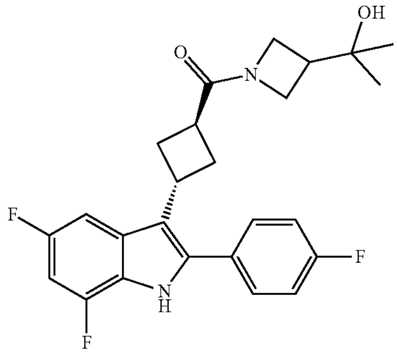 [SMILES: CC(C)(O)C1CN(C(=O)[C@H]2C[C@H](c3c(-c4ccc(F)cc4)[nH]c4c(F)cc(F)cc43)C2)C1]
87
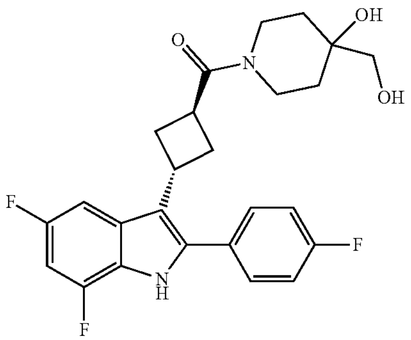 [SMILES: O=C([C@H]1C[C@H](c2c(-c3ccc(F)cc3)[nH]c3c(F)cc(F)cc32)C1)N1CCC(O)(CO)CC1]
TABLE 1-continued
Compounds 1 to 286
88
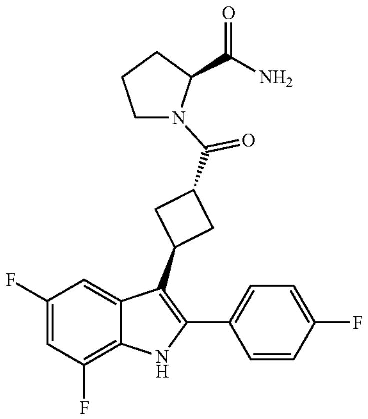 [SMILES: NC(=O)[C@@H]1CCCN1C(=O)[C@H]1C[C@H](c2c(-c3ccc(F)cc3)[nH]c3c(F)cc(F)cc32)C1]
89
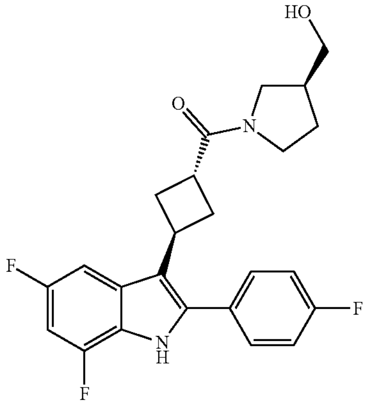 [SMILES: O=C([C@H]1C[C@H](c2c(-c3ccc(F)cc3)[nH]c3c(F)cc(F)cc32)C1)N1CC[C@H](CO)C1]
90
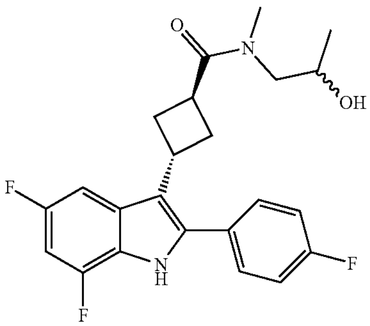 [SMILES: CC(O)CN(C)C(=O)[C@H]1C[C@H](c2c(-c3ccc(F)cc3)[nH]c3c(F)cc(F)cc32)C1]

TABLE 1-continued
| Compounds 1 to 286 |
|---|
91
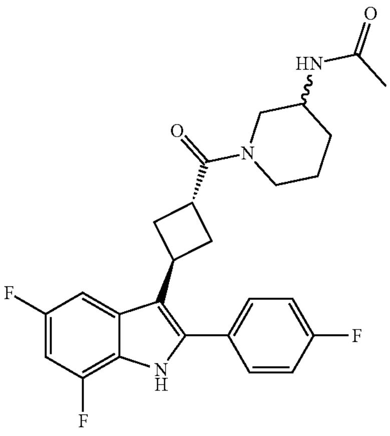 [SMILES: CC(=O)NC1CCCN(C(=O)[C@H]2C[C@H](c3c(-c4ccc(F)cc4)[nH]c4c(F)cc(F)cc43)C2)C1]
92
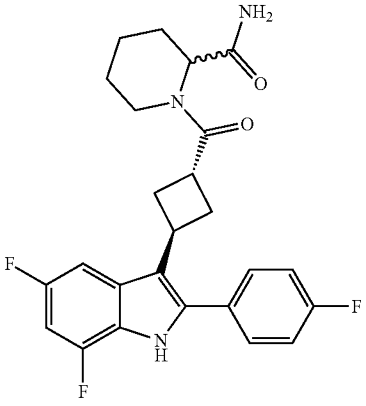 [SMILES: NC(=O)C1CCCCN1C(=O)[C@H]1C[C@H](c2c(-c3ccc(F)cc3)[nH]c3c(F)cc(F)cc32)C1]
93
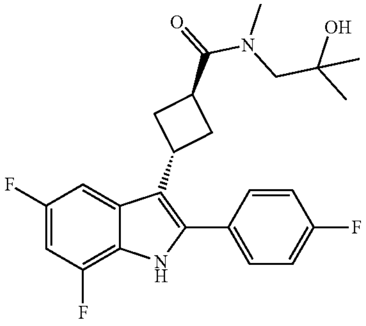 [SMILES: CN(CC(C)(C)O)C(=O)[C@H]1C[C@H](c2c(-c3ccc(F)cc3)[nH]c3c(F)cc(F)cc32)C1]
94
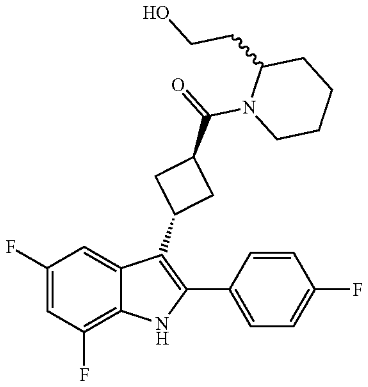 [SMILES: O=C([C@H]1C[C@H](c2c(-c3ccc(F)cc3)[nH]c3c(F)cc(F)cc32)C1)N1CCCCC1CCO]
95
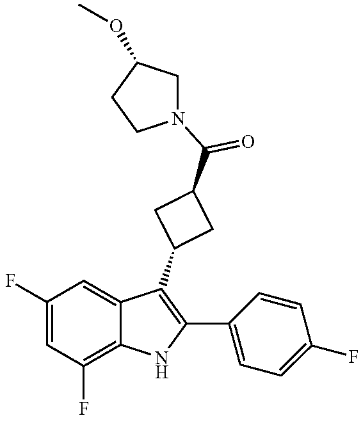 [SMILES: CO[C@H]1CCN(C(=O)[C@H]2C[C@H](c3c(-c4ccc(F)cc4)[nH]c4c(F)cc(F)cc43)C2)C1]
96
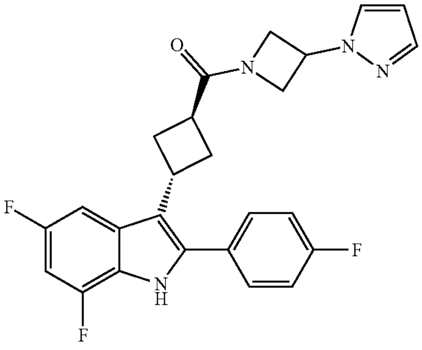 [SMILES: O=C([C@H]1C[C@H](c2c(-c3ccc(F)cc3)[nH]c3c(F)cc(F)cc32)C1)N1CC(n2cccn2)C1]

TABLE 1-continued
| Compounds 1 to 286 |
| --- |
97
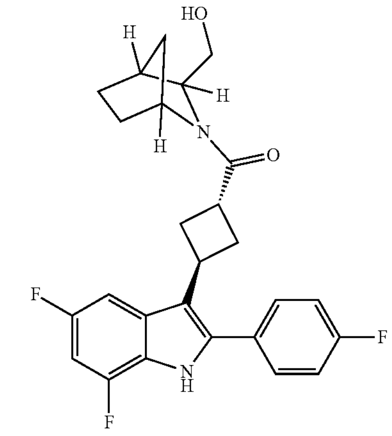 [SMILES: O=C([C@H]1C[C@H](c2c(-c3ccc(F)cc3)[nH]c3c(F)cc(F)cc32)C1)N1C2CCC(C2)C1CO]
98
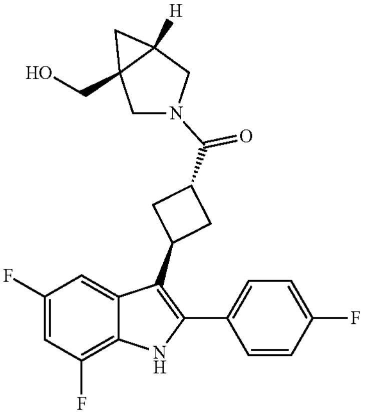 [SMILES: O=C([C@H]1C[C@H](c2c(-c3ccc(F)cc3)[nH]c3c(F)cc(F)cc32)C1)N1C[C@H]2C[C@@]2(CO)C1]
99
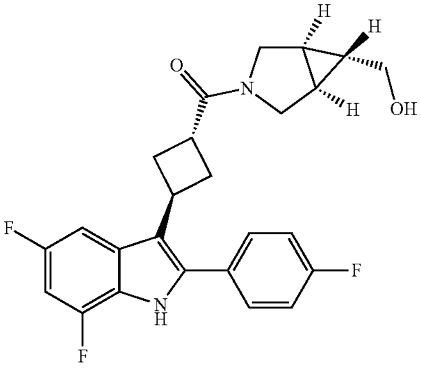 [SMILES: O=C([C@H]1C[C@H](c2c(-c3ccc(F)cc3)[nH]c3c(F)cc(F)cc32)C1)N1C[C@@H]2[C@@H](CO)[C@@H]2C1]
TABLE 1-continued
| Compounds 1 to 286 |
| --- |
100
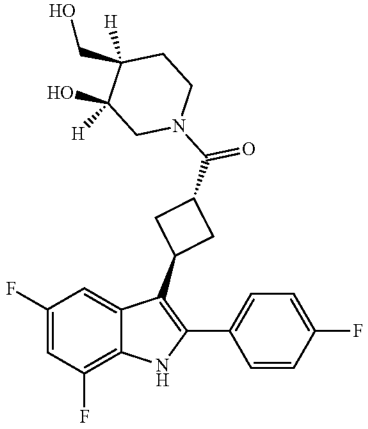 [SMILES: O=C([C@H]1C[C@H](c2c(-c3ccc(F)cc3)[nH]c3c(F)cc(F)cc32)C1)N1CC[C@H](CO)[C@H](O)C1]
101
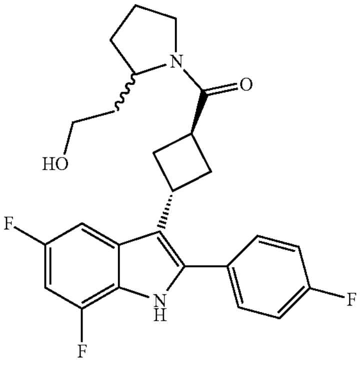 [SMILES: O=C([C@H]1C[C@H](c2c(-c3ccc(F)cc3)[nH]c3c(F)cc(F)cc32)C1)N1CCCC1CCO]
102
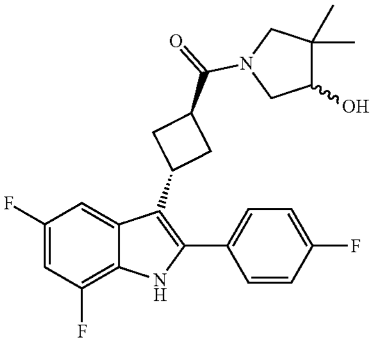 [SMILES: CC1(C)CN(C(=O)[C@H]2C[C@H](c3c(-c4ccc(F)cc4)[nH]c4c(F)cc(F)cc43)C2)CC1O]

TABLE 1-continued
Compounds 1 to 286
103
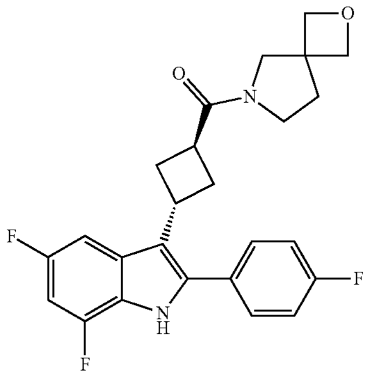 [SMILES: O=C([C@H]1C[C@H](c2c(-c3ccc(F)cc3)[nH]c3c(F)cc(F)cc32)C1)N1CCC2(COC2)C1]
104
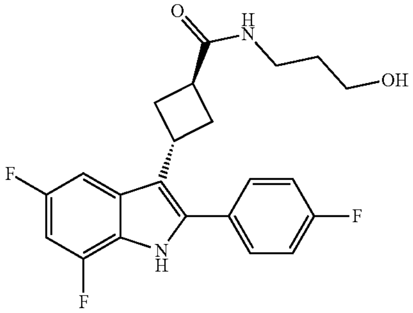 [SMILES: O=C(NCCCO)[C@H]1C[C@H](c2c(-c3ccc(F)cc3)[nH]c3c(F)cc(F)cc32)C1]
105
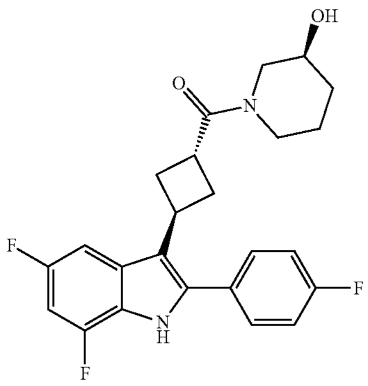 [SMILES: O=C([C@H]1C[C@H](c2c(-c3ccc(F)cc3)[nH]c3c(F)cc(F)cc32)C1)N1CCC[C@H](O)C1]
106
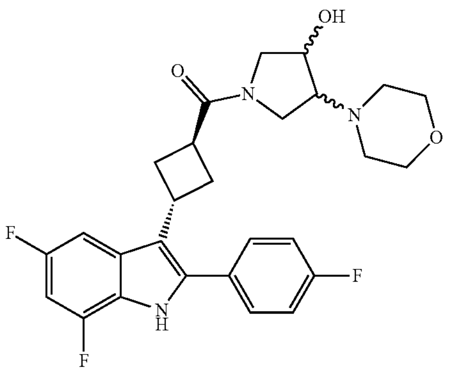 [SMILES: O=C([C@H]1C[C@H](c2c(-c3ccc(F)cc3)[nH]c3c(F)cc(F)cc32)C1)N1CC(O)C(N2CCOCC2)C1]
TABLE 1-continued
Compounds 1 to 286
107
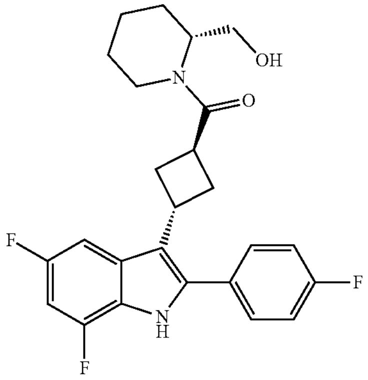 [SMILES: O=C([C@H]1C[C@H](c2c(-c3ccc(F)cc3)[nH]c3c(F)cc(F)cc32)C1)N1CCCC[C@@H]1CO]
108
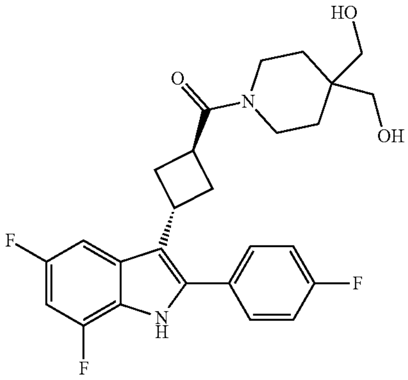 [SMILES: O=C([C@H]1C[C@H](c2c(-c3ccc(F)cc3)[nH]c3c(F)cc(F)cc32)C1)N1CCC(CO)(CO)CC1]
109
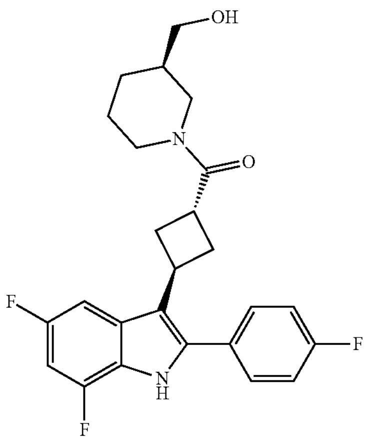 [SMILES: O=C([C@H]1C[C@H](c2c(-c3ccc(F)cc3)[nH]c3c(F)cc(F)cc32)C1)N1CCC[C@@H](CO)C1]

TABLE 1-continued
| Compounds 1 to 286 |
|---|
| 110 |
| 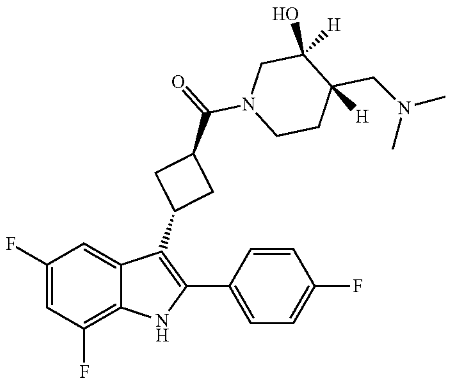 [SMILES: CN(C)C[C@@H]1CCN(C(=O)[C@H]2C[C@H](c3c(-c4ccc(F)cc4)[nH]c4c(F)cc(F)cc43)C2)C[C@H]1O] |
| 111 |
| 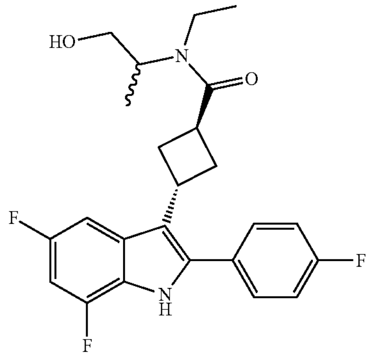 [SMILES: CCN(C(=O)[C@H]1C[C@H](c2c(-c3ccc(F)cc3)[nH]c3c(F)cc(F)cc32)C1)C(C)CO] |
| 112 |
| 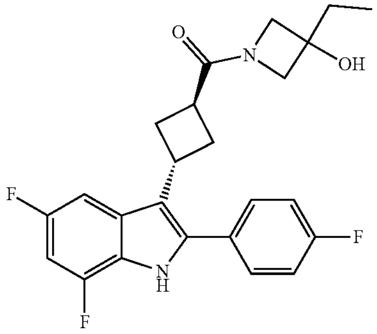 [SMILES: CCC1(O)CN(C(=O)[C@H]2C[C@H](c3c(-c4ccc(F)cc4)[nH]c4c(F)cc(F)cc43)C2)C1] |
TABLE 1-continued
| Compounds 1 to 286 |
|---|
| 113 |
| 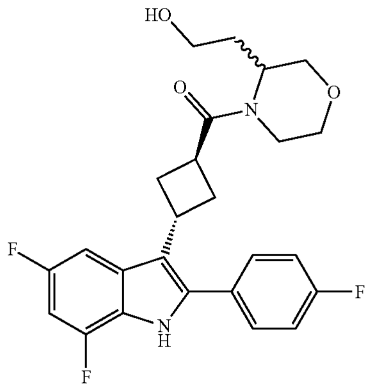 |
| 114 |
| 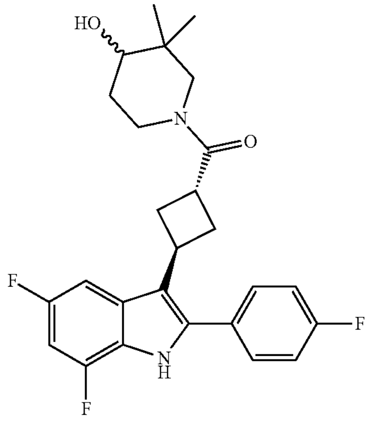 [SMILES: CC1(C)CN(C(=O)[C@H]2C[C@H](c3c(-c4ccc(F)cc4)[nH]c4c(F)cc(F)cc43)C2)CCC1O] |
| 115 |
| 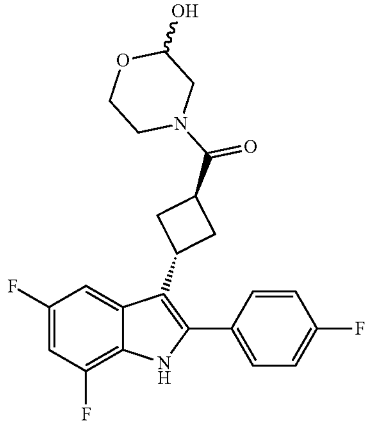 [SMILES: O=C([C@H]1C[C@H](c2c(-c3ccc(F)cc3)[nH]c3c(F)cc(F)cc32)C1)N1CCOC(O)C1] |

TABLE 1-continued
Compounds 1 to 286
116
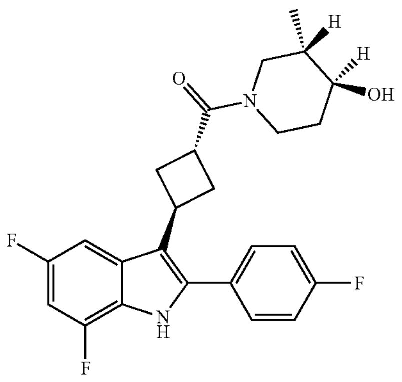 [SMILES: C[C@H]1CN(C(=O)[C@H]2C[C@H](c3c(-c4ccc(F)cc4)[nH]c4c(F)cc(F)cc43)C2)CC[C@@H]1O]
117
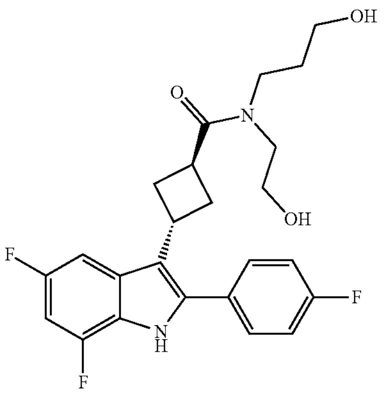 [SMILES: O=C([C@H]1C[C@H](c2c(-c3ccc(F)cc3)[nH]c3c(F)cc(F)cc32)C1)N(CCO)CCCO]
118
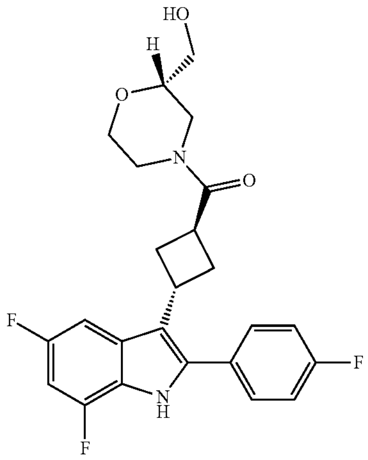 [SMILES: O=C([C@H]1C[C@H](c2c(-c3ccc(F)cc3)[nH]c3c(F)cc(F)cc32)C1)N1CCO[C@H](CO)C1]
TABLE 1-continued
Compounds 1 to 286
119
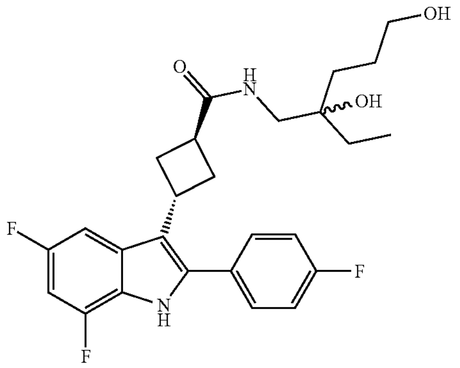 [SMILES: CCC(O)(CCCO)CNC(=O)[C@H]1C[C@H](c2c(-c3ccc(F)cc3)[nH]c3c(F)cc(F)cc32)C1]
120
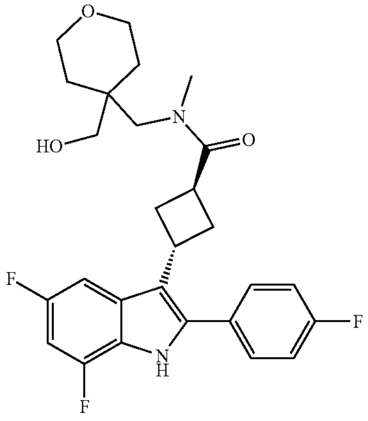 [SMILES: CN(CC1(CO)CCOCC1)C(=O)[C@H]1C[C@H](c2c(-c3ccc(F)cc3)[nH]c3c(F)cc(F)cc32)C1]
121
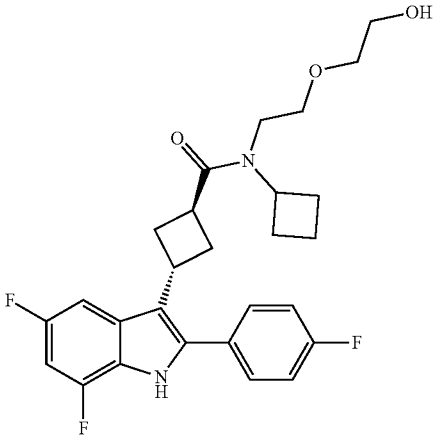 [SMILES: O=C([C@H]1C[C@H](c2c(-c3ccc(F)cc3)[nH]c3c(F)cc(F)cc32)C1)N(CCOCCO)C1CCC1]

TABLE 1-continued
Compounds 1 to 286
122
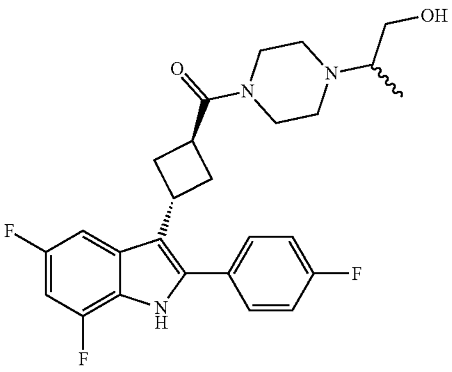 [SMILES: CC(CO)N1CCN(C(=O)[C@H]2C[C@H](c3c(-c4ccc(F)cc4)[nH]c4c(F)cc(F)cc43)C2)CC1]
123
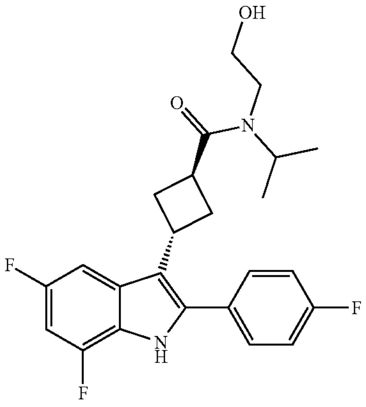 [SMILES: CC(C)N(CCO)C(=O)[C@H]1C[C@H](c2c(-c3ccc(F)cc3)[nH]c3c(F)cc(F)cc32)C1]
124
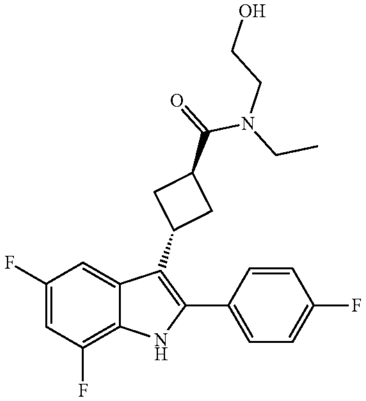 [SMILES: CCN(CCO)C(=O)[C@H]1C[C@H](c2c(-c3ccc(F)cc3)[nH]c3c(F)cc(F)cc32)C1]
TABLE 1-continued
Compounds 1 to 286
125
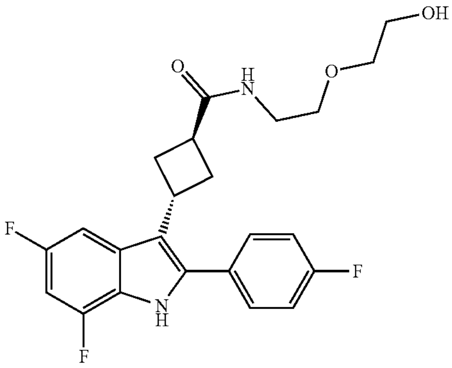 [SMILES: O=C(NCCOCCO)[C@H]1C[C@H](c2c(-c3ccc(F)cc3)[nH]c3c(F)cc(F)cc32)C1]
126
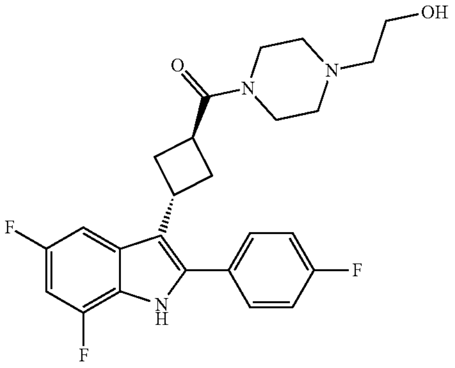
127
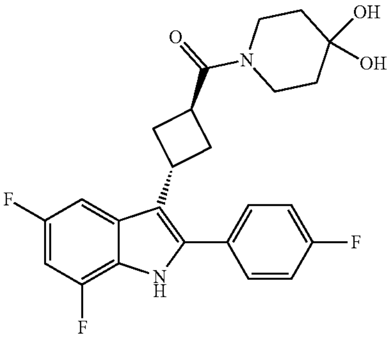 [SMILES: O=C([C@H]1C[C@H](c2c(-c3ccc(F)cc3)[nH]c3c(F)cc(F)cc32)C1)N1CCC(O)(O)CC1]
128
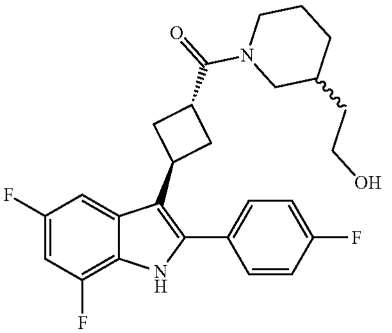 [SMILES: O=C([C@H]1C[C@H](c2c(-c3ccc(F)cc3)[nH]c3c(F)cc(F)cc32)C1)N1CCCC(CCO)C1]

TABLE 1-continued
Compounds 1 to 286
129
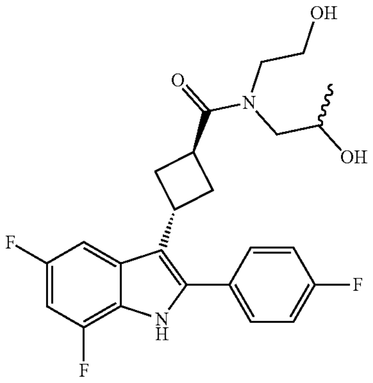 [SMILES: CC(O)CN(CCO)C(=O)[C@H]1C[C@H](c2c(-c3ccc(F)cc3)[nH]c3c(F)cc(F)cc32)C1]
130
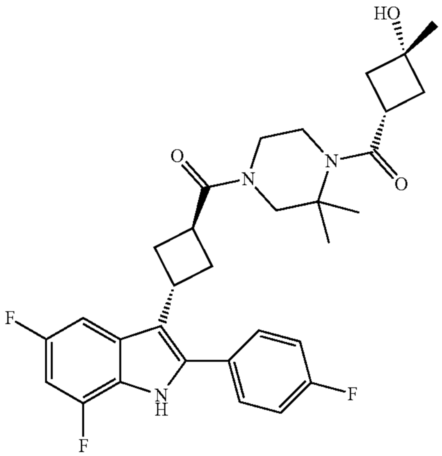 [SMILES: CC1(C)CN(C(=O)[C@H]2C[C@H](c3c(-c4ccc(F)cc4)[nH]c4c(F)cc(F)cc43)C2)CCN1C(=O)[C@H]1C[C@@](C)(O)C1]
131
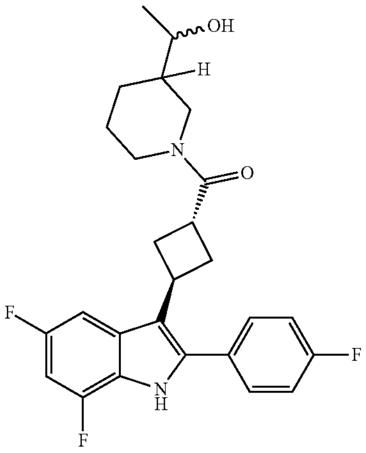 [SMILES: CC(O)C1CCCN(C(=O)[C@H]2C[C@H](c3c(-c4ccc(F)cc4)[nH]c4c(F)cc(F)cc43)C2)C1]
TABLE 1-continued
Compounds 1 to 286
132
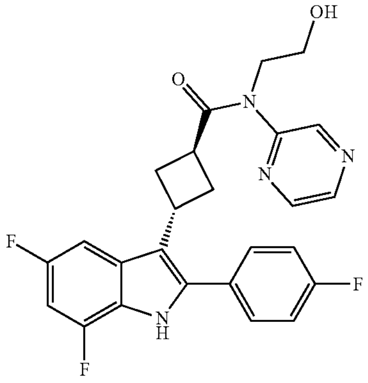 [SMILES: O=C([C@H]1C[C@H](c2c(-c3ccc(F)cc3)[nH]c3c(F)cc(F)cc32)C1)N(CCO)c1cnccn1]
133
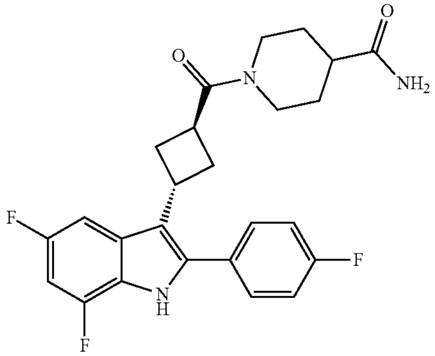 [SMILES: NC(=O)C1CCN(C(=O)[C@H]2C[C@H](c3c(-c4ccc(F)cc4)[nH]c4c(F)cc(F)cc43)C2)CC1]
134
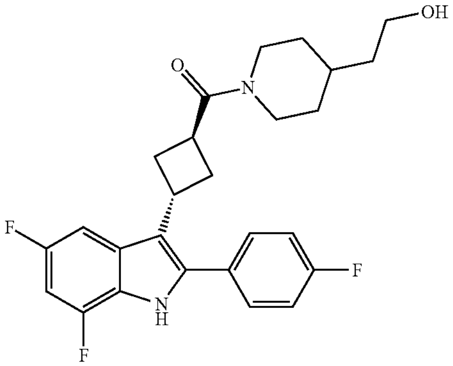
135
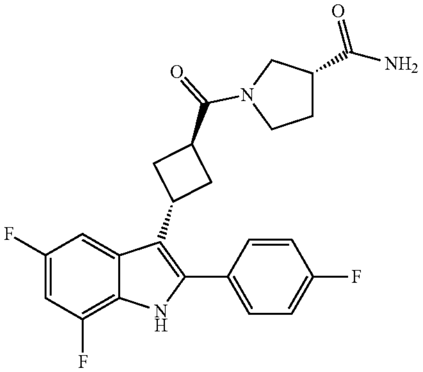 [SMILES: NC(=O)[C@@H]1CCN(C(=O)[C@H]2C[C@H](c3c(-c4ccc(F)cc4)[nH]c4c(F)cc(F)cc43)C2)C1]

TABLE 1-continued
Compounds 1 to 286
136
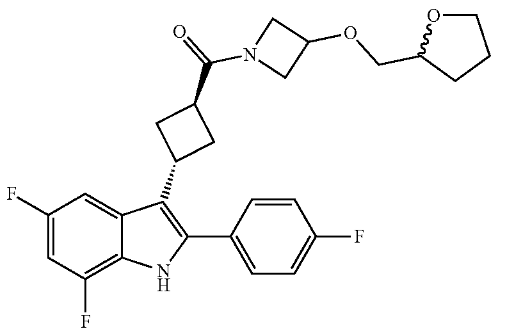 [SMILES: O=C([C@H]1C[C@H](c2c(-c3ccc(F)cc3)[nH]c3c(F)cc(F)cc32)C1)N1CC(OCC2CCCO2)C1]
137
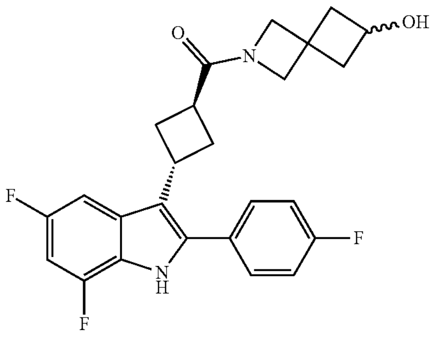 [SMILES: O=C([C@H]1C[C@H](c2c(-c3ccc(F)cc3)[nH]c3c(F)cc(F)cc32)C1)N1CC2(CC(O)C2)C1]
138
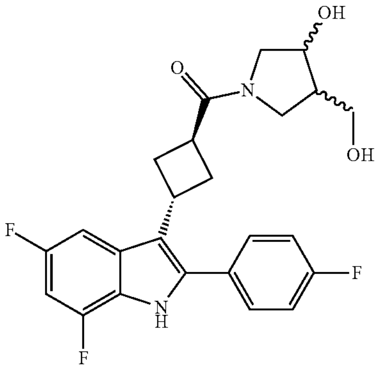 [SMILES: O=C([C@H]1C[C@H](c2c(-c3ccc(F)cc3)[nH]c3c(F)cc(F)cc32)C1)N1CC(O)C(CO)C1]
139
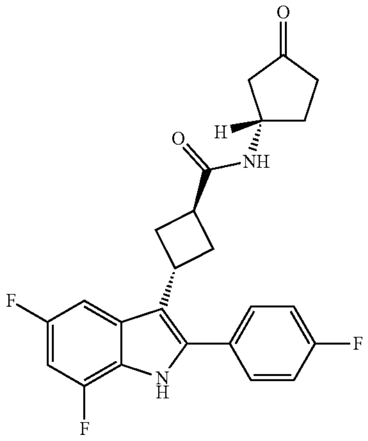 [SMILES: O=C1CC[C@H](NC(=O)[C@H]2C[C@H](c3c(-c4ccc(F)cc4)[nH]c4c(F)cc(F)cc43)C2)C1]
140
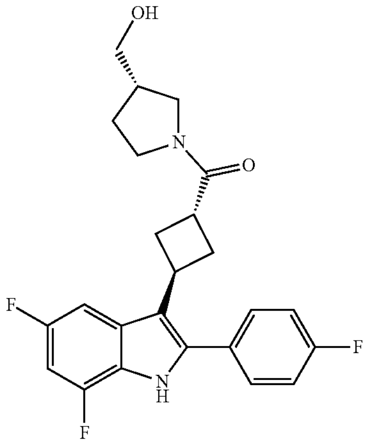 [SMILES: O=C([C@H]1C[C@H](c2c(-c3ccc(F)cc3)[nH]c3c(F)cc(F)cc32)C1)N1CC[C@H](CO)C1]
141
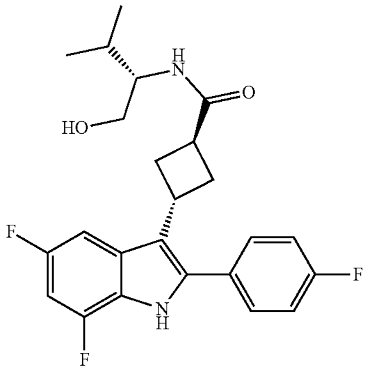 [SMILES: CC(C)[C@@H](CO)NC(=O)[C@H]1C[C@H](c2c(-c3ccc(F)cc3)[nH]c3c(F)cc(F)cc32)C1]

| Compounds 1 to 286 |
|---|
| 142 |
| 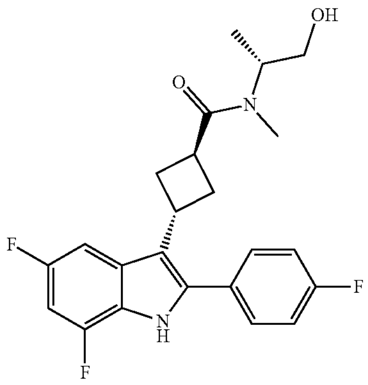 [SMILES: C[C@H](CO)N(C)C(=O)[C@H]1C[C@H](c2c(-c3ccc(F)cc3)[nH]c3c(F)cc(F)cc32)C1] |
| 143 |
| 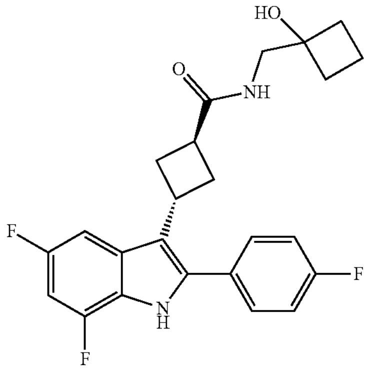 [SMILES: O=C(NCC1(O)CCC1)[C@H]1C[C@H](c2c(-c3ccc(F)cc3)[nH]c3c(F)cc(F)cc32)C1] |
| 144 |
| 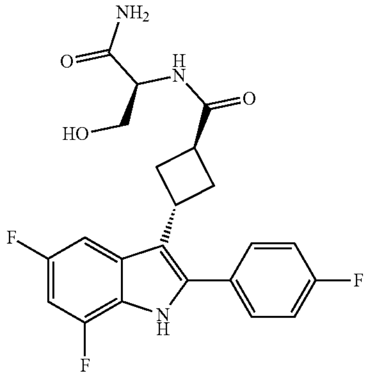 [SMILES: NC(=O)[C@H](CO)NC(=O)[C@H]1C[C@H](c2c(-c3ccc(F)cc3)[nH]c3c(F)cc(F)cc32)C1] |
| Compounds 1 to 286 |
|---|
| 145 |
| 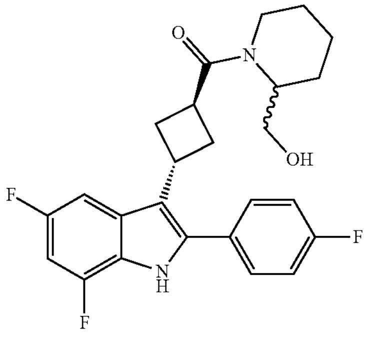 [SMILES: O=C([C@H]1C[C@H](c2c(-c3ccc(F)cc3)[nH]c3c(F)cc(F)cc32)C1)N1CCCCC1CO] |
| 146 |
| 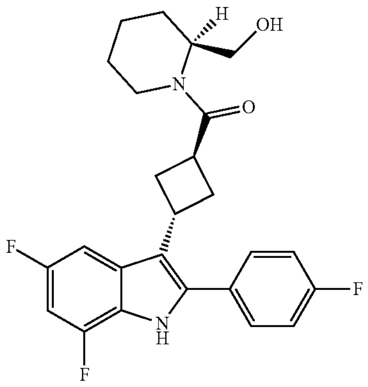 [SMILES: O=C([C@H]1C[C@H](c2c(-c3ccc(F)cc3)[nH]c3c(F)cc(F)cc32)C1)N1CCCC[C@H]1CO] |
| 147 |
| 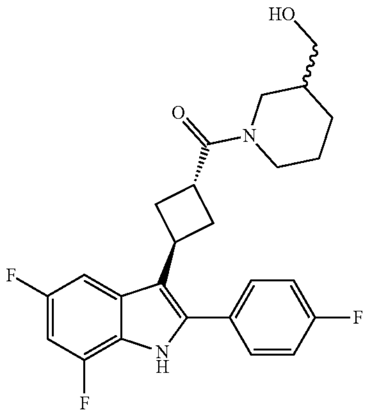 [SMILES: O=C([C@H]1C[C@H](c2c(-c3ccc(F)cc3)[nH]c3c(F)cc(F)cc32)C1)N1CCCC(CO)C1] |

TABLE 1-continued
| Compounds 1 to 286 |
|---|
148
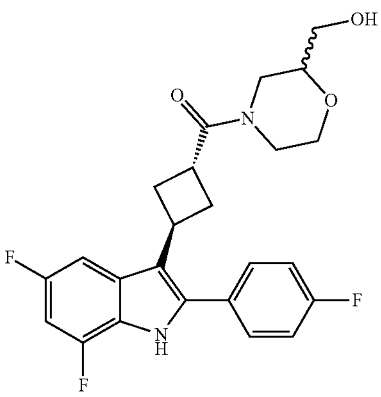 [SMILES: O=C([C@H]1C[C@H](c2c(-c3ccc(F)cc3)[nH]c3c(F)cc(F)cc32)C1)N1CCOC(CO)C1]
149
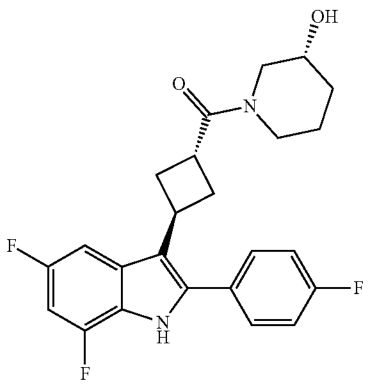 [SMILES: O=C([C@H]1C[C@H](c2c(-c3ccc(F)cc3)[nH]c3c(F)cc(F)cc32)C1)N1CCC[C@@H](O)C1]
150
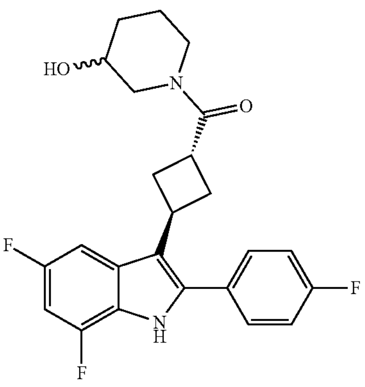 [SMILES: O=C([C@H]1C[C@H](c2c(-c3ccc(F)cc3)[nH]c3c(F)cc(F)cc32)C1)N1CCCC(O)C1]
TABLE 1-continued
| Compounds 1 to 286 |
|---|
151
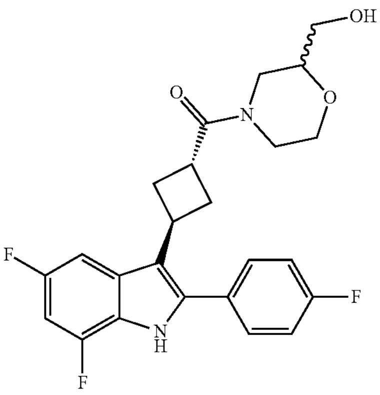 [SMILES: O=C([C@H]1C[C@H](c2c(-c3ccc(F)cc3)[nH]c3c(F)cc(F)cc32)C1)N1CCOC(CO)C1]
152
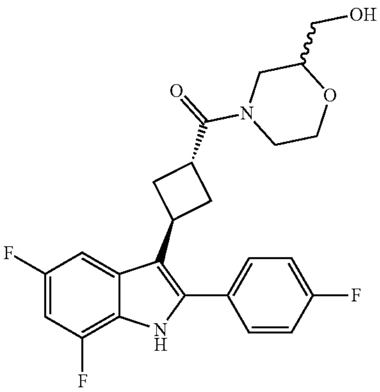 [SMILES: O=C([C@H]1C[C@H](c2c(-c3ccc(F)cc3)[nH]c3c(F)cc(F)cc32)C1)N1CCOC(CO)C1]
153
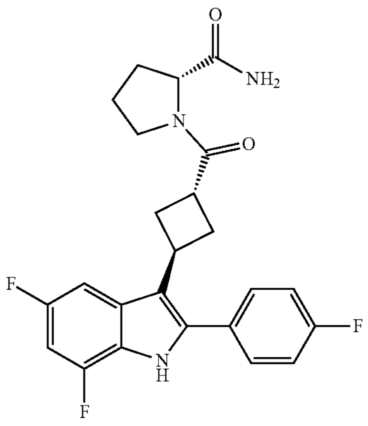 [SMILES: NC(=O)[C@H]1CCCN1C(=O)[C@H]1C[C@H](c2c(-c3ccc(F)cc3)[nH]c3c(F)cc(F)cc32)C1]

TABLE 1-continued
Compounds 1 to 286
154
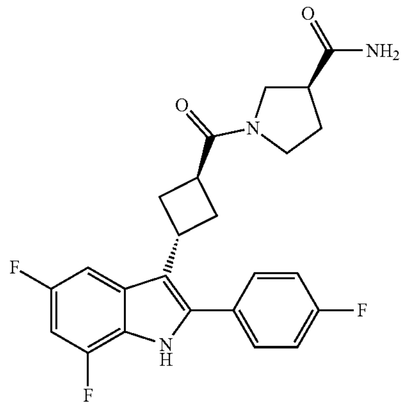 [SMILES: NC(=O)[C@H]1CCN(C(=O)[C@H]2C[C@H](c3c(-c4ccc(F)cc4)[nH]c4c(F)cc(F)cc43)C2)C1]
155
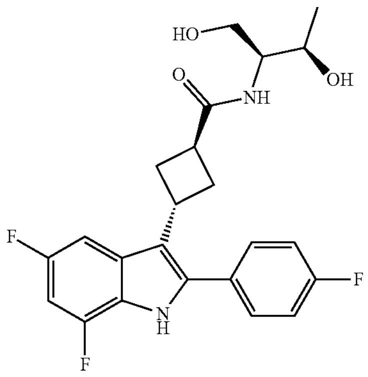 [SMILES: C[C@@H](O)[C@H](CO)NC(=O)[C@H]1C[C@H](c2c(-c3ccc(F)cc3)[nH]c3c(F)cc(F)cc32)C1]
156
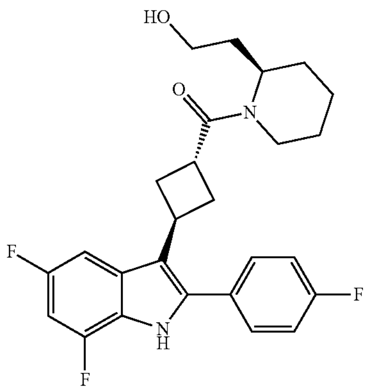 [SMILES: O=C([C@H]1C[C@H](c2c(-c3ccc(F)cc3)[nH]c3c(F)cc(F)cc32)C1)N1CCCC[C@@H]1CCO]
TABLE 1-continued
Compounds 1 to 286
157
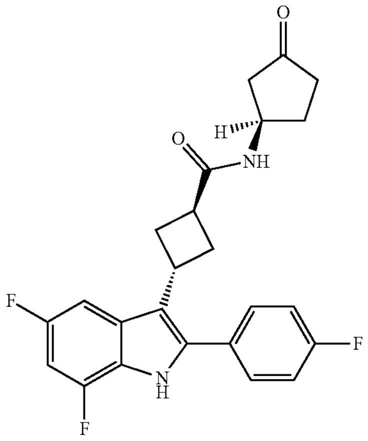 [SMILES: O=C1CC[C@@H](NC(=O)[C@H]2C[C@H](c3c(-c4ccc(F)cc4)[nH]c4c(F)cc(F)cc43)C2)C1]
158
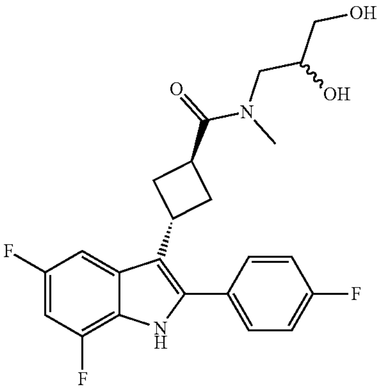 [SMILES: CN(CC(O)CO)C(=O)[C@H]1C[C@H](c2c(-c3ccc(F)cc3)[nH]c3c(F)cc(F)cc32)C1]
159
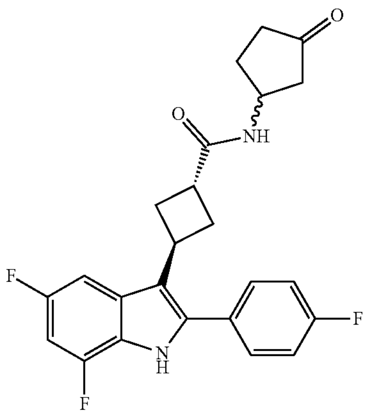 [SMILES: O=C1CCC(NC(=O)[C@H]2C[C@H](c3c(-c4ccc(F)cc4)[nH]c4c(F)cc(F)cc43)C2)C1]

TABLE 1-continued
Compounds 1 to 286
160
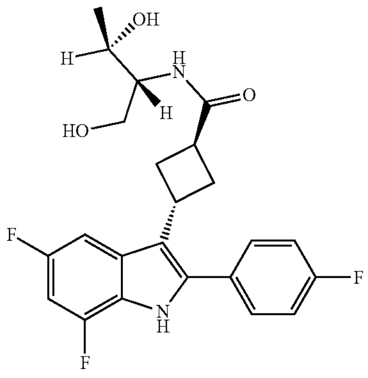 [SMILES: C[C@@H](O)[C@@H](CO)NC(=O)[C@H]1C[C@H](c2c(-c3ccc(F)cc3)[nH]c3c(F)cc(F)cc32)C1]
161
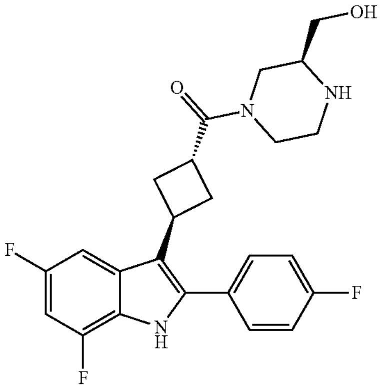 [SMILES: O=C([C@H]1C[C@H](c2c(-c3ccc(F)cc3)[nH]c3c(F)cc(F)cc32)C1)N1CCN[C@H](CO)C1]
162
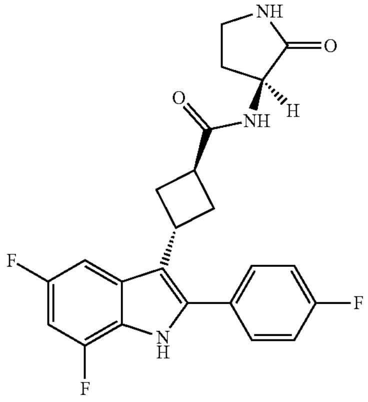 [SMILES: O=C1NCC[C@@H]1NC(=O)[C@H]1C[C@H](c2c(-c3ccc(F)cc3)[nH]c3c(F)cc(F)cc32)C1]
163
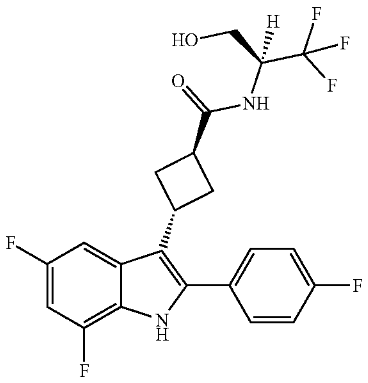 [SMILES: O=C(N[C@@H](CO)C(F)(F)F)[C@H]1C[C@H](c2c(-c3ccc(F)cc3)[nH]c3c(F)cc(F)cc32)C1]
164
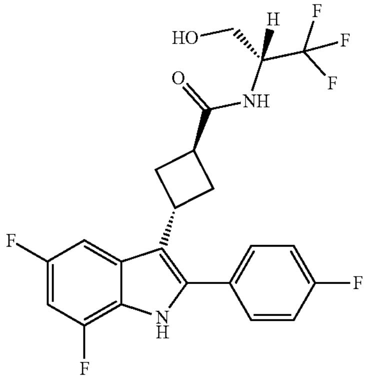 [SMILES: O=C(N[C@H](CO)C(F)(F)F)[C@H]1C[C@H](c2c(-c3ccc(F)cc3)[nH]c3c(F)cc(F)cc32)C1]
165
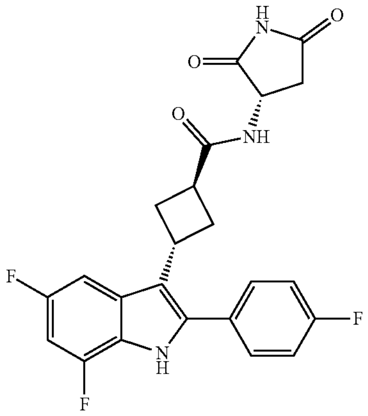

TABLE 1-continued
| Compounds 1 to 286 |
|---|
| 166 |
| 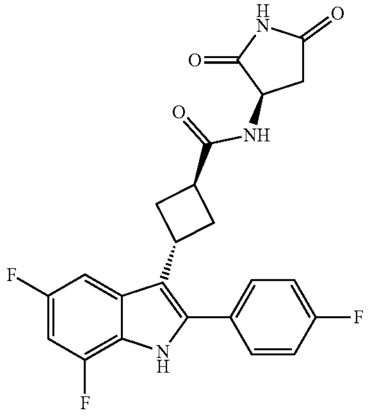 [SMILES: O=C1C[C@@H](NC(=O)[C@H]2C[C@H](c3c(-c4ccc(F)cc4)[nH]c4c(F)cc(F)cc43)C2)C(=O)N1] |
| 167 |
| 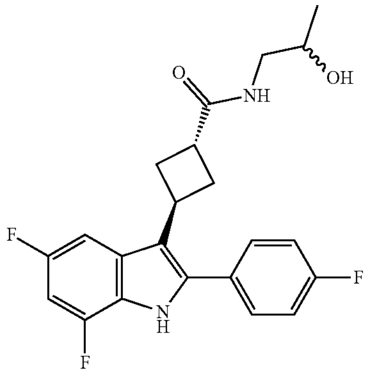 [SMILES: CC(O)CNC(=O)[C@H]1C[C@H](c2c(-c3ccc(F)cc3)[nH]c3c(F)cc(F)cc32)C1] |
| 168 |
| 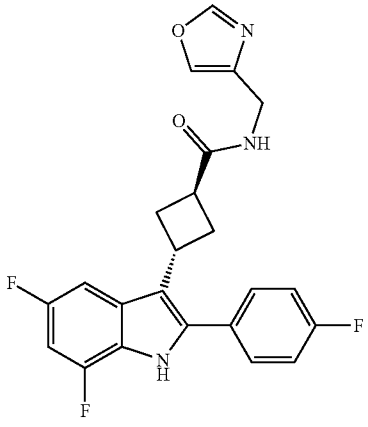 [SMILES: O=C(NCc1cocn1)[C@H]1C[C@H](c2c(-c3ccc(F)cc3)[nH]c3c(F)cc(F)cc32)C1] |
TABLE 1-continued
| Compounds 1 to 286 |
|---|
| 169 |
| 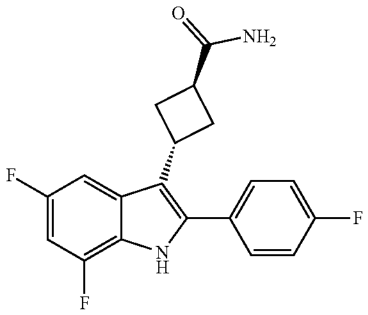 [SMILES: NC(=O)[C@H]1C[C@H](c2c(-c3ccc(F)cc3)[nH]c3c(F)cc(F)cc32)C1] |
| 170 |
| 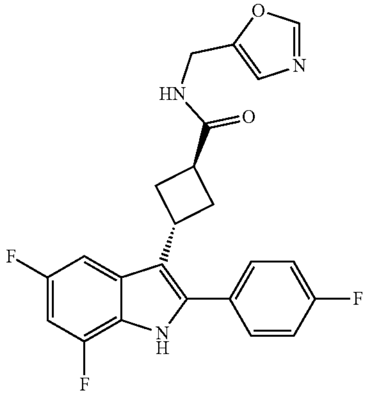 [SMILES: O=C(NCc1cnco1)[C@H]1C[C@H](c2c(-c3ccc(F)cc3)[nH]c3c(F)cc(F)cc32)C1] |
| 171 |
| 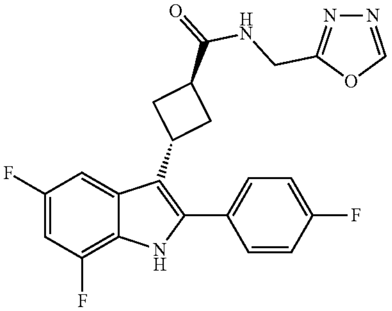 [SMILES: O=C(NCc1nnco1)[C@H]1C[C@H](c2c(-c3ccc(F)cc3)[nH]c3c(F)cc(F)cc32)C1] |
| 172 |
| 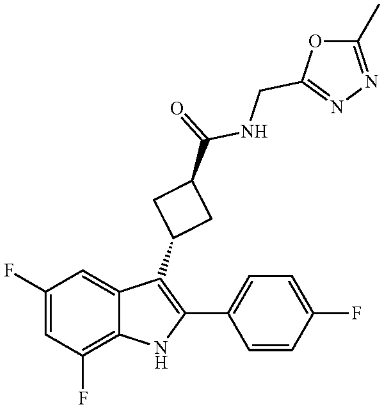 [SMILES: Cc1nnc(CNC(=O)[C@H]2C[C@H](c3c(-c4ccc(F)cc4)[nH]c4c(F)cc(F)cc43)C2)o1] |

TABLE 1-continued
Compounds 1 to 286
173
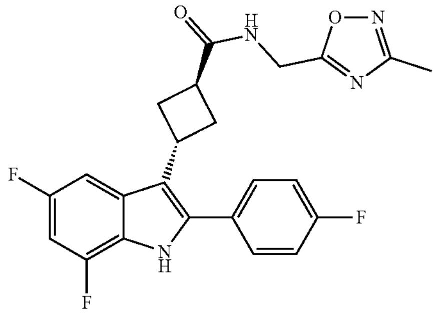 [SMILES: Cc1noc(CNC(=O)[C@H]2C[C@H](c3c(-c4ccc(F)cc4)[nH]c4c(F)cc(F)cc43)C2)n1]
174
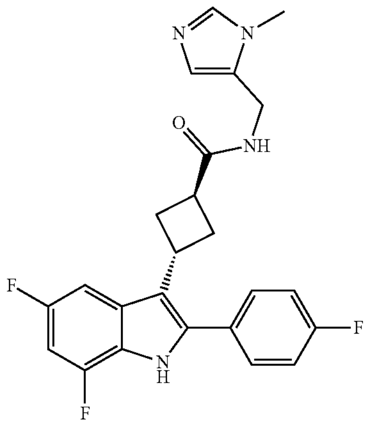 [SMILES: Cn1cncc1CNC(=O)[C@H]1C[C@H](c2c(-c3ccc(F)cc3)[nH]c3c(F)cc(F)cc32)C1]
175
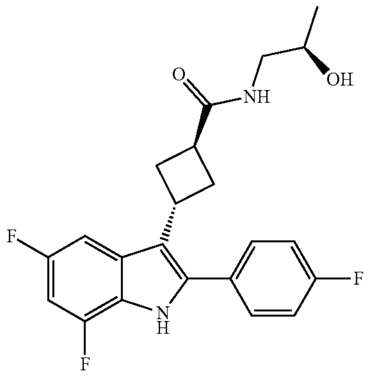 [SMILES: C[C@@H](O)CNC(=O)[C@H]1C[C@H](c2c(-c3ccc(F)cc3)[nH]c3c(F)cc(F)cc32)C1]
176
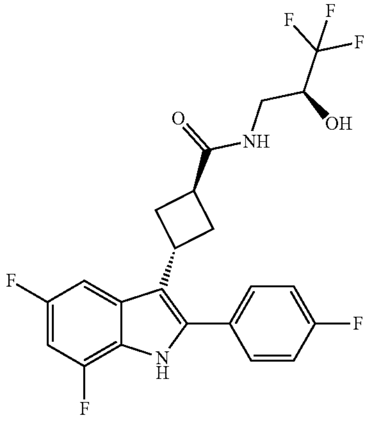 [SMILES: O=C(NC[C@H](O)C(F)(F)F)[C@H]1C[C@H](c2c(-c3ccc(F)cc3)[nH]c3c(F)cc(F)cc32)C1]
177
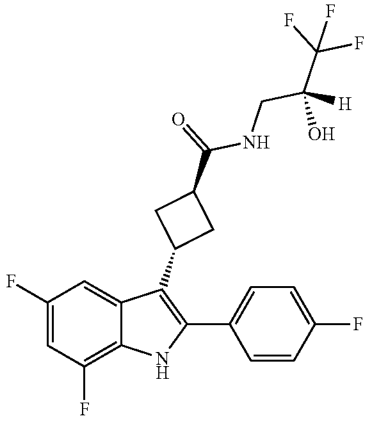 [SMILES: O=C(NC[C@@H](O)C(F)(F)F)[C@H]1C[C@H](c2c(-c3ccc(F)cc3)[nH]c3c(F)cc(F)cc32)C1]
178
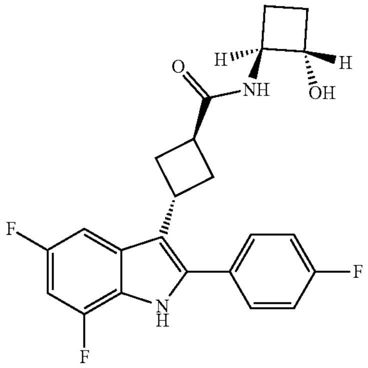 [SMILES: O=C(N[C@H]1CC[C@@H]1O)[C@H]1C[C@H](c2c(-c3ccc(F)cc3)[nH]c3c(F)cc(F)cc32)C1]

TABLE 1-continued
| Compounds 1 to 286 |
| --- |
| 179 |
| 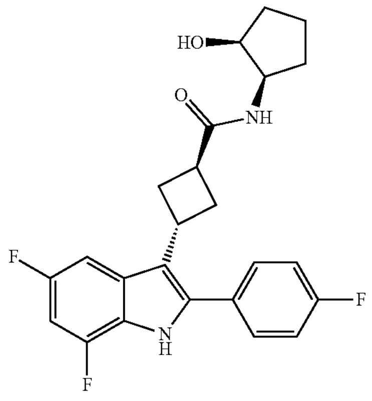 [SMILES: O=C(N[C@@H]1CCC[C@@H]1O)[C@H]1C[C@H](c2c(-c3ccc(F)cc3)[nH]c3c(F)cc(F)cc32)C1] |
| 180 |
| 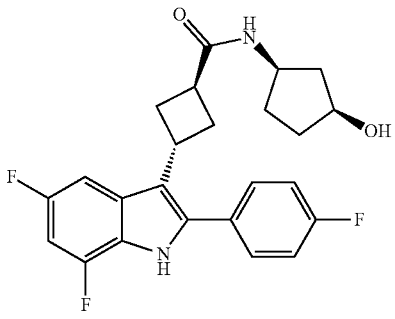 [SMILES: O=C(N[C@@H]1CC[C@H](O)C1)[C@H]1C[C@H](c2c(-c3ccc(F)cc3)[nH]c3c(F)cc(F)cc32)C1] |
| 181 |
| 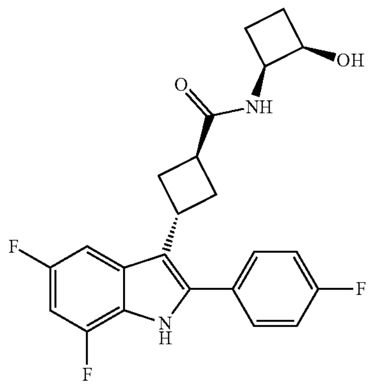 [SMILES: O=C(N[C@H]1CC[C@H]1O)[C@H]1C[C@H](c2c(-c3ccc(F)cc3)[nH]c3c(F)cc(F)cc32)C1] |
TABLE 1-continued
| Compounds 1 to 286 |
| --- |
| 182 |
| 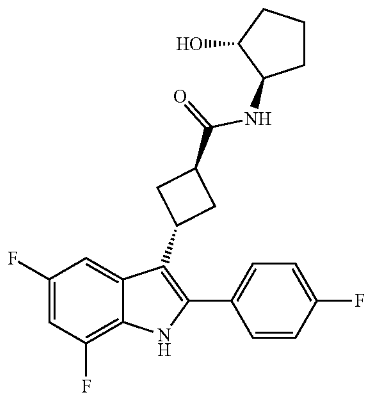 [SMILES: O=C(N[C@@H]1CCC[C@H]1O)[C@H]1C[C@H](c2c(-c3ccc(F)cc3)[nH]c3c(F)cc(F)cc32)C1] |
| 183 |
| 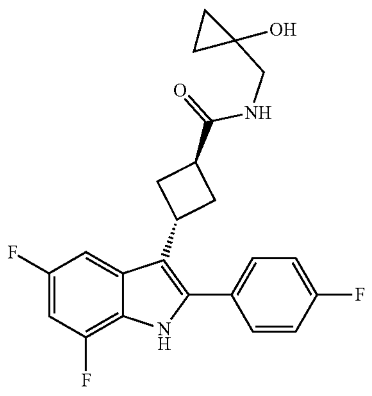 [SMILES: O=C(NCC1(O)CC1)[C@H]1C[C@H](c2c(-c3ccc(F)cc3)[nH]c3c(F)cc(F)cc32)C1] |
| 184 |
| 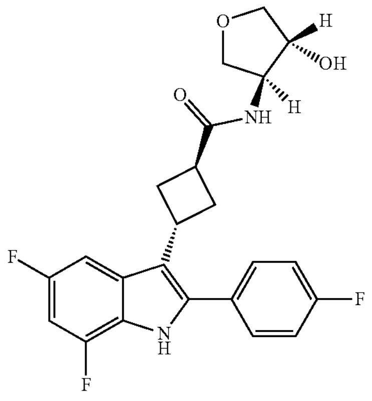 [SMILES: O=C(N[C@H]1COC[C@@H]1O)[C@H]1C[C@H](c2c(-c3ccc(F)cc3)[nH]c3c(F)cc(F)cc32)C1] |

TABLE 1-continued
Compounds 1 to 286
185
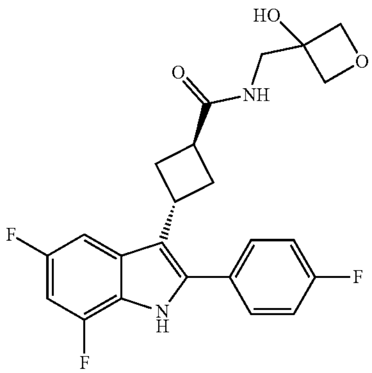 [SMILES: O=C(NCC1(O)COC1)[C@H]1C[C@H](c2c(-c3ccc(F)cc3)[nH]c3c(F)cc(F)cc32)C1]
186
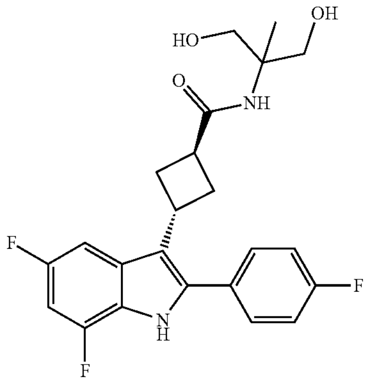 [SMILES: CC(CO)(CO)NC(=O)[C@H]1C[C@H](c2c(-c3ccc(F)cc3)[nH]c3c(F)cc(F)cc32)C1]
187
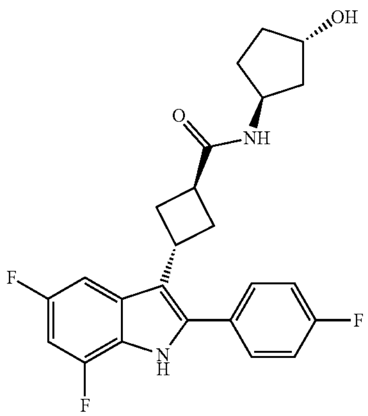 [SMILES: O=C(N[C@H]1CC[C@H](O)C1)[C@H]1C[C@H](c2c(-c3ccc(F)cc3)[nH]c3c(F)cc(F)cc32)C1]
188
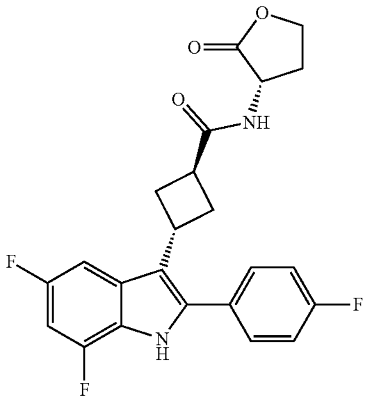 [SMILES: O=C1OCC[C@@H]1NC(=O)[C@H]1C[C@H](c2c(-c3ccc(F)cc3)[nH]c3c(F)cc(F)cc32)C1]
189
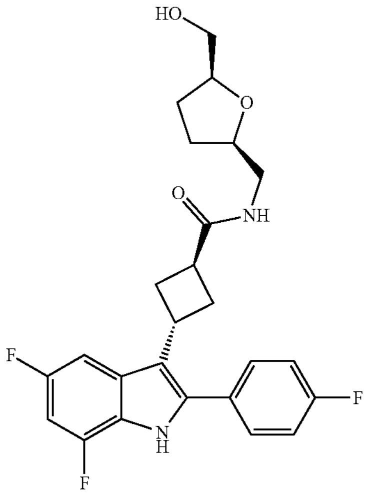 [SMILES: O=C(NC[C@H]1CC[C@@H](CO)O1)[C@H]1C[C@H](c2c(-c3ccc(F)cc3)[nH]c3c(F)cc(F)cc32)C1]
190
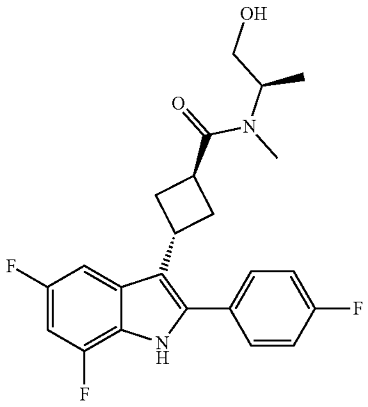 [SMILES: C[C@H](CO)N(C)C(=O)[C@H]1C[C@H](c2c(-c3ccc(F)cc3)[nH]c3c(F)cc(F)cc32)C1]

TABLE 1-continued
| Compounds 1 to 286 |
|---|
| 191 |
| 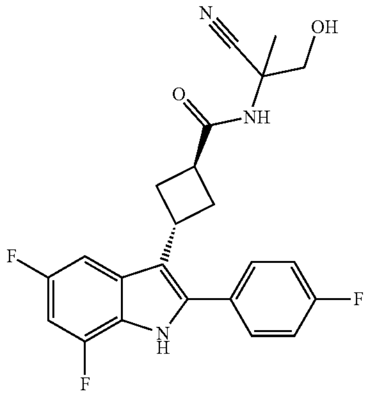 [SMILES: CC(C#N)(CO)NC(=O)[C@H]1C[C@H](c2c(-c3ccc(F)cc3)[nH]c3c(F)cc(F)cc32)C1] |
| 192 |
| 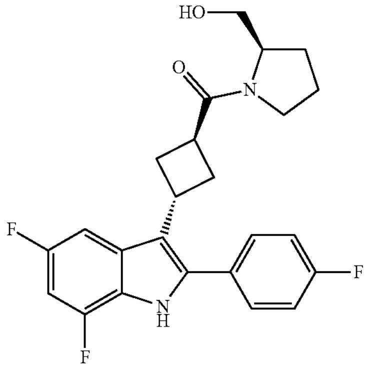 [SMILES: O=C([C@H]1C[C@H](c2c(-c3ccc(F)cc3)[nH]c3c(F)cc(F)cc32)C1)N1CCC[C@@H]1CO] |
| 193 |
| 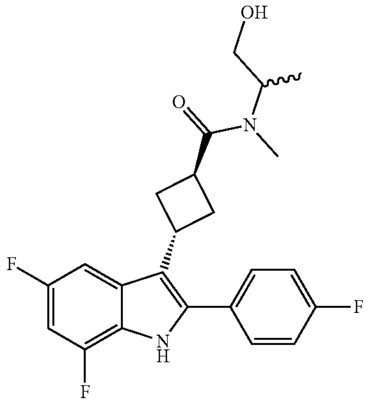 [SMILES: CC(CO)N(C)C(=O)[C@H]1C[C@H](c2c(-c3ccc(F)cc3)[nH]c3c(F)cc(F)cc32)C1] |
TABLE 1-continued
| Compounds 1 to 286 |
|---|
| 194 |
| 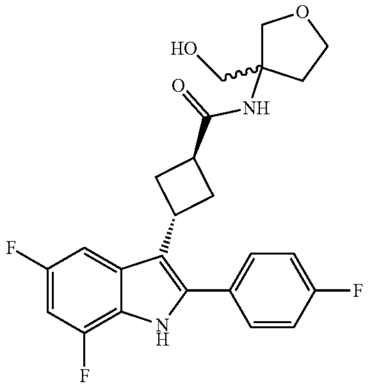 [SMILES: O=C(NC1(CO)CCOC1)[C@H]1C[C@H](c2c(-c3ccc(F)cc3)[nH]c3c(F)cc(F)cc32)C1] |
| 195 |
| 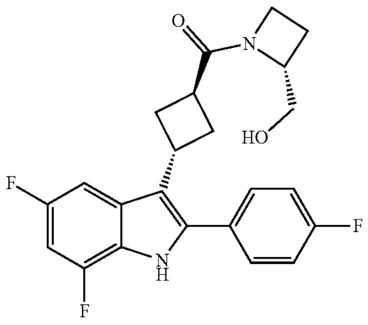 [SMILES: O=C([C@H]1C[C@H](c2c(-c3ccc(F)cc3)[nH]c3c(F)cc(F)cc32)C1)N1CC[C@@H]1CO] |
| 196 |
| 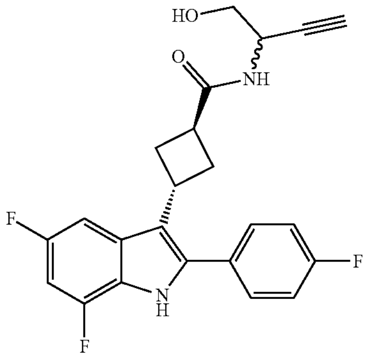 [SMILES: C#CC(CO)NC(=O)[C@H]1C[C@H](c2c(-c3ccc(F)cc3)[nH]c3c(F)cc(F)cc32)C1] |
| 197 |
| 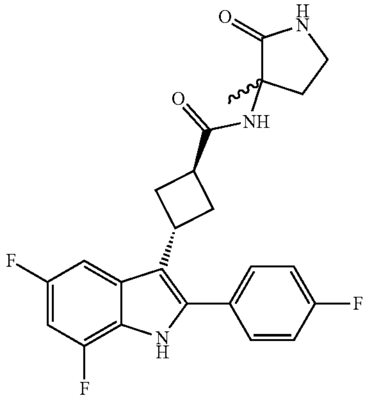 [SMILES: CC1(NC(=O)[C@H]2C[C@H](c3c(-c4ccc(F)cc4)[nH]c4c(F)cc(F)cc43)C2)CCNC1=O] |

TABLE 1-continued
Compounds 1 to 286
198
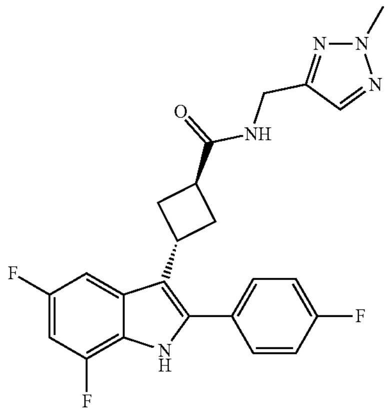 [SMILES: Cn1ncc(CNC(=O)[C@H]2C[C@H](c3c(-c4ccc(F)cc4)[nH]c4c(F)cc(F)cc43)C2)n1]
199
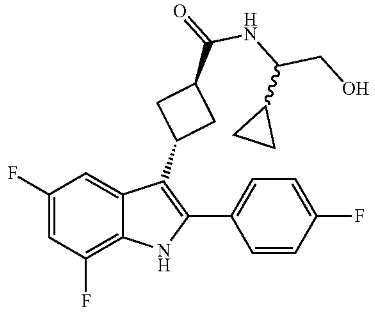 [SMILES: O=C(NC(CO)C1CC1)[C@H]1C[C@H](c2c(-c3ccc(F)cc3)[nH]c3c(F)cc(F)cc32)C1]
200
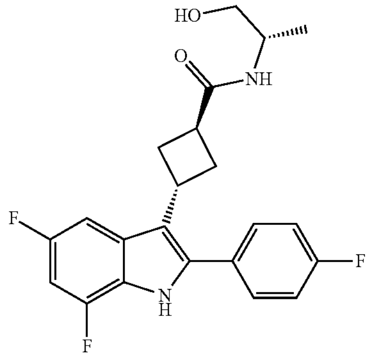 [SMILES: C[C@@H](CO)NC(=O)[C@H]1C[C@H](c2c(-c3ccc(F)cc3)[nH]c3c(F)cc(F)cc32)C1]
201
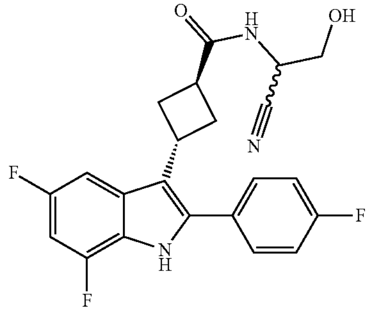 [SMILES: N#CC(CO)NC(=O)[C@H]1C[C@H](c2c(-c3ccc(F)cc3)[nH]c3c(F)cc(F)cc32)C1]
TABLE 1-continued
Compounds 1 to 286
202
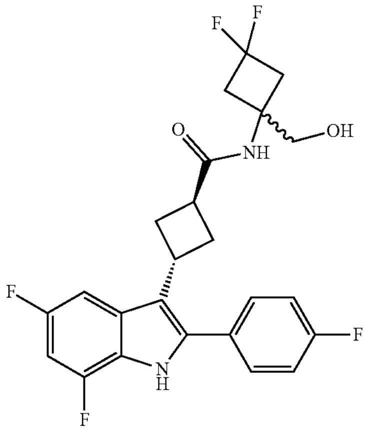 [SMILES: O=C(NC1(CO)CC(F)(F)C1)[C@H]1C[C@H](c2c(-c3ccc(F)cc3)[nH]c3c(F)cc(F)cc32)C1]
203
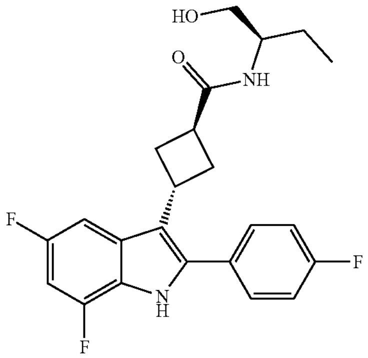 [SMILES: CC[C@H](CO)NC(=O)[C@H]1C[C@H](c2c(-c3ccc(F)cc3)[nH]c3c(F)cc(F)cc32)C1]
204
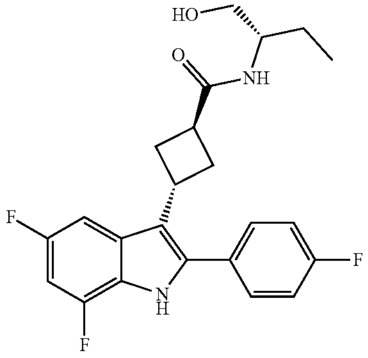 [SMILES: CC[C@@H](CO)NC(=O)[C@H]1C[C@H](c2c(-c3ccc(F)cc3)[nH]c3c(F)cc(F)cc32)C1]

TABLE 1-continued
| Compounds 1 to 286 |
|---|
205
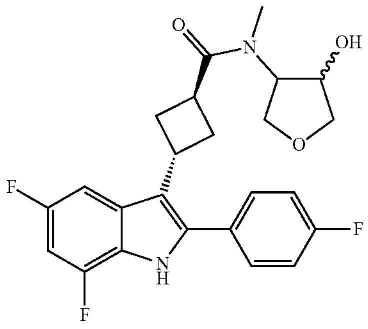 [SMILES: CN(C(=O)[C@H]1C[C@H](c2c(-c3ccc(F)cc3)[nH]c3c(F)cc(F)cc32)C1)C1COCC1O]
206
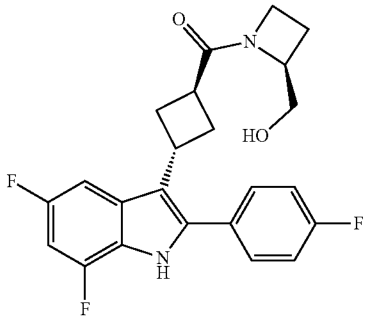 [SMILES: O=C([C@H]1C[C@H](c2c(-c3ccc(F)cc3)[nH]c3c(F)cc(F)cc32)C1)N1CC[C@H]1CO]
207
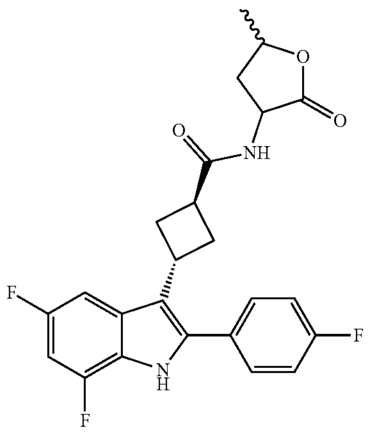 [SMILES: CC1CC(NC(=O)[C@H]2C[C@H](c3c(-c4ccc(F)cc4)[nH]c4c(F)cc(F)cc43)C2)C(=O)O1]
TABLE 1-continued
| Compounds 1 to 286 |
|---|
208
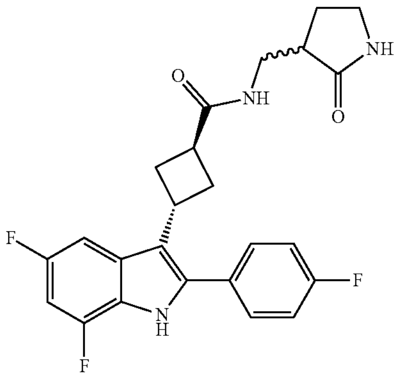 [SMILES: O=C1NCCC1CNC(=O)[C@H]1C[C@H](c2c(-c3ccc(F)cc3)[nH]c3c(F)cc(F)cc32)C1]
209
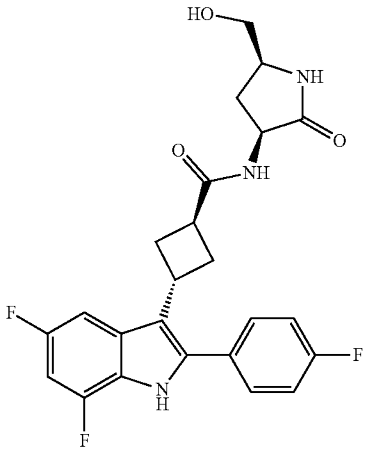 [SMILES: O=C1N[C@H](CO)C[C@@H]1NC(=O)[C@H]1C[C@H](c2c(-c3ccc(F)cc3)[nH]c3c(F)cc(F)cc32)C1]
210
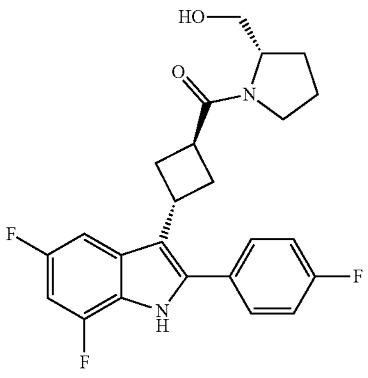 [SMILES: O=C([C@H]1C[C@H](c2c(-c3ccc(F)cc3)[nH]c3c(F)cc(F)cc32)C1)N1CCC[C@H]1CO]

TABLE 1-continued
Compounds 1 to 286
211
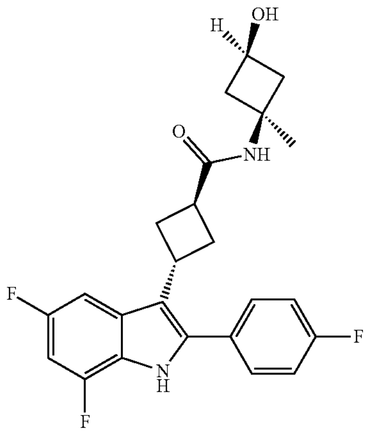 [SMILES: C[C@]1(NC(=O)[C@H]2C[C@H](c3c(-c4ccc(F)cc4)[nH]c4c(F)cc(F)cc43)C2)C[C@@H](O)C1]
212
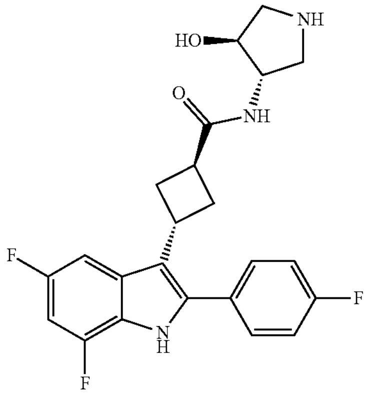 [SMILES: O=C(N[C@H]1CNC[C@@H]1O)[C@H]1C[C@H](c2c(-c3ccc(F)cc3)[nH]c3c(F)cc(F)cc32)C1]
213
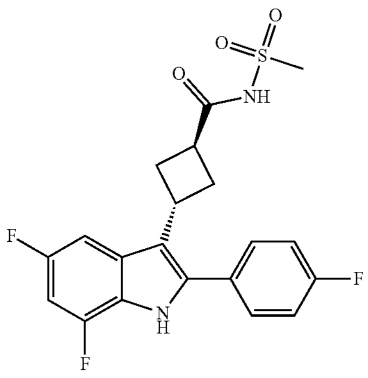 [SMILES: CS(=O)(=O)NC(=O)[C@H]1C[C@H](c2c(-c3ccc(F)cc3)[nH]c3c(F)cc(F)cc32)C1]
TABLE 1-continued
Compounds 1 to 286
214
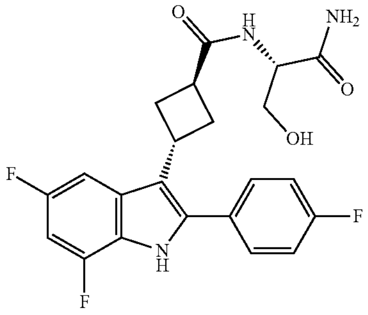 [SMILES: NC(=O)[C@H](CO)NC(=O)[C@H]1C[C@H](c2c(-c3ccc(F)cc3)[nH]c3c(F)cc(F)cc32)C1]
215
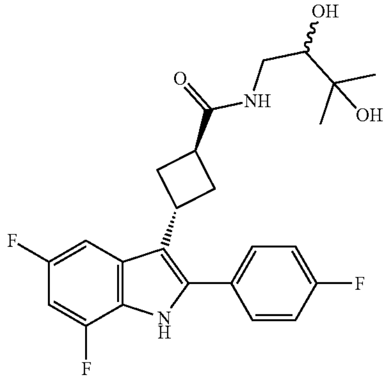 [SMILES: CC(C)(O)C(O)CNC(=O)[C@H]1C[C@H](c2c(-c3ccc(F)cc3)[nH]c3c(F)cc(F)cc32)C1]
216
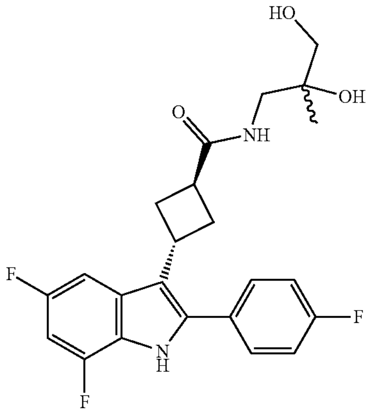 [SMILES: CC(O)(CO)CNC(=O)[C@H]1C[C@H](c2c(-c3ccc(F)cc3)[nH]c3c(F)cc(F)cc32)C1]
217
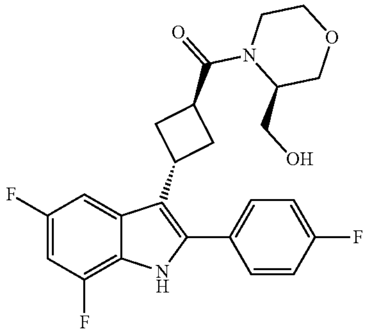 [SMILES: O=C([C@H]1C[C@H](c2c(-c3ccc(F)cc3)[nH]c3c(F)cc(F)cc32)C1)N1CCOC[C@H]1CO]

TABLE 1-continued
Compounds 1 to 286
218
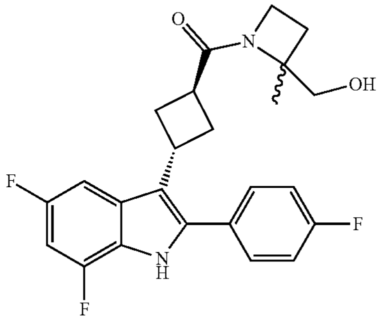 [SMILES: CC1(CO)CCN1C(=O)[C@H]1C[C@H](c2c(-c3ccc(F)cc3)[nH]c3c(F)cc(F)cc32)C1]
219
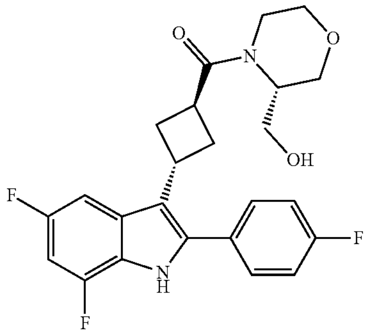 [SMILES: O=C([C@H]1C[C@H](c2c(-c3ccc(F)cc3)[nH]c3c(F)cc(F)cc32)C1)N1CCOC[C@@H]1CO]
220
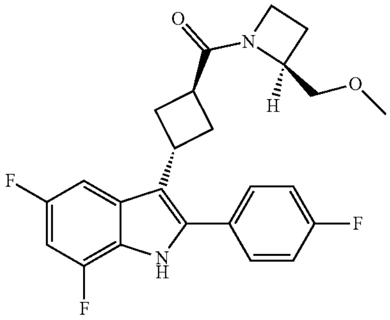 [SMILES: COC[C@@H]1CCN1C(=O)[C@H]1C[C@H](c2c(-c3ccc(F)cc3)[nH]c3c(F)cc(F)cc32)C1]
221
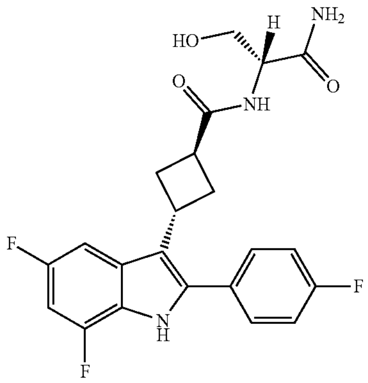 [SMILES: NC(=O)[C@@H](CO)NC(=O)[C@H]1C[C@H](c2c(-c3ccc(F)cc3)[nH]c3c(F)cc(F)cc32)C1]
TABLE 1-continued
Compounds 1 to 286
222
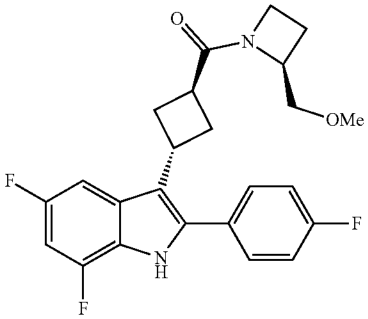 [SMILES: COC[C@@H]1CCN1C(=O)[C@H]1C[C@H](c2c(-c3ccc(F)cc3)[nH]c3c(F)cc(F)cc32)C1]
223
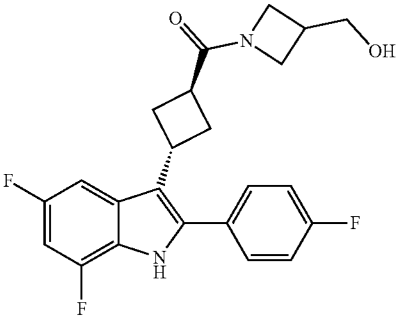 [SMILES: O=C([C@H]1C[C@H](c2c(-c3ccc(F)cc3)[nH]c3c(F)cc(F)cc32)C1)N1CC(CO)C1]
224
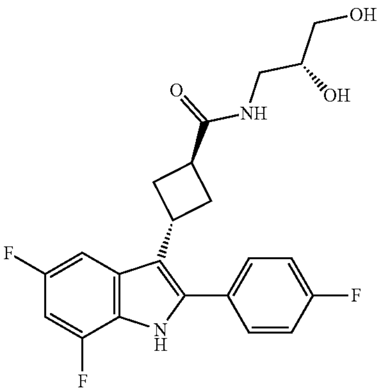 [SMILES: O=C(NC[C@@H](O)CO)[C@H]1C[C@H](c2c(-c3ccc(F)cc3)[nH]c3c(F)cc(F)cc32)C1]
225
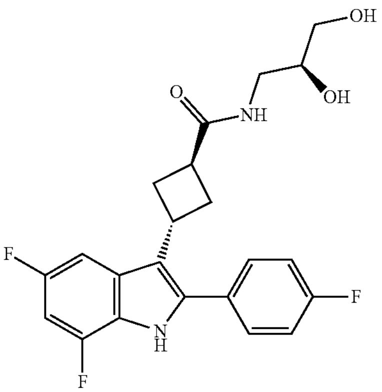 [SMILES: O=C(NC[C@H](O)CO)[C@H]1C[C@H](c2c(-c3ccc(F)cc3)[nH]c3c(F)cc(F)cc32)C1]

| Compounds 1 to 286 |
|---|
| 226 |
| 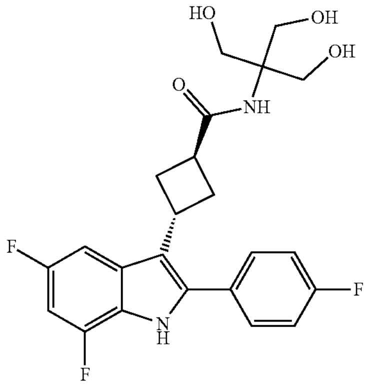 [SMILES: O=C(NC(CO)(CO)CO)[C@H]1C[C@H](c2c(-c3ccc(F)cc3)[nH]c3c(F)cc(F)cc32)C1] |
| 227 |
| 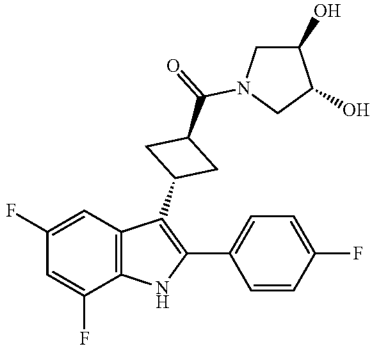 [SMILES: O=C([C@H]1C[C@H](c2c(-c3ccc(F)cc3)[nH]c3c(F)cc(F)cc32)C1)N1C[C@@H](O)[C@H](O)C1] |
| 228 |
| 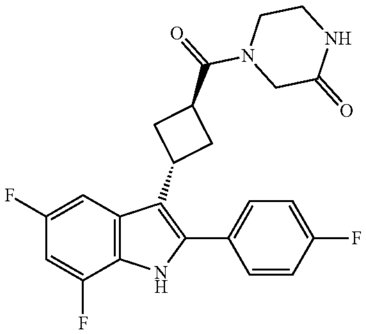 [SMILES: O=C1CN(C(=O)[C@H]2C[C@H](c3c(-c4ccc(F)cc4)[nH]c4c(F)cc(F)cc43)C2)CCN1] |
| Compounds 1 to 286 |
|---|
| 229 |
| 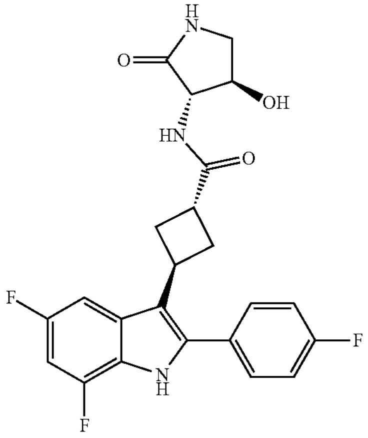 [SMILES: O=C1NC[C@@H](O)[C@@H]1NC(=O)[C@H]1C[C@H](c2c(-c3ccc(F)cc3)[nH]c3c(F)cc(F)cc32)C1] |
| 230 |
| 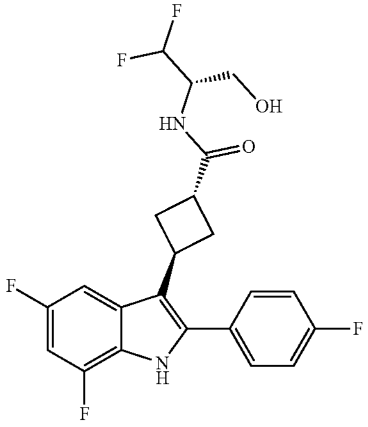 [SMILES: O=C(N[C@@H](CO)C(F)F)[C@H]1C[C@H](c2c(-c3ccc(F)cc3)[nH]c3c(F)cc(F)cc32)C1] |
| 231 |
| 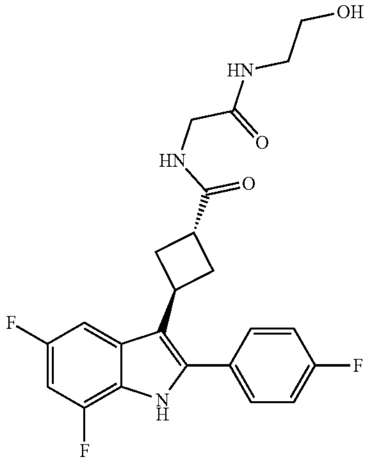 [SMILES: O=C(CNC(=O)[C@H]1C[C@H](c2c(-c3ccc(F)cc3)[nH]c3c(F)cc(F)cc32)C1)NCCO] |

TABLE 1-continued
Compounds 1 to 286
232
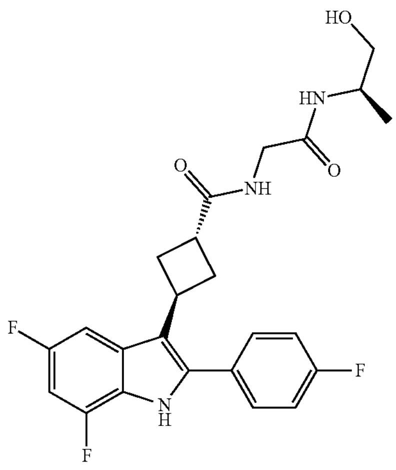 [SMILES: C[C@H](CO)NC(=O)CNC(=O)[C@H]1C[C@H](c2c(-c3ccc(F)cc3)[nH]c3c(F)cc(F)cc32)C1]
233
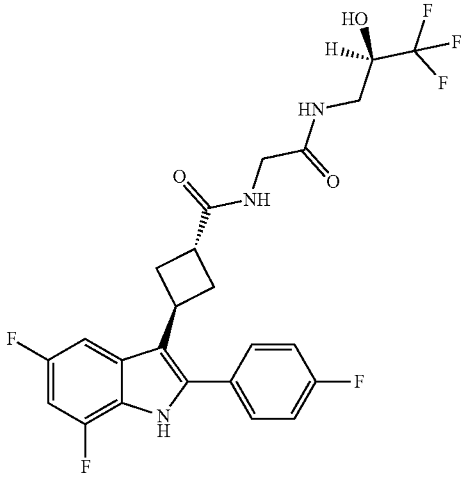 [SMILES: O=C(CNC(=O)[C@H]1C[C@H](c2c(-c3ccc(F)cc3)[nH]c3c(F)cc(F)cc32)C1)NC[C@@H](O)C(F)(F)F]
234
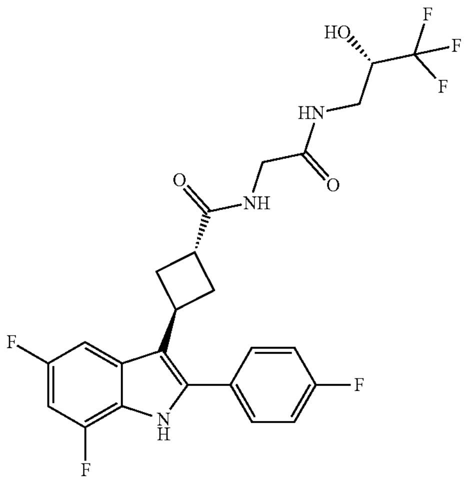 [SMILES: O=C(CNC(=O)[C@H]1C[C@H](c2c(-c3ccc(F)cc3)[nH]c3c(F)cc(F)cc32)C1)NC[C@H](O)C(F)(F)F]
TABLE 1-continued
Compounds 1 to 286
235
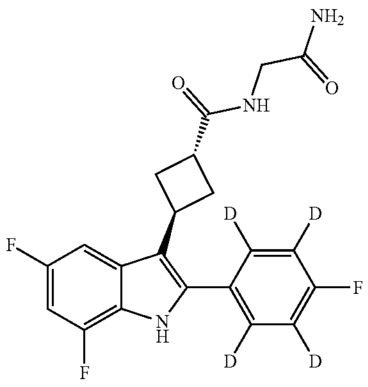 [SMILES: [2H]c1c([2H])c(-c2[nH]c3c(F)cc(F)cc3c2[C@H]2C[C@H](C(=O)NCC(N)=O)C2)c([2H])c([2H])c1F]
236
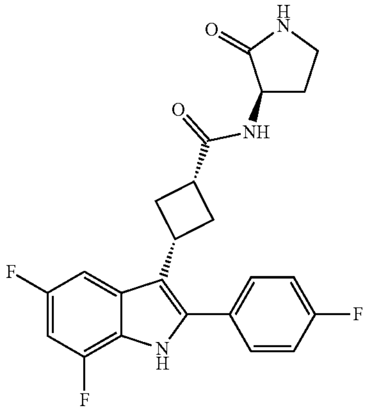 [SMILES: O=C1NCC[C@H]1NC(=O)[C@H]1C[C@@H](c2c(-c3ccc(F)cc3)[nH]c3c(F)cc(F)cc32)C1]
237
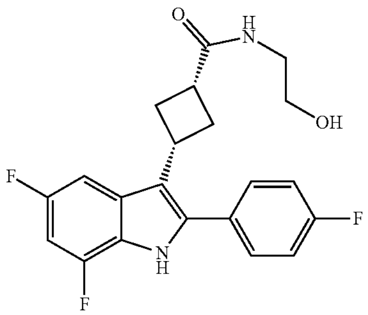 [SMILES: O=C(NCCO)[C@H]1C[C@@H](c2c(-c3ccc(F)cc3)[nH]c3c(F)cc(F)cc32)C1]
238
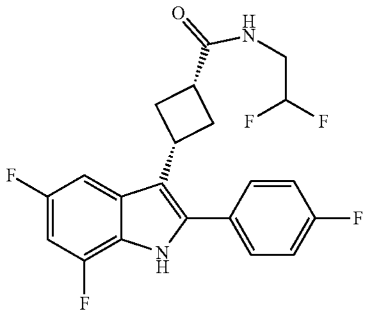 [SMILES: O=C(NCC(F)F)[C@H]1C[C@@H](c2c(-c3ccc(F)cc3)[nH]c3c(F)cc(F)cc32)C1]

TABLE 1-continued
Compounds 1 to 286
239
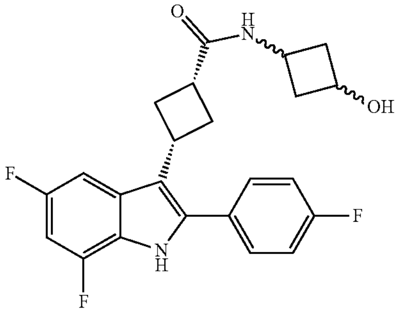 [SMILES: O=C(NC1CC(O)C1)[C@H]1C[C@@H](c2c(-c3ccc(F)cc3)[nH]c3c(F)cc(F)cc32)C1]
240
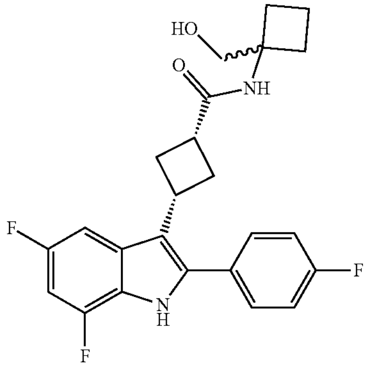 [SMILES: O=C(NC1(CO)CCC1)[C@H]1C[C@@H](c2c(-c3ccc(F)cc3)[nH]c3c(F)cc(F)cc32)C1]
241
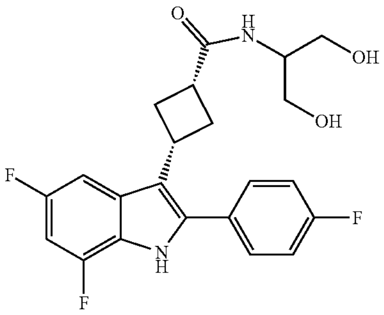 [SMILES: O=C(NC(CO)CO)[C@H]1C[C@@H](c2c(-c3ccc(F)cc3)[nH]c3c(F)cc(F)cc32)C1]
242
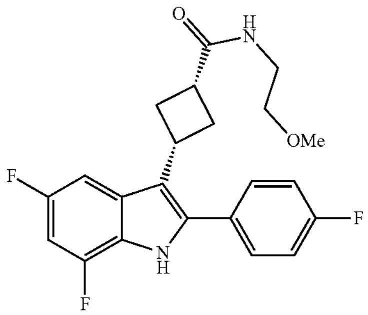 [SMILES: COCCNC(=O)[C@H]1C[C@@H](c2c(-c3ccc(F)cc3)[nH]c3c(F)cc(F)cc32)C1]
243
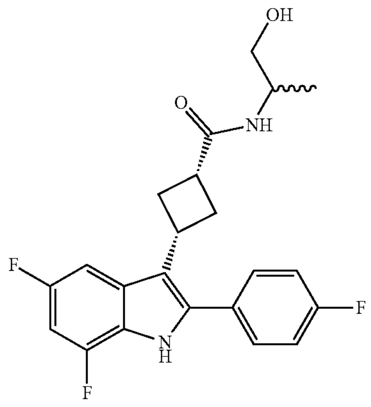 [SMILES: CC(CO)NC(=O)[C@H]1C[C@@H](c2c(-c3ccc(F)cc3)[nH]c3c(F)cc(F)cc32)C1]
244
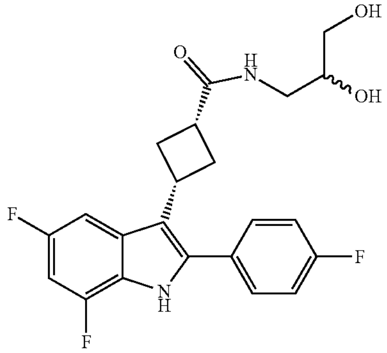 [SMILES: O=C(NCC(O)CO)[C@H]1C[C@@H](c2c(-c3ccc(F)cc3)[nH]c3c(F)cc(F)cc32)C1]
245
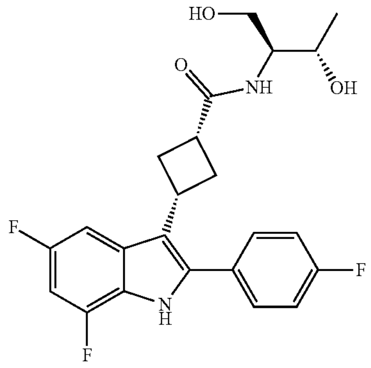 [SMILES: C[C@H](O)[C@H](CO)NC(=O)[C@H]1C[C@@H](c2c(-c3ccc(F)cc3)[nH]c3c(F)cc(F)cc32)C1]

TABLE 1-continued
Compounds 1 to 286
246
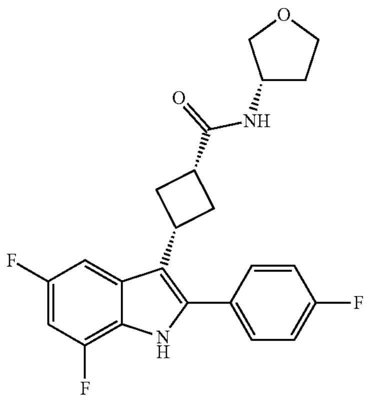 [SMILES: O=C(N[C@H]1CCOC1)[C@H]1C[C@@H](c2c(-c3ccc(F)cc3)[nH]c3c(F)cc(F)cc32)C1]
247
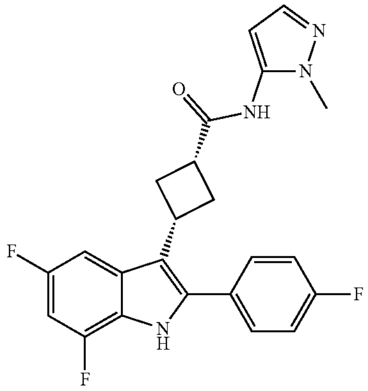 [SMILES: Cn1nccc1NC(=O)[C@H]1C[C@@H](c2c(-c3ccc(F)cc3)[nH]c3c(F)cc(F)cc32)C1]
248
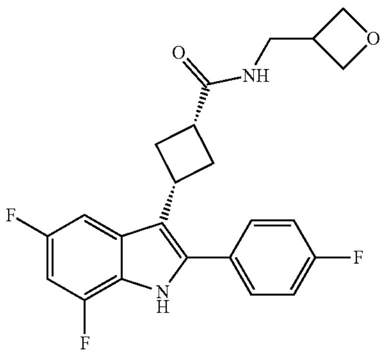 [SMILES: O=C(NCC1COC1)[C@H]1C[C@@H](c2c(-c3ccc(F)cc3)[nH]c3c(F)cc(F)cc32)C1]
249
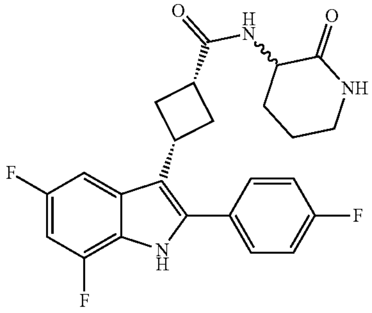 [SMILES: O=C1NCCCC1NC(=O)[C@H]1C[C@@H](c2c(-c3ccc(F)cc3)[nH]c3c(F)cc(F)cc32)C1]
250
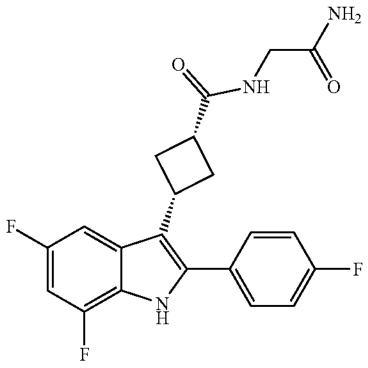 [SMILES: NC(=O)CNC(=O)[C@H]1C[C@@H](c2c(-c3ccc(F)cc3)[nH]c3c(F)cc(F)cc32)C1]
251
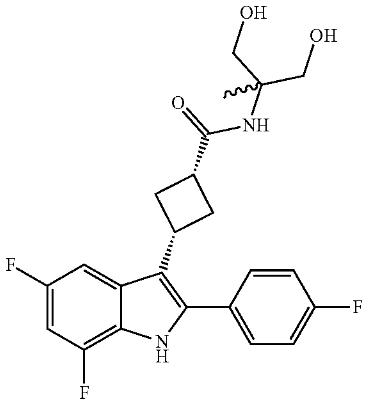
252
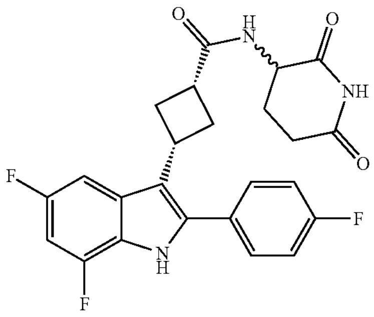 [SMILES: O=C1CCC(NC(=O)[C@H]2C[C@@H](c3c(-c4ccc(F)cc4)[nH]c4c(F)cc(F)cc43)C2)C(=O)N1]

TABLE 1-continued
| Compounds 1 to 286 |
|---|
| 253 |
| 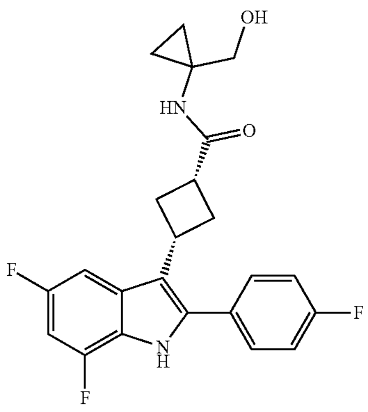 [SMILES: O=C(NC1(CO)CC1)[C@H]1C[C@@H](c2c(-c3ccc(F)cc3)[nH]c3c(F)cc(F)cc32)C1] |
| 254 |
| 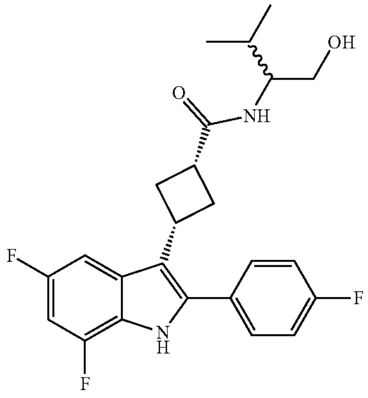 [SMILES: CC(C)C(CO)NC(=O)[C@H]1C[C@@H](c2c(-c3ccc(F)cc3)[nH]c3c(F)cc(F)cc32)C1] |
| 255 |
| 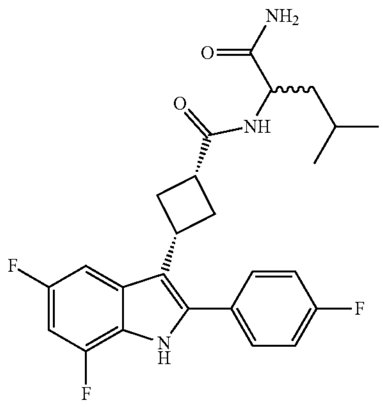 [SMILES: CC(C)CC(NC(=O)[C@H]1C[C@@H](c2c(-c3ccc(F)cc3)[nH]c3c(F)cc(F)cc32)C1)C(N)=O] |
TABLE 1-continued
| Compounds 1 to 286 |
|---|
| 256 |
| 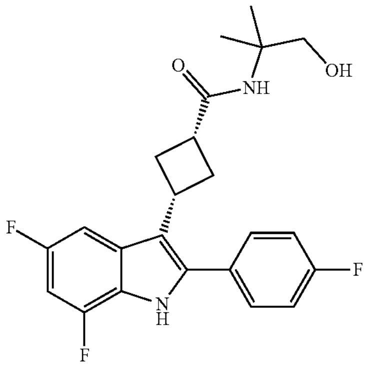 [SMILES: CC(C)(CO)NC(=O)[C@H]1C[C@@H](c2c(-c3ccc(F)cc3)[nH]c3c(F)cc(F)cc32)C1] |
| 257 |
| 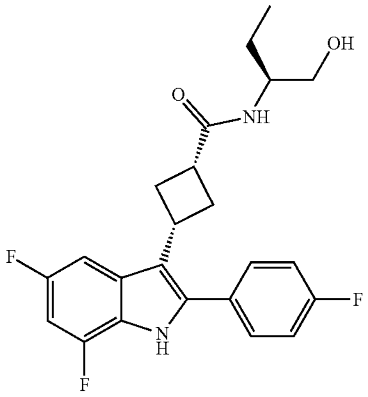 [SMILES: CC[C@@H](CO)NC(=O)[C@H]1C[C@@H](c2c(-c3ccc(F)cc3)[nH]c3c(F)cc(F)cc32)C1] |
| 258 |
| 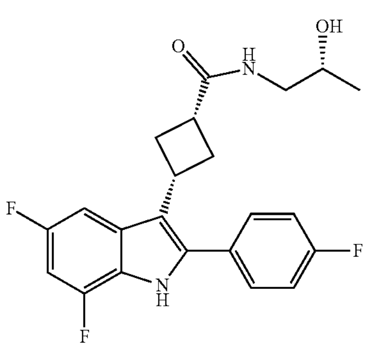 [SMILES: C[C@@H](O)CNC(=O)[C@H]1C[C@@H](c2c(-c3ccc(F)cc3)[nH]c3c(F)cc(F)cc32)C1] |

TABLE 1-continued
Compounds 1 to 286
259
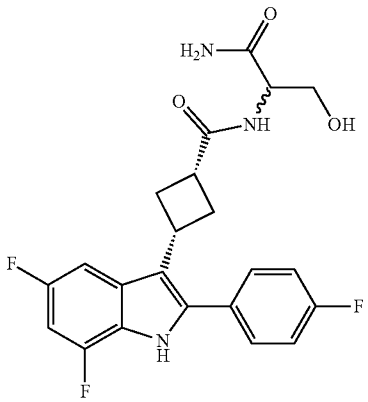 [SMILES: NC(=O)C(CO)NC(=O)[C@H]1C[C@@H](c2c(-c3ccc(F)cc3)[nH]c3c(F)cc(F)cc32)C1]
260
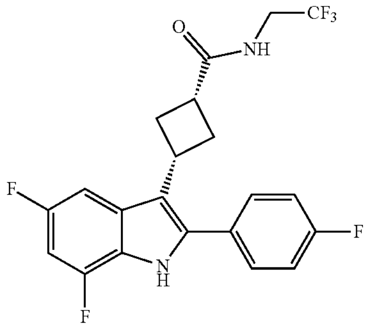 [SMILES: O=C(NCC(F)(F)F)[C@H]1C[C@@H](c2c(-c3ccc(F)cc3)[nH]c3c(F)cc(F)cc32)C1]
261
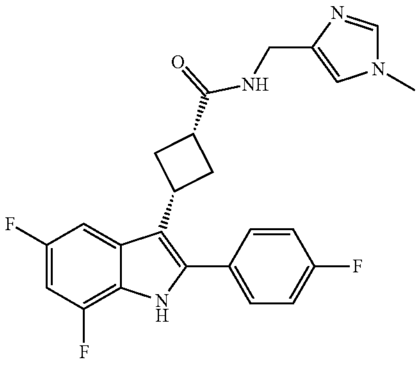 [SMILES: Cn1cnc(CNC(=O)[C@H]2C[C@@H](c3c(-c4ccc(F)cc4)[nH]c4c(F)cc(F)cc43)C2)c1]
262
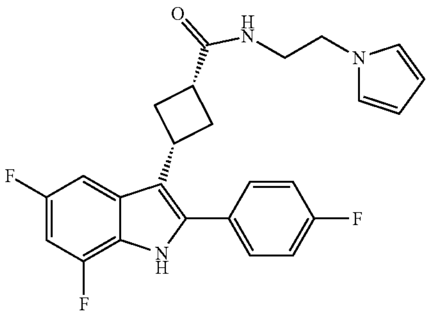 [SMILES: O=C(NCCn1cccc1)[C@H]1C[C@@H](c2c(-c3ccc(F)cc3)[nH]c3c(F)cc(F)cc32)C1]
TABLE 1-continued
Compounds 1 to 286
263
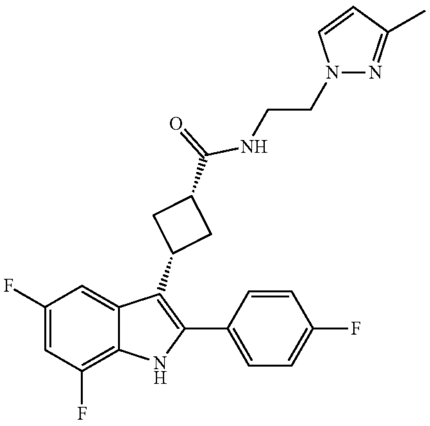 [SMILES: Cc1ccn(CCNC(=O)[C@H]2C[C@@H](c3c(-c4ccc(F)cc4)[nH]c4c(F)cc(F)cc43)C2)n1]
264
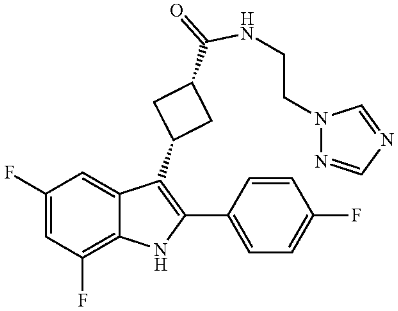 [SMILES: O=C(NCCn1cncn1)[C@H]1C[C@@H](c2c(-c3ccc(F)cc3)[nH]c3c(F)cc(F)cc32)C1]
265
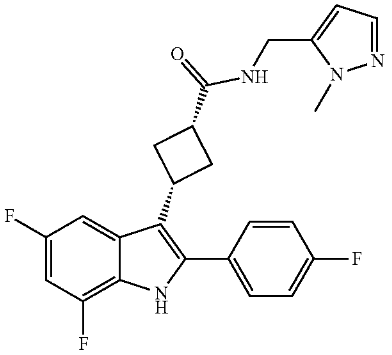 [SMILES: Cn1nccc1CNC(=O)[C@H]1C[C@@H](c2c(-c3ccc(F)cc3)[nH]c3c(F)cc(F)cc32)C1]

TABLE 1-continued
| Compounds 1 to 286 |
|---|
266
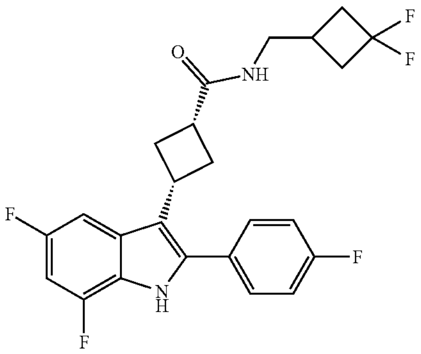 [SMILES: O=C(NCC1CC(F)(F)C1)[C@H]1C[C@@H](c2c(-c3ccc(F)cc3)[nH]c3c(F)cc(F)cc32)C1]
267
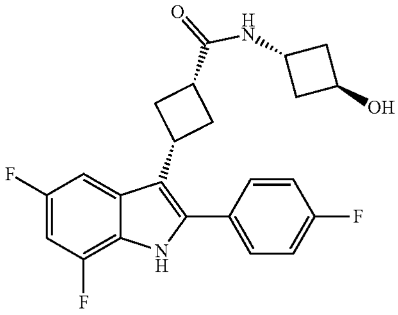 [SMILES: O=C(N[C@H]1C[C@H](O)C1)[C@H]1C[C@@H](c2c(-c3ccc(F)cc3)[nH]c3c(F)cc(F)cc32)C1]
268
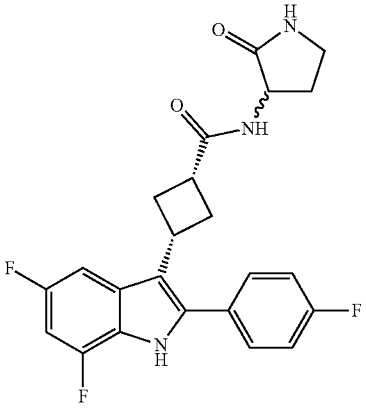 [SMILES: O=C1NCCC1NC(=O)[C@H]1C[C@@H](c2c(-c3ccc(F)cc3)[nH]c3c(F)cc(F)cc32)C1]
TABLE 1-continued
| Compounds 1 to 286 |
|---|
269
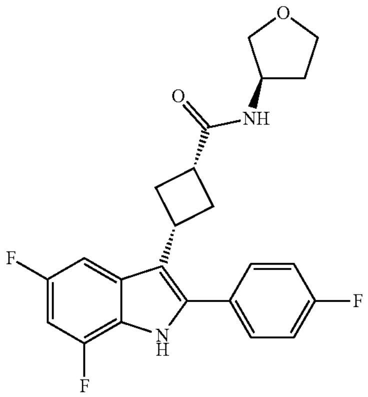 [SMILES: O=C(N[C@@H]1CCOC1)[C@H]1C[C@@H](c2c(-c3ccc(F)cc3)[nH]c3c(F)cc(F)cc32)C1]
270
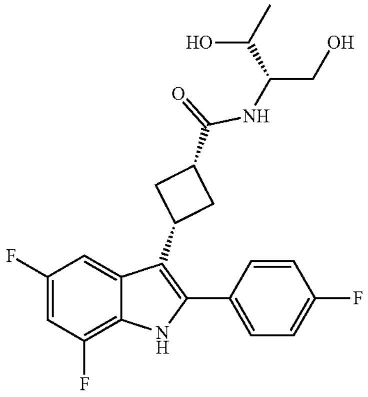 [SMILES: CC(O)[C@H](CO)NC(=O)[C@H]1C[C@@H](c2c(-c3ccc(F)cc3)[nH]c3c(F)cc(F)cc32)C1]
271
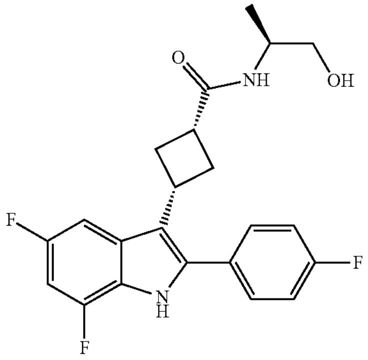 [SMILES: C[C@@H](CO)NC(=O)[C@H]1C[C@@H](c2c(-c3ccc(F)cc3)[nH]c3c(F)cc(F)cc32)C1]

TABLE 1-continued
| Compounds 1 to 286 |
|---|
272
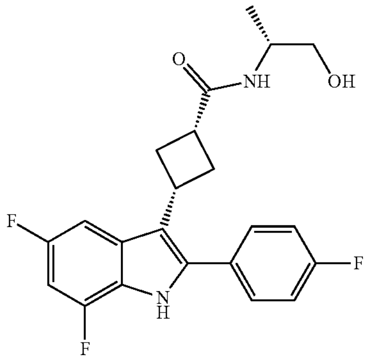 [SMILES: C[C@H](CO)NC(=O)[C@H]1C[C@@H](c2c(-c3ccc(F)cc3)[nH]c3c(F)cc(F)cc32)C1]
273
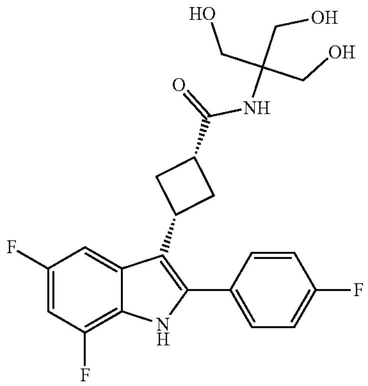 [SMILES: O=C(NC(CO)(CO)CO)[C@H]1C[C@@H](c2c(-c3ccc(F)cc3)[nH]c3c(F)cc(F)cc32)C1]
274
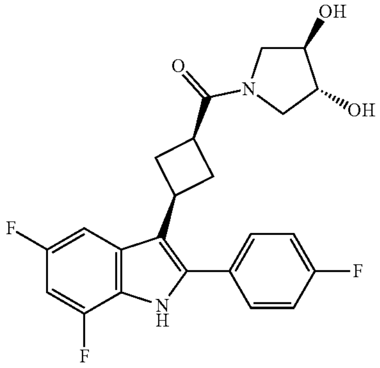 [SMILES: O=C([C@H]1C[C@@H](c2c(-c3ccc(F)cc3)[nH]c3c(F)cc(F)cc32)C1)N1C[C@@H](O)[C@H](O)C1]
TABLE 1-continued
| Compounds 1 to 286 |
|---|
275
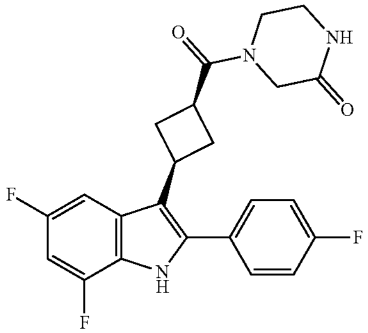 [SMILES: O=C1CN(C(=O)[C@H]2C[C@@H](c3c(-c4ccc(F)cc4)[nH]c4c(F)cc(F)cc43)C2)CCN1]
276
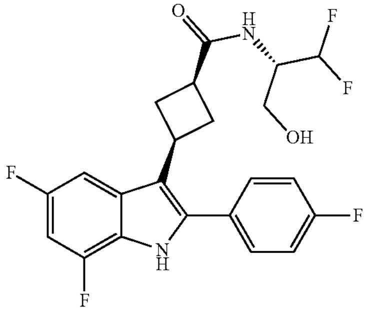 [SMILES: O=C(N[C@@H](CO)C(F)F)[C@H]1C[C@@H](c2c(-c3ccc(F)cc3)[nH]c3c(F)cc(F)cc32)C1]
277
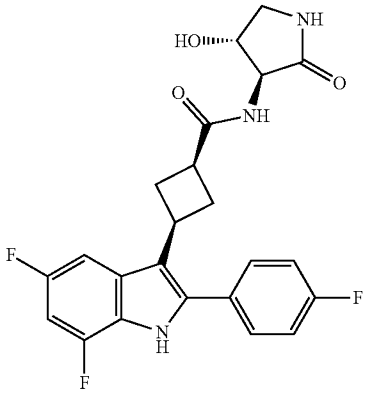 [SMILES: O=C1NC[C@@H](O)[C@@H]1NC(=O)[C@H]1C[C@@H](c2c(-c3ccc(F)cc3)[nH]c3c(F)cc(F)cc32)C1]
278
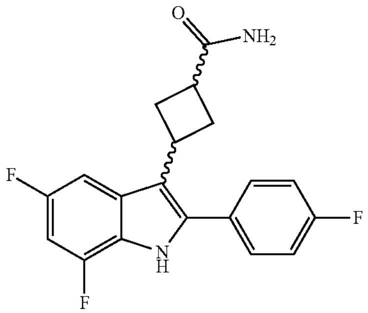 [SMILES: NC(=O)C1CC(c2c(-c3ccc(F)cc3)[nH]c3c(F)cc(F)cc23)C1]

TABLE 1-continued
| Compounds 1 to 286 |
|---|
| 279 |
| 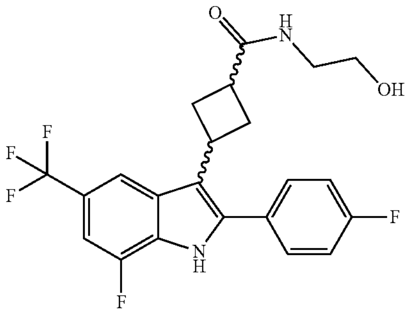 [SMILES: O=C(NCCO)C1CC(c2c(-c3ccc(F)cc3)[nH]c3c(F)cc(C(F)(F)F)cc23)C1] |
| 280 |
| 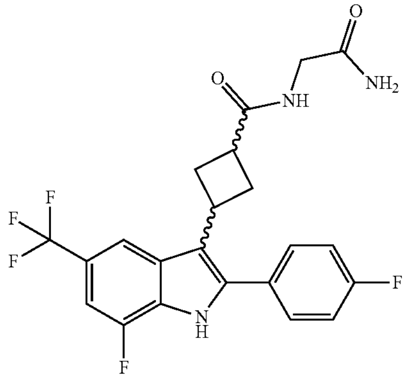 [SMILES: NC(=O)CNC(=O)C1CC(c2c(-c3ccc(F)cc3)[nH]c3c(F)cc(C(F)(F)F)cc23)C1] |
| 281 |
| 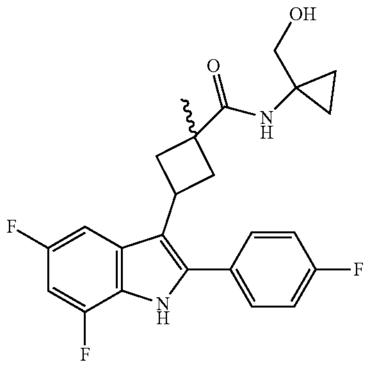 [SMILES: CC1(C(=O)NC2(CO)CC2)CC(c2c(-c3ccc(F)cc3)[nH]c3c(F)cc(F)cc23)C1] |
| 282 |
| 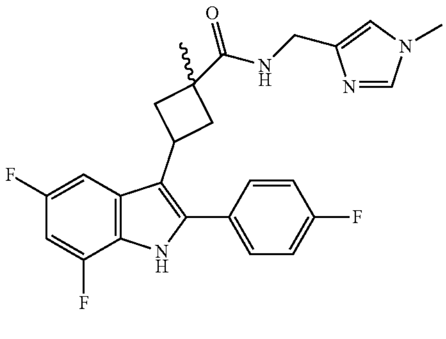 [SMILES: Cn1cnc(CNC(=O)C2(C)CC(c3c(-c4ccc(F)cc4)[nH]c4c(F)cc(F)cc34)C2)c1] |
TABLE 1-continued
| Compounds 1 to 286 |
|---|
| 283 |
| 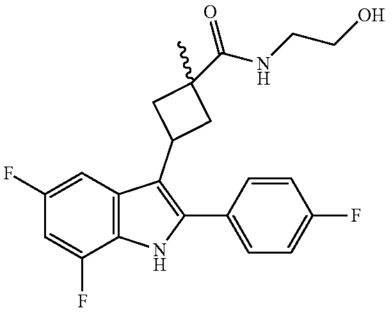 [SMILES: CC1(C(=O)NCCO)CC(c2c(-c3ccc(F)cc3)[nH]c3c(F)cc(F)cc23)C1] |
| 284 |
| 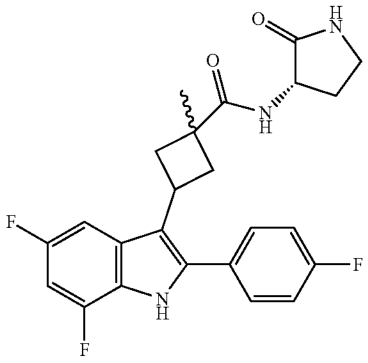 [SMILES: CC1(C(=O)N[C@H]2CCNC2=O)CC(c2c(-c3ccc(F)cc3)[nH]c3c(F)cc(F)cc23)C1] |
| 285 |
| 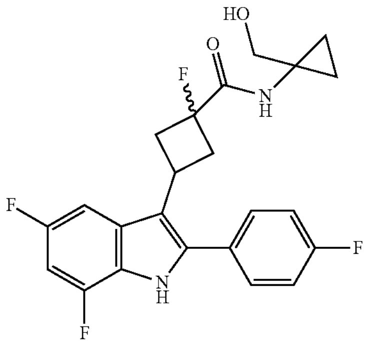 [SMILES: O=C(NC1(CO)CC1)C1(F)CC(c2c(-c3ccc(F)cc3)[nH]c3c(F)cc(F)cc23)C1] |
| 286 |
| 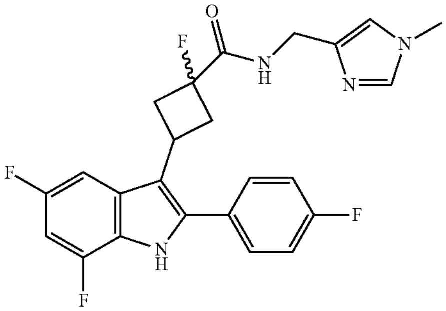 |
In some embodiments, the at least one entity of the disclosure is chosen from Compounds 287 to 465 depicted in Table 2 and pharmaceutically acceptable salts of any of those compounds, solvates of any of the foregoing, and deuterated derivatives of any of the foregoing. A wavy line in a compound in Table 2 (i.e.,  ) depicts a bond between two atoms and indicates a position of mixed stereochemistry for a collection of molecules, such as a racemic mixture, cis/trans isomers, or (E)/(Z) isomers.
TABLE 2
| Compounds 287 to 465 |
|---|
| 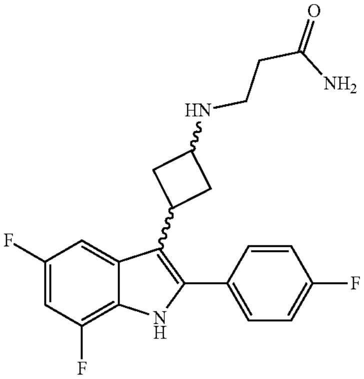 [SMILES: NC(=O)CCNC1CC(c2c(-c3ccc(F)cc3)[nH]c3c(F)cc(F)cc23)C1] 287 |
| 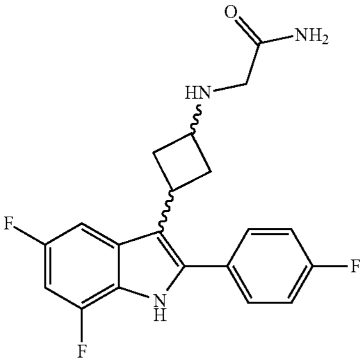 [SMILES: NC(=O)CNC1CC(c2c(-c3ccc(F)cc3)[nH]c3c(F)cc(F)cc23)C1] 288 |
| 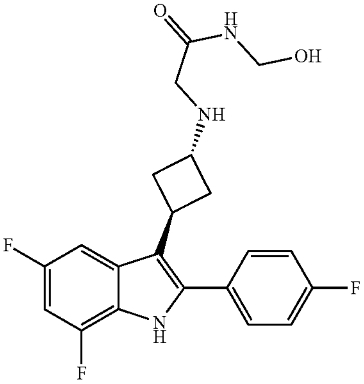 [SMILES: O=C(CN[C@H]1C[C@H](c2c(-c3ccc(F)cc3)[nH]c3c(F)cc(F)cc32)C1)NCO] 289 |
TABLE 2-continued
| Compounds 287 to 465 |
|---|
| 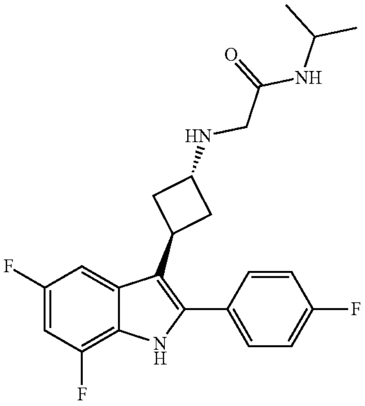 [SMILES: CC(C)NC(=O)CN[C@H]1C[C@H](c2c(-c3ccc(F)cc3)[nH]c3c(F)cc(F)cc32)C1] 290 |
| 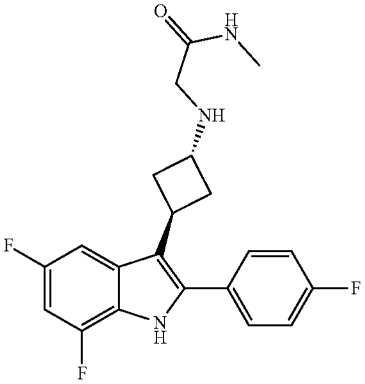 [SMILES: CNC(=O)CN[C@H]1C[C@H](c2c(-c3ccc(F)cc3)[nH]c3c(F)cc(F)cc32)C1] 291 |
| 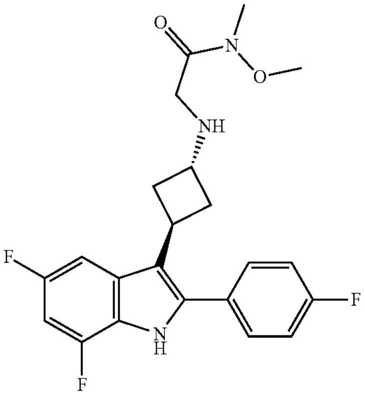 [SMILES: CON(C)C(=O)CN[C@H]1C[C@H](c2c(-c3ccc(F)cc3)[nH]c3c(F)cc(F)cc32)C1] 292 |
| 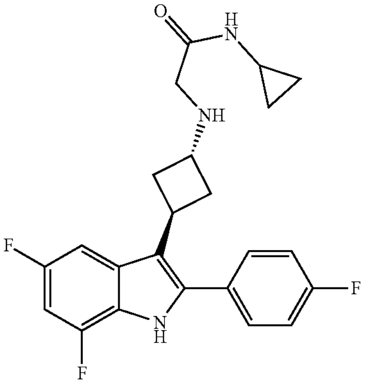 [SMILES: O=C(CN[C@H]1C[C@H](c2c(-c3ccc(F)cc3)[nH]c3c(F)cc(F)cc32)C1)NC1CC1] 293 |

TABLE 2-continued
Compounds 287 to 465
294
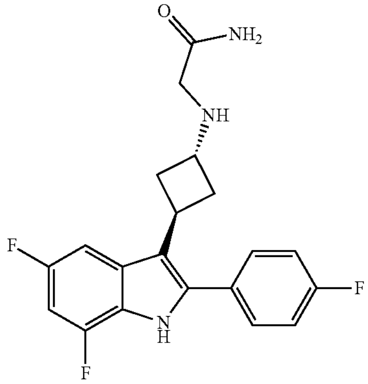 [SMILES: NC(=O)CN[C@H]1C[C@H](c2c(-c3ccc(F)cc3)[nH]c3c(F)cc(F)cc32)C1]
295
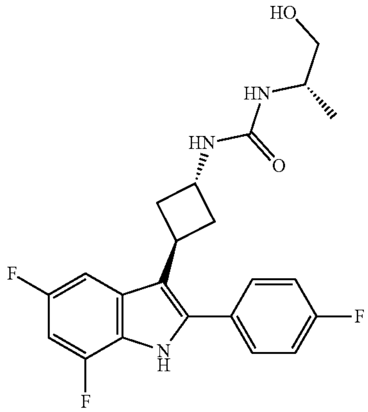 [SMILES: C[C@@H](CO)NC(=O)N[C@H]1C[C@H](c2c(-c3ccc(F)cc3)[nH]c3c(F)cc(F)cc32)C1]
296
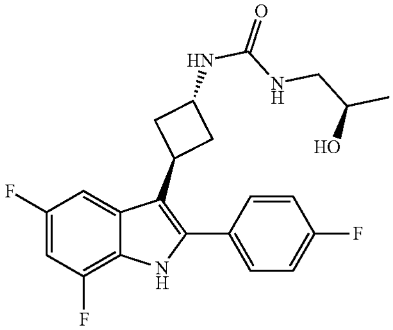 [SMILES: C[C@@H](O)CNC(=O)N[C@H]1C[C@H](c2c(-c3ccc(F)cc3)[nH]c3c(F)cc(F)cc32)C1]
297
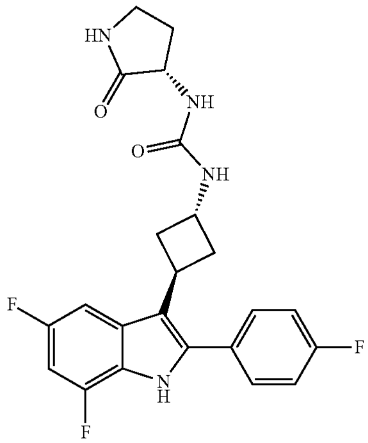 [SMILES: O=C(N[C@H]1CCNC1=O)N[C@H]1C[C@H](c2c(-c3ccc(F)cc3)[nH]c3c(F)cc(F)cc32)C1]
TABLE 2-continued
Compounds 287 to 465
298
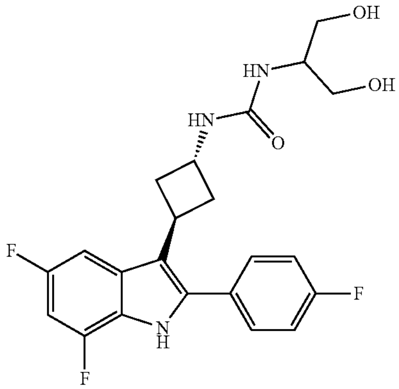 [SMILES: O=C(NC(CO)CO)N[C@H]1C[C@H](c2c(-c3ccc(F)cc3)[nH]c3c(F)cc(F)cc32)C1]
299
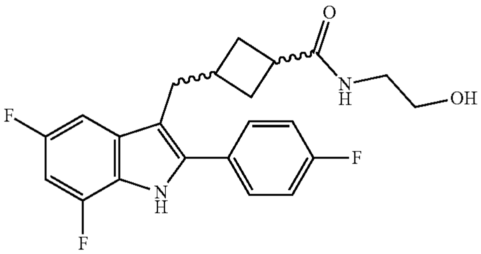 [SMILES: O=C(NCCO)C1CC(Cc2c(-c3ccc(F)cc3)[nH]c3c(F)cc(F)cc23)C1]
300
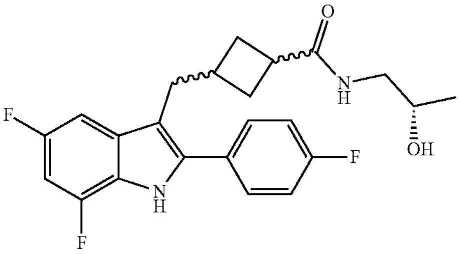 [SMILES: C[C@H](O)CNC(=O)C1CC(Cc2c(-c3ccc(F)cc3)[nH]c3c(F)cc(F)cc23)C1]
301
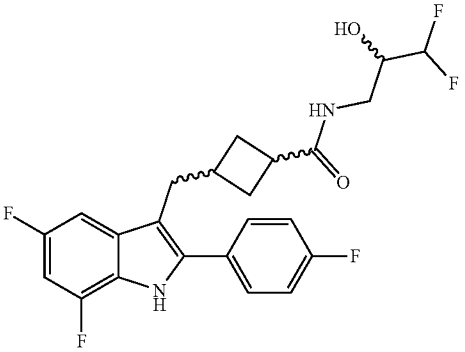 [SMILES: O=C(NCC(O)C(F)F)C1CC(Cc2c(-c3ccc(F)cc3)[nH]c3c(F)cc(F)cc23)C1]
302
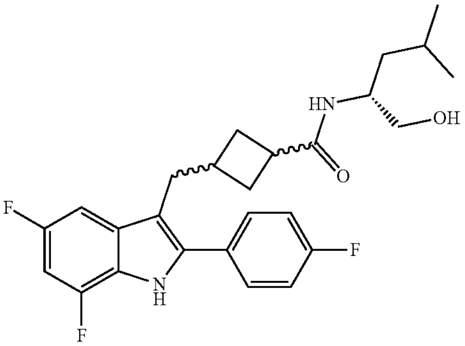 [SMILES: CC(C)C[C@H](CO)NC(=O)C1CC(Cc2c(-c3ccc(F)cc3)[nH]c3c(F)cc(F)cc23)C1]

TABLE 2-continued
Compounds 287 to 465
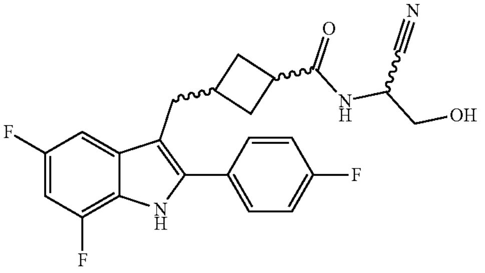 [SMILES: N#CC(CO)NC(=O)C1CC(Cc2c(-c3ccc(F)cc3)[nH]c3c(F)cc(F)cc23)C1]
303
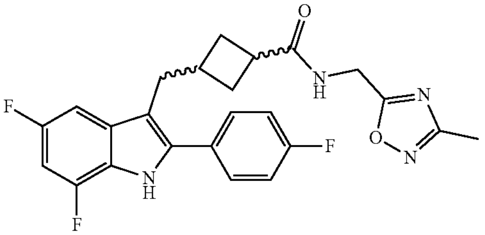 [SMILES: Cc1noc(CNC(=O)C2CC(Cc3c(-c4ccc(F)cc4)[nH]c4c(F)cc(F)cc34)C2)n1]
304
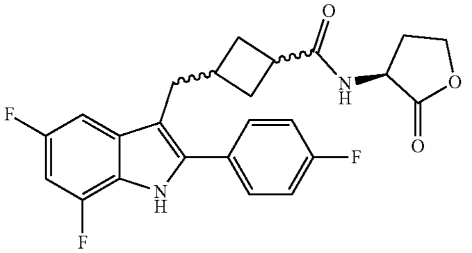 [SMILES: O=C(N[C@H]1CCOC1=O)C1CC(Cc2c(-c3ccc(F)cc3)[nH]c3c(F)cc(F)cc23)C1]
305
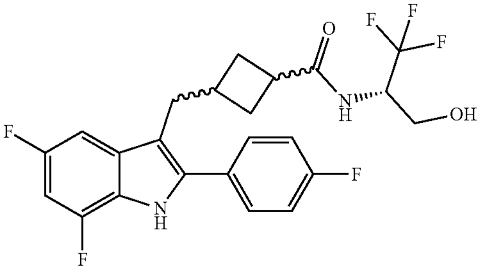 [SMILES: O=C(N[C@@H](CO)C(F)(F)F)C1CC(Cc2c(-c3ccc(F)cc3)[nH]c3c(F)cc(F)cc23)C1]
306
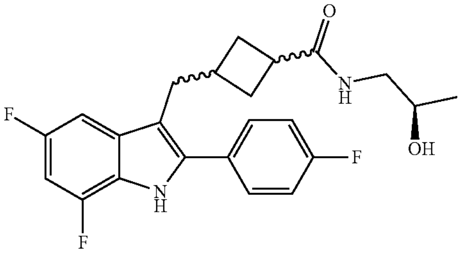 [SMILES: C[C@@H](O)CNC(=O)C1CC(Cc2c(-c3ccc(F)cc3)[nH]c3c(F)cc(F)cc23)C1]
307
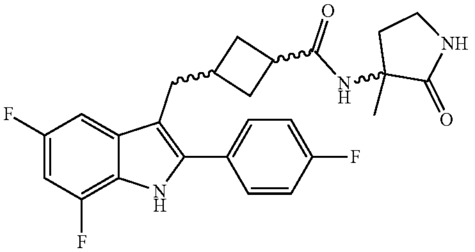 [SMILES: CC1(NC(=O)C2CC(Cc3c(-c4ccc(F)cc4)[nH]c4c(F)cc(F)cc34)C2)CCNC1=O]
308
TABLE 2-continued
Compounds 287 to 465
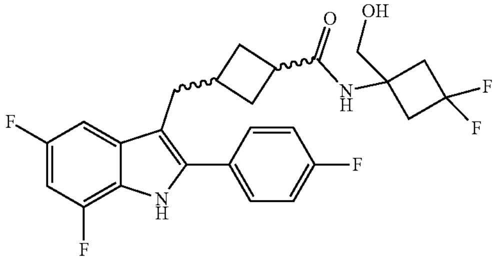 [SMILES: O=C(NC1(CO)CC(F)(F)C1)C1CC(Cc2c(-c3ccc(F)cc3)[nH]c3c(F)cc(F)cc23)C1]
309
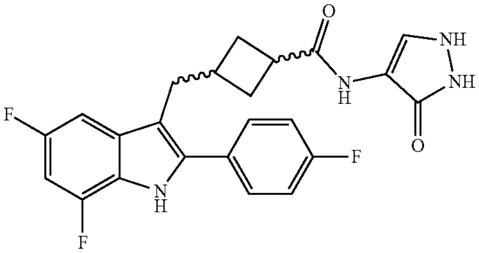 [SMILES: O=C(Nc1c[nH][nH]c1=O)C1CC(Cc2c(-c3ccc(F)cc3)[nH]c3c(F)cc(F)cc23)C1]
310
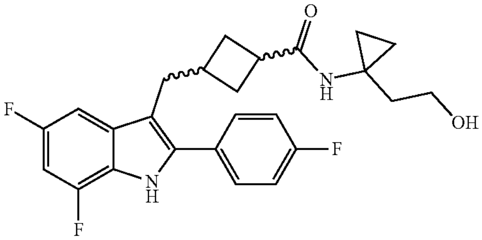 [SMILES: O=C(NC1(CCO)CC1)C1CC(Cc2c(-c3ccc(F)cc3)[nH]c3c(F)cc(F)cc23)C1]
311
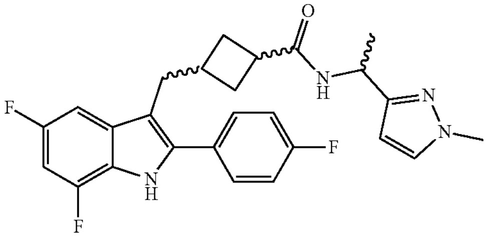 [SMILES: CC(NC(=O)C1CC(Cc2c(-c3ccc(F)cc3)[nH]c3c(F)cc(F)cc23)C1)c1ccn(C)n1]
312
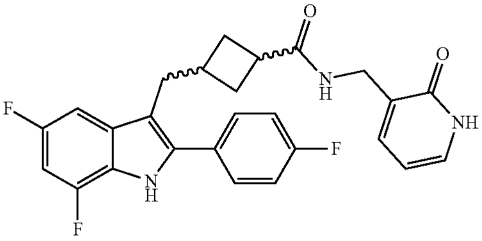 [SMILES: O=C(NCc1ccc[nH]c1=O)C1CC(Cc2c(-c3ccc(F)cc3)[nH]c3c(F)cc(F)cc23)C1]
313
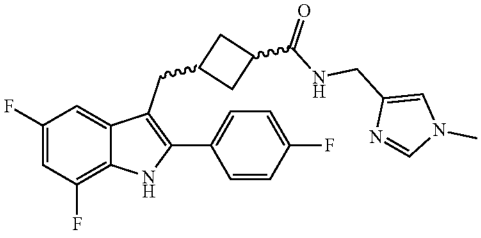 [SMILES: Cn1cnc(CNC(=O)C2CC(Cc3c(-c4ccc(F)cc4)[nH]c4c(F)cc(F)cc34)C2)c1]
314

TABLE 2-continued
Compounds 287 to 465
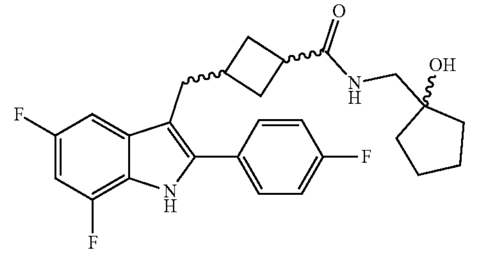 [SMILES: O=C(NCC1(O)CCCC1)C1CC(Cc2c(-c3ccc(F)cc3)[nH]c3c(F)cc(F)cc23)C1]
315
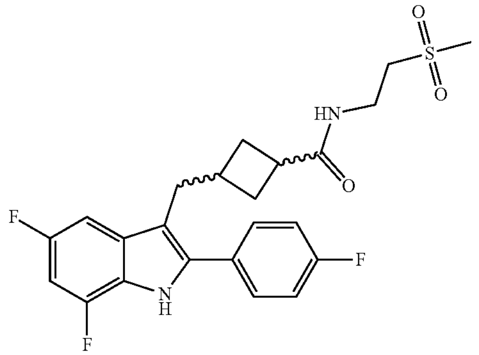 [SMILES: CS(=O)(=O)CCNC(=O)C1CC(Cc2c(-c3ccc(F)cc3)[nH]c3c(F)cc(F)cc23)C1]
316
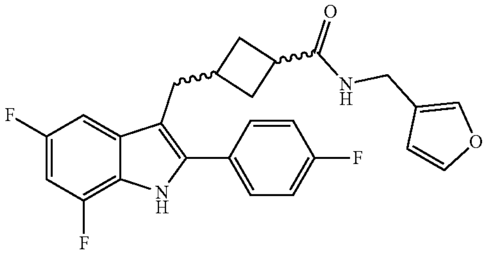 [SMILES: O=C(NCc1ccoc1)C1CC(Cc2c(-c3ccc(F)cc3)[nH]c3c(F)cc(F)cc23)C1]
317
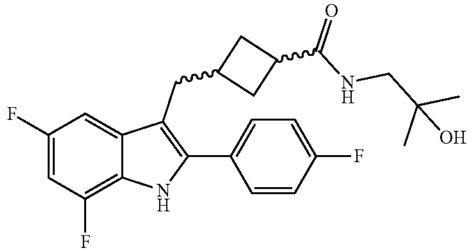 [SMILES: CC(C)(O)CNC(=O)C1CC(Cc2c(-c3ccc(F)cc3)[nH]c3c(F)cc(F)cc23)C1]
318
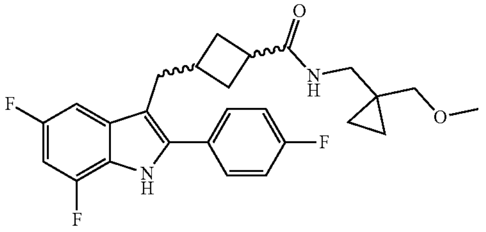 [SMILES: COCC1(CNC(=O)C2CC(Cc3c(-c4ccc(F)cc4)[nH]c4c(F)cc(F)cc34)C2)CC1]
319
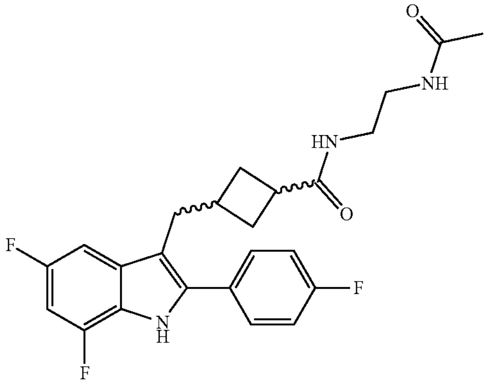 [SMILES: CC(=O)NCCNC(=O)C1CC(Cc2c(-c3ccc(F)cc3)[nH]c3c(F)cc(F)cc23)C1]
320
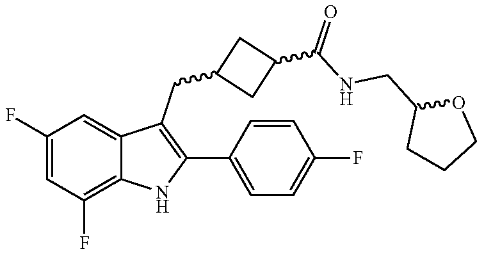 [SMILES: O=C(NCC1CCCO1)C1CC(Cc2c(-c3ccc(F)cc3)[nH]c3c(F)cc(F)cc23)C1]
321
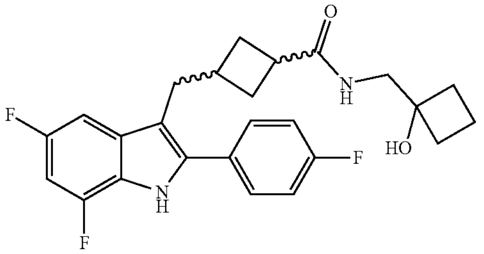 [SMILES: O=C(NCC1(O)CCC1)C1CC(Cc2c(-c3ccc(F)cc3)[nH]c3c(F)cc(F)cc23)C1]
322
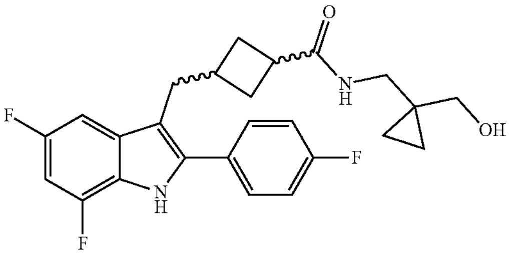 [SMILES: O=C(NCC1(CO)CC1)C1CC(Cc2c(-c3ccc(F)cc3)[nH]c3c(F)cc(F)cc23)C1]
323
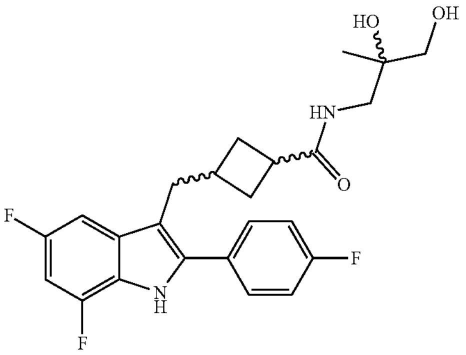 [SMILES: CC(O)(CO)CNC(=O)C1CC(Cc2c(-c3ccc(F)cc3)[nH]c3c(F)cc(F)cc23)C1]
324

TABLE 2-continued
Compounds 287 to 465
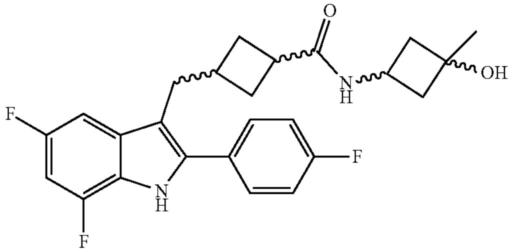 [SMILES: CC1(O)CC(NC(=O)C2CC(Cc3c(-c4ccc(F)cc4)[nH]c4c(F)cc(F)cc34)C2)C1]
325
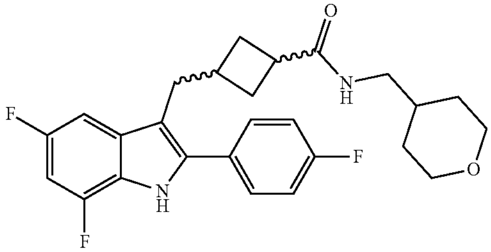 [SMILES: O=C(NCC1CCOCC1)C1CC(Cc2c(-c3ccc(F)cc3)[nH]c3c(F)cc(F)cc23)C1]
326
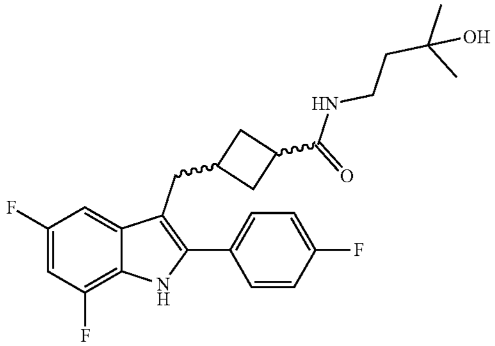 [SMILES: CC(C)(O)CCNC(=O)C1CC(Cc2c(-c3ccc(F)cc3)[nH]c3c(F)cc(F)cc23)C1]
327
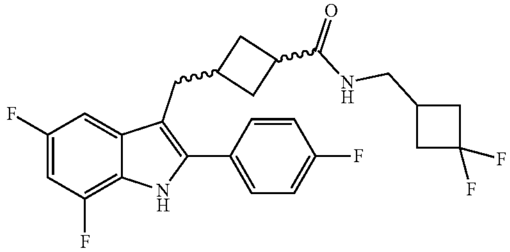 [SMILES: O=C(NCC1CC(F)(F)C1)C1CC(Cc2c(-c3ccc(F)cc3)[nH]c3c(F)cc(F)cc23)C1]
328
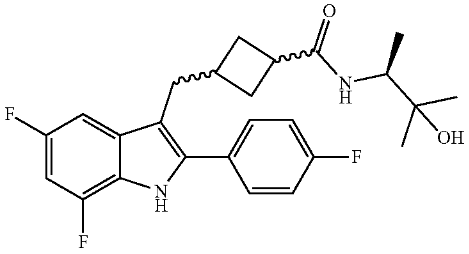 [SMILES: C[C@H](NC(=O)C1CC(Cc2c(-c3ccc(F)cc3)[nH]c3c(F)cc(F)cc23)C1)C(C)(C)O]
329
TABLE 2-continued
Compounds 287 to 465
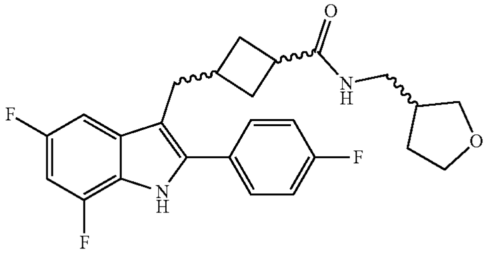 [SMILES: O=C(NCC1CCOC1)C1CC(Cc2c(-c3ccc(F)cc3)[nH]c3c(F)cc(F)cc23)C1]
330
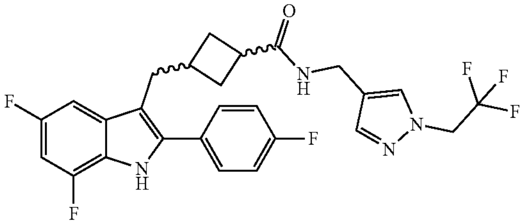 [SMILES: O=C(NCc1cnn(CC(F)(F)F)c1)C1CC(Cc2c(-c3ccc(F)cc3)[nH]c3c(F)cc(F)cc23)C1]
331
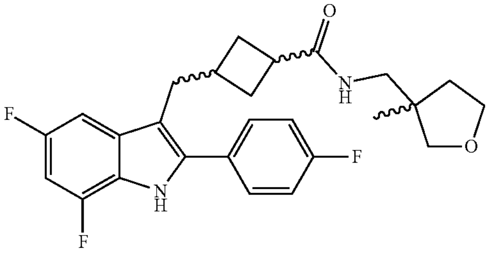 [SMILES: CC1(CNC(=O)C2CC(Cc3c(-c4ccc(F)cc4)[nH]c4c(F)cc(F)cc34)C2)CCOC1]
332
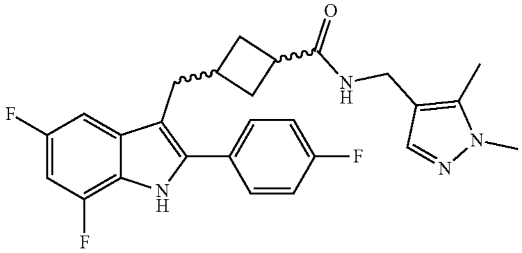 [SMILES: Cc1c(CNC(=O)C2CC(Cc3c(-c4ccc(F)cc4)[nH]c4c(F)cc(F)cc34)C2)cnn1C]
333
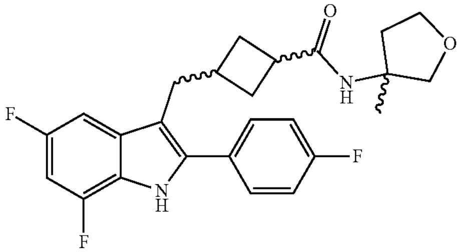 [SMILES: CC1(NC(=O)C2CC(Cc3c(-c4ccc(F)cc4)[nH]c4c(F)cc(F)cc34)C2)CCOC1]
334
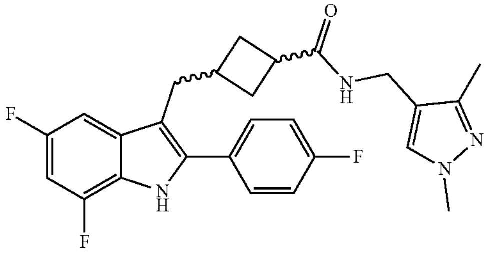 [SMILES: Cc1nn(C)cc1CNC(=O)C1CC(Cc2c(-c3ccc(F)cc3)[nH]c3c(F)cc(F)cc23)C1]
335

TABLE 2-continued
Compounds 287 to 465
336
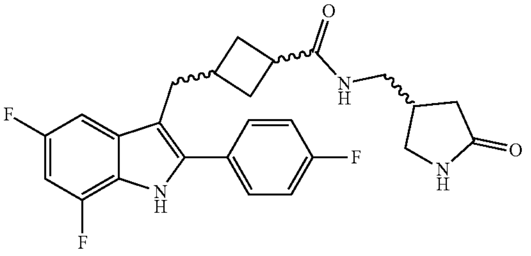 [SMILES: O=C1CC(CNC(=O)C2CC(Cc3c(-c4ccc(F)cc4)[nH]c4c(F)cc(F)cc34)C2)CN1]
337
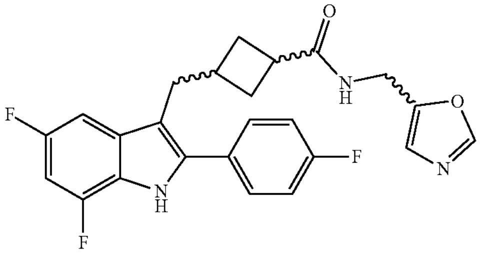 [SMILES: O=C(NCc1cnco1)C1CC(Cc2c(-c3ccc(F)cc3)[nH]c3c(F)cc(F)cc23)C1]
338
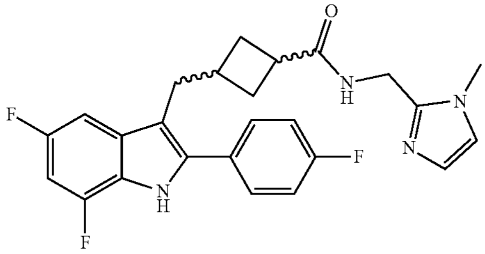 [SMILES: Cn1ccnc1CNC(=O)C1CC(Cc2c(-c3ccc(F)cc3)[nH]c3c(F)cc(F)cc23)C1]
339
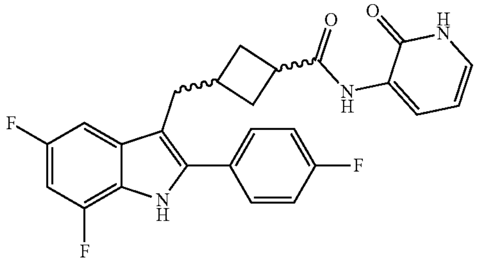 [SMILES: O=C(Nc1ccc[nH]c1=O)C1CC(Cc2c(-c3ccc(F)cc3)[nH]c3c(F)cc(F)cc23)C1]
340
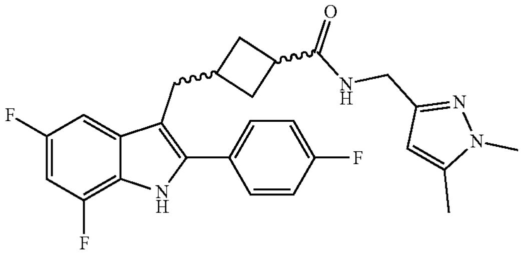 [SMILES: Cc1cc(CNC(=O)C2CC(Cc3c(-c4ccc(F)cc4)[nH]c4c(F)cc(F)cc34)C2)nn1C]
341
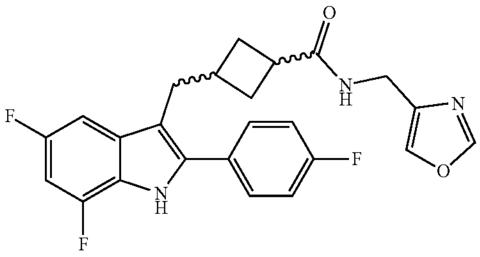 [SMILES: O=C(NCc1cocn1)C1CC(Cc2c(-c3ccc(F)cc3)[nH]c3c(F)cc(F)cc23)C1]
TABLE 2-continued
Compounds 287 to 465
342
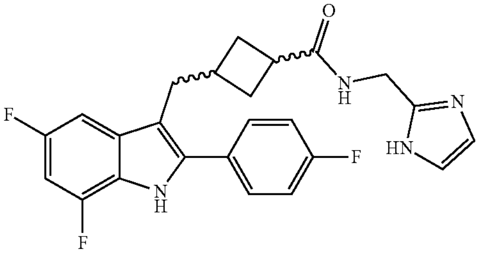 [SMILES: O=C(NCc1ncc[nH]1)C1CC(Cc2c(-c3ccc(F)cc3)[nH]c3c(F)cc(F)cc23)C1]
343
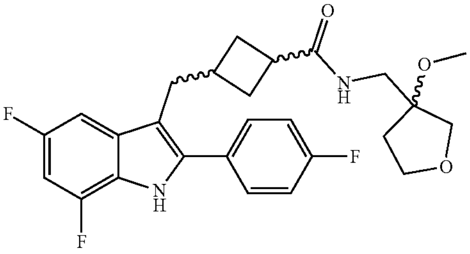 [SMILES: COC1(CNC(=O)C2CC(Cc3c(-c4ccc(F)cc4)[nH]c4c(F)cc(F)cc34)C2)CCOC1]
344
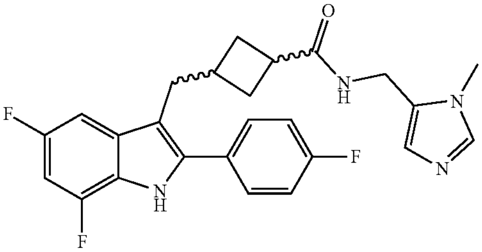 [SMILES: Cn1cncc1CNC(=O)C1CC(Cc2c(-c3ccc(F)cc3)[nH]c3c(F)cc(F)cc23)C1]
345
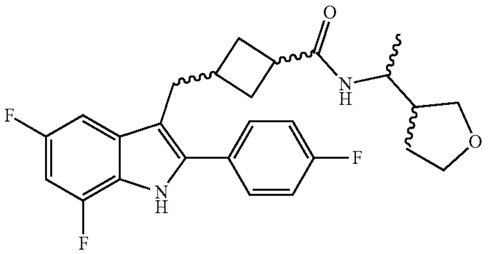 [SMILES: CC(NC(=O)C1CC(Cc2c(-c3ccc(F)cc3)[nH]c3c(F)cc(F)cc23)C1)C1CCOC1]
346
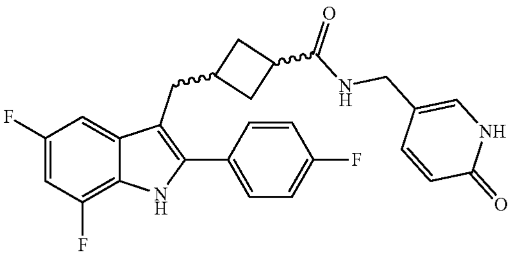 [SMILES: O=C(NCc1ccc(=O)[nH]c1)C1CC(Cc2c(-c3ccc(F)cc3)[nH]c3c(F)cc(F)cc23)C1]

TABLE 2-continued
| Compounds 287 to 465 |
|---|
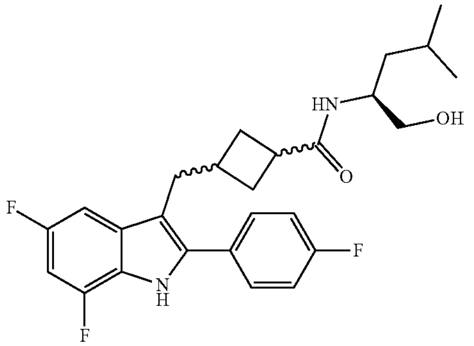 [SMILES: CC(C)C[C@@H](CO)NC(=O)C1CC(Cc2c(-c3ccc(F)cc3)[nH]c3c(F)cc(F)cc23)C1]
347
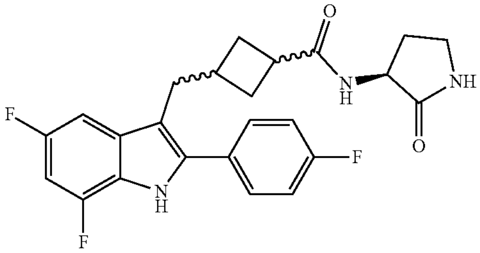 [SMILES: O=C(N[C@H]1CCNC1=O)C1CC(Cc2c(-c3ccc(F)cc3)[nH]c3c(F)cc(F)cc23)C1]
348
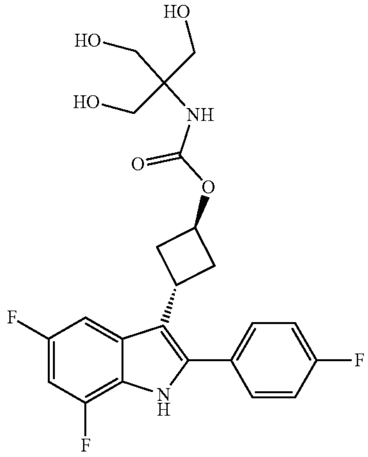 [SMILES: O=C(NC(CO)(CO)CO)O[C@H]1C[C@H](c2c(-c3ccc(F)cc3)[nH]c3c(F)cc(F)cc32)C1]
349
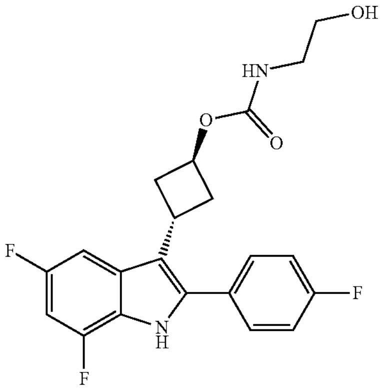 [SMILES: O=C(NCCO)O[C@H]1C[C@H](c2c(-c3ccc(F)cc3)[nH]c3c(F)cc(F)cc32)C1]
350
TABLE 2-continued
| Compounds 287 to 465 |
|---|
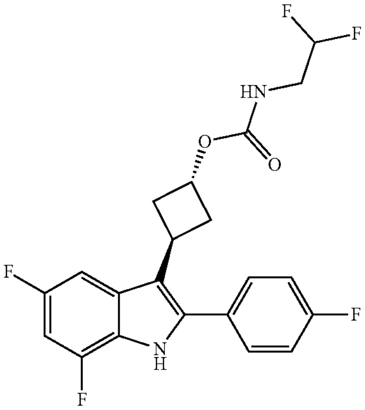 [SMILES: O=C(NCC(F)F)O[C@H]1C[C@H](c2c(-c3ccc(F)cc3)[nH]c3c(F)cc(F)cc32)C1]
351
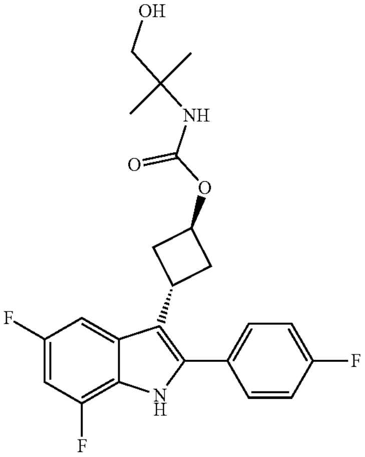 [SMILES: CC(C)(CO)NC(=O)O[C@H]1C[C@H](c2c(-c3ccc(F)cc3)[nH]c3c(F)cc(F)cc32)C1]
352
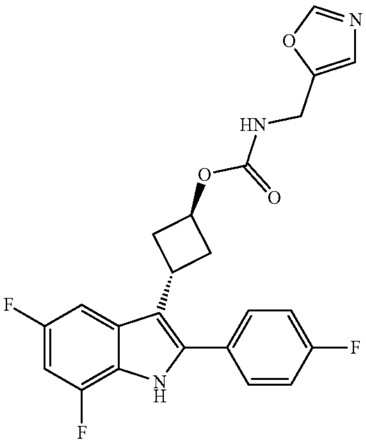 [SMILES: O=C(NCc1cnco1)O[C@H]1C[C@H](c2c(-c3ccc(F)cc3)[nH]c3c(F)cc(F)cc32)C1]
353

TABLE 2-continued
Compounds 287 to 465
354
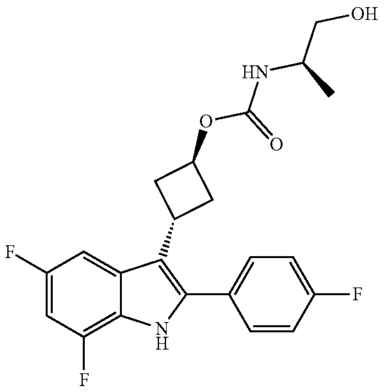 [SMILES: C[C@H](CO)NC(=O)O[C@H]1C[C@H](c2c(-c3ccc(F)cc3)[nH]c3c(F)cc(F)cc32)C1]
355
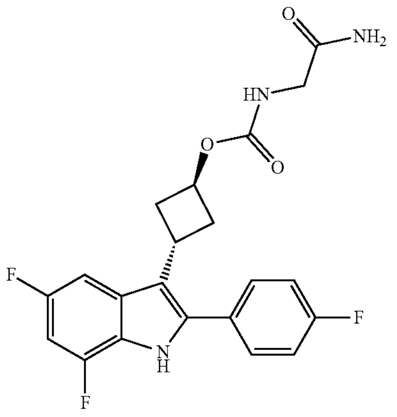 [SMILES: NC(=O)CNC(=O)O[C@H]1C[C@H](c2c(-c3ccc(F)cc3)[nH]c3c(F)cc(F)cc32)C1]
356
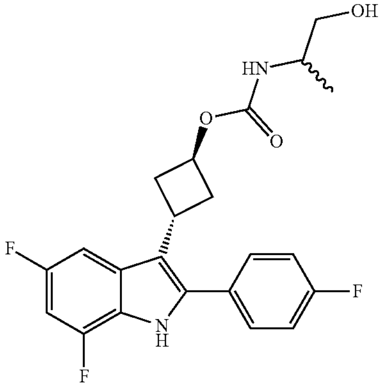 [SMILES: CC(CO)NC(=O)O[C@H]1C[C@H](c2c(-c3ccc(F)cc3)[nH]c3c(F)cc(F)cc32)C1]
357
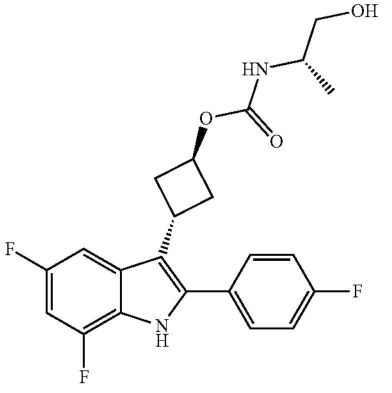 [SMILES: C[C@@H](CO)NC(=O)O[C@H]1C[C@H](c2c(-c3ccc(F)cc3)[nH]c3c(F)cc(F)cc32)C1]
358
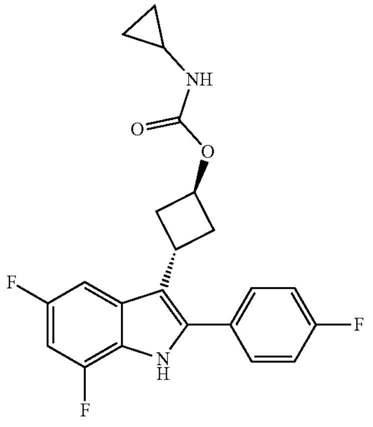 [SMILES: O=C(NC1CC1)O[C@H]1C[C@H](c2c(-c3ccc(F)cc3)[nH]c3c(F)cc(F)cc32)C1]
359
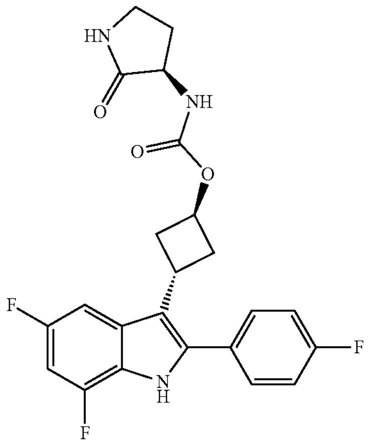 [SMILES: O=C(N[C@@H]1CCNC1=O)O[C@H]1C[C@H](c2c(-c3ccc(F)cc3)[nH]c3c(F)cc(F)cc32)C1]
360
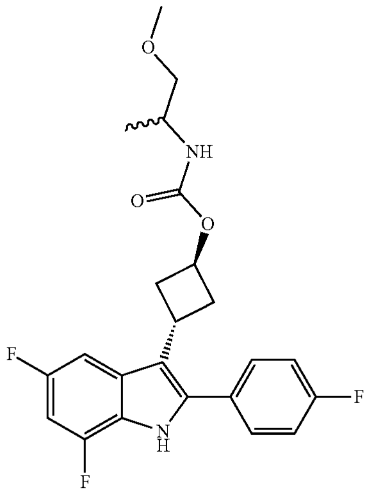 [SMILES: COCC(C)NC(=O)O[C@H]1C[C@H](c2c(-c3ccc(F)cc3)[nH]c3c(F)cc(F)cc32)C1]

TABLE 2-continued
| Compounds 287 to 465 |
|---|
| 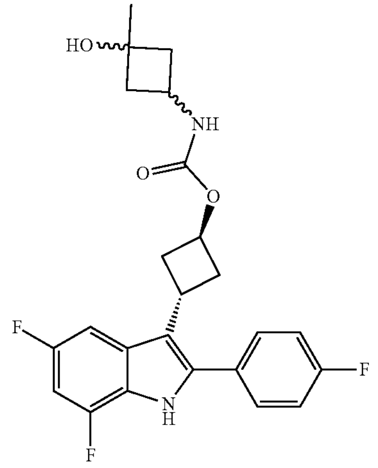 [SMILES: CC1(O)CC(NC(=O)O[C@H]2C[C@H](c3c(-c4ccc(F)cc4)[nH]c4c(F)cc(F)cc43)C2)C1] 361 |
| 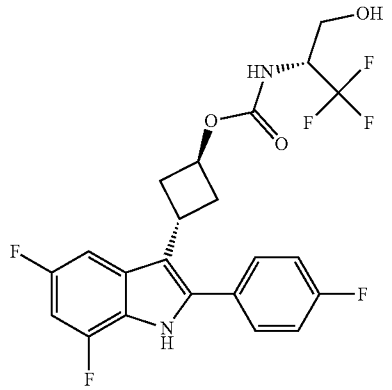 [SMILES: O=C(N[C@H](CO)C(F)(F)F)O[C@H]1C[C@H](c2c(-c3ccc(F)cc3)[nH]c3c(F)cc(F)cc32)C1] 362 |
| 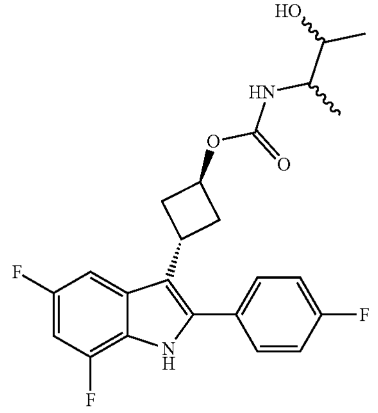 [SMILES: CC(O)C(C)NC(=O)O[C@H]1C[C@H](c2c(-c3ccc(F)cc3)[nH]c3c(F)cc(F)cc32)C1] 363 |
TABLE 2-continued
| Compounds 287 to 465 |
|---|
| 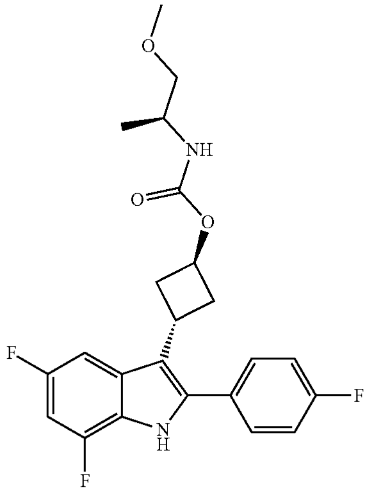 [SMILES: COC[C@H](C)NC(=O)O[C@H]1C[C@H](c2c(-c3ccc(F)cc3)[nH]c3c(F)cc(F)cc32)C1] 364 |
| 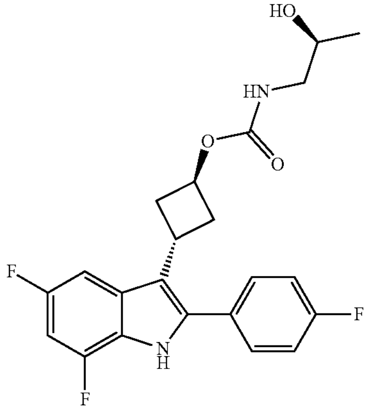 [SMILES: C[C@H](O)CNC(=O)O[C@H]1C[C@H](c2c(-c3ccc(F)cc3)[nH]c3c(F)cc(F)cc32)C1] 365 |
| 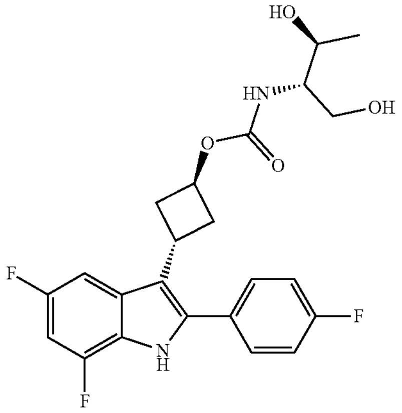 [SMILES: C[C@H](O)[C@H](CO)NC(=O)O[C@H]1C[C@H](c2c(-c3ccc(F)cc3)[nH]c3c(F)cc(F)cc32)C1] 366 |

TABLE 2-continued
Compounds 287 to 465
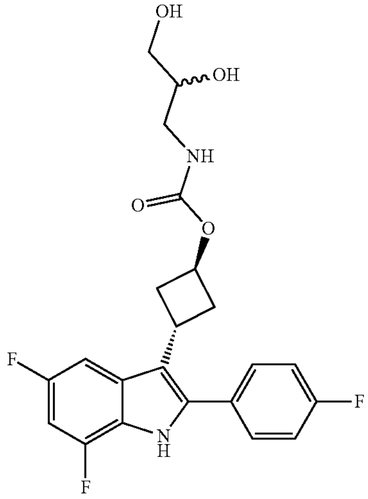 [SMILES: O=C(NCC(O)CO)O[C@H]1C[C@H](c2c(-c3ccc(F)cc3)[nH]c3c(F)cc(F)cc32)C1]
367
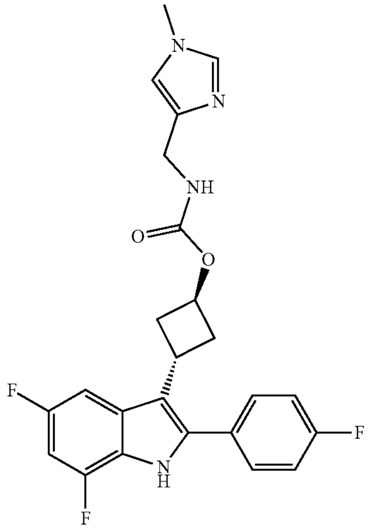 [SMILES: Cn1cnc(CNC(=O)O[C@H]2C[C@H](c3c(-c4ccc(F)cc4)[nH]c4c(F)cc(F)cc43)C2)c1]
368
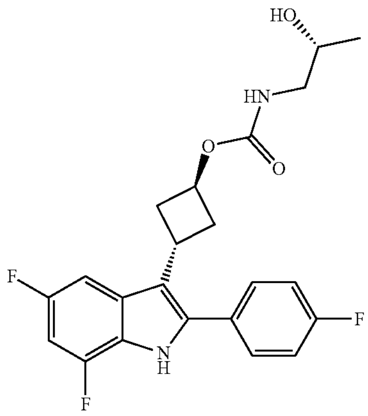 [SMILES: C[C@@H](O)CNC(=O)O[C@H]1C[C@H](c2c(-c3ccc(F)cc3)[nH]c3c(F)cc(F)cc32)C1]
369
TABLE 2-continued
Compounds 287 to 465
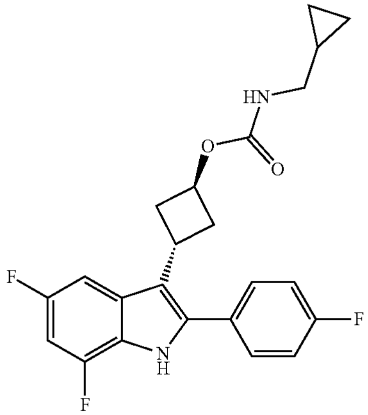 [SMILES: O=C(NCC1CC1)O[C@H]1C[C@H](c2c(-c3ccc(F)cc3)[nH]c3c(F)cc(F)cc32)C1]
370
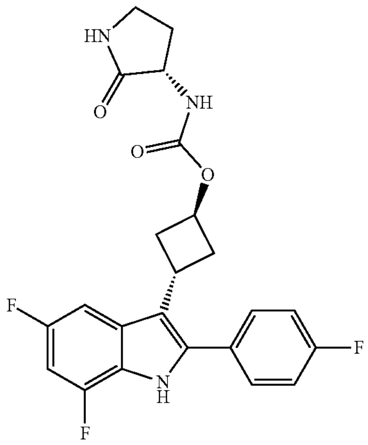 [SMILES: O=C(N[C@H]1CCNC1=O)O[C@H]1C[C@H](c2c(-c3ccc(F)cc3)[nH]c3c(F)cc(F)cc32)C1]
371
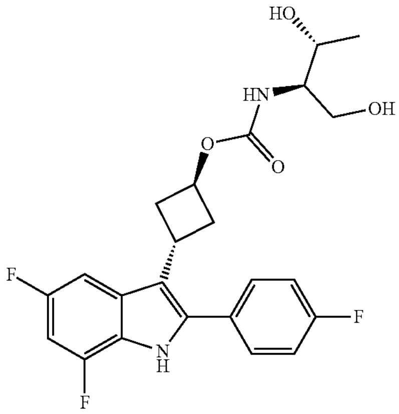 [SMILES: C[C@@H](O)[C@@H](CO)NC(=O)O[C@H]1C[C@H](c2c(-c3ccc(F)cc3)[nH]c3c(F)cc(F)cc32)C1]
372

TABLE 2-continued
Compounds 287 to 465
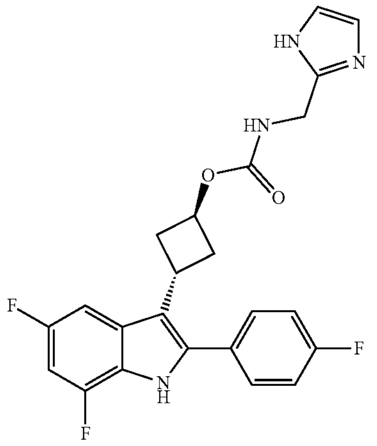 [SMILES: O=C(NCc1ncc[nH]1)O[C@H]1C[C@H](c2c(-c3ccc(F)cc3)[nH]c3c(F)cc(F)cc32)C1]
373
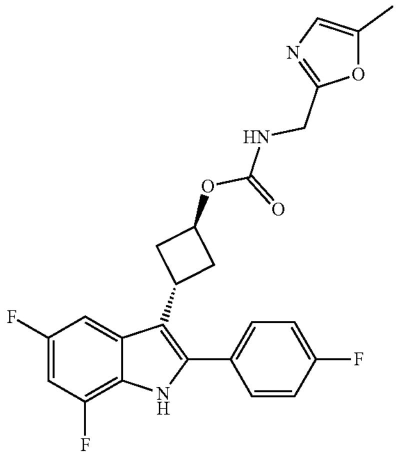 [SMILES: Cc1cnc(CNC(=O)O[C@H]2C[C@H](c3c(-c4ccc(F)cc4)[nH]c4c(F)cc(F)cc43)C2)o1]
374
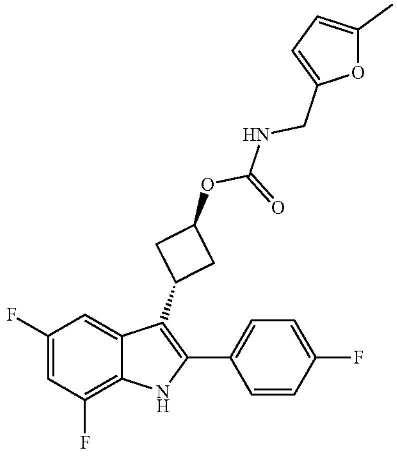 [SMILES: Cc1ccc(CNC(=O)O[C@H]2C[C@H](c3c(-c4ccc(F)cc4)[nH]c4c(F)cc(F)cc43)C2)o1]
375
TABLE 2-continued
Compounds 287 to 465
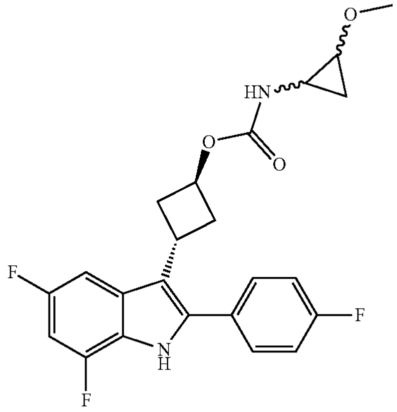 [SMILES: COC1CC1NC(=O)O[C@H]1C[C@H](c2c(-c3ccc(F)cc3)[nH]c3c(F)cc(F)cc32)C1]
376
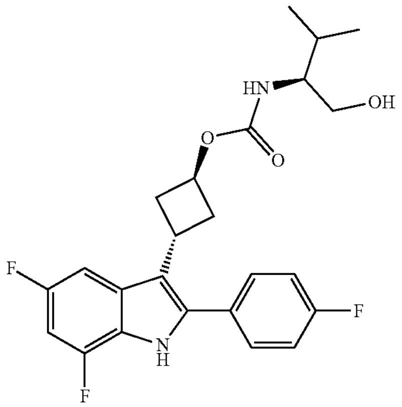 [SMILES: CC(C)[C@@H](CO)NC(=O)O[C@H]1C[C@H](c2c(-c3ccc(F)cc3)[nH]c3c(F)cc(F)cc32)C1]
377
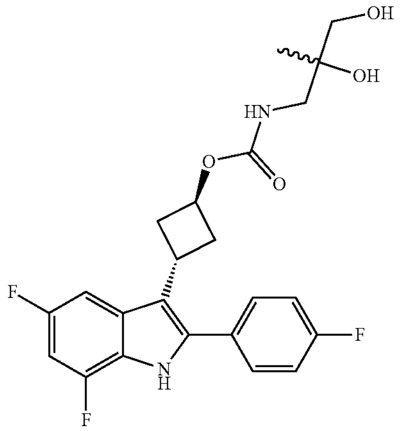 [SMILES: CC(O)(CO)CNC(=O)O[C@H]1C[C@H](c2c(-c3ccc(F)cc3)[nH]c3c(F)cc(F)cc32)C1]
378

TABLE 2-continued
Compounds 287 to 465
379
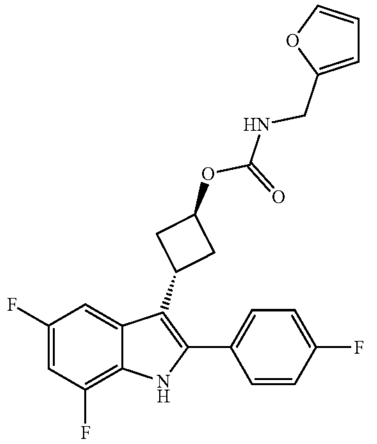 [SMILES: O=C(NCc1ccco1)O[C@H]1C[C@H](c2c(-c3ccc(F)cc3)[nH]c3c(F)cc(F)cc32)C1]
380
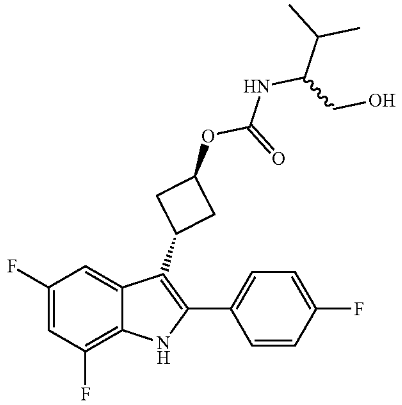 [SMILES: CC(C)C(CO)NC(=O)O[C@H]1C[C@H](c2c(-c3ccc(F)cc3)[nH]c3c(F)cc(F)cc32)C1]
381
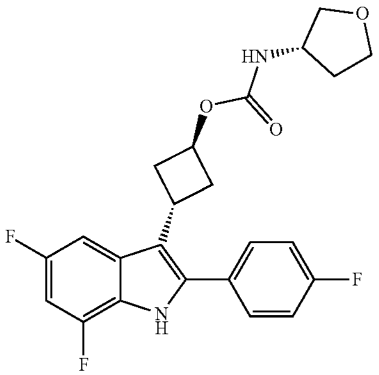 [SMILES: O=C(N[C@H]1CCOC1)O[C@H]1C[C@H](c2c(-c3ccc(F)cc3)[nH]c3c(F)cc(F)cc32)C1]
382
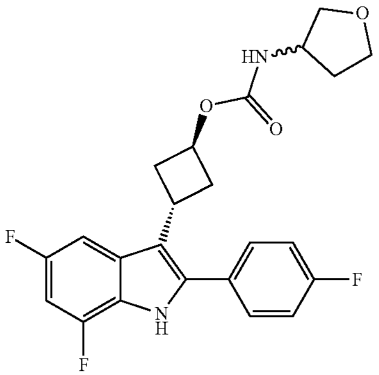 [SMILES: O=C(NC1CCOC1)O[C@H]1C[C@H](c2c(-c3ccc(F)cc3)[nH]c3c(F)cc(F)cc32)C1]
383
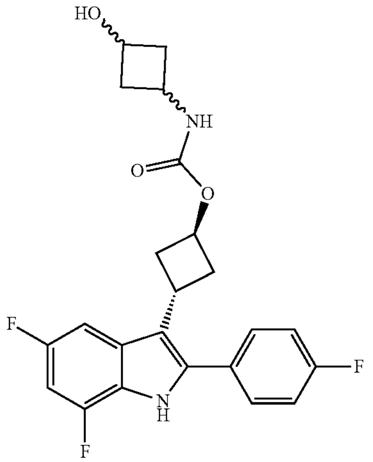 [SMILES: O=C(NC1CC(O)C1)O[C@H]1C[C@H](c2c(-c3ccc(F)cc3)[nH]c3c(F)cc(F)cc32)C1]
384
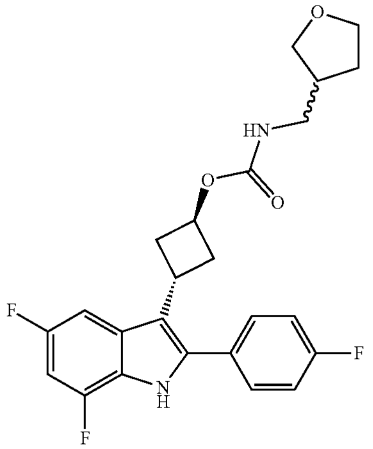 [SMILES: O=C(NCC1CCOC1)O[C@H]1C[C@H](c2c(-c3ccc(F)cc3)[nH]c3c(F)cc(F)cc32)C1]
385
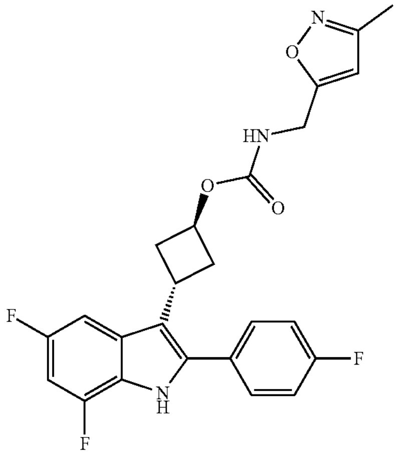 [SMILES: Cc1cc(CNC(=O)O[C@H]2C[C@H](c3c(-c4ccc(F)cc4)[nH]c4c(F)cc(F)cc43)C2)on1]

TABLE 2-continued
Compounds 287 to 465
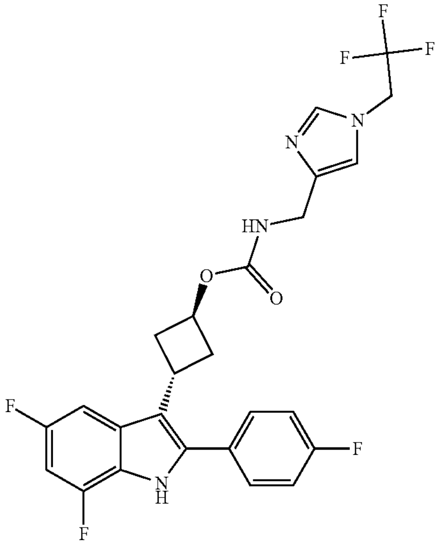 [SMILES: O=C(NCc1cn(CC(F)(F)F)cn1)O[C@H]1C[C@H](c2c(-c3ccc(F)cc3)[nH]c3c(F)cc(F)cc32)C1]
386
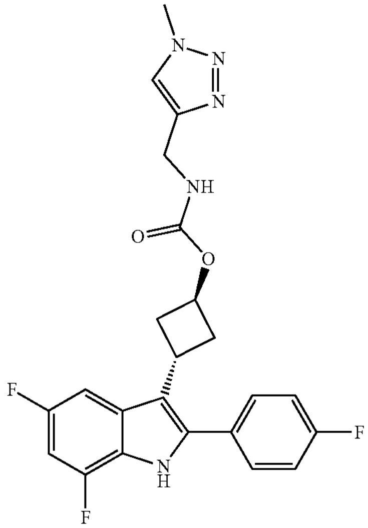 [SMILES: Cn1cc(CNC(=O)O[C@H]2C[C@H](c3c(-c4ccc(F)cc4)[nH]c4c(F)cc(F)cc43)C2)nn1]
387
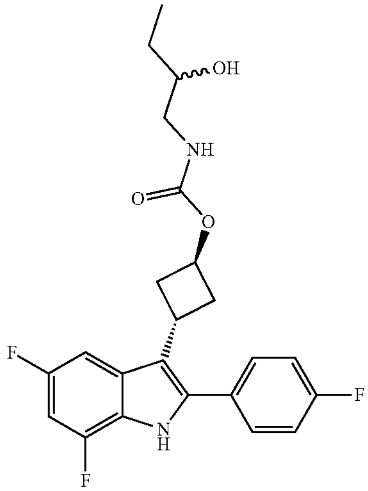 [SMILES: CCC(O)CNC(=O)O[C@H]1C[C@H](c2c(-c3ccc(F)cc3)[nH]c3c(F)cc(F)cc32)C1]
388
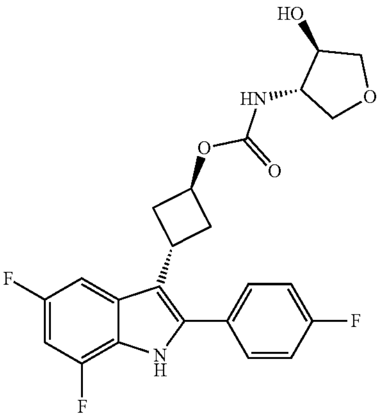 [SMILES: O=C(N[C@H]1COC[C@@H]1O)O[C@H]1C[C@H](c2c(-c3ccc(F)cc3)[nH]c3c(F)cc(F)cc32)C1]
389
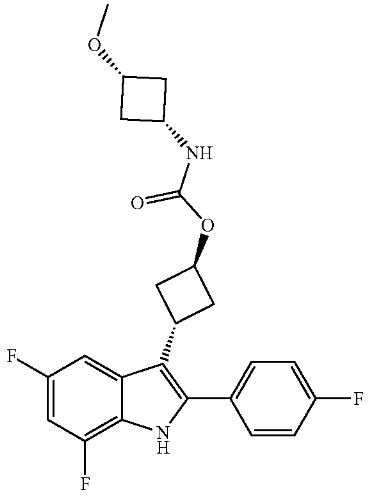 [SMILES: CO[C@H]1C[C@@H](NC(=O)O[C@H]2C[C@H](c3c(-c4ccc(F)cc4)[nH]c4c(F)cc(F)cc43)C2)C1]
390
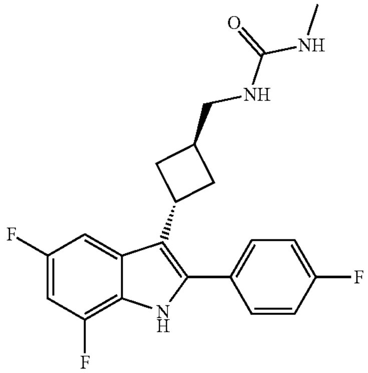 [SMILES: CNC(=O)NC[C@H]1C[C@H](c2c(-c3ccc(F)cc3)[nH]c3c(F)cc(F)cc32)C1]
391

TABLE 2-continued
| Compounds 287 to 465 |
|---|
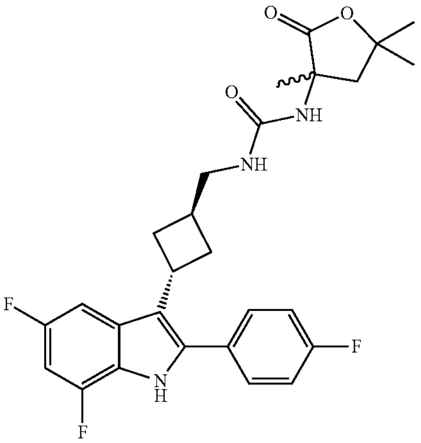 [SMILES: CC1(C)CC(C)(NC(=O)NC[C@H]2C[C@H](c3c(-c4ccc(F)cc4)[nH]c4c(F)cc(F)cc43)C2)C(=O)O1]
392
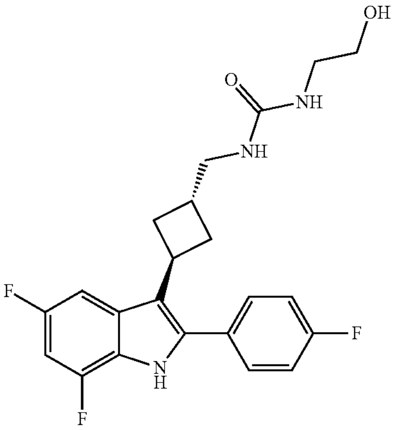 [SMILES: O=C(NCCO)NC[C@H]1C[C@H](c2c(-c3ccc(F)cc3)[nH]c3c(F)cc(F)cc32)C1]
393
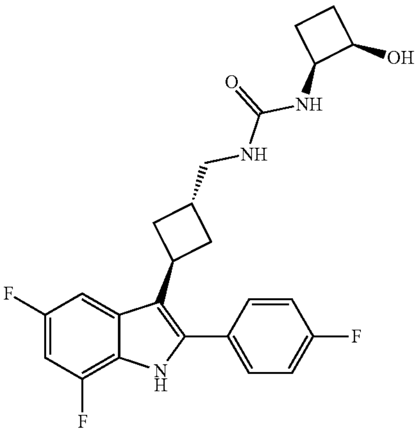 [SMILES: O=C(NC[C@H]1C[C@H](c2c(-c3ccc(F)cc3)[nH]c3c(F)cc(F)cc32)C1)N[C@H]1CC[C@H]1O]
394
TABLE 2-continued
| Compounds 287 to 465 |
|---|
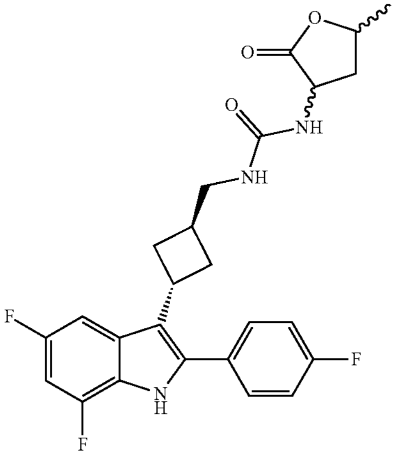 [SMILES: CC1CC(NC(=O)NC[C@H]2C[C@H](c3c(-c4ccc(F)cc4)[nH]c4c(F)cc(F)cc43)C2)C(=O)O1]
395
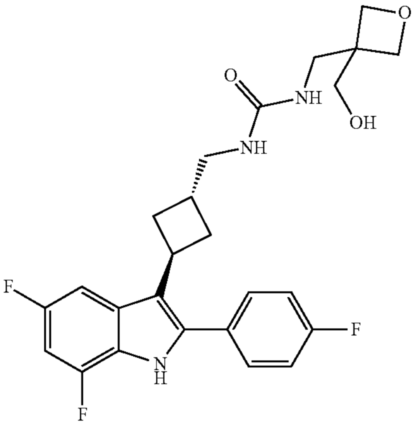 [SMILES: O=C(NCC1(CO)COC1)NC[C@H]1C[C@H](c2c(-c3ccc(F)cc3)[nH]c3c(F)cc(F)cc32)C1]
396
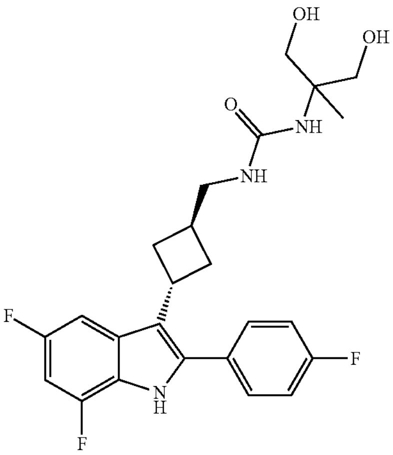 [SMILES: CC(CO)(CO)NC(=O)NC[C@H]1C[C@H](c2c(-c3ccc(F)cc3)[nH]c3c(F)cc(F)cc32)C1]
397

TABLE 2-continued
| Compounds 287 to 465 |
| --- |
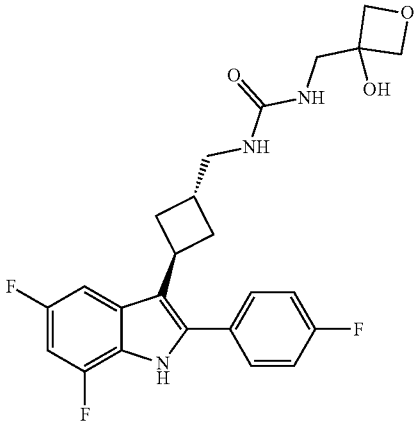 [SMILES: O=C(NCC1(O)COC1)NC[C@H]1C[C@H](c2c(-c3ccc(F)cc3)[nH]c3c(F)cc(F)cc32)C1]
398
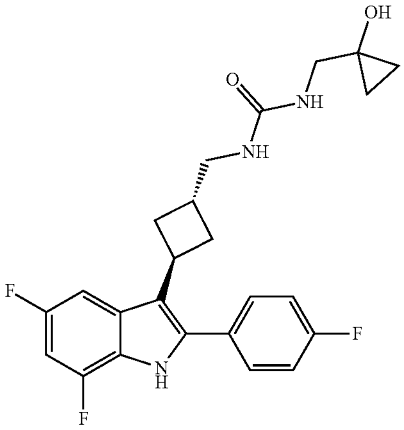 [SMILES: O=C(NCC1(O)CC1)NC[C@H]1C[C@H](c2c(-c3ccc(F)cc3)[nH]c3c(F)cc(F)cc32)C1]
399
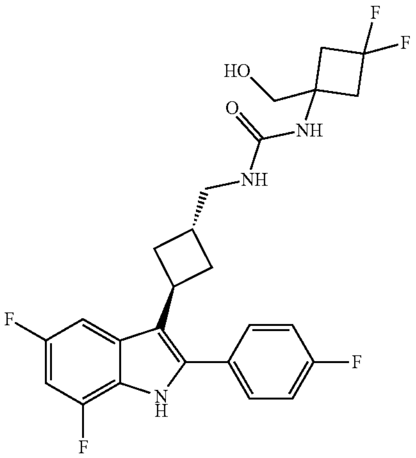 [SMILES: O=C(NC[C@H]1C[C@H](c2c(-c3ccc(F)cc3)[nH]c3c(F)cc(F)cc32)C1)NC1(CO)CC(F)(F)C1]
400
TABLE 2-continued
| Compounds 287 to 465 |
| --- |
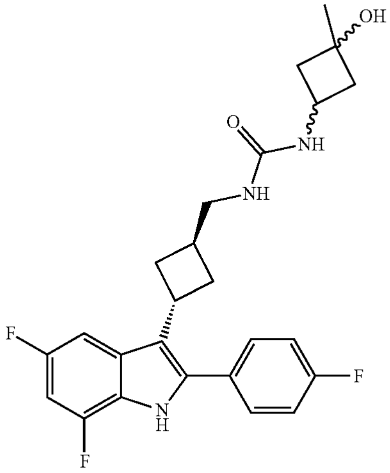 [SMILES: CC1(O)CC(NC(=O)NC[C@H]2C[C@H](c3c(-c4ccc(F)cc4)[nH]c4c(F)cc(F)cc43)C2)C1]
401
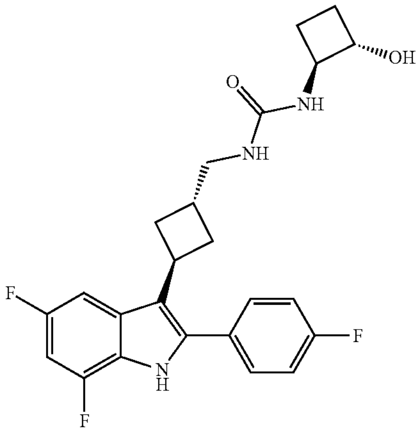 [SMILES: O=C(NC[C@H]1C[C@H](c2c(-c3ccc(F)cc3)[nH]c3c(F)cc(F)cc32)C1)N[C@H]1CC[C@@H]1O]
402
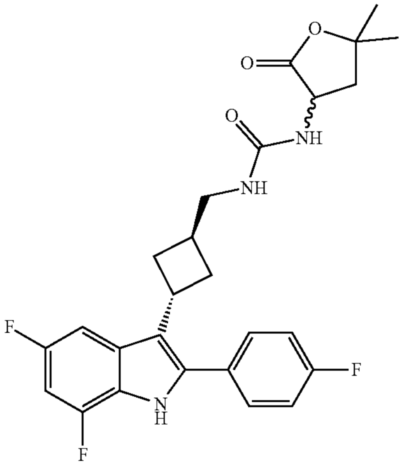 [SMILES: CC1(C)CC(NC(=O)NC[C@H]2C[C@H](c3c(-c4ccc(F)cc4)[nH]c4c(F)cc(F)cc43)C2)C(=O)O1]
403

TABLE 2-continued
Compounds 287 to 465
404
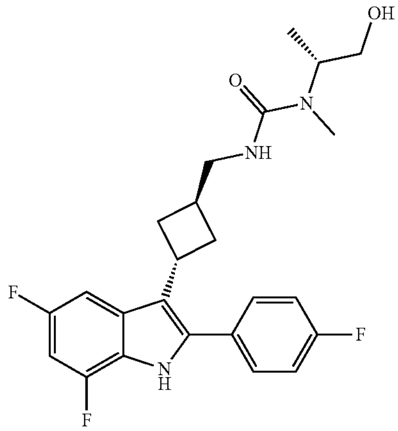 [SMILES: C[C@H](CO)N(C)C(=O)NC[C@H]1C[C@H](c2c(-c3ccc(F)cc3)[nH]c3c(F)cc(F)cc32)C1]
405
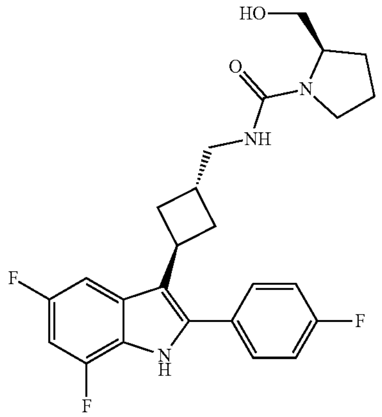 [SMILES: O=C(NC[C@H]1C[C@H](c2c(-c3ccc(F)cc3)[nH]c3c(F)cc(F)cc32)C1)N1CCC[C@@H]1CO]
406
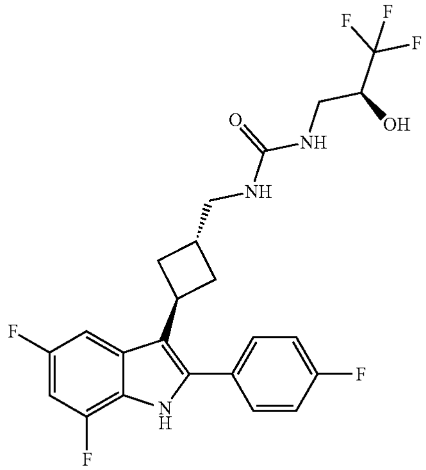 [SMILES: O=C(NC[C@H](O)C(F)(F)F)NC[C@H]1C[C@H](c2c(-c3ccc(F)cc3)[nH]c3c(F)cc(F)cc32)C1]
407
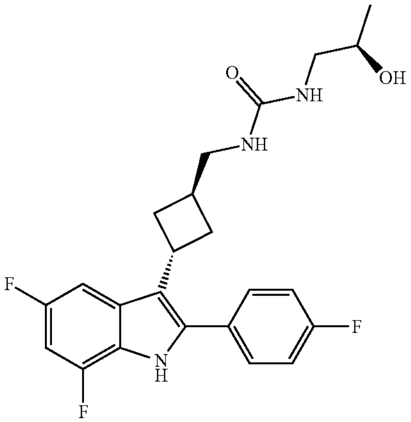 [SMILES: C[C@@H](O)CNC(=O)NC[C@H]1C[C@H](c2c(-c3ccc(F)cc3)[nH]c3c(F)cc(F)cc32)C1]
408
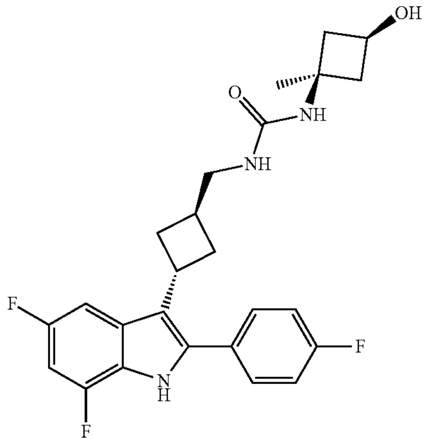 [SMILES: C[C@]1(NC(=O)NC[C@H]2C[C@H](c3c(-c4ccc(F)cc4)[nH]c4c(F)cc(F)cc43)C2)C[C@@H](O)C1]
409
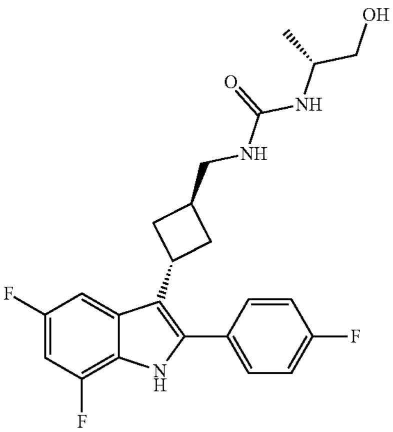 [SMILES: C[C@H](CO)NC(=O)NC[C@H]1C[C@H](c2c(-c3ccc(F)cc3)[nH]c3c(F)cc(F)cc32)C1]

TABLE 2-continued
| Compounds 287 to 465 | |
|---|---|
| 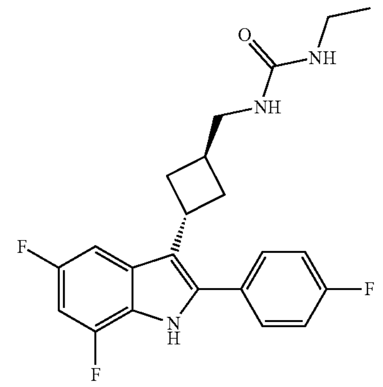 [SMILES: CCNC(=O)NC[C@H]1C[C@H](c2c(-c3ccc(F)cc3)[nH]c3c(F)cc(F)cc32)C1] | 410 |
| 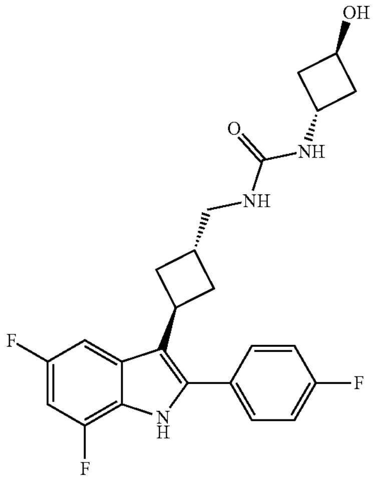 [SMILES: O=C(NC[C@H]1C[C@H](c2c(-c3ccc(F)cc3)[nH]c3c(F)cc(F)cc32)C1)N[C@H]1C[C@H](O)C1] | 411 |
| 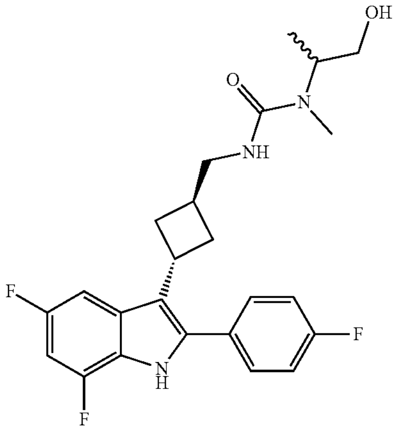 [SMILES: CC(CO)N(C)C(=O)NC[C@H]1C[C@H](c2c(-c3ccc(F)cc3)[nH]c3c(F)cc(F)cc32)C1] | 412 |
TABLE 2-continued
| Compounds 287 to 465 | |
|---|---|
| 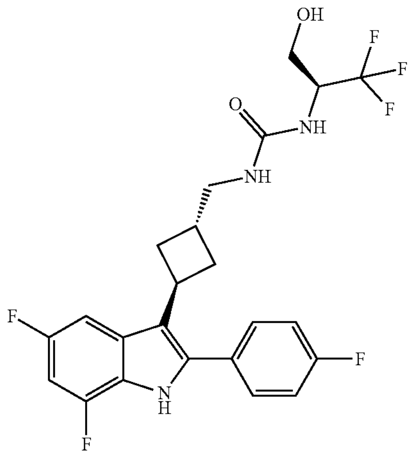 [SMILES: O=C(NC[C@H]1C[C@H](c2c(-c3ccc(F)cc3)[nH]c3c(F)cc(F)cc32)C1)N[C@@H](CO)C(F)(F)F] | 413 |
| 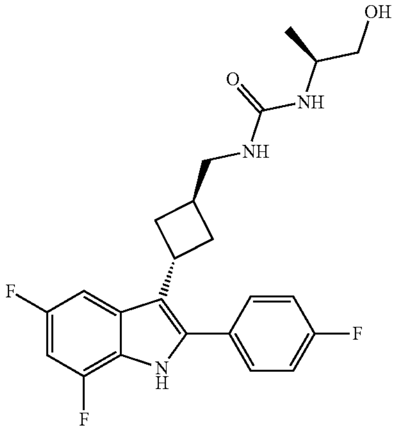 [SMILES: C[C@@H](CO)NC(=O)NC[C@H]1C[C@H](c2c(-c3ccc(F)cc3)[nH]c3c(F)cc(F)cc32)C1] | 414 |
| 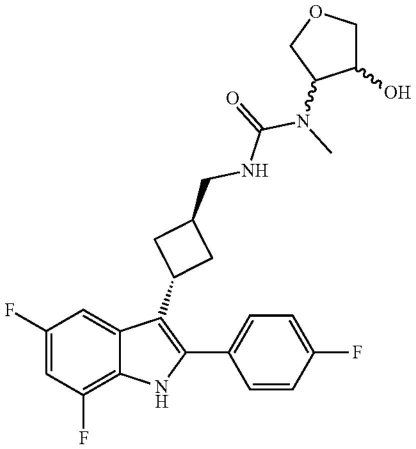 [SMILES: CN(C(=O)NC[C@H]1C[C@H](c2c(-c3ccc(F)cc3)[nH]c3c(F)cc(F)cc32)C1)C1COCC1O] | 415 |

Compounds 287 to 465
416
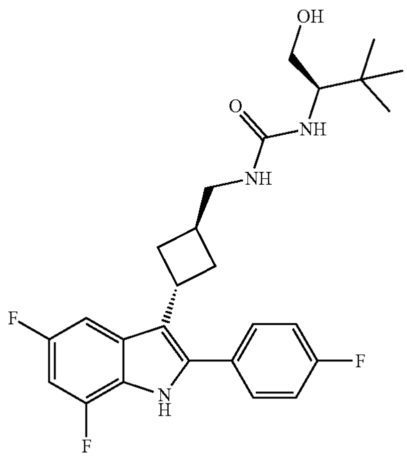 [SMILES: CC(C)(C)[C@H](CO)NC(=O)NC[C@H]1C[C@H](c2c(-c3ccc(F)cc3)[nH]c3c(F)cc(F)cc32)C1]
417
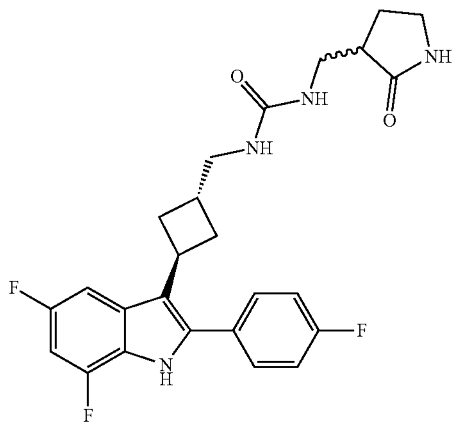 [SMILES: O=C(NCC1CCNC1=O)NC[C@H]1C[C@H](c2c(-c3ccc(F)cc3)[nH]c3c(F)cc(F)cc32)C1]
418
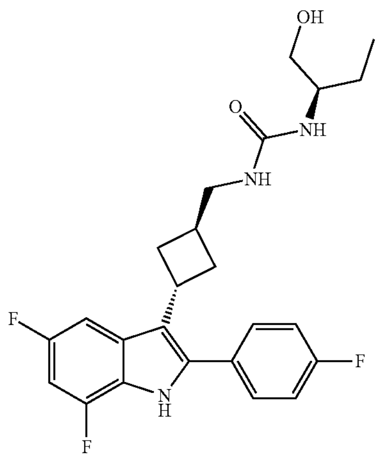 [SMILES: CC[C@H](CO)NC(=O)NC[C@H]1C[C@H](c2c(-c3ccc(F)cc3)[nH]c3c(F)cc(F)cc32)C1]
Compounds 287 to 465
419
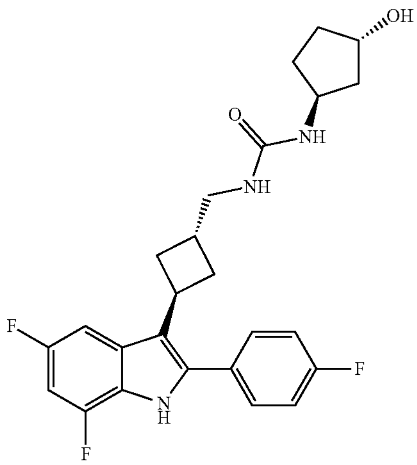 [SMILES: O=C(NC[C@H]1C[C@H](c2c(-c3ccc(F)cc3)[nH]c3c(F)cc(F)cc32)C1)N[C@H]1CC[C@H](O)C1]
420
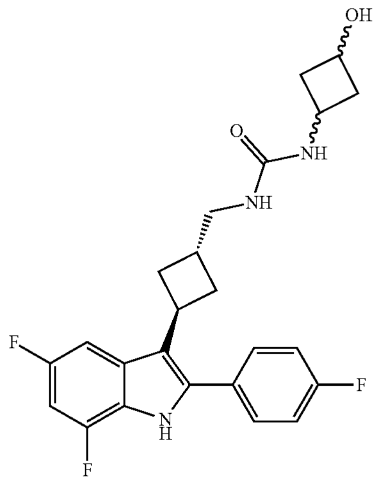 [SMILES: O=C(NC[C@H]1C[C@H](c2c(-c3ccc(F)cc3)[nH]c3c(F)cc(F)cc32)C1)NC1CC(O)C1]
421
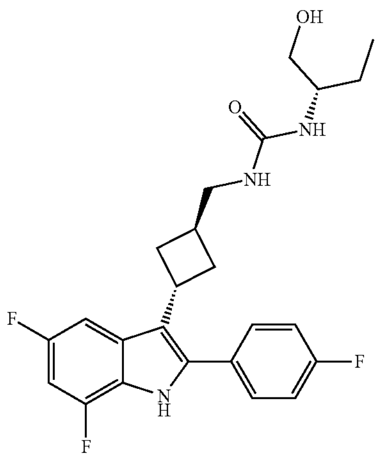 [SMILES: CC[C@@H](CO)NC(=O)NC[C@H]1C[C@H](c2c(-c3ccc(F)cc3)[nH]c3c(F)cc(F)cc32)C1]

TABLE 2-continued
Compounds 287 to 465
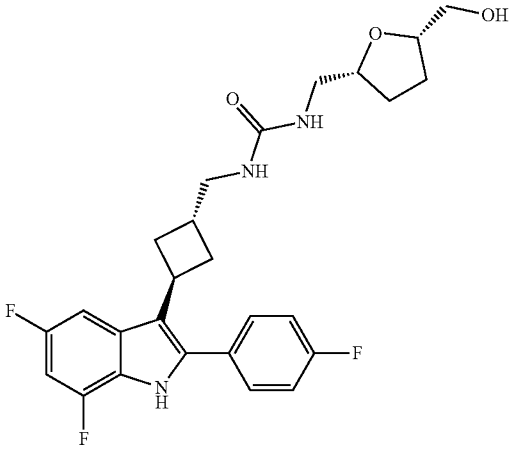 [SMILES: O=C(NC[C@H]1CC[C@@H](CO)O1)NC[C@H]1C[C@H](c2c(-c3ccc(F)cc3)[nH]c3c(F)cc(F)cc32)C1]
422
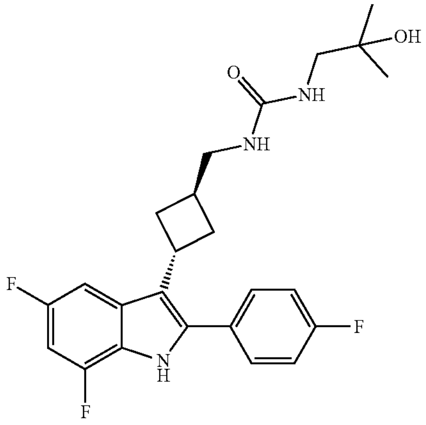 [SMILES: CC(C)(O)CNC(=O)NC[C@H]1C[C@H](c2c(-c3ccc(F)cc3)[nH]c3c(F)cc(F)cc32)C1]
423
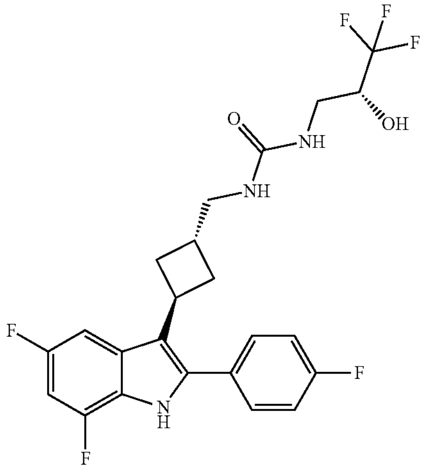 [SMILES: O=C(NC[C@@H](O)C(F)(F)F)NC[C@H]1C[C@H](c2c(-c3ccc(F)cc3)[nH]c3c(F)cc(F)cc32)C1]
424
TABLE 2-continued
Compounds 287 to 465
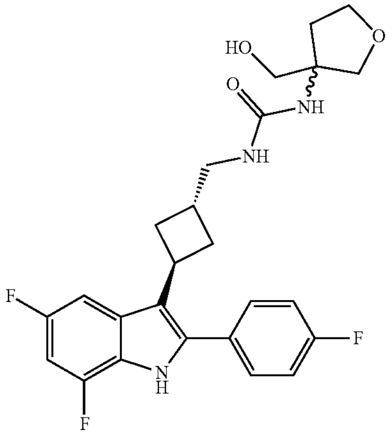 [SMILES: O=C(NC[C@H]1C[C@H](c2c(-c3ccc(F)cc3)[nH]c3c(F)cc(F)cc32)C1)NC1(CO)CCOC1]
425
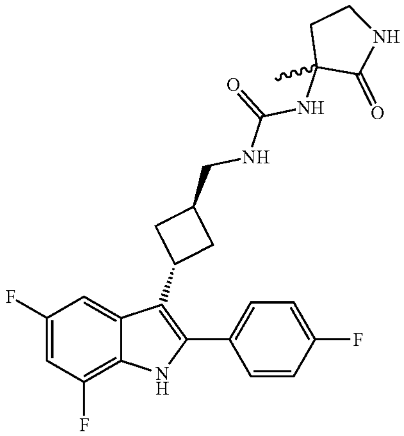 [SMILES: CC1(NC(=O)NC[C@H]2C[C@H](c3c(-c4ccc(F)cc4)[nH]c4c(F)cc(F)cc43)C2)CCNC1=O]
426
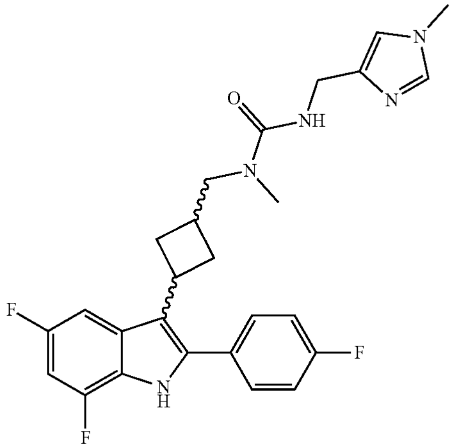 [SMILES: CN(CC1CC(c2c(-c3ccc(F)cc3)[nH]c3c(F)cc(F)cc23)C1)C(=O)NCc1cn(C)cn1]
427

TABLE 2-continued
Compounds 287 to 465
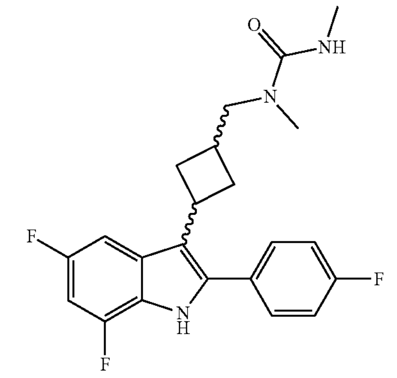 [SMILES: CNC(=O)N(C)CC1CC(c2c(-c3ccc(F)cc3)[nH]c3c(F)cc(F)cc23)C1]
428
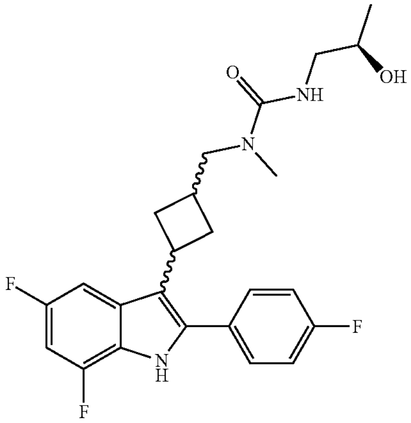 [SMILES: C[C@@H](O)CNC(=O)N(C)CC1CC(c2c(-c3ccc(F)cc3)[nH]c3c(F)cc(F)cc23)C1]
429
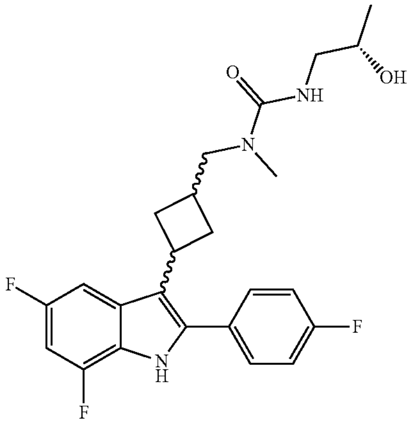 [SMILES: C[C@H](O)CNC(=O)N(C)CC1CC(c2c(-c3ccc(F)cc3)[nH]c3c(F)cc(F)cc23)C1]
430
TABLE 2-continued
Compounds 287 to 465
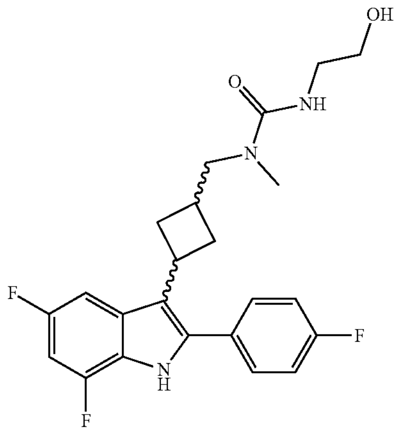 [SMILES: CN(CC1CC(c2c(-c3ccc(F)cc3)[nH]c3c(F)cc(F)cc23)C1)C(=O)NCCO]
431
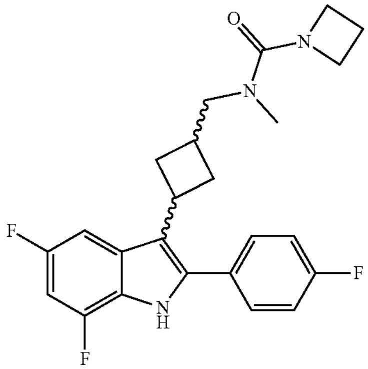 [SMILES: CN(CC1CC(c2c(-c3ccc(F)cc3)[nH]c3c(F)cc(F)cc23)C1)C(=O)N1CCC1]
432
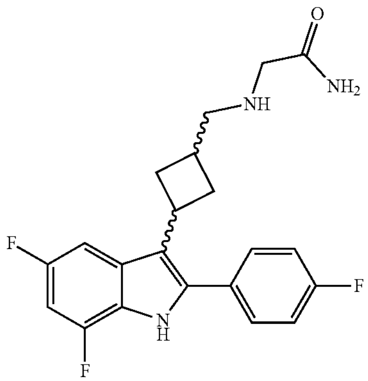 [SMILES: NC(=O)CNCC1CC(c2c(-c3ccc(F)cc3)[nH]c3c(F)cc(F)cc23)C1]
433
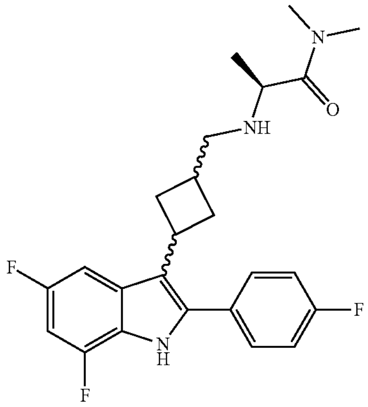 [SMILES: C[C@H](NCC1CC(c2c(-c3ccc(F)cc3)[nH]c3c(F)cc(F)cc23)C1)C(=O)N(C)C]
434

TABLE 2-continued
| Compounds 287 to 465 |
| --- |
435
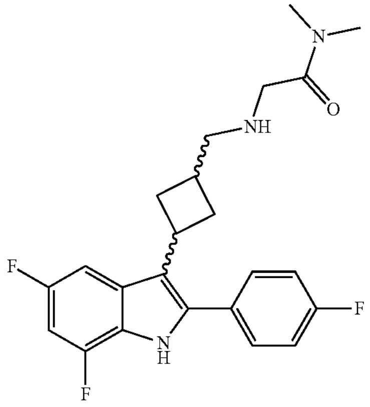 [SMILES: CN(C)C(=O)CNCC1CC(c2c(-c3ccc(F)cc3)[nH]c3c(F)cc(F)cc23)C1]
436
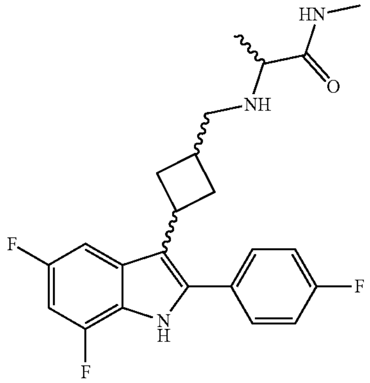 [SMILES: CNC(=O)C(C)NCC1CC(c2c(-c3ccc(F)cc3)[nH]c3c(F)cc(F)cc23)C1]
437
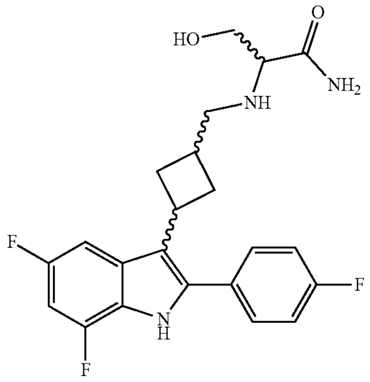 [SMILES: NC(=O)C(CO)NCC1CC(c2c(-c3ccc(F)cc3)[nH]c3c(F)cc(F)cc23)C1]
438
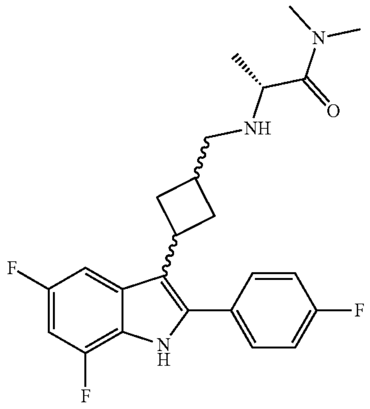 [SMILES: C[C@@H](NCC1CC(c2c(-c3ccc(F)cc3)[nH]c3c(F)cc(F)cc23)C1)C(=O)N(C)C]
TABLE 2-continued
| Compounds 287 to 465 |
| --- |
439
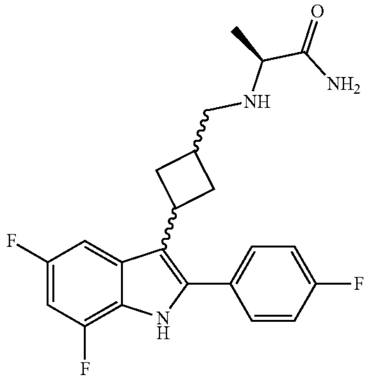 [SMILES: C[C@H](NCC1CC(c2c(-c3ccc(F)cc3)[nH]c3c(F)cc(F)cc23)C1)C(N)=O]
440
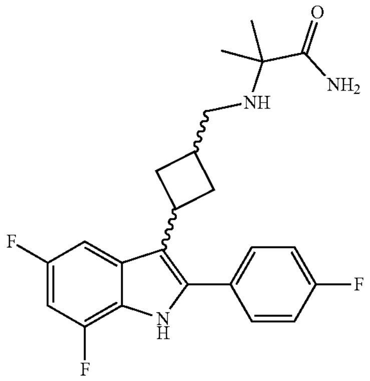 [SMILES: CC(C)(NCC1CC(c2c(-c3ccc(F)cc3)[nH]c3c(F)cc(F)cc23)C1)C(N)=O]
441
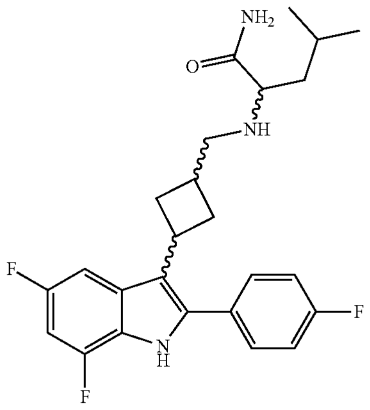 [SMILES: CC(C)CC(NCC1CC(c2c(-c3ccc(F)cc3)[nH]c3c(F)cc(F)cc23)C1)C(N)=O]

TABLE 2-continued
| Compounds 287 to 465 |
|---|
442
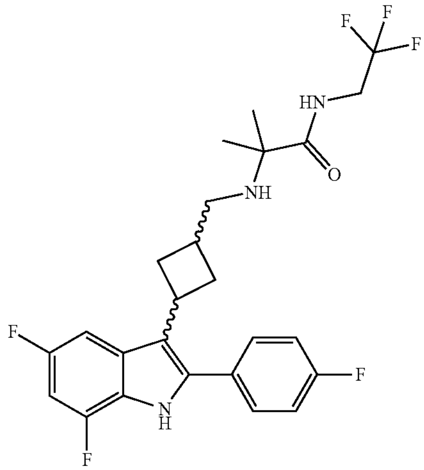 [SMILES: CC(C)(NCC1CC(c2c(-c3ccc(F)cc3)[nH]c3c(F)cc(F)cc23)C1)C(=O)NCC(F)(F)F]
443
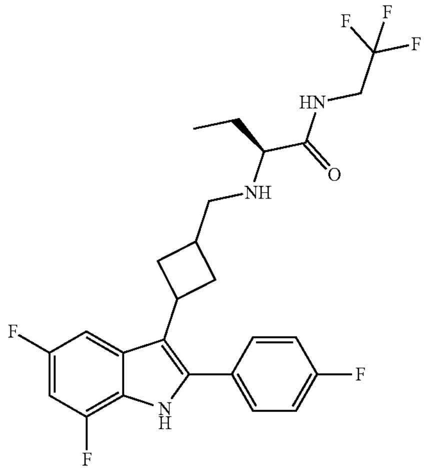 [SMILES: CC[C@H](NCC1CC(c2c(-c3ccc(F)cc3)[nH]c3c(F)cc(F)cc23)C1)C(=O)NCC(F)(F)F]
444
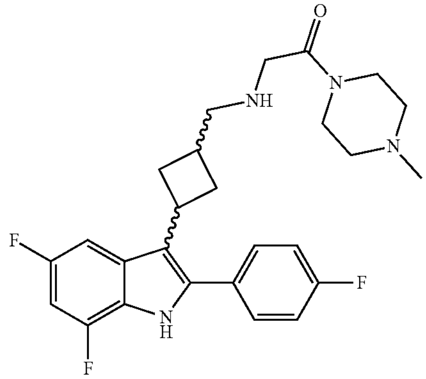 [SMILES: CN1CCN(C(=O)CNCC2CC(c3c(-c4ccc(F)cc4)[nH]c4c(F)cc(F)cc34)C2)CC1]
TABLE 2-continued
| Compounds 287 to 465 |
|---|
445
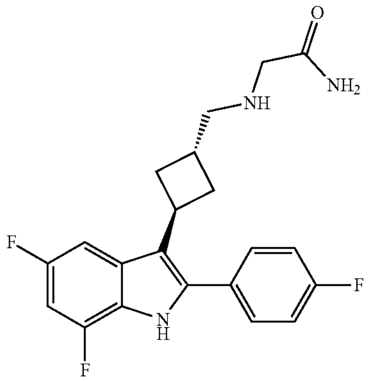 [SMILES: NC(=O)CNC[C@H]1C[C@H](c2c(-c3ccc(F)cc3)[nH]c3c(F)cc(F)cc32)C1]
446
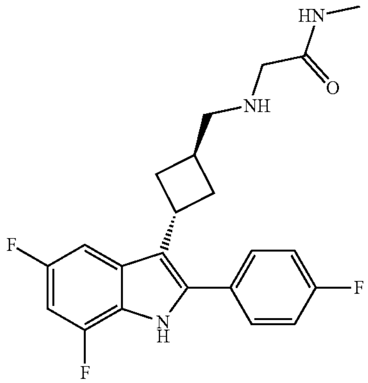 [SMILES: CNC(=O)CNC[C@H]1C[C@H](c2c(-c3ccc(F)cc3)[nH]c3c(F)cc(F)cc32)C1]
447
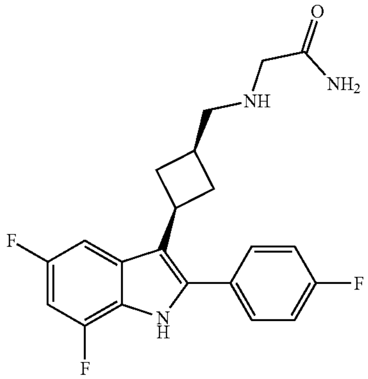 [SMILES: NC(=O)CNC[C@H]1C[C@@H](c2c(-c3ccc(F)cc3)[nH]c3c(F)cc(F)cc32)C1]
448
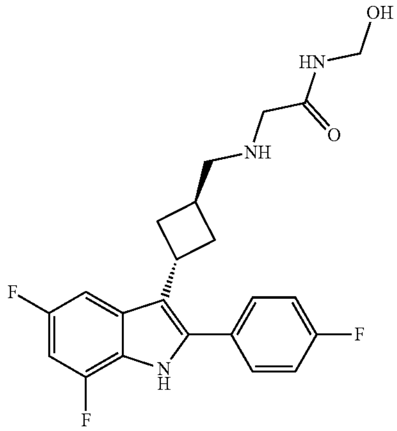 [SMILES: O=C(CNC[C@H]1C[C@H](c2c(-c3ccc(F)cc3)[nH]c3c(F)cc(F)cc32)C1)NCO]

TABLE 2-continued
Compounds 287 to 465
449
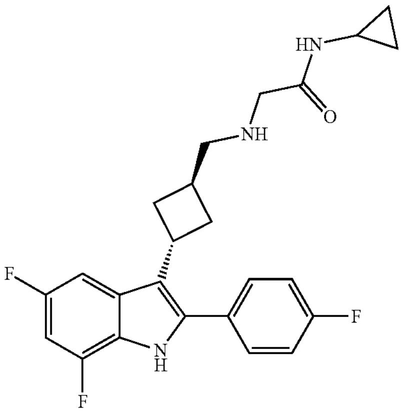 [SMILES: O=C(CNC[C@H]1C[C@H](c2c(-c3ccc(F)cc3)[nH]c3c(F)cc(F)cc32)C1)NC1CC1]
450
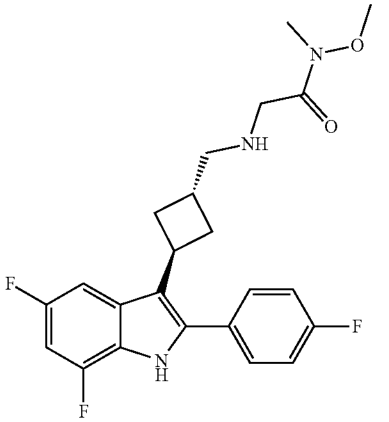 [SMILES: CON(C)C(=O)CNC[C@H]1C[C@H](c2c(-c3ccc(F)cc3)[nH]c3c(F)cc(F)cc32)C1]
451
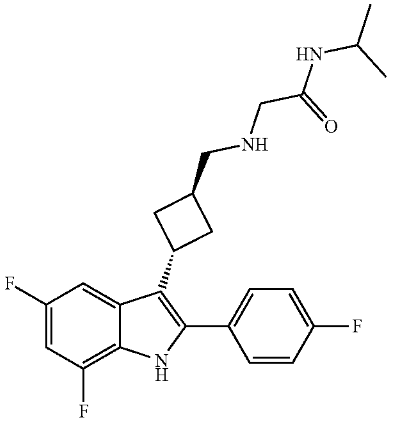 [SMILES: CC(C)NC(=O)CNC[C@H]1C[C@H](c2c(-c3ccc(F)cc3)[nH]c3c(F)cc(F)cc32)C1]
452
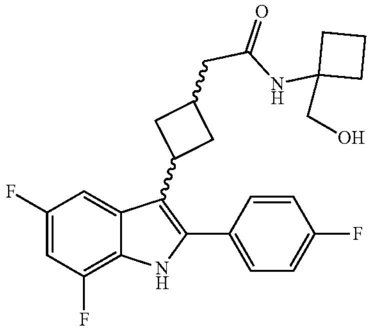 [SMILES: O=C(CC1CC(c2c(-c3ccc(F)cc3)[nH]c3c(F)cc(F)cc23)C1)NC1(CO)CCC1]
TABLE 2-continued
Compounds 287 to 465
453
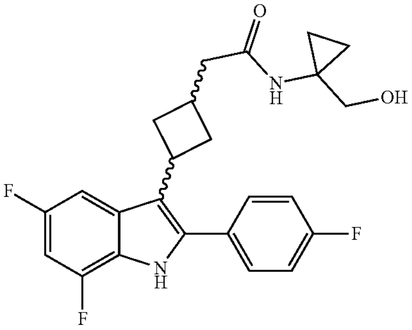 [SMILES: O=C(CC1CC(c2c(-c3ccc(F)cc3)[nH]c3c(F)cc(F)cc23)C1)NC1(CO)CC1]
454
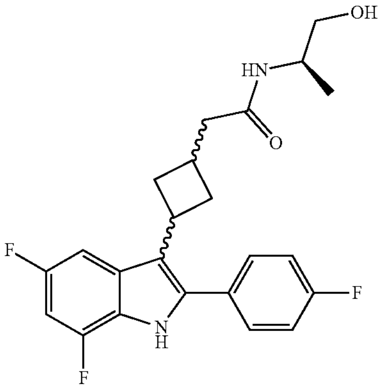 [SMILES: C[C@H](CO)NC(=O)CC1CC(c2c(-c3ccc(F)cc3)[nH]c3c(F)cc(F)cc23)C1]
455
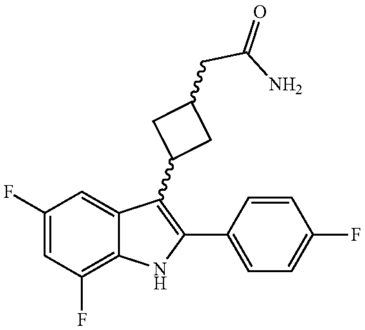 [SMILES: NC(=O)CC1CC(c2c(-c3ccc(F)cc3)[nH]c3c(F)cc(F)cc23)C1]
456
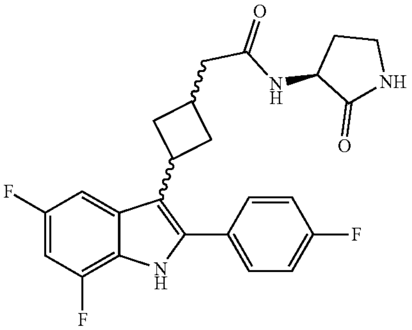 [SMILES: O=C(CC1CC(c2c(-c3ccc(F)cc3)[nH]c3c(F)cc(F)cc23)C1)N[C@H]1CCNC1=O]

TABLE 2-continued
| Compounds 287 to 465 |
| --- |
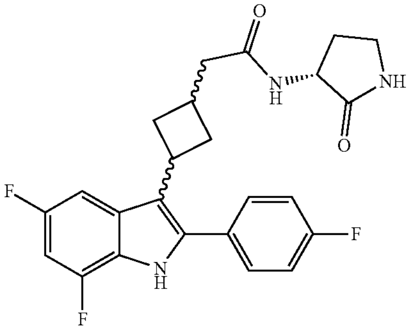 [SMILES: O=C(CC1CC(c2c(-c3ccc(F)cc3)[nH]c3c(F)cc(F)cc23)C1)N[C@@H]1CCNC1=O]
457
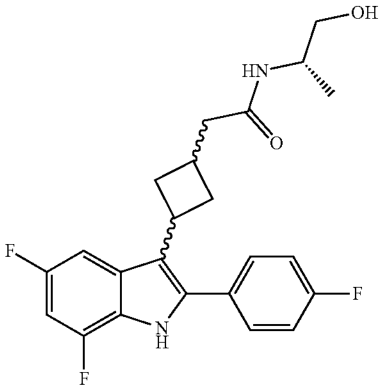 [SMILES: C[C@@H](CO)NC(=O)CC1CC(c2c(-c3ccc(F)cc3)[nH]c3c(F)cc(F)cc23)C1]
458
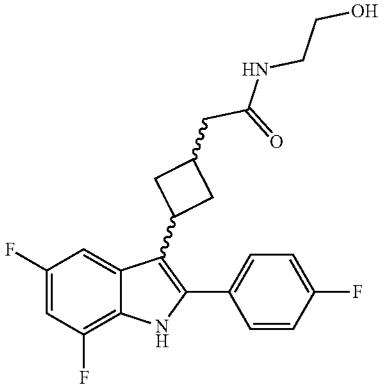 [SMILES: O=C(CC1CC(c2c(-c3ccc(F)cc3)[nH]c3c(F)cc(F)cc23)C1)NCCO]
459
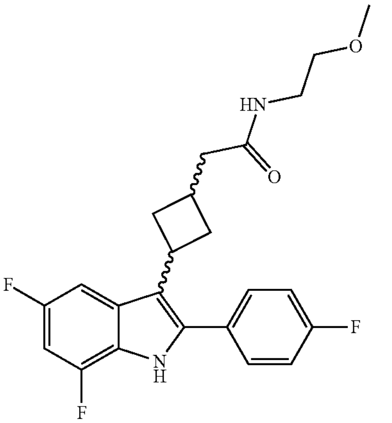 [SMILES: COCCNC(=O)CC1CC(c2c(-c3ccc(F)cc3)[nH]c3c(F)cc(F)cc23)C1]
460
TABLE 2-continued
| Compounds 287 to 465 |
| --- |
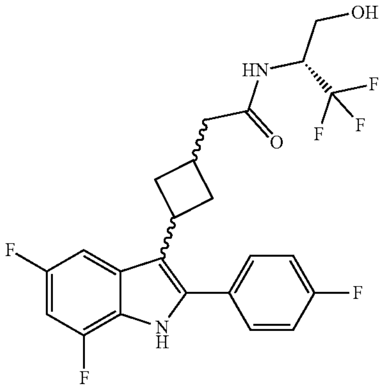 [SMILES: O=C(CC1CC(c2c(-c3ccc(F)cc3)[nH]c3c(F)cc(F)cc23)C1)N[C@H](CO)C(F)(F)F]
461
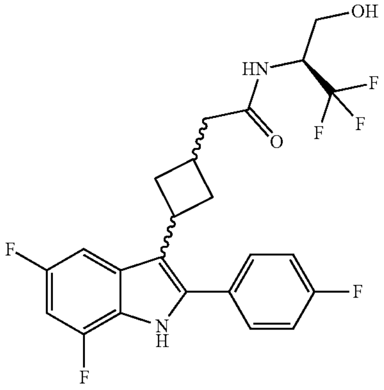 [SMILES: O=C(CC1CC(c2c(-c3ccc(F)cc3)[nH]c3c(F)cc(F)cc23)C1)N[C@@H](CO)C(F)(F)F]
462
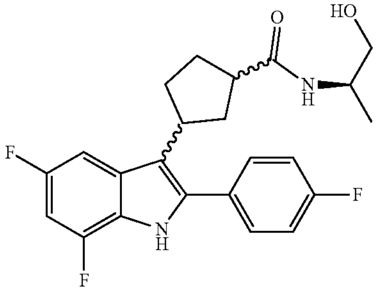 [SMILES: C[C@H](CO)NC(=O)C1CCC(c2c(-c3ccc(F)cc3)[nH]c3c(F)cc(F)cc23)C1]
463
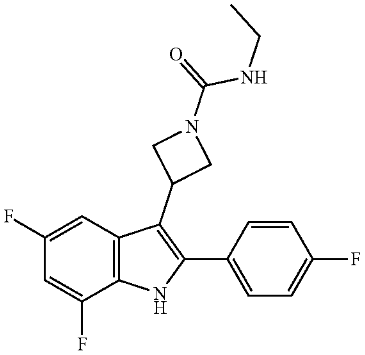 [SMILES: CCNC(=O)N1CC(c2c(-c3ccc(F)cc3)[nH]c3c(F)cc(F)cc23)C1]
464

TABLE 2-continued

| Compounds 287 to 465 |
|---|
| 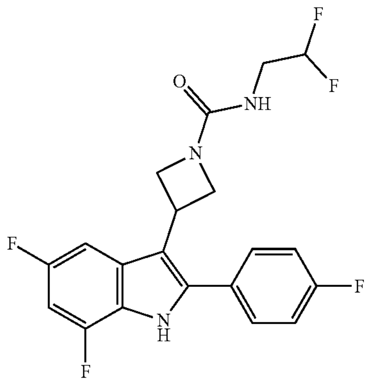 [SMILES: O=C(NCC(F)F)N1CC(c2c(-c3ccc(F)cc3)[nH]c3c(F)cc(F)cc23)C1] 465 |

Another aspect of the disclosure provides pharmaceutical compositions comprising at least one compound according to any one formula chosen from Formulae (I), (Ia), (II), (IIIa), (IIIb), (IV), (Va), and (Vb), Compounds 1 to 286 (Table 1) and Compounds 287 to 465 (Table 2), pharmaceutically acceptable salts of any of those compounds, solvates of any of the foregoing, and deuterated derivatives of any of the foregoing. In some embodiments, the pharmaceutical composition comprising at least one compound chosen from Formulae (I), (Ia), (II), (IIIa), (IIIb), (IV) (Va), and (Vb), Compounds 1 to 286 and Compounds 287 to 465, pharmaceutically acceptable salts of any of those compounds, solvates of any of the foregoing, and deuterated derivatives of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one additional active therapeutic agent. Alternatively, a pharmaceutical composition comprising at least one compound chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing can be administered as a separate composition concurrently with, prior to, or subsequent to, a composition comprising at least one other active therapeutic agent. In some embodiments, a pharmaceutical composition comprising at least one compound chosen from Compounds 1 to 286 (Table 1) and Compounds 287 to 465 (Table 2), pharmaceutically acceptable salts of any of those compounds, solvates of any of the foregoing, and deuterated derivatives of any of the foregoing can be administered as a separate composition concurrently with, prior to, or subsequent to, a composition comprising at least one other active therapeutic agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: The Science and Practice of Pharmacy, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In some embodiments of the disclosure, the compounds and the pharmaceutical compositions described herein are used to treat APOL1 mediated kidney disease. In some embodiments, the APOL1 mediated kidney disease is chosen from ESKD, FSGS, HIV-associated nephropathy, NDKD, arterionephrosclerosis, lupus nephritis, microalbuminuria, and chronic kidney disease. In some embodiments, the APOL1 mediated kidney disease treated with the compound, deuterated derivative, pharmaceutically acceptable salt, and/or composition of the invention is FSGS. In some embodiments, the APOL1 mediated kidney disease treated with the compound, deuterated derivative, pharmaceutically acceptable salt, and/or composition of the invention is NDKD. In some embodiments, the APOL1 mediated kidney disease treated with the compound, deuterated derivative, and pharmaceutically acceptable salt and/or composition of the invention is ESKD. In some embodiments, the patient with APOL1 mediated kidney disease to be treated with the compound, deuterated derivative, pharmaceutically acceptable salt, and/or composition of the invention has two APOL1 risk alleles. In some embodiments, the patient with APOL1 mediated kidney disease is homozygous for APOL1 genetic risk alleles G1: S342G:I384M. In some embodiments, the patient with APOL1 mediated kidney disease is homozygous for APOL1 genetic risk alleles G2: N388del: Y389del. In some embodiments, the patient with APOL1 mediated kidney disease is heterozygous for APOL1 genetic risk alleles G1: S342G:I384M and G2: N388de:Y389del.

In some embodiments, the methods of the disclosure comprise administering to a patient in need thereof at least one entity chosen from compounds of Formulae (I), (Ia), (II), (IIIa), (IIIb), (IV), (Va), and (Vb), pharmaceutically acceptable salts of any of those compounds, solvates of any of the foregoing, and deuterated derivatives of any of the foregoing. In some embodiments, the compound of Formula I is chosen from Compounds 1 to 286 (Table 1) and Compounds 287 to 465 (Table 2), pharmaceutically acceptable salts of any of those compounds, solvates of any of the foregoing, and deuterated derivatives of any of the foregoing. In some embodiments, said patient in need thereof possesses APOL1 genetic variants, i.e., G1: S342G:I384M and G2: N388del:Y389del.

Another aspect of the disclosure provides methods of inhibiting APOL1 activity comprising contacting said APOL1 with at least one entity chosen from compounds of Formulae (I), (Ia), (II), (IIIa), (IIIb), (IVa), (Va), and (Vb), pharmaceutically acceptable salts of any of those compounds, solvates of any of the foregoing, and deuterated derivatives of any of the foregoing. In some embodiments, the methods of inhibiting APOL1 activity comprise contacting said APOL1 with at least one entity chosen from Compounds 1 to 286 (Table 1) and Compounds 287 to 465 (Table 2), pharmaceutically acceptable salts of any of those compounds, solvates of any of the foregoing, and deuterated derivatives of any of the foregoing.

Non-Limiting Exemplary Embodiments

1. A compound chosen from compounds of Formula (I):

(I)

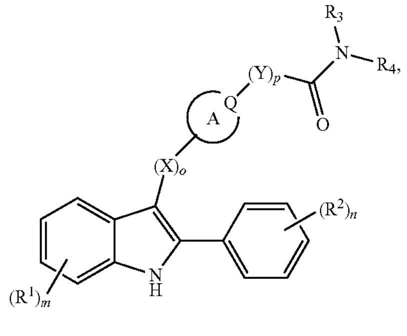

pharmaceutically acceptable salts thereof, solvates of any of the foregoing, and deuterated derivatives of any of the foregoing, wherein:

(i) Ring A is a 3- to 7-membered ring, wherein the ring is a cyclic alkyl or a heterocycle;

(ii) Q is N or $CR^5$;

(iii) each $R_1$ is independently chosen from
halogen groups,
hydroxy,
thiol,
amino,
cyano,
—$OC(O)C_1$-$C_6$ linear, branched, and cyclic alkyl groups,
—$C(O)OC_1$-$C_6$ linear, branched, and cyclic alkyl groups,
—$NHC(O)C_1$-$C_6$ linear, branched, and cyclic alkyl groups,
—$C(O)NHC_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—$NHS(O)_2C_1$-$C_6$ linear, branched, and cyclic alkyl groups,
—$S(O)_2NHC_1$-$C_6$ linear, branched, and cyclic alkyl groups,
—$NHS(O)_2$aryl groups,
—$S(O)_2$NHaryl groups,
—$NHS(O)_2$heteroaryl groups,
—$S(O)_2$NHheteroaryl groups,
—$NHC(O)NHC_1$-$C_6$ linear, branched, and cyclic alkyl groups,
—NHC(O)NHaryl groups,
—NHC(O)NHheteroaryl groups,
$C_1$-$C_6$ linear, branched, and cyclic alkyl groups,
$C_2$-$C_6$ linear, branched, and cyclic alkenyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3- to 6-membered heterocycloalkenyl groups,
3- to 6-membered heterocycloalkyl groups, and
5- and 6-membered heteroaryl groups; or two $R_1$ groups, together with the carbon atoms to which they are attached, form a $C_4$-$C_8$ cycloalkyl group, an aryl group, or a heteroaryl group;

(iv) each $R_2$ is independently chosen from
halogen groups,
hydroxy,
thiol,
amino,
cyano,
—$NHC(O)C_1$-$C_6$ linear, branched, and cyclic alkyl groups,
—$C(O)NHC_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—$NHS(O)_2C_1$-$C_6$ linear, branched, and cyclic alkyl groups,
—$S(O)_2NHC_1$-$C_6$ linear, branched, and cyclic alkyl groups,
—$NHS(O)_2$aryl groups,
—$S(O)_2$NHaryl groups,
—$NHS(O)_2$heteroaryl groups,
—$S(O)_2$NHheteroaryl groups,
—$NHC(O)NHC_1$-$C_4$ linear, branched, and cyclic alkyl groups, —NHC(O)NHaryl groups, —NHC(O)NHheteroaryl groups, $C_1$-$C_4$ linear, branched, and cyclic alkyl groups, $C_2$-$C_4$ linear, branched, and cyclic alkenyl groups, $C_1$-$C_4$ linear, branched, and cyclic hydroxyalkyl groups, $C_1$-$C_4$ linear, branched, and cyclic alkoxy groups, $C_1$-$C_4$ linear, branched, and cyclic thioalkyl groups, $C_1$-$C_4$ linear, branched, and cyclic haloalkyl groups, $C_1$-$C_4$ linear, branched, and cyclic haloaminoalkyl groups, $C_1$-$C_4$ linear, branched, and cyclic halothioalkyl groups, and $C_1$-$C_4$ linear, branched, and cyclic haloalkoxy groups;

(v) m is chosen from 0, 1, 2, 3, and 4;

(vi) n is chosen from 0, 1, 2, 3, 4, and 5;

(vii) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with one to four groups independently chosen from:

$C_1$-$C_6$ alkyl groups, aryl groups, heteroaryl groups, halogen groups, hydroxy, and amino;

(viii) Y is chosen from divalent amino, divalent oxygen, divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with one to three groups independently chosen from $C_1$-$C_6$ alkyl groups optionally substituted with hydroxy, $C_3$-$C_6$ cyclic alkyl, aryl groups, heteroaryl groups, halogen groups, hydroxy, and amino, or wherein the divalent alkyl groups, divalent alkoxy groups, divalent aminoalkyl groups, and divalent thioalkyl groups are optionally fused to a $C_3$-$C_6$ cyclic alkyl;

(ix) o is chosen from 0, 1, 2, 3, and 4;

(x) p is chosen from 0, 1, 2, 3, and 4;

(xi) $R_3$ and $R_4$ are independently chosen from:

hydrogen, $C_1$-$C_6$ linear and branched alkylsulfonyl groups, $C_1$-$C_6$ linear and branched alkoxy groups optionally substituted with a $C_3$-$C_6$ cyclic alkyl group or a 3- to 6-membered heterocycle;

$C_1$-$C_6$ cyclic alkyl groups optionally substituted with one to four groups independently chosen from:

halogen groups, hydroxy, oxo, $C_1$-$C_6$ linear and branched alkoxy groups, $C_1$-$C_6$ linear and branched alkyl groups optionally substituted with one or two groups independently chosen from hydroxy and $C_1$-$C_6$ linear and branched alkoxy groups, and amido groups, heterocyclic groups optionally substituted with one to four groups independently chosen from:

halogen groups, oxo, hydroxy, and $C_1$-$C_6$ linear and branched alkyl groups optionally substituted with one or two groups independently chosen from hydroxy and $C_1$-$C_6$ linear and branched alkoxy groups, aryl groups optionally substituted with one to four groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, heteroaryl groups optionally substituted with one to four groups independently chosen from hydroxy and $C_1$-$C_6$ linear alkyl groups, and $C_1$-$C_7$ linear and branched alkyl groups, wherein the alkyl groups are optionally substituted with one to five groups independently chosen from:

amino groups, hydroxy, oxo, cyano, carboxylic acid, halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, $C_1$-$C_6$ linear and branched alkylsulfonyl groups, aryl groups optionally substituted with one or two groups independently chosen from halogen groups, hydroxy, $C_1$-$C_6$ linear and branched alkyl groups optionally substituted with one or two groups independently chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups, or $R_3$ and $R_4$, together with the nitrogen atom to which they are attached, form a 4- to 10-membered heterocyclyl group optionally substituted with one to four groups independently chosen from hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups; and (xii) $R_5$ is absent or is chosen from:

hydrogen, halogen groups, hydroxy, thiol, amino, and $C_1$-$C_6$ linear and branched alkyl groups, wherein when $R_5$ is absent, Q is a bridgehead atom.

2. The compound, deuterated derivative, or pharmaceutically acceptable salt according to embodiment 1, wherein Ring A is a 4- to 6-membered ring.

3. The compound, deuterated derivative, or pharmaceutically acceptable salt according to embodiment 2, wherein Ring A is a 4-membered ring.

4. The compound, deuterated derivative, or pharmaceutically acceptable salt according to embodiment 2, wherein Ring A is a cyclobutyl.

5. The compound, deuterated derivative, or pharmaceutically acceptable salt according to embodiment 2, wherein Ring A is chosen from:

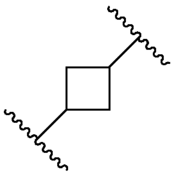

,

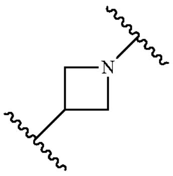

,

-continued

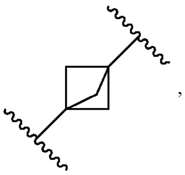

, and

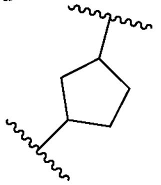

.

6. The compound, deuterated derivative, or pharmaceutically acceptable salt according to any one of embodiments 1-4, wherein Q is $CR^5$.

7. The compound, deuterated derivative, or pharmaceutically acceptable salt according to any one of embodiments 1-6, wherein each $R_1$ is independently chosen from:

halogen groups, hydroxy, thiol, amino, cyano, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups, $C_1$-$C_6$ linear, branched, and cyclic halothioalkyl groups, and $C_1$-$C_6$ linear, branched, and cyclic haloalkoxy groups.

8. The compound, deuterated derivative, or pharmaceutically acceptable salt according to any one of embodiments 1-7, wherein each $R_1$ is independently chosen from halogen groups and $C_1$-$C_6$ linear, branched, and cyclic haloalkyl groups.

9. The compound, deuterated derivative, or pharmaceutically acceptable salt according to any one of embodiments 1-8, wherein each $R_1$ is independently chosen from fluoro and $CF_3$.

10. The compound, salt, or deuterated derivative according to any one of embodiments 1-9, wherein each $R_1$ is fluoro.

11. The compound, deuterated derivative, or pharmaceutically acceptable salt according to any one of embodiments 1-10, wherein each $R_2$ is independently chosen from:

halogen groups, hydroxy, thiol, amino, cyano, $C_1$-$C_4$ linear, branched, and cyclic alkyl groups, $C_2$-$C_4$ linear, branched, and cyclic alkenyl groups, $C_1$-$C_4$ linear, branched, and cyclic hydroxyalkyl groups, $C_1$-$C_4$ linear, branched, and cyclic alkoxy groups, $C_1$-$C_4$ linear, branched, and cyclic thioalkyl groups, $C_1$-$C_4$ linear, branched, and cyclic haloalkyl groups, $C_1$-$C_4$ linear, branched, and cyclic haloaminoalkyl groups, $C_1$-$C_4$ linear, branched, and cyclic halothioalkyl groups, and $C_1$-$C_4$ linear, branched, and cyclic haloalkoxy groups.

12. The compound, deuterated derivative, or pharmaceutically acceptable salt according to any one of embodiments 1-11, wherein each $R_2$ is independently chosen from halogen groups.

13. The compound, salt, or deuterated derivative according to any one of embodiments 1-12, wherein each $R_2$ is fluoro.

14. The compound, salt, or deuterated derivative according to any one of embodiments 1-13, wherein m is 2.

15. The compound, salt, or deuterated derivative according to any one of embodiments 1-14, wherein n is 1.

16. The compound, salt, or deuterated derivative according to any one of embodiments 1-15, wherein X is chosen from divalent $C_1$-$C_8$ linear, branched, and cyclic alkyl groups, wherein the divalent alkyl groups are optionally substituted with one to four groups chosen from:

$C_1$-$C_6$ alkyl groups,
aryl groups,
heteroaryl groups,
halogen groups,
hydroxy, and
amino.

17. The compound, salt, or deuterated derivative according to any one of embodiments 1-16, wherein X is chosen from —$CH_2$— and —$CH_2$—$CH_2$—.

18. The compound, salt, or deuterated derivative according to any one of embodiments 1-17, wherein Y is chosen from divalent amino, divalent oxygen, divalent $C_1$-$C_8$ linear, branched, and cyclic alkyl groups, and divalent $C_1$-$C_8$ linear, branched, and cyclic aminoalkyl groups, wherein the divalent alkyl groups and divalent aminoalkyl groups are optionally substituted with one to three groups independently chosen from $C_1$-$C_6$ alkyl groups optionally substituted with hydroxy,
$C_3$-$C_6$ cyclic alkyl,
oxo, and
hydroxy,
or wherein the divalent alkyl groups, divalent alkoxy groups, divalent aminoalkyl groups, and divalent thioalkyl groups are optionally fused to a $C_3$-$C_6$ cyclic alkyl.

19. The compound, salt, or deuterated derivative according to any one of embodiments 1-18, wherein Y is chosen from

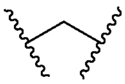, 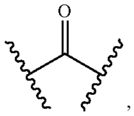, 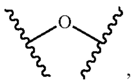, 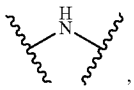,

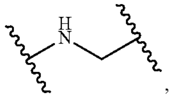, 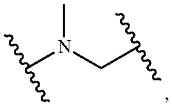, 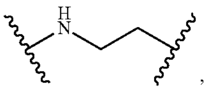,

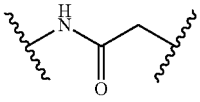, 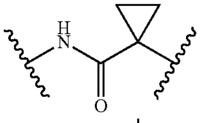,

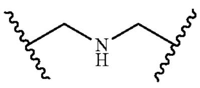, 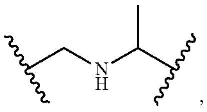,

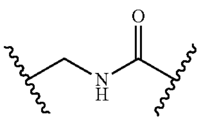, 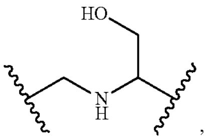,

-continued

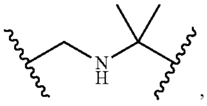, 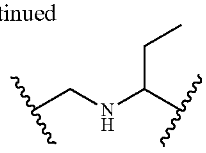,

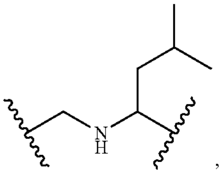, 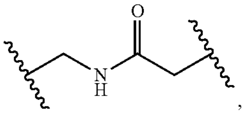,

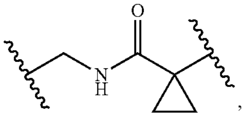, and 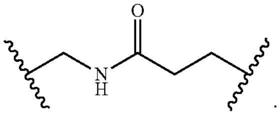.

20. The compound, salt, or deuterated derivative according to any one of embodiments 1-19, wherein o is 0.

21. The compound, salt, or deuterated derivative according to any one of embodiments 1-19, wherein o is 1.

22. The compound, salt, or deuterated derivative according to any one of embodiments 1-21, wherein p is 0.

23. The compound, salt, or deuterated derivative according to any one of embodiments 1-21, wherein p is 1.

24. The compound, salt, or deuterated derivative according to any one of embodiments 1-23, wherein $R_3$ is hydrogen, and $R_4$ is chosen from:

hydrogen,
$C_1$-$C_6$ linear and branched alkylsulfonyl groups,
$C_1$-$C_6$ linear and branched alkoxy groups optionally substituted with a $C_3$-$C_6$ cyclic alkyl group or a 3- to 6-membered heterocycle;
$C_1$-$C_6$ cyclic alkyl groups optionally substituted with one to four groups independently chosen from:
- halogen groups,
- hydroxy,
- oxo,
- $C_1$-$C_6$ linear and branched alkoxy groups,
- $C_1$-$C_6$ linear and branched alkyl groups optionally substituted with one or two groups independently chosen from hydroxy and $C_1$-$C_6$ linear and branched alkoxy groups, and
- amido groups, heterocyclic groups optionally substituted with one to four groups independently chosen from:
- halogen groups,
- oxo,
- hydroxy, and
- $C_1$-$C_6$ linear and branched alkyl groups optionally substituted with one or two groups independently chosen from hydroxy and $C_1$-$C_6$ linear and branched alkoxy groups, heteroaryl groups optionally substituted with one to four groups independently chosen from hydroxy and $C_1$-$C_6$ linear alkyl groups, and $C_1$-$C_7$ linear and branched alkyl groups, wherein the alkyl groups are optionally substituted with one to five groups independently chosen from:
- amino groups,
- hydroxy,
- oxo,
- cyano,
- carboxylic acid,
- halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups.

25. The compound, salt, or deuterated derivative according to any one of embodiments 1-23, wherein $R_3$ and $R_4$, together with the nitrogen atom to which they are attached, form a 4- to 10-membered heterocyclyl group optionally substituted with one to four groups independently chosen from:

hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups.

26. The compound, salt, or deuterated derivative according to any one of embodiments 1-25, wherein R is independently chosen from hydrogen, halogen groups, and $C_1$-$C_6$ linear and branched alkyl groups.

27. The compound, salt, or deuterated derivative according to any one of embodiments 1-26, wherein $R_5$ is independently chosen from hydrogen, fluoro, and methyl.

28. The compound, salt, or deuterated derivative according to embodiment 1, wherein the compound is selected from compounds of Formula (V-a) and (V-b):

(V-a)

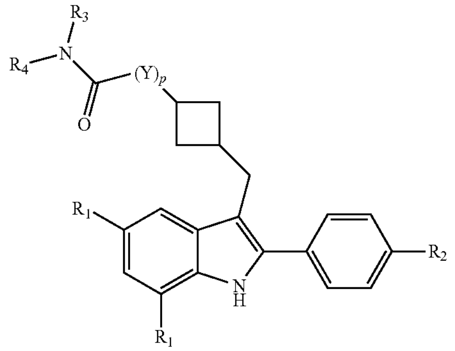

and (V-b)

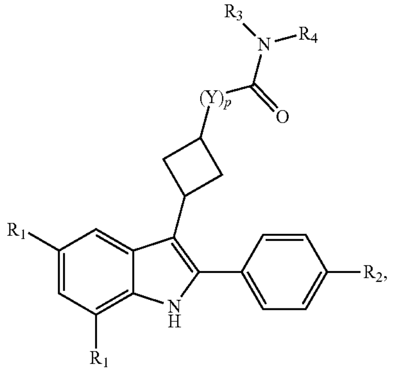

pharmaceutically acceptable salts thereof, solvates of any of the foregoing, and deuterated derivatives of any of the foregoing, wherein $R^1$, $R_2$, $R_3$, $R_4$, Y, and p are as defined in embodiment 1.

29. The compound, deuterated derivative, or pharmaceutically acceptable salt according to embodiment 28, wherein each $R_1$ is independently chosen from:

halogen groups, hydroxy, thiol, amino, cyano, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups, $C_1$-$C_6$ linear, branched, and cyclic halothioalkyl groups, and $C_1$-$C_6$ linear, branched, and cyclic haloalkoxy groups.

30. The compound, deuterated derivative, or pharmaceutically acceptable salt according to embodiment 28 or 29, wherein each $R_1$ is independently chosen from halogen groups and $C_1$-$C_6$ linear, branched, and cyclic haloalkyl groups.

31. The compound, deuterated derivative, or pharmaceutically acceptable salt according to any one of embodiments 28-30, wherein each $R_1$ is independently chosen from fluoro and $CF_3$.

32. The compound, salt, or deuterated derivative according to any one of embodiments 28-31, wherein each $R_1$ is fluoro.

33. The compound, deuterated derivative, or pharmaceutically acceptable salt according to any one of embodiments 28-32, wherein $R_2$ is chosen from:

halogen groups,
hydroxy,
thiol,
amino,
cyano,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups.

34. The compound, deuterated derivative, or pharmaceutically acceptable salt according to any one of embodiments 28-33, wherein $R_2$ is chosen from halogen groups.

35. The compound, salt, or deuterated derivative according to any one of embodiments 28-34, wherein $R_2$ is fluoro.

36. The compound, salt, or deuterated derivative according to any one of embodiments 28-35, wherein Y is chosen from divalent amino, divalent oxygen, divalent $C_1$-$C_8$ linear, branched, and cyclic alkyl groups, and divalent $C_1$-$C_8$ linear, branched, and cyclic aminoalkyl groups, wherein the divalent alkyl groups and divalent aminoalkyl groups are optionally substituted with one to three groups independently chosen from $C_1$-$C_6$ alkyl groups optionally substituted with hydroxy,
$C_3$-$C_6$ cyclic alkyl,
oxo, and
hydroxy,
or wherein the divalent alkyl groups, divalent alkoxy groups, divalent aminoalkyl groups, and divalent thioalkyl groups are optionally fused to a $C_3$-$C_6$ cyclic alkyl.

37. The compound, salt, or deuterated derivative according to any one of embodiments 28-36, wherein Y is chosen from

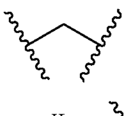,
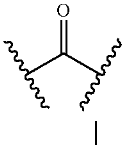,
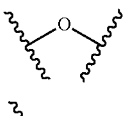,
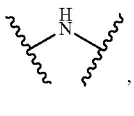,
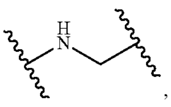,
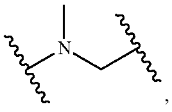,
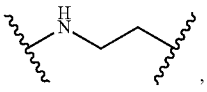, -continued

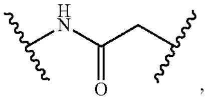,
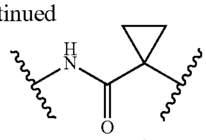,
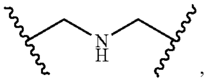,
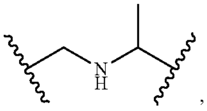,
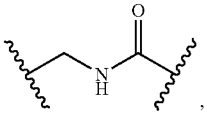,
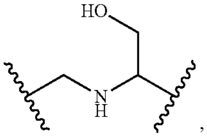,
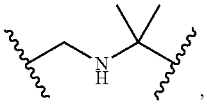,
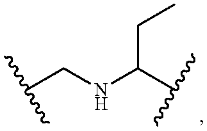,
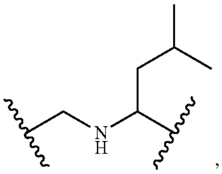,
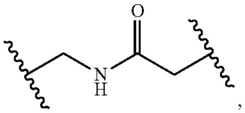,
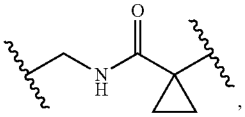, and
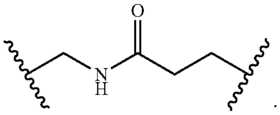.

38. The compound, salt, or deuterated derivative according to any one of embodiments 28-37, wherein p is 0.

39. The compound, salt, or deuterated derivative according to any one of embodiments 28-37, wherein p is 1.

40. The compound, salt, or deuterated derivative according to any one of embodiments 28-39, wherein $R_3$ is hydrogen and $R_4$ is chosen from:

hydrogen,
$C_1$-$C_6$ linear and branched alkylsulfonyl groups,
$C_1$-$C_6$ linear and branched alkoxy groups optionally substituted with a $C_3$-$C_6$ cyclic alkyl group or a 3- to 6-membered heterocycle;
$C_1$-$C_6$ cyclic alkyl groups optionally substituted with one to four groups independently chosen from:
  halogen groups,
  hydroxy,
  oxo,
  $C_1$-$C_6$ linear and branched alkoxy groups,
  $C_1$-$C_6$ linear and branched alkyl groups optionally substituted with one or two groups independently chosen from hydroxy and $C_1$-$C_6$ linear and branched alkoxy groups, and
  amido groups,
heterocyclic groups optionally substituted with one to four groups independently chosen from:
  halogen groups,
  oxo,
  hydroxy, and
  $C_1$-$C_6$ linear and branched alkyl groups optionally substituted with one or two groups independently chosen from hydroxy and $C_1$-$C_6$ linear and branched alkoxy groups,
heteroaryl groups optionally substituted with one to four groups independently chosen from hydroxy and $C_1$-$C_6$ linear alkyl groups, and $C_1$-$C_7$ linear and branched alkyl groups, wherein the alkyl groups are optionally substituted with one to five groups independently chosen from:

amino groups, hydroxy, oxo, cyano, carboxylic acid, halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups.

41. The compound, salt, or deuterated derivative according to any one of embodiments 28-39, wherein $R_3$ and $R_4$, together with the nitrogen atom to which they are attached, form a 4 to 10-membered heterocyclyl group optionally substituted with one to four groups independently chosen from:

hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups.

42. A compound chosen from compounds of Formula (Ia):

(Ia)

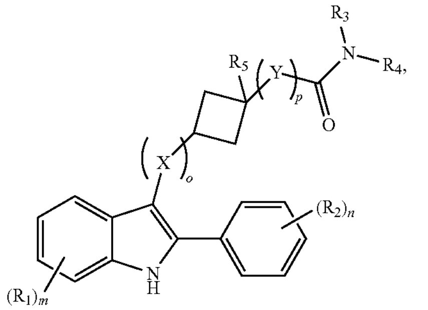

pharmaceutically acceptable salts thereof, solvates of any of the foregoing, and deuterated derivatives of any of the foregoing, wherein:

(i) each $R_1$ is independently chosen from halogen groups, hydroxy, thiol, amino, cyano, —OC(O)$C_1$-$C_6$ linear, branched, and cyclic alkyl groups, —C(O)O$C_1$-$C_6$ linear, branched, and cyclic alkyl groups, —NHC(O)$C_1$-$C_6$ linear, branched, and cyclic alkyl groups, —C(O)NH$C_1$-$C_6$ linear, branched, and cyclic alkyl groups, —NHC(O)aryl groups, —C(O)NHaryl groups, —NHC(O)heteroaryl groups, —C(O)NHheteroaryl groups, —NHS$(O)_2C_1$-$C_6$ linear, branched, and cyclic alkyl groups, —S$(O)_2$NH$C_1$-$C_6$ linear, branched, and cyclic alkyl groups, —NHS$(O)_2$aryl groups, —S$(O)_2$NHaryl groups, —NHS$(O)_2$heteroaryl groups, —S$(O)_2$NHheteroaryl groups, —NHC(O)NH$C_1$-$C_6$ linear, branched, and cyclic alkyl groups, —NHC(O)NHaryl groups, —NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3- to 6-membered heterocycloalkenyl groups,
3- to 6-membered heterocycloalkyl groups, and
5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2$$C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(iii) m is chosen from 0, 1, 2, 3, and 4;

(iv) n is chosen from 0, 1, 2, 3 4, and 5;

(v) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with at least one group chosen from
$C_1$-$C_6$ alkyl groups,
aryl groups,
heteroaryl groups,
halogen groups,
hydroxy, and
amino;

(vi) Y is chosen from divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with at least one group chosen from
$C_1$-$C_6$ alkyl groups,
aryl groups,
heteroaryl groups,
halogen groups,
hydroxy, and
amino;

(vii) o is chosen from 0, 1, 2, 3, and 4;

(viii) p is chosen from 0, 1, 2, 3, and 4;

(ix) $R_3$ and $R_4$ are independently chosen from
hydrogen,
$C_1$-$C_6$ linear and branched alkylsulfonyl groups,
$C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups,
heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
heteroaryl groups optionally substituted with at least one group chosen from $C_1$-$C_6$ linear alkyl groups, and
$C_1$-$C_6$ linear and branched alkyl groups, wherein the alkyl groups are optionally substituted with at least one group chosen from:
amino groups,
hydroxy,
cyano,
carboxylic acid,
halogen groups,
amido groups optionally substituted with one or two groups chosen from $C_1$-$C_6$ linear, branched, and cyclic alkyl groups and $C_1$-$C_6$ linear, branched, and cyclic hydroxyalkyl groups,
$C_3$-$C_6$ cyclic alkyl groups optionally substituted with one or two groups chosen from halogen groups and hydroxy,
$C_1$-$C_6$ linear and branched alkynyl groups,
$C_1$-$C_6$ linear and branched alkoxy groups optionally substituted with at least one hydroxy,
$C_1$-$C_6$ linear and branched alkylsulfonyl groups,
aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups,
carbonyl-(4-methylpiperazin-1-yl),
carbonyl-(N-morpholino),
4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each R is independently chosen from hydrogen, halogen groups, hydroxy, thiol, amino, and $C_1$-$C_6$ linear and branched alkyl groups.

43. The compound, salt, or deuterated derivative of embodiment 42, wherein $R_3$ is hydrogen or methyl.

44. The compound, salt, or deuterated derivative of embodiment 42 or 43, wherein $R_3$ is hydrogen.

45. The compound, salt, or deuterated derivative of any one of embodiments 42-44, wherein each $R_1$ is independently chosen from halogen groups.

46. The compound, salt, or deuterated derivative of any one of embodiments 42-45, wherein each $R_1$ is fluoro.

47. The compound, salt, or deuterated derivative of any one of embodiments 42-46, wherein each $R_2$ is independently chosen from halogen groups and methyl.

48. The compound, salt, or deuterated derivative of any one of embodiments 42-47, wherein each $R_2$ is independently chosen from halogen groups.

49. The compound, salt, or deuterated derivative of any one of embodiments 42-48, wherein each $R_2$ is fluoro.

50. The compound, salt, or deuterated derivative of any one of embodiments 42-49, wherein m is 1 or 2.

51. The compound, salt, or deuterated derivative of any one of embodiments 42-50, wherein m is 2.

52. The compound, salt, or deuterated derivative of any one of embodiments 42-51, wherein n is 1 or 2.

53. The compound, salt, or deuterated derivative of any one of embodiments 42-52, wherein o is 1.

54. The compound, salt, or deuterated derivative of any one of embodiments 42-53, wherein p is 1.

55. The compound, salt, or deuterated derivative of any one of embodiments 42-52 or 54, wherein o is 0.

56. The compound, salt, or deuterated derivative of any one of embodiments 42-51 or 53, wherein p is 0.

57. The compound, salt, or deuterated derivative of any one of embodiments 42-56, wherein R is hydrogen.

58. A compound chosen from compounds of Formula (II):

(II)

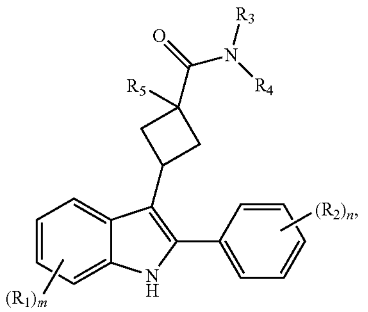

pharmaceutically acceptable salts thereof, solvates of any of the foregoing, and deuterated derivatives of any of the foregoing, wherein:

(i) each $R_1$ is independently chosen from halogen groups, hydroxy, thiol, amino, cyano, —OC(O)$C_1$-$C_6$ linear, branched, and cyclic alkyl groups, —C(O)O$C_1$-$C_6$ linear, branched, and cyclic alkyl groups, —NHC(O)$C_1$-$C_6$ linear, branched, and cyclic alkyl groups, —C(O)NH$C_1$-$C_6$ linear, branched, and cyclic alkyl groups, —NHC(O)aryl groups, —C(O)NHaryl groups, —NHC(O)heteroaryl groups, —C(O)NHheteroaryl groups, —NHS$(O)_2C_1$-$C_6$ linear, branched, and cyclic alkyl groups, —S$(O)_2$NH$C_1$-$C_6$ linear, branched, and cyclic alkyl groups, —NHS$(O)_2$aryl groups, —S$(O)_2$NHaryl groups, —NHS$(O)_2$heteroaryl groups, —S$(O)_2$NHheteroaryl groups, —NHC(O)NH$C_1$-$C_6$ linear, branched, and cyclic alkyl groups, —NHC(O)NHaryl groups, —NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3- to 6-membered heterocycloalkenyl groups,
3- to 6-membered heterocycloalkyl groups, and
5- and 6-membered heteroaryl groups; or
two $R_1$ groups, together with the carbon atoms to which they are attached, form a $C_4$-$C_8$ cycloalkyl group, an aryl group, or a heteroaryl group;

(ii) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(iii) m is chosen from 0, 1, 2, 3, and 4;

(iv) n is chosen from 0, 1, 2, 3, 4, and 5;

(v) $R_3$ and $R_4$ are independently chosen from
hydrogen,
$C_1$-$C_6$ linear and branched alkylsulfonyl groups,
$C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups,
heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
heteroaryl groups optionally substituted with at least one group chosen from $C_1$-$C_6$ linear alkyl groups, and
$C_1$-$C_6$ linear and branched alkyl groups, wherein the alkyl groups are optionally substituted with at least one group chosen from:
amino groups,
hydroxy,
cyano,
carboxylic acid,
halogen groups,
amido groups optionally substituted with one or two groups chosen from $C_1$-$C_6$ linear, branched, and cyclic alkyl groups and $C_1$-$C_6$ linear, branched, and cyclic hydroxyalkyl groups,
$C_3$-$C_6$ cyclic alkyl groups optionally substituted with one or two groups chosen from halogen groups and hydroxy,
$C_1$-$C_6$ linear and branched alkynyl groups,
$C_1$-$C_6$ linear and branched alkoxy groups optionally substituted with at least one hydroxy,
$C_1$-$C_6$ linear and branched alkylsulfonyl groups,
aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups,
carbonyl-(4-methylpiperazin-1-yl),
carbonyl-(N-morpholino),
4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and
4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups,
or $R_3$ and $R_4$, together with the nitrogen atom to which they are attached, form a 4- to 10-membered heterocyclyl group optionally substituted with at least one group chosen from
hydroxy,
oxo,
$C_1$-$C_6$ linear, branched, and cyclic alkyl groups optionally substituted with at least one groups chosen from hydroxy, amino groups, $C_1$-$C_6$ linear, branched, and cyclic alkoxy groups,
amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each R is independently chosen from hydrogen, halogen groups, hydroxy, thiol, amino, and $C_1$-$C_6$ linear and branched alkyl groups.

59. The compound, salt, or deuterated derivative of embodiment 58, wherein (i) each $R_1$ is independently chosen from halogen groups, and $C_1$-$C_6$ linear and branched alkyl groups;

(ii) each $R_2$ is independently chosen from halogen groups, and $C_1$-$C_6$ linear and branched alkyl groups;

(iii) m is chosen from 0, 1, 2, and 3; and (iv) n is 1 or 2.

60. The compound, salt, or deuterated derivative embodiment 58 or 59, wherein:

(i) each $R_1$ is independently chosen from halogen groups, and methyl;

(ii) each $R_2$ is independently chosen from halogen groups, and methyl;

(iii) m is 0, 1 or 2; and (iv) n is 1 or 2.

61. The compound, salt, or deuterated derivative of any one of embodiments 58-60, wherein each $R_1$ is fluoro.

62. The compound, salt, or deuterated derivative of any one of embodiments 58-61, wherein each $R_2$ is fluoro.

63. The compound, salt, or deuterated derivative of any one of embodiments 58-62, wherein m is 0, 1 or 2.

64. The compound, salt, or deuterated derivative of any one of embodiments 58-63, wherein m is 2.

65. The compound, salt, or deuterated derivative of any one of embodiments 58-63, wherein m is 0.

66. The compound, salt, or deuterated derivative of any one of embodiments 58-65, wherein n is 1 or 2.

67. The compound, salt, or deuterated derivative of any one of embodiments 58-65, wherein n is 1.

68. The compound, salt, or deuterated derivative of any one of embodiments 58-67, wherein $R_5$ is chosen from hydrogen, amino, alkyl, and halo.

69. The compound, salt, or deuterated derivative of any one of embodiments 58-67, wherein R is chosen from hydrogen and $C_1$-$C_6$ linear alkyl groups.

70. The compound, salt, or deuterated derivative of any one of embodiments 58-69, wherein R is hydrogen.

71. The compound, salt, or deuterated derivative of any one of embodiments 58-70, wherein $R_3$ is chosen from hydrogen and $C_1$-$C_6$ linear and branched alkyl groups.

72. The compound, salt, or deuterated derivative of any one of embodiments 58-71, wherein $R_3$ is chosen from hydrogen and methyl.

73. The compound, salt, or deuterated derivative of any one of embodiments 58-72, wherein $R_4$ is chosen from:

$C_1$-$C_6$ linear and branched alkyl groups optionally substituted with at least one group chosen from:

amino groups, hydroxy, cyano, amido groups optionally substituted with one or two groups chosen from $C_1$-$C_6$ linear, branched, and cyclic alkyl groups and $C_1$-$C_6$ linear, branched, and cyclic hydroxyalkyl groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups.

74. The compound, salt, or deuterated derivative of any one of embodiments 58-73, wherein $R_4$ is chosen from:

$C_1$-$C_6$ linear and branched alkyl groups optionally substituted with at least one group chosen from:

hydroxy, amido groups optionally substituted with one or two groups chosen from $C_1$-$C_6$ linear, branched, and cyclic alkyl groups and $C_1$-$C_6$ linear, branched, and cyclic hydroxyalkyl groups, and 5- or 6-membered heteroaryl groups optionally substituted with one or two groups chosen from $C_1$-$C_6$ linear and branched alkyl groups optionally substituted with one or two groups chosen from hydroxy and $C_1$-$C_6$ linear and branched alkoxy groups.

75. The compound, salt, or deuterated derivative of any one of embodiments 58-74, wherein $R_4$ is chosen from $C_1$-$C_6$ linear and branched alkyl groups optionally substituted with at least one group chosen from:

hydroxy, amido groups optionally substituted with one or two groups chosen from $C_1$-$C_6$ linear alkyl groups, and 5- or 6-membered heteroaryl groups optionally substituted with one or two groups chosen from $C_1$-$C_6$ linear alkyl groups.

76. The compound, salt, or deuterated derivative of any one of embodiments 58-70, wherein $R_3$ and $R_4$, together with the nitrogen atom to which they are attached, form a 4- to 10-membered heterocyclyl group optionally substituted with at least one group chosen from:

hydroxy, $C_1$-$C_6$ linear alkyl groups, and amide groups optionally substituted with at least one group chosen from $C_1$-$C_6$ linear, branched, and cyclic alkyl groups.

77. A compound chosen from Compounds 1 to 286 (Table 1), pharmaceutically acceptable salts thereof, solvates of any of the foregoing, and deuterated derivatives of any of the foregoing.

78. A compound chosen from Compounds 287 to 465 (Table 2), pharmaceutically acceptable salts thereof, solvates of any of the foregoing, and deuterated derivatives of any of the foregoing.

79. A pharmaceutical composition comprising the compound, salt, or deuterated derivative according to any one of embodiments 1-78 and a pharmaceutically acceptable carrier.

80. A method of treating APOL1 mediated kidney disease comprising administering to a patient in need thereof the compound, salt, or deuterated derivative according to any one of embodiments 1-78 or a pharmaceutical composition according to embodiment 79.

81. The method according to embodiment 80, wherein the APOL1 mediated kidney disease is chosen from ESKD, NDKD, FSGS, HIV-associated nephropathy, arterionephrosclerosis, lupus nephritis, microalbuminuria, and chronic kidney disease.

82. The method according to embodiment 80, wherein the APOL1 mediated kidney disease is FSGS.

83. The method according to embodiment 80, wherein the APOL1 mediated kidney disease is NDKD.

84. The method according to embodiment 80, wherein the APOL1 mediated kidney disease is ESKD.

85. The method according to any one of embodiments 80-84, wherein the APOL1 mediated kidney disease is associated with APOL1 genetic alleles chosen from homozygous G1: S342G:I384M and homozygous G2: N388del:Y389del.

86. The method according to any one of embodiments 80-84, wherein the APOL1 mediated kidney disease is associated with compound heterozygous G1: S342G:I384M and G2: N388del:Y389del APOL1 genetic alleles.

87. A method of inhibiting APOL1 activity comprising contacting said APOL1 with the compound, salt, or deuterated derivative according to any one of embodiments 1-78 or a pharmaceutical composition according to embodiment 79.

88. The method according to embodiment 87, wherein the APOL1 is associated with APOL1 genetic alleles chosen from homozygous G1: S342G:I384M and homozygous G2: N388del:Y389del.

89. The method according to embodiment 87, wherein the APOL1 is associated with compound heterozygous G1: S342G:I384M and G2: N388del:Y389del APOL1 genetic alleles.

General Synthetic Schemes

Another aspect of the disclosure provides methods for making compounds of Formulae (I), (Ia), (II), (IIIa), (IIIb), (IV), (Va), and (Vb), Compounds 1 to 286 and Compounds 287 to 465, pharmaceutically acceptable salts of any of those compounds, solvates of any of the foregoing, and deuterated derivatives of any of the foregoing, and intermediates for making any of the foregoing. Throughout the synthetic schemes and descriptions for preparing compounds of Formulae (I), (Ia), (I), (IIIa), (IIIb), (IV), (Va), and (Vb), Compounds 1 to 286 (Table 1) and Compound 287 to 465 (Table 2), pharmaceutically acceptable salts of any of those compounds, solvates of any of the foregoing, and deuterated derivatives of any of the foregoing, the following abbreviations are used:

Abbreviations

AIBN=Azobisisobutyronitrile
ARP=assay ready plate
BBBPY=4,4'-Di-tert-butyl-2,2'-dipyridyl
CBzCl=Benzyl chloroformate
CDMT=2-Chloro-4,6-dimethoxy-1,3,5-triazine
DIPEA=N,N-Diisopropylethylamine or N-ethyl-N-isopropyl-propan-2-amine
DMAP=dimethylamino pyridine
DMA=dimethyl acetamide
DME=dimethoxyethane
DMEM=Dulbecco's modified Eagle's medium
DMF=dimethylformamide
DMSO=dimethyl sulfoxide
DPPA=diphenylphosphoryl azide
EtOAc=Ethyl Acetate
EtOH=ethanol
FBS=fetal bovine serum
FLU=fluorescent values
HATU=[dimethylamino(triazolo[4,5-b]pyridin-3-yloxy)methylene]-dimethyl-ammonium (Phosphorus Hexafluoride Ion)
HDMC=N-[(5-Chloro-3-oxido-1H-benzotriazol-1-yl)-4-morpholinylmethylene]-N-methylmethanaminium hexafluorophosphate
HEPES=4-(2-hydroxyethyl)-1-piperazineethanesulfonic acid
HBSS=Hank's balanced salt solution
IPA=isopropyl alcohol
LDA=lithium diisopropyl amide
LED=light emitting diode
MeOH=methanol
MTBE=Methyl tert-butyl ether
NMM=N-methyl morpholine
NMP=N-methyl pyrrolidine
PBS=phosphate-buffered saline
$Pd(dppf)_2Cl_2$=[1,1'-Bis(diphenylphosphino)ferrocene]dichloropalladium(II)
$PdCl_2(PPh_3)_2$=Bis(triphenylphosphine)palladium(II) dichloride
PP=polypropylene
PTSA=p-Toluenesulfonic acid monohydrate
T3P=2,4,6-Tripropyl-1,3,5,2,4,6-trioxatriphosphorinane-2,4,6-trioxide
TEA=triethylamine
Tet=tetracycline
TFA=trifluoroacetic acid
THE=tetrahydrofuran
THP=tetrahydropyran
TMSS=Tris(trimethylsilyl)silane Scheme 1 provides processes suitable for the preparation of indoles of Formula 1-4. In some embodiments, X is a halogen. In some embodiments, the halogen is Cl, I, or Br. $R^1$, $R^2$, m and n are as defined above. Any suitable conditions for coupling an alkyne can be used to convert aryl halides of Formula 1-1 and alkynes of formula 1-2 to afford an amino aryl alkyne of Formula 1-3. For example, in some embodiments, the coupling is performed in the presence of a CuI and $Pd(PPh_3)_2Cl_2$ catalyst system. In some embodiments, the reaction is performed in the presence of at least one base. In some embodiments, the at least one base is DIPEA or $NEt_3$. In some embodiments, conversion of compounds of formula 1-3 to indoles of Formula 1-4 is accomplished by treatment with CuI or $PdCl_2$ in at least one polar solvent in the presence of added heat. In some embodiments, the at least one polar solvent is chosen from DMF and MeCN. In some embodiments, the added heat is greater than 100° C.

Scheme I

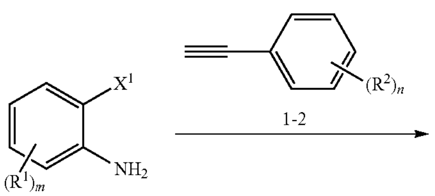

1-1

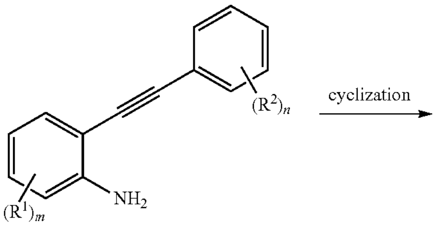

1-3

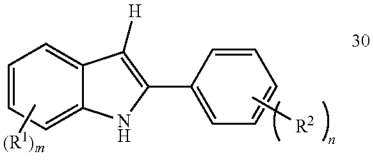

1-4

Scheme 2 describes processes for the preparation of formula I. Indoles of formula 1-4 may react with carbonyl compounds of formula 2-1, to afford compounds of formula 2-2. Compound 2-1 are any ketones or aldehydes which are suitable to form a compound of formula 2-2 upon reductive coupling with a compound of formula 1-4. For example, X' may be CH, or X' may be absent (o=0). In some embodiments, the reaction is performed in the presence of at least one acid and at least one reducing agent. In some embodiments, the acid is chosen from trifluoroacetic acid and methanesulfonic acid. In some embodiments, the reducing agent is $Et_3SiH$. The reaction may be performed in a solvent such as dichloromethane. Processes for the preparation of a compound of formula I involve coupling of a carboxylic acid of formula 2-2 and amines 1-5 using any suitable method for the formation of an amide bond.

Scheme 2

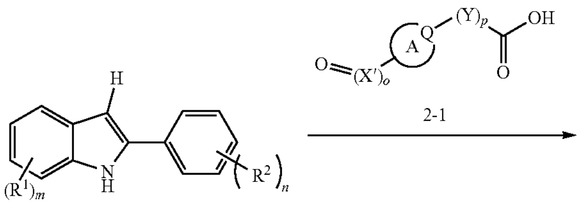

1-4

-continued

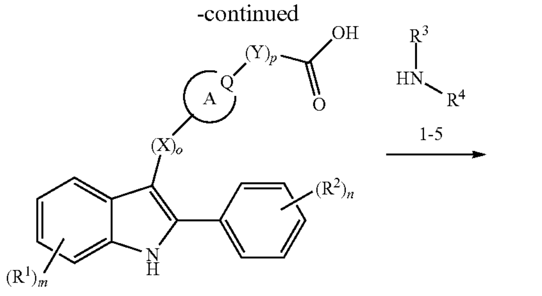

2-2

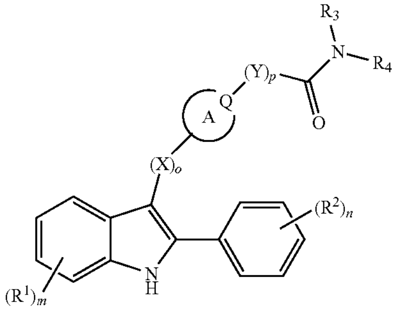

I

Scheme 3 describes processes for preparation of compounds of Formulae (II), In some embodiments, compounds of formula 3-2 are prepared from indoles of formula 1-4 and ketones of formula 3-1. In some embodiments, the reaction is performed in the presence of at least one acid and at least one reducing agent. In some embodiments, the acid is chosen from trifluoroacetic acid and methanesulfonic acid. In some embodiments, the reducing agent is $Et_3SiH$. In some embodiments, the reaction is performed in the at least one solvent. In some embodiments, the one solvent is dichloromethane. In some embodiments, processes for preparing compounds of Formulae (I), (Ia), (II), (IIIa), (IIIb), and (IVa), comprise reacting a compound of formula 3-2 with an amine of formula 1-5 in the presence of at least one amide coupling agent (e.g. HATU, CDMT, HDMC, or T3P) and at least one suitable base (e.g. DIPEA or TEA), as depicted in Scheme 3. In some embodiments, the amide coupling agent is chosen from HATU, CDMT, HDMC, and T3P. In some embodiments, a suitable base is chosen from DIPEA and TEA. In some embodiments, HATU and triethylamine in at least one solvent is used. In some embodiments, the solvent is DMF. Other suitable conditions for amide bond formation may be used to prepare compounds of Formulae (I), (Ia), (II), (IIIa), (IIIb), and (IVa) from compounds of Formula 1-5 and 3-2.

Scheme 3

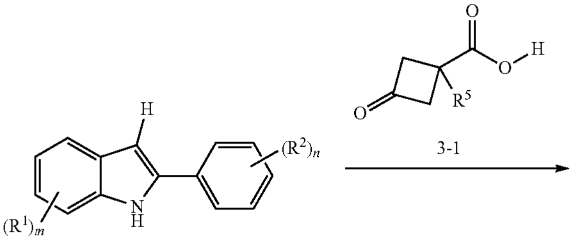

1-4

-continued

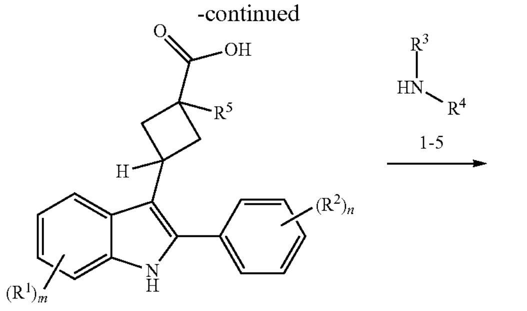

3-2

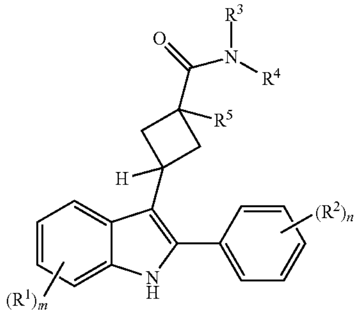

II

Processes for the preparation of compounds of formula 4-3 and 4-5 are shown in Scheme 4. $LG^1$ is any suitable leaving group, for example, p-nitrophenol. In some embodiments, where $LG^1$ is a p-nitrophenol group, amines of formula 4-1 may be converted to an intermediate of formula 4-2, by treatment with any suitable reagent for the formation of a p-nitrophenol carbamate. For example, the reaction may be performed in the presence of p-nitrophenol carbonate or (4-nitrophenyl) carbonochloridate. The reaction may be performed in a basic solvent such as pyridine. In alternative conditions, compounds of formula 4-2 may be prepared by treatment with p-nitrophenol carbonate in the presence of a base such as DIPEA, in a solvent such as DMF. Addition of an amine of formula 1-5 to a solution of an intermediate of formula 4-2 affords compounds of formula 4-3. In some embodiments, the reaction may be performed in the presence of a base such as triethylamine and a solvent such as DMF. The reaction may be performed at room temperature or with added heat.

Scheme 4

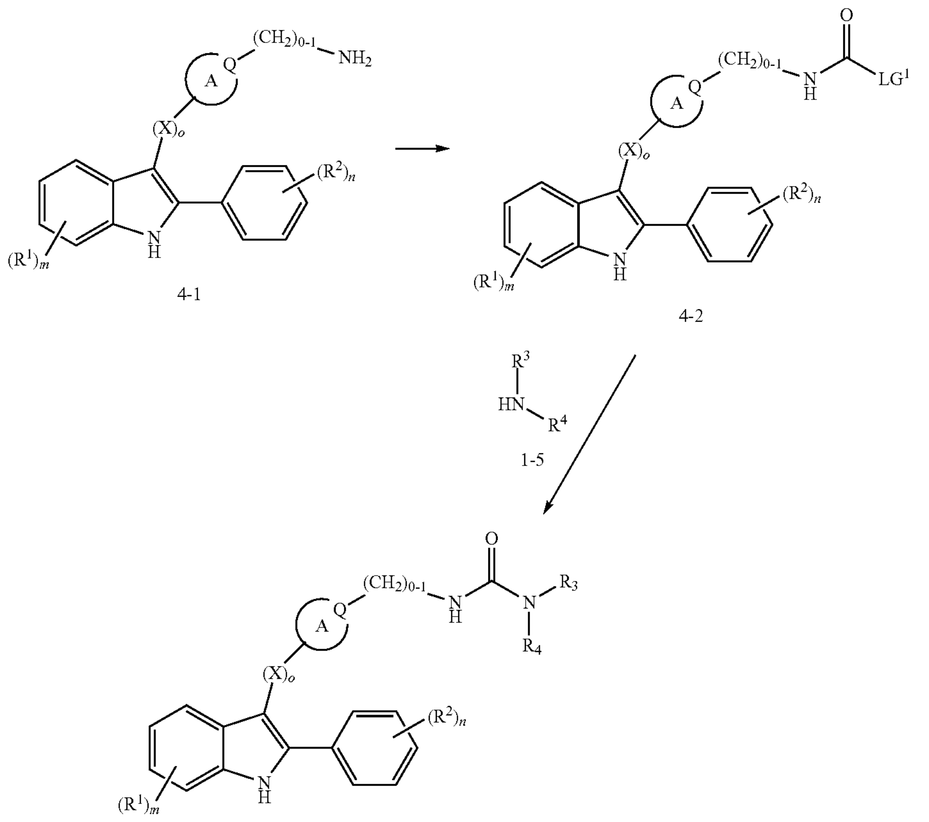

4-3

Scheme 5 shows a process for the preparation of compounds of formula 5-2. An amine of formula 4-1 may react with an alkyl halide if formula 5-1 in the presence of a base and solvent. In some embodiments, the base may be triethylamine. In some embodiments, the solvent may be DMF. In some embodiments, the reaction may be performed at room temperature.

Scheme 5

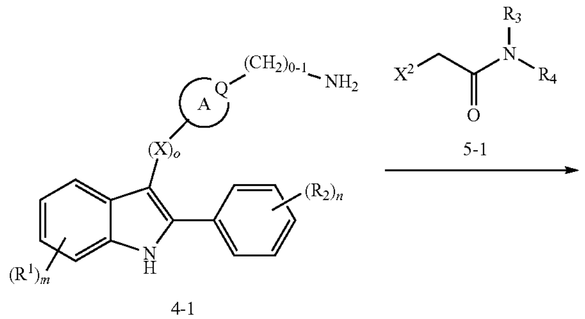

4-1

5-1

-continued

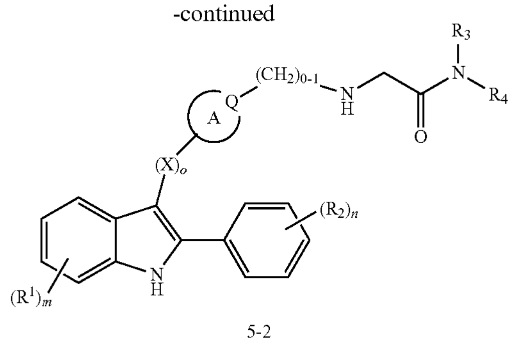

5-2

Scheme 6 depicts processes for the preparation of amines of formula 6-3 and 6-6. Amines of formula 6-3 and 6-6 may be used as compounds of formula 4-1 in scheme 4 and scheme 5. $PG^1$ is any suitable nitrogen protecting group, for example, CBz or Boc. Compounds of formula 6-2 may be prepared from indoles of formula 1-4 and ketones of formula 6-2 using any condition suitable for performing a reductive alkylation. An acid and a reducing agent may be used in the reductive alkylation step. In some embodiments, the acid used is trifluoroacetic acid or methanesulfonic acid. In some embodiments, the reducing agent may be triethylsilane. A compound of formula 6-3 may be prepared from 6-2 using any suitable condition for removal of a nitrogen protecting group. For example, where $PG^1$ is CBz, hydrogenolysis using hydrogen gas and a palladium on carbon catalyst affords compounds of formula 6-3. In some embodiments, the reaction is performed in a solvent mixture such as THE and Methanol. Compounds of formula 6-6 may be prepared from indoles of formula 1-4 and aldehydes of formula 6-5 using processes described for the preparation of compounds of formula 6-3.

Scheme 6

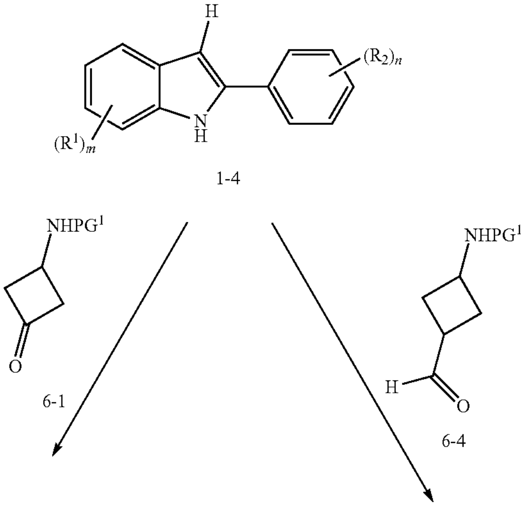

1-4

6-1

6-4

-continued

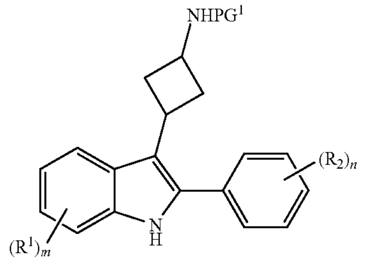

6-2

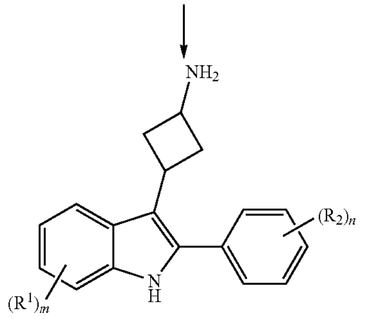

6-3

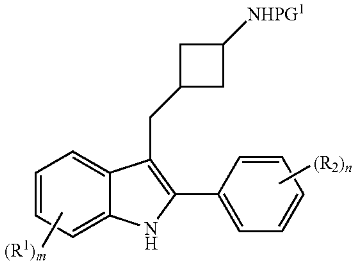

6-5

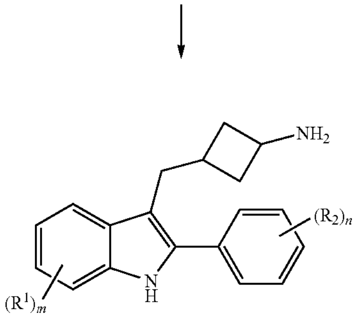

6-6

Scheme 7 shows processes for the preparation of compounds of formula 7-3. Compounds of formula 7-2 may be prepared from 1-4 and 7-1 using any suitable conditions for reductive alkylation. Compounds of formula 7-3 may be prepared using any suitable method for the reduction of a nitrile group to an amine. In some embodiments, hydrogenation using a catalyst such as Raney Nickel may be used. The reaction may be performed in a solvent such as a solution of ammonia in methanol. The reaction may be performed at elevated pressure, for example 60 psi hydrogen atmosphere. In some alterative embodiments, reduction with $LiAlH_4$ may be used. The reaction may be performed in a solvent such as THF. The reaction may be performed in the presence of added heat (e.g. 60° C.). Compounds of formula 7-3 may be used as compounds of formula 4-1.

Scheme 7

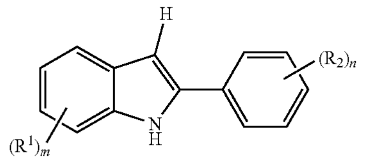

1-4

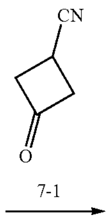

7-1

-continued

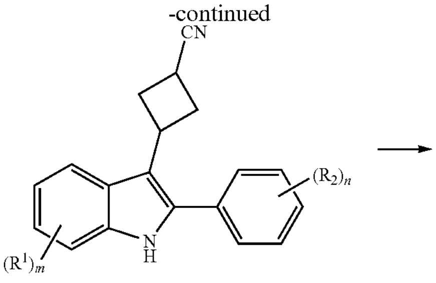

7-2

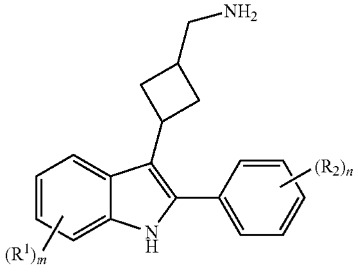

7-3

Scheme 8 shows processes for the preparation of compounds of formula 8-3 from alcohols of formula 8-1. $LG^2$ is any suitable activated alcohol which forms a carbonate. Compound of formula 8-2 may be prepared from alcohols of formula 8-1 using any suitable reagent for the preparation of a carbamate. For example, where $LG^2$ is a p-nitrophenol, compounds of formula 8-2 may be prepared by treatment of 8-1 with p-nitrophenol carbonate or (4-nitrophenyl) carbonochloridate. The reaction is performed in the presence of a suitable base, for example, triethylamine or pyridine. A solvent such as dichloromethane may be used. A compound of formula 8-3 may be prepared from carbamates of formula 8-2 and amines of formula 1-5 in the presence of base and solvent. In some embodiments, a base such as pyridine and a solvent such as DMF may be use. The reaction may be performed in the presence of added heat. For example, the reaction may be performed at 80° C.

Scheme 8

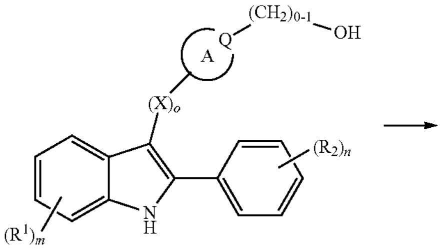

8-1

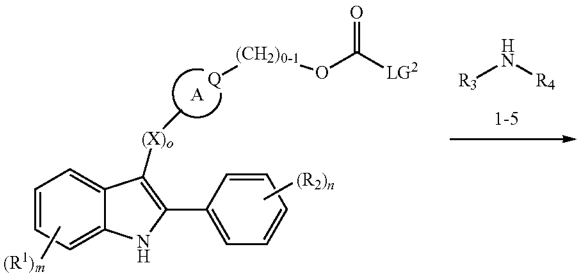

8-2

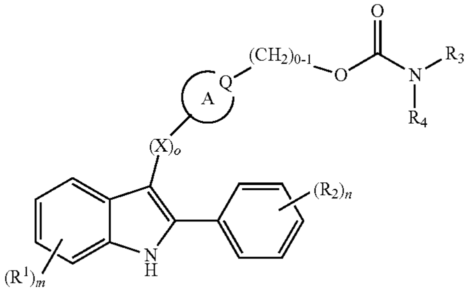

8-3

Scheme 9 shows processes for the preparation of alcohols of formula 9-3. Alcohols of formula 9-3 may be used as compound of formula 8-1. $PG^2$ is any suitable alcohol protecting group. For example, $PG^2$ may be an acetate group. Compounds of formula 9-2 may be prepared by reductive alkylation of compounds of formula 9-1 with indoles of formula 1-4. Any suitable conditions for reductive alkylation may be used. In some embodiments, a reducing agent such as $Et_3SiH$ may be used. An acid such as TFA may be used. The reaction may be performed in a solvent such as dichloromethane. A compound of formula 9-3 may be prepared from a compound of formula 9-2 using and suitable method for the removal of an alcohol protecting group. For example, where $PG^2$ is an acetate group, treatment with a base such as $K_2CO_3$ in a solvent such as methanol may be used to afford compounds of formula 9-3.

Scheme 9

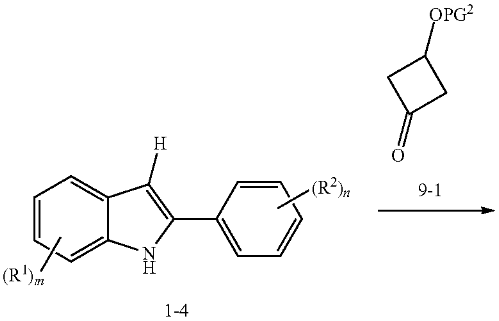

1-4

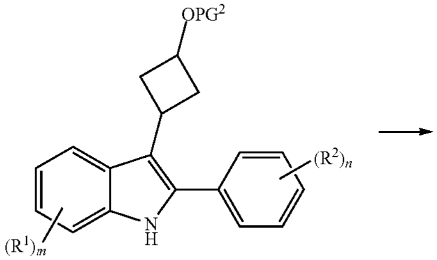

9-2

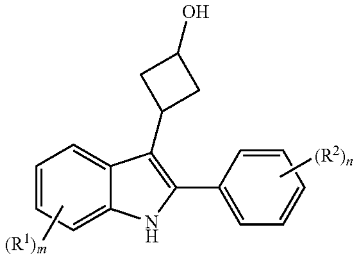

9-3

Scheme 10 shows processes for the preparation of compounds of formula 10-3. Ring A in compounds of formula 10-3 contains a nitrogen atom. A compound of formula 10-3 may be prepared from an amine 10-3 and an isocyanate of formula 10-2. In some embodiments, the reaction may be performed in the presence of a base such as DIPEA. In some embodiments, the reaction is performed in a solvent such as DMSO.

Scheme 10

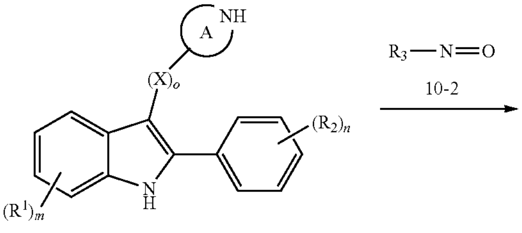

10-1

-continued

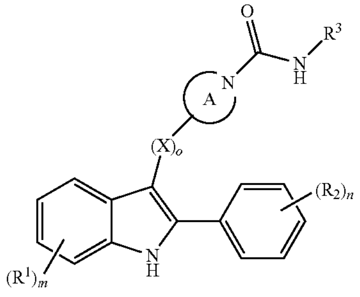

10-3

EXAMPLES

In order that the disclosure described herein may be more fully understood, the following examples are set forth. It should be understood that these examples are for illustrative purposes only and are not to be construed as limiting this disclosure in any manner.

Example 1. Synthesis of Compounds

General Purification and Analysis Methods

Unless otherwise stated, all final products were purified, as necessary, by reversed-phase HPLC (Method: C18 Waters Sunfire column (30×150 mm, 5 micron). Gradient: 10-100% MeCN in $H_2O$. Modifier: 0.2% formic acid or 0.1% Trifluoroacetic acid).

Products were analyzed by LCMS methods A, B, or C. LCMS m/z and retention times were collected.

LCMS Method A: HPLC Sunfire C18 column. Gradient: 2-98% MeCN/$H_2O$ over 3.8 minutes. TFA Modifier.

LCMS Method B: UPLC CSH C18 column. Gradient: 5-95% MeCN/$H_2O$. TFA Modifier.

LCMS Method C: UPLC CSH C18 column. Gradient: 10-60% MeCN/$H_2O$. TFA Modifier.

Preparations of S1-S3

3-[5,7-difluoro-2-(4-fluorophenyl)-1H-indol-3-yl]cyclobutanecarboxylic acid (S1), 3-[5,7-difluoro-2-(4-fluorophenyl)-1H-indol-3-yl]cyclobutanecarboxylic acid [TRANS] (S2) and 3-[5,7-difluoro-2-(4-fluorophenyl)-1H-indol-3-yl]cyclobutanecarboxylic acid [CIS] (S3)

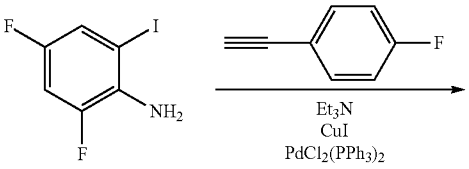

C1

-continued

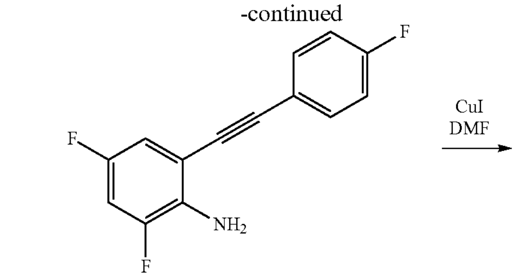

C2

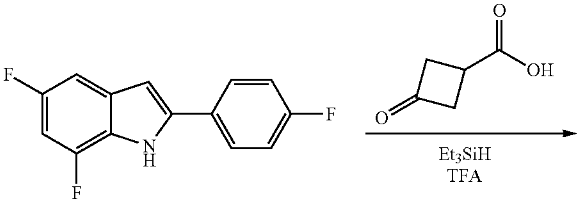

C3

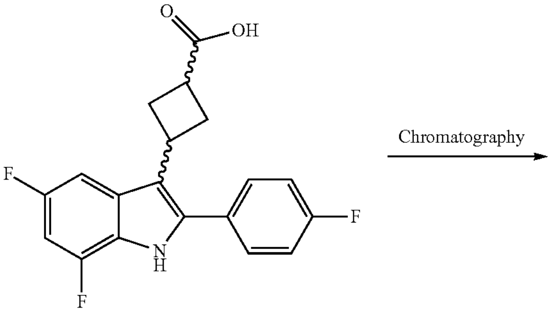

S1

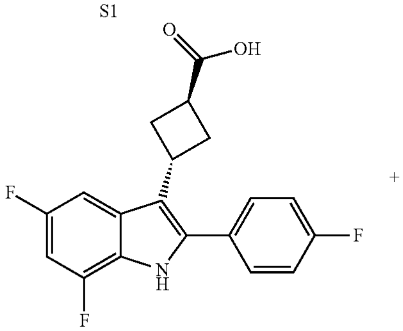

S2

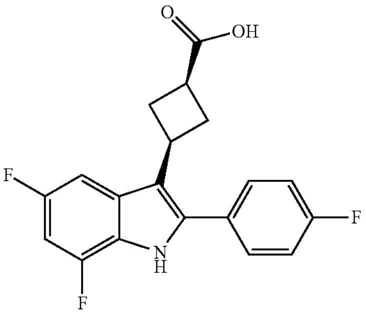

S3

Step 1. Synthesis of 2,4-difluoro-6-[2-(4-fluorophenyl)ethynyl]aniline (C2)

To a flask containing 2,4-difluoro-6-iodo-aniline C2 (134 g, 525.5 mmol) was added $NEt_3$ (1.3 L), followed by DMF (250 mL), 1-ethynyl-4-fluoro-benzene (83.5 g, 695.1 mmol), CuI (20.5 g, 107.6 mmol), and $PdCl_2(PPh_3)_2$ (25 g, 35.6 mmol). The mixture was allowed to stir at room temperature for 2 h. Solvent was removed under reduced pressure and water (500 mL) was added. The mixture was extracted with Ethyl acetate, filtered and concentrated in vacuo. The product mixture was filtered through a silica gel plug (Eluent: $CH_2Cl_2$), followed by a second silica plug filtration (Eluent: 30-40% EtOAc in Heptane). Silica gel chromatography (Gradient: 0-20% EtOAc in heptane) afforded the product as a pale yellow solid. (87 g, 60%). $^1H$ NMR (300 MHz, $CDCl_3$) δ 7.58-7.45 (m, 2H), 7.14-7.02 (m, 2H), 6.92 (ddd, J=8.8, 2.8, 1.7 Hz, 1H), 6.87-6.71 (m, 1H), 4.15 (s, 2H) ppm. LCMS m/z 248.0 $[M+H]^+$.

Step 2. Synthesis of 5,7-difluoro-2-(4-fluorophenyl)-1H-indole (C3)

To a solution of 2,4-difluoro-6-[2-(4-fluorophenyl)ethynyl]aniline C2 (46 g, 167.5 mmol) in DMF (600 mL) was added CuI (1.9 g, 10.0 mmol) and the reaction was heated at reflux. Water (800 mL) was added and the mixture extracted with MTBE. The mixture was then washed with sat. NaCl solution, dried over $Na_2SO_4$ and then concentrated in vacuo to afford the product, which was used in subsequent steps without further purification (41 g, 87%). $^1H$ NMR (300 MHz, $CDCl_3$) δ 8.43 (s, 1H), 7.72-7.58 (m, 2H), 7.27-7.15 (m, 2H), 7.09 (dd, J=9.0, 2.1 Hz, 1H), 6.85-6.63 (m, 2H) ppm. LCMS m/z 248.0 $[M+H]^+$.

Step 3. Synthesis of 3-[5,7-difluoro-2-(4-fluorophenyl)-1H-indol-3-yl]cyclobutanecarboxylic acid (S1)

To a solution of 5,7-difluoro-2-(4-fluorophenyl)-1H-indole (100 mg, 0.4045 mmol) in $CH_2Cl_2$ (5 mL) and added 3-oxocyclobutanecarboxylic acid (47 mg, 0.4119 mmol), $Et_3SiH$ (235 mg, 2.021 mmol) and TFA (230 mg, 2.017 mmol). The reaction mixture was stirred at room temperature overnight, then concentrated and re-dissolved in a water/ethyl acetate mixture. The organic layer was washed with $NaHCO_3$(aq), then dried with $Na_2SO_4$. 3-[5,7-difluoro-2-(4-fluorophenyl)-1H-indol-3-yl]cyclobutanecarboxylic acid (Trifluoroacetate salt) (40 mg, 21%). $^1H$ NMR (300 MHz, DMSO-$d_6$) δ12.20 (s, 1H), 11.72 (d, J=3.9 Hz, 1H), 7.71-7.29 (m, 5H), 7.00 (ddt, J=11.7, 9.8, 2.1 Hz, 1H), 4.14-3.83 (m, 1H), 3.26-2.91 (m, 1H), 2.77-2.54 (m, 2H, obscured by solvent peak) ppm. LCMS m/z 346.22 $[M+H]^+$.

Preparation of 3-[5,7-difluoro-2-(4-fluorophenyl)-1H-indol-3-yl]cyclobutanecarboxylic acid [TRANS] (S2) and 3-[5,7-difluoro-2-(4-fluorophenyl)-1H-indol-3-yl]cyclobutanecarboxylic acid [CIS] (S3)

To a solution of 5,7-difluoro-2-(4-fluorophenyl)-1H-indole (20 g, 80.90 mmol) and 3-oxocyclobutanecarboxylic acid (13.9 g, 121.8 mmol) in $CH_2Cl_2$ (160 mL) was added $Et_3SiH$ (65 mL, 407.0 mmol). TFA (31 mL, 402.4 mmol) was added slowly via an addition funnel while monitoring the temperature. A slight exotherm (2-3° C.) was observed during addition. After 1 h, the temperature rose to 24° C. The mixture was allowed to stir at room temperature overnight. The solvent was removed under reduced pressure, then quenched with saturated $NaHCO_3$ to afford pH 7. The organic layer was separated and washed with brine. Solvent was removed under reduced pressure. Dichloromethane (25 mL) was added and the solids were triturated. The mixture was filtered and solvent removed under reduced pressure. The mixture contained the product as a mixture of cis and trans isomers. Silica gel chromatography (Gradient: 0-20% MeOH in dichloromethane) afforded the product.

SFC Analysis was used to distinguish the cis and trans isomers by chromatography. Column: Daicel Chiralpak® AD-H, 4.6×100 mm. Mobile Phase: 20% Methanol (containing 5 mM Ammonia), 80% carbon dioxide. Flow: 5 mL/min.

Peak A (first eluting peak, retention time 0.86 minutes). Trans isomer.

Peak B (second eluting peak, retention time 0.98 minutes). Cis isomer.

3-[5,7-difluoro-2-(4-fluorophenyl)-1H-indol-3-yl]cyclobutanecarboxylic acid [TRANS] S2 (8.49 g, 30%). $^1H$ NMR (300 MHz, Acetone-$d_6$) δ 10.71 (s, 1H), 7.79-7.56 (m, 2H), 7.45 (dd, J=9.8, 2.2 Hz, 1H), 7.39-7.21 (m, 2H), 6.85 (ddd, J=11.1, 9.6, 2.2 Hz, 1H), 4.14 (pd, J=9.3, 1.3 Hz, 1H), 3.29 (dddd, J=9.4, 7.3, 3.6, 1.3 Hz, 1H), 2.89-2.56 (m, 4H) ppm. LCMS m/z 346.07 $[M+H]^+$.

3-[5,7-difluoro-2-(4-fluorophenyl)-1H-indol-3-yl]cyclobutanecarboxylic acid [CIS] S3 (11.7 g, 42%). $^1H$ NMR (400 MHz, Acetone-$d_6$) δ 10.69 (s, 1H), 7.74-7.56 (m, 3H), 7.37-7.21 (m, 2H), 6.84 (ddd, J=11.1, 9.6, 2.2 Hz, 1H), 3.89 (tt, J=10.2, 8.5 Hz, 1H), 3.19 (tt, J=9.6, 8.4 Hz, 1H), 2.85-2.71 (m, 2H), 2.69-2.55 (m, 2H), 2.05 (m, J=2.2 Hz, 2H) ppm.

Preparation S4

1-Ethynyl-4-fluorobenzene-2,3,5,6-$d_4$ (S4)

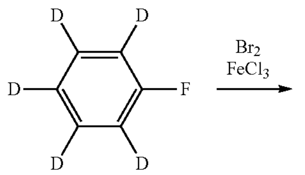

C4

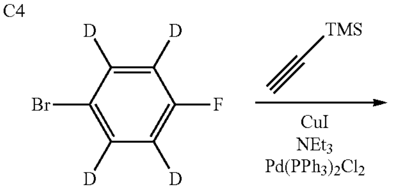

C5

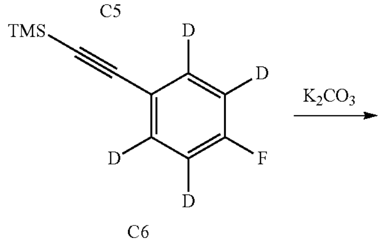

C6

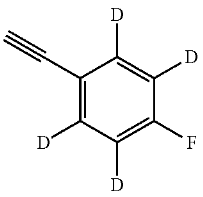

S4

Step 1. Synthesis of 1-Bromo-4-fluorobenzene-2,3,5,6-$d_4$ (C5)

A solution of bromine (34.8 g, 218 mmol, 1.1 equiv) in $CH_2Cl_2$ (40 mL) was added dropwise to a solution of 1-fluorobenzene-2,3,4,5,6-$d_5$ C4 (20 g, 200 mol, 1 equiv) and $FeCl_3$ (0.6 g, 3.7 mmol, 0.02 equiv) in $CH_2Cl_2$ (40 mL) at 18-20° C. After stirring at room temperature for 1.5 h, the mixture was washed with water (3×50 mL), sodium thiosulfate solution (0.72 M, 50 mL) and additional water (50 mL). The organic layer was dried over sodium sulfate and filtered. A small scale run of this reaction (5 g of 1-fluorobenzene-2,3,4,5,6-d) which was processed in same manner was combined for distillation to remove solvent. The combined organic layers were evaporated under atmospheric distillation to remove dichloromethane and then distilled to afford the product (33.3 g, 75% yield, b.p. 150-152° C.) as a colorless oil.

Step 2. Synthesis of ((4-Fluorophenyl-2,3,5,6-$d_4$) ethynyl)trimethylsilane (C6)

(Trimethylsilyl) acetylene (32.9 mL, 232.5 mmol, 1.3 equiv), copper(I) iodide (3.5 g, 18.6 mmol, 0.1 equiv) and $PdCl_2(PPh_3)_2$ (6.5 g, 9.3 mmol, 0.05 equiv) were added to a mixture of 1-Bromo-4-fluorobenzene-2,3,5,6-$d_4$ C5 (33.3 g, 186.0 mmol, 1 equiv) in $NEt_3$ (310 mL) at room temperature. The mixture was purged with nitrogen for 10 minutes, then stirred at 70-80° C. for 18 h. After cooling to room temperature, the mixture was diluted with EtOAc (300 mL), filtered through Celite®, which was washed with EtOAc (2×100 mL). The filtrate was concentrated under reduced pressure at 30° C. to afford the product (45.3 g) as a dark-brown oil, which was used subsequently.

Step 3. Synthesis of 1-Ethynyl-4-fluorobenzene-2,3,5,6-$d_4$ (S4)

Potassium carbonate (128.5 g, 930 mmol, 5 equiv) was added to a mixture of ((4-Fluorophenyl-2,3,5,6-$d_4$)ethynyl) trimethylsilane C6 (45.3 g, 186 mmol, 1 equiv) in MeOH (620 mL) at room temperature. The mixture was stirred at room temperature for 2 h. The mixture was filtered through Celite®, washing with MeOH (50 mL) and hexanes (3×50 mL). The filtrate was diluted with water (2000 mL) and separated. The aqueous layer was extracted with hexanes (3×500 mL). The combined organic layers were washed with water (200 mL), dried over sodium sulfate, filtered and concentrated under reduced pressure (50 mbar, 5° C.) to give the product (30 g, theoretical yield 23.09 g) as a dark oil. (Note: 1-Ethynyl-4-fluorobenzene-2,3,5,6-$d_4$ is volatile, and it was co-distilled with other solvents (MeOH, hexanes) under reduced pressure or under atmospheric distillation. The crude 1-Ethynyl-4-fluorobenzene-2,3,5,6-$d_4$ S4 was used in next step without column purification in order to minimize the loss during evaporation of solvents.)

Compound 1

N-(2-amino-2-oxo-ethyl)-3-[5,7-difluoro-2-(4-fluorophenyl)-1H-indol-3-yl]cyclobutanecarboxamide (1)

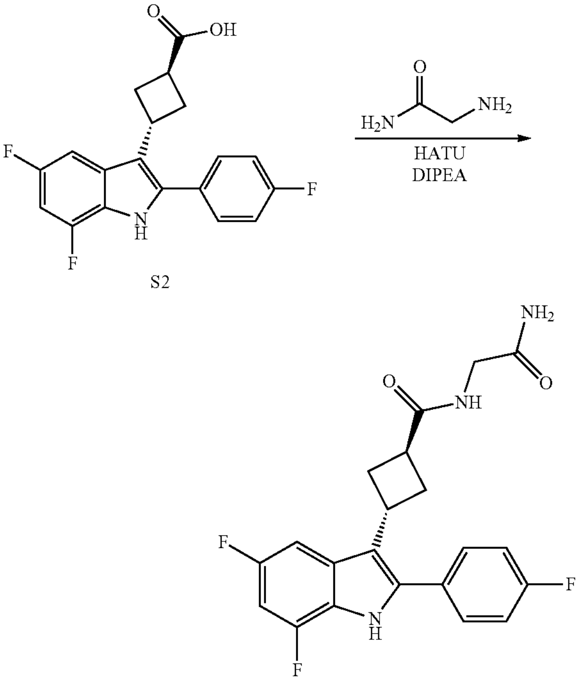

S2

1

To a solution of 3-[5,7-difluoro-2-(4-fluorophenyl)-1H-indol-3-yl]cyclobutanecarboxylic acid (130 g, 376.5 mmol) in DMF (920 mL) was added HATU (217 g, 570.7 mmol) and the mixture stirred for 10 min. The reaction was cooled to 5° C. on an ice bath. 2-aminoacetamide (Hydrochloride salt) (48 g, 434.2 mmol) and DIPEA (197 mL, 1.131 mol) were added slowly via an addition funnel maintaining the temperature below 30° C. The ice bath was removed and stirred for 1 h at room temperature. The mixture was quenched with sat $NaHCO_3$ (2 L) and EtOAc (1 L) was added. The product crystallized out during the quench. The solids were filtered off and washed with water (1 L). The filtrate layers were separated and washed with EtOAc (1 L), then combined organic layers were washed with water (2 L) and brine (2 L). The product precipitated out of the organic layer and the solids were filtered off. The filtrate was concentrated by 90% of the original volume under reduced pressure (no additional product). The combined solid was slurried in 4:1 water/acetone (500 mL) for 12 h. The solids were filtered, washed with water (400 mL) and dried overnight in vacuum oven at 55° C. N-(2-amino-2-oxo-ethyl)-3-[5,7-difluoro-2-(4-fluorophenyl)-1H-indol-3-yl]cyclobutanecarboxamide (109.75 g, 72%). $^1H$ NMR (300 MHz, Methanol-$d_4$) δ 7.56-7.44 (m, 2H), 7.32 (dd, J=9.7, 2.2 Hz, 1H), 7.20 (t, J=8.8 Hz, 2H), 6.74 (ddd, J=11.0, 9.6, 2.2 Hz, 1H), 4.18-4.02 (m, 1H), 3.88 (s, 2H), 3.25 (dtd, J=9.2, 4.9, 2.3 Hz, 1H), 2.75-2.56 (m, 4H) ppm. LCMS m/z 402.24 $[M+H]^+$. SFC analysis indicates 99:1 trans/cis ratio (Column: Daicel Chiralpak® AD-H, 10×250 mm; Mobile Phase: 40% MeOH (containing 5 mM Ammonia), 70% carbon dioxide. Flow: 75 mL/min).

Trans stereochemistry was confirmed by single crystal X-ray structure.

Compounds 2-45

Compounds 2-45 (Table 3) were prepared from S2 and a commercially available amine by HATU coupling as described in standard procedure A.

Standard Procedure A. HATU Coupling of Amines

To a solution of 3-[5,7-difluoro-2-(4-fluorophenyl)-1H-indol-3-yl]cyclobutanecarboxylic acid S2 (25 mg, 0.07 mmol) in DMF (2 mL) and amine (0.07 mmol), HATU (~36 mg, 0.09 mmol) and $Et_3N$ (approximately 7.3 mg, 10.1 μL, 0.07 mmol). The reaction mixture was stirred at room temperature overnight. The reaction mixture was filtered and purified by reversed-phase HPLC. Method: C18 Waters Sunfire column (30×150 mm, 5 micron). Gradient: MeCN in $H_2O$ with 0.1% trifluoroacetic acid.

TABLE 3

Structure, physicochemical properties, and LCMS analysis for compounds 2-45

| Compound | Structure | $^1H$ NMR (ppm); LCMS m/z $[M + H]^+$ | LCMS Method; LCMS retention time (min) |
|---|---|---|---|
| 2 | 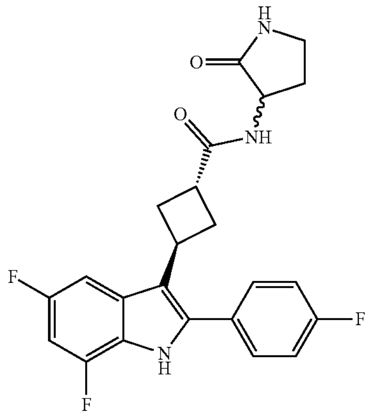 [SMILES: O=C1NCCC1NC(=O)[C@H]1C[C@H](c2c(-c3ccc(F)cc3)[nH]c3c(F)cc(F)cc32)C1] | LCMS m/z 428.16 $[M + H]^+$ | A; 3.32 |
| 3 | 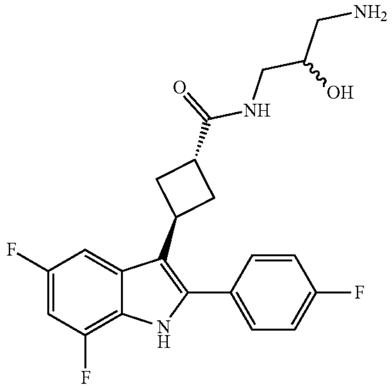 [SMILES: NCC(O)CNC(=O)[C@H]1C[C@H](c2c(-c3ccc(F)cc3)[nH]c3c(F)cc(F)cc32)C1] | LCMS m/z 418.16 $[M + H]^+$ | A; 2.66 |
| 4 | 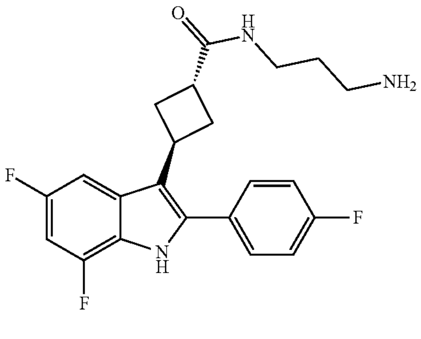 [SMILES: NCCCNC(=O)[C@H]1C[C@H](c2c(-c3ccc(F)cc3)[nH]c3c(F)cc(F)cc32)C1] | LCMS m/z 402.2 $[M + H]^+$ | A; 2.7 |

TABLE 3-continued
| Compound | Structure | $^1H$ NMR (ppm); LCMS m/z $[M + H]^+$ | LCMS Method; LCMS retention time (min) |
|---|---|---|---|
| Structure, physicochemical properties, and LCMS analysis for compounds 2-45 | | | |
| 5 | 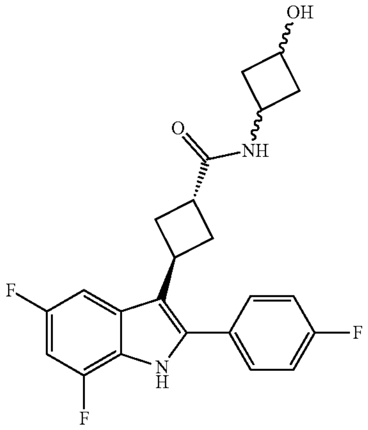 [SMILES: O=C(NC1CC(O)C1)[C@H]1C[C@H](c2c(-c3ccc(F)cc3)[nH]c3c(F)cc(F)cc32)C1] | LCMS m/z 415.19 $[M + H]^+$ | A; 3.41 |
| 6 | 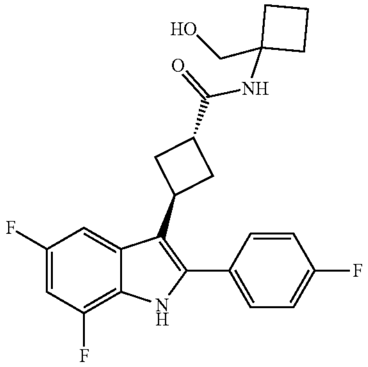 [SMILES: O=C(NC1(CO)CCC1)[C@H]1C[C@H](c2c(-c3ccc(F)cc3)[nH]c3c(F)cc(F)cc32)C1] | LCMS m/z 429.17 $[M + H]^+$ | A; 3.8 |
| 7 | 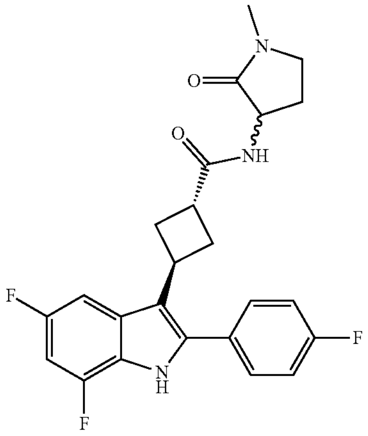 [SMILES: CN1CCC(NC(=O)[C@H]2C[C@H](c3c(-c4ccc(F)cc4)[nH]c4c(F)cc(F)cc43)C2)C1=O] | LCMS m/z 442.17 $[M + H]^+$ | A; 3.46 |

TABLE 3-continued
| Compound | Structure | ¹H NMR (ppm); LCMS m/z [M + H]⁺ | LCMS Method; LCMS retention time (min) |
|---|---|---|---|
| Structure, physicochemical properties, and LCMS analysis for compounds 2-45 | | | |
| 8 | 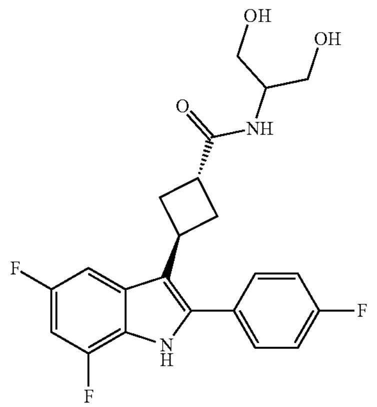 [SMILES: O=C(NC(CO)CO)[C@H]1C[C@H](c2c(-c3ccc(F)cc3)[nH]c3c(F)cc(F)cc32)C1] | LCMS m/z 419.17 [M + H]⁺ | A; 3.14 |
| 9 | 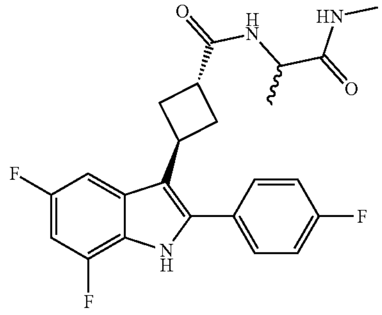 [SMILES: CNC(=O)C(C)NC(=O)[C@H]1C[C@H](c2c(-c3ccc(F)cc3)[nH]c3c(F)cc(F)cc32)C1] | LCMS m/z 430.18 [M + H]⁺ | A; 3.44 |
| 10 | 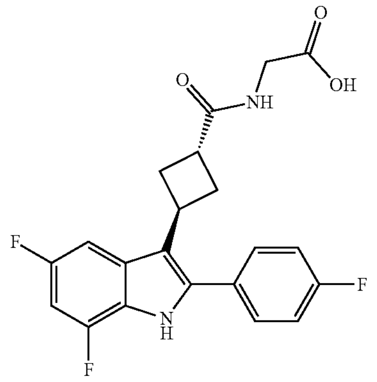 [SMILES: O=C(O)CNC(=O)[C@H]1C[C@H](c2c(-c3ccc(F)cc3)[nH]c3c(F)cc(F)cc32)C1] | LCMS m/z 403.14 [M + H]⁺ | A; 3.42 |
| 11 | 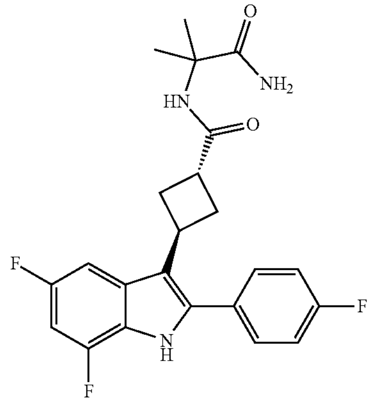 [SMILES: CC(C)(NC(=O)[C@H]1C[C@H](c2c(-c3ccc(F)cc3)[nH]c3c(F)cc(F)cc32)C1)C(N)=O] | LCMS m/z 430.18 [M + H]⁺ | A; 3.42 |

TABLE 3-continued
| Compound | Structure | $^1$H NMR (ppm); LCMS m/z $[M + H]^+$ | LCMS Method; LCMS retention time (min) |
| --- | --- | --- | --- |
| Structure, physicochemical properties, and LCMS analysis for compounds 2-45 | | | |
| 12 | 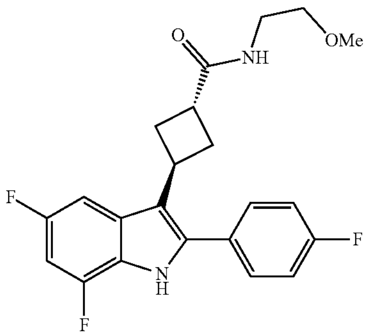 [SMILES: COCCNC(=O)[C@H]1C[C@H](c2c(-c3ccc(F)cc3)[nH]c3c(F)cc(F)cc32)C1] | LCMS m/z 403.17 $[M + H]^+$ | A; 3.8 |
| 13 | 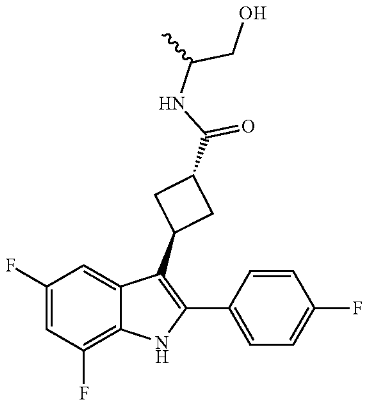 [SMILES: CC(CO)NC(=O)[C@H]1C[C@H](c2c(-c3ccc(F)cc3)[nH]c3c(F)cc(F)cc32)C1] | LCMS m/z 403.17 $[M + H]^+$ | A; 3.5 |
| 14 | 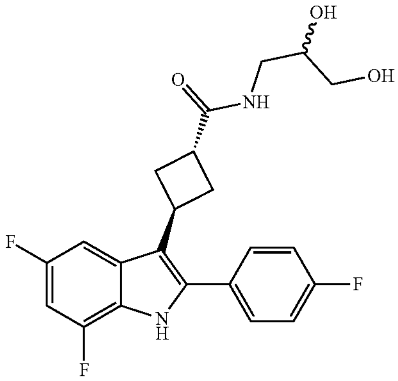 [SMILES: O=C(NCC(O)CO)[C@H]1C[C@H](c2c(-c3ccc(F)cc3)[nH]c3c(F)cc(F)cc32)C1] | LCMS m/z 419.17 $[M + H]^+$ | A; 3.16 |
| 15 | 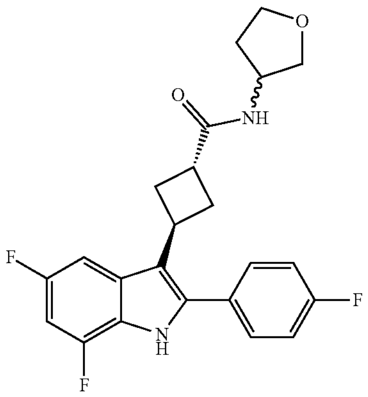 [SMILES: O=C(NC1CCOC1)[C@H]1C[C@H](c2c(-c3ccc(F)cc3)[nH]c3c(F)cc(F)cc32)C1] | LCMS m/z 415.16 $[M + H]^+$ | A; 3.72 |

TABLE 3-continued
| Structure, physicochemical properties, and LCMS analysis for compounds 2-45 | | | |
|---|---|---|---|
| Compound | Structure | $^1$H NMR (ppm); LCMS m/z $[M + H]^+$ | LCMS Method; LCMS retention time (min) |
| 16 | 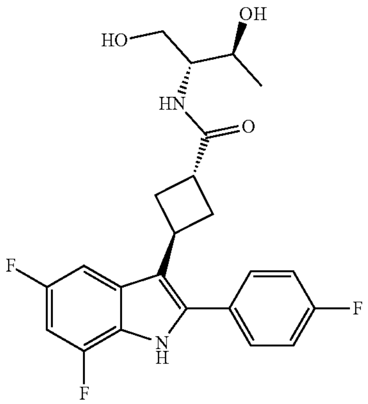 [SMILES: C[C@H](O)[C@@H](CO)NC(=O)[C@H]1C[C@H](c2c(-c3ccc(F)cc3)[nH]c3c(F)cc(F)cc32)C1] | LCMS m/z 433.18 $[M + H]^+$ | A; 3.24 |
| 17 | 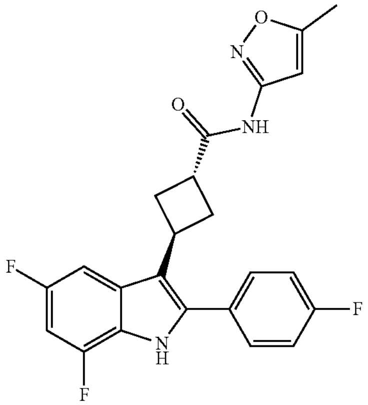 [SMILES: Cc1cc(NC(=O)[C@H]2C[C@H](c3c(-c4ccc(F)cc4)[nH]c4c(F)cc(F)cc43)C2)no1] | LCMS m/z 426.14 $[M + H]^+$ | A; 4.12 |
| 18 | 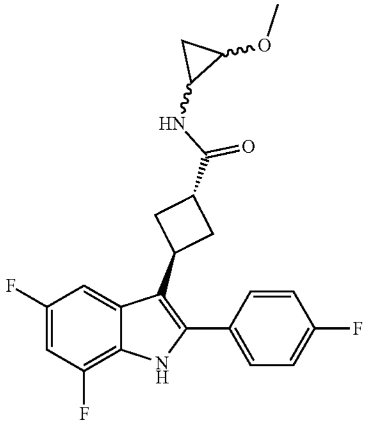 [SMILES: COC1CC1NC(=O)[C@H]1C[C@H](c2c(-c3ccc(F)cc3)[nH]c3c(F)cc(F)cc32)C1] | LCMS m/z 415.16 $[M + H]^+$ | A; 3.84 |

TABLE 3-continued
| Structure, physicochemical properties, and LCMS analysis for compounds 2-45 | | | |
|---|---|---|---|
| Compound | Structure | $^1H$ NMR (ppm); LCMS m/z $[M + H]^+$ | LCMS Method; LCMS retention time (min) |
| 19 | 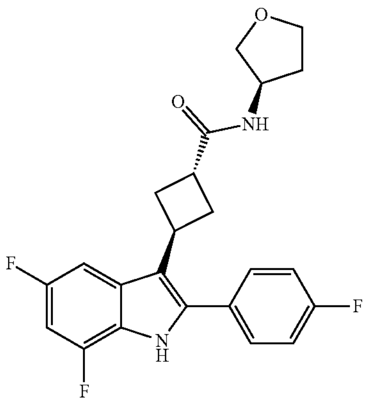 [SMILES: O=C(N[C@@H]1CCOC1)[C@H]1C[C@H](c2c(-c3ccc(F)cc3)[nH]c3c(F)cc(F)cc32)C1] | LCMS m/z 415.16 $[M + H]^+$ | A; 3.72 |
| 20 | 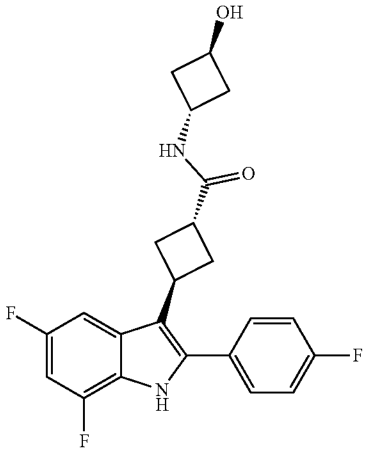 [SMILES: O=C(N[C@H]1C[C@H](O)C1)[C@H]1C[C@H](c2c(-c3ccc(F)cc3)[nH]c3c(F)cc(F)cc32)C1] | LCMS m/z 415.19 $[M + H]^+$ | A; 3.38 |
| 21 | 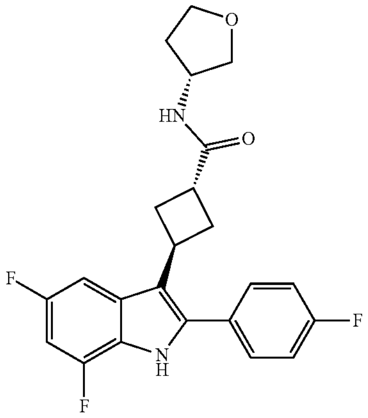 [SMILES: O=C(N[C@@H]1CCOC1)[C@H]1C[C@H](c2c(-c3ccc(F)cc3)[nH]c3c(F)cc(F)cc32)C1] | LCMS m/z 415.19 $[M + H]^+$ | A; 3.67 |

TABLE 3-continued
| Structure, physicochemical properties, and LCMS analysis for compounds 2-45 | | | |
|---|---|---|---|
| Compound | Structure | $^1$H NMR (ppm); LCMS m/z $[M + H]^+$ | LCMS Method; LCMS retention time (min) |
| 22 | 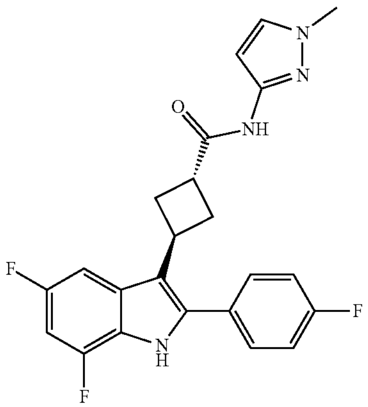 [SMILES: Cn1ccc(NC(=O)[C@H]2C[C@H](c3c(-c4ccc(F)cc4)[nH]c4c(F)cc(F)cc43)C2)n1] | LCMS m/z 425.19 $[M + H]^+$ | A; 3.81 |
| 23 | 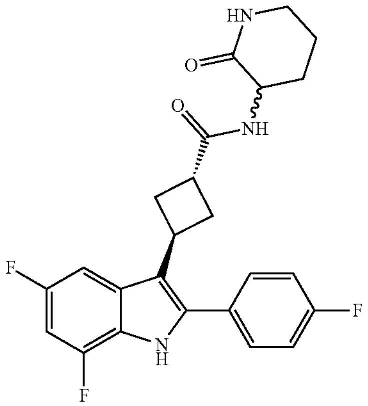 [SMILES: O=C1NCCCC1NC(=O)[C@H]1C[C@H](c2c(-c3ccc(F)cc3)[nH]c3c(F)cc(F)cc32)C1] | LCMS m/z 442.17 $[M + H]^+$ | A; 3.42 |
| 24 | 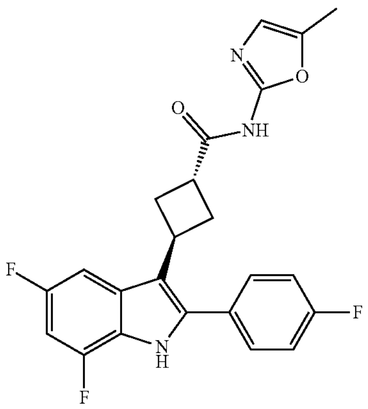 [SMILES: Cc1cnc(NC(=O)[C@H]2C[C@H](c3c(-c4ccc(F)cc4)[nH]c4c(F)cc(F)cc43)C2)o1] | LCMS m/z 426.17 $[M + H]^+$ | A; 3.18 |

TABLE 3-continued
| Structure, physicochemical properties, and LCMS analysis for compounds 2-45 | | | |
|---|---|---|---|
| Compound | Structure | $^1$H NMR (ppm); LCMS m/z $[M + H]^+$ | LCMS Method; LCMS retention time (min) |
| 25 | 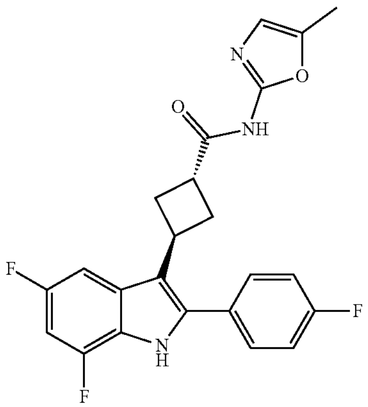 | LCMS m/z 433.18 $[M + H]^+$ | A; 3.24 |
| 26 | 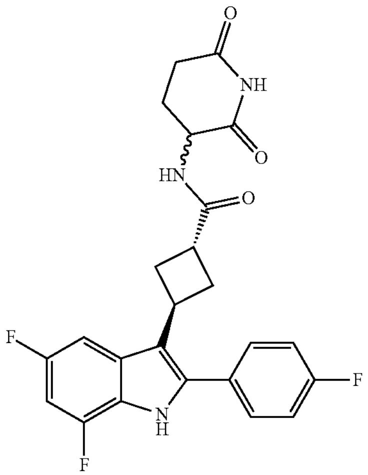 [SMILES: O=C1CCC(NC(=O)[C@H]2C[C@H](c3c(-c4ccc(F)cc4)[nH]c4c(F)cc(F)cc43)C2)C(=O)N1] | LCMS m/z 456.14 $[M + H]^+$ | A; 3.46 |
| 27 | 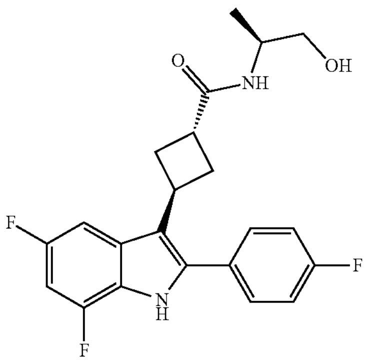 [SMILES: C[C@@H](CO)NC(=O)[C@H]1C[C@H](c2c(-c3ccc(F)cc3)[nH]c3c(F)cc(F)cc32)C1] | LCMS m/z 403.17 $[M + H]^+$ | A; 3.48 |

TABLE 3-continued
| Structure, physicochemical properties, and LCMS analysis for compounds 2-45 | | | |
|---|---|---|---|
| Compound | Structure | $^1$H NMR (ppm); LCMS m/z [M + H]$^+$ | LCMS Method; LCMS retention time (min) |
| 28 | 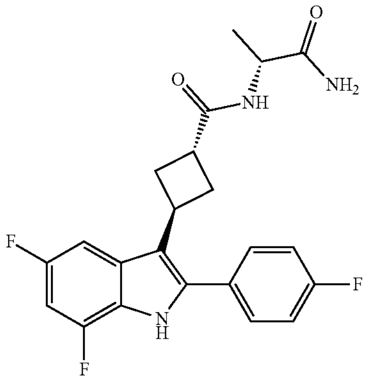 [SMILES: C[C@@H](NC(=O)[C@H]1C[C@H](c2c(-c3ccc(F)cc3)[nH]c3c(F)cc(F)cc32)C1)C(N)=O] | LCMS m/z 416.04 [M + H]$^+$ | A; 3.32 |
| 29 | 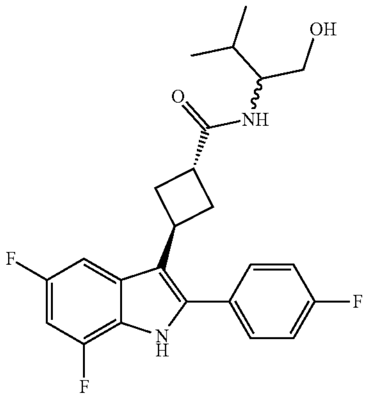 [SMILES: CC(C)C(CO)NC(=O)[C@H]1C[C@H](c2c(-c3ccc(F)cc3)[nH]c3c(F)cc(F)cc32)C1] | LCMS m/z 431.19 [M + H]$^+$ | A; 3.8 |
| 30 | 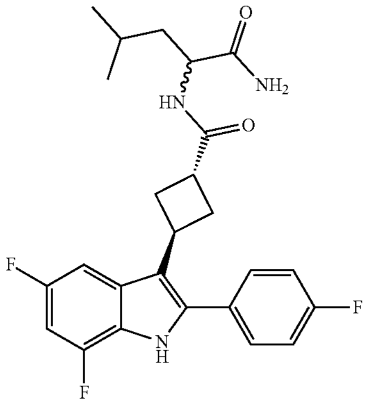 [SMILES: CC(C)CC(NC(=O)[C@H]1C[C@H](c2c(-c3ccc(F)cc3)[nH]c3c(F)cc(F)cc32)C1)C(N)=O] | LCMS m/z 458.32 [M + H]$^+$ | A; 3.74 |

TABLE 3-continued
| Structure, physicochemical properties, and LCMS analysis for compounds 2-45 | | | |
|---|---|---|---|
| Compound | Structure | $^1$H NMR (ppm); LCMS m/z $[M + H]^+$ | LCMS Method; LCMS retention time (min) |
| 31 | 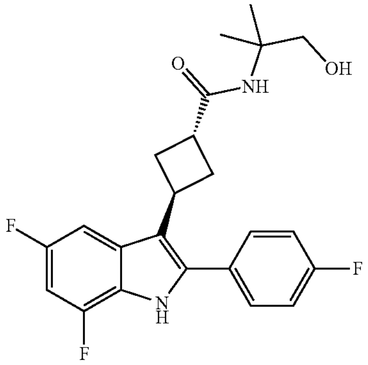 [SMILES: CC(C)(CO)NC(=O)[C@H]1C[C@H](c2c(-c3ccc(F)cc3)[nH]c3c(F)cc(F)cc32)C1] | LCMS m/z 417.18 $[M + H]^+$ | A; 3.84 |
| 32 | 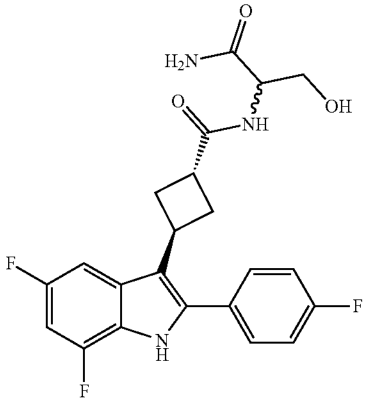 [SMILES: NC(=O)C(CO)NC(=O)[C@H]1C[C@H](c2c(-c3ccc(F)cc3)[nH]c3c(F)cc(F)cc32)C1] | LCMS m/z 432.13 $[M + H]^+$ | A; 3.07 |
| 33 | 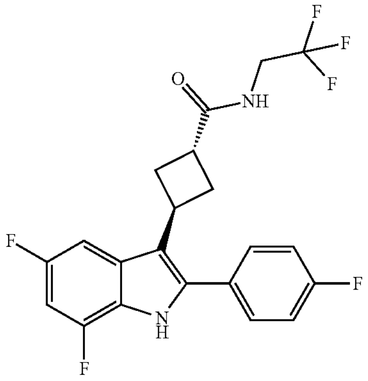 [SMILES: O=C(NCC(F)(F)F)[C@H]1C[C@H](c2c(-c3ccc(F)cc3)[nH]c3c(F)cc(F)cc32)C1] | LCMS m/z 427.21 $[M + H]^+$ | A; 4.09 |

TABLE 3-continued
| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds 2-45 | | | |
| 34 | 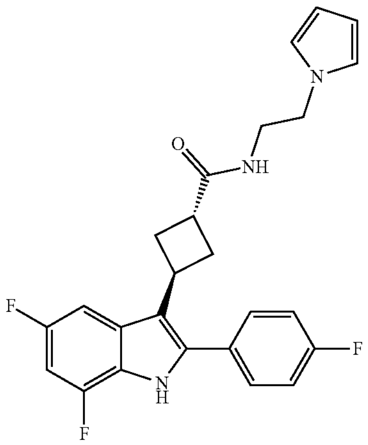 [SMILES: O=C(NCCn1cccc1)[C@H]1C[C@H](c2c(-c3ccc(F)cc3)[nH]c3c(F)cc(F)cc32)C1] | LCMS m/z 438.16 [M + H]$^+$ | A; 4.05 |
| 35 | 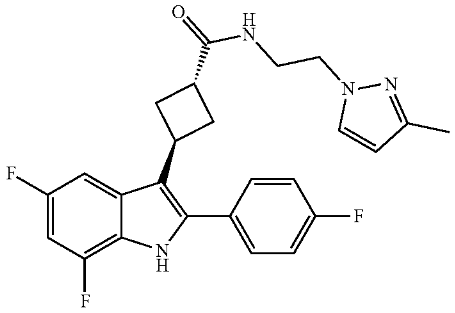 [SMILES: Cc1ccn(CCNC(=O)[C@H]2C[C@H](c3c(-c4ccc(F)cc4)[nH]c4c(F)cc(F)cc43)C2)n1] | LCMS m/z 453.21 [M + H]$^+$ | A; 3.48 |
| 36 | 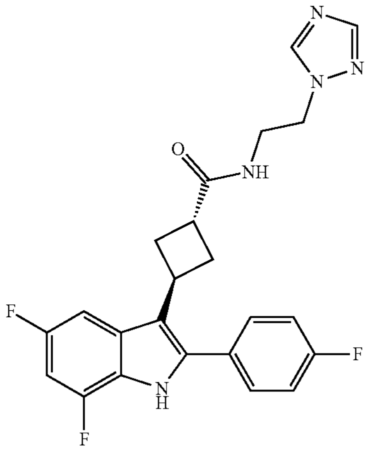 [SMILES: O=C(NCCn1cncn1)[C@H]1C[C@H](c2c(-c3ccc(F)cc3)[nH]c3c(F)cc(F)cc32)C1] | LCMS m/z 440.15 [M + H]$^+$ | A; 3.25 |

TABLE 3-continued
| Structure, physicochemical properties, and LCMS analysis for compounds 2-45 | | | |
|---|---|---|---|
| Compound | Structure | $^1$H NMR (ppm); LCMS m/z $[M + H]^+$ | LCMS Method; LCMS retention time (min) |
| 37 | 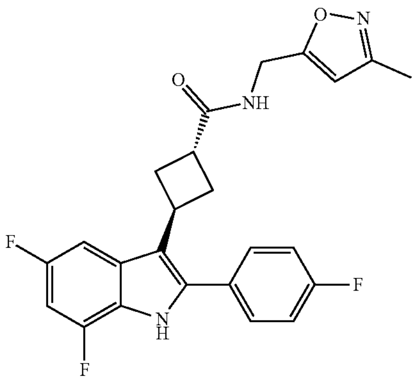 [SMILES: Cc1cc(CNC(=O)[C@H]2C[C@H](c3c(-c4ccc(F)cc4)[nH]c4c(F)cc(F)cc43)C2)on1] | LCMS m/z 440.15 $[M + H]^+$ | A; 3.82 |
| 38 | 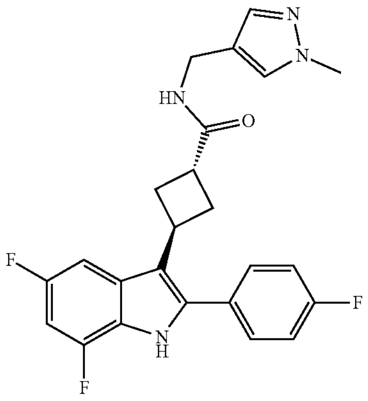 [SMILES: Cn1cc(CNC(=O)[C@H]2C[C@H](c3c(-c4ccc(F)cc4)[nH]c4c(F)cc(F)cc43)C2)cn1] | LCMS m/z 439.17 $[M + H]^+$ | A; 3.53 |
| 39 | 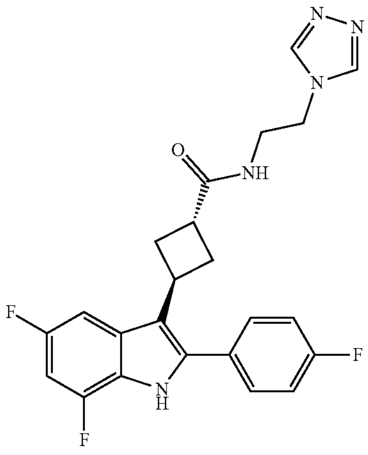 [SMILES: O=C(NCCn1cnnc1)[C@H]1C[C@H](c2c(-c3ccc(F)cc3)[nH]c3c(F)cc(F)cc32)C1] | LCMS m/z 440.15 $[M + H]^+$ | A; 2.87 |

TABLE 3-continued
Structure, physicochemical properties, and LCMS analysis for compounds 2-45
| Compound | Structure | $^1$H NMR (ppm); LCMS m/z $[M + H]^+$ | LCMS Method; LCMS retention time (min) |
| --- | --- | --- | --- |
| 40 | 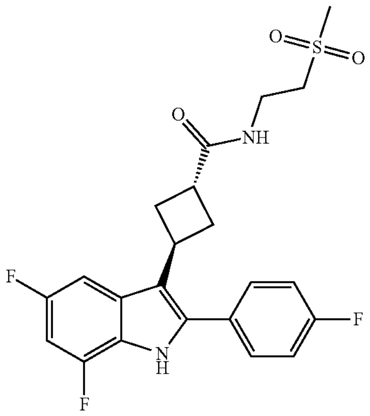 [SMILES: CS(=O)(=O)CCNC(=O)[C@H]1C[C@H](c2c(-c3ccc(F)cc3)[nH]c3c(F)cc(F)cc32)C1] | LCMS m/z 451.26 $[M + H]^+$ | B; 0.81 |
| 41 | 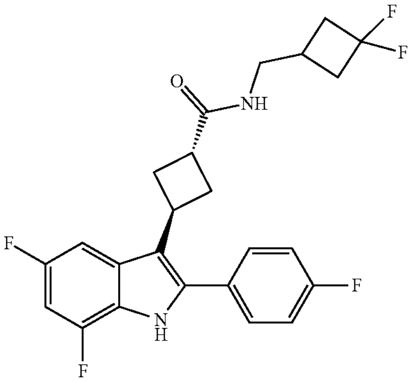 [SMILES: O=C(NCC1CC(F)(F)C1)[C@H]1C[C@H](c2c(-c3ccc(F)cc3)[nH]c3c(F)cc(F)cc32)C1] | LCMS m/z 449.14 $[M + H]^+$ | A; 4.12 |
| 42 | 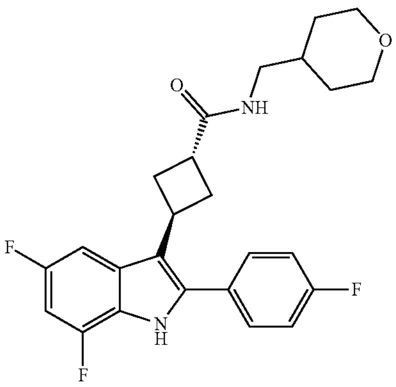 [SMILES: O=C(NCC1CCOCC1)[C@H]1C[C@H](c2c(-c3ccc(F)cc3)[nH]c3c(F)cc(F)cc32)C1] | LCMS m/z 443.18 $[M + H]^+$ | A; 3.82 |

TABLE 3-continued
Structure, physicochemical properties, and LCMS analysis for compounds 2-45
| Compound | Structure | $^1$H NMR (ppm); LCMS m/z $[M + H]^+$ | LCMS Method; LCMS retention time (min) |
|---|---|---|---|
| 43 | 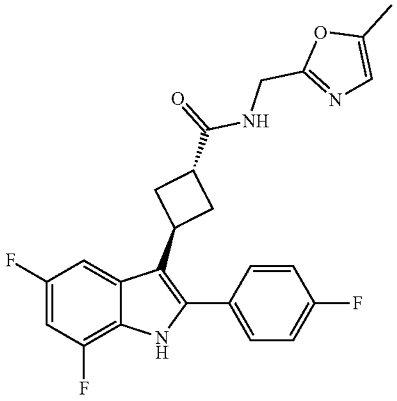 [SMILES: Cc1cnc(CNC(=O)[C@H]2C[C@H](c3c(-c4ccc(F)cc4)[nH]c4c(F)cc(F)cc43)C2)o1] | LCMS m/z 440.02 $[M + H]^+$ | A; 3.74 |
| 44 | 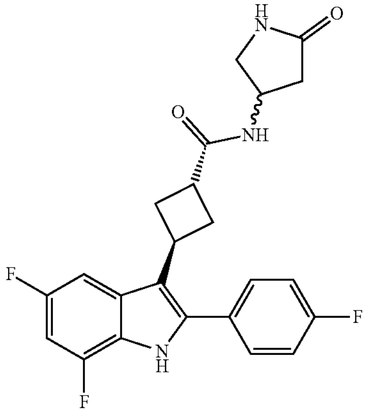 | LCMS m/z 428.29 $[M + H]^+$ | A; 3.23 |
| 45 | 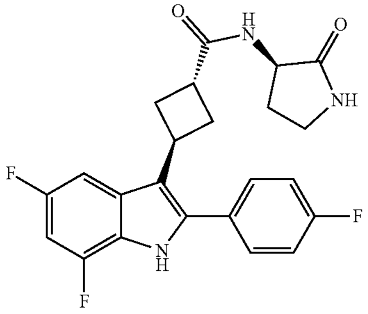 [SMILES: O=C1NCC[C@H]1NC(=O)[C@H]1C[C@H](c2c(-c3ccc(F)cc3)[nH]c3c(F)cc(F)cc32)C1] | $^1$H NMR (300 MHz, Methanol-$d_4$) δ 7.56 – 7.40 (m, 2H), 7.32 (dd, J = 9.8, 2.2 Hz, 1H), 7.27 – 7.07 (m, 2H), 6.74 (ddd, J = 11.1, 9.6, 2.2 Hz, 1H), 4.52 (dd, J = 10.3, 8.8 Hz, 1H), 4.11 (m, 1H), 3.41 – 3.32 (m, 2H), 3.24 – 3.13 (m, 1H), 2.79 – 2.61 (m, 3H), 2.58 – 2.38 (m, 1H), 2.04 – 1.87 (m, 1H). LCMS m/z 428.16 $[M + H]^+$ | A; 3.32 |

Compound 46

3-[5,7-difluoro-2-(4-fluorophenyl)-1H-indol-3-yl]-N-(2-hydroxyethyl)cyclobutanecarboxamide (46

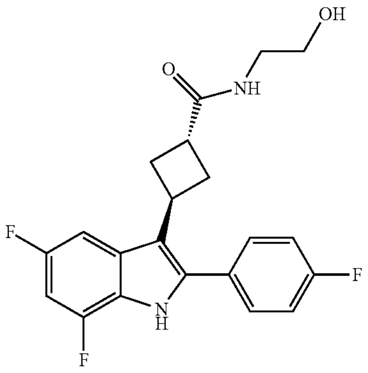 [SMILES: O=C(NCCO)[C@H]1C[C@H](c2c(-c3ccc(F)cc3)[nH]c3c(F)cc(F)cc32)C1]

A 250 mL round bottom flask was charged with a magnetic stir bar, 3-[5,7-difluoro-2-(4-fluorophenyl)-1H-indol-3-yl]cyclobutanecarboxylic acid (5.63 g, 16.3 mmol), DMF (30 mL), DIPEA (8.5 g, 65.77 mmol), ethanolamine (2.2 g, 36.02 mmol) and HATU (12 g, 31.56 mmol). The reaction was allowed to stir at room temperature. The mixture was diluted with water (~250 mL) and extracted with EtOAc (2×200 mL). The combined organic extracts were washed with water (200 mL), brine (~200 mL), and dried with $MgSO_4$. The mixture was filtered and concentrated in vacuo to a volume of 50 mL. The product formed a white precipitate which was collected via vacuum filtration using Buchner funnel. The filter cake was washed with EtOAc, collected and dried under vacuum to afford 3-[5,7-difluoro-2-(4-fluorophenyl)-1H-indol-3-yl]-N-(2-hydroxyethyl) cyclobutanecarboxamide (4.86 g, 770). $^1H$ NMR (300 MHz, Acetone) 610.69 (s, 1H), 7.77-7.51 (m, 2H), 7.41 (dd, J=9.8, 2.2 Hz, 1H), 7.36-7.21 (m, 2H), 7.11 (s, 1H), 6.85 (ddd, J=11.1, 9.7, 2.2 Hz, 1H), 4.25-3.99 (m, 1H), 3.94 (td, J=5.5, 0.7 Hz, 1H), 3.60 (q, J=5.5 Hz, 2H), 3.34 (q, J=5.6 Hz, 2H), 3.29-3.11 (m, 1H), 2.71-2.46 (m, 4H) ppm. LCMS m/z 389.29 $[M+H]^+$.

Compounds 47-48

Compounds 47-48 (Table 4) were prepared by coupling of S2and the appropriate commercially available amine according to standard procedure A.

TABLE 4

Structure, physicochemical properties, and LCMS analysis for compounds 47-48

| Compound | Structure | $^1H$ NMR (ppm); LCMS m/z $[M + H]^+$ | LCMS Method; LCMS retention time (min) |
|---|---|---|---|
| 47[(1)] | 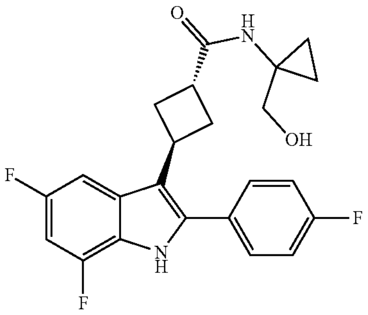 [SMILES: O=C(NC1(CO)CC1)[C@H]1C[C@H](c2c(-c3ccc(F)cc3)[nH]c3c(F)cc(F)cc32)C1] | $^1H$ NMR (300 MHz, Acetone-$d_6$) δ 10.69 (s, 1H), 7.69-7.57 (m, 2H), 7.38 (dd, J = 9.8, 2.2 Hz, 1H), 7.35-7.21 (m, 2H), 6.85 (ddd, J = 11.1, 9.7, 2.2 Hz, 1H), 4.21-4.03 (m, 1H), 3.54 (s, 1H), 3.27 (s, 2H), 3.24-3.08 (m, 1H), 2.61 (ddd, J = 9.7, 6.7, 3.0 Hz, 3H), 0.90-0.65 (m, 3H). LCMS m/z 415.2 $[M + H]^+$ | A; 2.195 |
| 48 | 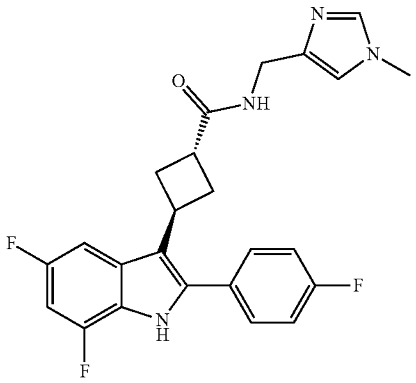 [SMILES: Cn1cnc(CNC(=O)[C@H]2C[C@H](c3c(-c4ccc(F)cc4)[nH]c4c(F)cc(F)cc43)C2)c1] | $^1H$ NMR (300 MHz, Acetone) δ 8.80 (s, 1H), 7.77-7.54 (m, 2H), 7.54-7.36 (m, 2H), 7.39-7.15 (m, 2H), 6.84 (ddd, J = 11.5, 9.7, 2.2 Hz, 1H), 4.52 (d, J = 4.1 Hz, 2H), 4.27-4.08 (m, 1H), 4.04 (s, 3H), 3.29-2.81 (m, 2H), 2.84-2.43 (m, 3H). LCMS m/z 439.185 $[M + H]^+$ | A; 1.73 |

(1)Purification by reversed-phase chromatography (Column: C18. Gradient: 0-100% MeCN in water with 0.1% trifluoroacetic acid) afforded the product. DIPEA was used as the base in the coupling reaction.

Compounds 49-82

Compounds 49-82 (Table 5) were prepared from S2 and the appropriate commercially available amine by HATU coupling according to standard procedure A.

TABLE 5

Structure, physicochemical properties, and LCMS analysis for compounds 49-82

| Compound | Structure | $^1$H NMR (ppm); LCMS m/z [M + H]$^+$ | LCMS Method; LCMS retention time (min) |
|---|---|---|---|
| 49 | 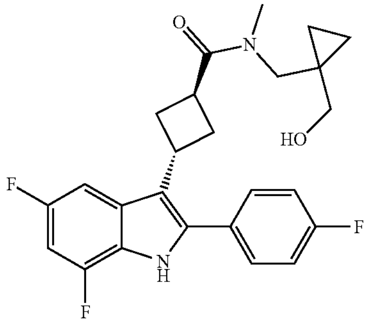 [SMILES: CN(CC1(CO)CC1)C(=O)[C@H]1C[C@H](c2c(-c3ccc(F)cc3)[nH]c3c(F)cc(F)cc32)C1] | LCMS m/z 443.18 [M + H]$^+$ | A; 4.02 |
| 50 | 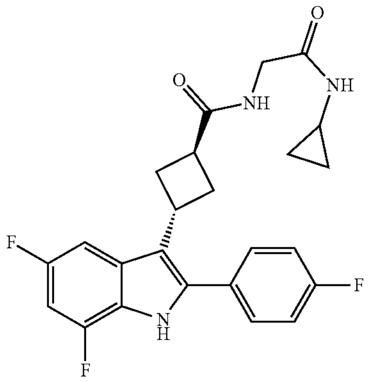 [SMILES: O=C(CNC(=O)[C@H]1C[C@H](c2c(-c3ccc(F)cc3)[nH]c3c(F)cc(F)cc32)C1)NC1CC1] | LCMS m/z 442.17 [M + H]$^+$ | A; 3.49 |
| 51 | 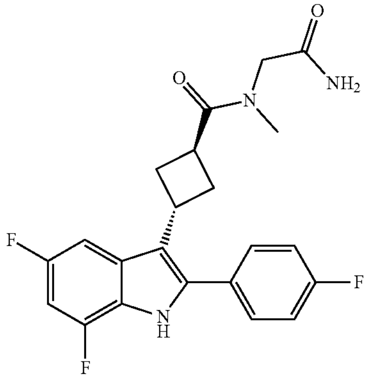 [SMILES: CN(CC(N)=O)C(=O)[C@H]1C[C@H](c2c(-c3ccc(F)cc3)[nH]c3c(F)cc(F)cc32)C1] | LCMS m/z 416.17 [M + H]$^+$ | A; 3.3 |

TABLE 5-continued
| Structure, physicochemical properties, and LCMS analysis for compounds 49-82 | | | |
|---|---|---|---|
| Compound | Structure | $^1$H NMR (ppm); LCMS m/z $[M + H]^+$ | LCMS Method; LCMS retention time (min) |
| 52 | 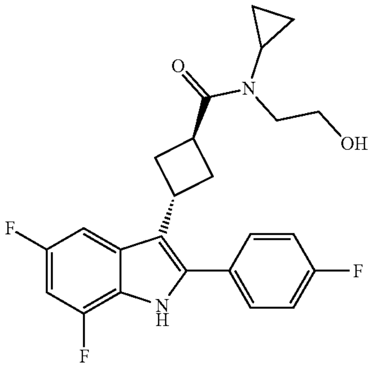 [SMILES: O=C([C@H]1C[C@H](c2c(-c3ccc(F)cc3)[nH]c3c(F)cc(F)cc32)C1)N(CCO)C1CC1] | LCMS m/z 429.17 $[M + H]^+$ | A; 3.85 |
| 53 | 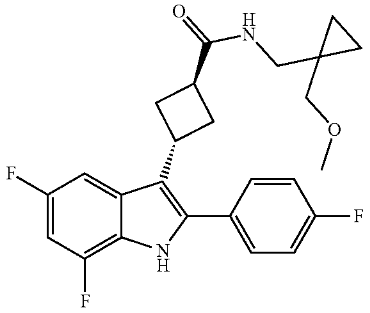 [SMILES: COCC1(CNC(=O)[C@H]2C[C@H](c3c(-c4ccc(F)cc4)[nH]c4c(F)cc(F)cc43)C2)CC1] | LCMS m/z 443.31 $[M + H]^+$ | A; 4.07 |
| 54 | 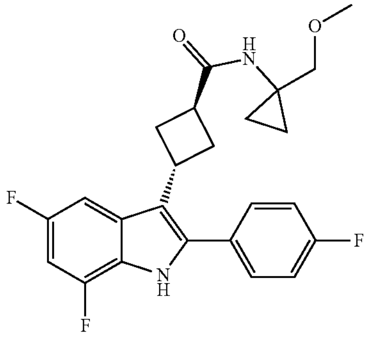 [SMILES: COCC1(NC(=O)[C@H]2C[C@H](c3c(-c4ccc(F)cc4)[nH]c4c(F)cc(F)cc43)C2)CC1] | LCMS m/z 429.17 $[M + H]^+$ | A; 3.88 |
| 55 | 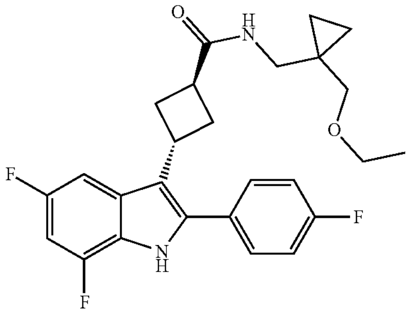 [SMILES: CCOCC1(CNC(=O)[C@H]2C[C@H](c3c(-c4ccc(F)cc4)[nH]c4c(F)cc(F)cc43)C2)CC1] | $^1$H NMR (300 MHz, Acetone-$d_6$) δ 10.71 (s, 1H), 7.62 (td, J = 8.9, 5.5 Hz, 2H), 7.41 (dd, J = 9.8, 2.2 Hz, 1H), 7.35-7.21 (m, 2H), 7.14 (s, 1H), 6.92-6.77 (m, 1H), 4.22-4.04 (m, 1H), 3.40-3.33 (m, 1H), 3.38-3.27 (m, 2H), 3.32-3.10 (m, 1H), 2.94-2.76 (m, 1H), 2.75-2.57 (m, 3H), 2.48 (qd, J = 8.5, 2.7 Hz, 1H), 1.83-1.69 (m, 2H), 1.75-1.51 (m, 5H). LCMS m/z 457.21 $[M + H]^+$ | A; 4.25 |

TABLE 5-continued
Structure, physicochemical properties, and LCMS analysis for compounds 49-82
| Compound | Structure | $^1H$ NMR (ppm); LCMS m/z $[M + H]^+$ | LCMS Method; LCMS retention time (min) |
| --- | --- | --- | --- |
| 56 | 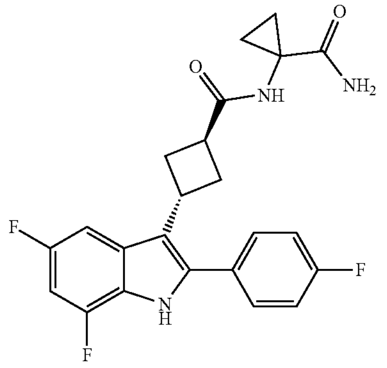 [SMILES: NC(=O)C1(NC(=O)[C@H]2C[C@H](c3c(-c4ccc(F)cc4)[nH]c4c(F)cc(F)cc43)C2)CC1] | LCMS m/z 428.16 $[M + H]^+$ | A; 3.34 |
| 57 | 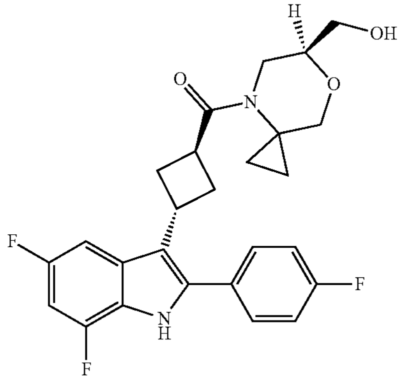 [SMILES: O=C([C@H]1C[C@H](c2c(-c3ccc(F)cc3)[nH]c3c(F)cc(F)cc32)C1)N1C[C@@H](CO)OCC12CC2] | LCMS m/z 471.32 $[M + H]^+$ | A; 3.7 |
| 58 | 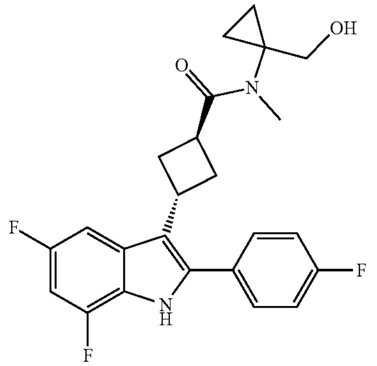 [SMILES: CN(C(=O)[C@H]1C[C@H](c2c(-c3ccc(F)cc3)[nH]c3c(F)cc(F)cc32)C1)C1(CO)CC1] | LCMS m/z 429.2 $[M + H]^+$ | A; 3.77 |
| 59 | 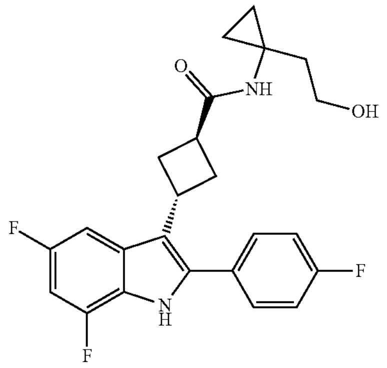 [SMILES: O=C(NC1(CCO)CC1)[C@H]1C[C@H](c2c(-c3ccc(F)cc3)[nH]c3c(F)cc(F)cc32)C1] | LCMS m/z 429.17 $[M + H]^+$ | A; 3.68 |

TABLE 5-continued
| Compound | Structure | $^1$H NMR (ppm); LCMS m/z [M + H]$^+$ | LCMS Method; LCMS retention time (min) |
|---|---|---|---|
| 60 | 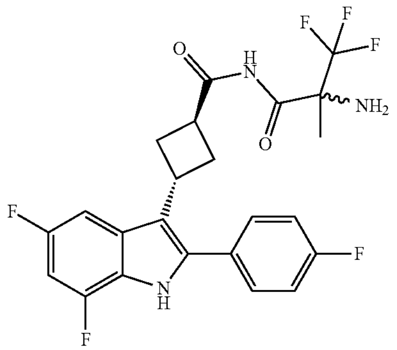 [SMILES: CC(N)(C(=O)NC(=O)[C@H]1C[C@H](c2c(-c3ccc(F)cc3)[nH]c3c(F)cc(F)cc32)C1)C(F)(F)F] | LCMS m/z 484.12 [M + H]$^+$ | A; 3.68 |
| 61 | 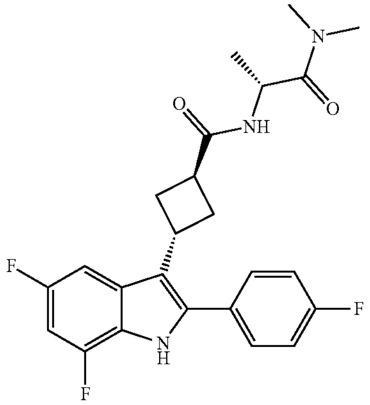 [SMILES: C[C@@H](NC(=O)[C@H]1C[C@H](c2c(-c3ccc(F)cc3)[nH]c3c(F)cc(F)cc32)C1)C(=O)N(C)C] | LCMS m/z 444.19 [M + H]$^+$ | A; 3.66 |
| 62 | 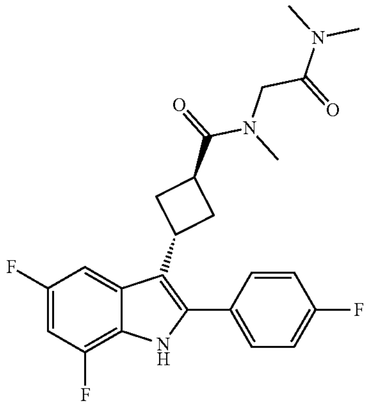 [SMILES: CN(C)C(=O)CN(C)C(=O)[C@H]1C[C@H](c2c(-c3ccc(F)cc3)[nH]c3c(F)cc(F)cc32)C1] | $^1$H NMR (300 MHz, Acetone-$d_6$) δ 7.70-7.37 (m, 3H), 7.34-7.18 (m, 2H), 6.85 (dddd, J = 11.1, 9.6, 3.6, 2.2 Hz, 1H), 4.35-3.75 (m, 4H), 3.68-3.26 (m, 1H), 3.15-2.93 (m, 5H), 2.93-2.85 (m, 3H), 2.82-2.61 (m, 4H). LCMS m/z 444.02 [M + H]$^+$ | A; 3.66 |
| 63 | 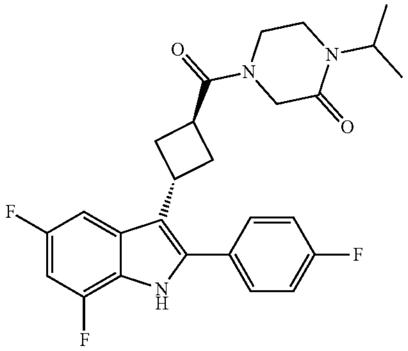 [SMILES: CC(C)N1CCN(C(=O)[C@H]2C[C@H](c3c(-c4ccc(F)cc4)[nH]c4c(F)cc(F)cc43)C2)CC1=O] | LCMS m/z 470.18 [M + H]$^+$ | A; 3.82 |
Structure, physicochemical properties, and LCMS analysis for compounds 49-82

TABLE 5-continued
| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds 49-82 | | | |
| 64 | 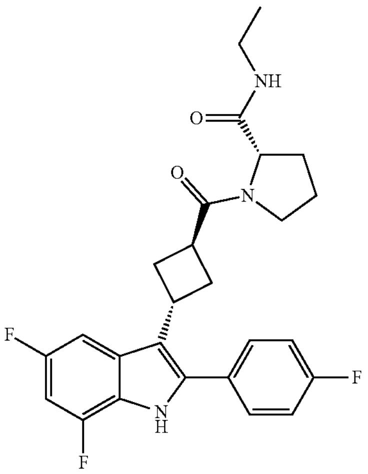 [SMILES: CCNC(=O)[C@@H]1CCCN1C(=O)[C@H]1C[C@H](c2c(-c3ccc(F)cc3)[nH]c3c(F)cc(F)cc32)C1] | LCMS m/z 470.3 [M + H]$^+$ | A; 3.83 |
| 65 | 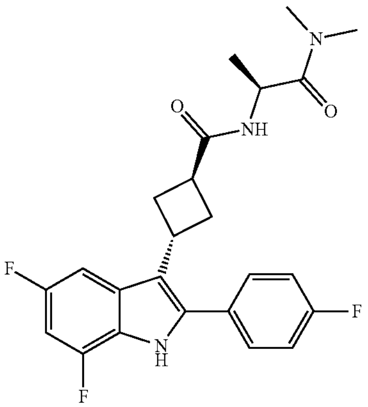 [SMILES: C[C@H](NC(=O)[C@H]1C[C@H](c2c(-c3ccc(F)cc3)[nH]c3c(F)cc(F)cc32)C1)C(=O)N(C)C] | LCMS m/z 444.3 [M + H]$^+$ | A; 3.74 |
| 66 | 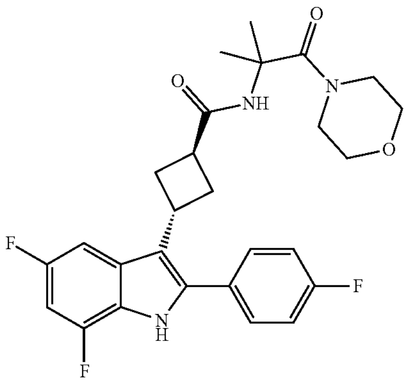 [SMILES: CC(C)(NC(=O)[C@H]1C[C@H](c2c(-c3ccc(F)cc3)[nH]c3c(F)cc(F)cc32)C1)C(=O)N1CCOCC1] | LCMS m/z 500.32 [M + H]$^+$ | A; 3.65 |

TABLE 5-continued

| Structure, physicochemical properties, and LCMS analysis for compounds 49-82 | | | |
|---|---|---|---|
| Compound | Structure | $^1$H NMR (ppm); LCMS m/z [M + H]$^+$ | LCMS Method; LCMS retention time (min) |
| 67 | 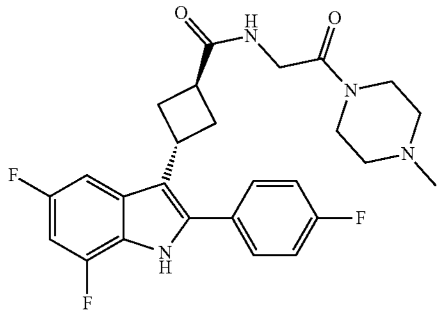 [SMILES: CN1CCN(C(=O)CNC(=O)[C@H]2C[C@H](c3c(-c4ccc(F)cc4)[nH]c4c(F)cc(F)cc43)C2)CC1] | LCMS m/z 485.34 [M + H]$^+$ | A; 2.86 |
| 68 | 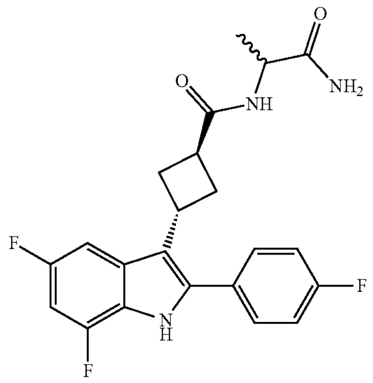 [SMILES: CC(NC(=O)[C@H]1C[C@H](c2c(-c3ccc(F)cc3)[nH]c3c(F)cc(F)cc32)C1)C(N)=O] | $^1$H NMR (300 MHz, Acetone-$d_6$) δ 10.69 (s, 1H), 8.05 (dd, J = 10.1, 2.2 Hz, 1H), 7.77-7.52 (m, 2H), 7.52-7.15 (m, 3H), 6.84 (ddt, J = 12.6, 9.6, 2.6 Hz, 1H), 4.63-4.41 (m, 1H), 4.12 (t, J = 9.0 Hz, 1H), 3.82 (p, J = 9.3, 8.9 Hz, 1H), 3.42-3.08 (m, 1H), 2.82 (dt, J = 16.4, 7.7 Hz, 1H), 2.65 (dd, J = 9.3, 6.4 Hz, 2H), 2.55-2.36 (m, 1H), 1.33 (dd, J = 6.9, 3.7 Hz, 3H). LCMS m/z 416.29 [M + H]$^+$ | A; 3.45 |
| 69 | 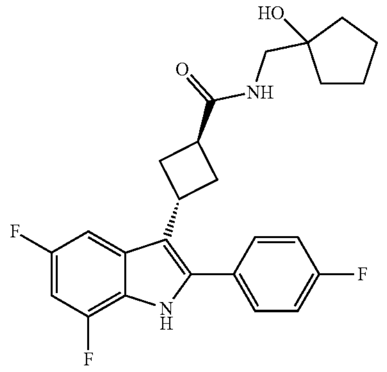 [SMILES: O=C(NCC1(O)CCCC1)[C@H]1C[C@H](c2c(-c3ccc(F)cc3)[nH]c3c(F)cc(F)cc32)C1] | $^1$H NMR (300 MHz, Acetone-$d_6$) δ 10.71 (s, 1H), 8.06 (dd, J = 10.2, 2.2 Hz, 1H), 7.68-7.55 (m, 2H), 7.41 (dd, J = 9.8, 2.2 Hz, 1H), 7.35-7.21 (m, 2H), 7.14 (s, 1H), 6.84 (ddt, J = 11.2, 9.6, 2.5 Hz, 1H), 4.22-4.04 (m, 1H), 3.40-3.33 (m, 1H), 3.38-3.23 (m, 2H), 2.94-2.76 (m, 1H), 2.75-2.57 (m, 3H), 2.48 (qd, J = 8.6, 2.7 Hz, 1H), 1.81-1.69 (m, 1H), 1.69-1.51 (m, 2H), 1.59 (s, 4H). LCMS m/z 443.33 [M + H]$^+$ | A; 3.93 |
| 70 | 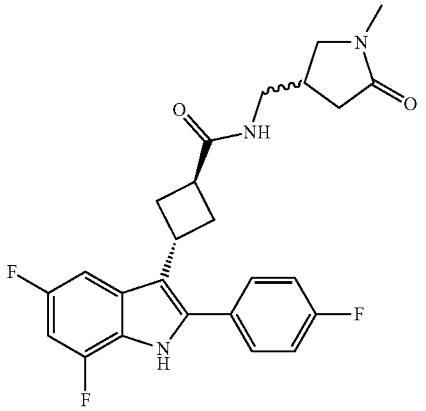 [SMILES: CN1CC(CNC(=O)[C@H]2C[C@H](c3c(-c4ccc(F)cc4)[nH]c4c(F)cc(F)cc43)C2)CC1=O] | LCMS m/z 456.33 [M + H]$^+$ | A; 3.55 |

TABLE 5-continued

Structure, physicochemical properties, and LCMS analysis for compounds 49-82

| Compound | Structure | $^1$H NMR (ppm); LCMS m/z [M + H]$^+$ | LCMS Method; LCMS retention time (min) |
|---|---|---|---|
| 71 | 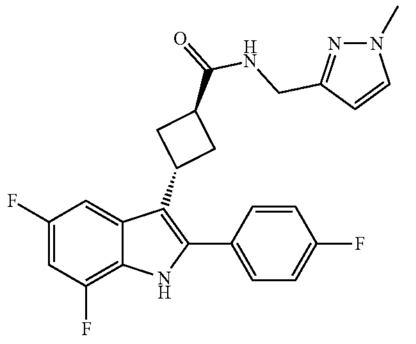 [SMILES: Cn1ccc(CNC(=O)[C@H]2C[C@H](c3c(-c4ccc(F)cc4)[nH]c4c(F)cc(F)cc43)C2)n1] | LCMS m/z 456.33 [M + H]$^+$ | A; 3.68 |
| 72 | 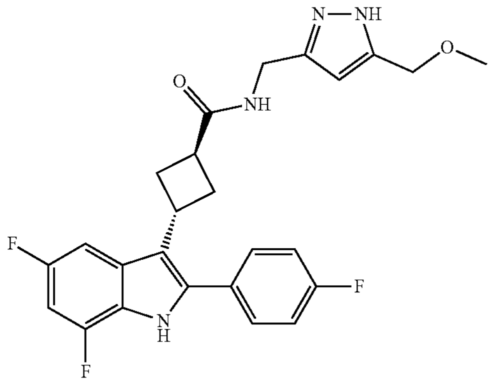 | LCMS m/z 456.33 [M + H]$^+$ | A; 3.49 |
| 73 | 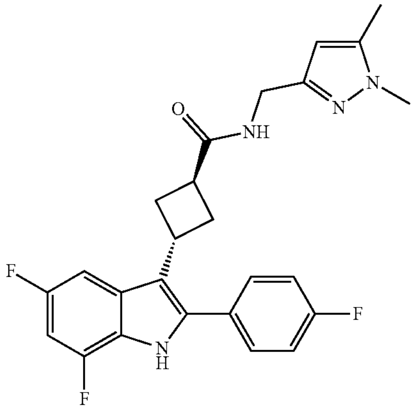 | $^1$H NMR (300 MHz, Acetone-$d_6$) δ 10.71 (s, 1H), 7.69-7.54 (m, 2H), 7.40 (dd, J = 9.8, 2.2 Hz, 1H), 7.35-7.23 (m, 2H), 6.84 (ddt, J = 10.9, 9.6, 1.6 Hz, 1H), 6.17 (s, 1H), 4.41 (dd, J = 5.5, 3.1 Hz, 1H), 4.11 (q, J = 8.8 Hz, 1H), 3.84 (d, J = 1.8 Hz, 3H), 3.28 (t, J = 5.5 Hz, 1H), 3.28-3.11 (m, 1H), 2.84 (q, J = 9.6, 8.0 Hz, 1H), 2.75-2.59 (m, 3H), 2.49 (dd, J = 11.1, 8.3 Hz, 1H), 2.33 (d, J = 2.2 Hz, 3H). LCMS m/z 456.33 [M + H]$^+$ | A; 3.58 |
| 74 | 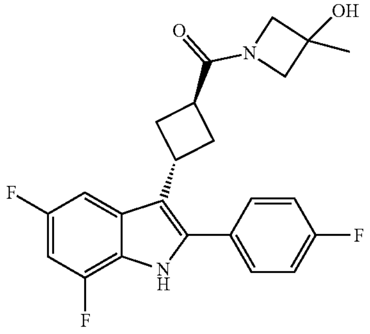 | $^1$H NMR (300 MHz, Acetone-$d_6$) δ 10.70 (s, 1H), 7.73-7.55 (m, 2H), 7.44 (dd, J = 9.8, 2.2 Hz, 1H), 7.37-7.09 (m, 2H), 6.85 (dddd, J = 11.1, 9.6, 3.8, 2.2 Hz, 1H), 4.20-3.66 (m, 5H), 3.43-3.05 (m, 1H), 2.95-2.30 (m, 4H), 1.48 (s, 3H). LCMS m/z 456.33 [M + H]$^+$ | A; 3.65 |

TABLE 5-continued
| Compound | Structure | $^1H$ NMR (ppm); LCMS m/z $[M + H]^+$ | LCMS Method; LCMS retention time (min) |
| --- | --- | --- | --- |
| 75 | 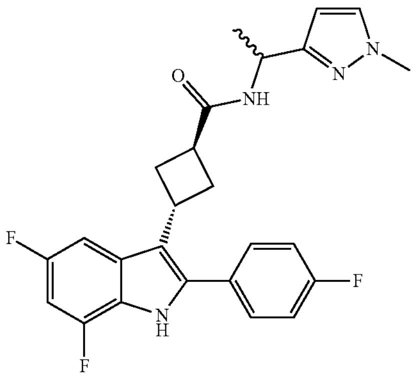 | LCMS m/z 456.33 $[M + H]^+$ | A; 3.83 |
| 76 | 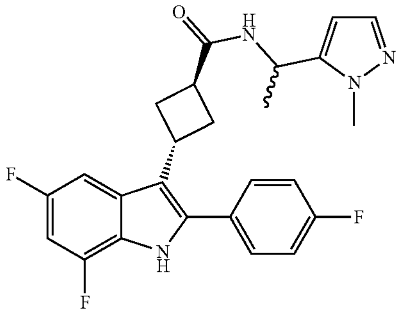 | LCMS m/z 456.33 $[M + H]^+$ | A; 3.81 |
| 77 | 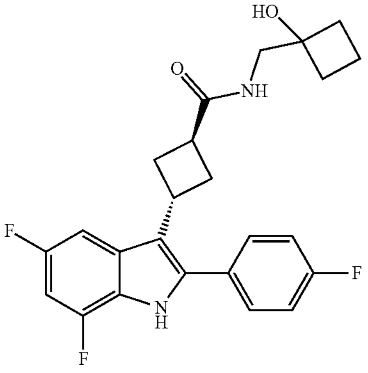 [SMILES: O=C(NCC1(O)CCC1)[C@H]1C[C@H](c2c(-c3ccc(F)cc3)[nH]c3c(F)cc(F)cc32)C1] | LCMS m/z 456.33 $[M + H]^+$ | A; 3.81 |
| 78 | 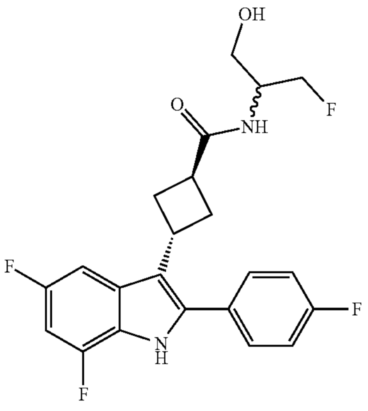 [SMILES: O=C(NC(CO)CF)[C@H]1C[C@H](c2c(-c3ccc(F)cc3)[nH]c3c(F)cc(F)cc32)C1] | LCMS m/z 456.33 $[M + H]^+$ | A; 3.63 |
Structure, physicochemical properties, and LCMS analysis for compounds 49-82

TABLE 5-continued
| Compound | Structure | $^1$H NMR (ppm); LCMS m/z [M + H]$^+$ | LCMS Method; LCMS retention time (min) |
|---|---|---|---|
| 79 | 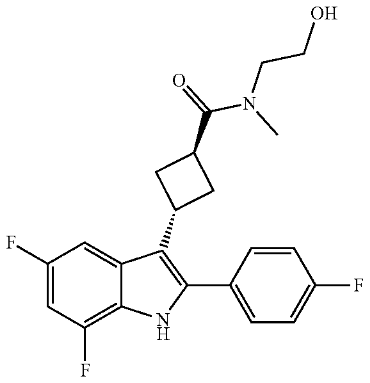 | LCMS m/z 456.33 [M + H]$^+$ | A; 3.68 |
| 80 | 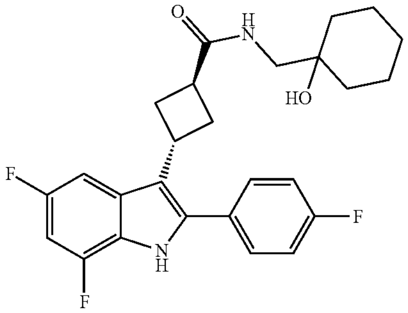 [SMILES: O=C(NCC1(O)CCCCC1)[C@H]1C[C@H](c2c(-c3ccc(F)cc3)[nH]c3c(F)cc(F)cc32)C1] | LCMS m/z 456.33 [M + H]$^+$ | A; 4.11 |
| 81 | 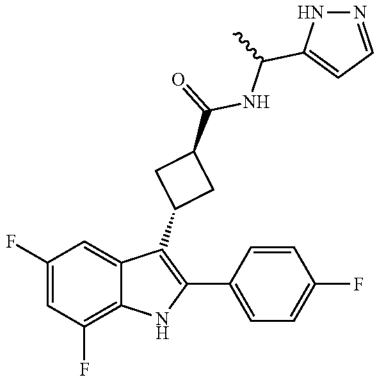 [SMILES: CC(NC(=O)[C@H]1C[C@H](c2c(-c3ccc(F)cc3)[nH]c3c(F)cc(F)cc32)C1)c1ccn[nH]1] | $^1$H NMR (300 MHz, Acetone-$d_6$) δ 10.71 (s, 1H), 7.84 (dd, J = 3.7, 2.3 Hz, 1H), 7.70-7.53 (m, 2H), 7.43-7.20 (m, 3H), 6.84 (dddd, J = 11.1, 9.6, 3.3, 2.2 Hz, 1H), 6.63 (s, 2H), 6.48-6.41 (m, 1H), 5.30 (p, J = 7.1 Hz, 1H), 4.21-4.03 (m, 1H), 3.37-3.09 (m, 1H), 2.65 (dddd, J = 10.9, 9.3, 6.4, 1.3 Hz, 4H), 1.54 (dd, J = 7.0, 2.8 Hz, 3H). LCMS m/z 456.33 [M + H]$^+$. | A; 3.49 |
| 82 | 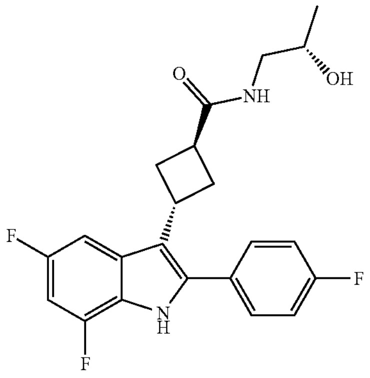 | $^1$H NMR (300 MHz, Acetone-$d_6$) δ 10.69 (s, 1H), 7.60 (ddd, J = 8.9, 4.5, 1.7 Hz, 2H), 7.41 (dd, J = 9.8, 2.2 Hz, 1H), 7.36-7.22 (m, 2H), 6.85 (ddd, J = 11.1, 9.6, 2.2 Hz, 1H), 4.22-3.99 (m, 1H), 3.90-3.74 (m, 1H), 3.37-3.20 (m, 2H), 3.14 (ddd, J =13.5, 6.9, 5.4 Hz, 1H), 2.69-2.57 (m, 3H), 1.10 (dd, J = 6.2, 1.4 Hz, 3H). LCMS m/z 456.33 [M + H]$^+$. | A; 3.47 |

Compounds 83-161

Compounds 83-161 (Table 6) were prepared from S2 and the appropriate commercially available amine by HATU coupling according to standard procedure A.

TABLE 6

Structure, physicochemical properties, and LCMS analysis for compounds for compounds 83-161

| Compound | Structure | $^1$H NMR (ppm); LCMS m/z [M + H]$^+$ | LCMS Method; LCMS retention time (min) |
|---|---|---|---|
| 83 | 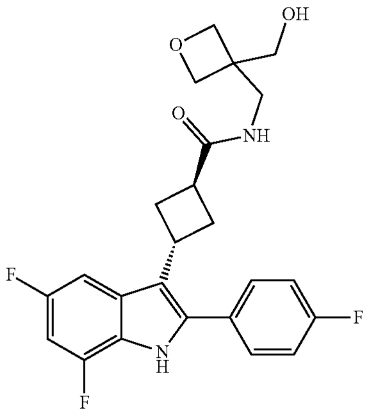 [SMILES: O=C(NCC1(CO)COC1)[C@H]1C[C@H](c2c(-c3ccc(F)cc3)[nH]c3c(F)cc(F)cc32)C1] | LCMS m/z 445.1 [M + H]$^+$ | A; 2.835 |
| 84 | 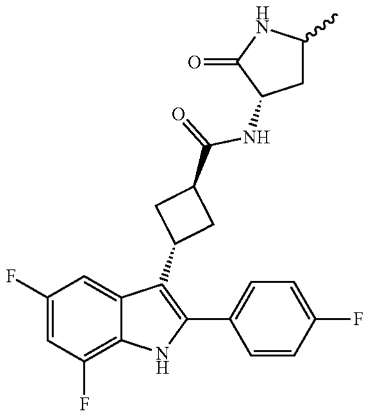 [SMILES: CC1C[C@H](NC(=O)[C@H]2C[C@H](c3c(-c4ccc(F)cc4)[nH]c4c(F)cc(F)cc43)C2)C(=O)N1] | LCMS m/z 442.29 [M + H]$^+$ | A; 3.215 |
| 85 | 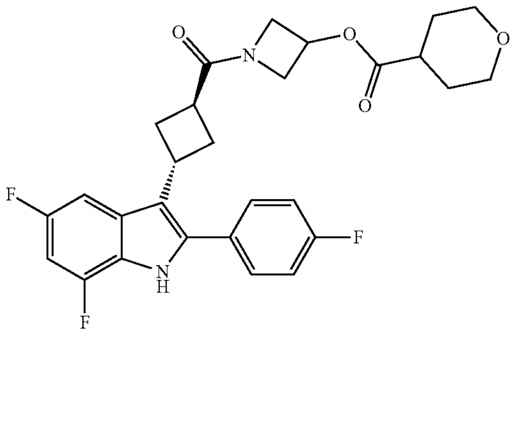 [SMILES: O=C(OC1CN(C(=O)[C@H]2C[C@H](c3c(-c4ccc(F)cc4)[nH]c4c(F)cc(F)cc43)C2)C1)C1CCOCC1] | LCMS m/z 513.17 [M + H]$^+$ | A; 3.95 |

TABLE 6-continued
Structure, physicochemical properties, and LCMS analysis for compounds for compounds 83-161
| Compound | Structure | $^1$H NMR (ppm); LCMS m/z [M + H]$^+$ | LCMS Method; LCMS retention time (min) |
|---|---|---|---|
| 86 | 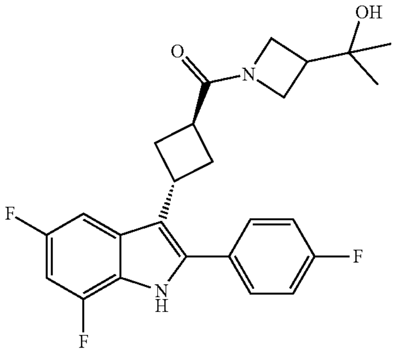 [SMILES: CC(C)(O)C1CN(C(=O)[C@H]2C[C@H](c3c(-c4ccc(F)cc4)[nH]c4c(F)cc(F)cc43)C2)C1] | LCMS m/z 443.17 [M + H]$^+$ | A; 3.72 |
| 87 | 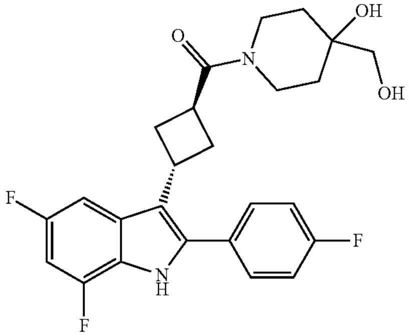 [SMILES: O=C([C@H]1C[C@H](c2c(-c3ccc(F)cc3)[nH]c3c(F)cc(F)cc32)C1)N1CCC(O)(CO)CC1] | LCMS m/z 459.17 [M + H]$^+$ | A; 3.29 |
| 88 | 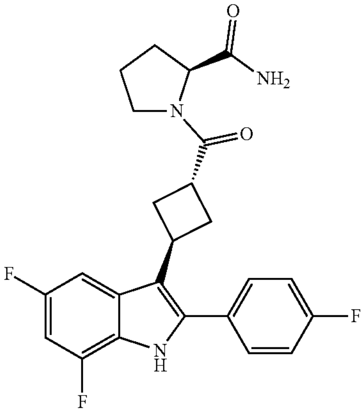 [SMILES: NC(=O)[C@@H]1CCCN1C(=O)[C@H]1C[C@H](c2c(-c3ccc(F)cc3)[nH]c3c(F)cc(F)cc32)C1] | LCMS m/z 442.16 [M + H]$^+$ | A; 3.44 |
| 89 | 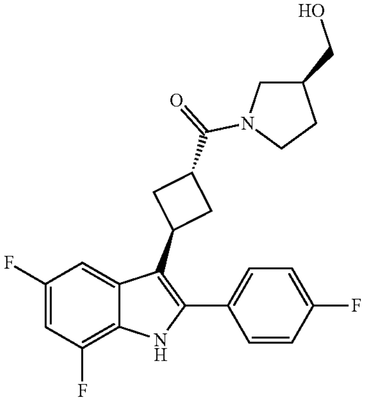 [SMILES: O=C([C@H]1C[C@H](c2c(-c3ccc(F)cc3)[nH]c3c(F)cc(F)cc32)C1)N1CC[C@H](CO)C1] | LCMS m/z 429.16 [M + H]$^+$ | A; 3.55 |

TABLE 6-continued
| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds for compounds 83-161 | | | |
| 90 | 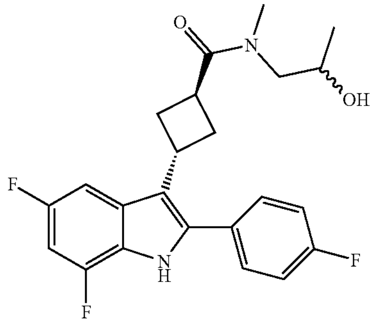 [SMILES: CC(O)CN(C)C(=O)[C@H]1C[C@H](c2c(-c3ccc(F)cc3)[nH]c3c(F)cc(F)cc32)C1] | LCMS m/z 417.18 [M + H]$^+$ | A; 3.71 |
| 91 | 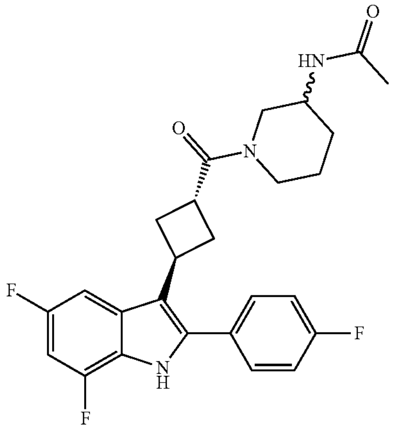 [SMILES: CC(=O)NC1CCCN(C(=O)[C@H]2C[C@H](c3c(-c4ccc(F)cc4)[nH]c4c(F)cc(F)cc43)C2)C1] | LCMS m/z 470.18 [M + H]$^+$ | A; 3.62 |
| 92 | 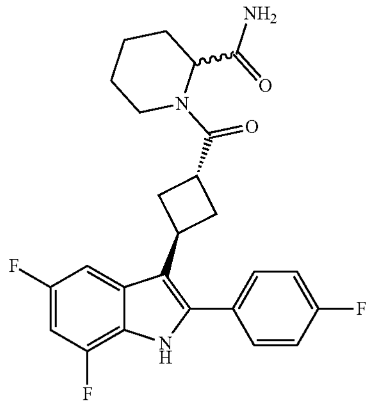 [SMILES: NC(=O)C1CCCCN1C(=O)[C@H]1C[C@H](c2c(-c3ccc(F)cc3)[nH]c3c(F)cc(F)cc32)C1] | LCMS m/z 456.23 [M + H]$^+$ | A; 3.74 |
| 93 | 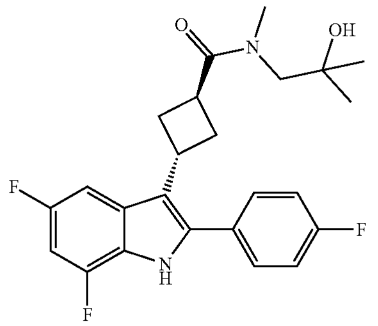 [SMILES: CN(CC(C)(C)O)C(=O)[C@H]1C[C@H](c2c(-c3ccc(F)cc3)[nH]c3c(F)cc(F)cc32)C1] | LCMS m/z 431.09 [M + H]$^+$ | A; 3.87 |

TABLE 6-continued
| Structure, physicochemical properties, and LCMS analysis for compounds for compounds 83-161 | | | |
|---|---|---|---|
| Compound | Structure | ¹H NMR (ppm); LCMS m/z $[M + H]^+$ | LCMS Method; LCMS retention time (min) |
| 94 | 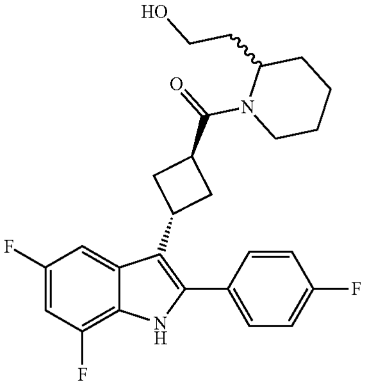 [SMILES: O=C([C@H]1C[C@H](c2c(-c3ccc(F)cc3)[nH]c3c(F)cc(F)cc32)C1)N1CCCCC1CCO] | LCMS m/z 457.21 $[M + H]^+$ | A; 4.08 |
| 95 | 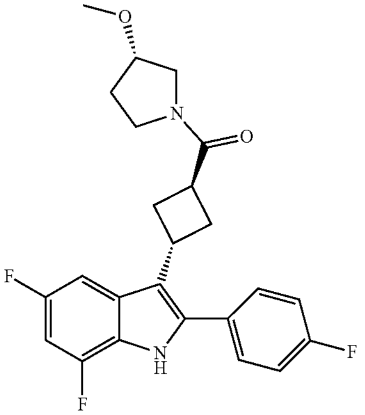 [SMILES: CO[C@H]1CCN(C(=O)[C@H]2C[C@H](c3c(-c4ccc(F)cc4)[nH]c4c(F)cc(F)cc43)C2)C1] | LCMS m/z 429.16 $[M + H]^+$ | A; 3.97 |
| 96 | 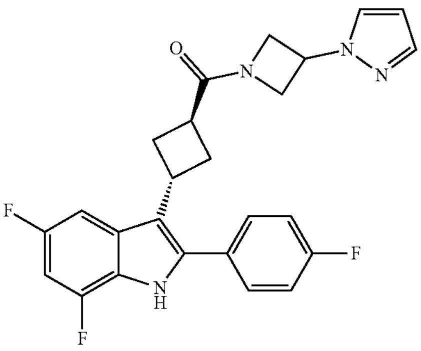 [SMILES: O=C([C@H]1C[C@H](c2c(-c3ccc(F)cc3)[nH]c3c(F)cc(F)cc32)C1)N1CC(n2cccn2)C1] | LCMS m/z 451.15 $[M + H]^+$ | A; 3.83 |

TABLE 6-continued
Structure, physicochemical properties, and LCMS analysis for compounds for compounds 83-161
| Compound | Structure | $^{1}H$ NMR (ppm); LCMS m/z [M + H]$^{+}$ | LCMS Method; LCMS retention time (min) |
|---|---|---|---|
| 97 | 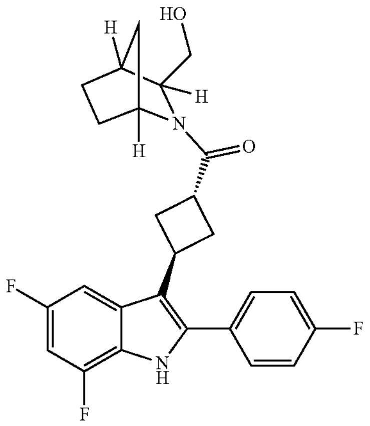 [SMILES: O=C([C@H]1C[C@H](c2c(-c3ccc(F)cc3)[nH]c3c(F)cc(F)cc32)C1)N1C2CCC(C2)C1CO] | LCMS m/z 455.03 [M + H]$^{+}$ | A; 4.09 |
| 98 | 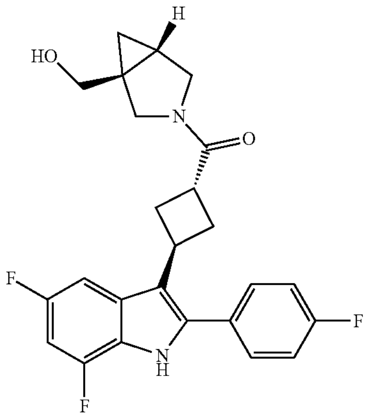 [SMILES: O=C([C@H]1C[C@H](c2c(-c3ccc(F)cc3)[nH]c3c(F)cc(F)cc32)C1)N1C[C@H]2C[C@@]2(CO)C1] | LCMS m/z 441.05 [M + H]$^{+}$ | A; 3.64 |
| 99 | 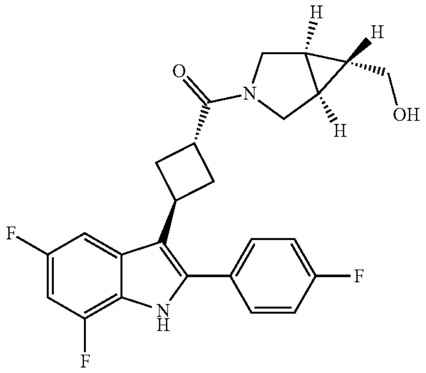 [SMILES: O=C([C@H]1C[C@H](c2c(-c3ccc(F)cc3)[nH]c3c(F)cc(F)cc32)C1)N1C[C@@H]2[C@@H](CO)[C@@H]2C1] | LCMS m/z 440.96 [M + H]$^{+}$ | A; 3.57 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z [M + H]$^+$ | LCMS Method; LCMS retention time (min) |
| 100 | 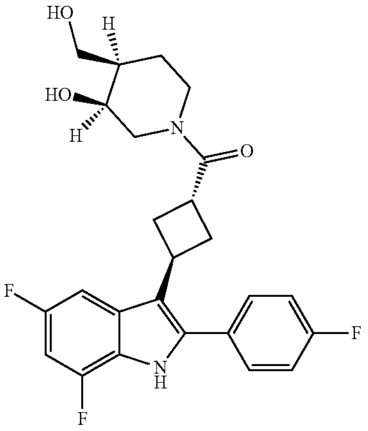 [SMILES: O=C([C@H]1C[C@H](c2c(-c3ccc(F)cc3)[nH]c3c(F)cc(F)cc32)C1)N1CC[C@H](CO)[C@H](O)C1] | LCMS m/z 459.17 [M + H]$^+$ | A; 3.33 |
| 101 | 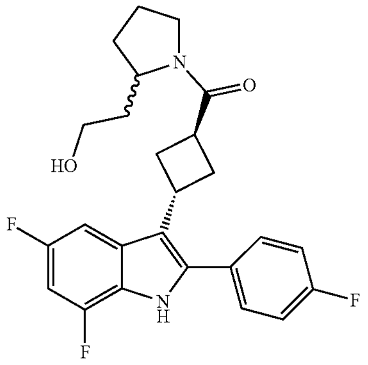 [SMILES: O=C([C@H]1C[C@H](c2c(-c3ccc(F)cc3)[nH]c3c(F)cc(F)cc32)C1)N1CCCC1CCO] | LCMS m/z 443.07 [M + H]$^+$ | A; 3.97 |
| 102 | 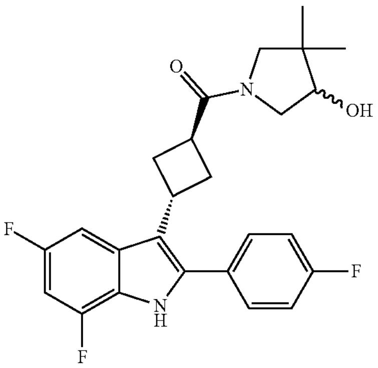 [SMILES: CC1(C)CN(C(=O)[C@H]2C[C@H](c3c(-c4ccc(F)cc4)[nH]c4c(F)cc(F)cc43)C2)CC1O] | LCMS m/z 443.17 [M + H]$^+$ | A; 3.82 |

TABLE 6-continued
Structure, physicochemical properties, and LCMS analysis for compounds for compounds 83-161
| Compound | Structure | $^{1}$H NMR (ppm); LCMS m/z [M + H]$^{+}$ | LCMS Method; LCMS retention time (min) |
|---|---|---|---|
| 103 | 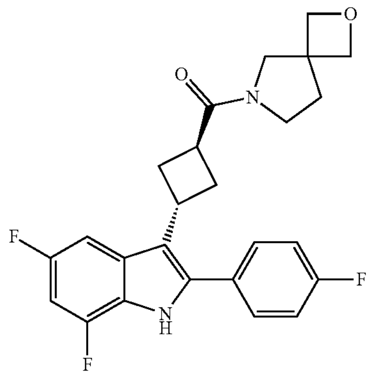 [SMILES: O=C([C@H]1C[C@H](c2c(-c3ccc(F)cc3)[nH]c3c(F)cc(F)cc32)C1)N1CCC2(COC2)C1] | LCMS m/z 441.15 [M + H]$^{+}$ | A; 3.78 |
| 104 | 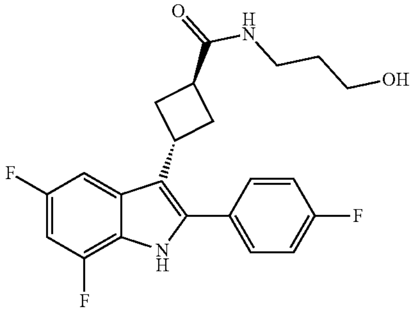 [SMILES: O=C(NCCCO)[C@H]1C[C@H](c2c(-c3ccc(F)cc3)[nH]c3c(F)cc(F)cc32)C1] | LCMS m/z 403.17 [M + H]$^{+}$ | A; 3.44 |
| 105 | 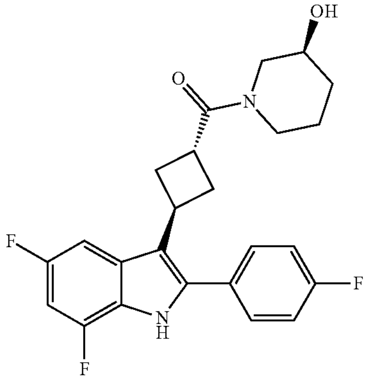 [SMILES: O=C([C@H]1C[C@H](c2c(-c3ccc(F)cc3)[nH]c3c(F)cc(F)cc32)C1)N1CCC[C@H](O)C1] | LCMS m/z 429.16 [M + H]$^{+}$ | A; 3.7 |
| 106 | 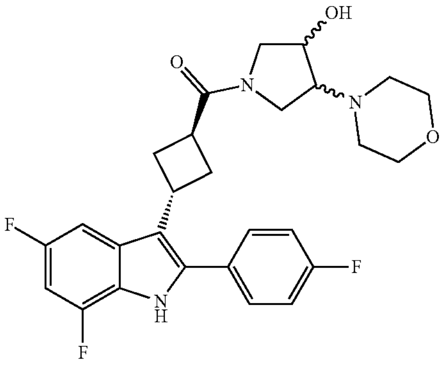 [SMILES: O=C([C@H]1C[C@H](c2c(-c3ccc(F)cc3)[nH]c3c(F)cc(F)cc32)C1)N1CC(O)C(N2CCOCC2)C1] | LCMS m/z 500.21 [M + H]$^{+}$ | A; 2.72 |

TABLE 6-continued
Structure, physicochemical properties, and LCMS analysis for compounds for compounds 83-161
| Compound | Structure | $^1H$ NMR (ppm); LCMS m/z $[M + H]^+$ | LCMS Method; LCMS retention time (min) |
|---|---|---|---|
| 107 | 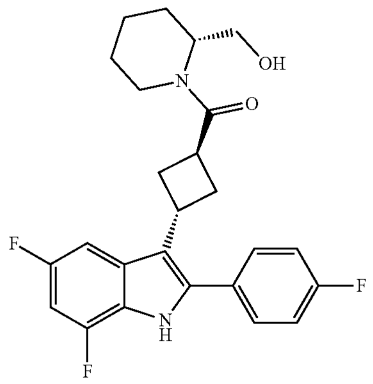 [SMILES: O=C([C@H]1C[C@H](c2c(-c3ccc(F)cc3)[nH]c3c(F)cc(F)cc32)C1)N1CCCC[C@@H]1CO] | LCMS m/z 443.17 $[M + H]^+$ | A; 3.92 |
| 108 | 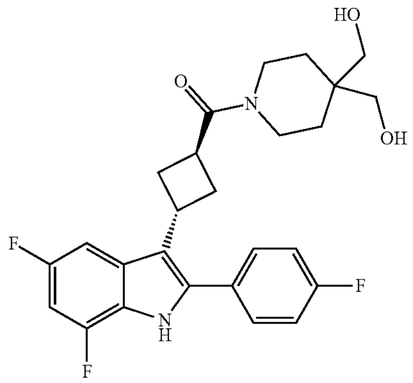 [SMILES: O=C([C@H]1C[C@H](c2c(-c3ccc(F)cc3)[nH]c3c(F)cc(F)cc32)C1)N1CCC(CO)(CO)CC1] | LCMS m/z 473.17 $[M + H]^+$ | A; 3.35 |
| 109 | 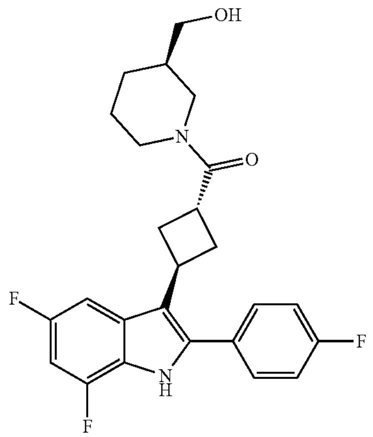 [SMILES: O=C([C@H]1C[C@H](c2c(-c3ccc(F)cc3)[nH]c3c(F)cc(F)cc32)C1)N1CCC[C@@H](CO)C1] | LCMS m/z 443.17 $[M + H]^+$ | A; 3.81 |

TABLE 6-continued
Structure, physicochemical properties, and LCMS analysis for compounds for compounds 83-161
| Compound | Structure | $^1$H NMR (ppm); LCMS m/z $[M + H]^+$ | LCMS Method; LCMS retention time (min) |
|---|---|---|---|
| 110 | 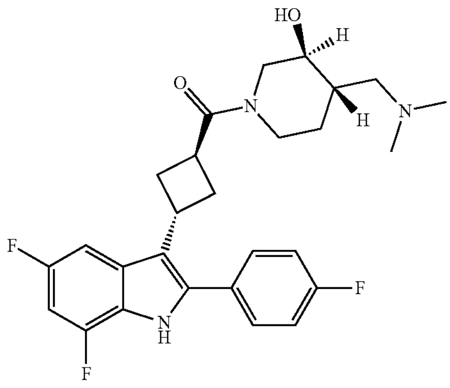 [SMILES: CN(C)C[C@@H]1CCN(C(=O)[C@H]2C[C@H](c3c(-c4ccc(F)cc4)[nH]c4c(F)cc(F)cc43)C2)C[C@H]1O] | LCMS m/z 486.2 $[M + H]^+$ | A; 2.77 |
| 111 | 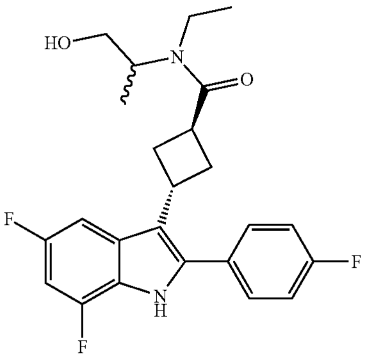 [SMILES: CCN(C(=O)[C@H]1C[C@H](c2c(-c3ccc(F)cc3)[nH]c3c(F)cc(F)cc32)C1)C(C)CO] | LCMS m/z 431.18 $[M + H]^+$ | A; 3.88 |
| 112 | 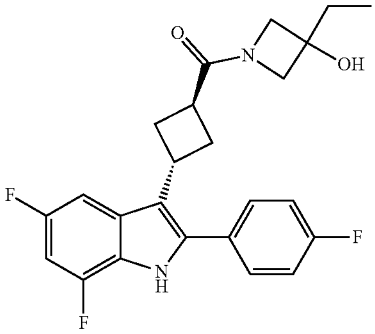 [SMILES: CCC1(O)CN(C(=O)[C@H]2C[C@H](c3c(-c4ccc(F)cc4)[nH]c4c(F)cc(F)cc43)C2)C1] | LCMS m/z 429.16 $[M + H]^+$ | A; 3.72 |
| 113 | 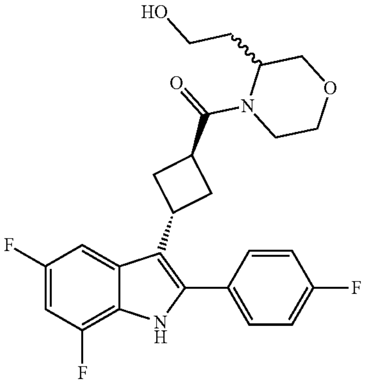 [SMILES: O=C([C@H]1C[C@H](c2c(-c3ccc(F)cc3)[nH]c3c(F)cc(F)cc32)C1)N1CCOCC1CCO] | LCMS m/z 459.17 $[M + H]^+$ | A; 3.66 |

TABLE 6-continued
| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds for compounds 83-161 | | | |
| 114 | 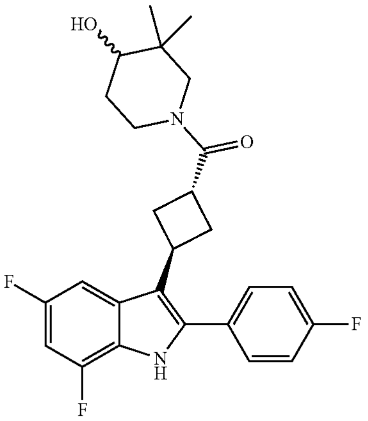 [SMILES: CC1(C)CN(C(=O)[C@H]2C[C@H](c3c(-c4ccc(F)cc4)[nH]c4c(F)cc(F)cc43)C2)CCC1O] | LCMS m/z 457.18 [M + H]$^+$ | A; 3.87 |
| 115 | 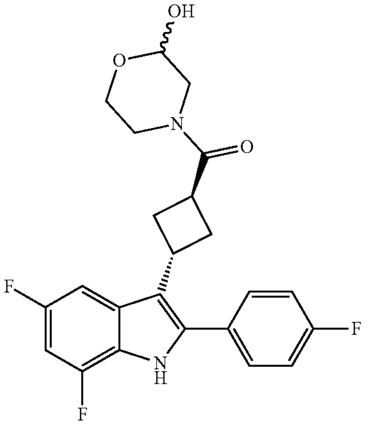 [SMILES: O=C([C@H]1C[C@H](c2c(-c3ccc(F)cc3)[nH]c3c(F)cc(F)cc32)C1)N1CCOC(O)C1] | LCMS m/z 431.12 [M + H]$^+$ | A; 3.52 |
| 116 | 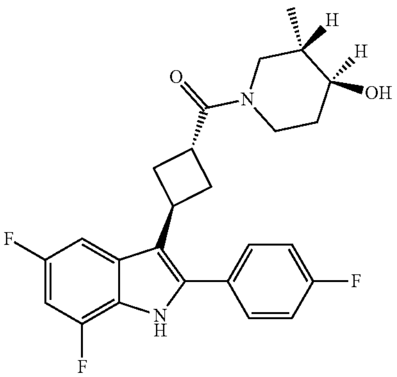 [SMILES: C[C@H]1CN(C(=O)[C@H]2C[C@H](c3c(-c4ccc(F)cc4)[nH]c4c(F)cc(F)cc43)C2)CC[C@@H]1O] | LCMS m/z 443.14 [M + H]$^+$ | A; 3.73 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z [M + H]$^+$ | LCMS Method; LCMS retention time (min) |
| 117 | 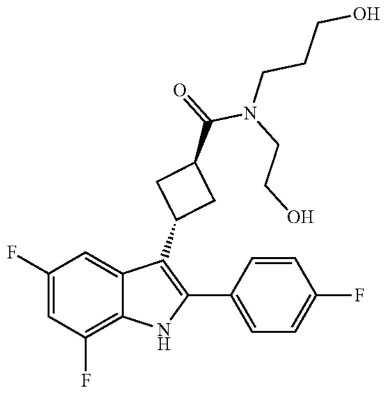 [SMILES: O=C([C@H]1C[C@H](c2c(-c3ccc(F)cc3)[nH]c3c(F)cc(F)cc32)C1)N(CCO)CCCO] | LCMS m/z 447.15 [M + H]$^+$ | A; 3.29 |
| 118 | 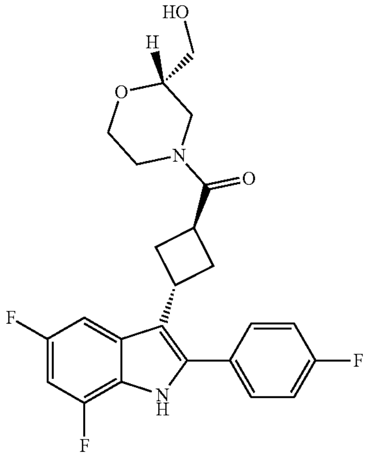 [SMILES: O=C([C@H]1C[C@H](c2c(-c3ccc(F)cc3)[nH]c3c(F)cc(F)cc32)C1)N1CCO[C@H](CO)C1] | LCMS m/z 445.08 [M + H]$^+$ | A, A; 3.5 |
| 119 | 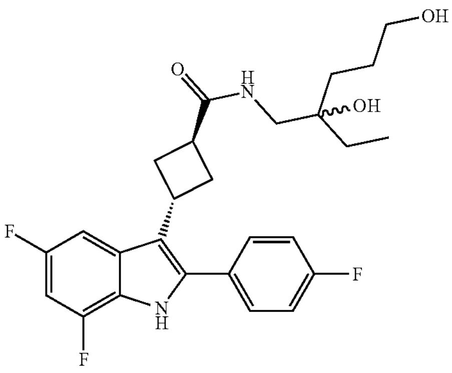 [SMILES: CCC(O)(CCCO)CNC(=O)[C@H]1C[C@H](c2c(-c3ccc(F)cc3)[nH]c3c(F)cc(F)cc32)C1] | LCMS m/z 475.19 [M + H]$^+$ | A; 3.44 |

TABLE 6-continued
| Compound | Structure | $^1H$ NMR (ppm); LCMS m/z [M + H]$^+$ | LCMS Method; LCMS retention time (min) |
|---|---|---|---|
| Structure, physicochemical properties, and LCMS analysis for compounds for compounds 83-161 | | | |
| 120 | 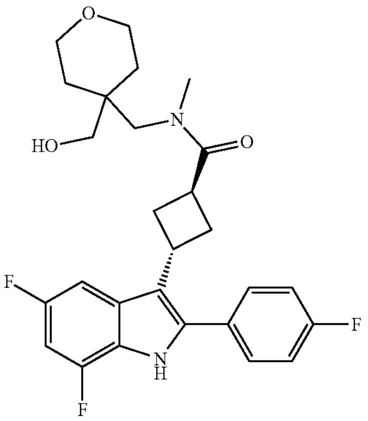 [SMILES: CN(CC1(CO)CCOCC1)C(=O)[C@H]1C[C@H](c2c(-c3ccc(F)cc3)[nH]c3c(F)cc(F)cc32)C1] | LCMS m/z 487.18 [M + H]$^+$ | A; 3.97 |
| 121 | 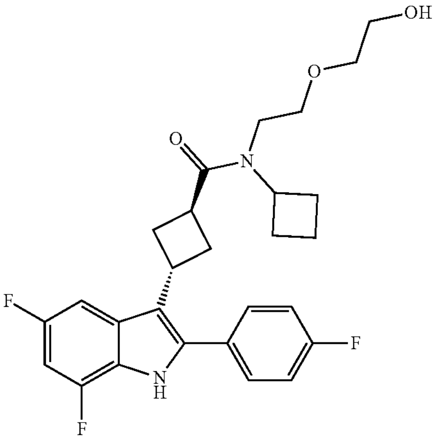 [SMILES: O=C([C@H]1C[C@H](c2c(-c3ccc(F)cc3)[nH]c3c(F)cc(F)cc32)C1)N(CCOCCO)C1CCC1] | LCMS m/z 487.05 [M + H]$^+$ | A; 4.03 |
| 122 | 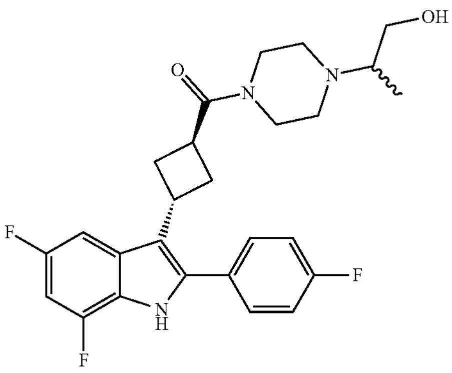 [SMILES: CC(CO)N1CCN(C(=O)[C@H]2C[C@H](c3c(-c4ccc(F)cc4)[nH]c4c(F)cc(F)cc43)C2)CC1] | LCMS m/z 472.2 [M + H]$^+$ | A; 2.75 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z $[M + H]^+$ | LCMS Method; LCMS retention time (min) |
| 123 | 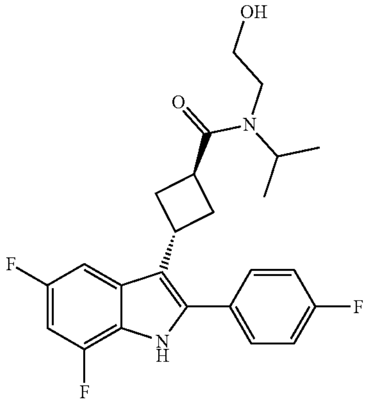 [SMILES: CC(C)N(CCO)C(=O)[C@H]1C[C@H](c2c(-c3ccc(F)cc3)[nH]c3c(F)cc(F)cc32)C1] | LCMS m/z 431.15 $[M + H]^+$ | A; 3.93 |
| 124 | 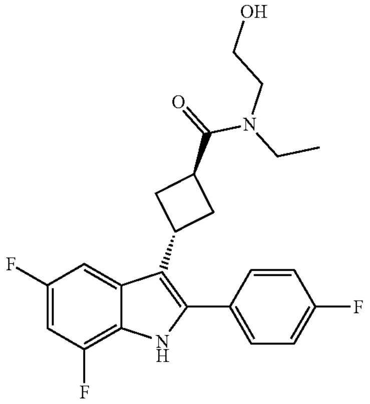 [SMILES: CCN(CCO)C(=O)[C@H]1C[C@H](c2c(-c3ccc(F)cc3)[nH]c3c(F)cc(F)cc32)C1] | LCMS m/z 417.14 $[M + H]^+$ | A; 3.74 |
| 125 | 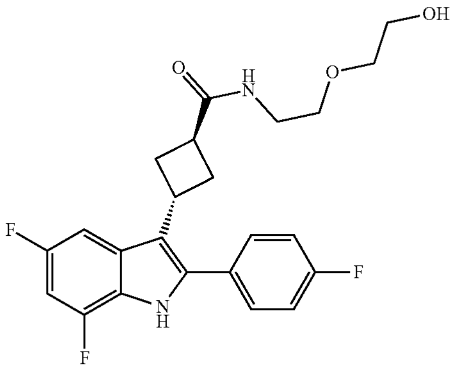 [SMILES: O=C(NCCOCCO)[C@H]1C[C@H](c2c(-c3ccc(F)cc3)[nH]c3c(F)cc(F)cc32)C1] | LCMS m/z 433.17 $[M + H]^+$ | A; 3.36 |

TABLE 6-continued
Structure, physicochemical properties, and LCMS analysis for compounds for compounds 83-161
| Compound | Structure | $^1$H NMR (ppm); LCMS m/z [M + H]$^+$ | LCMS Method; LCMS retention time (min) |
|---|---|---|---|
| 126 | 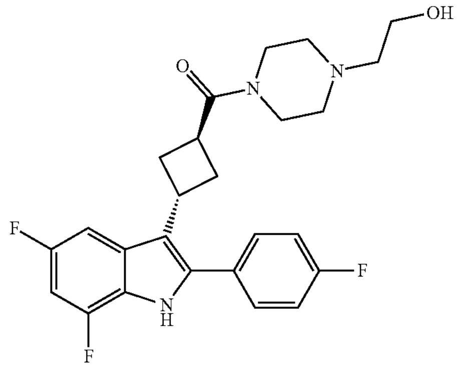 | LCMS m/z 458.19 [M + H]$^+$ | A; 2.7 |
| 127 | 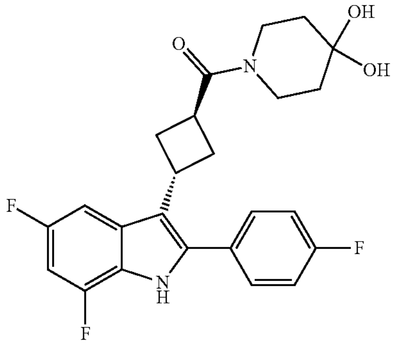 [SMILES: O=C([C@H]1C[C@H](c2c(-c3ccc(F)cc3)[nH]c3c(F)cc(F)cc32)C1)N1CCC(O)(O)CC1] | LCMS m/z 445.22 [M + H]$^+$ | A; 3.8 |
| 128 | 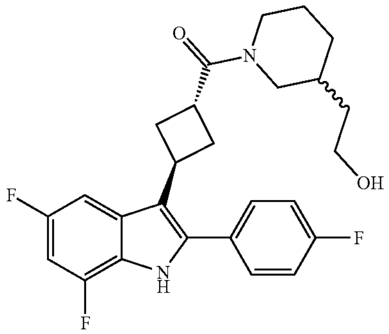 [SMILES: O=C([C@H]1C[C@H](c2c(-c3ccc(F)cc3)[nH]c3c(F)cc(F)cc32)C1)N1CCCC(CCO)C1] | LCMS m/z 457.18 [M + H]$^+$ | A; 3.91 |
| 129 | 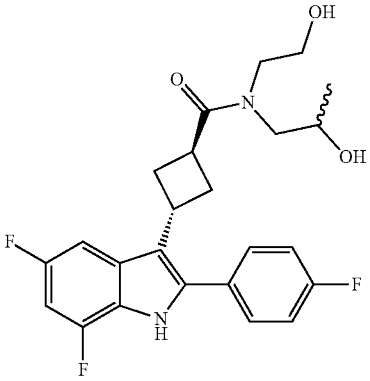 [SMILES: CC(O)CN(CCO)C(=O)[C@H]1C[C@H](c2c(-c3ccc(F)cc3)[nH]c3c(F)cc(F)cc32)C1] | LCMS m/z 447.05 [M + H]$^+$ | A; 3.39 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z [M + H]$^+$ | LCMS Method; LCMS retention time (min) |
| 130 | 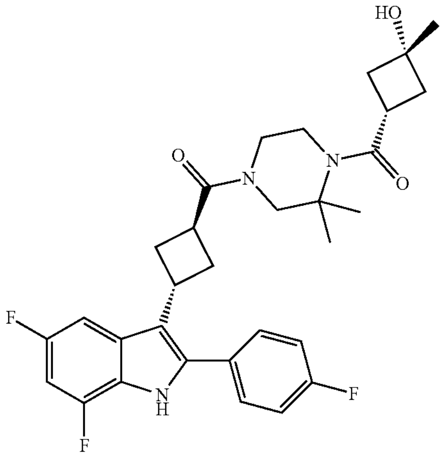 [SMILES: CC1(C)CN(C(=O)[C@H]2C[C@H](c3c(-c4ccc(F)cc4)[nH]c4c(F)cc(F)cc43)C2)CCN1C(=O)[C@H]1C[C@@](C)(O)C1] | LCMS m/z 554.25 [M + H]$^+$ | A; 3.65 |
| 131 | 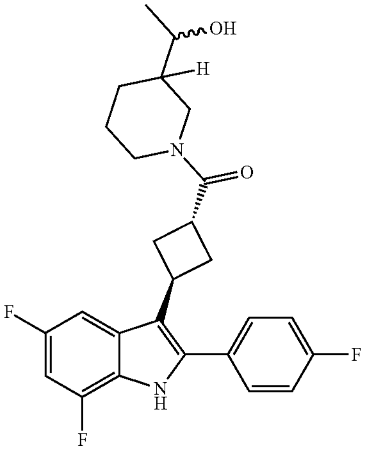 [SMILES: CC(O)C1CCCN(C(=O)[C@H]2C[C@H](c3c(-c4ccc(F)cc4)[nH]c4c(F)cc(F)cc43)C2)C1] | LCMS m/z 457.18 [M + H]$^+$ | A; 3.9 |
| 132 | 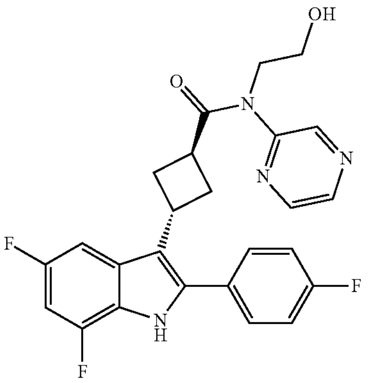 [SMILES: O=C([C@H]1C[C@H](c2c(-c3ccc(F)cc3)[nH]c3c(F)cc(F)cc32)C1)N(CCO)c1cnccn1] | LCMS m/z 467.15 [M + H]$^+$ | A; 3.7 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z [M + H]$^+$ | LCMS Method; LCMS retention time (min) |
| 133 | 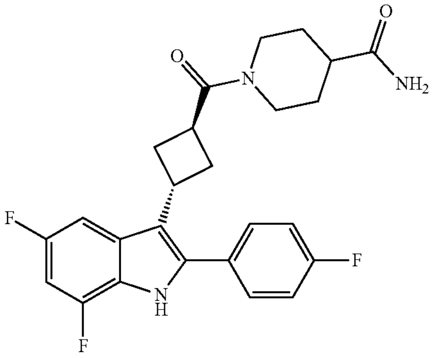 [SMILES: NC(=O)C1CCN(C(=O)[C@H]2C[C@H](c3c(-c4ccc(F)cc4)[nH]c4c(F)cc(F)cc43)C2)CC1] | LCMS m/z 456.17 [M + H]$^+$ | A; 3.39 |
| 134 | 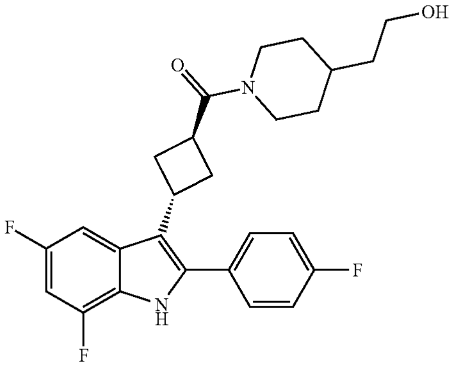 [SMILES: O=C([C@H]1C[C@H](c2c(-c3ccc(F)cc3)[nH]c3c(F)cc(F)cc32)C1)N1CCC(CCO)CC1] | LCMS m/z 457.02 [M + H]$^+$ | A; 3.79 |
| 135 | 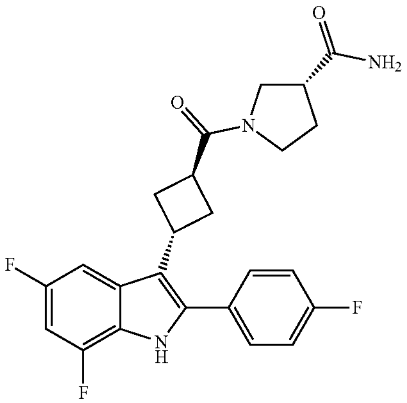 [SMILES: NC(=O)[C@@H]1CCN(C(=O)[C@H]2C[C@H](c3c(-c4ccc(F)cc4)[nH]c4c(F)cc(F)cc43)C2)C1] | LCMS m/z 442.13 [M + H]$^+$ | A; 3.32 |
| 136 | 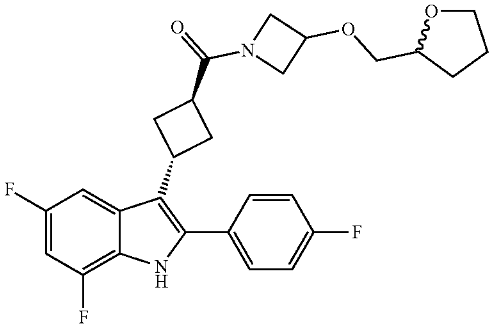 [SMILES: O=C([C@H]1C[C@H](c2c(-c3ccc(F)cc3)[nH]c3c(F)cc(F)cc32)C1)N1CC(OCC2CCCO2)C1] | LCMS m/z 485.16 [M + H]$^+$ | A; 3.99 |

TABLE 6-continued
| Compound | Structure | $^1$H NMR (ppm); LCMS m/z [M + H]$^+$ | LCMS Method; LCMS retention time (min) |
| --- | --- | --- | --- |
| Structure, physicochemical properties, and LCMS analysis for compounds for compounds 83-161 | | | |
| 137 | 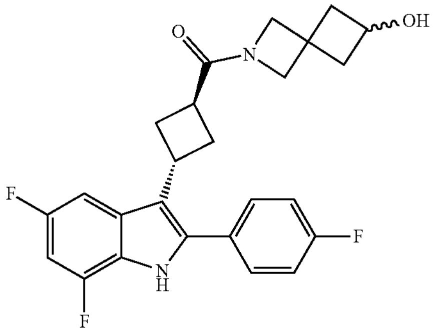 [SMILES: O=C([C@H]1C[C@H](c2c(-c3ccc(F)cc3)[nH]c3c(F)cc(F)cc32)C1)N1CC2(CC(O)C2)C1] | LCMS m/z 441.25 [M + H]$^+$ | A; 3.52 |
| 138 | 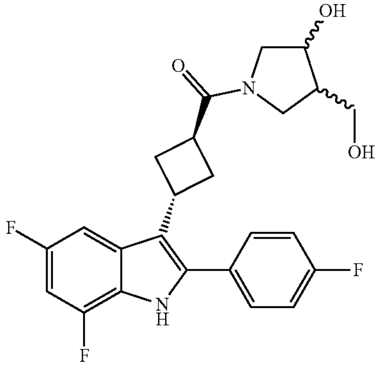 [SMILES: O=C([C@H]1C[C@H](c2c(-c3ccc(F)cc3)[nH]c3c(F)cc(F)cc32)C1)N1CC(O)C(CO)C1] | LCMS m/z 445.13 [M + H]$^+$ | A; 3.15 |
| 139 | 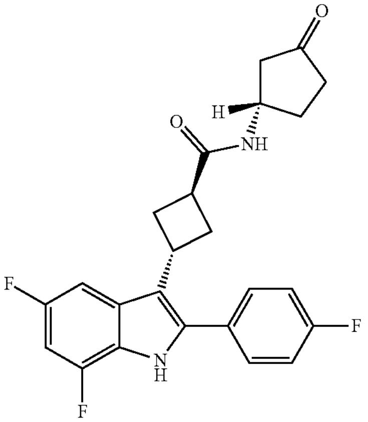 [SMILES: O=C1CC[C@H](NC(=O)[C@H]2C[C@H](c3c(-c4ccc(F)cc4)[nH]c4c(F)cc(F)cc43)C2)C1] | LCMS m/z 427.14 [M + H]$^+$ | A; 3.7 |

TABLE 6-continued
Structure, physicochemical properties, and LCMS analysis for compounds for compounds 83-161
| Compound | Structure | $^1$H NMR (ppm); LCMS m/z [M + H]$^+$ | LCMS Method; LCMS retention time (min) |
|---|---|---|---|
| 140 | 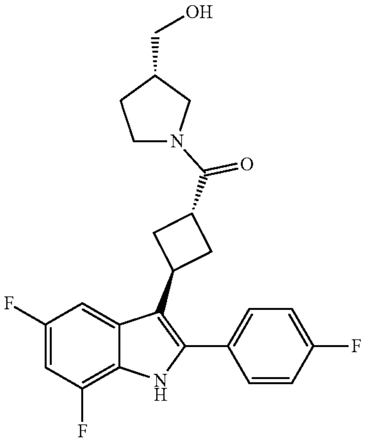 [SMILES: O=C([C@H]1C[C@H](c2c(-c3ccc(F)cc3)[nH]c3c(F)cc(F)cc32)C1)N1CC[C@H](CO)C1] | LCMS m/z 429.16 [M + H]$^+$ | A; 3.55 |
| 141 | 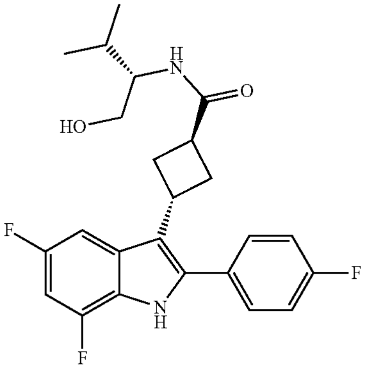 [SMILES: CC(C)[C@@H](CO)NC(=O)[C@H]1C[C@H](c2c(-c3ccc(F)cc3)[nH]c3c(F)cc(F)cc32)C1] | LCMS m/z 431.18 [M + H]$^+$ | A; 3.77 |
| 142 | 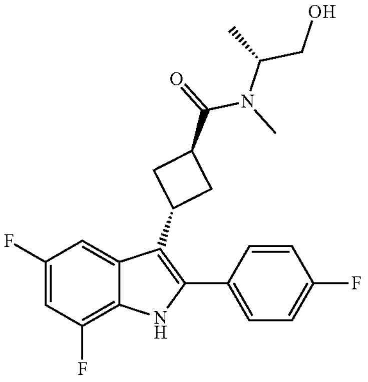 [SMILES: C[C@H](CO)N(C)C(=O)[C@H]1C[C@H](c2c(-c3ccc(F)cc3)[nH]c3c(F)cc(F)cc32)C1] | LCMS m/z 417.18 [M + H]$^+$ | A; 3.69 |

TABLE 6-continued
| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds for compounds 83-161 | | | |
| 143 | 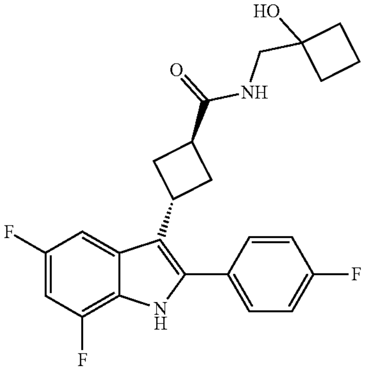 [SMILES: O=C(NCC1(O)CCC1)[C@H]1C[C@H](c2c(-c3ccc(F)cc3)[nH]c3c(F)cc(F)cc32)C1] | LCMS m/z 429.16 [M + H]$^+$ | A; 3.75 |
| 144 | 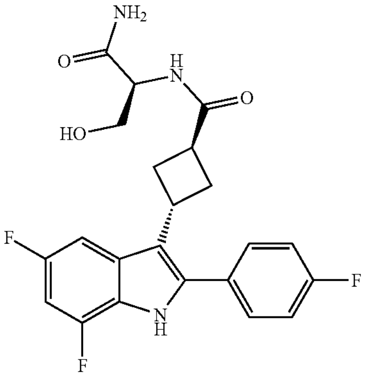 [SMILES: NC(=O)[C@H](CO)NC(=O)[C@H]1C[C@H](c2c(-c3ccc(F)cc3)[nH]c3c(F)cc(F)cc32)C1] | LCMS m/z 432.13 [M + H]$^+$ | A; 3.07 |
| 145 | 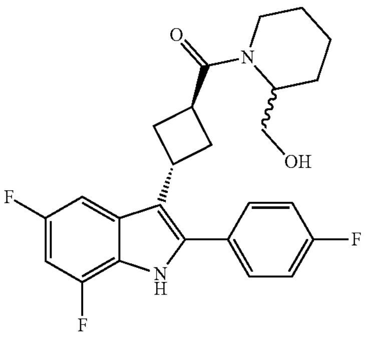 [SMILES: O=C([C@H]1C[C@H](c2c(-c3ccc(F)cc3)[nH]c3c(F)cc(F)cc32)C1)N1CCCCC1CO] | LCMS m/z 443.14 [M + H]$^+$ | A; 3.92 |
| 146 | 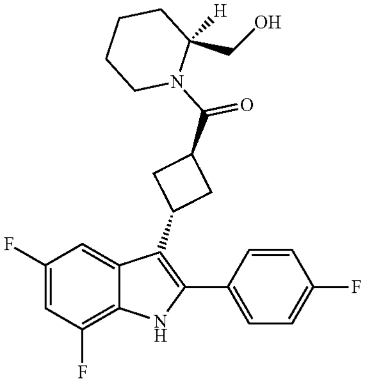 [SMILES: O=C([C@H]1C[C@H](c2c(-c3ccc(F)cc3)[nH]c3c(F)cc(F)cc32)C1)N1CCCC[C@H]1CO] | LCMS m/z 443.17 [M + H]$^+$ | A; 3.92 |

TABLE 6-continued
Structure, physicochemical properties, and LCMS analysis for compounds for compounds 83-161
| Compound | Structure | $^1$H NMR (ppm); LCMS m/z [M + H]$^+$ | LCMS Method; LCMS retention time (min) |
|---|---|---|---|
| 147 | 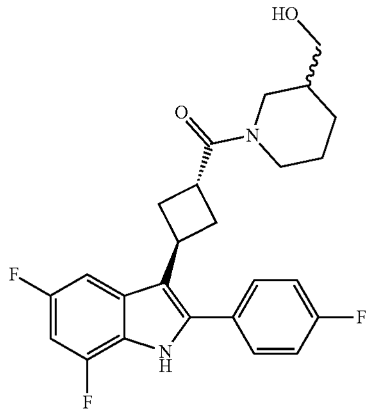 [SMILES: O=C([C@H]1C[C@H](c2c(-c3ccc(F)cc3)[nH]c3c(F)cc(F)cc32)C1)N1CCCC(CO)C1] | LCMS m/z 443.33 [M + H]$^+$ | A; 3.82 |
| 148 | 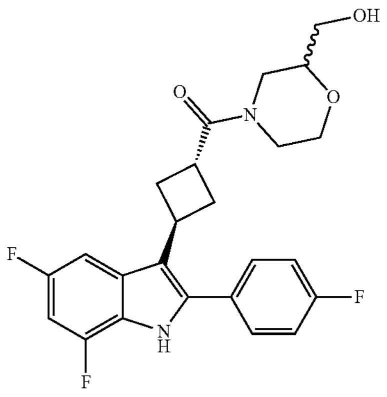 [SMILES: O=C([C@H]1C[C@H](c2c(-c3ccc(F)cc3)[nH]c3c(F)cc(F)cc32)C1)N1CCOC(CO)C1] | LCMS m/z 445.13 [M + H]$^+$ | A; 3.5 |
| 149 | 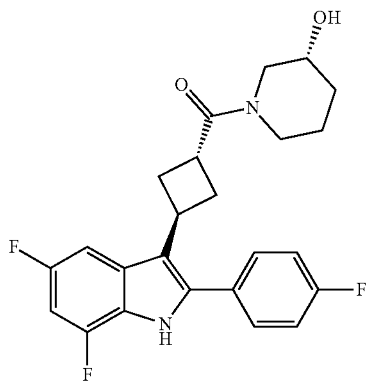 [SMILES: O=C([C@H]1C[C@H](c2c(-c3ccc(F)cc3)[nH]c3c(F)cc(F)cc32)C1)N1CCC[C@@H](O)C1] | LCMS m/z 429.16 [M + H]$^+$ | A; 3.71 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z [M + H]$^+$ | LCMS Method; LCMS retention time (min) |
| 150 | 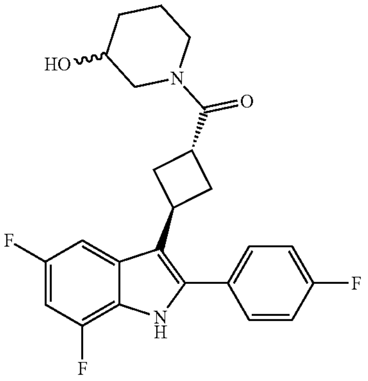 [SMILES: O=C([C@H]1C[C@H](c2c(-c3ccc(F)cc3)[nH]c3c(F)cc(F)cc32)C1)N1CCCC(O)C1] | LCMS m/z 429.16 [M + H]$^+$ | A; 3.7 |
| 151 | 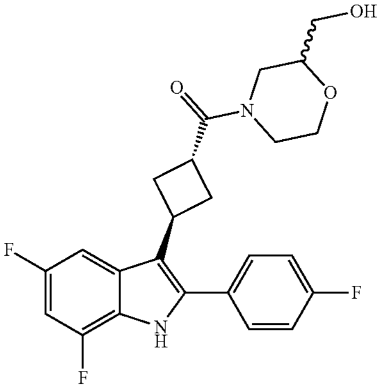 [SMILES: O=C([C@H]1C[C@H](c2c(-c3ccc(F)cc3)[nH]c3c(F)cc(F)cc32)C1)N1CCOC(CO)C1] | LCMS m/z 445.16 [M + H]$^+$ | A; 3.5 |
| 152 | 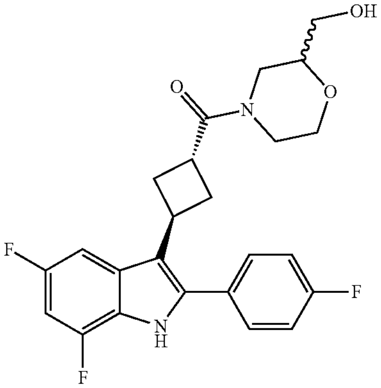 [SMILES: O=C([C@H]1C[C@H](c2c(-c3ccc(F)cc3)[nH]c3c(F)cc(F)cc32)C1)N1CCOC(CO)C1] | LCMS m/z 445.16 [M + H]$^+$ | A; 3.5 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z $[M + H]^+$ | LCMS Method; LCMS retention time (min) |
| 153 | 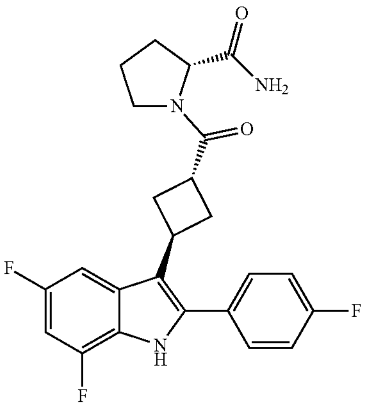 [SMILES: NC(=O)[C@H]1CCCN1C(=O)[C@H]1C[C@H](c2c(-c3ccc(F)cc3)[nH]c3c(F)cc(F)cc32)C1] | LCMS m/z 442.13 $[M + H]^+$ | A; 3.44 |
| 154 | 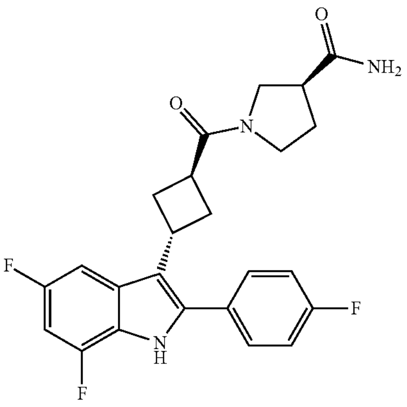 [SMILES: NC(=O)[C@H]1CCN(C(=O)[C@H]2C[C@H](c3c(-c4ccc(F)cc4)[nH]c4c(F)cc(F)cc43)C2)C1] | LCMS m/z 442.13 $[M + H]^+$ | A; 3.32 |
| 155 | 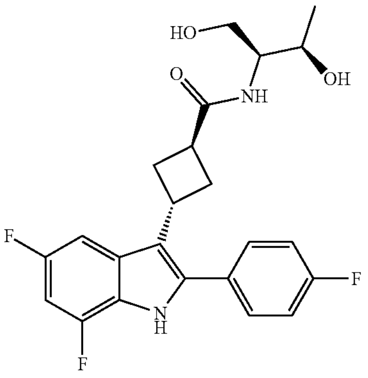 [SMILES: C[C@@H](O)[C@H](CO)NC(=O)[C@H]1C[C@H](c2c(-c3ccc(F)cc3)[nH]c3c(F)cc(F)cc32)C1] | LCMS m/z 433.14 $[M + H]^+$ | A; 3.22 |

TABLE 6-continued
| Structure, physicochemical properties, and LCMS analysis for compounds for compounds 83-161 | | | |
|---|---|---|---|
| Compound | Structure | $^1$H NMR (ppm); LCMS m/z [M + H]$^+$ | LCMS Method; LCMS retention time (min) |
| 156 | 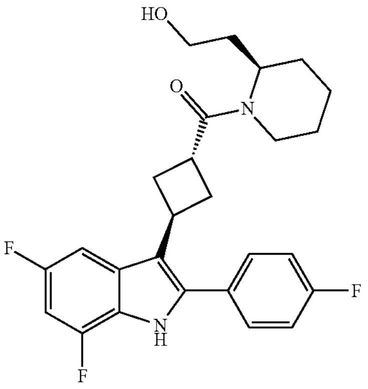 [SMILES: O=C([C@H]1C[C@H](c2c(-c3ccc(F)cc3)[nH]c3c(F)cc(F)cc32)C1)N1CCCC[C@@H]1CCO] | LCMS m/z 457.18 [M + H]$^+$ | A; 4.13 |
| 157 | 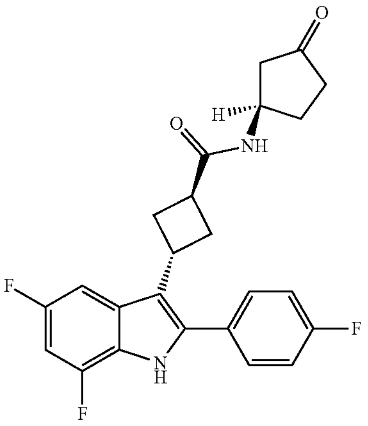 [SMILES: O=C1CC[C@@H](NC(=O)[C@H]2C[C@H](c3c(-c4ccc(F)cc4)[nH]c4c(F)cc(F)cc43)C2)C1] | LCMS m/z 427.14 [M + H]$^+$ | A; 3.7 |
| 158 | 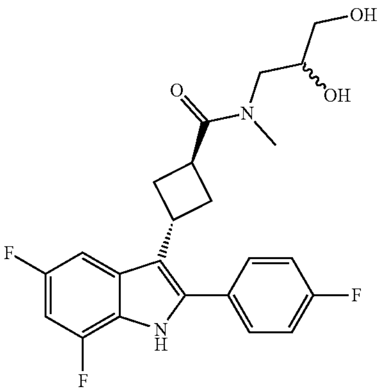 [SMILES: CN(CC(O)CO)C(=O)[C@H]1C[C@H](c2c(-c3ccc(F)cc3)[nH]c3c(F)cc(F)cc32)C1] | LCMS m/z 433.17 [M + H]$^+$ | A; 3.33 |

TABLE 6-continued

| Compound | Structure | $^1$H NMR (ppm); LCMS m/z [M + H]$^+$ | LCMS Method; LCMS retention time (min) |
|---|---|---|---|
| 159 | 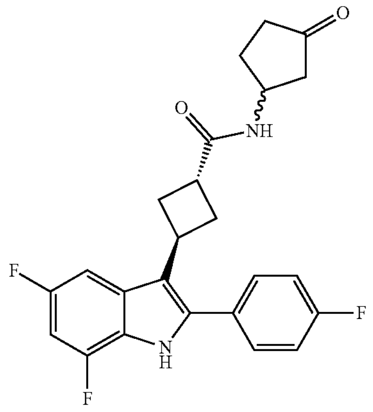 [SMILES: O=C1CCC(NC(=O)[C@H]2C[C@H](c3c(-c4ccc(F)cc4)[nH]c4c(F)cc(F)cc43)C2)C1] | LCMS m/z 427.14 [M + H]$^+$ | A; 3.7 |
| 160 | 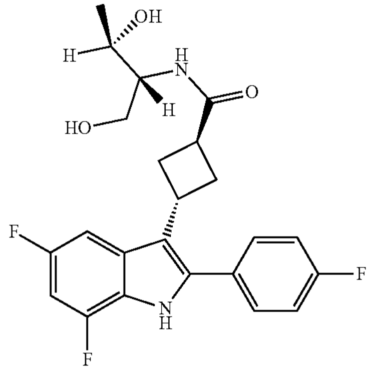 [SMILES: C[C@@H](O)[C@@H](CO)NC(=O)[C@H]1C[C@H](c2c(-c3ccc(F)cc3)[nH]c3c(F)cc(F)cc32)C1] | LCMS m/z 433.17 [M + H]$^+$ | A; 3.24 |
| 161 | 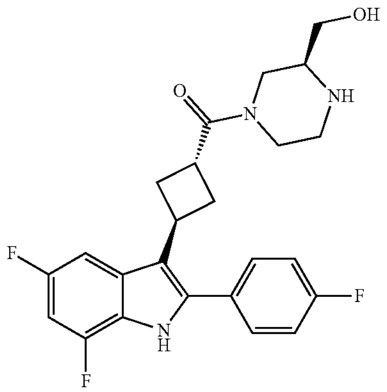 [SMILES: O=C([C@H]1C[C@H](c2c(-c3ccc(F)cc3)[nH]c3c(F)cc(F)cc32)C1)N1CCN[C@H](CO)C1] | LCMS m/z 444.18 [M + H]$^+$ | A; 0.27 |

Structure, physicochemical properties, and LCMS analysis for compounds for compounds 83-161

Compounds 162-234

Compounds 162-234 (Table 7) were prepared from S2 and the appropriate commercially available amine by HATU coupling according to standard procedure A.

TABLE 7

| Structure, physicochemical properties, and LCMS analysis for compounds 162-234 | | | |
|---|---|---|---|
| Compound | Structure | $^1$H NMR (ppm); LCMS m/z $[M + H]^+$ | LCMS Method; LCMS retention time (min) |
| 162 | 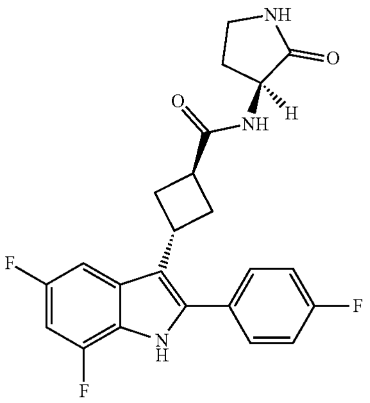 [SMILES: O=C1NCC[C@@H]1NC(=O)[C@H]1C[C@H](c2c(-c3ccc(F)cc3)[nH]c3c(F)cc(F)cc32)C1] | $^1$H NMR (300 MHz, Methanol-$d_4$) 7.97 (s, 1H), 7.57 - 7.44 (m, 2H), 7.32 (dd, J = 9.8, 2.2 Hz, 1H), 7.29 - 7.09 (m, 2H), 6.73 (dddd, J = 11.0, 9.6, 5.4, 2.2 Hz, 1H), 4.51 (ddd, J = 10.3, 8.8, 3.2 Hz, 1H), 4.18 - 3.99 (m, 1H), 3.44 - 3.31 (m, 2H), 3.25 - 3.15 (m, 1H), 2.73 - 2.56 (m, 3H), 2.55 - 2.45 (m, 1H), 2.01 (ddt, J = 12.6, 10.4, 9.2 Hz, 1H). LCMS m/z 428.2 $[M + H]^+$ | C; 0.97 |
| 163 | 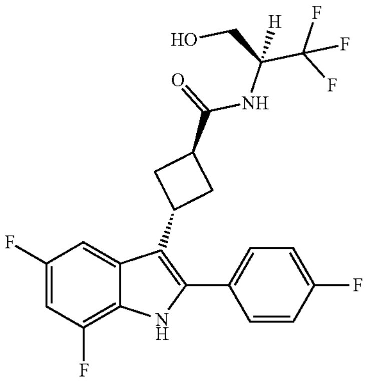 [SMILES: O=C(N[C@@H](CO)C(F)(F)F)[C@H]1C[C@H](c2c(-c3ccc(F)cc3)[nH]c3c(F)cc(F)cc32)C1] | $^1$H NMR (300 MHz, Methanol-$d_4$) δ 8.34 (d, J = 9.3 Hz, 1H), 7.56 - 7.43 (m, 2H), 7.34 (dd, J = 9.7, 2.2 Hz, 1H), 7.27 - 7.12 (m, 2H), 6.75 (ddd, J = 11.1, 9.6, 2.1 Hz, 1H), 4.81 - 4.56 (m, 1H), 4.10 (p, J = 9.1 Hz, 1H), 3.83 (dd, J = 11.7, 4.6 Hz, 1H), 3.71 (dd, J = 11.7, 6.9 Hz, 1H), 2.77 - 2.46 (m, 3H). LCMS m/z 457.12 $[M + H]^+$ | A; 3.81 |
| 164 | 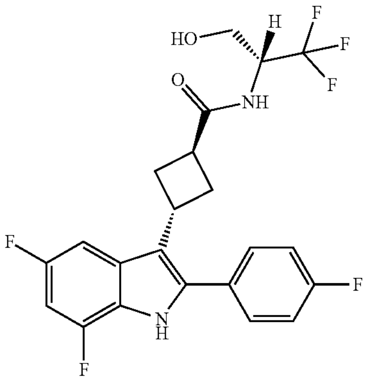 [SMILES: O=C(N[C@H](CO)C(F)(F)F)[C@H]1C[C@H](c2c(-c3ccc(F)cc3)[nH]c3c(F)cc(F)cc32)C1] | $^1$H NMR (300 MHz, Methanol-$d_4$) δ 8.34 (d, J = 9.3 Hz, 1H), 7.58 - 7.44 (m, 2H), 7.34 (dd, J = 9.7, 2.2 Hz, 1H), 7.28 - 7.14 (m, 2H), 6.82 - 6.68 (m, 1H), 4.68 (s, 1H), 4.10 (p, J = 9.1 Hz, 1H), 3.89 - 3.65 (m, 2H), 3.32 - 3.08 (m, 1H), 2.80 - 2.44 (m, 4H). LCMS m/z 457.21 $[M + H]^+$ | A; 3.81 |

TABLE 7-continued
Structure, physicochemical properties, and LCMS analysis for compounds 162-234
| Compound | Structure | $^1$H NMR (ppm); LCMS m/z [M + H]$^+$ | LCMS Method; LCMS retention time (min) |
|---|---|---|---|
| 165 | 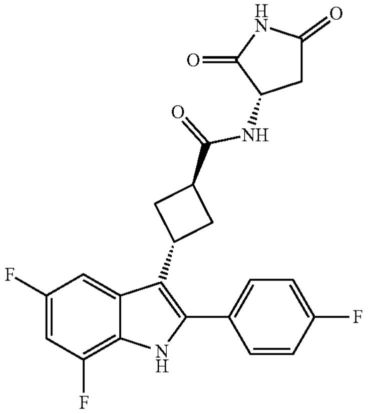 [SMILES: O=C1C[C@H](NC(=O)[C@H]2C[C@H](c3c(-c4ccc(F)cc4)[nH]c4c(F)cc(F)cc43)C2)C(=O)N1] | LCMS m/z 442.2 [M + H]$^+$ | A; 3.4 |
| 166 | 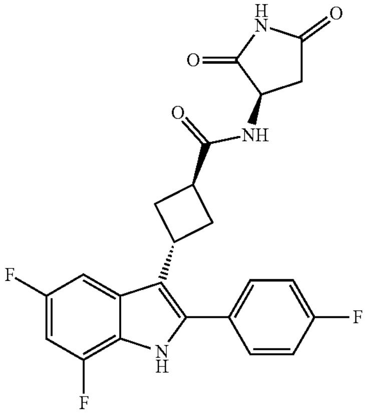 [SMILES: O=C1C[C@@H](NC(=O)[C@H]2C[C@H](c3c(-c4ccc(F)cc4)[nH]c4c(F)cc(F)cc43)C2)C(=O)N1] | LCMS m/z 442.2 [M + H]$^+$ | A; 3.4 |
| 167 | 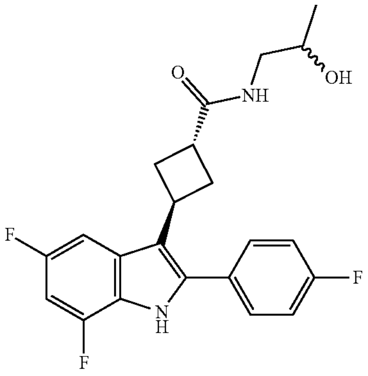 [SMILES: CC(O)CNC(=O)[C@H]1C[C@H](c2c(-c3ccc(F)cc3)[nH]c3c(F)cc(F)cc32)C1] | $^1$H NMR (300 MHz, Acetone-$d_6$) δ 10.70 (s, 1H), 7.69 - 7.49 (m, 2H), 7.41 (dd, J = 9.8, 2.2 Hz, 1H), 7.36 - 7.21 (m, 2H), 7.12 (s, 1H), 6.85 (ddd, J = 11.1, 9.7, 2.2 Hz, 1H), 4.25 - 4.03 (m, 1H), 3.84 - 3.67 (m, 3H), 3.30 (ddt, J = 10.7, 8.9, 5.2 Hz, 2H), 3.20 - 3.01 (m, 1H), 2.71 - 2.58 (m, 3H), 1.11 (d, J = 6.3 Hz, 3H). LCMS m/z 403.21 [M + H]$^+$ | A; 3.48 |

TABLE 7-continued

Structure, physicochemical properties, and LCMS analysis for compounds 162-234

| Compound | Structure | $^1H$ NMR (ppm); LCMS m/z $[M + H]^+$ | LCMS Method; LCMS retention time (min) |
|---|---|---|---|
| 168 | 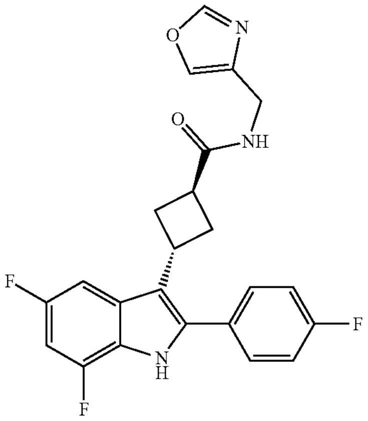 [SMILES: O=C(NCc1cocn1)[C@H]1C[C@H](c2c(-c3ccc(F)cc3)[nH]c3c(F)cc(F)cc32)C1] | $^1H$ NMR (300 MHz, Methanol-$d_4$) δ 8.14 (dd, J = 4.2, 1.0 Hz, 1H), 7.81 (dq, J = 1.7, 1.0 Hz, 1H), 7.56 - 7.44 (m, 2H), 7.32 (dd, J = 9.8, 2.2 Hz, 1H), 7.21 (ddt, J = 8.8, 6.6, 2.4 Hz, 2H), 6.74 (dddd, J = 13.9, 9.6, 4.3, 2.1 Hz, 1H), 4.34 (d, J = 1.0 Hz, 2H), 4.17 - 4.03 (m, 1H), 3.25-3.17 (m, 1H), 2.81 - 2.49 (m, 4H). LCMS m/z 426.17 $[M + H]^+$ | A; 3.66 |
| 169 | 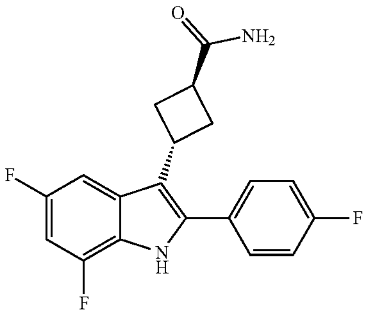 [SMILES: NC(=O)[C@H]1C[C@H](c2c(-c3ccc(F)cc3)[nH]c3c(F)cc(F)cc32)C1] | LCMS m/z 345.12 $[M + H]^+$ | A; 3.53 |
| 170 | 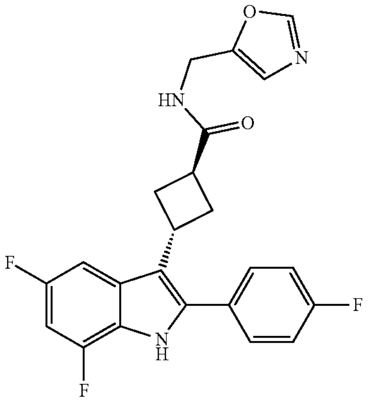 [SMILES: O=C(NCc1cnco1)[C@H]1C[C@H](c2c(-c3ccc(F)cc3)[nH]c3c(F)cc(F)cc32)C1] | $^1H$ NMR (300 MHz, Methanol-$d_4$) δ 8.15 (d, J = 0.5 Hz, 1H), 7.58 - 7.41 (m, 2H), 7.32 (dd, J = 9.7, 2.2 Hz, 1H), 7.26 - 7.14 (m, 2H), 7.03 (q, J = 0.8 Hz, 1H), 6.74 (ddd, J = 11.0, 9.6, 2.2 Hz, 1H), 4.48 (d, J = 1.0 Hz, 2H), 4.20 - 4.03 (m, 1H), 3.25 - 3.13 (m, 1H), 2.84 - 2.43 (m, 4H). LCMS m/z 426.17 $[M + H]^+$ | A; 3.63 |
| 171 | 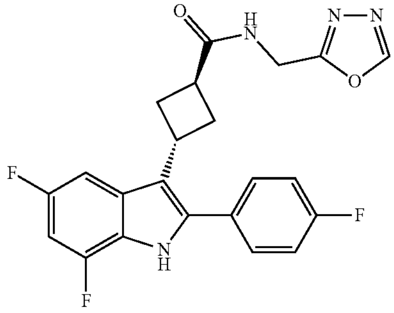 [SMILES: O=C(NCc1nnco1)[C@H]1C[C@H](c2c(-c3ccc(F)cc3)[nH]c3c(F)cc(F)cc32)C1] | LCMS m/z 427.15 $[M + H]^+$ | A; 3.63 |

TABLE 7-continued
| Compound | Structure | $^1H$ NMR (ppm); LCMS m/z $[M + H]^+$ | LCMS Method; LCMS retention time (min) |
| --- | --- | --- | --- |
| Structure, physicochemical properties, and LCMS analysis for compounds 162-234 | | | |
| 172 | 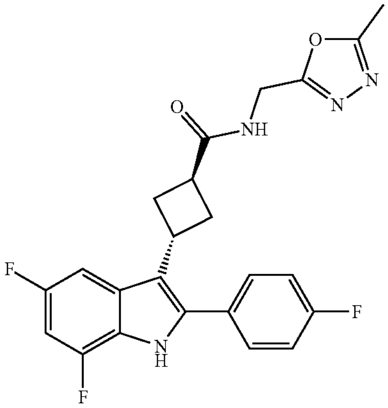 [SMILES: Cc1nnc(CNC(=O)[C@H]2C[C@H](c3c(-c4ccc(F)cc4)[nH]c4c(F)cc(F)cc43)C2)o1] | LCMS m/z 441.16 $[M + H]^+$ | A; 3.52 |
| 173 | 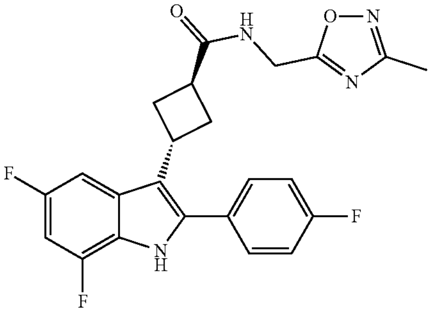 [SMILES: Cc1noc(CNC(=O)[C@H]2C[C@H](c3c(-c4ccc(F)cc4)[nH]c4c(F)cc(F)cc43)C2)n1] | LCMS m/z 441.12 $[M + H]^+$ | A; 3.78 |
| 174 | 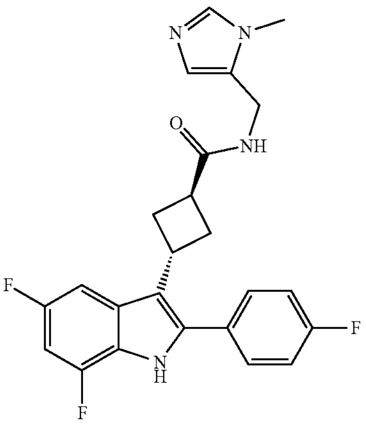 [SMILES: Cn1cncc1CNC(=O)[C@H]1C[C@H](c2c(-c3ccc(F)cc3)[nH]c3c(F)cc(F)cc32)C1] | $^1H$ NMR (300 MHz, Methanol-$d_4$) δ 8.64 (s, 1H), 8.43 (d, J = 7.4 Hz, 2H), 8.24 (d, J = 9.6 Hz, 1H), 8.15 (d, J = 8.7 Hz, 2H), 7.88 (s, 1H), 7.64 (d, J = 11.1 Hz, 1H), 5.36 (s, 2H), 5.01 (d, J = 9.0 Hz, 1H), 4.61 (s, 3H), 4.05 (d, J = 37.4 Hz, 1H), 3.73 - 3.26 (m, 4H). LCMS m/z 439.17 $[M + H]^+$ | A; 2.76 |

TABLE 7-continued
Structure, physicochemical properties, and LCMS analysis for compounds 162-234
| Compound | Structure | $^1$H NMR (ppm); LCMS m/z $[M + H]^+$ | LCMS Method; LCMS retention time (min) |
| --- | --- | --- | --- |
| 175 | 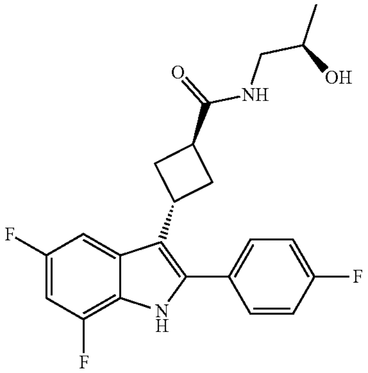 [SMILES: C[C@@H](O)CNC(=O)[C@H]1C[C@H](c2c(-c3ccc(F)cc3)[nH]c3c(F)cc(F)cc32)C1] | LCMS m/z 403.26 $[M + H]^+$ | A; 3 |
| 176 | 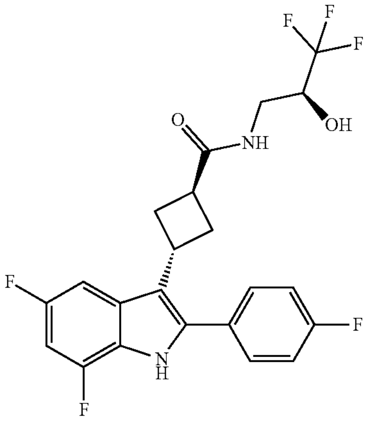 [SMILES: O=C(NC[C@H](O)C(F)(F)F)[C@H]1C[C@H](c2c(-c3ccc(F)cc3)[nH]c3c(F)cc(F)cc32)C1] | LCMS m/z 457.23 $[M + H]^+$ | A; 3.36 |
| 177 | 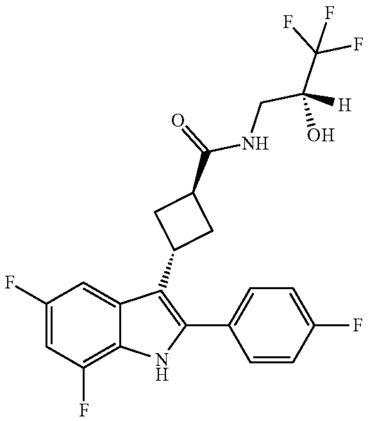 [SMILES: O=C(NC[C@@H](O)C(F)(F)F)[C@H]1C[C@H](c2c(-c3ccc(F)cc3)[nH]c3c(F)cc(F)cc32)C1] | LCMS m/z 457.19 $[M + H]^+$ | A; 3.37 |

TABLE 7-continued
| Structure, physicochemical properties, and LCMS analysis for compounds 162-234 | | | |
|---|---|---|---|
| Compound | Structure | $^1$H NMR (ppm); LCMS m/z $[M + H]^+$ | LCMS Method; LCMS retention time (min) |
| 178 | 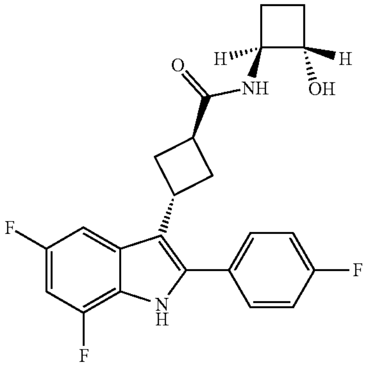 [SMILES: O=C(N[C@H]1CC[C@@H]1O)[C@H]1C[C@H](c2c(-c3ccc(F)cc3)[nH]c3c(F)cc(F)cc32)C1] | LCMS m/z 415.28 $[M + H]^+$ | A; 3.06 |
| 179 | 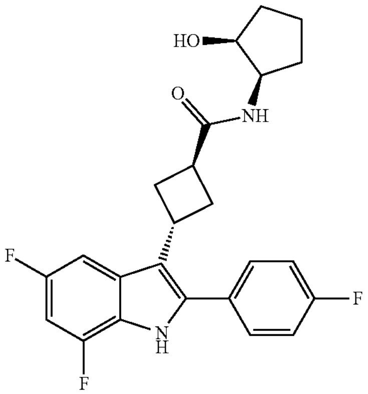 [SMILES: O=C(N[C@@H]1CCC[C@@H]1O)[C@H]1C[C@H](c2c(-c3ccc(F)cc3)[nH]c3c(F)cc(F)cc32)C1] | LCMS m/z 429.29 $[M + H]^+$ | A; 3.22 |
| 180 | 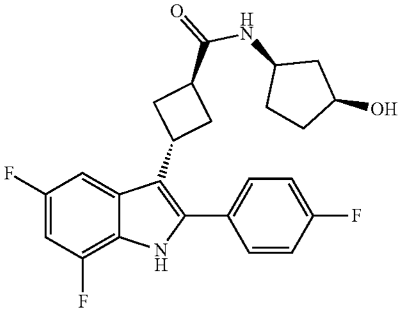 [SMILES: O=C(N[C@@H]1CC[C@H](O)C1)[C@H]1C[C@H](c2c(-c3ccc(F)cc3)[nH]c3c(F)cc(F)cc32)C1] | LCMS m/z 429.29 $[M + H]^+$ | A; 3.06 |
| 181 | 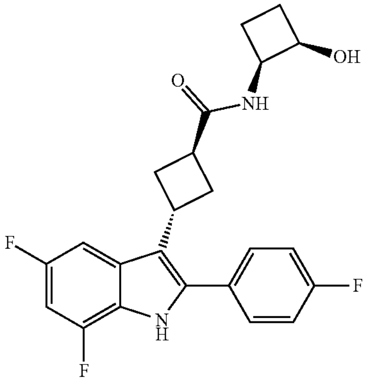 [SMILES: O=C(N[C@H]1CC[C@H]1O)[C@H]1C[C@H](c2c(-c3ccc(F)cc3)[nH]c3c(F)cc(F)cc32)C1] | LCMS m/z 415.25 $[M + H]^+$ | A; 3.13 |

TABLE 7-continued
Structure, physicochemical properties, and LCMS analysis for compounds 162-234
| Compound | Structure | $^1$H NMR (ppm); LCMS m/z $[M + H]^+$ | LCMS Method; LCMS retention time (min) |
|---|---|---|---|
| 182 | 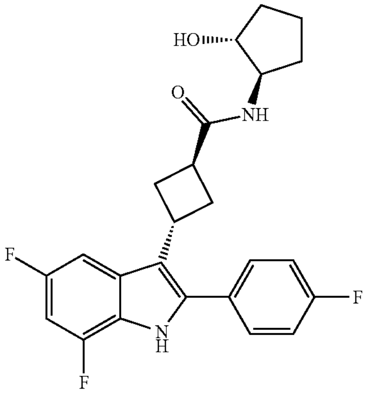 [SMILES: O=C(N[C@@H]1CCC[C@H]1O)[C@H]1C[C@H](c2c(-c3ccc(F)cc3)[nH]c3c(F)cc(F)cc32)C1] | LCMS m/z 429.29 $[M + H]^+$ | A; 3.21 |
| 183 | 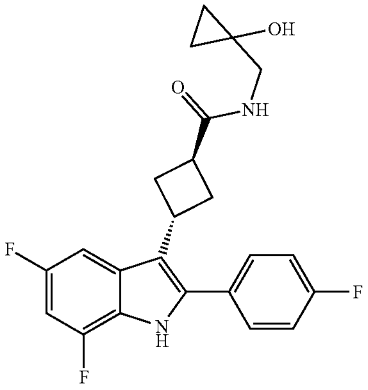 [SMILES: O=C(NCC1(O)CC1)[C@H]1C[C@H](c2c(-c3ccc(F)cc3)[nH]c3c(F)cc(F)cc32)C1] | LCMS m/z 415.28 $[M + H]^+$ | A; 3.09 |
| 184 | 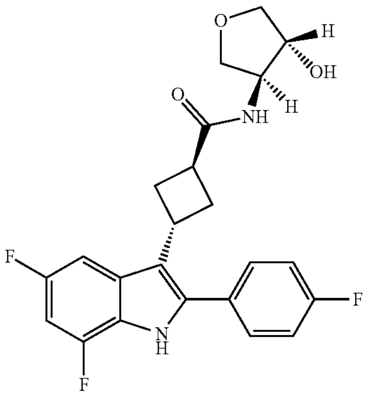 [SMILES: O=C(N[C@H]1COC[C@@H]1O)[C@H]1C[C@H](c2c(-c3ccc(F)cc3)[nH]c3c(F)cc(F)cc32)C1] | LCMS m/z 431.27 $[M + H]^+$ | A; 2.91 |

TABLE 7-continued
| Structure, physicochemical properties, and LCMS analysis for compounds 162-234 | | | |
|---|---|---|---|
| Compound | Structure | $^1$H NMR (ppm); LCMS m/z [M + H]$^+$ | LCMS Method; LCMS retention time (min) |
| 185 | 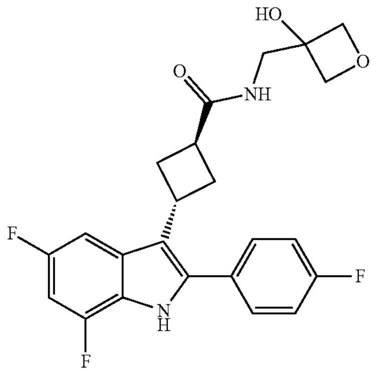 [SMILES: O=C(NCC1(O)COC1)[C@H]1C[C@H](c2c(-c3ccc(F)cc3)[nH]c3c(F)cc(F)cc32)C1] | LCMS m/z 431.27 [M + H]$^+$ | A; 2.93 |
| 186 | 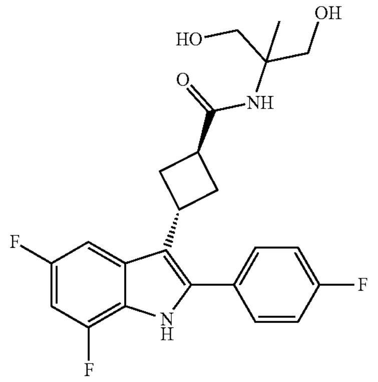 [SMILES: CC(CO)(CO)NC(=O)[C@H]1C[C@H](c2c(-c3ccc(F)cc3)[nH]c3c(F)cc(F)cc32)C1] | LCMS m/z 433.28 [M + H]$^+$ | A; 2.97 |
| 187 | 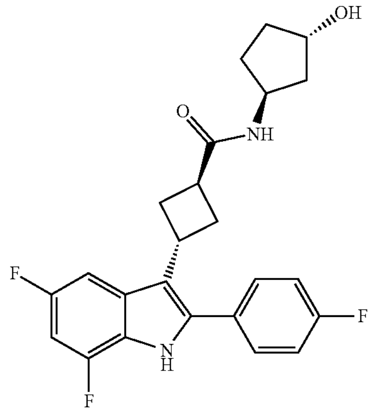 [SMILES: O=C(N[C@H]1CC[C@H](O)C1)[C@H]1C[C@H](c2c(-c3ccc(F)cc3)[nH]c3c(F)cc(F)cc32)C1] | LCMS m/z 429.29 [M + H]$^+$ | A; 3.01 |

TABLE 7-continued
| Compound | Structure | $^1$H NMR (ppm); LCMS m/z $[M + H]^+$ | LCMS Method; LCMS retention time (min) |
|---|---|---|---|
| Structure, physicochemical properties, and LCMS analysis for compounds 162-234 | | | |
| 188 | 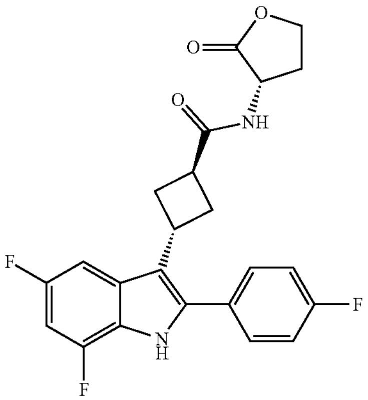 [SMILES: O=C1OCC[C@@H]1NC(=O)[C@H]1C[C@H](c2c(-c3ccc(F)cc3)[nH]c3c(F)cc(F)cc32)C1] | LCMS m/z 429.25 $[M + H]^+$ | A; 3.16 |
| 189 | 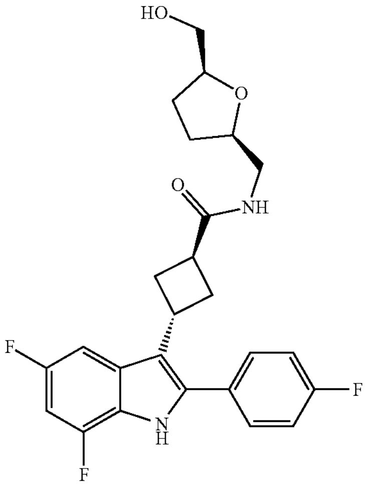 [SMILES: O=C(NC[C@H]1CC[C@@H](CO)O1)[C@H]1C[C@H](c2c(-c3ccc(F)cc3)[nH]c3c(F)cc(F)cc32)C1] | LCMS m/z 459.31 $[M + H]^+$ | A; 3.03 |
| 190 | 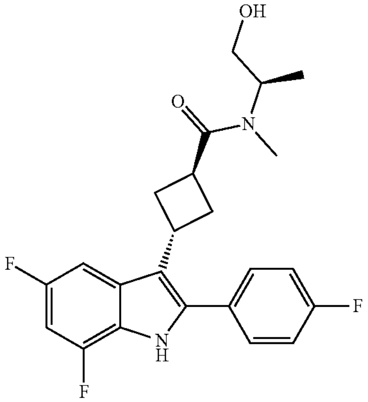 [SMILES: C[C@H](CO)N(C)C(=O)[C@H]1C[C@H](c2c(-c3ccc(F)cc3)[nH]c3c(F)cc(F)cc32)C1] | LCMS m/z 417.3 $[M + H]^+$ | A; 3.18 |

TABLE 7-continued
| Structure, physicochemical properties, and LCMS analysis for compounds 162-234 | | | |
|---|---|---|---|
| Compound | Structure | $^1$H NMR (ppm); LCMS m/z [M + H]$^+$ | LCMS Method; LCMS retention time (min) |
| 191 | 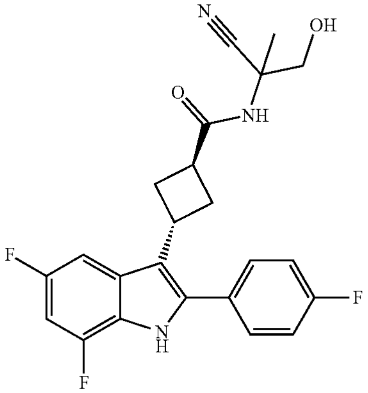 [SMILES: CC(C#N)(CO)NC(=O)[C@H]1C[C@H](c2c(-c3ccc(F)cc3)[nH]c3c(F)cc(F)cc32)C1] | LCMS m/z 428.24 [M + H]$^+$ | A; 3.15 |
| 192 | 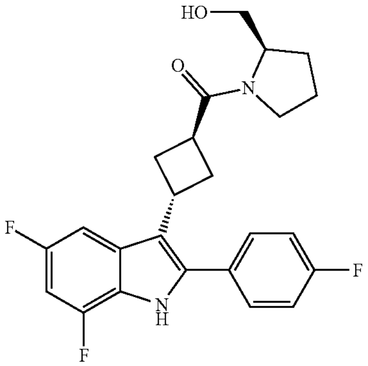 [SMILES: O=C([C@H]1C[C@H](c2c(-c3ccc(F)cc3)[nH]c3c(F)cc(F)cc32)C1)N1CCC[C@@H]1CO] | $^1$H NMR (300 MHz, Methanol-$d_4$) δ 7.55 - 7.49 (m, 2H), 7.38 (ddd, J = 9.7, 5.7, 2.3 Hz, 1H), 7.27 - 7.07 (m, 2H), 6.77 (ddd, J = 11.4, 9.6, 2.1 Hz, 1H), 4.15 (d, J = 4.2 Hz, 2H), 3.74 - 3.62 (m, 2H), 3.44 (t, J = 6.6 Hz, 2H), 2.90 - 2.49 (m, 5H), 2.03 - 1.79 (m, 4H). LCMS m/z 429.29 [M + H]$^+$ | A; 3.33 |
| 193 | 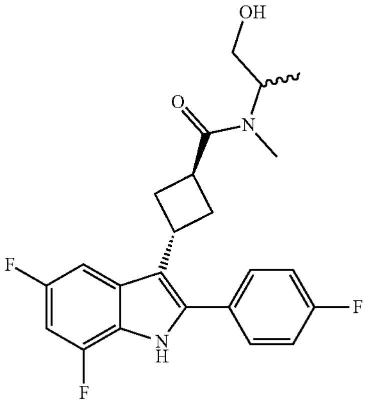 [SMILES: CC(CO)N(C)C(=O)[C@H]1C[C@H](c2c(-c3ccc(F)cc3)[nH]c3c(F)cc(F)cc32)C1] | LCMS m/z 417.3 [M + H]$^+$ | A; 3.18 |

TABLE 7-continued
| Compound | Structure | ¹H NMR (ppm); LCMS m/z [M + H]⁺ | LCMS Method; LCMS retention time (min) |
|---|---|---|---|
| Structure, physicochemical properties, and LCMS analysis for compounds 162-234 | | | |
| 194 | 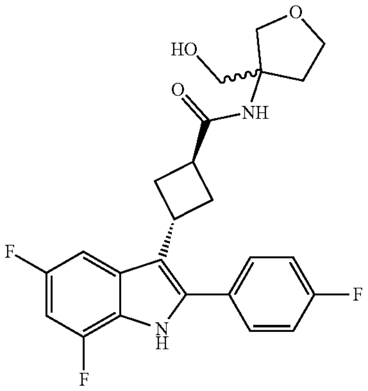 [SMILES: O=C(NC1(CO)CCOC1)[C@H]1C[C@H](c2c(-c3ccc(F)cc3)[nH]c3c(F)cc(F)cc32)C1] | LCMS m/z 445.27 [M + H]⁺ | A; 3.01 |
| 195 | 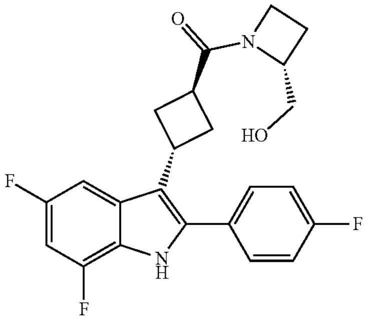 [SMILES: O=C([C@H]1C[C@H](c2c(-c3ccc(F)cc3)[nH]c3c(F)cc(F)cc32)C1)N1CC[C@@H]1CO] | LCMS m/z 415.28 [M + H]⁺ | A; 3.2 |
| 196 | 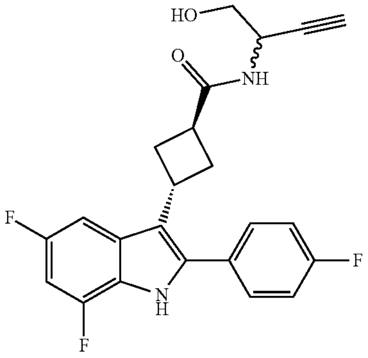 [SMILES: C#CC(CO)NC(=O)[C@H]1C[C@H](c2c(-c3ccc(F)cc3)[nH]c3c(F)cc(F)cc32)C1] | LCMS m/z 413.27 [M + H]⁺ | A; 3.08 |
| 197 | 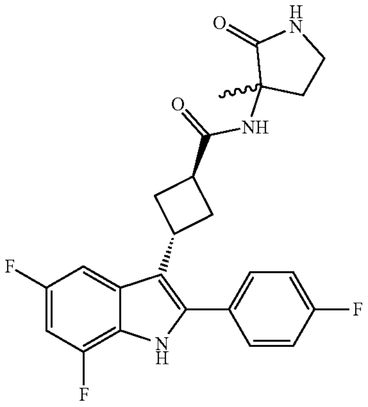 [SMILES: CC1(NC(=O)[C@H]2C[C@H](c3c(-c4ccc(F)cc4)[nH]c4c(F)cc(F)cc43)C2)CCNC1=O] | LCMS m/z 442.29 [M + H]⁺ | A; 2.93 |

TABLE 7-continued
| Compound | Structure | $^1H$ NMR (ppm); LCMS m/z $[M + H]^+$ | LCMS Method; LCMS retention time (min) |
|---|---|---|---|
| Structure, physicochemical properties, and LCMS analysis for compounds 162-234 | | | |
| 198 | 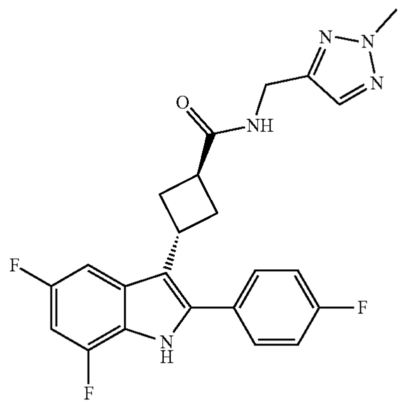 [SMILES: Cn1ncc(CNC(=O)[C@H]2C[C@H](c3c(-c4ccc(F)cc4)[nH]c4c(F)cc(F)cc43)C2)n1] | LCMS m/z 440.27 $[M + H]^+$ | A; 3.2 |
| 199 | 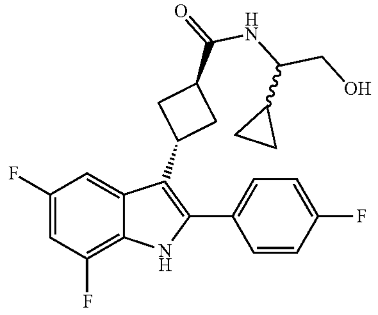 [SMILES: O=C(NC(CO)C1CC1)[C@H]1C[C@H](c2c(-c3ccc(F)cc3)[nH]c3c(F)cc(F)cc32)C1] | LCMS m/z 429.29 $[M + H]^+$ | A; 3.18 |
| 200 | 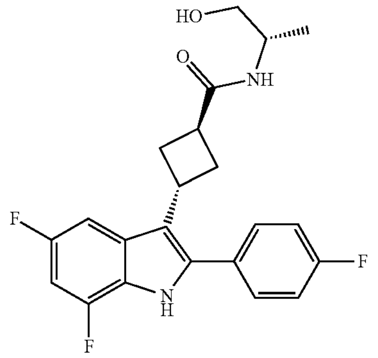 [SMILES: C[C@@H](CO)NC(=O)[C@H]1C[C@H](c2c(-c3ccc(F)cc3)[nH]c3c(F)cc(F)cc32)C1] | LCMS m/z 403.26 $[M + H]^+$ | A; 3.01 |
| 201 | 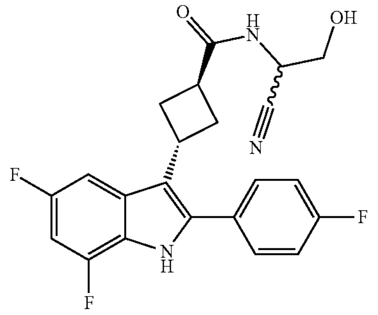 [SMILES: N#CC(CO)NC(=O)[C@H]1C[C@H](c2c(-c3ccc(F)cc3)[nH]c3c(F)cc(F)cc32)C1] | LCMS m/z 414.28 $[M + H]^+$ | A; 3.09 |

TABLE 7-continued
Structure, physicochemical properties, and LCMS analysis for compounds 162-234
| Compound | Structure | $^{1}$H NMR (ppm); LCMS m/z $[M + H]^+$ | LCMS Method; LCMS retention time (min) |
|---|---|---|---|
| 202 | 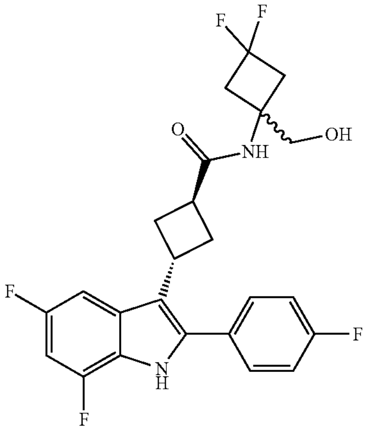 [SMILES: O=C(NC1(CO)CC(F)(F)C1)[C@H]1C[C@H](c2c(-c3ccc(F)cc3)[nH]c3c(F)cc(F)cc32)C1] | LCMS m/z 465.26 $[M + H]^+$ | A; 3.33 |
| 203 | 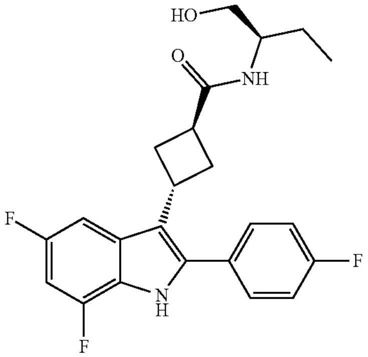 [SMILES: CC[C@H](CO)NC(=O)[C@H]1C[C@H](c2c(-c3ccc(F)cc3)[nH]c3c(F)cc(F)cc32)C1] | LCMS m/z 417.3 $[M + H]^+$ | A; 3.13 |
| 204 | 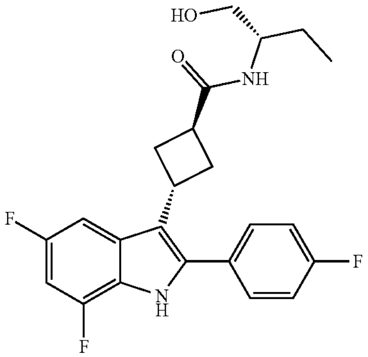 [SMILES: CC[C@@H](CO)NC(=O)[C@H]1C[C@H](c2c(-c3ccc(F)cc3)[nH]c3c(F)cc(F)cc32)C1] | LCMS m/z 417.3 $[M + H]^+$ | A; 3.13 |
| 205 | 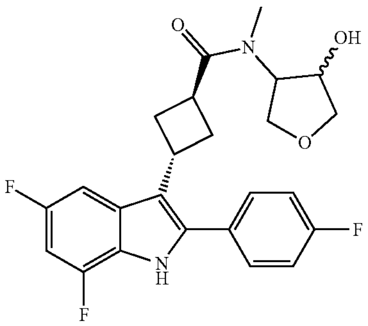 [SMILES: CN(C(=O)[C@H]1C[C@H](c2c(-c3ccc(F)cc3)[nH]c3c(F)cc(F)cc32)C1)C1COCC1O] | LCMS m/z 445.27 $[M + H]^+$ | A; 3.08 |

TABLE 7-continued
| Structure, physicochemical properties, and LCMS analysis for compounds 162-234 | | | |
|---|---|---|---|
| Compound | Structure | $^1$H NMR (ppm); LCMS m/z [M + H]$^+$ | LCMS Method; LCMS retention time (min) |
| 206 | 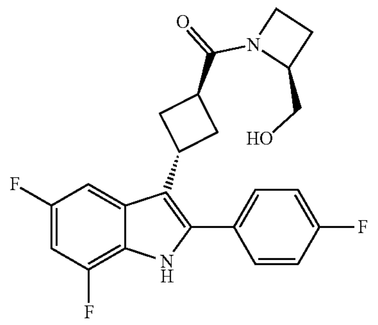 [SMILES: O=C([C@H]1C[C@H](c2c(-c3ccc(F)cc3)[nH]c3c(F)cc(F)cc32)C1)N1CC[C@H]1CO] | LCMS m/z 415.28 [M + H]$^+$ | A; 3.2 |
| 207 | 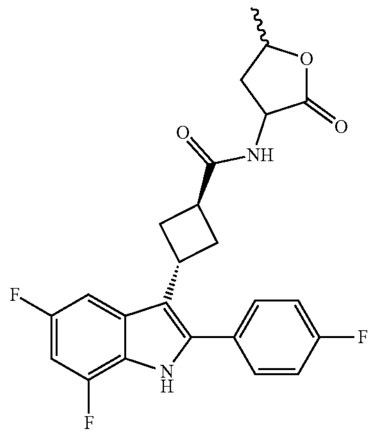 [SMILES: CC1CC(NC(=O)[C@H]2C[C@H](c3c(-c4ccc(F)cc4)[nH]c4c(F)cc(F)cc43)C2)C(=O)O1] | LCMS m/z 443.26 [M + H]$^+$ | A; 3.31 |
| 208 | 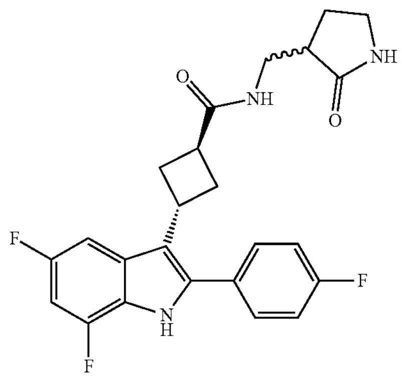 [SMILES: O=C1NCCC1CNC(=O)[C@H]1C[C@H](c2c(-c3ccc(F)cc3)[nH]c3c(F)cc(F)cc32)C1] | LCMS m/z 442.29 [M + H]$^+$ | A; 2.89 |

TABLE 7-continued
Structure, physicochemical properties, and LCMS analysis for compounds 162-234
| Compound | Structure | $^1$H NMR (ppm); LCMS m/z $[M + H]^+$ | LCMS Method; LCMS retention time (min) |
|---|---|---|---|
| 209 | 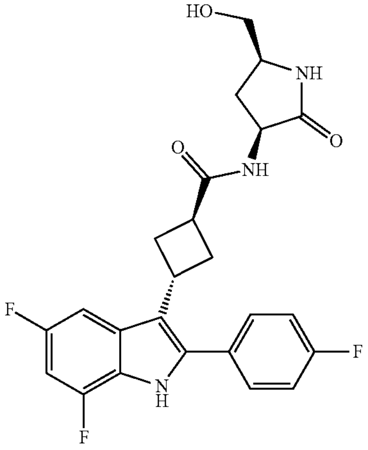 [SMILES: O=C1N[C@H](CO)C[C@@H]1NC(=O)[C@H]1C[C@H](c2c(-c3ccc(F)cc3)[nH]c3c(F)cc(F)cc32)C1] | LCMS m/z 458.27 $[M + H]^+$ | A; 2.67 |
| 210 | 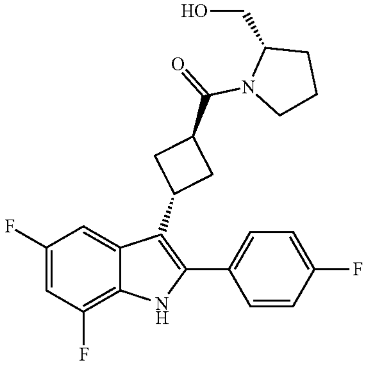 [SMILES: O=C([C@H]1C[C@H](c2c(-c3ccc(F)cc3)[nH]c3c(F)cc(F)cc32)C1)N1CCC[C@H]1CO] | LCMS m/z 429.29 $[M + H]^+$ | A; 3.32 |
| 211 | 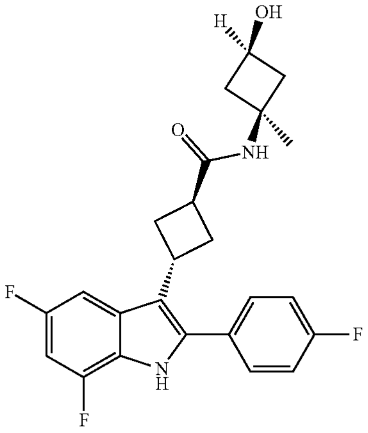 [SMILES: C[C@]1(NC(=O)[C@H]2C[C@H](c3c(-c4ccc(F)cc4)[nH]c4c(F)cc(F)cc43)C2)C[C@@H](O)C1] | LCMS m/z 429.29 $[M + H]^+$ | A; 3.09 |

TABLE 7-continued
| Compound | Structure | $^1$H NMR (ppm); LCMS m/z $[M + H]^+$ | LCMS Method; LCMS retention time (min) |
|---|---|---|---|
| Structure, physicochemical properties, and LCMS analysis for compounds 162-234 | | | |
| 212 | 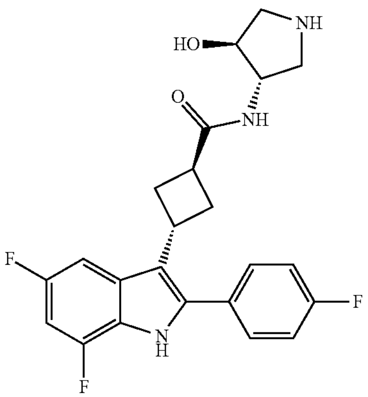 [SMILES: O=C(N[C@H]1CNC[C@@H]1O)[C@H]1C[C@H](c2c(-c3ccc(F)cc3)[nH]c3c(F)cc(F)cc32)C1] | LCMS m/z 430.41 $[M + H]^+$ | B; 0.67 |
| 213 | 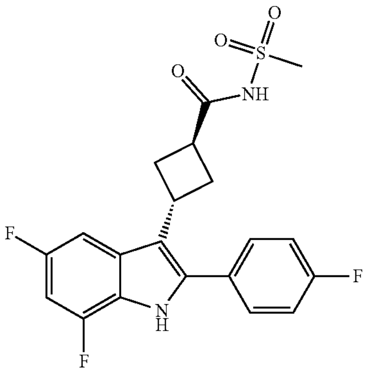 [SMILES: CS(=O)(=O)NC(=O)[C@H]1C[C@H](c2c(-c3ccc(F)cc3)[nH]c3c(F)cc(F)cc32)C1] | $^1$H NMR (300 MHz, Methanol-$d_4$) δ 7.59 - 7.43 (m, 2H), 7.33 (dd, J = 9.8, 2.2 Hz, 1H), 7.30 - 7.18 (m, 2H), 6.77 (ddd, J = 11.1, 9.6, 2.2 Hz, 1H), 4.17 - 3.98 (m, 1H), 3.29 (s, 3H), 3.29 - 3.17 (m, 1H), 2.81 - 2.60 (m, 4H). LCMS m/z 423.23 $[M + H]^+$ | A; 3.76 |
| 214 | 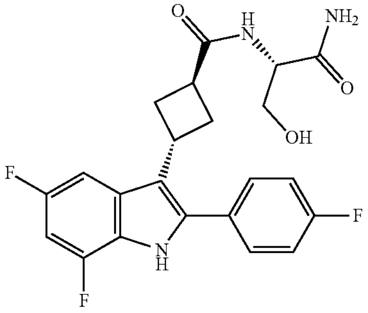 [SMILES: NC(=O)[C@H](CO)NC(=O)[C@H]1C[C@H](c2c(-c3ccc(F)cc3)[nH]c3c(F)cc(F)cc32)C1] | LCMS m/z 431.96 $[M + H]^+$ | A; 3.08 |
| 215 | 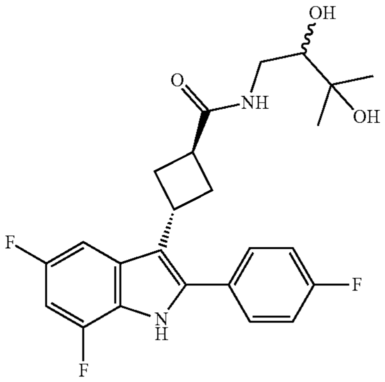 [SMILES: CC(C)(O)C(O)CNC(=O)[C@H]1C[C@H](c2c(-c3ccc(F)cc3)[nH]c3c(F)cc(F)cc32)C1] | LCMS m/z 447.15 $[M + H]^+$ | A; 3.37 |

TABLE 7-continued
Structure, physicochemical properties, and LCMS analysis for compounds 162-234
| Compound | Structure | $^1$H NMR (ppm); LCMS m/z $[M + H]^+$ | LCMS Method; LCMS retention time (min) |
|---|---|---|---|
| 216 | 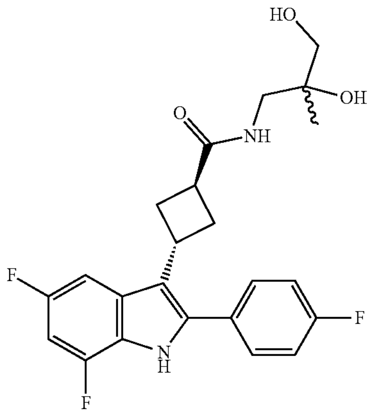 [SMILES: CC(O)(CO)CNC(=O)[C@H]1C[C@H](c2c(-c3ccc(F)cc3)[nH]c3c(F)cc(F)cc32)C1] | LCMS m/z 433.17 $[M + H]^+$ | A; 3.32 |
| 217 | 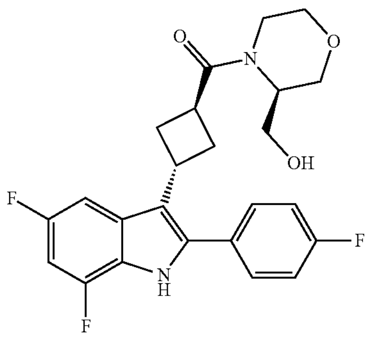 [SMILES: O=C([C@H]1C[C@H](c2c(-c3ccc(F)cc3)[nH]c3c(F)cc(F)cc32)C1)N1CCOC[C@H]1CO] | LCMS m/z 445.13 $[M + H]^+$ | A; 3.53 |
| 218 | 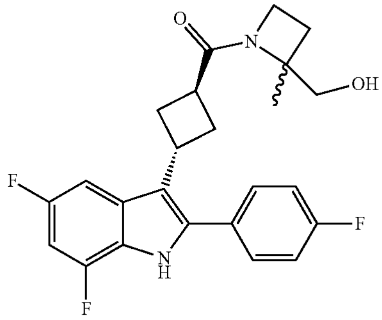 [SMILES: CC1(CO)CCN1C(=O)[C@H]1C[C@H](c2c(-c3ccc(F)cc3)[nH]c3c(F)cc(F)cc32)C1] | LCMS m/z 429.16 $[M + H]^+$ | A; 3.9 |
| 219 | 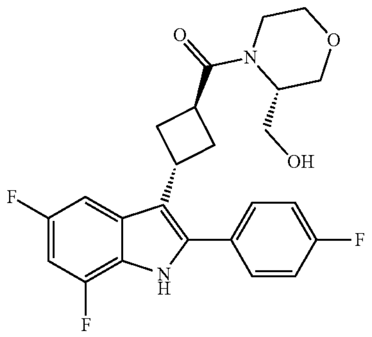 [SMILES: O=C([C@H]1C[C@H](c2c(-c3ccc(F)cc3)[nH]c3c(F)cc(F)cc32)C1)N1CCOC[C@@H]1CO] | LCMS m/z 445.16 $[M + H]^+$ | A; 3.55 |

TABLE 7-continued
| Compound | Structure | $^1$H NMR (ppm); LCMS m/z [M + H]$^+$ | LCMS Method; LCMS retention time (min) |
| --- | --- | --- | --- |
| Structure, physicochemical properties, and LCMS analysis for compounds 162-234 | | | |
| 220 | 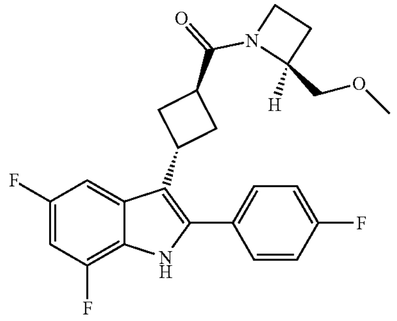 [SMILES: COC[C@@H]1CCN1C(=O)[C@H]1C[C@H](c2c(-c3ccc(F)cc3)[nH]c3c(F)cc(F)cc32)C1] | LCMS m/z 429.03 [M + H]$^+$ | A; 4.06 |
| 221 | 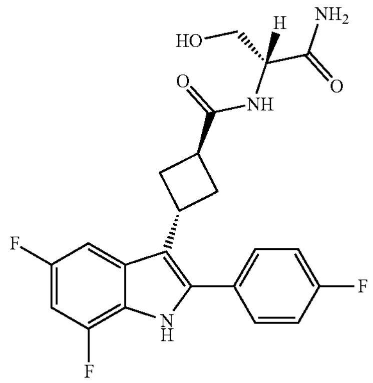 [SMILES: NC(=O)[C@@H](CO)NC(=O)[C@H]1C[C@H](c2c(-c3ccc(F)cc3)[nH]c3c(F)cc(F)cc32)C1] | LCMS m/z 432.23 [M + H]$^+$ | A; 3.07 |
| 222 | 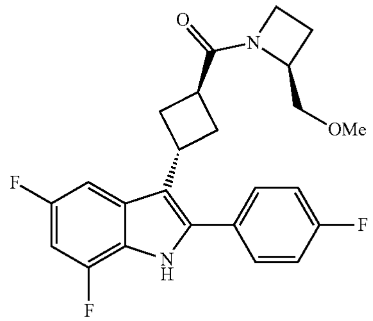 [SMILES: COC[C@@H]1CCN1C(=O)[C@H]1C[C@H](c2c(-c3ccc(F)cc3)[nH]c3c(F)cc(F)cc32)C1] | LCMS m/z 429.16 [M + H]$^+$ | A; 4.07 |
| 223 | 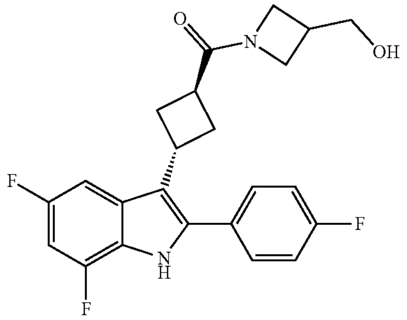 [SMILES: O=C([C@H]1C[C@H](c2c(-c3ccc(F)cc3)[nH]c3c(F)cc(F)cc32)C1)N1CC(CO)C1] | LCMS m/z 415.16 [M + H]$^+$ | A; 3.42 |

TABLE 7-continued

| Structure, physicochemical properties, and LCMS analysis for compounds 162-234 | | | |
|---|---|---|---|
| Compound | Structure | $^1$H NMR (ppm); LCMS m/z $[M + H]^+$ | LCMS Method; LCMS retention time (min) |
| 224 | 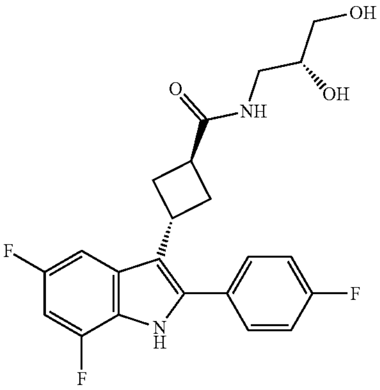 [SMILES: O=C(NC[C@@H](O)CO)[C@H]1C[C@H](c2c(-c3ccc(F)cc3)[nH]c3c(F)cc(F)cc32)C1] | $^1$H NMR (300 MHz, DMSO-$d_6$) 11.69 (s, 1H), 7.74 (t, J = 5.8 Hz, 1H), 7.52 (ddd, J = 8.6, 5.4, 2.6 Hz, 2H), 7.47 - 7.23 (m, 3H), 7.00 (ddd, J = 11.7, 9.7, 2.2 Hz, 1H), 3.94 (p, J = 8.9 Hz, 1H), 3.58 - 3.36 (m, 2H), 3.36 - 3.09 (m, 6H), 3.10 - 2.91 (m, 2H). LCMS m/z 419.13 $[M + H]^+$ | A; 3.17 |
| 225 | 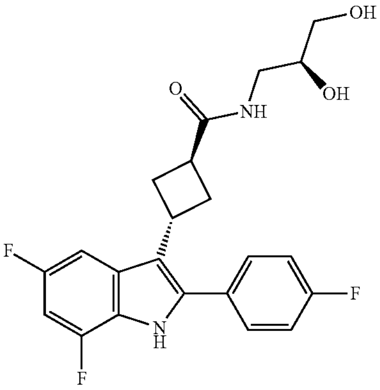 [SMILES: O=C(NC[C@H](O)CO)[C@H]1C[C@H](c2c(-c3ccc(F)cc3)[nH]c3c(F)cc(F)cc32)C1] | $^1$H NMR (300 MHz, DMSO-$d_6$) 11.67 (s, 1H), 7.72 (m, 1H), 7.63 - 7.42 (m, 2H), 7.42 - 7.23 (m, 3H), 6.99 (ddd, J = 11.7, 9.7, 2.1 Hz, 2H), 3.93 (t, J = 9.0 Hz, 2H), 3.47 (m, 2H), 3.35 - 3.10 (m, 4H), 2.99 (m 1H). LCMS m/z 419.16 $[M + H]^+$ | A; 3.17 |
| 226 | 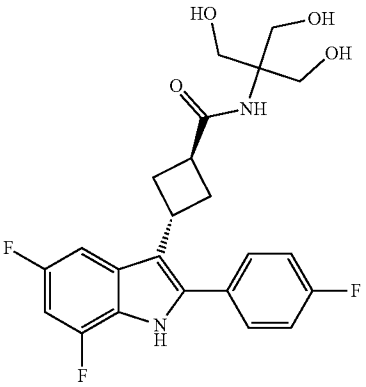 [SMILES: O=C(NC(CO)(CO)CO)[C@H]1C[C@H](c2c(-c3ccc(F)cc3)[nH]c3c(F)cc(F)cc32)C1] | $^1$H NMR (300 MHz, DMSO-$d_6$) δ 11.68 (s, 1H), 7.59 - 7.48 (m, 2H), 7.45 - 7.31 (m, 3H), 7.02 (s, 1H), 7.01 (ddd, J = 11.6, 9.7, 2.1 Hz, 1H), 4.76 (t, J = 5.8 Hz, 3H), 3.99 - 3.87 (m, 2H), 3.57 (d, J = 5.8 Hz, 6H), 2.50 - 2.44 (m, 4H). LCMS m/z 448.88 $[M + H]^+$ | B , A; 1.95 |

TABLE 7-continued

| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds 162-234 | | | |
| 227 | 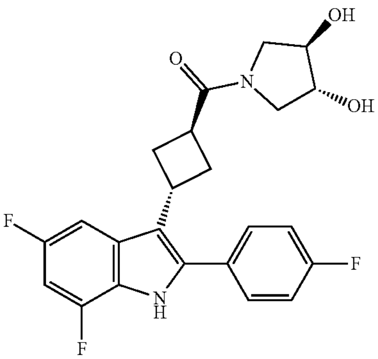 [SMILES: O=C([C@H]1C[C@H](c2c(-c3ccc(F)cc3)[nH]c3c(F)cc(F)cc32)C1)N1C[C@@H](O)[C@H](O)C1] | $^1$H NMR (300 MHz, $CD_3OD$) 7.62 – 7.41 (m, 2H), 7.34 (dd, J = 9.7, 2.1 Hz, 1H), 7.29 – 7.07 (m, 2H), 6.74 (ddd, J = 11.1, 9.6, 2.2 Hz, 1H), 4.19 – 3.93 (m, 3H), 3.76 – 3.57 (m, 2H), 3.52-3.48 (m, 1H), 3.45 – 3.33 (m, 2H), 2.86 – 2.48 (m, 4H). LCMS m/z 431.15 [M + H]$^+$ | A; 3.14 |
| 228 | 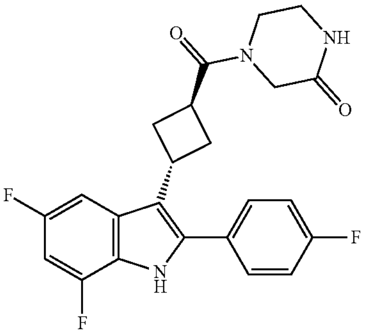 [SMILES: O=C1CN(C(=O)[C@H]2C[C@H](c3c(-c4ccc(F)cc4)[nH]c4c(F)cc(F)cc43)C2)CCN1] | $^1$H NMR (300 MHz, $CD_3OD$) 7.50 (dd, J = 8.8, 5.4 Hz, 2H), 7.36 (d, J = 9.8 Hz, 1H), 7.21 (t, J = 8.8 Hz, 2H), 6.74 (ddd, J = 11.3, 9.4, 2.3 Hz, 1H), 4.19-4.15 (m, 2H), 3.86-3.60 (m, 3H), 3.49-3.25 (m, 3H), 2.75-2.60 (m, 2H), 2.59-2.50 (m, 2H). LCMS m/z 427.99 [M + H]$^+$ | A; 3.36 |
| 229 | 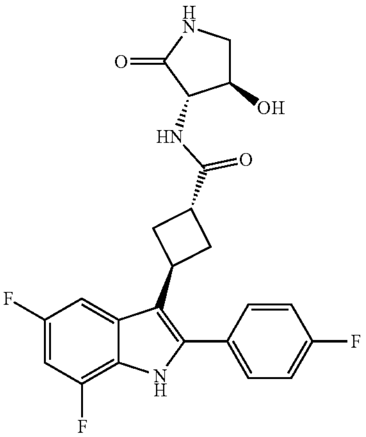 [SMILES: O=C1NC[C@@H](O)[C@@H]1NC(=O)[C@H]1C[C@H](c2c(-c3ccc(F)cc3)[nH]c3c(F)cc(F)cc32)C1] | $^1$H NMR (300 MHz, Methanol-$d_4$) δ 7.57 – 7.45 (m, 2H), 7.32 (dd, J = 9.8, 2.2 Hz, 1H), 7.24 – 7.11 (m, 2H), 6.73 (dddd, J = 11.7, 8.9, 6.7, 2.1 Hz, 1H), 4.57 – 4.35 (m, 1H), 4.24 (dd, J = 7.8, 3.8 Hz, 1H), 4.20-4.03 (m, 1H), 3.60 (ddd, J = 9.9, 7.6, 3.8 Hz, 1H), 3.24 (q, J = 7.0 Hz, 1H), 3.12 (ddd, J = 9.9, 7.0, 4.0 Hz, 1H), 2.78 – 2.51 (m, 4H). LCMS m/z 444.12 [M + H]$^+$ | A; 3.07 |

TABLE 7-continued
| Structure, physicochemical properties, and LCMS analysis for compounds 162-234 | | | |
|---|---|---|---|
| Compound | Structure | $^1$H NMR (ppm); LCMS m/z $[M + H]^+$ | LCMS Method; LCMS retention time (min) |
| 230 | 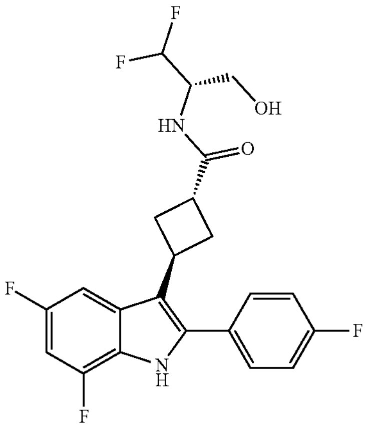 [SMILES: O=C(N[C@@H](CO)C(F)F)[C@H]1C[C@H](c2c(-c3ccc(F)cc3)[nH]c3c(F)cc(F)cc32)C1] | $^1$H NMR (300 MHz, Methanol-$d_4$) δ 7.61 – 7.44 (m, 2H), 7.33 (dd, J = 9.7, 2.2 Hz, 1H), 7.25 – 7.03 (m, 2H), 6.89 – 6.66 (m, 1H), 5.98 (td, J = 55.6, 3.4 Hz, 1H), 4.32 (dddd, J = 14.0, 8.3, 5.8, 3.0 Hz, 1H), 4.12 (dt, J = 9.9, 8.6 Hz, 1H), 3.82 – 3.67 (m, 2H), 3.30 – 3.15 (m, 2H), 2.91 – 2.53 (m, 3H). LCMS m/z 439.1 $[M + H]^+$ | A; 3.65 |
| 231 | 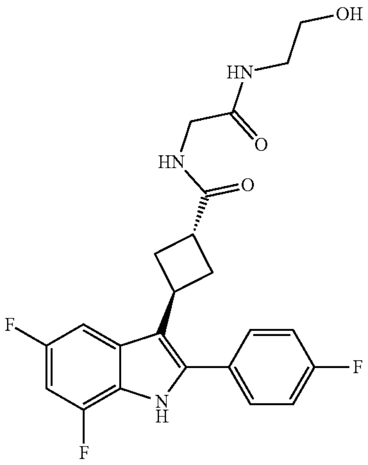 [SMILES: O=C(CNC(=O)[C@H]1C[C@H](c2c(-c3ccc(F)cc3)[nH]c3c(F)cc(F)cc32)C1)NCCO] | LCMS m/z 445.97 $[M + H]^+$ | A; 3.11 |
| 232 | 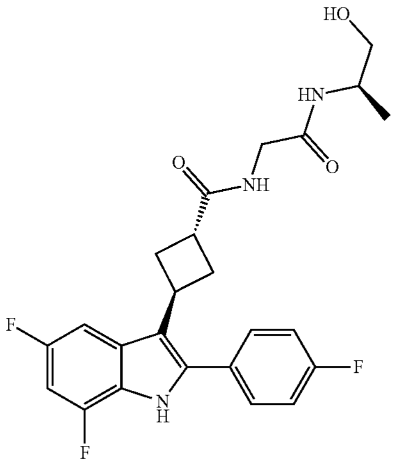 [SMILES: C[C@H](CO)NC(=O)CNC(=O)[C@H]1C[C@H](c2c(-c3ccc(F)cc3)[nH]c3c(F)cc(F)cc32)C1] | LCMS m/z 460.14 $[M + H]^+$ | A; 3.21 |

TABLE 7-continued
| Structure, physicochemical properties, and LCMS analysis for compounds 162-234 | | | |
|---|---|---|---|
| Compound | Structure | $^1$H NMR (ppm); LCMS m/z [M + H]$^+$ | LCMS Method; LCMS retention time (min) |
| 233 | 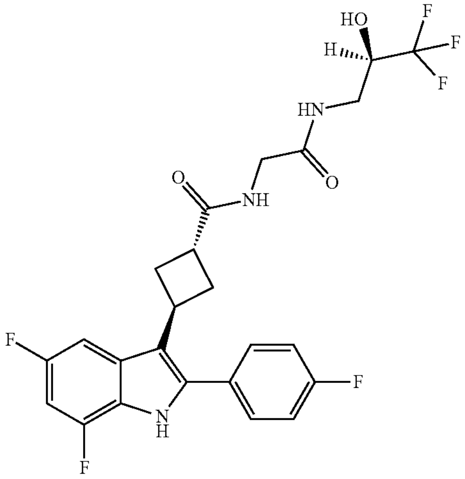 [SMILES: O=C(CNC(=O)[C@H]1C[C@H](c2c(-c3ccc(F)cc3)[nH]c3c(F)cc(F)cc32)C1)NC[C@@H](O)C(F)(F)F] | LCMS m/z 514.38 [M + H]$^+$ | A; 3.54 |
| 234 | 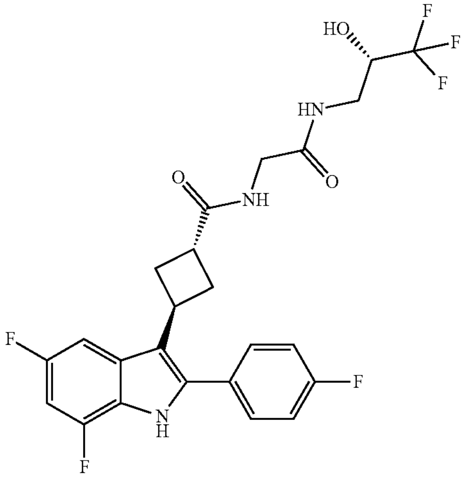 [SMILES: O=C(CNC(=O)[C@H]1C[C@H](c2c(-c3ccc(F)cc3)[nH]c3c(F)cc(F)cc32)C1)NC[C@H](O)C(F)(F)F] | LCMS m/z 514.31 [M + H]$^+$ | A; 3.54 |

Compound 235

N-(2-amino-2-oxo-ethyl)-3-[5,7-difluoro-2-(2,3,5,6-tetradeuterio-4-fluoro-phenyl)-1H-indol-3-yl]cyclobutanecarboxamide (235)

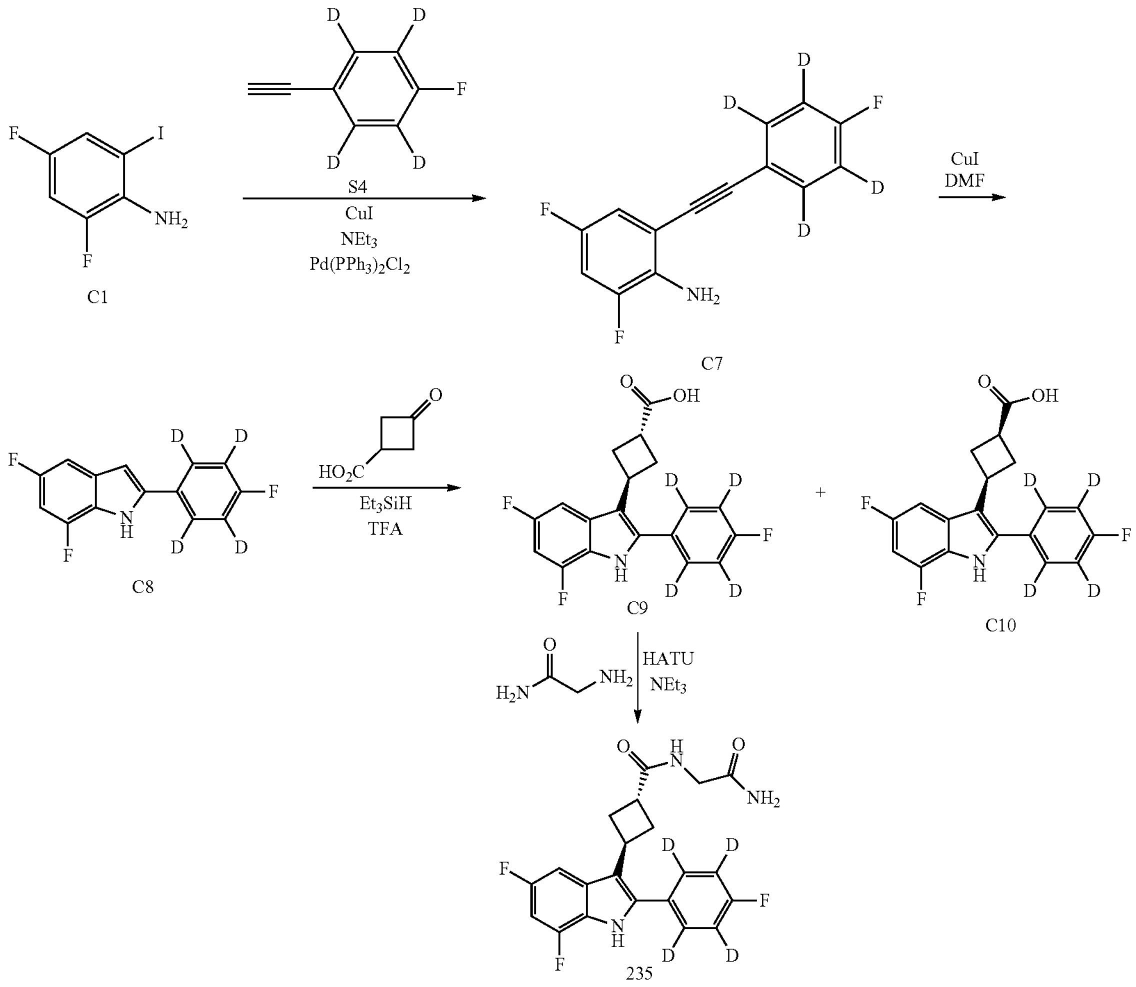

C1 C7 C8 C9 C10 235

Step 1. 2,4-Difluoro-6-((4-fluorophenyl-2,3,5,6-$d_4$)ethynyl)aniline (C8)

A mixture of crude 2,4-difluoro-6-iodoaniline C7 (59.7 g, 58% purity, 135.8 mmol, 1 equiv) and crude 1-Ethynyl-4-fluorobenzene-2,3,5,6-$d_4$ C56 (28.1 g, 60% purity, 135.80 mmol, 1 equiv) in $NEt_3$ (550 mL) was purged with nitrogen for 10 minutes. CuI (5.2 g, 27.2 mmol, 0.2 equiv) and $Pd(PPh_3)Cl_2$ (9.5 g, 13.6 mmol, 0.1 equiv) were added. The mixture was stirred at room temperature for 20 h, and then the mixture was concentrated under reduced pressure at 40° C. The residue was purified twice over silica gel (800 g silica gel, dry-loading, eluting each time with a gradient of 0 to 10% dichloromethane in heptanes) to give the product C8 (40.5 g) as a brown solid which was used in subsequent steps without further purification. (This material still contained some unreacted 2,4-difluoro-6-iodoaniline (40% based on LCMS)).

Step 2. 5,7-Difluoro-2-(4-fluorophenyl-2,3,5,6-$d_4$)-1H-indole (C9)

A solution of 2,4-Difluoro-6-((4-fluorophenyl-2,3,5,6-$d_4$)ethynyl)aniline C8 (39.5 g, 60% purity, 157.2 mmol, 1 equiv) in DMF (400 mL) was purged with nitrogen for 10 minutes. CuI (3.0 g, 15.7 mmol, 0.1 equiv) was added, and the mixture was purged with nitrogen for an additional 10 minutes. The mixture was heated at 145° C. for 20 h and cooled to room temperature. The mixture was concentrated under reduced pressure at 60° C. to remove most of DMF. The residue was diluted with water (500 mL) and t-butyl methyl ether (300 mL). The mixture was filtered through Celite®, which was washed with t-butyl methyl ether (100 mL). The layers of the filtrate were separated, and the aqueous layer was extracted with t-butyl methyl ether (2×200 mL). The combined organic layers were washed with saturated brine (500 mL), dried over sodium sulfate, filtered and concentrated under reduced pressure at 40° C. Purification by silica gel chromatography (Gradient: 0-10%

EtOAc in heptanes) afforded 5,7-Difluoro-2-(4-fluorophenyl-2,3,5,6-$d_4$)-1H-indole as an orange-brown solid (19 g, 80% yield). (1r,3r)-3-(5,7-Difluoro-2-(4-fluorophenyl-2,3,5,6-$d_4$)-1H-indol-3-yl)cyclobutane-1-carboxylic acid (C10)

Trifluoroacetic acid (30.64 mL, 400.09 mmol, 6.02 equiv) was added dropwise to a solution of compound C9 (16.7 g, 66.47 mmol, 1 equiv), 3-oxocyclobutanecarboxylic acid (11.38 g, 99.71 mmol, 1.5 equiv) and triethylsilane (64.3 mL, 402.28 mmol, 6.05 equiv) in dichloromethane (200 mL) at room temperature. After stirring for 20 hours at room temperature, the reaction mixture was concentrated under reduced pressure to ~100 mL and the solid (cis isomer C11) was filtered and washed with dichloromethane (2×10 mL). The filtrate was concentrated under reduced pressure and the residue was purified twice on an InterChim auto-chromatography system (330 g Sorbtech silica gel column), eluting each time with a gradient of 0 to 10% ethyl acetate in dichloromethane to give compound C10 (19.3 g, 83% yield) as a pale-yellow oil.

(1r,3r)-N-(2-Amino-2-oxoethyl)-3-(5,7-difluoro-2-(4-fluorophenyl-2,3,5,6-$d_4$)-1H-indol-3-yl)cyclobutane-1-carboxamide (235)

HATU (24.0 g, 63.15 mmol, 1.5 equiv) was added to a solution of compound C10 (19.3 g, 42.1 mmol, 1 equiv) in DMF (200 mL) and the mixture was sparged with nitrogen for 10 minutes. The mixture was cooled to 5° C. in an ice bath, and glycinamide hydrochloride (5.12 g, 46.31 mmol, 1.1 equiv) was added, followed by the dropwise addition of N,N-diisopropylethylamine (22.0 mL, 126.3 mmol, 3 equiv). The mixture was stirred at room temperature for 2 hours. Saturated sodium bicarbonate (250 mL) was added and the mixture was extracted with ethyl acetate (3×300 mL). The combined organic layers were washed with saturated brine (400 mL), filtered and concentrated under reduced pressure at 40° C. The residue was purified on an InterChim auto-chromatography system (330 g SorbTech silica gel column), eluting with a gradient of 0 to 100% ethyl acetate in heptanes to give crude compound 236 (30 g) as a yellow solid. This material (30 g) was dissolved in a mixture of ethyl acetate (600 mL) and water (200 mL). The layers were separated, and the organic layer was washed with water (200 mL) and saturated brine (200 mL). The organic layer was concentrated under reduced pressure to give a pale yellow sticky solid (21 g), which was triturated twice in a 4 to 1 mixture of water and acetone (250 mL) to give compound 235 (13.9 g, 95% purity) as an off-white solid. This material was further purified by SFC separation. Column: Daicel Chiralpak® AD-H, 20×250 mm; Mobile Phase: 30% Methanol (containing 0.15% diethylamine), 70% carbon dioxide. Flow: 65 mL/min. The second eluting peak was the product compound 235 (7.5 g, 99.9% purity), obtained as a white solid. The cis isomer of compound 235 was isolated in the first eluting peak, obtained as a yellow solid (1.8 g, 95.8% purity).

Compound 235 was further purified by SFC an additional time. Column: achiral, 20×250 mm; Mobile Phase: 45% Methanol, 65% carbon dioxide. Flow: 75 mL/min.

Compound 236-273

Compound 236-273 (Table 8) was prepared from S3 and the appropriate commercially available amine by HATU coupling according to standard procedure A.

TABLE 8

Structure, physicochemical properties, and LCMS analysis for compounds 236-273

| Compound | Structure | $^1$H NMR (ppm); LCMS m/z $[M + H]^+$ | LCMS Method; LCMS retention time (min) |
|---|---|---|---|
| 236 | 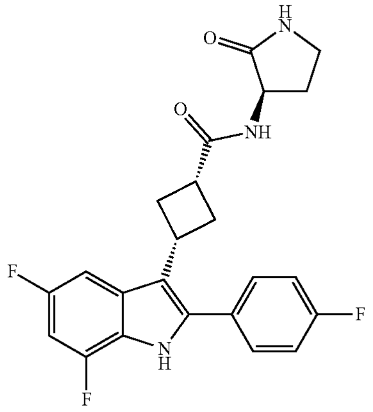 [SMILES: O=C1NCC[C@H]1NC(=O)[C@H]1C[C@@H](c2c(-c3ccc(F)cc3)[nH]c3c(F)cc(F)cc32)C1] | LCMS m/z 428.16 $[M + H]^+$ | A; 3.33 |

TABLE 8-continued

| Compound | Structure | $^1H$ NMR (ppm); LCMS m/z $[M + H]^+$ | LCMS Method; LCMS retention time (min) |
|---|---|---|---|
| Structure, physicochemical properties, and LCMS analysis for compounds 236-273 | | | |
| 237 | 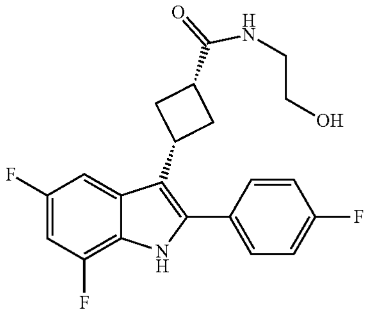 [SMILES: O=C(NCCO)[C@H]1C[C@@H](c2c(-c3ccc(F)cc3)[nH]c3c(F)cc(F)cc32)C1] | $^1H$ NMR (300 MHz, Acetone-$d_6$) 10.66 (s, 1H), 8.09 (dd, J = 10.2, 2.2 Hz, 1H), 7.77 - 7.51 (m, 2H), 7.37 - 7.03 (m, 3H), 6.84 (ddd, J = 11.6, 9.6, 2.2 Hz, 1H), 3.97 - 3.68 (m, 1H), 3.59 (q, J = 5.6 Hz, 2H), 3.34 (q, J = 5.6 Hz, 2H), 3.24 - 3.03 (m, 1H), 3.01 - 2.74 (m, 2H), 2.45 (qd, J = 8.4, 2.6 Hz, 2H). LCMS m/z 389.155 $[M + H]^+$. | A; 2.085 |
| 238 | 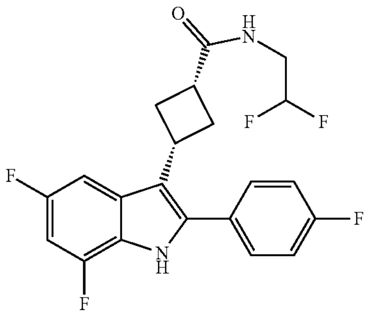 [SMILES: O=C(NCC(F)F)[C@H]1C[C@@H](c2c(-c3ccc(F)cc3)[nH]c3c(F)cc(F)cc32)C1] | LCMS m/z 409.01 $[M + H]^+$ | A; 3.96 |
| 239 | 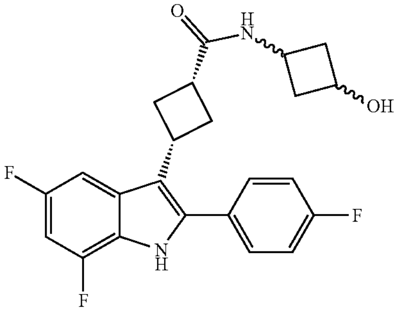 [SMILES: O=C(NC1CC(O)C1)[C@H]1C[C@@H](c2c(-c3ccc(F)cc3)[nH]c3c(F)cc(F)cc32)C1] | $^1H$ NMR (300 MHz, Acetone-$d_6$) δ 10.69 (s, 1H), 8.08 (dd, J = 10.2, 2.2 Hz, 1H), 7.73 - 7.47 (m, 2H), 7.38 - 7.14 (m, 3H), 6.83 (ddd, J = 11.1, 9.6, 2.2 Hz, 1H), 4.08 - 3.61 (m, 3H), 3.14 - 2.88 (m, 1H), 2.92 - 2.67 (m, 2H), 2.70 - 2.53 (m, 2H), 2.53 - 2.33 (m, 2H), 1.89 - 1.68 (m, 2H). LCMS m/z 415.16 $[M + H]^+$ | A; 3.43 |
| 240 | 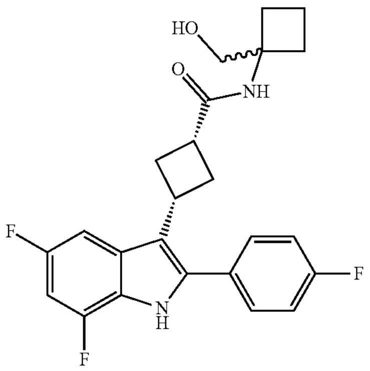 [SMILES: O=C(NC1(CO)CCC1)[C@H]1C[C@@H](c2c(-c3ccc(F)cc3)[nH]c3c(F)cc(F)cc32)C1] | LCMS m/z 429.2 $[M + H]^+$ | A; 3.83 |

TABLE 8-continued
Structure, physicochemical properties, and LCMS analysis for compounds 236-273
| Compound | Structure | $^{1}H$ NMR (ppm); LCMS m/z $[M + H]^+$ | LCMS Method; LCMS retention time (min) |
|---|---|---|---|
| 241 | 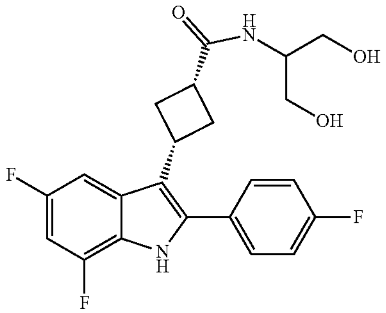 [SMILES: O=C(NC(CO)CO)[C@H]1C[C@@H](c2c(-c3ccc(F)cc3)[nH]c3c(F)cc(F)cc32)C1] | LCMS m/z 419.17 $[M + H]^+$ | A; 3.17 |
| 242 | 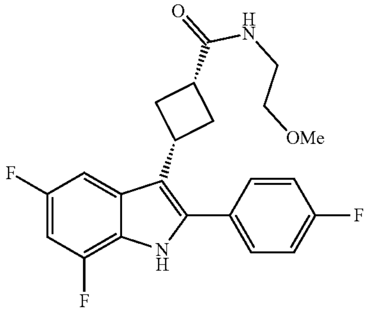 [SMILES: COCCNC(=O)[C@H]1C[C@@H](c2c(-c3ccc(F)cc3)[nH]c3c(F)cc(F)cc32)C1] | LCMS m/z 403.17 $[M + H]^+$ | A; 3.8 |
| 243 | 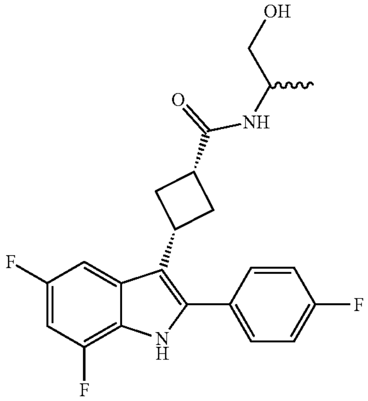 [SMILES: CC(CO)NC(=O)[C@H]1C[C@@H](c2c(-c3ccc(F)cc3)[nH]c3c(F)cc(F)cc32)C1] | LCMS m/z 403.21 $[M + H]^+$ | A; 3.52 |
| 244 | 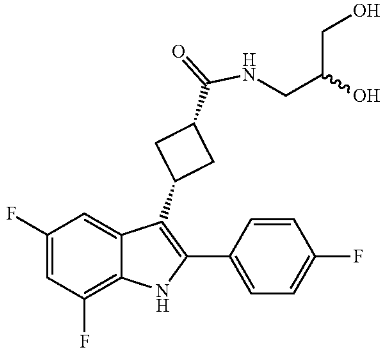 [SMILES: O=C(NCC(O)CO)[C@H]1C[C@@H](c2c(-c3ccc(F)cc3)[nH]c3c(F)cc(F)cc32)C1] | $^{1}H$ NMR (300 MHz, Acetone-$d_6$) δ 10.67 (s, 1H), 8.03 (dd, J = 10.1, 2.2 Hz, 1H), 7.63 (ddt, J = 8.3, 5.3, 2.5 Hz, 2H), 7.40 - 7.13 (m, 3H), 6.84 (ddd, J = 11.3, 9.6, 2.2 Hz, 1H), 3.83 (tt, J = 10.4, 8.5 Hz, 1H), 3.67 (qd, J = 5.8, 4.7 Hz, 1H), 3.54 - 3.26 (m, 4H), 3.25 - 3.09 (m, 1H), 2.84 (dtd, J = 11.9, 9.9, 2.1 Hz, 2H), 2.49 (ddddd, J = 10.3, 8.4, 6.1, 4.0, 2.3 Hz, 2H). LCMS m/z 419.2 $[M + H]^+$ | A; 3.18 |

TABLE 8-continued

Structure, physicochemical properties, and LCMS analysis for compounds 236-273

| Compound | Structure | $^1$H NMR (ppm); LCMS m/z $[M + H]^+$ | LCMS Method; LCMS retention time (min) |
|---|---|---|---|
| 245 | 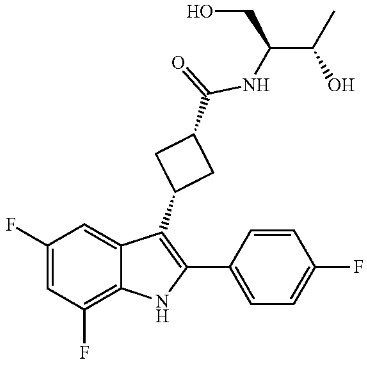 [SMILES: C[C@H](O)[C@H](CO)NC(=O)[C@H]1C[C@@H](c2c(-c3ccc(F)cc3)[nH]c3c(F)cc(F)cc32)C1] | $^1$H NMR (300 MHz, Acetone-$d_6$) δ 10.68 (s, 1H), 8.12 - 8.02 (m, 1H), 7.70 - 7.53 (m, 2H), 7.35 - 7.21 (m, 2H), 6.93 - 6.77 (m, 2H), 4.09 (qd, J = 6.4, 2.9 Hz, 1H), 4.01 - 3.83 (m, 1H), 3.83 - 3.73 (m, 1H), 3.72 - 3.57 (m, 2H), 3.26 (tt, J = 9.4, 8.2 Hz, 1H), 2.98 - 2.76 (m, 2H), 2.74 - 2.58 (m, 1H), 2.58 - 2.39 (m, 2H), 2.12 - 2.04 (m, 1H), 1.12 (d, J = 6.4 Hz, 3H). LCMS m/z 433.21 $[M + H]^+$ | A; 3.27 |
| 246 | 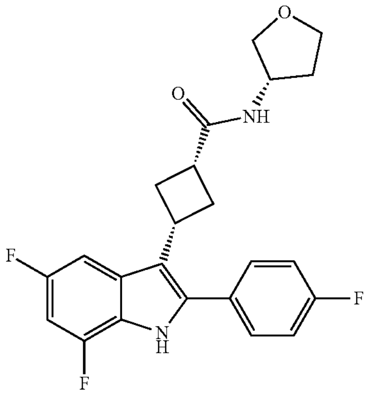 [SMILES: O=C(N[C@H]1CCOC1)[C@H]1C[C@@H](c2c(-c3ccc(F)cc3)[nH]c3c(F)cc(F)cc32)C1] | $^1$H NMR (300 MHz, Acetone-$d_6$) δ 10.68 (s, 1H), 8.03 (dd, J = 10.1, 2.2 Hz, 1H), 7.75 - 7.52 (m, 2H), 7.49 - 7.21 (m, 3H), 6.92 - 6.70 (m, 2H), 4.69 - 4.37 (m, 1H), 3.98 - 3.70 (m, 1H), 3.40 (dd, J = 9.2, 4.2 Hz, 2H), 3.19 (p, J = 8.8 Hz, 1H), 2.84 (q, J = 10.2 Hz, 2H), 2.70 - 2.35 (m, 3H), 2.03 - 1.84 (m, 1H). LCMS m/z 415.29 $[M + H]^+$ | A; 3.73 |
| 247 | 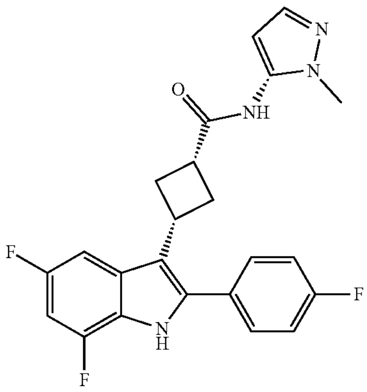 | $^1$H NMR (300 MHz, Acetone-$d_6$) δ 7.97 (dd, J = 10.1, 2.2 Hz, 1H), 7.69 - 7.56 (m, 2H), 7.36 - 7.22 (m, 2H), 6.85 (ddd, J = 11.1, 9.7, 2.2 Hz, 1H), 3.90 - 3.71 (m, 1H), 3.07 (p, J = 8.4 Hz, 1H), 2.80 (dt, J = 12.3, 9.6 Hz, 2H), 2.63 (s, 6H), 2.57 - 2.39 (m, 2H). LCMS m/z 425.16 $[M + H]^+$ | A; 3.67 |

TABLE 8-continued
| Compound | Structure | $^1$H NMR (ppm); LCMS m/z $[M + H]^+$ | LCMS Method; LCMS retention time (min) |
|---|---|---|---|
| Structure, physicochemical properties, and LCMS analysis for compounds 236-273 | | | |
| 248 | 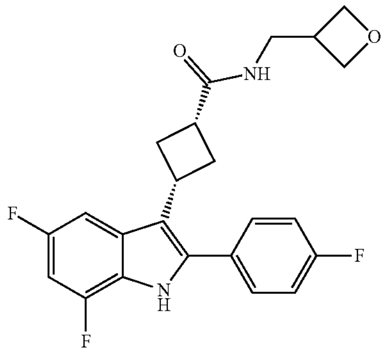 [SMILES: O=C(NCC1COC1)[C@H]1C[C@@H](c2c(-c3ccc(F)cc3)[nH]c3c(F)cc(F)cc32)C1] | LCMS m/z 415.16 $[M + H]^+$ | A; 2.77 |
| 249 | 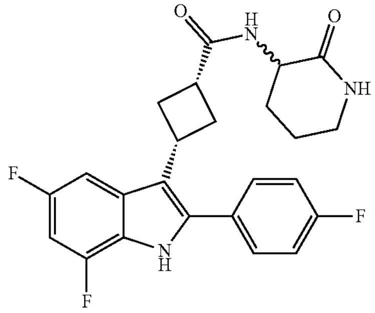 [SMILES: O=C1NCCCC1NC(=O)[C@H]1C[C@@H](c2c(-c3ccc(F)cc3)[nH]c3c(F)cc(F)cc32)C1] | LCMS m/z 442.17 $[M + H]^+$ | A; 3.42 |
| 250 | 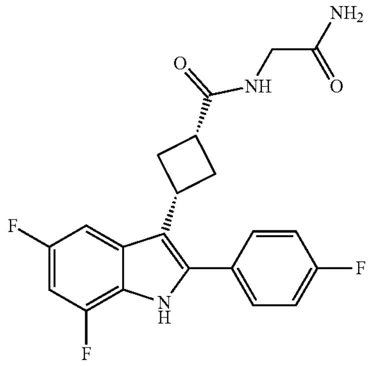 [SMILES: NC(=O)CNC(=O)[C@H]1C[C@@H](c2c(-c3ccc(F)cc3)[nH]c3c(F)cc(F)cc32)C1] | LCMS m/z 402.16 $[M + H]^+$ | A; 3.22 |
| 251 | 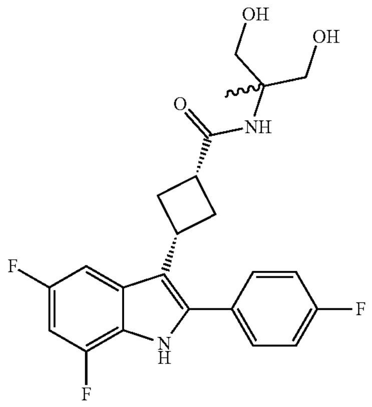 | LCMS m/z 433.18 $[M + H]^+$ | A; 3.45 |

TABLE 8-continued
| Structure, physicochemical properties, and LCMS analysis for compounds 236-273 | | | |
|---|---|---|---|
| Compound | Structure | $^1$H NMR (ppm); LCMS m/z $[M + H]^+$ | LCMS Method; LCMS retention time (min) |
| 252 | 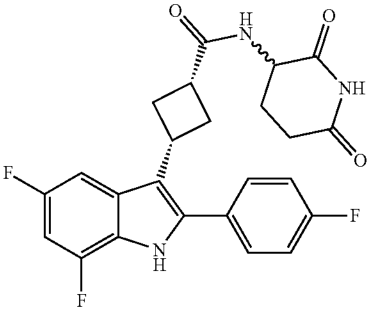 [SMILES: O=C1CCC(NC(=O)[C@H]2C[C@@H](c3c(-c4ccc(F)cc4)[nH]c4c(F)cc(F)cc43)C2)C(=O)N1] | LCMS m/z 456.14 $[M + H]^+$ | A; 3.48 |
| 253 | 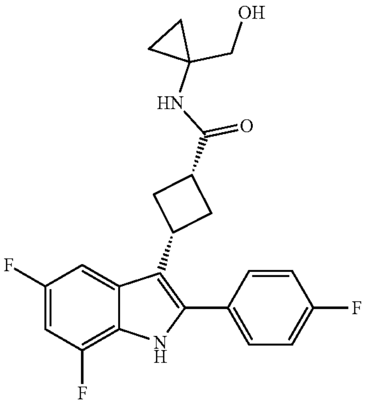 [SMILES: O=C(NC1(CO)CC1)[C@H]1C[C@@H](c2c(-c3ccc(F)cc3)[nH]c3c(F)cc(F)cc32)C1] | $^1$H NMR (300 MHz, Acetone-$d_6$) δ 7.92 (dd, J = 10.1, 2.2 Hz, 1H), 7.69 – 7.57 (m, 2H), 7.36 – 7.22 (m, 2H), 6.85 (ddd, J = 11.1, 9.6, 2.2 Hz, 1H), 3.92 – 3.74 (m, 1H), 3.60 (s, 2H), 3.17 (p, J = 8.5 Hz, 1H), 2.81 (qd, J = 9.6, 2.6 Hz, 2H), 2.49 (qd, J = 8.4, 2.6 Hz, 2H), 0.91 – 0.74 (m, 4H). LCMS m/z 415.19 $[M + H]^+$ | A; 3.57 |
| 254 | 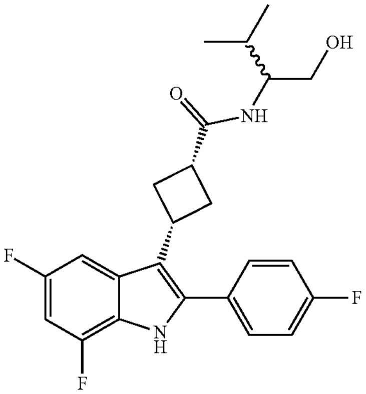 [SMILES: CC(C)C(CO)NC(=O)[C@H]1C[C@@H](c2c(-c3ccc(F)cc3)[nH]c3c(F)cc(F)cc32)C1] | LCMS m/z 431.19 $[M + H]^+$ | A; 3.8 |

TABLE 8-continued
| Structure, physicochemical properties, and LCMS analysis for compounds 236-273 | | | |
|---|---|---|---|
| Compound | Structure | $^1$H NMR (ppm); LCMS m/z $[M + H]^+$ | LCMS Method; LCMS retention time (min) |
| 255 | 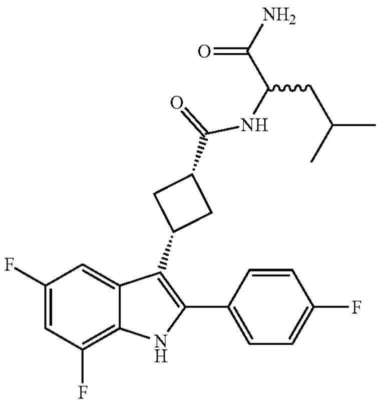 [SMILES: CC(C)CC(NC(=O)[C@H]1C[C@@H](c2c(-c3ccc(F)cc3)[nH]c3c(F)cc(F)cc32)C1)C(N)=O] | LCMS m/z 458.19 $[M + H]^+$ | A; 3.76 |
| 256 | 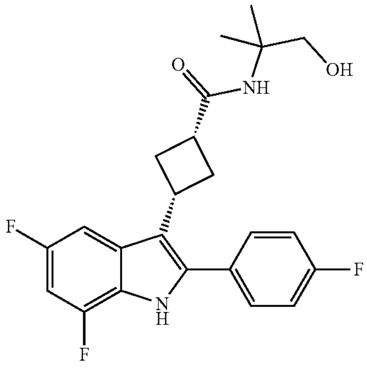 [SMILES: CC(C)(CO)NC(=O)[C@H]1C[C@@H](c2c(-c3ccc(F)cc3)[nH]c3c(F)cc(F)cc32)C1] | LCMS m/z 417.18 $[M + H]^+$ | A; 3.85 |
| 257 | 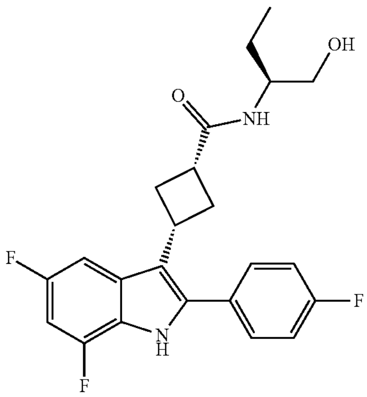 [SMILES: CC[C@@H](CO)NC(=O)[C@H]1C[C@@H](c2c(-c3ccc(F)cc3)[nH]c3c(F)cc(F)cc32)C1] | LCMS m/z 417.15 $[M + H]^+$ | A; 3.65 |

TABLE 8-continued
| Compound | Structure | $^1H$ NMR (ppm); LCMS m/z $[M + H]^+$ | LCMS Method; LCMS retention time (min) |
| --- | --- | --- | --- |
| Structure, physicochemical properties, and LCMS analysis for compounds 236-273 | | | |
| 258 | 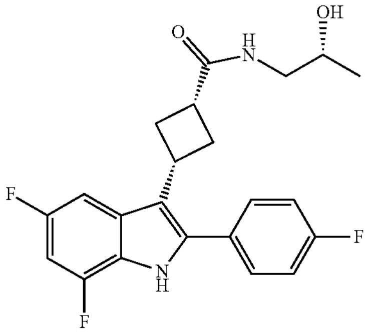 [SMILES: C[C@@H](O)CNC(=O)[C@H]1C[C@@H](c2c(-c3ccc(F)cc3)[nH]c3c(F)cc(F)cc32)C1] | LCMS m/z 403.24 $[M + H]^+$ | A; 3.7 |
| 259 | 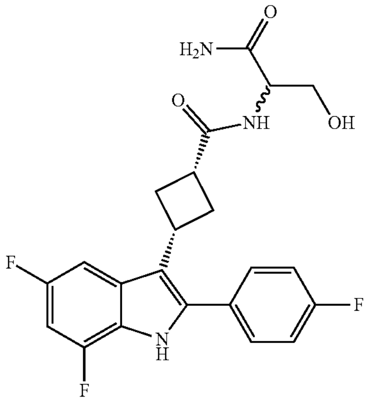 [SMILES: NC(=O)C(CO)NC(=O)[C@H]1C[C@@H](c2c(-c3ccc(F)cc3)[nH]c3c(F)cc(F)cc32)C1] | LCMS m/z 432.13 $[M + H]^+$ | A; 3.08 |
| 260 | 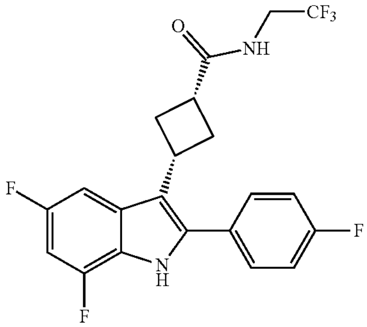 [SMILES: O=C(NCC(F)(F)F)[C@H]1C[C@@H](c2c(-c3ccc(F)cc3)[nH]c3c(F)cc(F)cc32)C1] | LCMS m/z 426.99 $[M + H]^+$ | A; 4.11 |
| 261 | 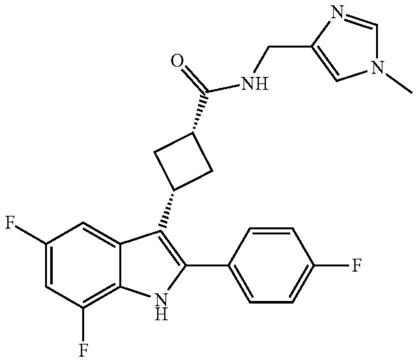 [SMILES: Cn1cnc(CNC(=O)[C@H]2C[C@@H](c3c(-c4ccc(F)cc4)[nH]c4c(F)cc(F)cc43)C2)c1] | LCMS m/z 439.14 $[M + H]^+$ | A; 2.77 |

TABLE 8-continued
Structure, physicochemical properties, and LCMS analysis for compounds 236-273
| Compound | Structure | $^1$H NMR (ppm); LCMS m/z [M + H]$^+$ | LCMS Method; LCMS retention time (min) |
|---|---|---|---|
| 262 | 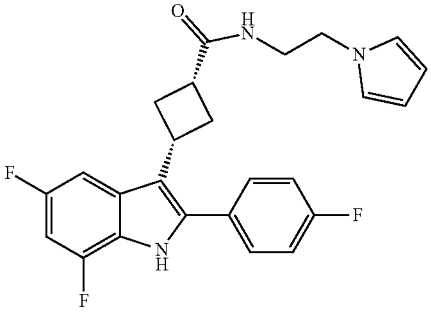 [SMILES: O=C(NCCn1cccc1)[C@H]1C[C@@H](c2c(-c3ccc(F)cc3)[nH]c3c(F)cc(F)cc32)C1] | LCMS m/z 438.16 [M + H]$^+$ | A; 4.1 |
| 263 | 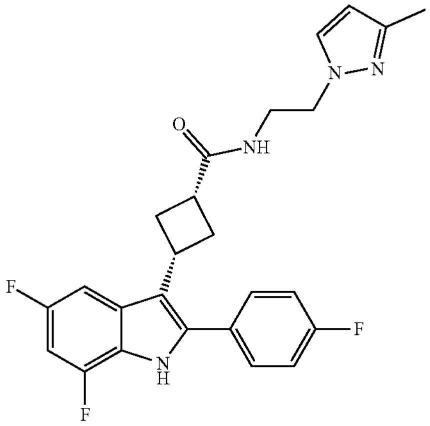 [SMILES: Cc1ccn(CCNC(=O)[C@H]2C[C@@H](c3c(-c4ccc(F)cc4)[nH]c4c(F)cc(F)cc43)C2)n1] | $^1$H NMR (300 MHz, Acetone-$d_6$) δ 8.02 (dd, J = 10.3, 2.2 Hz, 1H), 7.81 – 7.51 (m, 3H), 7.49 – 7.12 (m, 2H), 6.85 (ddd, J = 11.1, 9.6, 2.2 Hz, 1H), 6.06 (dd, J = 2.3, 0.6 Hz, 1H), 4.26 (dd, J = 6.5, 5.5 Hz, 2H), 3.89 – 3.69 (m, 1H), 3.69 – 3.54 (m, 2H), 3.17 – 2.96 (m, 1H), 2.80 (dt, J = 12.3, 9.5 Hz, 2H), 2.44 (qd, J = 8.4, 2.6 Hz, 2H), 2.21 (s, 2H). LCMS m/z 453.21 [M + H]$^+$ | A; 3.47 |
| 264 | 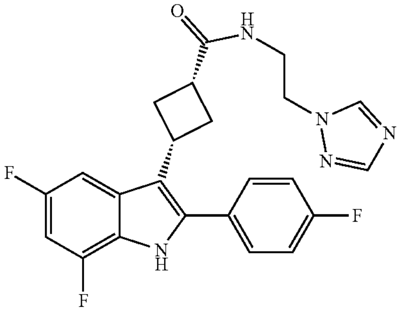 [SMILES: O=C(NCCn1cncn1)[C@H]1C[C@@H](c2c(-c3ccc(F)cc3)[nH]c3c(F)cc(F)cc32)C1] | LCMS m/z 440.15 [M + H]$^+$ | A; 3.26 |
| 265 | 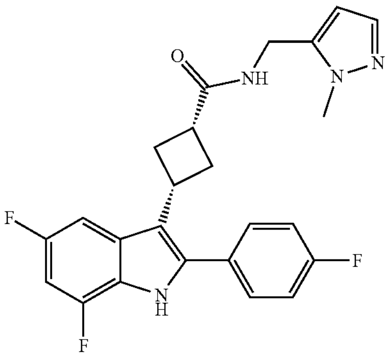 [SMILES: Cn1nccc1CNC(=O)[C@H]1C[C@@H](c2c(-c3ccc(F)cc3)[nH]c3c(F)cc(F)cc32)C1] | LCMS m/z 439.27 [M + H]$^+$ | A; 3.58 |

TABLE 8-continued
| Structure, physicochemical properties, and LCMS analysis for compounds 236-273 | | | |
|---|---|---|---|
| Compound | Structure | $^1$H NMR (ppm); LCMS m/z [M + H]$^+$ | LCMS Method; LCMS retention time (min) |
| 266 | 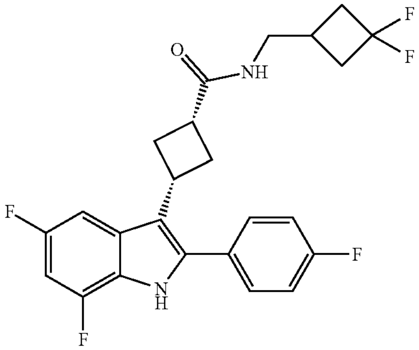 [SMILES: O=C(NCC1CC(F)(F)C1)[C@H]1C[C@@H](c2c(-c3ccc(F)cc3)[nH]c3c(F)cc(F)cc32)C1] | LCMS m/z 449.14 [M + H]$^+$ | A; 4.13 |
| 267 | 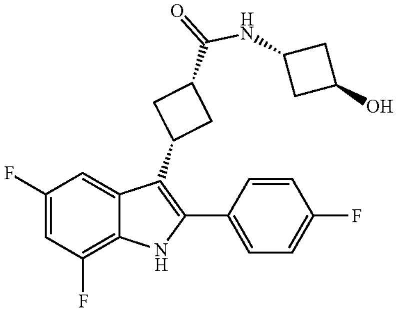 [SMILES: O=C(N[C@H]1C[C@H](O)C1)[C@H]1C[C@@H](c2c(-c3ccc(F)cc3)[nH]c3c(F)cc(F)cc32)C1] | LCMS m/z 415.16 [M + H]$^+$ | A; 3.42 |
| 268 | 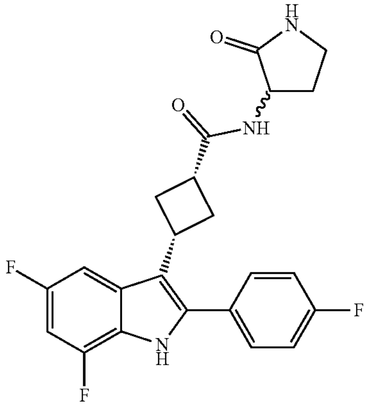 [SMILES: O=C1NCCC1NC(=O)[C@H]1C[C@@H](c2c(-c3ccc(F)cc3)[nH]c3c(F)cc(F)cc32)C1] | LCMS m/z 428.16 [M + H]$^+$ | A; 3.33 |
| 269 | 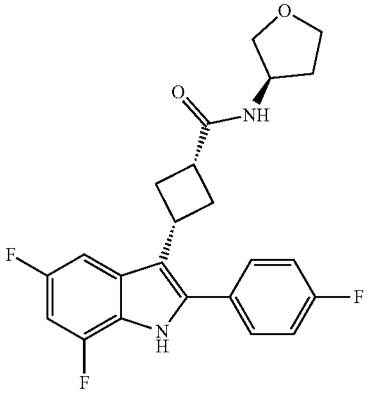 [SMILES: O=C(N[C@@H]1CCOC1)[C@H]1C[C@@H](c2c(-c3ccc(F)cc3)[nH]c3c(F)cc(F)cc32)C1] | LCMS m/z 415.19 [M + H]$^+$ | A; 3.74 |

TABLE 8-continued
| Compound | Structure | $^1$H NMR (ppm); LCMS m/z [M + H]$^+$ | LCMS Method; LCMS retention time (min) |
|---|---|---|---|
| Structure, physicochemical properties, and LCMS analysis for compounds 236-273 | | | |
| 270 | 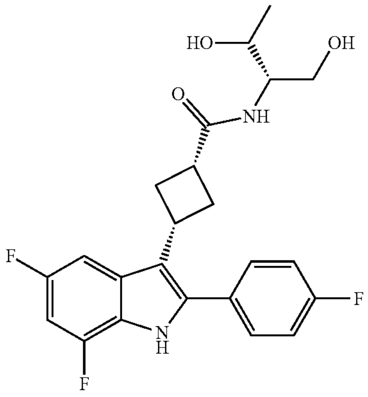 [SMILES: CC(O)[C@H](CO)NC(=O)[C@H]1C[C@@H](c2c(-c3ccc(F)cc3)[nH]c3c(F)cc(F)cc32)C1] | LCMS m/z 433.18 [M + H]$^+$ | A; 3.26 |
| 271 | 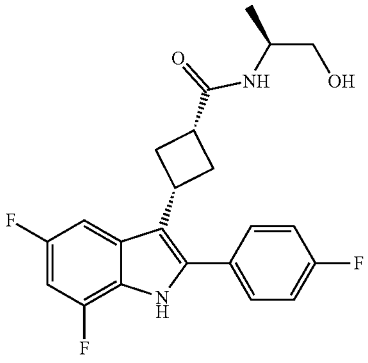 [SMILES: C[C@@H](CO)NC(=O)[C@H]1C[C@@H](c2c(-c3ccc(F)cc3)[nH]c3c(F)cc(F)cc32)C1] | LCMS m/z 403.17 [M + H]$^+$ | A; 3.51 |
| 272 | 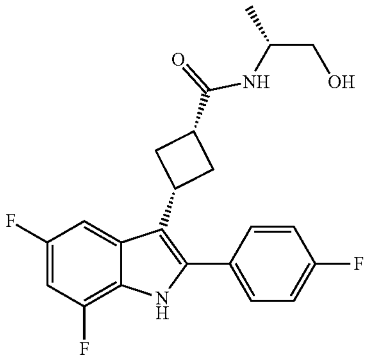 [SMILES: C[C@H](CO)NC(=O)[C@H]1C[C@@H](c2c(-c3ccc(F)cc3)[nH]c3c(F)cc(F)cc32)C1] | LCMS m/z 403.14 [M + H]$^+$ | A; 3.82 |

TABLE 8-continued

| Compound | Structure | $^1H$ NMR (ppm); LCMS m/z $[M + H]^+$ | LCMS Method; LCMS retention time (min) |
|---|---|---|---|
| Structure, physicochemical properties, and LCMS analysis for compounds 236-273 | | | |
| 273 | 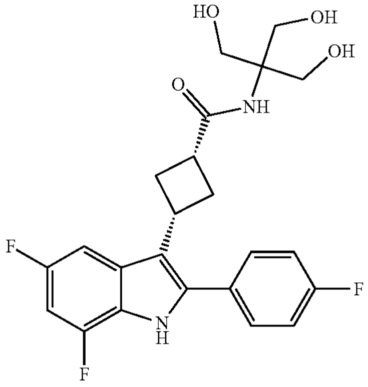 [SMILES: O=C(NC(CO)(CO)CO)[C@H]1C[C@@H](c2c(-c3ccc(F)cc3)[nH]c3c(F)cc(F)cc32)C1] | LCMS m/z 449.17 $[M + H]^+$ | A; 3.23 |

Compound 274-277

Compounds 274-277 (Table 9) were prepared from S3 and the appropriate commercially available amine by HATU coupling according to standard procedure A.

TABLE 9

| Compound | Structure | $^1H$ NMR (ppm); LCMS m/z $[M + H]^+$ | LCMS Method; LCMS retention time (min) |
|---|---|---|---|
| Structure, physicochemical properties, and LCMS analysis for compounds 274-277 | | | |
| 274 | 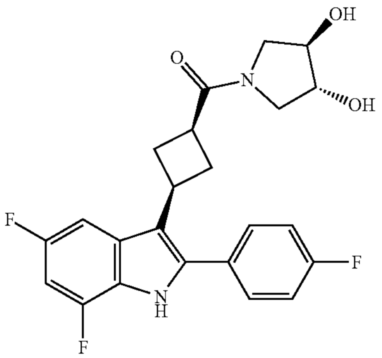 [SMILES: O=C([C@H]1C[C@@H](c2c(-c3ccc(F)cc3)[nH]c3c(F)cc(F)cc32)C1)N1C[C@@H](O)[C@H](O)C1] | $^1H$ NMR (300 MHz, $CD_3OD$) 7.64-7.45 (m, 3H), 7.22 (t, J = 8.8 Hz, 2H), 6.72 (ddd, J = 11.6, 9.6, 2.1 Hz, 1H), 4.10 (dd, J = 12.3, 3.8 Hz, 2H), 3.91-3.67 (m, 2H), 3.62 (dd, J = 13.0, 4.2 Hz, 1H), 3.55-3.32 (m, 3H), 2.75 (m, 2H), 2.62-2.47 (m, 2H). LCMS m/z 431.12 $[M + H]^+$ | A; 3.14 |
| 275 | 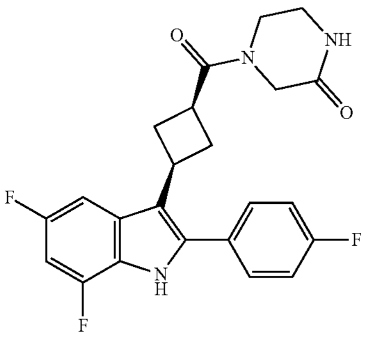 [SMILES: O=C1CN(C(=O)[C@H]2C[C@@H](c3c(-c4ccc(F)cc4)[nH]c4c(F)cc(F)cc43)C2)CCN1] | $^1H$ NMR (300 MHz, $CD_3OD$) 7.59-7.39 (m, 3H), 7.22 (t, J = 8.7 Hz, 2H), 6.80-6.65 (m, 1H), 4.15 (d, J = 11.3 Hz, 2H), 3.93-3.66 (m, 3H), 3.51-3.31 (m, 3H), 2.72 (m, 2H), 2.55 (m, 2H). LCMS m/z 428.15 $[M + H]^+$ | A; 3.33 |

TABLE 9-continued

Structure, physicochemical properties, and LCMS analysis for compounds 274-277

| Compound | Structure | $^1H$ NMR (ppm); LCMS m/z $[M + H]^+$ | LCMS Method; LCMS retention time (min) |
|---|---|---|---|
| 276 | 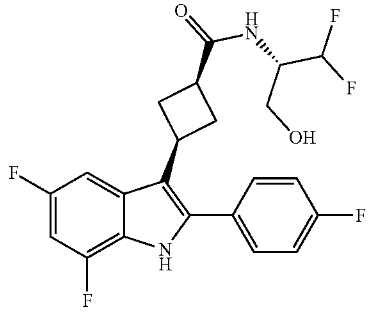 [SMILES: O=C(N[C@@H](CO)C(F)F)[C@H]1C[C@@H](c2c(-c3ccc(F)cc3)[nH]c3c(F)cc(F)cc32)C1] | LCMS m/z 439.1 $[M + H]^+$ | A; 3.66 |
| 277 | 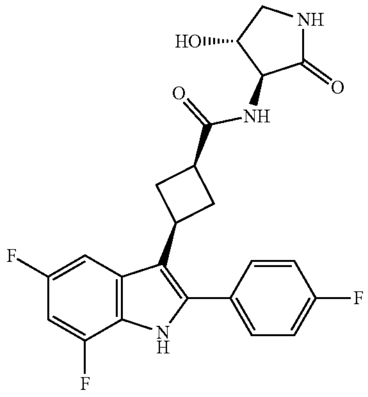 [SMILES: O=C1NC[C@@H](O)[C@@H]1NC(=O)[C@H]1C[C@@H](c2c(-c3ccc(F)cc3)[nH]c3c(F)cc(F)cc32)C1] | LCMS m/z 444.12 $[M + H]^+$ | A; 3.1 |

Compounds 278

3-[5,7-difluoro-2-(4-fluorophenyl)-1H-indol-3-yl] cyclobutanecarboxamide (278)

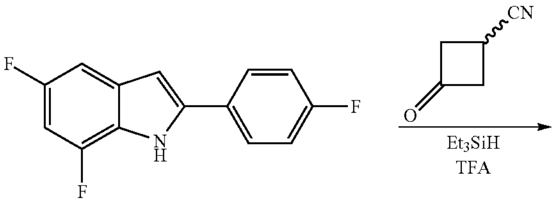

C3

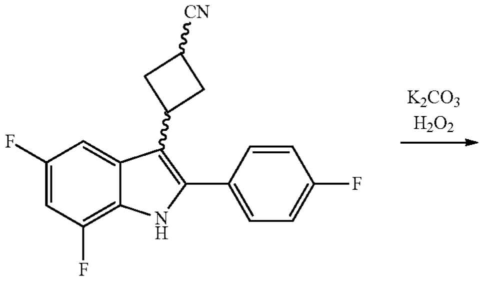

C11

-continued

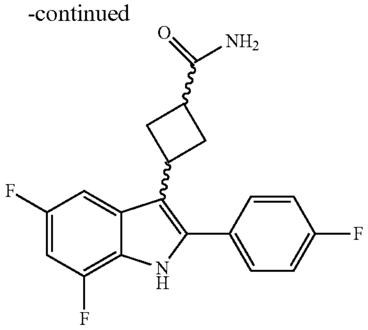

278

Step 1. Synthesis of 3-[5,7-difluoro-2-(4-fluorophenyl)-1H-indol-3-yl]cyclobutanecarbonitrile (C12)

5,7-difluoro-2-(4-fluorophenyl)-1H-indole (200 mg, 0.81 mmol) was taken in $CH_2Cl_2$ (10 mL) and added 3-oxocyclobutanecarbonitrile (100 mg, 1.1 mmol). $Et_3SiH$ (800 mg, 6.9 mmol) and TFA (600 mg, 5.3 mmol). The reaction mixture was stirred overnight. The reaction mixture was concentrated and diluted with saturated $NaHCO_3$/Ethyl acetate. The organic layer was dried with brine and $Na_2SO_4$ then concentrated to afford a solid. Purification by reversed-phase HPLC (Method: C18 Waters Sunfire column (30×150 mm, 5 micron). Gradient: MeCN in $H_2O$ with 0.1% trifluoroacetic acid) afforded the product. 3-[5,7-difluoro-2-(4-fluorophenyl)-1H-indol-3-yl]cyclobutanecarbonitrile (Trifluoroacetate salt) (220 mg, 55%). $^1$H NMR (300 MHz, DMSO-$d_6$) δ 11.81 (s, 1H), 7.73-7.47 (m, 2H), 7.47-7.23 (m, 3H), 7.14-6.90 (m, 1H), 3.82 (tt, J=10.2, 8.2 Hz, 1H), 3.36-3.22 (m, 1H), 2.86-2.66 (m, 2H), 2.57 (ddd, J=11.8, 9.0, 2.3 Hz, 2H). LCMS m/z 327.08 $[M+H]^+$.

Step 2. Synthesis of 3-[5,7-difluoro-2-(4-fluorophenyl)-1H-indol-3-yl]cyclobutanecarboxamide (278)

3-[5,7-difluoro-2-(4-fluorophenyl)-1H-indol-3-yl]cyclobutanecarbonitrile (C12) (50 mg, 0.1066 mmol) was dissolved in DMSO (2 mL) and added $K_2CO3$ (15 mg, 0.11 mmol) and hydrogen peroxide (5 mg, 0.15 mmol). The frothy reaction mixture was stirred at room temperature for 2 hours. The reaction mixture was diluted with ethyl acetate, filtered, and concentrated. Purification by reversed-phase HPLC (Method: C18 Waters Sunfire column (30×150 mm, 5 micron). Gradient: MeCN in $H_2O$ with 0.1% trifluoroacetic acid afforded the product). 3-[5,7-difluoro-2-(4-fluorophenyl)-1H-indol-3-yl]cyclobutanecarboxamide (Trifluoroacetate salt) (4 mg, 7%). $^1$H NMR (300 MHz, Methanol-$d_4$) δ 9.56 (s, 1H), 6.11 (dd, J=9.9, 2.2 Hz, 1H), 6.08-5.88 (m, 2H), 5.88-5.57 (m, 2H), 5.40-5.03 (m, 1H), 2.24 (tt, J=10.3, 8.3 Hz, 1H), 1.72-1.42 (m, 1H), 1.31-1.06 (m, 2H), 0.95 (qd, J=8.3, 2.6 Hz, 2H) ppm. LCMS m/z 345.28 $[M+1]^+$.

Compounds 279-280

Compounds 279 and 280 (Table 10) were prepared from 3-[7-fluoro-2-(4-fluorophenyl)-5-(trifluoromethyl)-1H-indol-3-yl]cyclobutanecarboxylic acid [CIS/TRANS mix] and the appropriate commercially available amine using standard method A. 3-[7-fluoro-2-(4-fluorophenyl)-5-(trifluoromethyl)-1H-indol-3-yl]cyclobutanecarboxylic acid [CIS/TRANS mix] was prepared from 7-fluoro-2-(4-fluorophenyl)-5-(trifluoromethyl)-1H-indole and 3-oxocyclobutanecarboxylic acid using the method described for the preparation of S1.

TABLE 10

Structure, physicochemical properties, and LCMS analysis for compounds 279-280

| Compound | Structure | LCMS m/z $[M + H]^+$ | LCMS Method; LCMS retention time (min) |
|---|---|---|---|
| 279 | 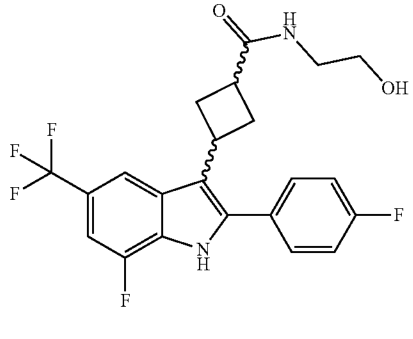 [SMILES: O=C(NCCO)C1CC(c2c(-c3ccc(F)cc3)[nH]c3c(F)cc(C(F)(F)F)cc23)C1] | LCMS m/z 438.97 $[M + H]^+$ | A; 3.63 |
| 280 | 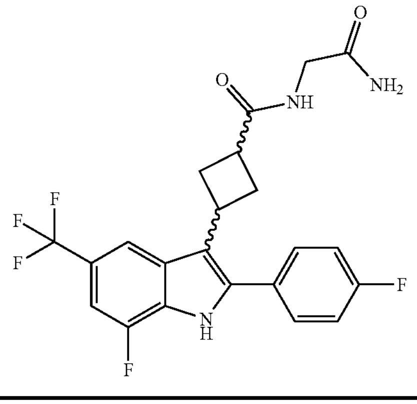 | LCMS m/z 452.14 $[M + H]^+$ | B; 0.82 |

Compound 281-286

Compound 281-286 (Table 11) were prepared from the appropriate acid and commerically available amine by coupling with HATU according to standard method A.

TABLE 11

Structure, physicochemical properties, and LCMS analysis for compounds 281-286

| Compound | Structure | $^1H$ NMR (ppm); LCMS m/z $[M + H]^+$ | LCMS Method; LCMS retention time (min) |
|---|---|---|---|
| 281(1) | 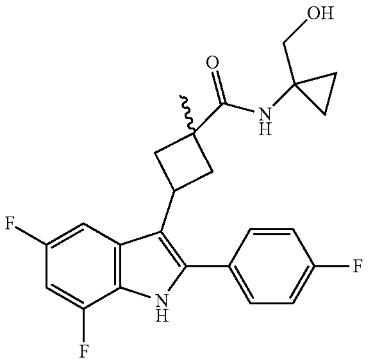 [SMILES: CC1(C(=O)NC2(CO)CC2)CC(c2c(-c3ccc(F)cc3)[nH]c3c(F)cc(F)cc23)C1] | LCMS m/z 429.2 $[M + H]^+$ | A; 3.63 |
| 282(1) | 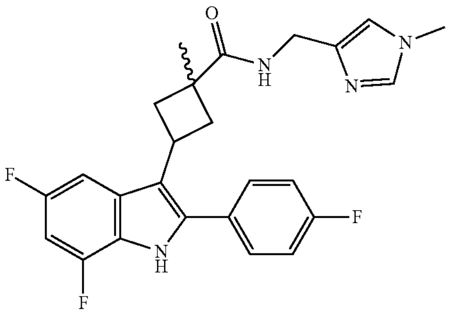 [SMILES: Cn1cnc(CNC(=O)C2(C)CC(c3c(-c4ccc(F)cc4)[nH]c4c(F)cc(F)cc34)C2)c1] | LCMS m/z 453.21 $[M + H]^+$ | A; 2.82 |
| 283(1) | 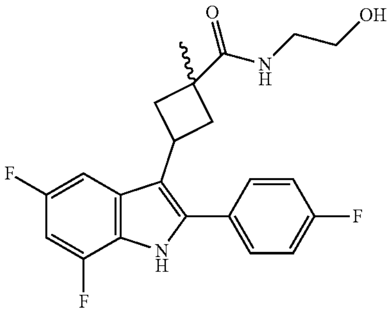 [SMILES: CC1(C(=O)NCCO)CC(c2c(-c3ccc(F)cc3)[nH]c3c(F)cc(F)cc23)C1] | LCMS m/z 403.17 $[M + H]^+$ | A; 3.47 |
| 284(1) | 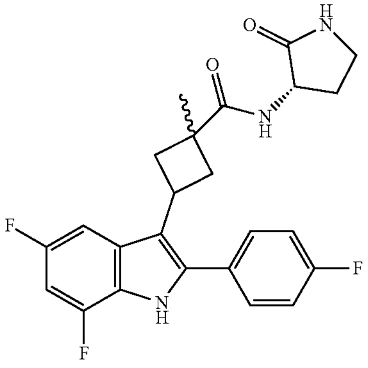 [SMILES: CC1(C(=O)N[C@H]2CCNC2=O)CC(c2c(-c3ccc(F)cc3)[nH]c3c(F)cc(F)cc23)C1] | LCMS m/z 442.17 $[M + H]^+$ | A; 3.41 |

TABLE 11-continued

| Structure, physicochemical properties, and LCMS analysis for compounds 281-286 | | | |
|---|---|---|---|
| Compound | Structure | $^1$H NMR (ppm); LCMS m/z [M + H]$^+$ | LCMS Method; LCMS retention time (min) |
| 285(2) | 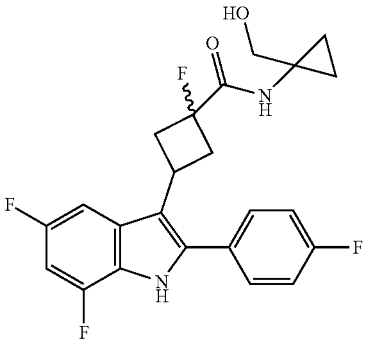 [SMILES: O=C(NC1(CO)CC1)C1(F)CC(c2c(-c3ccc(F)cc3)[nH]c3c(F)cc(F)cc23)C1] | $^1$H NMR (300 MHz, Acetone-$d_6$) δ 10.77 (s, 1H), 8.08 (dd, J = 10.1, 2.2 Hz, 1H), 7.77 (s, 1H), 7.75-7.52 (m, 2H), 7.31 (s, 2H), 6.87 (d, J = 0.7 Hz, 1H), 4.19 (p, J = 9.5 Hz, 1H), 3.60 (s, 2H), 3.43-3.14 (m, 2H), 3.13-2.86 (m, 1H), 2.70-2.47 (m, 2H), 0.98-0.70 (m, 4H). LCMS m/z 433.14 [M + H]$^+$. | A; 3.78 |
| 286(2) | 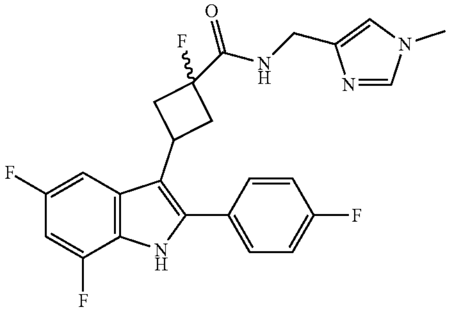 [SMILES: Cn1cnc(CNC(=O)C2(F)CC(c3c(-c4ccc(F)cc4)[nH]c4c(F)cc(F)cc34)C2)c1] | LCMS m/z 457.15 [M + H]$^+$ | A; 2.87 |

(1)Prepared from 3-[5,7-difluoro-2-(4-fluorophenyl)-1H-indol-3-yl]-1-methyl-cyclobutanecarboxylic acid. 3-[5,7-difluoro-2-(4-fluorophenyl)-1H-indol-3-yl]-1-methyl-cyclobutanecarboxylic acid was prepared from C3 and 1-methyl-3-oxo-cyclobutanecarboxylic acid by reductive coupling with Et3SiH in the presence of TFA, as described for the preparation of S1.
(2)Prepared from 3-[5,7-difluoro-2-(4-fluorophenyl)-1H-indol-3-yl]-1-fluoro-cyclobutanecarboxylic acid.

All amines used in the preparation of compounds in Tables 3-11 are shown in Table 12. Amines in Table 12 were either purchased commercially or prepared by standard literature processes.

TABLE 12

| Amines used in the preparation of compounds in Tables 3-11 | | |
|---|---|---|
| Compound Number | Table | Amine |
| 2 | 3 | 3-aminopyrrolidin-2-one |
| 3 | 3 | 1,3-diaminopropan-2-ol |
| 4 | 3 | propane-1,3-diamine |
| 5 | 3 | 3-aminocyclobutanol |
| 6 | 3 | (1-aminocyclobutyl)methanol |
| 7 | 3 | 3-amino-1-methyl-pyrrolidin-2-one |
| 8 | 3 | 2-aminopropane-1,3-diol |
| 9 | 3 | 2-amino-N-methyl-propanamide |
| 10 | 3 | 2-aminoacetic acid |
| 11 | 3 | 2-amino-2-methyl-propanamide |
| 12 | 3 | 2-methoxyethanamine |
| 13 | 3 | 2-aminopropan-1-ol |
| 14 | 3 | 3-aminopropane-1,2-diol |
| 15 | 3 | tetrahydrofuran-3-amine |
| 16 | 3 | (2S,3S)-2-aminobutane-1,3-diol |
| 17 | 3 | 5-methylisoxazol-3-amine |
| 18 | 3 | 2-methoxy cyclopropanamine |
| 19 | 3 | (3S)-tetrahydrofuran-3-amine |
| 20 | 3 | 3-aminocyclobutanol |
| 21 | 3 | (3R)-tetrahydrofuran-3-amine |
| 22 | 3 | 1-methylpyrazol-3-amine |
| 23 | 3 | 3-aminopiperidin-2-one |

TABLE 12-continued

| Amines used in the preparation of compounds in Tables 3-11 | | |
|---|---|---|
| Compound Number | Table | Amine |
| 24 | 3 | 5-methyloxazol-2-amine |
| 25 | 3 | (2S)-2-aminobutane-1,3-diol |
| 26 | 3 | 3-aminopiperidine-2,6-dione |
| 27 | 3 | (2R)-2-aminopropan-1-ol |
| 28 | 31 | (2R)-2-aminopropanamide |
| 29 | 3 | 2-amino-3-methyl-butan-1-ol |
| 30 | 3 | 2-amino-4-methyl-pentanamide |
| 31 | 3 | 2-amino-2-methyl-propan-1-ol |
| 32 | 3 | 2-amino-3-hydroxy-propanamide |
| 33 | 3 | 2,2,2-trifluoroethanamine |
| 34 | 3 | 2-pyrrol-1-ylethanamine |
| 35 | 3 | 2-(3-methylpyrazol-1-yl)ethanamine |
| 36 | 3 | 2-(1,2,4-triazol-1-yl)ethanamine |
| 37 | 3 | (3-methylisoxazol-5-yl)methanamine |
| 38 | 3 | (1-methylpyrazol-4-yl)methanamine |
| 39 | 3 | 2-(1,2,4-triazol-4-yl)ethanamine |
| 40 | 3 | 2-methylsulfonylethanamine |
| 41 | 3 | (3,3-difluorocyclobutyl)methanamine |
| 42 | 3 | tetrahydropyran-4-ylmethanamine |
| 43 | 3 | (5-methyloxazol-2-yl)methanamine |
| 44 | 3 | 4-aminopyrrolidin-2-one |
| 45 | 3 | (3R)-3-aminopyrrolidin-2-one |
| 47 | 4 | (1-aminocyclopropyl)methanol |
| 48 | 4 | (1-methylimidazol-4-yl)m ethanamine |
| 49 | 5 | [1-(methylaminomethyl)cyclopropyl]methanol |
| 50 | 5 | 2-amino-N-cyclopropyl-acetamide |
| 51 | 5 | 2-(methylamino)acetamide |
| 52 | 5 | 2-(cyclopropylamino)ethanol |

TABLE 12-continued

Amines used in the preparation of compounds in Tables 3-11

| Compound Number | Table | Amine |
|---|---|---|
| 53 | 5 | [1-(methoxymethyl)cyclopropyl]methanamine |
| 54 | 5 | 1-(methoxymethyl)cyclopropanamine |
| 55 | 5 | [1-(ethoxymethyl)cyclopropyl]methanamine |
| 56 | 5 | 1-aminocyclopropanecarboxamide |
| 57 | 5 | [(6R)-7-oxa-4-azaspiro[2.5]octan-6-yl]methanol |
| 58 | 5 | [1-(methylamino)cyclopropyl]methanol |
| 59 | 5 | 2-(1-aminocyclopropyl)ethanol |
| 60 | 5 | 2-amino-3,3,3-trifluoro-2-methyl-propanamide |
| 61 | 5 | (2R)-2-amino-N,N-dimethyl-propanamide |
| 62 | 5 | N,N-dimethyl-2-(methylamino)acetamide |
| 63 | 5 | 1-isopropylpiperazin-2-one |
| 64 | 5 | (2S)-N-ethylpyrrolidine-2-carboxamide |
| 65 | 5 | (2S)-2-amino-N,N-dimethyl-propanamide |
| 66 | 5 | 2-amino-2-methyl-1-morpholino-propan-1-one |
| 67 | 5 | 2-amino-1-(4-methylpiperazin-1-yl)ethanone |
| 68 | 5 | 2-aminopropanamide |
| 69 | 5 | 1-(aminomethyl)cyclopentanol |
| 70 | 5 | 4-(aminom ethyl)-1-methyl-pyrrolidin-2-one |
| 71 | 5 | (1-methylpyrazol-3-yl)methanamine |
| 72 | 5 | [5-(methoxymethyl)-1H-pyrazol-3-yl]methanamine |
| 73 | 5 | (1,5-dimethylpyrazol-3-yl)methanamine |
| 74 | 5 | 3-methylazetidin-3-ol |
| 75 | 5 | 1-(1-methylpyrazol-3-yl)ethanamine |
| 76 | 5 | l-(2-methylpyrazol-3-yl)ethanamine |
| 77 | 5 | 1-(aminomethyl)cyclobutanol |
| 78 | 5 | 2-amino-3-fluoro-propan-1-ol |
| 79 | 5 | 2-(methylamino)ethanol |
| 80 | 5 | 1-(aminomethyl)cyclohexanol |
| 81 | 5 | 1-(1H-pyrazol-5-yl)ethanamine |
| 82 | 5 | (2S)-1-aminopropan-2-ol |
| 83 | 6 | [3-(aminomethyl)oxetan-3-yl]methanol |
| 84 | 6 | (3S)-3-amino-5-methyl-pyrrolidin-2-one |
| 85 | 6 | azetidin-3-yl tetrahydropyran-4-carboxylate |
| 86 | 6 | 2-(azetidin-3-yl)propan-2-ol |
| 87 | 6 | 4-(hydroxymethyl)piperidin-4-ol |
| 88 | 6 | (2S)-pyrrolidine-2-carboxamide |
| 89 | 6 | [(3R)-pyrrolidin-3-yl]methanol |
| 90 | 6 | 1-(methylamino)propan-2-ol |
| 91 | 6 | N-(3-piperidyl)acetamide |
| 92 | 6 | piperidine-2-carboxamide |
| 93 | 6 | 2-methyl-1-(methylamino)propan-2-ol |
| 94 | 6 | 2-(2-piperidyl)ethanol |
| 95 | 6 | (3S)-3-methoxypyrrolidine |
| 96 | 6 | 1-(azetidin-3-yl)pyrazole |
| 97 | 6 | 2-azabicyclo[2.2.1]heptan-3-ylmethanol |
| 98 | 6 | [(1S,5S)-3-azabicyclo[3.1.0]hexan-1-yl]methanol |
| 99 | 6 | [(1R,5S)-3-azabicyclo[3.1.0]hexan-6-yl]methanol |
| 100 | 6 | (3S,4R)-4-(hydroxymethyl)piperidin-3-ol |
| 101 | 6 | 2-pyrrolidin-2-ylethanol |
| 102 | 6 | 4,4-dimethylpyrrolidin-3-ol |
| 103 | 6 | 2-oxa-7-azaspiro[3,4]octane |
| 104 | 6 | 3-aminopropan-1-ol |
| 105 | 6 | (3S)-piperidin-3-ol |
| 106 | 6 | 4-morpholinopyrrolidin-3-ol |
| 107 | 6 | [(2R)-2-piperidyl]methanol |
| 108 | 6 | [4-(hydroxymethyl)-4-piperidyl]methanol |
| 109 | 6 | [(3R)-3-piperidyl]methanol |
| 110 | 6 | (3S,4S)-4-[(dimethylamino)methyl]piperidin-3-ol |
| 111 | 6 | 2-(ethylamino)propan-1-ol |
| 112 | 6 | 3-ethylazetidin-3-ol |
| 113 | 6 | 2-morpholin-3-ylethanol |
| 114 | 6 | 3,3-dimethylpiperidin-4-ol |
| 115 | 6 | morpholin-2-ol |
| 116 | 6 | (3S,4S)-3-methylpiperidin-4-ol |
| 117 | 6 | 3-(2-hydroxyethylamino)propan-1-ol |
| 118 | 6 | [(2S)-morpholin-2-yl]methanol |
| 119 | 6 | 4-(aminomethyl)hexane-1,4-diol |
| 120 | 6 | [4-(methylaminomethyl)tetrahydropyran-4-yl]methanol |
| 121 | 6 | 2-[2-(cyclobutylamino)ethoxy]ethanol |
| 122 | 6 | 2-piperazin-1-ylpropan-1-ol |
| 123 | 6 | 2-(isopropylamino)ethanol |
| 124 | 6 | 2-(ethylamino)ethanol |
| 125 | 6 | 2-(2-aminoethoxy)ethanol |
| 126 | 6 | 2-piperazin-1-ylethanol |
| 127 | 6 | piperidine-4,4-diol |
| 128 | 6 | 2-(3-piperidyl)ethanol |
| 129 | 6 | 1-(2-hydroxyethylamino)propan-2-ol |
| 130 | 6 | (2,2-dimethylpiperazin-1-yl)-(3-hydroxy-3-methyl-cyclobutyl)methanone |
| 131 | 6 | 1-(3-piperidyl)ethanol |
| 132 | 6 | 2-(pyrazin-2-ylamino)ethanol |
| 133 | 6 | piperidine-4-carboxamide |
| 134 | 6 | 2-(4-piperidyl)ethanol |
| 135 | 6 | (3R)-pyrrolidine-3-carboxamide |
| 136 | 6 | 3-(tetrahydrofuran-2-ylmethoxy)azetidine |
| 137 | 6 | 2-azaspiro[3.3]heptan-6-ol |
| 138 | 6 | 4-(hydroxymethyl)pyrrolidin-3-ol |
| 139 | 6 | (3R)-3-aminocyclopentanone |
| 140 | 6 | [(3S)-pyrrolidin-3-yl]methanol |
| 141 | 6 | (2S)-2-amino-3-methyl-butan-1-ol |
| 142 | 6 | (2R)-2-(methylamino)propan-1-ol |
| 143 | 6 | 1-(aminomethyl)cyclobutanol |
| 144 | 6 | (2S)-2-amino-3-hydroxy-propanamide |
| 145 | 6 | 2-piperidylmethanol |
| 146 | 6 | [(2S)-2-piperidyl]methanol |
| 147 | 6 | 3-piperidylmethanol |
| 148 | 6 | morpholin-2-ylmethanol |
| 149 | 6 | (3R)-piperidin-3-ol |
| 150 | 6 | piperidin-3-ol |
| 151 | 6 | morpholin-2-ylmethanol |
| 152 | 6 | morpholin-2-ylmethanol |
| 153 | 6 | (2R)-pyrrolidine-2-carboxamide |
| 154 | 6 | (3S)-pyrrolidine-3-carboxamide |
| 155 | 6 | (2S,3R)-2-aminobutane-1,3-diol |
| 156 | 6 | 2-[(2R)-2-piperidyl]ethanol |
| 157 | 6 | (3S)-3-aminocyclopentanone |
| 158 | 6 | 3-(methylamino)propane-1,2-diol |
| 159 | 6 | 3-aminocyclopentanone |
| 160 | 6 | (2R,3R)-2-aminobutane-1,3-diol |
| 161 | 6 | [(2S)-piperazin-2-yl]methanol |
| 162 | 7 | (3S)-3-aminopyrrolidin-2-one |
| 163 | 7 | (2S)-2-amino-3,3,3-trifluoro-propan-1-ol |
| 164 | 7 | (2R)-2-amino-3,3,3-trifluoro-propan-1-ol |
| 165 | 7 | (3S)-3-aminopyrrolidine-2,5-dione |
| 166 | 7 | (3R)-3-aminopyrrolidine-2,5-dione |
| 167 | 7 | 1-aminopropan-2-ol |
| 168 | 7 | oxazol-4-ylmethanamine |
| 169 | 7 | ammonia |
| 170 | 7 | oxazol-5-ylmethanamine |
| 171 | 7 | 1,3,4-oxadiazol-2-ylmethanamine |
| 172 | 7 | (5-methyl-1,3,4-oxadiazol-2-yl)methanamine |
| 173 | 7 | (3-methyl-1,2,4-oxadiazol-5-yl)methanamine |
| 174 | 7 | (3-methylimidazol-4-yl)methanamine |
| 175 | 7 | (2R)-1-aminopropan-2-ol |
| 176 | 7 | (2S)-3-amino-1,1,1-trifluoro-propan-2-ol |
| 177 | 7 | (2R)-3-amino-1,1,1-trifluoro-propan-2-ol |
| 178 | 7 | (1S,2S)-2-aminocyclobutanol |
| 179 | 7 | (1S,2R)-2-aminocyclopentanol |
| 180 | 7 | (1R,3S)-3-aminocyclopentanol |
| 181 | 7 | (1R,2S)-2-aminocyclobutanol |
| 182 | 7 | (1R,2R)-2-aminocyclopentanol |
| 183 | 7 | 1-(aminomethyl)cyclopropanol |
| 184 | 7 | (3R,4S)-4-aminotetrahydrofuran-3-ol |
| 185 | 7 | 3-(aminomethyl)oxetan-3-ol |
| 186 | 7 | 2-amino-2-methyl-propane-1,3-diol |
| 187 | 7 | (1S,3S)-3-aminocyclopentanol |
| 188 | 7 | (3S)-3-aminotetrahydrofuran-2-one |
| 189 | 7 | [(2S,5R)-5-(aminomethyl)tetrahydrofuran-2-yl]methanol |
| 190 | 7 | (2R)-2-(methylamino)propan-1-ol |
| 191 | 7 | 2-amino-3-hydroxy-2-methyl-propanenitrile |
| 192 | 7 | [(2R)-pyrrolidin-2-yl]methanol |
| 193 | 7 | 2-(methylamino)propan-1-ol |
| 194 | 7 | (3-aminotetrahydrofuran-3-yl)methanol |
| 195 | 7 | [(2R)-azetidin-2-yl]methanol |
| 196 | 7 | 2-aminobut-3-yn-1-ol |
| 197 | 7 | 3-amino-3-methyl-pyrrolidin-2-one |

TABLE 12-continued

Amines used in the preparation of compounds in Tables 3-11

| Compound Number | Table | Amine |
|---|---|---|
| 198 | 7 | (2-methyltriazol-4-yl)methanamine |
| 199 | 7 | 2-amino-2-cyclopropyl-ethanol |
| 200 | 7 | (2S)-2-aminopropan-1-ol |
| 201 | 7 | 2-amino-3-hydroxy-propanenitrile |
| 202 | 7 | (1-amino-3,3-difluoro-cyclobutyl)methanol |
| 203 | 7 | (2R)-2-aminobutan-1-ol |
| 204 | 7 | (2S)-2-aminobutan-1-ol |
| 205 | 7 | 4-(methylamino)tetrahydrofuran-3-ol |
| 206 | 7 | [(2S)-azetidin-2-yl]methanol |
| 207 | 7 | 3-amino-5-methyl-tetrahydrofuran-2-one |
| 208 | 7 | 3-(aminomethyl)pyrrolidin-2-one |
| 209 | 7 | (3S,5S)-3-amino-5-(hydroxymethyl)pyrrolidin-2-one |
| 210 | 7 | [(2S)-pyrrolidin-2-yl]methanol |
| 211 | 7 | 3-amino-3-methyl-cyclobutanol |
| 212 | 7 | (3S,4S)-4-aminopyrrolidin-3-ol |
| 213 | 7 | methanesulfonamide |
| 214 | 7 | (2S)-2-amino-3-hydroxy-propanamide |
| 215 | 7 | 1-amino-3-methyl-butane-2,3-diol |
| 216 | 7 | 3-amino-2-methyl-propane-1,2-diol |
| 217 | 7 | [(3R)-morpholin-3-yl]methanol |
| 218 | 7 | (2-methylazetidin-2-yl)methanol |
| 219 | 7 | [(3S)-morpholin-3-yl]methanol |
| 220 | 7 | (2S)-2-(methoxymethyl)azetidine |
| 221 | 7 | (2R)-2-amino-3-hydroxy-propanamide |
| 222 | 7 | (2R)-2-(methoxymethyl)azetidine |
| 223 | 7 | azetidin-3-ylmethanol |
| 224 | 7 | (2R)-3-aminopropane-1,2-diol |
| 225 | 7 | (2S)-3-aminopropane-1,2-diol |
| 226 | 7 | 2-amino-2-(hydroxymethyl)propane-1,3-diol |
| 227 | 7 | (3R,4R)-pyrrolidine-3,4-diol |
| 228 | 7 | piperazin-2-one |
| 229 | 7 | (3S,4R)-3-amino-4-hydroxy-pyrrolidin-2-one |
| 230 | 7 | (2S)-2-amino-3,3-difluoro-propan-1-ol |
| 231 | 7 | 2-amino-N-(2-hydroxy ethyl)acetamide |
| 232 | 7 | 2-amino-N-[(1R)-2-hydroxy-1-methyl-ethyl]acetamide |
| 233 | 7 | 2-amino-N-[(2R)-3,3,3-trifluoro-2-hydroxy-propyl]acetamide |
| 234 | 7 | 2-amino-N-[(2S)-3,3,3-trifluoro-2-hydroxy-propyl]acetamide |
| 236 | 8 | (3R)-3-aminopyrrolidin-2-one |
| 237 | 8 | 2-aminoethanol |
| 238 | 8 | 2,2-difluoroethanamine |
| 239 | 8 | 3-aminocyclobutanol |
| 240 | 8 | (1-aminocyclobutyl)methanol |
| 241 | 8 | 2-aminopropane-1,3-diol |
| 242 | 8 | 2-methoxyethanamine |
| 243 | 8 | 2-aminopropan-1-ol |
| 244 | 8 | 3-aminopropane-1,2-diol |
| 245 | 8 | (2S,3S)-2-aminobutane-1,3-diol |
| 246 | 8 | (3S)-tetrahydrofuran-3-amine |
| 247 | 8 | 2-methylpyrazol-3-amine |
| 248 | 8 | oxetan-3-ylmethanamine |
| 249 | 8 | 3-aminopiperidin-2-one |
| 250 | 8 | 2-aminoacetamide |
| 251 | 8 | 2-amino-2-methyl-propane-1,3-diol |
| 252 | 8 | 3-aminopiperidine-2,6-dione |
| 253 | 8 | (1-aminocyclopropyl)methanol |
| 254 | 8 | 2-amino-3-methyl-butan-1-ol |
| 255 | 8 | 2-amino-4-methyl-pentanamide |
| 256 | 8 | 2-amino-2-methyl-propan-1-ol |
| 257 | 8 | (2S)-2-aminobutan-1-ol |
| 258 | 8 | (2R)-1-aminopropan-2-ol |
| 259 | 8 | 2-amino-3-hydroxy-propanamide |
| 260 | 8 | 2,2,2-trifluoroethanamine |
| 261 | 8 | (1-methylimidazol-4-yl)methanamine |
| 262 | 8 | 2-pyrrol-1-ylethanamine |
| 263 | 8 | 2-(3-methylpyrazol-1-yl)ethanamine |
| 264 | 8 | 2-(1,2,4-triazol-1-yl)ethanamine |
| 265 | 8 | (2-methylpyrazol-3-yl)methanamine |
| 266 | 8 | (3,3-difluorocyclobutyl)methanamine |
| 267 | 8 | 3-aminocyclobutanol |
| 268 | 8 | 3-aminopyrrolidin-2-one |
| 269 | 8 | (3R)-tetrahydrofuran-3-amine |
| 270 | 8 | (2S)-2-aminobutane-1,3-diol |
| 271 | 8 | (2S)-2-aminopropan-1-ol |
| 272 | 8 | (2R)-2-aminopropan-1-ol |
| 273 | 8 | 2-amino-2-(hydroxymethyl)propane-1,3-diol |
| 274 | 9 | (3R,4R)-pyrrolidine-3,4-diol |
| 275 | 9 | piperazin-2-one |
| 276 | 9 | (2S)-2-amino-3,3-difluoro-propan-1-ol |
| 277 | 9 | (3S,4R)-3-amino-4-hydroxy-pyrrolidin-2-one |
| 279 | 10 | 2-aminoethanol |
| 280 | 10 | 2-aminoacetamide |
| 281 | 11 | (1-aminocyclopropyl)methanol |
| 282 | 11 | (1-methylimidazol-4-yl)methanamine |
| 283 | 11 | 2-aminoethanol |
| 284 | 11 | (3S)-3-aminopyrrolidin-2-one |
| 285 | 11 | (1-aminocyclopropyl)methanol |
| 286 | 11 | (1-methylimidazol-4-yl)methanamine |

Preparation S5

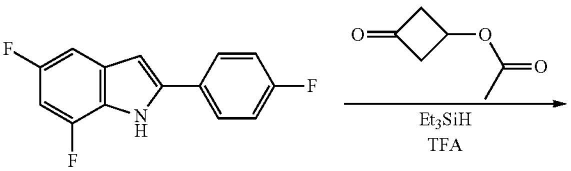

C3

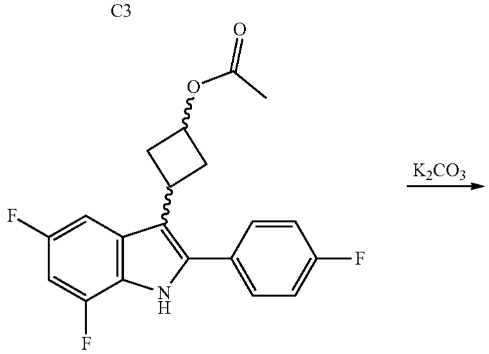

C12

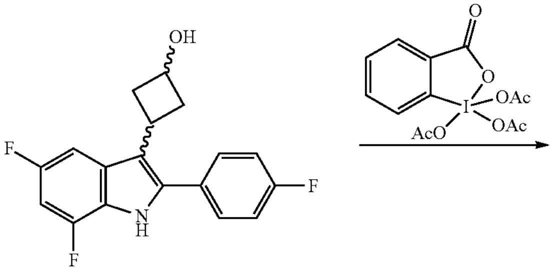

C13

-continued

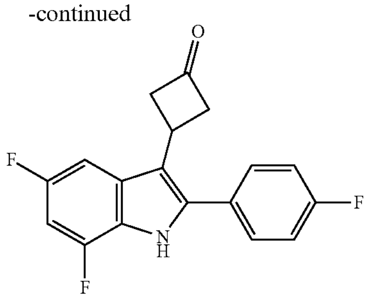

S5

Step 1. Synthesis of [3-[5,7-difluoro-2-(4-fluorophenyl)-1H-indol-3-yl]cyclobutyl] acetate (C12)

To a solution of 5,7-difluoro-2-(4-fluorophenyl)-1H-indole C3 (5 g, 20 mmol) in dichloromethane (25 mL) was added (3-oxocyclobutyl) acetate (3.8 g, 0.030 mol) followed by $Et_3SiH$ (12 g, 100 mmol) and trifluoroacetic acid (12 g, 110 mmol). The mixture was stirred at room temperature overnight. The mixture was then partitioned between ethyl acetate and aqueous sat. sodium bicarbonate solution. The organic phase was separated and washed with brine. The organic layer was dried over sodium sulfate, filtered, and concentrated in vacuo. The residue was purified by silica gel chromatography (Gradient: 0-40% EtOAc in heptane) to afford the product. [3-[5,7-Difluoro-2-(4-fluorophenyl)-1H-indol-3-yl]cyclobutyl] acetate (7 g, 67%). LCMS m/z 360.2 $[M+H]^+$.

Step 2. Synthesis of 3-[5,7-difluoro-2-(4-fluorophenyl)-1H-indol-3-yl]cyclobutanol (C13)

To a solution of [3-[5,7-difluoro-2-(4-fluorophenyl)-1H-indol-3-yl]cyclobutyl] acetate C12 (7 g, 12 mmol) in methanol (60 mL) was added potassium carbonate (2.2 g, 16 mmol). The mixture was stirred at room temperature for 4 h. The mixture was then partitioned between ethyl acetate and brine. The organic phase was separated and dried over sodium sulfate, filtered, and concentrated in vacuo. The residue was purified by silica gel chromatography using EtOAc in heptane to afford the product. 3-[5,7-Difluoro-2-(4-fluorophenyl)-1H-indol-3-yl]cyclobutanol (4 g, 95%). $^1H$ NMR (300 MHz, DMSO-$d_6$) δ 11.67 (d, J=7.4 Hz, 1H), 7.75-7.15 (m, 5H), 6.99 (t, J=10.5 Hz, 1H), 4.43 (d, J=7.0 Hz, 1H), 3.99 (dd, J=13.0, 7.0 Hz, 1H), 2.57 (d, J=8.5 Hz, 2H), 2.21 (p, J=10.8, 10.2 Hz, 2H). LCMS m/z 318.2 $[M+H]^+$.

Step 3. Synthesis of 3-[5,7-difluoro-2-(4-fluorophenyl)-1H-indol-3-yl]cyclobutanone (S5)

To a solution of 3-[5,7-difluoro-2-(4-fluorophenyl)-1H-indol-3-yl]cyclobutanol C13 (500 mg, 1.1 mmol) in dichloromethane (25 mL) was added 3-oxo-1,3-dihydro-1λ5,2-benziodoxole-1,1,1-triyl triacetate (580 mg, 1.4 mmol). The mixture was stirred at room temperature for 3 h. The precipitate was removed by filtration, and the filtrate was concentrated in vacuo. The residue was purified by silica gel chromatography (Gradient: 0-50% EtOAc in heptane) to afford the product. 3-[5,7-Difluoro-2-(4-fluorophenyl)-1H-indol-3-yl]cyclobutanone (200 mg, 37%). $^1H$ NMR (400 MHz, DMSO-$d_6$) δ 11.83 (s, 1H), 7.67-7.59 (m, 2H), 7.37 (t, J 8.8 Hz, 2H), 7.16 (dd, J=9.8, 2.2 Hz, 1H), 7.07-6.97 (m, 1H), 3.92 (p, J=8.2 Hz, 1H), 3.53-3.41 (m, 2H), 3.31-3.25 (m, 1H). LCMS m/z 316.3 $[M+H]^+$.

Preparation S6

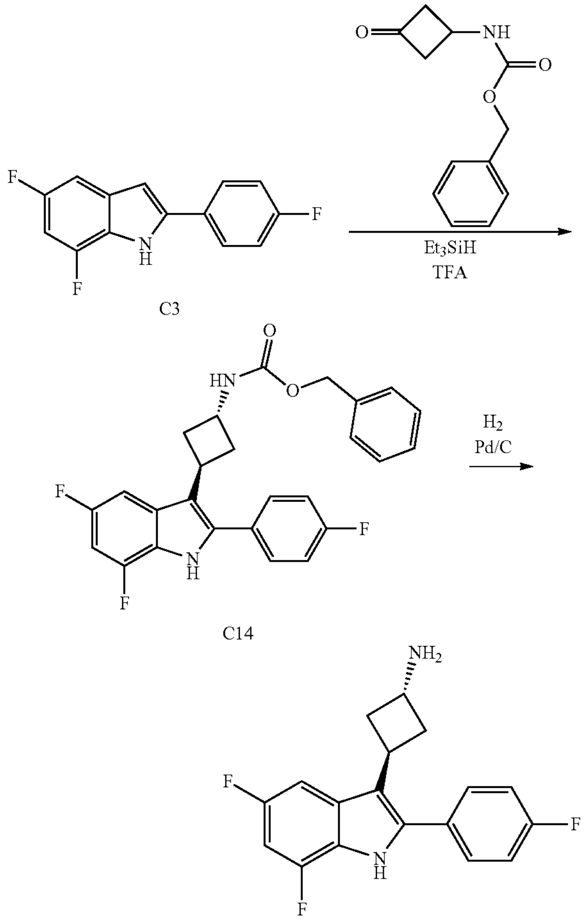

C3

C14

S6

Step 1. Synthesis of benzyl (1r,3r)-3-(5,7-difluoro-2-(4-fluorophenyl)-1H-indol-3-yl)cyclobutyl)carbamate (C14)

To a solution of 5,7-difluoro-2-(4-fluorophenyl)-1H-indole S1 (5.05 g, 20.4 mmol) in dichloromethane (100 mL) under a nitrogen atmosphere was added benzyl N-(3-oxocyclobutyl)carbamate (4.9 g, 22 mmol) followed by $Et_3SiH$ (20 mL, 130 mmol) and trifluoroacetic acid (9.5 mL, 120 mmol). The mixture was stirred at room temperature overnight. The mixture was then concentrated in vacuo and partitioned between ethyl acetate and aqueous sat. sodium bicarbonate solution. The organic phase was separated and washed with brine. The organic layer was dried over sodium sulfate, filtered, and concentrated in vacuo. The residue was purified by silica gel chromatography (Gradient: 0-100% EtOAc in heptane) to afford the isomeric mixture of product. The isomeric mixture (6.5 g, 14 mmol) was separated by chiral SFC separation (Column: Daicel Chiralpak® AD-H, 20×250 mm; Mobile Phase: 40% methanol (containing 5 mM ammonia), 60% carbon dioxide. Flow: 75 mL/min) into trans isomer. Benzyl (1r,3r)-3-(5,7-difluoro-2-(4-fluorophenyl)-1H-indol-3-yl)cyclobutyl)carbamate (1.1 g, 52%). $^1$H NMR (300 MHz, Acetone-$d_6$) δ 7.64-7.57 (m, 2H), 7.43-7.24 (m, 7H), 6.90-6.80 (m, 2H), 5.10 (2, 2H), 4.35 (d, J=6.9 Hz, 1H), 4.21-4.07 (m, 1H), 2.81-2.74 (m, 2H), 2.50-2.40 (m, 2H). LCMS m/z 451.24 [M+H]$^+$.

Step 2. Synthesis of (1r,3r)-3-[5,7-difluoro-2-(4-fluorophenyl)-1H-indol-3-yl]cyclobutanamine (S6)

To a solution of benzyl N-[(1r,3r)-3-[5,7-difluoro-2-(4-fluorophenyl)-1H-indol-3-yl]cyclobutyl]carbamate C14 (1.7 g, 3.8 mmol) in MeOH (20 mL) and THE (5 mL) was added 10% palladium on carbon catalyst (1 g, 50% water). The reaction mixture was placed on Parr shaker at 30 psi for 6 h. Then the mixture was filtered through Celite®. The filtrate was removed in vacuo, and the resulting mixture was triturated with DCM (10 mL) to provide the product. (1r,3r)-3-[5,7-Difluoro-2-(4-fluorophenyl)-1H-indol-3-yl]cyclobutanamine (948.2 mg, 75%). $^1$H NMR (300 MHz, Methanol-$d_4$) δ 7.51 (ddt, J=8.3, 5.2, 2.5 Hz, 2H), 7.26 (dtd, J=8.8, 6.8, 2.2 Hz, 3H), 6.78 (ddd, J=11.1, 9.6, 2.1 Hz, 1H), 4.25 (p, J=9.0 Hz, 1H), 3.96 (dddt, J=8.2, 7.0, 3.5, 1.9 Hz, 1H), 2.97-2.80 (m, 2H), 2.50 (ddt, J=12.5, 9.6, 3.3 Hz, 2H). LCMS m/z 317.13 [M+H]$^+$.

Preparation S7

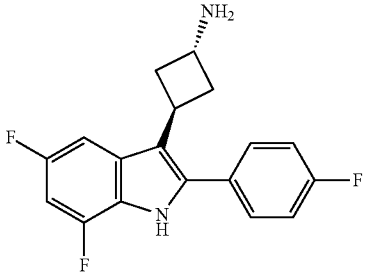

S6

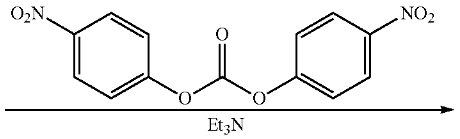

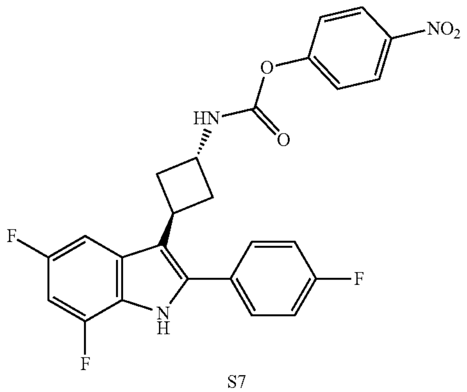

S7

Preparation of 4-nitrophenyl ((1r,3r)-3-(5,7-difluoro-2-(4-fluorophenyl)-1H-indol-3-yl)cyclo-butyl) carbamate (S7)

To a solution of 3-[5,7-difluoro-2-(4-fluorophenyl)-1H-indol-3-yl]cyclobutanamine S6 (600 mg, 1.9 mmol) in THE (20 mL) was added bis(4-nitrophenyl) carbonate (285 mg, 0.937 mmol), followed by $Et_3N$ (200 mg, 2.0 mmol). The reaction mixture was stirred for a few hours. The mixture was then concentrated in vacuo to provide the product. 4-Nitrophenyl ((1r,3r)-3-(5,7-difluoro-2-(4-fluorophenyl)-1H-indol-3-yl)cyclobutyl)carbamate (600 mg, 12%). LCMS m/z 482.27 [M+H]$^+$.

Preparation S8

3-[[5,7-difluoro-2-(4-fluorophenyl)-1H-indol-3-yl]methyl]cyclobutanecarboxylic acid (S8)

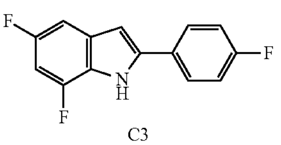

C3

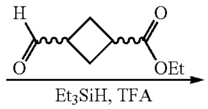

-continued

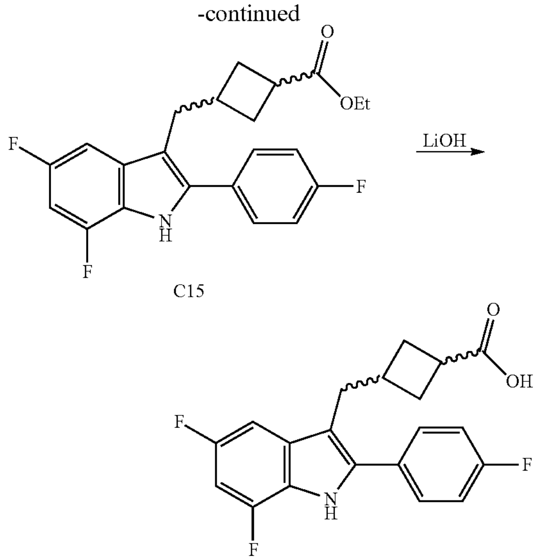

C15

S8

Step 1. Synthesis of ethyl 3-[[5,7-difluoro-2-(4-fluorophenyl)-1H-indol-3-yl]methyl]cyclobutanecarboxylate (C5)

5,7-difluoro-2-(4-fluorophenyl)-1H-indole C3 (750 mg, 3.034 mmol) and ethyl 3-formylcyclobutanecarboxylate (2.4 g, 15.37 mmol) were dissolved in $CH_2Cl_2$ (8 mL) and added $Et_3SiH$ (1.8 g, 15.48 mmol) and TFA (1.7 g, 14.91 mmol). The reaction mixture was stirred at room temperature overnight. The organic solvent (including TFA) was removed under reduced pressure. The resulting crude material was quenched with aqueous $NaHCO_3$solution and extracted with EtOAc. The organic layer was washed with brine and dried over $Na_2SO_4$, concentrated and purified by silica gel chromatography using hexane and EtOAc to provide the product. Ethyl 3-[[5,7-difluoro-2-(4-fluorophenyl)-1H-indol-3-yl]methyl]cyclobutanecarboxylate (1.1 g, 90%). $^1H$ NMR (300 MHz, Acetone-$d_6$) δ 10.70 (s, 1H), 7.74 (dddd, J=8.4, 7.5, 5.2, 3.1 Hz, 2H), 7.39-7.15 (m, 3H), 6.82 (ddd, J=11.1, 9.7, 2.2 Hz, 1H), 4.03 (qd, J=7.1, 2.6 Hz, 2H), 3.11-2.93 (m, 2H), 2.93-2.78 (m, 1H), 2.79-2.48 (m, 1H), 2.26-2.10 (m, 2H), 1.97-1.77 (m, 2H), 1.43-1.20 (m, 1H), 1.16 (td, J=7.1, 1.5 Hz, 3H). LCMS m/z 388.35 $[M+H]^+$.

Step 2. Synthesis of 3-[[5,7-difluoro-2-(4-fluorophenyl)-1H-indol-3-yl]methyl]cyclobutanecarboxylic acid (S8)

Ethyl 3-[[5,7-difluoro-2-(4-fluorophenyl)-1H-indol-3-yl]methyl]cyclobutanecarboxylate C15 (1 g, 1.862 mmol) was dissolved in THE (10 mL), water (10 mL) and then LiOH (90 mg, 3.758 mmol) was added. The reaction mixture was stirred overnight. The reaction mixture was then concentrated, diluted with water and EtOAc. The organic layer was neutralized with 1N HCl and extracted with EtOAc. The combined organic layers were washed with brine and dried over $Na_2SO_4$. The organic layer was then concentrated and purified by silica gel chromatography (Gradient 0-20% MeOH in DCM) to provide the product. 3-[[5,7-Difluoro-2-(4-fluorophenyl)-1H-indol-3-yl]methyl]cyclobutanecarboxylic acid (800 mg, quantitative). $^1H$ NMR (300 MHz, Acetone-$d_6$) δ 10.71 (s, 1H), 7.88-7.64 (m, 2H), 7.43-7.08 (m, 3H), 6.82 (ddd, J=11.0, 9.7, 2.2 Hz, 1H), 3.15-3.04 (m, 1H), 3.01-2.94 (m, 1H), 2.94-2.79 (m, 1H), 2.79-2.48 (m, 1H), 2.29-2.11 (m, 2H), 1.90 (qdd, J=9.4, 5.3, 2.4 Hz, 2H). LCMS m/z 360.31 $[M+H]^+$.

Preparation S9

(1r,3r)-3-(5,7-difluoro-2-(4-fluorophenyl)-1H-indol-3-yl)cyclobutyl (4-nitrophenyl) carbonate (S9)

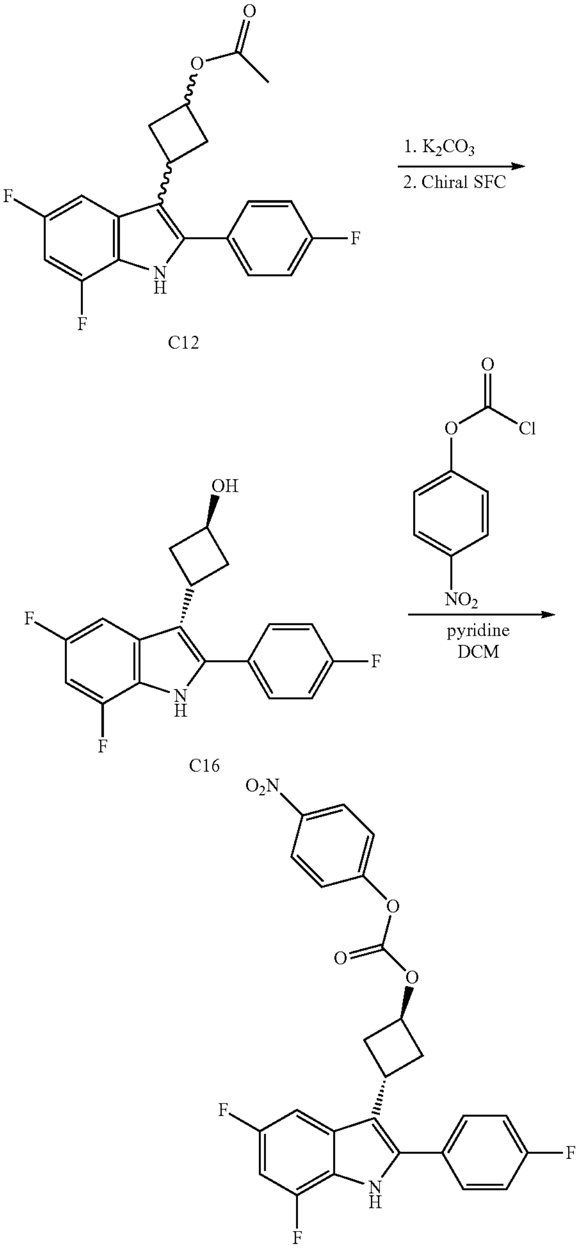

C12

C16

S9

Step 1. Synthesis of (1r,3r)-3-(5,7-difluoro-2-(4-fluorophenyl)-1H-indol-3-yl)cyclobutan-1-ol (C16)

To a solution of [3-[5,7-difluoro-2-(4-fluorophenyl)-1H-indol-3-yl]cyclobutyl] acetate C12 (700 mg, 1.2 mmol) in MeOH (10 mL) was added $K_2CO3$ (200 mg, 1.4 mmol) at room temperature. The mixture was then partitioned between EtOAc and aqueous saturated sodium bicarbonate solution. The organic phase was separated, dried over magnesium sulfate, filtered, and concentrated in vacuo. The residue was purified by chiral SFC separation (Column: Daicel Chiralpak® OJ-H, 20×250 mm; Mobile Phase: 20% isopropanol (containing 5 mM Ammonia), 80% carbon dioxide. Flow: 75 mL/min) to afford the trans isomer. (1r,3r)-3-(5,7-Difluoro-2-(4-fluorophenyl)-1H-indol-3-yl) cyclobutan-1-ol (100 mg, 46%). $^1$H NMR (300 MHz, Acetone-$d_6$) δ 10.67 (s, 1H), 7.81-7.51 (m, 2H), 7.51-7.07 (m, 3H), 6.99-6.62 (m, 1H), 4.58 (dt, J=6.9, 3.5 Hz, 1H), 4.13 (ttd, J=9.2, 7.9, 1.1 Hz, 2H), 2.79-2.55 (m, 2H), 2.50-2.25 (m, 2H). LCMS m/z 318.28 $[M+H]^+$.

Step 2. Synthesis of (1r,3r)-3-(5,7-difluoro-2-(4-fluorophenyl)-1H-indol-3-yl)cyclobutyl (4-nitrophenyl) carbonate (S9)

To a solution of (1r,3r)-3-(5,7-difluoro-2-(4-fluorophenyl)-1H-indol-3-yl)cyclobutan-1-01 C16 (2000 mg, 6.30 mmol) in DCM (20 mL) was added (4-nitrophenyl) carbonochloridate (2 g, 10 mmol), followed by pyridine (750 mg, 9.5 mmol). The mixture was stirred for 5 h at room temperature. The mixture was concentrated in vacuo, and the residue was dissolved in ethyl acetate. The solution was washed with 2 M aqueous NaOH (×3) and brine, dried over sodium sulfate, filtered, and concentrated in vacuo to afford the product. (1r,3r)-3-(5,7-Difluoro-2-(4-fluorophenyl)-1H-indol-3-yl)cyclobutyl (4-nitrophenyl) carbonate. LCMS m/z 483.26 $[M+H]^+$.

Preparation of S10 and S11

((1r,3r)-3-(5,7-difluoro-2-(4-fluorophenyl)-1H-indol-3-yl)cyclobutyl)methanamine (S10) and ((1s,3s)-3-(5,7-difluoro-2-(4-fluorophenyl)-1H-indol-3-yl)cyclobutyl)methanamine (S11)

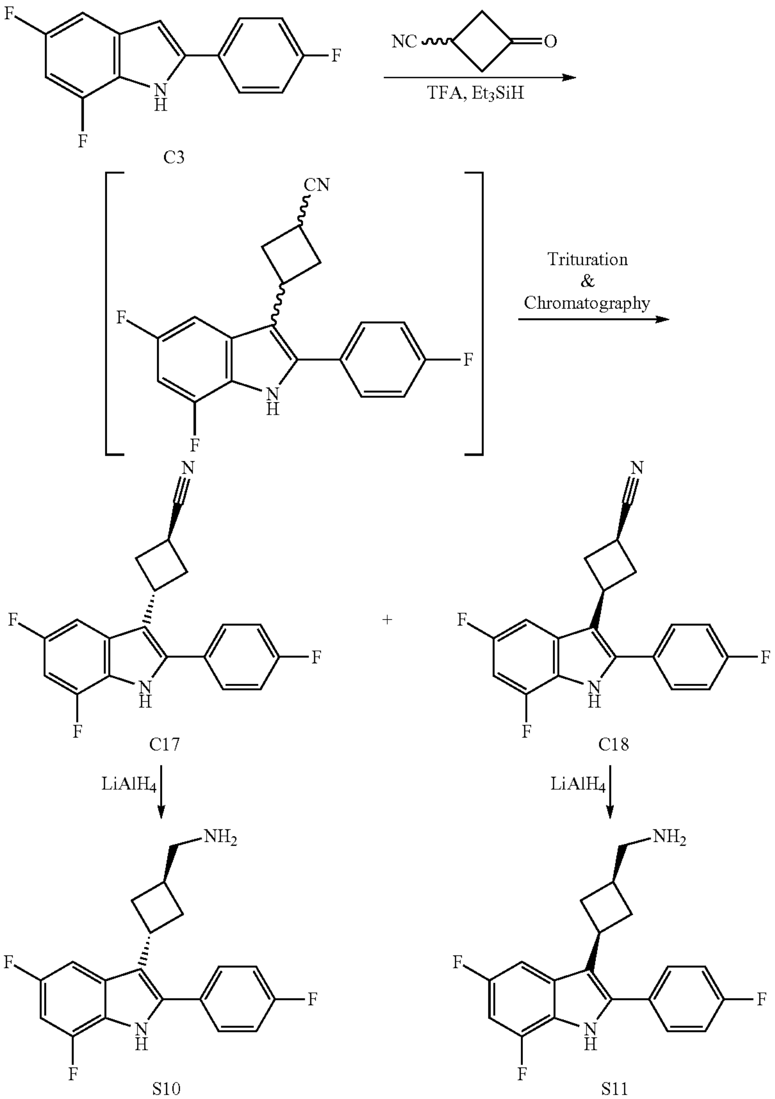

Step 1. Synthesis of 3-(5,7-difluoro-2-(4-fluorophenyl)-1H-indol-3-yl)cyclobutane-1-carbonitrile (C17)

A 250 mL round bottom flask was charged with a magnetic stir bar, 5,7-difluoro-2-(4-fluorophenyl)-1H-indole S1 (3.8 g, 13.8 mmol), 3-oxocyclobutanecarbonitrile (1.7 g, 17.8 mmol), DCM (100 mL), $Et_3SiH$ (9.6 g, 82.5 mmol), and then TFA (9.5 g, 83.3 mmol) was added drop wise via syringe. After 16 h additional 3-oxocyclobutanecarbonitrile (1.7 g, 17.8 mmol), $Et_3SiH$ (9.6 g, 82.5 mmol), and TFA (9.5 g, 83.3 mmol) were added and the mixture was allowed to stir for another 20 h. The reaction was then judged to be complete by LCMS and was then carefully inverse quenched onto a solution of saturated aqueous $NaHCO_3$. Once a neutral pH was obtained the mixture was poured into a separatory funnel and extracted with DCM (2×500 mL). The organic extract was then combined, dried with $MgSO_4$, filtered through a bed of Celite and conc. in vacuo to afford the title compound as a ~1:1 mixture of cis/trans.

Upon standing solids formed which were triturated with DCM (~50 mL). The resulting white solids were then collected via vacuum filtration using a Buchner funnel. The solids were determined to be the cis-product and the filtrate was mostly trans. The filtrate (trans) material was pre-absorbed onto Celite and further purified via $SiO_2$ chromatography (120 g) using heptanes/ethyl acetate (8:1) as eluent to afford pure trans-3-[5,7-difluoro-2-(4-fluorophenyl)-1H-indol-3-yl]cyclobutanecarbonitrile C17 (1.7 g, 26%). LCMS m/z 327.28 $[M+H]^+$ and 3-[5,7-difluoro-2-(4-fluorophenyl)-1H-indol-3-yl]cyclobutanecarbonitrile C18 (2.2 g, 45%). LCMS m/z 327.28 $[M+H]^+$.

Synthesis of ((1r, 3r)-3-(5,7-difluoro-2-(4-fluorophenyl)-1H-indol-3-yl)cyclobutyl)methanamine (S10)

To a solution of (1r,3r)-3-(5,7-difluoro-2-(4-fluorophenyl)-1H-indol-3-yl)cyclo-butane-1-carbonitrile C17 (901 mg, 2.62 mmol) in anhydrous THE (29 mL) at 0° C. under a nitrogen atmosphere was added lithium aluminum hydride (5.7 mL of 2 M, 11 mmol) slowly. The reaction was stirred at 0° C. for additional 10 min, slowly warmed to room temperature, and heated to 60° C. for 1 h. The reaction was then cooled to room temperature and slowly added to a cold solution of 1 M aqueous Rochelle's salt. The mixture was extracted with ethyl acetate, and the organic layer was washed with water and brine, dried over anhydrous sodium sulfate, filtered, and concentrated in vacuo. The residue was triturated with DCM to afford the product. ((1r,3r)-3-(5,7-Difluoro-2-(4-fluorophenyl)-1H-indol-3-yl)cyclobutyl) methanamine (535 mg, 57%). $^1H$ NMR (300 MHz, Acetone-$d_6$) δ 7.66-7.55 (m, 2H), 7.41 (ddd, J=9.9, 5.6, 2.2 Hz, 1H), 7.32-7.24 (m, 2H), 6.84 (ddd, J=11.1, 9.6, 2.2 Hz, 1H), 4.10-3.95 (m, 1H), 3.42 (s, 1H), 2.82 (d, J=7.3 Hz, 1H), 2.68-2.48 (m, 3H), 2.25-2.16 (m, 2H). LCMS m/z 331.33 $[M+H]^+$.

Synthesis of ((1s,3s)-3-(5,7-difluoro-2-(4-fluorophenyl)-1H-indol-3-yl)cyclobutyl)methanamine (S11)

To a solution of (1r,3r)-3-(5,7-difluoro-2-(4-fluorophenyl)-1H-indol-3-yl)cyclo-butane-1-carbonitrile C18 (3 g, 9 mmol) in anhydrous THE (45 mL) at 0° C. under an argon atmosphere was added lithium aluminum hydride (1.8 g, 48 mmol) in portions. The reaction was stirred at 0° C. for additional 10 min, slowly warmed to room temperature, and heated to 60° C. for 1 h. The reaction was then cooled to room temperature and quenched with aqueous sodium sulfate solution slowly. The mixture was filtered through a pad of Celite®, washed with ethyl acetate, and concentrated in vacuo. The residue was triturated with DCM to afford the product. ((1s,3s)-3-(5,7-difluoro-2-(4-fluorophenyl)-1H-indol-3-yl)cyclobutyl)methanamine (3 g, 95%). H NMR (400 MHz, DMSO-$d_6$) δ 11.62 (s, 1H), 7.57 (dd, J=8.5, 5.5 Hz, 2H), 7.46 (dd, J=10.0, 2.2 Hz, 1H), 7.34 (t, J=8.7 Hz, 2H), 7.01-6.91 (m, 1H), 3.59 (q, J=9.6, 8.9 Hz, 1H), 2.56-2.50 (m, 2H), 2.3-2.22 (m, 3H), 2.02-1.97 (m, 2H). LCMS m/z 331.0 $[M+H]^+$.

Preparation S12

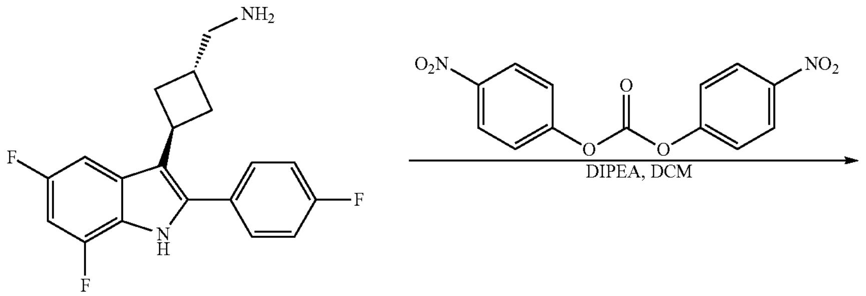

S10

-continued

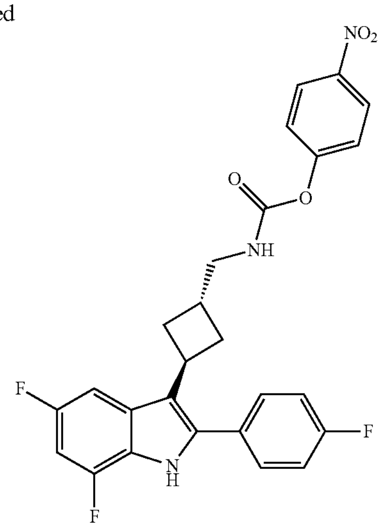

S12

Preparation of 4-nitrophenyl (((1r,3r)-3-(5,7-difluoro-2-(4-fluorophenyl)-1H-indol-3-yl)cyclo-butyl) methyl)carbamate (S12)

To a solution of bis(4-nitrophenyl) carbonate (2.2 g, 7.3 mmol) in DCM (40 mL) was added DIPEA (2 mL, 10 mmol) followed by a solution of ((1r,3r)-3-(5,7-difluoro-2-(4-fluorophenyl)-1H-indol-3-yl)cyclobutyl)methanamine S10 (1.89 g, 5.72 mmol) in DCM (5 mL). The reaction mixture was stirred at room temperature for 1 h then diluted with water and extracted with EtOAc. The organic layer was dried over sodium sulfate, filtered, and concentrated in vacuo to afford the product. (((1r,3r)-3-(5,7-Difluoro-2-(4-fluorophenyl)-1H-indol-3-yl)cyclobutyl)-methyl)carbamate (2.3 g, 81%). LCMS m/z 496.22 [M+H]$^+$.

Preparation S13

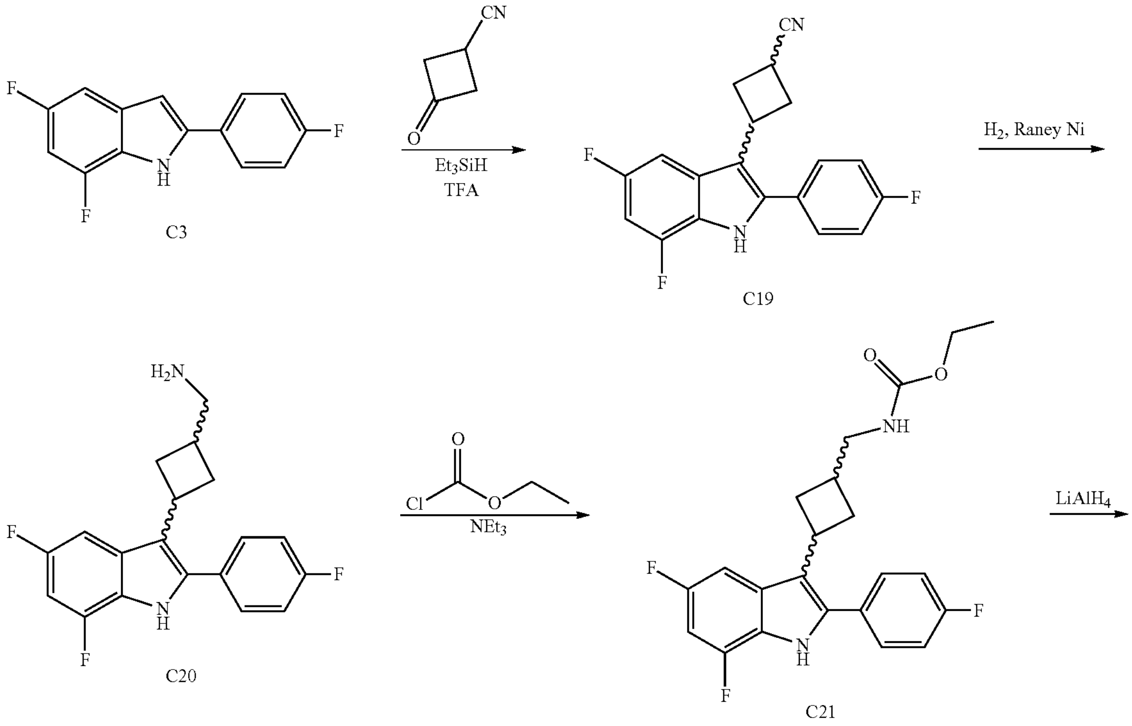

-continued

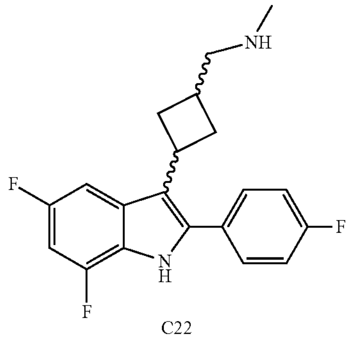

C22

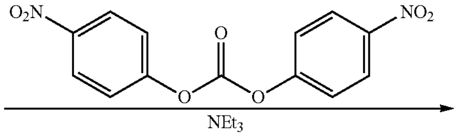

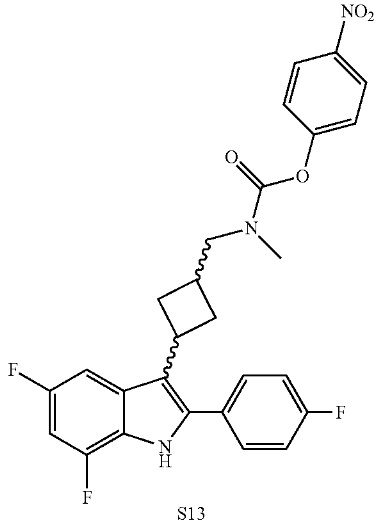

S13

Step 1. Synthesis of 3-(5,7-difluoro-2-(4-fluorophenyl)-1H-indol-3-yl)cyclobutane-1-carbonitrile (C9)

To a solution of 5,7-difluoro-2-(4-fluorophenyl)-1H-indole C3 (200 mg, 0.81 mmol) and 3-oxocyclobutanecarbonitrile (100 mg, 1.1 mmol) in DCM (10 mL) was added $Et_3SiH$ (800 mg, 6.9 mmol), followed by trifluoroacetic acid (600 mg, 5.3 mmol). The mixture was stirred overnight and partitioned between saturated aqueous sodium bicarbonate solution and ethyl acetate. The organic layer was separated, washed with brine, dried over sodium sulfate, filtered, and concentrated in vacuo to afford the product. 3-(5,7-Difluoro-2-(4-fluorophenyl)-1H-indol-3-yl)cyclobutane-1-carbonitrile (220 mg, 55%). $^1H$ NMR (300 MHz, DMSO-$d_6$) δ 11.81 (s, 1H), 7.73-7.47 (m, 2H), 7.47-7.23 (m, 3H), 7.14-6.90 (m, 1H), 3.82 (tt, J=10.2, 8.2 Hz, 1H), 3.36-3.22 (m, 1H), 2.86-2.66 (m, 2H), 2.57 (ddd, J=11.8, 9.0, 2.3 Hz, 2H). LCMS m/z 327.08 $[M+H]^+$.

Step 2. Synthesis of (3-(5,7-difluoro-2-(4-fluorophenyl)-1H-indol-3-yl)cyclobutyl)methanamine (C20)

To a suspension of Raney Ni (50 mg, 0.9 mmol) in methanol (50 mL) was added 3-[5,7-difluoro-2-(4-fluorophenyl)-1H-indol-3-yl]cyclobutanecarbonitrile C19 (2.5 g, 4.7 mmol), followed by ammonia solution (400 mL, 7 M in methanol). The mixture was stirred at room temperature for 2 days under hydrogen atmosphere (60 psi). The mixture was filtered, and the filtrate was concentrated in vacuo to afford the product. (3-(5,7-Difluoro-2-(4-fluorophenyl)-1H-indol-3-yl)cyclobutyl)methanamine (1.2 g, 77%). $^1H$ NMR (300 MHz, Methanol-$d_4$) δ 6.25 (ddd, J=8.6, 5.4, 2.7 Hz, 2H), 6.01-5.85 (m, 3H), 5.46 (ddd, J=11.4, 9.7, 2.1 Hz, 1H), 2.52 (dq, J=10.2, 7.7 Hz, 1H), 1.69 (d, J=6.1 Hz, 2H), 1.28 (td, J=7.3, 3.9 Hz, 3H), 0.88-0.69 (m, 2H). LCMS m/z 331.37 $[M+H]^+$.

Step 3. Synthesis of ethyl ((3-(5,7-difluoro-2-(4-fluorophenyl)-1H-indol-3-yl)cyclobutyl)methyl) carbamate (C21)

To a solution of (3-(5,7-difluoro-2-(4-fluorophenyl)-1H-indol-3-yl)cyclobutyl)-methanamine C20 (423 mg, 1.06 mmol) and ethyl chloroformate (0.135 mL, 1.41 mmol) in DCM (6 mL) was added $Et_3N$ (0.450 mL, 3.23 mmol). The reaction mixture was stirred at room temperature for 2 h then diluted with water. The aqueous layer was extracted with DCM, then the combined organics were washed successively with water and brine, dried over sodium sulfate, filtered, and concentrated in vacuo. The crude product was purified by silica gel chromatography (Gradient: 0-100% EtOAc in hexanes) to afford the product. Ethyl ((3-(5,7-difluoro-2-(4-fluorophenyl)-1H-indol-3-yl)cyclobutyl) methyl)carbamate (315 mg, 70%). LCMS m/z 403.42 $[M+H]^+$.

Step 4. Synthesis of 1-(3-(5,7-difluoro-2-(4-fluorophenyl)-1H-indol-3-yl)cyclobutyl)-N-methylmethanamine (C22)

To a solution of ethyl ((3-(5,7-difluoro-2-(4-fluorophenyl)-1H-indol-3-yl)cyclobutyl)methyl)carbamate C21 (309 mg, 0.73 mmol) in THF (4 mL) at 0° C. was added $LiAlH_4$ (1.3 mL, 2.99 mmol, 2.3 M in 2-methyltetrahydrofuran). The reaction mixture was warmed to room temperature and stirred for 2 h, then quenched with an aqueous solution of Rochelle's salt and extracted with EtOAc. The organic layer was washed successively with water and brine, dried over sodium sulfate, filtered, and concentrated in vacuo to afford the product. 1-(3-(5,7-Difluoro-2-(4-fluorophenyl)-1H-indol-3-yl)cyclobutyl)-N-methylmethanamine (219 mg, 73%). LCMS m/z 344.92 $[M+H]^+$.

Step 5. Synthesis of 4-nitrophenyl ((3-(5,7-difluoro-2-(4-fluorophenyl)-1H-indol-3-yl)cyclobutyl)methyl)(methyl)carbamate (S13)

To a solution of bis(4-nitrophenyl) carbonate (308 mg, 1.01 mmol) in DCM (5 mL) was added $Et_3N$ (295 μL, 2.12 mmol) followed by a solution of 1-(3-(5,7-difluoro-2-(4-fluorophenyl)-1H-indol-3-yl)cyclobutyl)-N-methylmethanamine C22 (290 mg, 0.84 mmol) in DCM (5 mL). The reaction mixture was stirred at room temperature for 1 h then partitioned between water and EtOAc. The organic layer was dried over sodium sulfate, filtered, and concentrated in vacuo to afford the product. 4-Nitrophenyl ((3-(5,7-difluoro-2-(4-fluorophenyl)-1H-indol-3-yl)cyclobutyl)methyl)(methyl)carbamate (266 mg, 62%). LCMS m/z 510.24 $[M+H]^+$.

Preparation S4

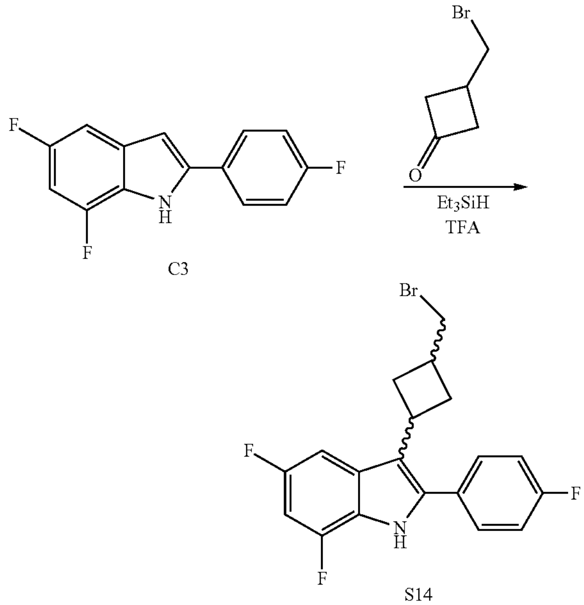

C3

S14

Preparation of 3-(3-(bromomethyl)cyclobutyl)-5,7-difluoro-2-(4-fluorophenyl)-1H-indole (S14)

To a solution of 5,7-difluoro-2-(4-fluorophenyl)-1H-indole C3 (380 mg, 1.5 mmol) in DCM (5 mL) was added 3-(bromomethyl)cyclobutanone (250 mg, 1.5 mmol), $Et_3SiH$ (900 mg, 7.7 mmol), and TFA (525 mg, 4.60 mmol). The reaction mixture was allowed to stir overnight at ambient temperature. The reaction mixture was then diluted with EtOAc (~100 mL) and then washed with saturated aqueous $NaHCO_3$. The organic layer was washed with brine, dried over anhydrous $Na_2SO_4$, filtered through Celite®, and concentrated in vacuo. The residue was purified by silica gel chromatography (Gradient: 0-40% EtOAc in hexanes) to afford the product. 3-(3-(Bromomethyl)cyclobutyl)-5,7-difluoro-2-(4-fluorophenyl)-1H-indole (504 mg, 34%). LCMS m/z 394.38 $[M+H]^+$.

Preparation S15

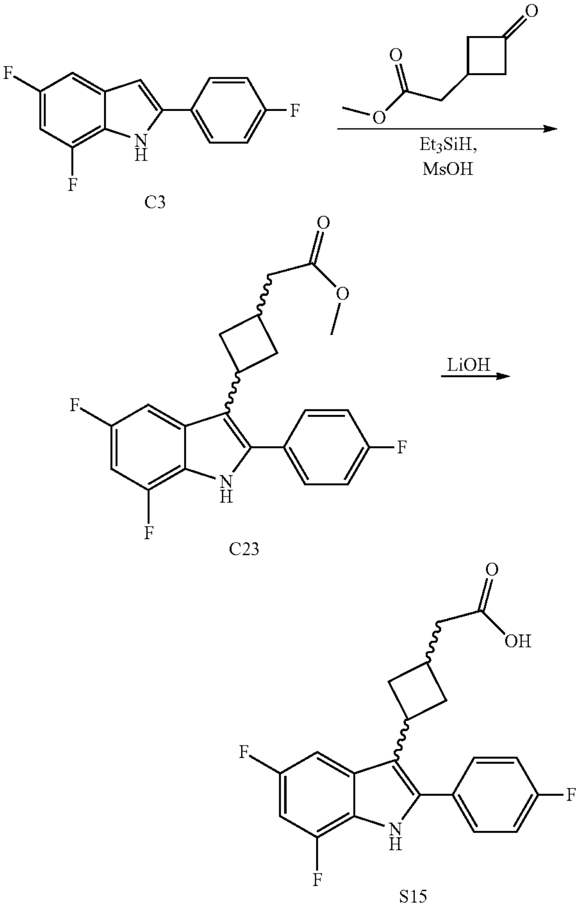

C3

C23

S15

Step 1. Synthesis of methyl 2-(3-(5,7-difluoro-2-(4-fluorophenyl)-1H-indol-3-yl)cyclobutyl)acetate (C23)

To a solution of 5,7-difluoro-2-(4-fluorophenyl)-1H-indole C3 (460 mg, 1.9 mmol) and methyl 2-(3-oxocyclobutyl)acetate (291 mg, 2.05 mmol) in DCE (5 mL) was added triethylsilane (1.2 mL, 7.5 mmol) followed by methanesulfonic acid (365 μL, 5.63 mmol) at 70° C. The mixture was heated at 70° C. for 2 h, and additional methyl 2-(3-oxocyclobutyl)acetate (291 mg, 2.05 mmol) was added. The mixture was stirred at 70° C. for additional 2 h. After cooling to room temperature, the mixture was diluted with DCM (80 mL) and washed with saturated aqueous sodium carbonate solution and brine. The organic layer was separated and concentrated in vacuo. The residue was purified by silica gel chromatography (Gradient: 0-10% EtOAc in hexanes) to afford the product. Methyl 2-(3-(5,7-difluoro-2-(4-fluorophenyl)-1H-indol-3-yl)cyclobutyl)acetate (450.7 mg, 65%). LCMS m/z 374.19 $[M+H]^+$.

Step 2. Synthesis of 2-(3-(5,7-difluoro-2-(4-fluorophenyl)-1H-indol-3-yl)cyclobutyl)acetic acid (S15)

To a solution of methyl 2-[3-[5,7-difluoro-2-(4-fluorophenyl)-1H-indol-3-yl]cyclobutyl]acetate C23 (488 mg, 1.30 mmol) in THE (10 mL) was added saturated aqueous LiOH (5 mL). The mixture was then warmed to 50° C. and allowed to stir overnight. The mixture was then allowed to cool to ambient temperature and concentrated in vacuo. The resulting residue was then diluted with DCM (50 mL) and acidified to pH 3 with 10% HCl, and the aqueous layer was extracted with DCM (3x25 mL). The combined organic phase was washed with brine, dried with anhydrous $MgSO_4$, filtered, and concentrated in vacuo to afford the product. 2-(3-(5,7-Difluoro-2-(4-fluorophenyl)-1H-indol-3-yl)cyclobutyl)acetic acid (508 mg, quantitative). $^1H$ NMR (300 MHz, Chloroform-d) δ 8.05 (s, 1H), 7.57-7.39 (m, 2H), 7.29-7.16 (m, 4H), 6.87-6.64 (m, 1H), 3.86-3.72 (m, 2H), 2.80-2.47 (m, 3H), 2.06 (q, J=10.8, 9.2 Hz, 1H), 1.88 (td, J=5.7, 4.9, 3.1 Hz, 2H). LCMS m/z 360.19 $[M+H]^+$.

Preparation S16

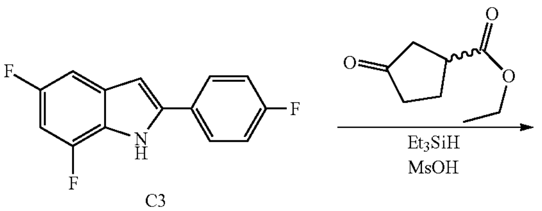

C3

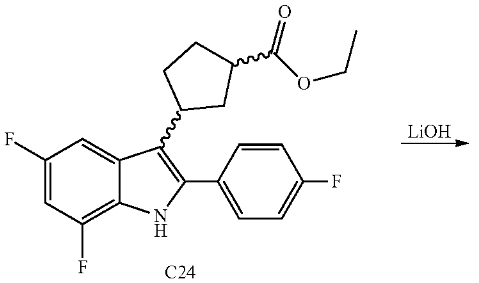

C24

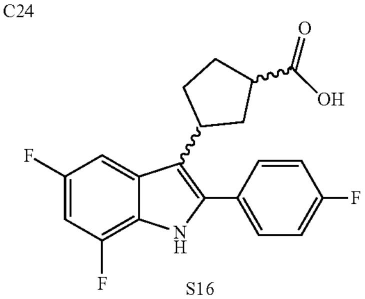

S16

Step 1. Synthesis of ethyl 3-[5,7-difluoro-2-(4-fluorophenyl)-1H-indol-3-yl]cyclopentanecarboxylate (C24)

To a solution of 5,7-difluoro-2-(4-fluorophenyl)-1H-indole C3 (501 mg, 1.89 mmol) and ethyl 3-oxocyclopentanecarboxylate (390 mg, 2.5 mmol) in DCE (8 mL) at 70° C.

was added methanesulfonic acid (201 μL, 3.10 mmol), triethylsilane (1 mL, 6 mmol). The mixture was heated to 180° C. for 1 h. Then, additional ethyl 3-oxocyclopentanecarboxylate (390 mg, 2.5 mmol), methanesulfonic acid (201 μL, 3.10 mmol), and triethylsilane (1 mL, 6 mmol) were added, and the mixture was stirred at 90° C. for 3 days. Water (100 mL) was added to the mixture, and the aqueous layer was extracted with DCM (3x70 mL). Purification by silica gel chromatography (Gradient: 0-100% EtOAc in heptane) afforded the product. Ethyl 3-[5,7-difluoro-2-(4-fluorophenyl)-1H-indol-3-yl]cyclopentanecarboxylate (300 mg, 40%). $^1H$ NMR (300 MHz, Chloroform-d) δ 8.13 (s, 1H), 7.61-7.42 (m, 2H), 7.36-7.01 (m, 3H), 6.76 (ddd, J 10.8, 9.4, 2.1 Hz, 1H), 5.97-5.20 (m, 1H), 4.24-4.06 (m, 2H), 3.61-3.30 (m, 1H), 3.23-2.91 (m, 1H), 2.25 (ddt, J=15.2, 6.5, 2.7 Hz, 2H), 2.13-2.01 (m, 3H), 1.36-1.27 (m, 3H). LCMS m/z 388.1 $[M+H]^+$.

Step 2. Synthesis of 3-[5,7-difluoro-2-(4-fluorophenyl)-1H-indol-3-yl]cyclopentanecarboxylic acid (S16)

A solution of ethyl 3-[5,7-difluoro-2-(4-fluorophenyl)-1H-indol-3-yl]cyclopentanecarboxylate C24 (290 mg, 0.74 mmol) and LiOH (360 mg, 15 mmol) in MeOH (3 mL), THE (4 mL), and water (4 mL) was heated to 50° C. overnight. The mixture was concentrated in vacuo. Water (30 mL) was added to the residue, followed by HCl to adjust the pH to 1. The mixture was extracted with DCM (3x30 mL), and the combined organic phase was washed with brine and concentrated in vacuo to afford the product. 3-[5,7-Difluoro-2-(4-fluorophenyl)-1H-indol-3-yl]cyclopentanecarboxylic acid (264 mg, 99%). $^1H$ NMR (300 MHz, Chloroform-d) δ 8.04 (s, 1H), 7.61-7.38 (m, 2H), 7.27-7.06 (m, 3H), 6.76 (dddd, J=10.6, 9.3, 2.1, 1.0 Hz, 1H), 3.57-3.33 (m, 1H), 3.30-2.95 (m, 1H), 2.55-1.83 (m, 6H). LCMS m/z 360.07 $[M+H]^+$.

Preparation S17

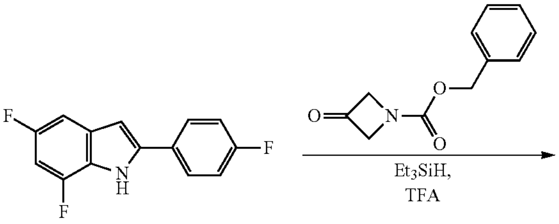

C3

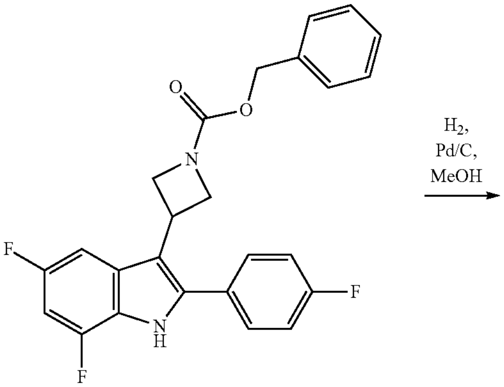

C25

-continued

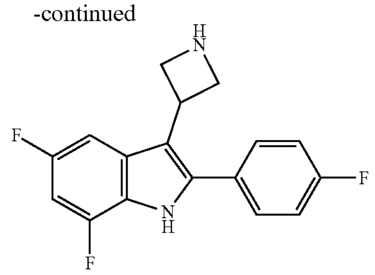

S17

Step 1. Synthesis of benzyl 3-(5,7-difluoro-2-(4-fluorophenyl)-1H-indol-3-yl)azetidine-1-carboxylate (C25)

To a solution of 5,7-difluoro-2-(4-fluorophenyl)-1H-indole C3 (500 mg, 1.35 mmol) and benzyl 3-oxoazetidine-1-carboxylate (277 mg, 1.35 mmol) in DCM (15 mL) was added $Et_3SiH$ (470 mg, 4.0 mmol), and TFA (310 mg, 2.71 mmol). The reaction mixture was allowed to stir overnight at ambient temperature and then concentrated in vacuo. The residue was dissolved in EtOAc (~50 mL) and washed with saturated aqueous $NaHCO_3$. The organic layer was separated, dried with anhydrous $MgSO_4$, filtered, and concentrated in vacuo. The residue was purified by silica gel chromatography (Gradient: 0-100% EtOAc in heptane) to afford the product. Benzyl 3-(5,7-difluoro-2-(4-fluorophenyl)-1H-indol-3-yl)azetidine-1-carboxylate (536 mg, 84%). LCMS m/z 524.04 $[M+H]^+$.

Step 2. Synthesis of 3-(azetidin-3-yl)-5,7-difluoro-2-(4-fluorophenyl)-1H-indole (S17)

A mixture of 10 wt % Pd/C (20 mg) in MeOH (10 mL) and benzyl 3-[5,7-difluoro-2-(4-fluorophenyl)-1H-indol-3-yl]azetidine-1-carboxylate C25 (500 mg, 1.1 mmol) in MeOH (20 mL) was placed under an atmosphere of hydrogen. The resulting mixture was stirred at ambient temperature for 3 h. The mixture was filtered through Celite® and concentrated in vacuo. The residue was purified by reversed-phase chromatography (C18 column; Gradient: MeCN in $H_2O$ with 0.1% trifluoroacetic acid) to afford the product. 3-(Azetidin-3-yl)-5,7-difluoro-2-(4-fluorophenyl)-1H-indole (380 mg, 81%). $^1H$ NMR (300 MHz, Methanol-$d_4$) δ 7.63-7.48 (m, 2H), 7.41 (dd, J=9.5, 2.1 Hz, 1H), 7.37-7.18 (m, 2H), 6.85 (ddd, J=11.0, 9.6, 2.1 Hz, 1H), 4.70-4.52 (m, 1H), 4.45 (dd, J=11.0, 9.1 Hz, 2H), 4.36-4.17 (m, 2H). LCMS m/z 303.26 $[M+H]^+$.

Compound 287

3-[[3-[5,7-difluoro-2-(4-fluorophenyl)-1H-indol-3-yl]cyclobutyl]amino]propanamide (287)

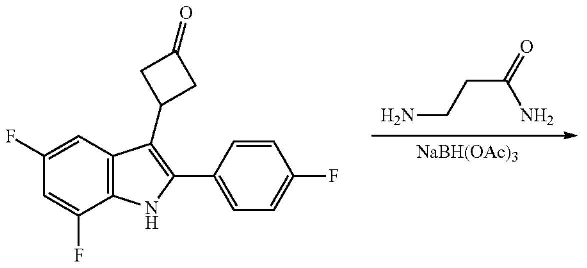

S5

-continued

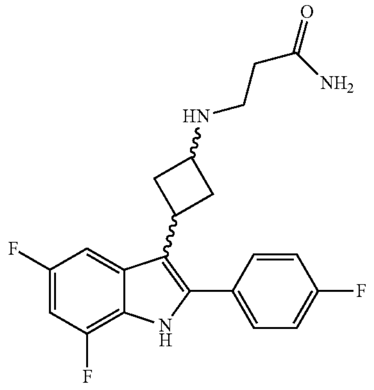

287

Preparation of 3-[[3-[5,7-difluoro-2-(4-fluorophenyl)-1H-indol-3-yl]cyclobutyl]amino]propanamide (287)

To a solution of 3-aminopropanamide (14 mg, 0.11 mmol) and 3-[5,7-difluoro-2-(4-fluorophenyl)-1H-indol-3-yl]cyclobutanone S5 (30 mg, 0.1 mmol) in DMF (2.5 mL) was added triacetoxy(sodio)boron (24 mg, 0.11 mmol) followed by acetic acid (4 mg, 0.01 mmol) The mixture was allowed to stir at room temperature overnight. The reaction mixture was then filtered, and the filtrate was purified by reversed-phase HPLC (Method: C18 Waters Sunfire column (30×150 mm, 5 micron). Gradient: MeCN in $H_2O$ with 0.1% trifluoroacetic acid) to afford the product. 3-[[3-[5,7-Difluoro-2-(4-fluorophenyl)-1H-indol-3-yl]cyclobutyl]amino]propanamide (12 mg, 25%). LCMS m/z 388.16 $[M+H]^+$.

Compound 288

2-[[3-[5,7-difluoro-2-(4-fluorophenyl)-1H-indol-3-yl]cyclobutyl]amino]acetamide (288)

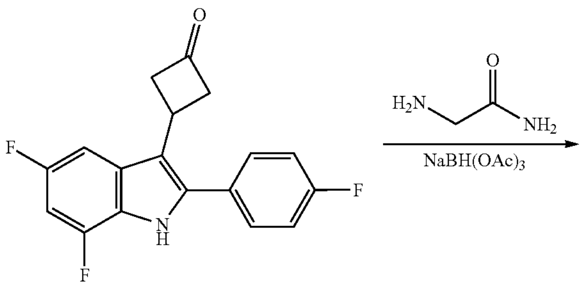

S5

-continued

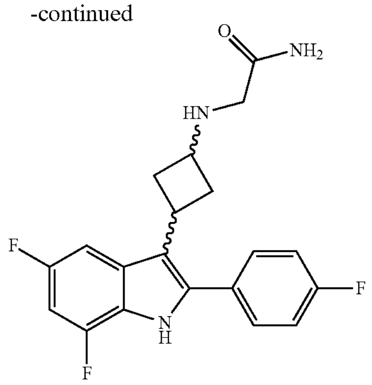

288

Preparation of 2-[[3-[5,7-difluoro-2-(4-fluorophenyl)-1H-indol-3-yl]cyclobutyl]amino]acetamide (288)

To a solution of 2-aminoacetamide (12 mg, 0.11 mmol) and 3-[5,7-difluoro-2-(4-fluorophenyl)-1H-indol-3-yl]cyclobutanone S5 (30 mg, 0.1 mmol) in DMF (2.5 mL) was added triacetoxy(sodio)boron (24 mg, 0.11 mmol) followed by acetic acid (4 mg, 0.01 mmol) The mixture was allowed to stir at room temperature overnight. The reaction mixture was then filtered, and the filtrate was purified by reversed-phase HPLC (Method: C18 Waters Sunfire column (30×150 mm, 5 micron). Gradient: MeCN in $H_2O$ with 0.1% trifluoroacetic acid) to afford the product. 2-[[3-[5,7-Difluoro-2-(4-fluorophenyl)-1H-indol-3-yl]cyclobutyl]amino]acetamide (9 mg, 19%). LCMS m/z 374.15 $[M+H]^+$.

Compound 289

N-[3-[5,7-difluoro-2-(4-fluorophenyl)-1H-indol-3-yl]cyclobutyl]-2-hydroxy-acetamide (289)

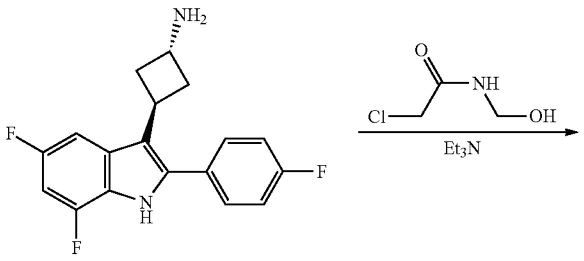

S6

-continued

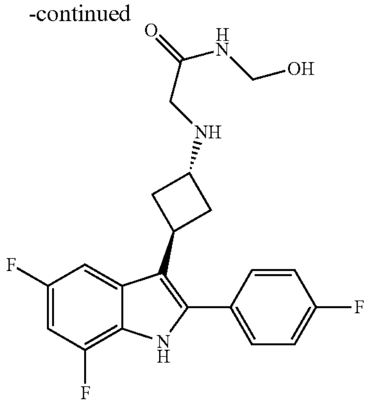

289

Preparation of N-[3-[5,7-difluoro-2-(4-fluorophenyl)-1H-indol-3-yl]cyclobutyl]-2-hydroxy-acetamide (289)

Standard Procedure B: N-Alkylation Method

To a solution of 3-[5,7-difluoro-2-(4-fluorophenyl)-1H-indol-3-yl]cyclobutanamine S6 (50 mg, 0.16 mmol) in DMF (2 mL) was added 2-chloro-N-(hydroxymethyl)acetamide (29 mg, 0.24 mmol) followed by $Et_3N$ (32 mg, 44 μL, 0.32 mmol). The reaction mixture was stirred at room temperature overnight. Purification by reversed-phase HPLC (Method: C18 Waters Sunfire column (30×150 mm, 5 micron). Gradient: MeCN in $H_2O$ with 0.1% trifluoroacetic acid) afforded the product. N-[3-[5,7-difluoro-2-(4-fluorophenyl)-1H-indol-3-yl]cyclobutyl]-2-hydroxy-acetamide (3.8 mg, 4.6%). LCMS m/z 404.18 $[M+H]^+$.

Compounds 290-294

Compounds 290-294 (see Table 13) were prepared in a single step from compound S6 using standard method described for the synthesis of compound 289. Alkyl halides were obtained from commercial sources. Any modifications to methods are noted in Table 13 and accompanying footnotes.

TABLE 13
| Structure and physiochemical data for compounds 290-294 | | | |
|---|---|---|---|
| Cmpound | Product | Alkyl halide | $^1$H NMR; LCMS m/z $[M + H]^+$ |
| 290 | 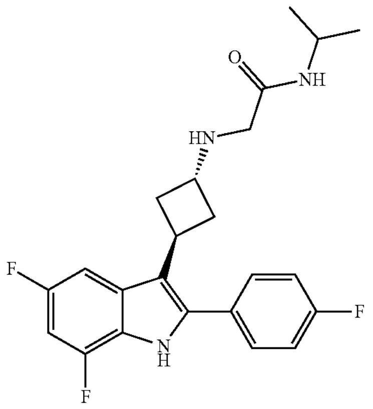 [SMILES: CC(C)NC(=O)CN[C@H]1C[C@H](c2c(-c3ccc(F)cc3)[nH]c3c(F)cc(F)cc32)C1] | 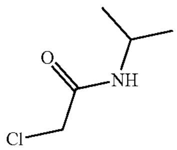 | LCMS m/z 416.2 $[M + H]^+$ |
| 291 | 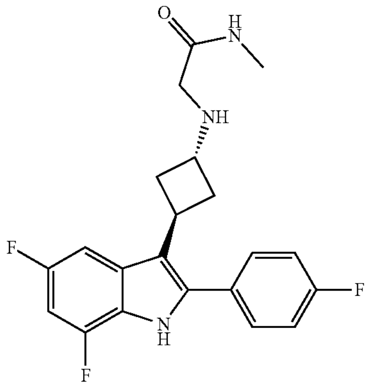 [SMILES: CNC(=O)CN[C@H]1C[C@H](c2c(-c3ccc(F)cc3)[nH]c3c(F)cc(F)cc32)C1] | 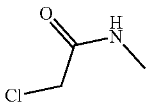 | LCMS m/z 388.16 $[M + H]^+$ |
| 292 | 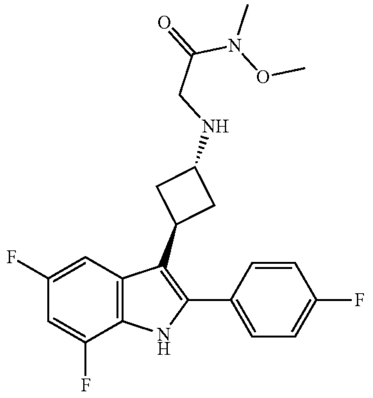 [SMILES: CON(C)C(=O)CN[C@H]1C[C@H](c2c(-c3ccc(F)cc3)[nH]c3c(F)cc(F)cc32)C1] | 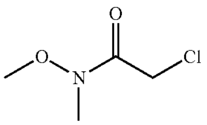 | LCMS m/z 418.19 $[M + H]^+$ |

TABLE 13-continued

| Structure and physiochemical data for compounds 290-294 | | | |
|---|---|---|---|
| Cmpound | Product | Alkyl halide | $^1$H NMR; LCMS m/z [M + H]$^+$ |
| 293 | 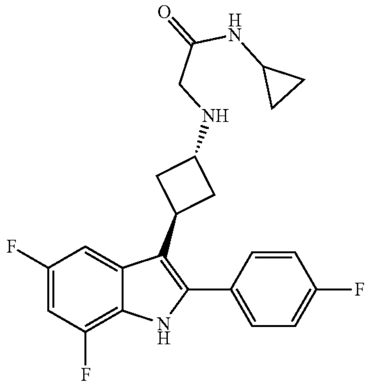 [SMILES: O=C(CN[C@H]1C[C@H](c2c(-c3ccc(F)cc3)[nH]c3c(F)cc(F)cc32)C1)NC1CC1] | 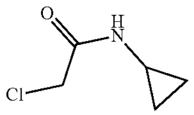 | LCMS m/z 414.31 [M + H]$^+$ |
| 294 | 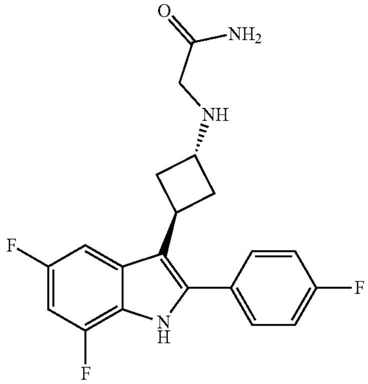 [SMILES: NC(=O)CN[C@H]1C[C@H](c2c(-c3ccc(F)cc3)[nH]c3c(F)cc(F)cc32)C1] | 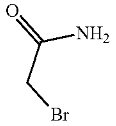 | LCMS m/z 374.18 [M + H]$^+$ |

Compound 295

1-((1r,3S)-3-(5,7-difluoro-2-(4-fluorophenyl)-1H-indol-3-yl)cyclobutyl)-3-((S)-1-hydroxypropan-2-yl) urea (295)

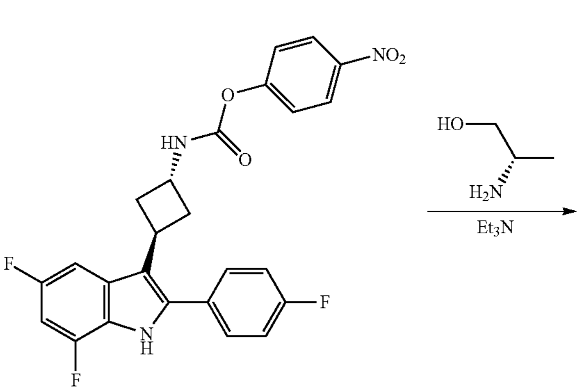

S7

-continued

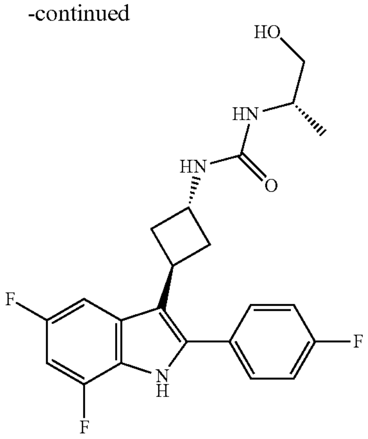

295

Preparation of 1-((1r,3S)-3-(5,7-difluoro-2-(4-fluorophenyl)-1H-indol-3-yl)cyclobutyl)-3-((S)-1-hydroxypropan-2-yl)urea (295)

Standard procedure C: Urea Formation

To a solution of (4-nitrophenyl) N-[3-[5,7-difluoro-2-(4-fluorophenyl)-1H-indol-3-yl]cyclobutyl]carbamate S7 (50 mg, 0.1 mmol) in DMF (2 mL) was added (2S)-2-aminopropan-1-ol (7.8 mg, 0.1039 mmol) followed by $Et_3N$ (10.5 mg, 14.5 μL, 0.104 mmol). The reaction mixture was stirred at room temperature overnight. Purification by reversed-phase HPLC (Method: C18 Waters Sunfire column (30×150 mm, 5 micron). Gradient: MeCN in $H_2O$ with 0.1% trifluoroacetic acid) afforded the product. 1-((1r,3S)-3-(5,7-Difluoro-2-(4-fluorophenyl)-1H-indol-3-yl)cyclobutyl)-3-((S)-1-hydroxypropan-2-yl)urea (19.7 mg, 36%). LCMS m/z 418.15 $[M+H]^+$.

Compounds 296-298

Compounds 296-298 (see Table 14) were prepared in a single step from intermediate S7 using standard method described for the synthesis of compound 295. Amines were obtained from commercial sources. Any modifications to methods are noted in Table 14 and accompanying footnotes.

TABLE 14

Structure and physicochemical data for compounds 296-298

| Cmpound | Product | Amine | $^1H$ NMR; LCMS m/z $[M + H]^+$ |
|---|---|---|---|
| 296 | 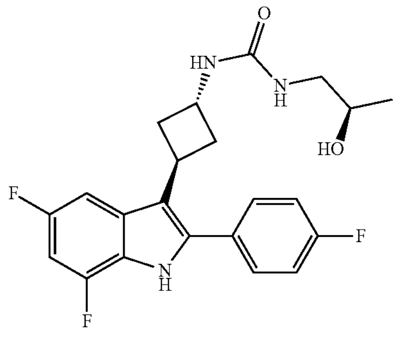 [SMILES: C[C@@H](O)CNC(=O)N[C@H]1C[C@H](c2c(-c3ccc(F)cc3)[nH]c3c(F)cc(F)cc32)C1] | 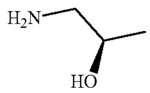 | LCMS m/z 418.15 $[M + H]^+$ |
| 297 | 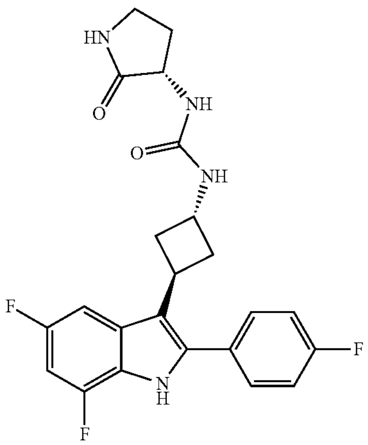 [SMILES: O=C(N[C@H]1CCNC1=O)N[C@H]1C[C@H](c2c(-c3ccc(F)cc3)[nH]c3c(F)cc(F)cc32)C1] | 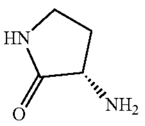 | LCMS m/z 443.14 $[M + H]^+$ |
| 298 | 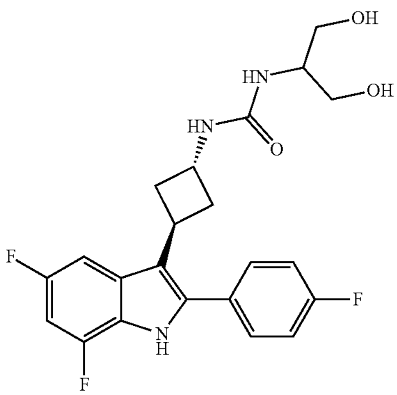 [SMILES: O=C(NC(CO)CO)N[C@H]1C[C@H](c2c(-c3ccc(F)cc3)[nH]c3c(F)cc(F)cc32)C1] | 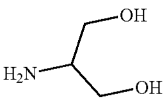 | LCMS m/z 434.15 $[M + H]^+$ |

Compound 299

3-[[5,7-difluoro-2-(4-fluorophenyl)-1H-indol-3-yl] methyl]-N-(2-hydroxyethyl)cyclobutane-1-carboxamide (299)

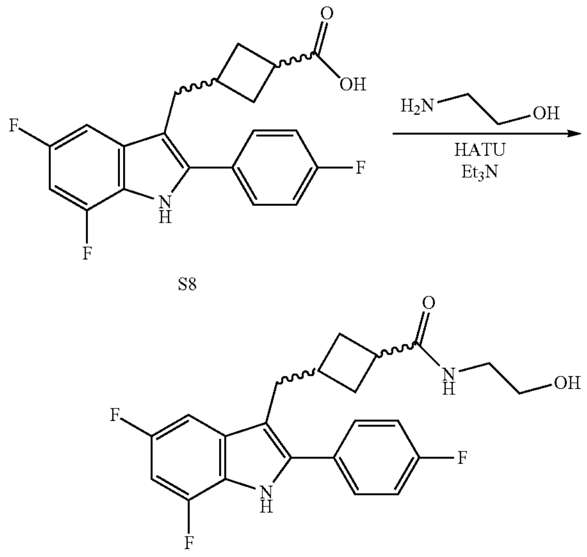

S8

299

Preparation of 3-[[5,7-difluoro-2-(4-fluorophenyl)-1H-indol-3-yl]methyl]-N-(2-hydroxyethyl)-cyclobutane-1-carboxamide (299)

Standard procedure D: Amide Coupling with HATU

To a solution of 3-[[5,7-difluoro-2-(4-fluorophenyl)-1H-indol-3-yl]methyl]cyclobutanecarboxylic acid S8 (30 mg, 0.08 mmol) and 2-aminoethanol (6.6 mg, 0.11 mmol) in DMF (2 mL) was added HATU (38 mg, 0.10 mmol), followed by $Et_3N$ (16.9 mg, 0.167 mmol). The reaction mixture was stirred at room temperature overnight. The reaction mixture was filtered. Purification by reversed-phase HPLC (Method: C18 Waters Sunfire column (30×150 mm, 5 micron). Gradient: MeCN in $H_2O$ with 0.1% trifluoroacetic acid) afforded the product. 3-[[5,7-Difluoro-2-(4-fluorophenyl)-1H-indol-3-yl]methyl]-N-(2-hydroxyethyl) cyclobutane-1-carboxamide (2.2 mg, 5.1%). LCMS m/z 403.17 $[M+H]^+$.

Compounds 300-348

Compounds 300-348 (see Table 15) were prepared in a single step from intermediate S8 using standard method described for the synthesis of compound 299. Amines were obtained from commercial sources. Any modifications to methods are noted in Table 15 and accompanying footnotes.

TABLE 15

Structure and physicochemical data for compounds 300-348

| Cmpound | Product | Amine | $^1H$ NMR; LCMS m/z $[M + H]^+$ |
|---|---|---|---|
| 300 | 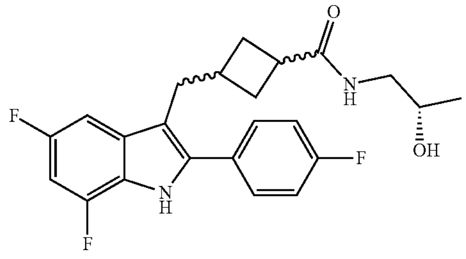 [SMILES: C[C@H](O)CNC(=O)C1CC(Cc2c(-c3ccc(F)cc3)[nH]c3c(F)cc(F)cc23)C1] | 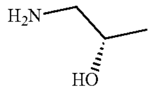 | LCMS m/z 417.18 $[M + H]^+$ |
| 301 | 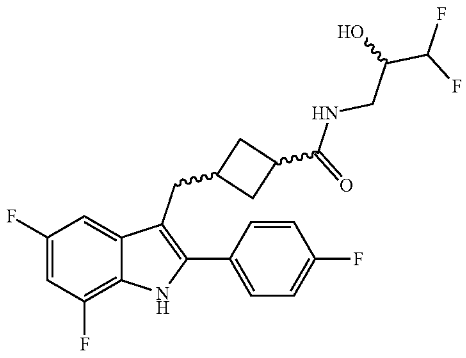 [SMILES: O=C(NCC(O)C(F)F)C1CC(Cc2c(-c3ccc(F)cc3)[nH]c3c(F)cc(F)cc23)C1] | 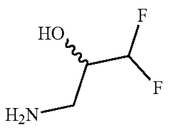 | LCMS m/z 453.14 $[M + H]^+$ |

TABLE 15-continued
| Structure and physicochemical data for compounds 300-348 | | | |
|---|---|---|---|
| Cmpound | Product | Amine | $^1$H NMR; LCMS m/z $[M + H]^+$ |
| 302 | 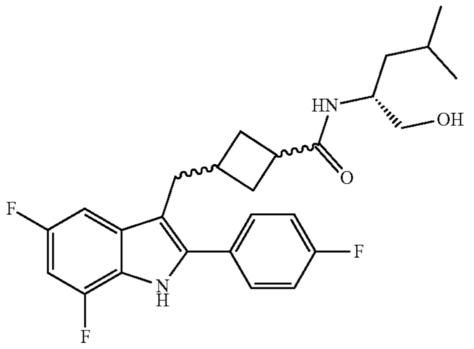 [SMILES: CC(C)C[C@H](CO)NC(=O)C1CC(Cc2c(-c3ccc(F)cc3)[nH]c3c(F)cc(F)cc23)C1] | 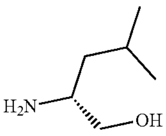 | LCMS m/z 459.17 $[M + H]^+$ |
| 303 | 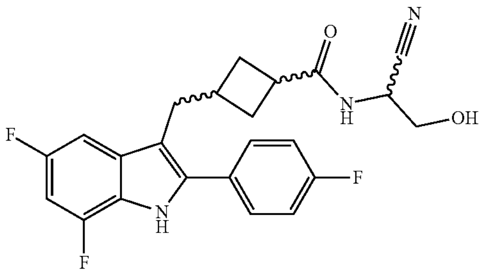 [SMILES: N#CC(CO)NC(=O)C1CC(Cc2c(-c3ccc(F)cc3)[nH]c3c(F)cc(F)cc23)C1] | 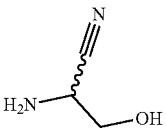 | LCMS m/z 428.16 $[M + H]^+$ |
| 304 | 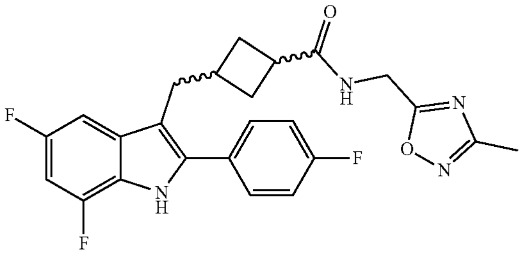 [SMILES: Cc1noc(CNC(=O)C2CC(Cc3c(-c4ccc(F)cc4)[nH]c4c(F)cc(F)cc34)C2)n1] | 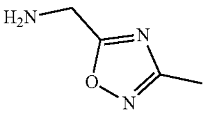 | LCMS m/z 455.16 $[M + H]^+$ |
| 305 | 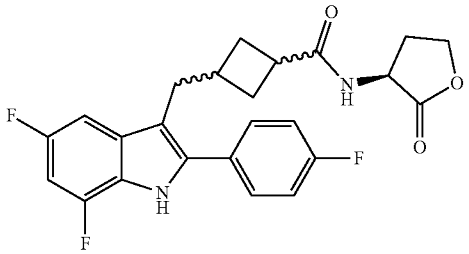 [SMILES: O=C(N[C@H]1CCOC1=O)C1CC(Cc2c(-c3ccc(F)cc3)[nH]c3c(F)cc(F)cc23)C1] | 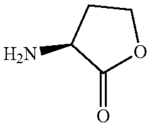 | LCMS m/z 443.11 $[M + H]^+$ |
| 306 | 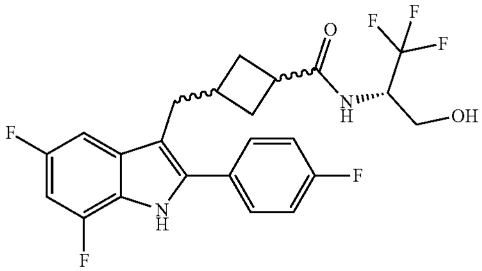 [SMILES: O=C(N[C@@H](CO)C(F)(F)F)C1CC(Cc2c(-c3ccc(F)cc3)[nH]c3c(F)cc(F)cc23)C1] | 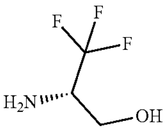 | LCMS m/z 471.25 $[M + H]^+$ |

TABLE 15-continued
| Structure and physicochemical data for compounds 300-348 | | | |
|---|---|---|---|
| Cmpound | Product | Amine | $^1$H NMR; LCMS m/z [M + H]$^+$ |
| 307 | 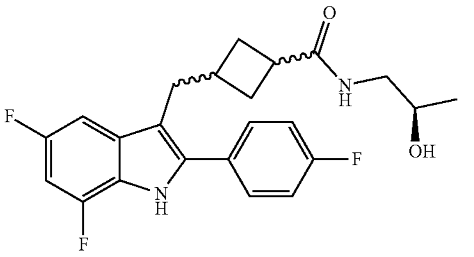 [SMILES: C[C@@H](O)CNC(=O)C1CC(Cc2c(-c3ccc(F)cc3)[nH]c3c(F)cc(F)cc23)C1] | 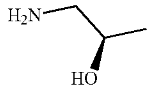 | LCMS m/z 417.18 [M + H]$^+$ |
| 308 | 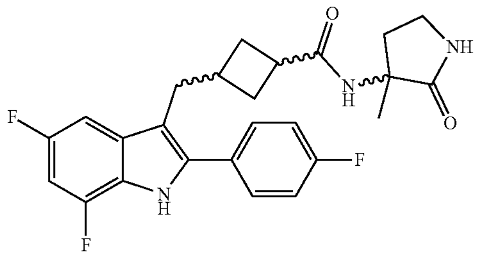 [SMILES: CC1(NC(=O)C2CC(Cc3c(-c4ccc(F)cc4)[nH]c4c(F)cc(F)cc34)C2)CCNC1=O] | 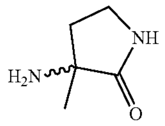 | LCMS m/z 456.17 [M + H]$^+$ |
| 309 | 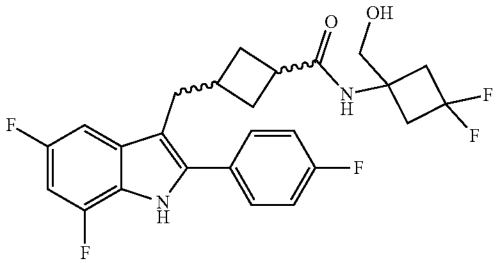 [SMILES: O=C(NC1(CO)CC(F)(F)C1)C1CC(Cc2c(-c3ccc(F)cc3)[nH]c3c(F)cc(F)cc23)C1] | 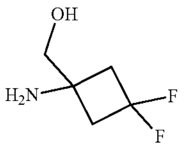 | LCMS m/z 479.17 [M + H]$^+$ |
| 310 | 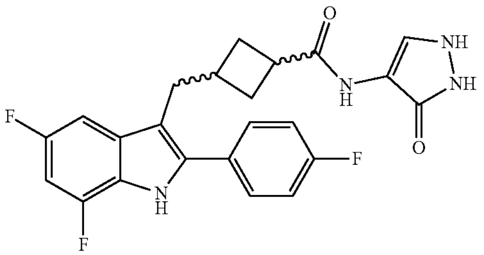 [SMILES: O=C(Nc1c[nH][nH]c1=O)C1CC(Cc2c(-c3ccc(F)cc3)[nH]c3c(F)cc(F)cc23)C1] | 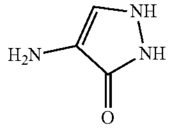 | LCMS m/z 441.12 [M + H]$^+$ |
| 311 | 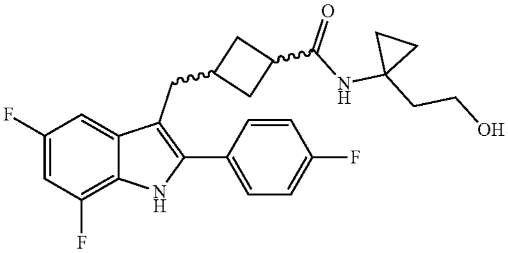 [SMILES: O=C(NC1(CCO)CC1)C1CC(Cc2c(-c3ccc(F)cc3)[nH]c3c(F)cc(F)cc23)C1] | 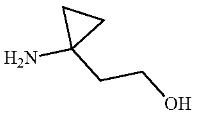 | LCMS m/z 443.18 [M + H]$^+$ |

TABLE 15-continued
Structure and physicochemical data for compounds 300-348
| Cmpound | Product | Amine | $^1$H NMR; LCMS m/z $[M + H]^+$ |
|---|---|---|---|
| 312 | 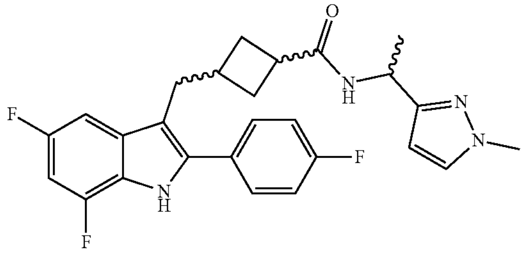 [SMILES: CC(NC(=O)C1CC(Cc2c(-c3ccc(F)cc3)[nH]c3c(F)cc(F)cc23)C1)c1ccn(C)n1] | 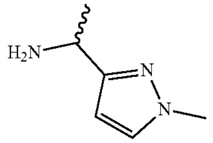 | LCMS m/z 467.18 $[M + H]^+$ |
| 313 | 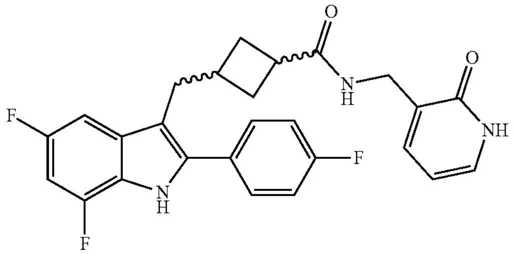 [SMILES: O=C(NCc1ccc[nH]c1=O)C1CC(Cc2c(-c3ccc(F)cc3)[nH]c3c(F)cc(F)cc23)C1] | 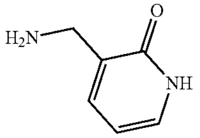 | LCMS m/z 466.14 $[M + H]^+$ |
| 314 | 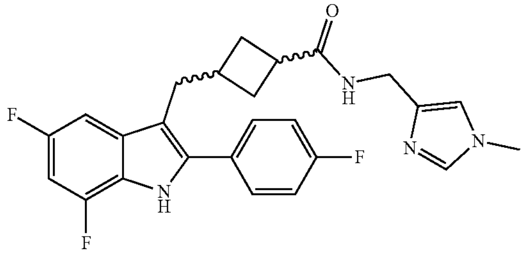 [SMILES: Cn1cnc(CNC(=O)C2CC(Cc3c(-c4ccc(F)cc4)[nH]c4c(F)cc(F)cc34)C2)c1] | 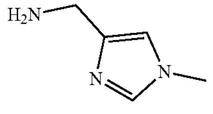 | $^1$H NMR (300 MHz, Acetone-$d_6$) δ 10.71 (s, 1H), 8.92 (s, 1H), 7.91-7.68 (m, 3H), 7.60-7.47 (m, 1H), 7.40-7.11 (m, 3H), 6.83 (ddd, J = 11.0, 9.7, 2.2 Hz, 1H), 4.43 (d, J = 5.6 Hz, 2H), 4.04 (d, J = 6.4 Hz, 3H), 2.94 (d, J = 7.2 Hz, 2H), 2.90-2.79 (m, 1H), 2.54 (tt, J = 9.3, 7.3 Hz, 1H), 2.26-2.08 (m, 2H), 1.90 (qd, J = 9.2, 2.5 Hz, 2H); LCMS m/z 453.14 $[M + H]^+$ |
| 315 | 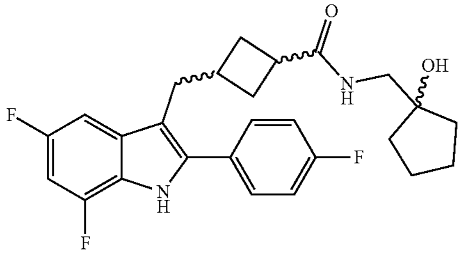 [SMILES: O=C(NCC1(O)CCCC1)C1CC(Cc2c(-c3ccc(F)cc3)[nH]c3c(F)cc(F)cc23)C1] | 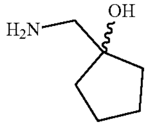 | LCMS m/z 457.33 $[M + H]^+$ |
| 316 | 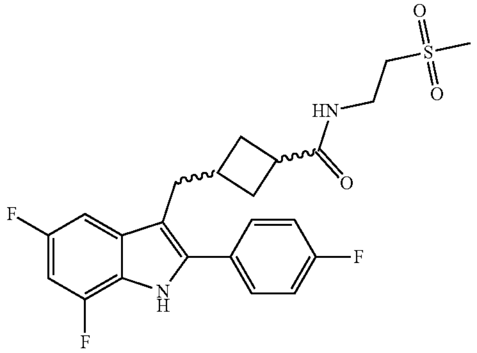 [SMILES: CS(=O)(=O)CCNC(=O)C1CC(Cc2c(-c3ccc(F)cc3)[nH]c3c(F)cc(F)cc23)C1] | 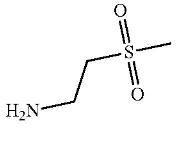 | LCMS m/z 465.13 $[M + H]^+$ |

TABLE 15-continued
| Structure and physicochemical data for compounds 300-348 | | | |
|---|---|---|---|
| Cmpound | Product | Amine | $^1$H NMR; LCMS m/z [M + H]+ |
| 317 | 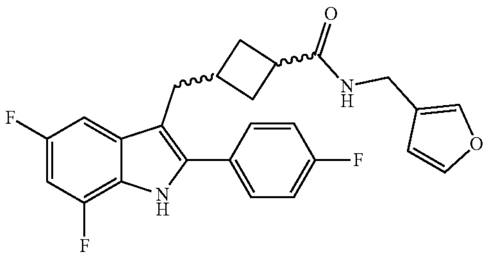 [SMILES: O=C(NCc1ccoc1)C1CC(Cc2c(-c3ccc(F)cc3)[nH]c3c(F)cc(F)cc23)C1] | 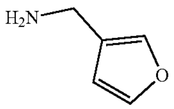 | LCMS m/z 439.14 [M + H]+ |
| 318 | 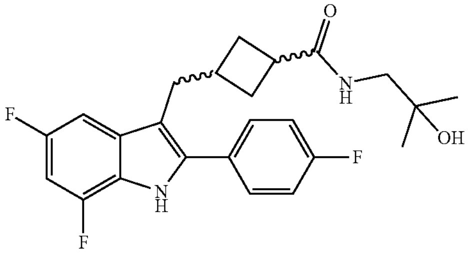 [SMILES: CC(C)(O)CNC(=O)C1CC(Cc2c(-c3ccc(F)cc3)[nH]c3c(F)cc(F)cc23)C1] | 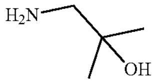 | LCMS m/z 431.19 [M + H]+ |
| 319 | 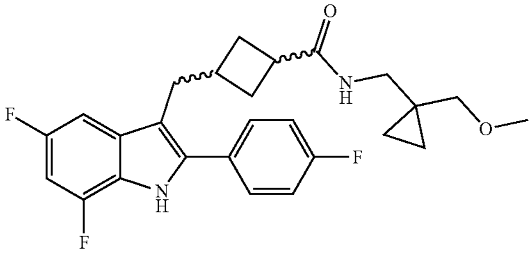 [SMILES: COCC1(CNC(=O)C2CC(Cc3c(-c4ccc(F)cc4)[nH]c4c(F)cc(F)cc34)C2)CC1] | 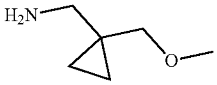 | LCMS m/z 457.21 [M + H]+ |
| 320 | 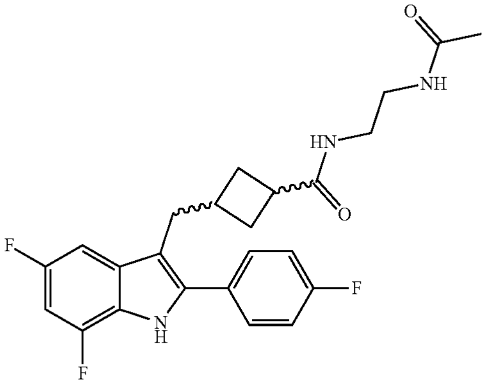 [SMILES: CC(=O)NCCNC(=O)C1CC(Cc2c(-c3ccc(F)cc3)[nH]c3c(F)cc(F)cc23)C1] | 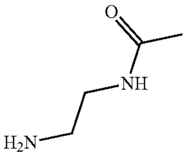 | LCMS m/z 444.19 [M + H]+ |
| 321 | 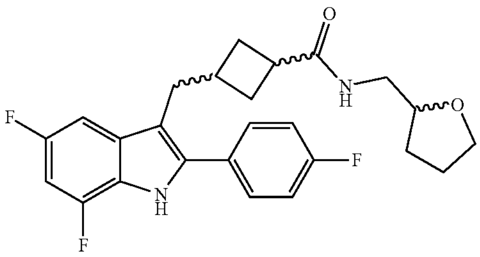 [SMILES: O=C(NCC1CCCO1)C1CC(Cc2c(-c3ccc(F)cc3)[nH]c3c(F)cc(F)cc23)C1] | 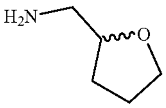 | LCMS m/z 443.18 [M + H]+ |

TABLE 15-continued
| Structure and physicochemical data for compounds 300-348 | | | |
|---|---|---|---|
| Cmpound | Product | Amine | 1H NMR; LCMS m/z [M + H]+ |
| 322 | 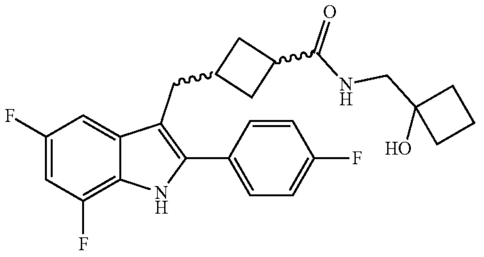 [SMILES: O=C(NCC1(O)CCC1)C1CC(Cc2c(-c3ccc(F)cc3)[nH]c3c(F)cc(F)cc23)C1] | 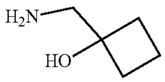 | LCMS m/z 443.18 [M + H]+ |
| 323 | 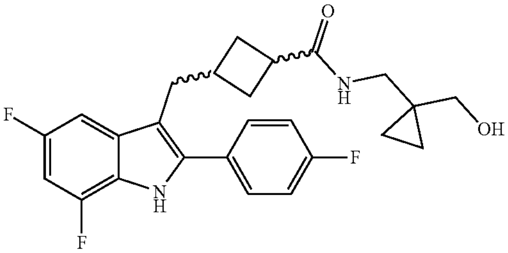 [SMILES: O=C(NCC1(CO)CC1)C1CC(Cc2c(-c3ccc(F)cc3)[nH]c3c(F)cc(F)cc23)C1] | 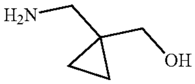 | LCMS m/z 443.18 [M + H]+ |
| 324 | 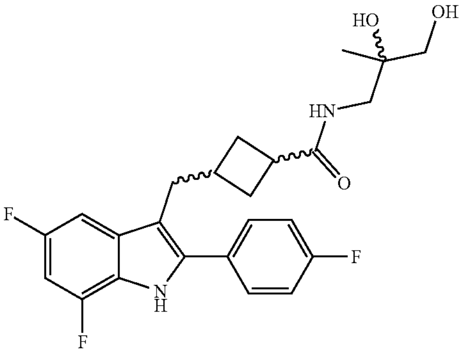 [SMILES: CC(O)(CO)CNC(=O)C1CC(Cc2c(-c3ccc(F)cc3)[nH]c3c(F)cc(F)cc23)C1] | 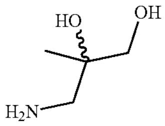 | LCMS m/z 447.18 [M + H]+ |
| 325 | 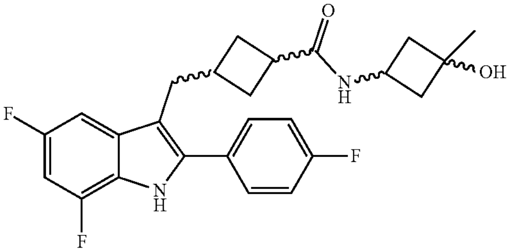 [SMILES: CC1(O)CC(NC(=O)C2CC(Cc3c(-c4ccc(F)cc4)[nH]c4c(F)cc(F)cc34)C2)C1] | 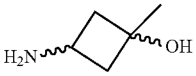 | LCMS m/z 443.18 [M + H]+ |
| 326 | 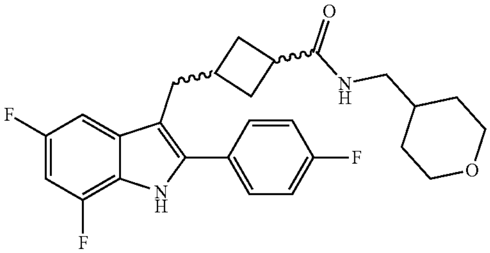 [SMILES: O=C(NCC1CCOCC1)C1CC(Cc2c(-c3ccc(F)cc3)[nH]c3c(F)cc(F)cc23)C1] | 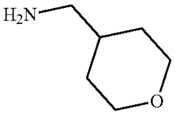 | LCMS m/z 457.18 [M + H]+ |

TABLE 15-continued
| Structure and physicochemical data for compounds 300-348 | | | |
|---|---|---|---|
| Cmpound | Product | Amine | $^1$H NMR; LCMS m/z [M + H]+ |
| 327 | 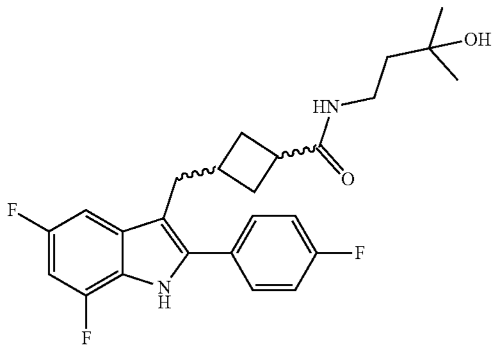 [SMILES: CC(C)(O)CCNC(=O)C1CC(Cc2c(-c3ccc(F)cc3)[nH]c3c(F)cc(F)cc23)C1] | 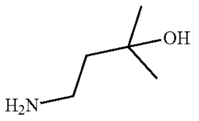 | LCMS m/z 445.19 [M + H]+ |
| 328 | 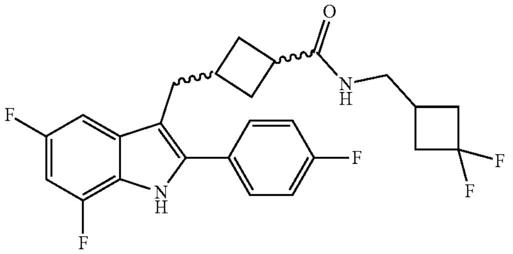 [SMILES: O=C(NCC1CC(F)(F)C1)C1CC(Cc2c(-c3ccc(F)cc3)[nH]c3c(F)cc(F)cc23)C1] | 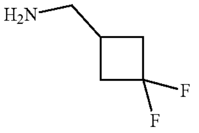 | LCMS m/z 463.14 [M + H]+ |
| 329 | 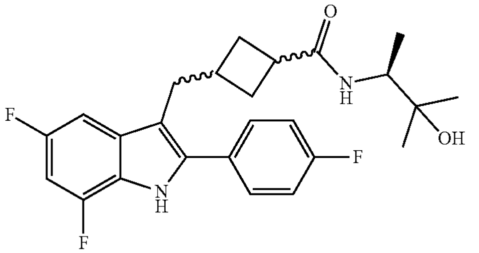 [SMILES: C[C@H](NC(=O)C1CC(Cc2c(-c3ccc(F)cc3)[nH]c3c(F)cc(F)cc23)C1)C(C)(C)O] | 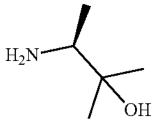 | LCMS m/z 445.19 [M + H]+ |
| 330 | 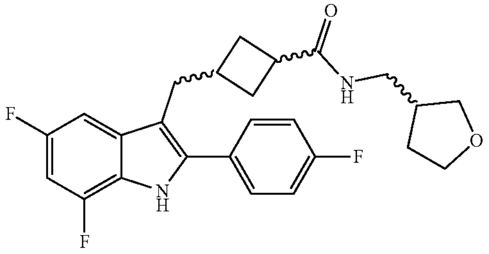 [SMILES: O=C(NCC1CCOC1)C1CC(Cc2c(-c3ccc(F)cc3)[nH]c3c(F)cc(F)cc23)C1] | 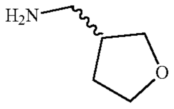 | LCMS m/z 443.18 [M + H]+ |
| 331 | 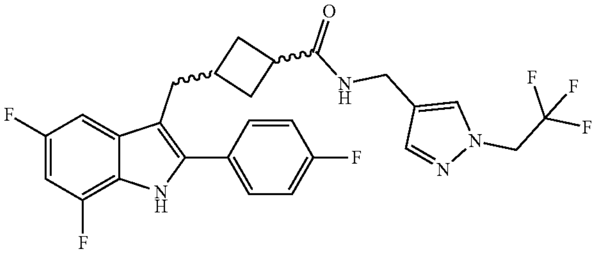 [SMILES: O=C(NCc1cnn(CC(F)(F)F)c1)C1CC(Cc2c(-c3ccc(F)cc3)[nH]c3c(F)cc(F)cc23)C1] | 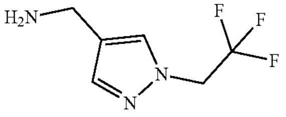 [SMILES: NCc1cnn(CC(F)(F)F)c1] | LCMS m/z 521.15 [M + H]+ |

TABLE 15-continued
| Structure and physicochemical data for compounds 300-348 | | | |
|---|---|---|---|
| Cmpound | Product | Amine | $^1$H NMR; LCMS m/z [M + H]$^+$ |
| 332 | 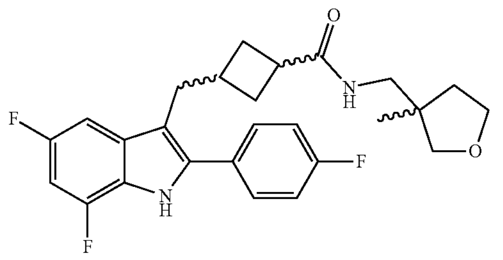 [SMILES: CC1(CNC(=O)C2CC(Cc3c(-c4ccc(F)cc4)[nH]c4c(F)cc(F)cc34)C2)CCOC1] | 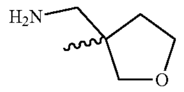 | LCMS m/z 457.21 [M + H]$^+$ |
| 333 | 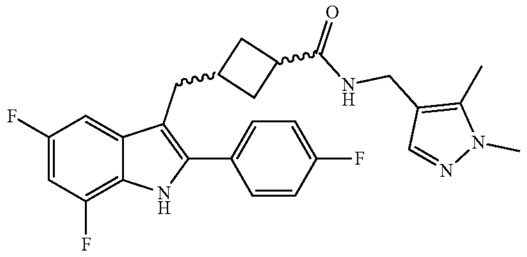 [SMILES: Cc1c(CNC(=O)C2CC(Cc3c(-c4ccc(F)cc4)[nH]c4c(F)cc(F)cc34)C2)cnn1C] | 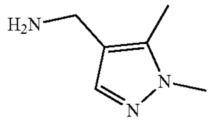 | LCMS m/z 467.18 [M + H]$^+$ |
| 334 | 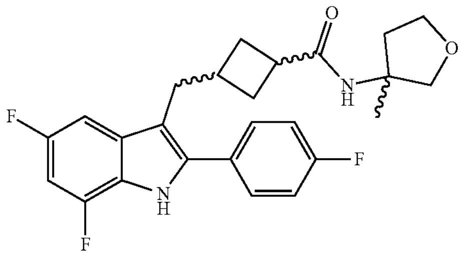 [SMILES: CC1(NC(=O)C2CC(Cc3c(-c4ccc(F)cc4)[nH]c4c(F)cc(F)cc34)C2)CCOC1] | 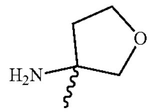 | LCMS m/z 443.18 [M + H]$^+$ |
| 335 | 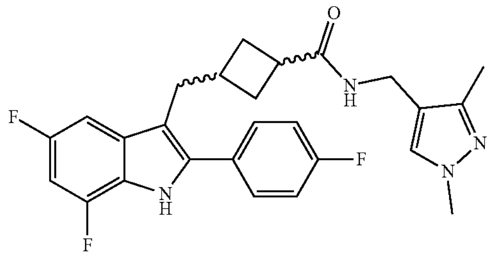 [SMILES: Cc1nn(C)cc1CNC(=O)C1CC(Cc2c(-c3ccc(F)cc3)[nH]c3c(F)cc(F)cc23)C1] | 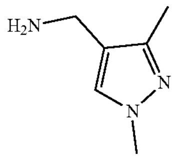 | LCMS m/z 467.18 [M + H]$^+$ |
| 336 | 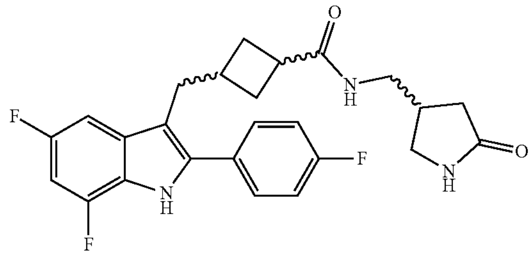 [SMILES: O=C1CC(CNC(=O)C2CC(Cc3c(-c4ccc(F)cc4)[nH]c4c(F)cc(F)cc34)C2)CN1] | 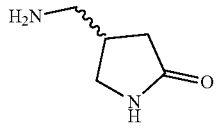 | LCMS m/z 456.17 [M + H]$^+$ |

TABLE 15-continued
Structure and physicochemical data for compounds 300-348
| Cmpound | Product | Amine | $^1$H NMR; LCMS m/z [M + H]$^+$ |
|---|---|---|---|
| 337 | 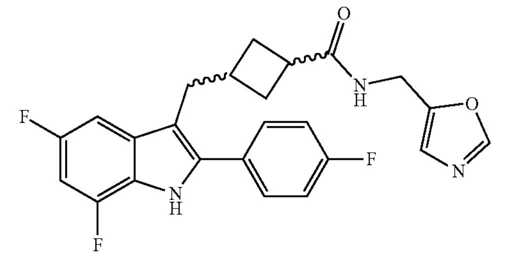 [SMILES: O=C(NCc1cnco1)C1CC(Cc2c(-c3ccc(F)cc3)[nH]c3c(F)cc(F)cc23)C1] | 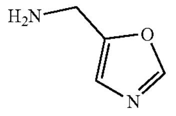 | LCMS m/z 440.15 [M + H]$^+$ |
| 338 | 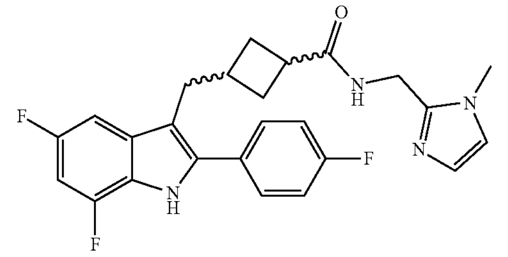 [SMILES: Cn1ccnc1CNC(=O)C1CC(Cc2c(-c3ccc(F)cc3)[nH]c3c(F)cc(F)cc23)C1] | 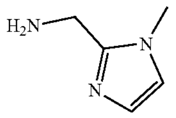 | LCMS m/z 453.37 [M + H]$^+$ |
| 339 | 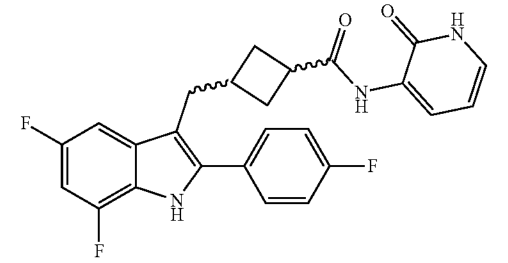 [SMILES: O=C(Nc1ccc[nH]c1=O)C1CC(Cc2c(-c3ccc(F)cc3)[nH]c3c(F)cc(F)cc23)C1] | 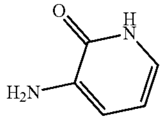 | LCMS m/z 452.13 [M + H]$^+$ |
| 340 | 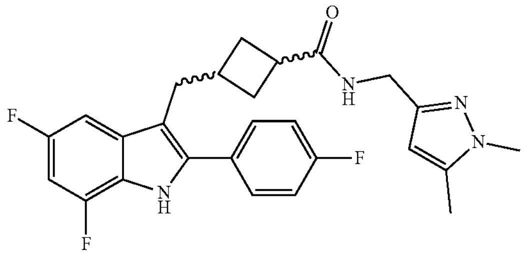 [SMILES: Cc1cc(CNC(=O)C2CC(Cc3c(-c4ccc(F)cc4)[nH]c4c(F)cc(F)cc34)C2)nn1C] | 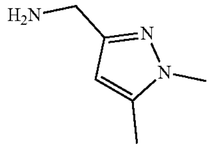 | LCMS m/z 467.18 [M + H]$^+$ |
| 341 | 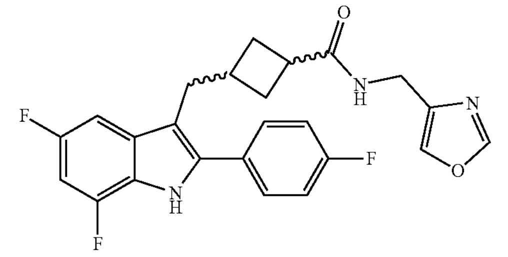 [SMILES: O=C(NCc1cocn1)C1CC(Cc2c(-c3ccc(F)cc3)[nH]c3c(F)cc(F)cc23)C1] | 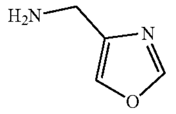 | LCMS m/z 440.15 [M + H]$^+$ |

TABLE 15-continued
| Structure and physicochemical data for compounds 300-348 | | | |
|---|---|---|---|
| Cmpound | Product | Amine | $^1$H NMR; LCMS m/z [M + H]$^+$ |
| 342 | 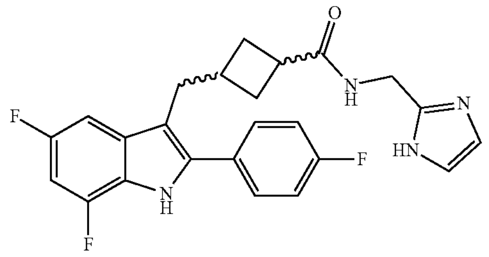 [SMILES: O=C(NCc1ncc[nH]1)C1CC(Cc2c(-c3ccc(F)cc3)[nH]c3c(F)cc(F)cc23)C1] | 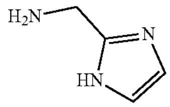 | LCMS m/z 439.14 [M + H]$^+$ |
| 343 | 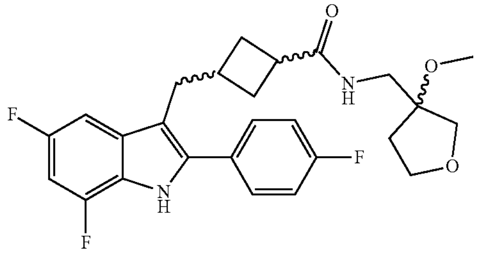 [SMILES: COC1(CNC(=O)C2CC(Cc3c(-c4ccc(F)cc4)[nH]c4c(F)cc(F)cc34)C2)CCOC1] | 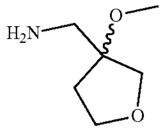 | LCMS m/z 473.17 [M + H]$^+$ |
| 344 | 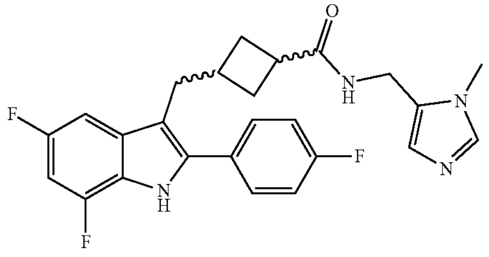 [SMILES: Cn1cncc1CNC(=O)C1CC(Cc2c(-c3ccc(F)cc3)[nH]c3c(F)cc(F)cc23)C1] | 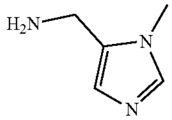 | LCMS m/z 453.18 [M + H]$^+$ |
| 345 | 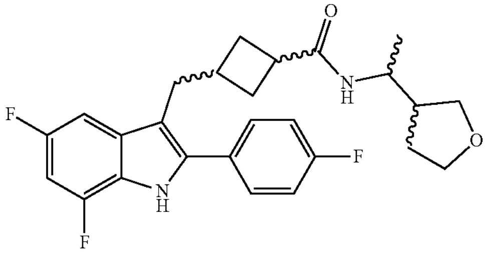 [SMILES: CC(NC(=O)C1CC(Cc2c(-c3ccc(F)cc3)[nH]c3c(F)cc(F)cc23)C1)C1CCOC1] | 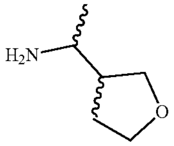 | LCMS m/z 457.21 [M + H]$^+$ |
| 346 | 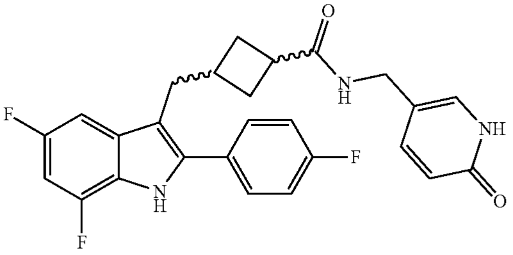 [SMILES: O=C(NCc1ccc(=O)[nH]c1)C1CC(Cc2c(-c3ccc(F)cc3)[nH]c3c(F)cc(F)cc23)C1] | 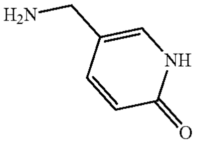 | LCMS m/z 466.14 [M + H]$^+$ |

TABLE 15-continued

| Structure and physicochemical data for compounds 300-348 | | | |
|---|---|---|---|
| Cmpound | Product | Amine | $^1$H NMR; LCMS m/z $[M + H]^+$ |
| 347 | 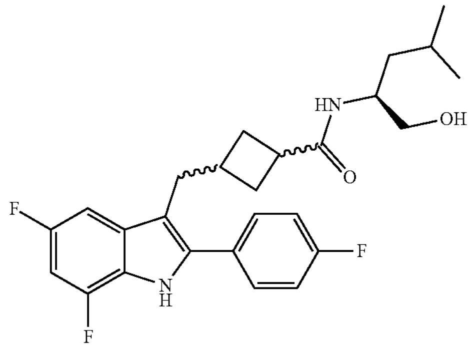 [SMILES: CC(C)C[C@@H](CO)NC(=O)C1CC(Cc2c(-c3ccc(F)cc3)[nH]c3c(F)cc(F)cc23)C1] | 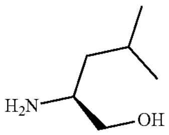 | LCMS m/z 459.2 $[M + H]^+$ |
| 348 | 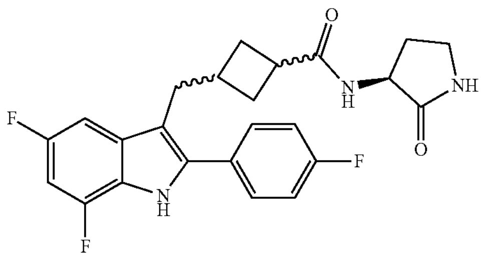 [SMILES: O=C(N[C@H]1CCNC1=O)C1CC(Cc2c(-c3ccc(F)cc3)[nH]c3c(F)cc(F)cc23)C1] | 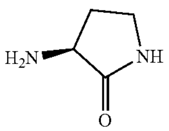 | LCMS m/z 442.17 $[M + H]^+$ |

Compound 349

(1r, 3r)-3-(5,7-difluoro-2-(4fluorophenyl)-1H-indol-3-yl)cyclobutyl (1,3-dihydroxy-2-(hydroxymethyl) propan-2-yl)carbamate (349)

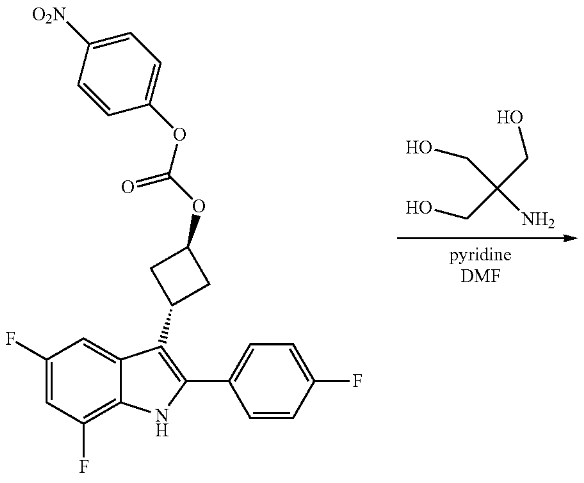

S9

-continued

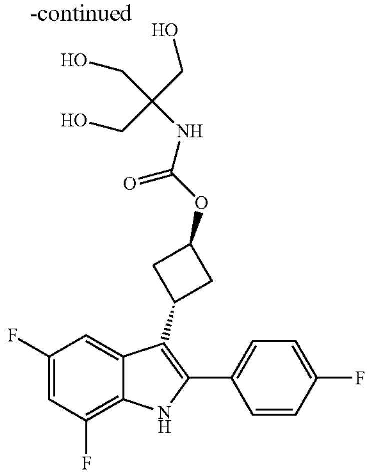

349

Preparation of (1r, 3r)-3-(5,7-difluoro-2-(4-fluorophenyl)-1H-indol-3-yl)cyclobutyl (1,3-dihydroxy-2-(hydroxymethyl)propan-2-yl)carbamate (349)

Standard procedure E: Carbamate Coupling Method

To a solution of (1r,3r)-3-(5,7-difluoro-2-(4-fluorophenyl)-1H-indol-3-yl)cyclobutyl (4-nitrophenyl) carbonate S9 (50 mg, 0.1 mmol) in DMF (2 mL) was added 2-amino-2-(hydroxymethyl)propane-1,3-diol (19 mg, 0.16 mmol), followed by pyridine (16 mg, 0.21 mmol). The mixture was heated to 80° C. overnight. The mixture was filtered and purified by reversed-phase HPLC (Method: C18 Waters Sunfire column (30×150 mm, 5 micron). Gradient: MeCN in $H_2O$ with 0.1% trifluoroacetic acid) to yield the product. (1r,3r)-3-(5,7-Difluoro-2-(4-fluorophenyl)-1H-indol-3-yl) cyclobutyl (1,3-dihydroxy-2-(hydroxymethyl)propan-2-yl) carbamate (12 mg, 20%). LCMS m/z 465.26 $[M+H]^+$.

Compounds 350-390

Compounds 350-390 (see Table 16) were prepared from intermediate S9 using the appropriate amine and using the carbamate coupling method as described for compound 349. Amines were obtained from commercial sources. Any modifications to methods are noted in Table 16 and accompanying footnotes.

TABLE 16

Structure and physicochemical data for compounds 350-390

| Cmpound | Product | Amine reagent | $^1H$ NMR; LCMS m/z $[M + H]^+$ |
|---|---|---|---|
| 350 | 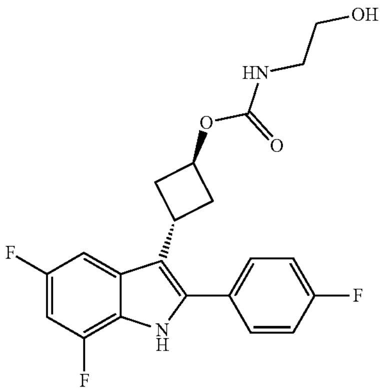 [SMILES: O=C(NCCO)O[C@H]1C[C@H](c2c(-c3ccc(F)cc3)[nH]c3c(F)cc(F)cc32)C1] | 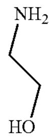 | LCMS m/z 405.29 $[M + H]^+$. |
| 351 | 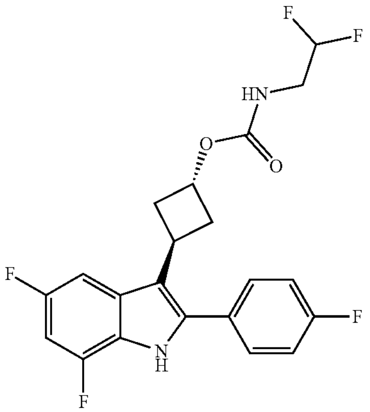 [SMILES: O=C(NCC(F)F)O[C@H]1C[C@H](c2c(-c3ccc(F)cc3)[nH]c3c(F)cc(F)cc32)C1] | 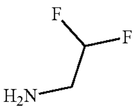 | LCMS m/z 425.06 $[M + H]^+$. |
| 352 | 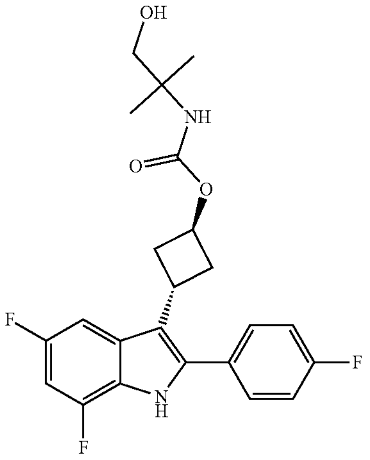 [SMILES: CC(C)(CO)NC(=O)O[C@H]1C[C@H](c2c(-c3ccc(F)cc3)[nH]c3c(F)cc(F)cc32)C1] | 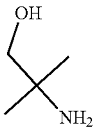 | LCMS m/z 433.11 $[M + H]^+$. |

TABLE 16-continued
| Structure and physicochemical data for compounds 350-390 | | | |
|---|---|---|---|
| Cmpound | Product | Amine reagent | $^1$H NMR; LCMS m/z $[M + H]^+$ |
| 353 | 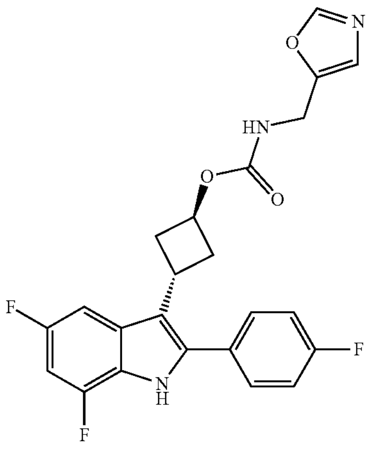 [SMILES: O=C(NCc1cnco1)O[C@H]1C[C@H](c2c(-c3ccc(F)cc3)[nH]c3c(F)cc(F)cc32)C1] | 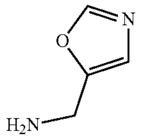 | LCMS m/z 442.1 $[M + H]^+$. |
| 354 | 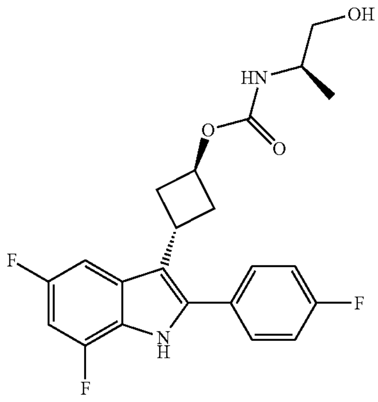 [SMILES: C[C@H](CO)NC(=O)O[C@H]1C[C@H](c2c(-c3ccc(F)cc3)[nH]c3c(F)cc(F)cc32)C1] | 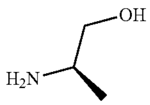 | LCMS m/z 419.16 $[M + H]^+$. |
| 355 | 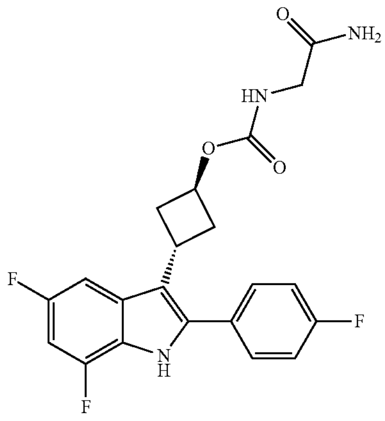 [SMILES: NC(=O)CNC(=O)O[C@H]1C[C@H](c2c(-c3ccc(F)cc3)[nH]c3c(F)cc(F)cc32)C1] | 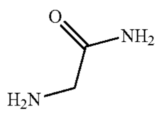 | LCMS m/z 418.02 $[M + H]^+$. |

TABLE 16-continued
| Structure and physicochemical data for compounds 350-390 | | | |
|---|---|---|---|
| Cmpound | Product | Amine reagent | $^1$H NMR; LCMS m/z $[M + H]^+$ |
| 356 | 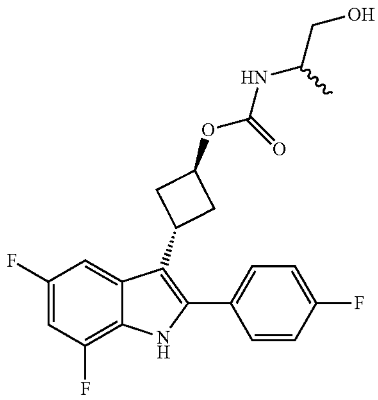 [SMILES: CC(CO)NC(=O)O[C@H]1C[C@H](c2c(-c3ccc(F)cc3)[nH]c3c(F)cc(F)cc32)C1] | 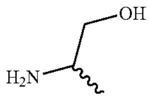 | LCMS m/z 419 $[M + H]^+$. |
| 357 | 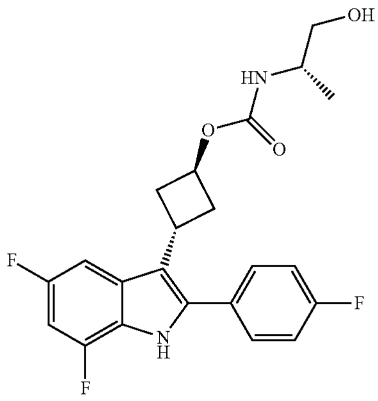 [SMILES: C[C@@H](CO)NC(=O)O[C@H]1C[C@H](c2c(-c3ccc(F)cc3)[nH]c3c(F)cc(F)cc32)C1] | 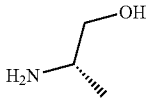 | LCMS m/z 419.29 $[M + H]^+$. |
| 358 | 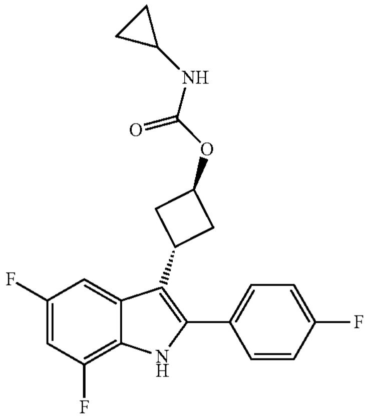 [SMILES: O=C(NC1CC1)O[C@H]1C[C@H](c2c(-c3ccc(F)cc3)[nH]c3c(F)cc(F)cc32)C1] | 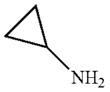 | LCMS m/z 401.15 $[M + H]^+$. |

TABLE 16-continued
| Structure and physicochemical data for compounds 350-390 | | | |
|---|---|---|---|
| Cmpound | Product | Amine reagent | $^1H$ NMR; LCMS m/z $[M + H]^+$ |
| 359 | 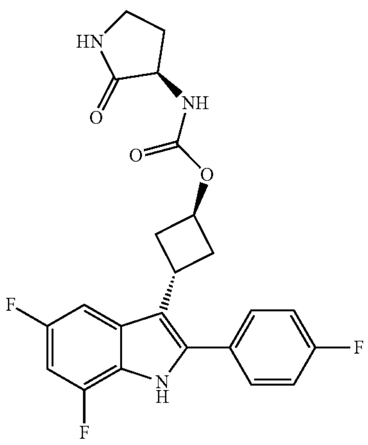 [SMILES: O=C(N[C@@H]1CCNC1=O)O[C@H]1C[C@H](c2c(-c3ccc(F)cc3)[nH]c3c(F)cc(F)cc32)C1] | 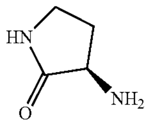 | LCMS m/z 444.31 $[M + H]^+$. |
| 360 | 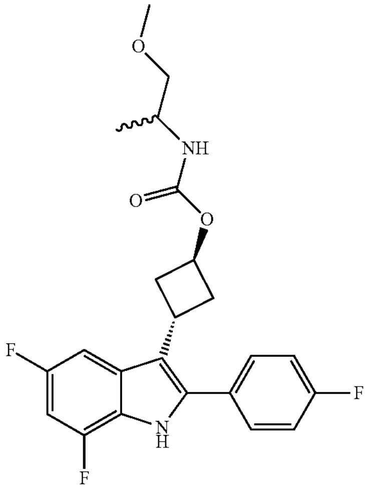 [SMILES: COCC(C)NC(=O)O[C@H]1C[C@H](c2c(-c3ccc(F)cc3)[nH]c3c(F)cc(F)cc32)C1] | 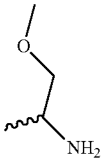 | LCMS m/z 433.04 $[M + H]^+$. |
| 361 | 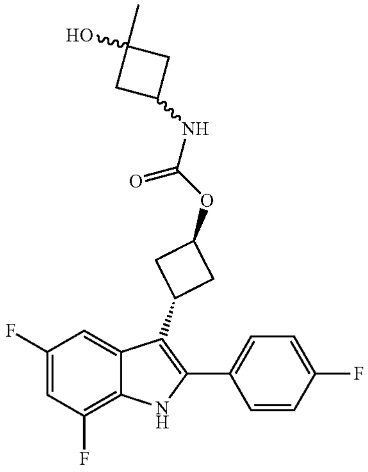 [SMILES: CC1(O)CC(NC(=O)O[C@H]2C[C@H](c3c(-c4ccc(F)cc4)[nH]c4c(F)cc(F)cc43)C2)C1] | 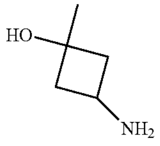 | LCMS m/z 445.13 $[M + H]^+$. |

TABLE 16-continued
| Structure and physicochemical data for compounds 350-390 | | | |
|---|---|---|---|
| Cmpound | Product | Amine reagent | $^1$H NMR; LCMS m/z [M + H]$^+$ |
| 362 | 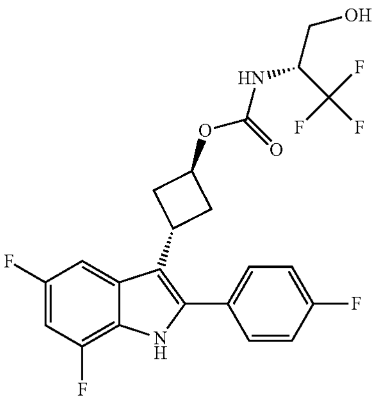 [SMILES: O=C(N[C@H](CO)C(F)(F)F)O[C@H]1C[C@H](c2c(-c3ccc(F)cc3)[nH]c3c(F)cc(F)cc32)C1] | 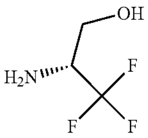 | LCMS m/z 473.21 [M + H]$^+$. |
| 363 | 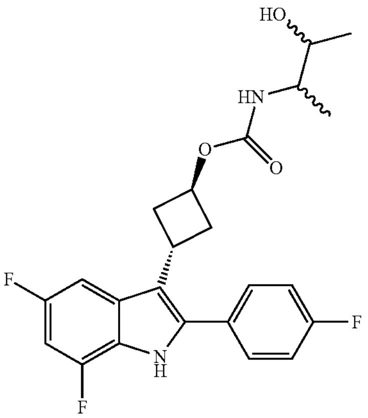 [SMILES: CC(O)C(C)NC(=O)O[C@H]1C[C@H](c2c(-c3ccc(F)cc3)[nH]c3c(F)cc(F)cc32)C1] | 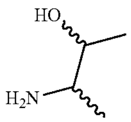 | LCMS m/z 433.3 [M + H]$^+$. |
| 364 | 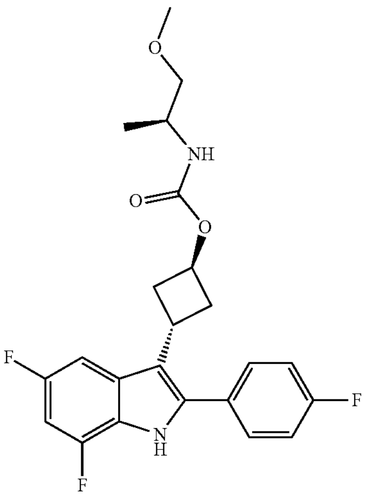 [SMILES: COC[C@H](C)NC(=O)O[C@H]1C[C@H](c2c(-c3ccc(F)cc3)[nH]c3c(F)cc(F)cc32)C1] | 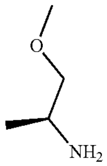 | LCMS m/z 433.2 [M + H]$^+$. |

TABLE 16-continued
| Structure and physicochemical data for compounds 350-390 | | | |
|---|---|---|---|
| Cmpound | Product | Amine reagent | $^1$H NMR; LCMS m/z [M + H]$^+$ |
| 365 | 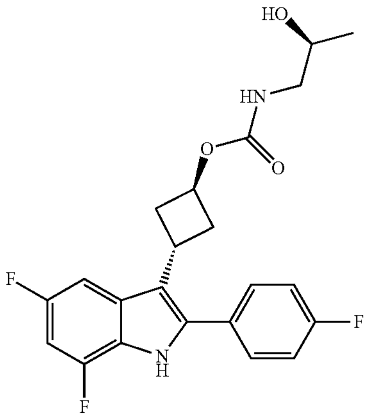 [SMILES: C[C@H](O)CNC(=O)O[C@H]1C[C@H](c2c(-c3ccc(F)cc3)[nH]c3c(F)cc(F)cc32)C1] | 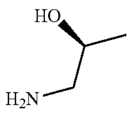 | LCMS m/z 419.2 [M + H]$^+$. |
| 366 | 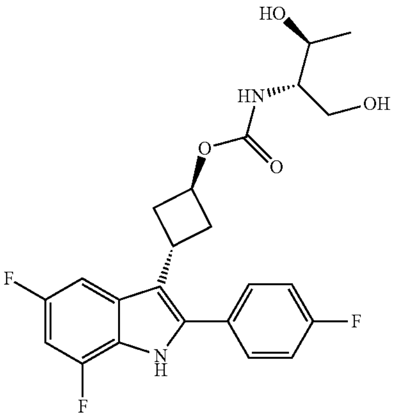 [SMILES: C[C@H](O)[C@H](CO)NC(=O)O[C@H]1C[C@H](c2c(-c3ccc(F)cc3)[nH]c3c(F)cc(F)cc32)C1] | 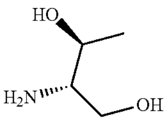 | LCMS m/z 449.39 [M + H]$^+$. |
| 367 | 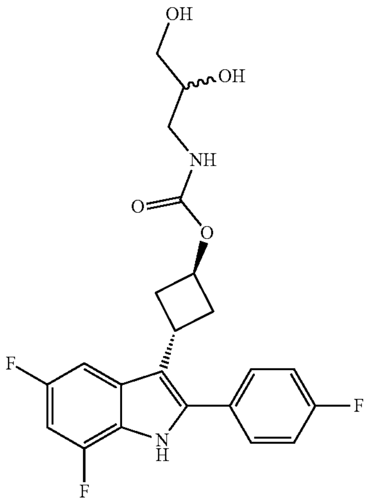 [SMILES: O=C(NCC(O)CO)O[C@H]1C[C@H](c2c(-c3ccc(F)cc3)[nH]c3c(F)cc(F)cc32)C1] | 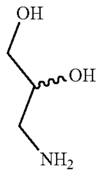 | LCMS m/z 435.12 [M + H]$^+$. |

TABLE 16-continued
| Structure and physicochemical data for compounds 350-390 | | | |
|---|---|---|---|
| Cmpound | Product | Amine reagent | $^1$H NMR; LCMS m/z $[M + H]^+$ |
| 368 | 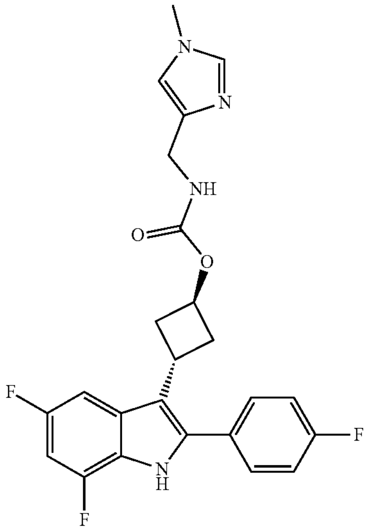 [SMILES: Cn1cnc(CNC(=O)O[C@H]2C[C@H](c3c(-c4ccc(F)cc4)[nH]c4c(F)cc(F)cc43)C2)c1] | 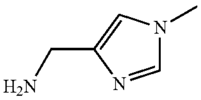 | $^1$H NMR (300 MHz, Acetone-$d_6$) δ 10.74 (s, 1H), 8.63 (s, 1H), 7.61 (dt, J = 10.5, 6.8 Hz, 2H), 7.46-7.17 (m, 4H), 6.86 (ddd, J = 11.0, 9.6, 2.1 Hz, 1H), 5.20 (dt, J = 6.8, 3.6 Hz, 1H), 4.37 (d, J = 6.1 Hz, 2H), 4.12 (q, J = 8.7 Hz, 1H), 4.00 (s, 3H), 2.84-2.64 (m, 3H), 2.62-2.38 (m, 2H). LCMS m/z 455.16 $[M + H]^+$. |
| 369 | 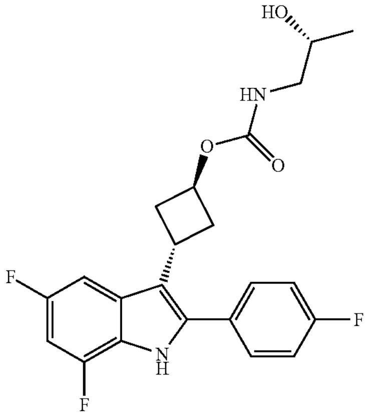 [SMILES: C[C@@H](O)CNC(=O)O[C@H]1C[C@H](c2c(-c3ccc(F)cc3)[nH]c3c(F)cc(F)cc32)C1] | 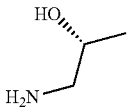 | LCMS m/z 419.26 $[M + H]^+$. |
| 370 | 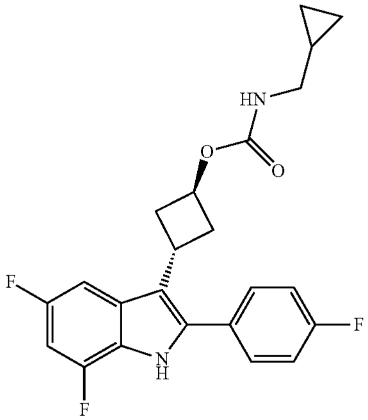 [SMILES: O=C(NCC1CC1)O[C@H]1C[C@H](c2c(-c3ccc(F)cc3)[nH]c3c(F)cc(F)cc32)C1] | 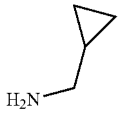 | LCMS m/z 415.32 $[M + H]^+$. |

TABLE 16-continued
| Structure and physicochemical data for compounds 350-390 | | | |
|---|---|---|---|
| Cmpound | Product | Amine reagent | $^{1}H$ NMR; LCMS m/z $[M + H]^{+}$ |
| 371 | 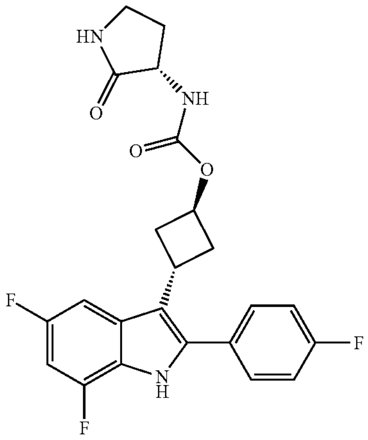 [SMILES: O=C(N[C@H]1CCNC1=O)O[C@H]1C[C@H](c2c(-c3ccc(F)cc3)[nH]c3c(F)cc(F)cc32)C1] | 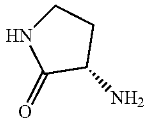 | LCMS m/z 444.18 $[M + H]^{+}$. |
| 372 | 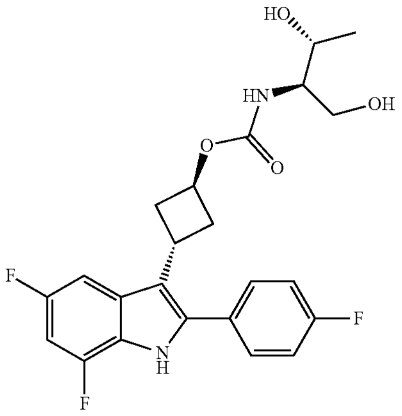 [SMILES: C[C@@H](O)[C@@H](CO)NC(=O)O[C@H]1C[C@H](c2c(-c3ccc(F)cc3)[nH]c3c(F)cc(F)cc32)C1] | 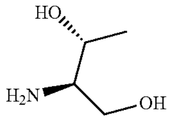 | LCMS m/z 449.36 $[M + H]^{+}$. |
| 373 | 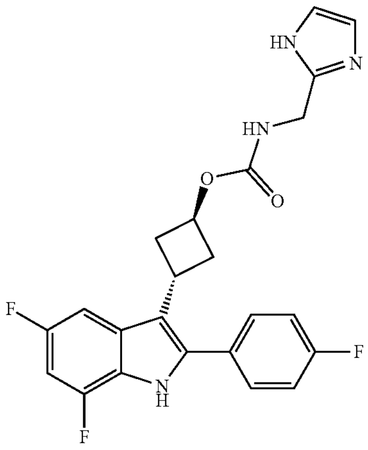 [SMILES: O=C(NCc1ncc[nH]1)O[C@H]1C[C@H](c2c(-c3ccc(F)cc3)[nH]c3c(F)cc(F)cc32)C1] | 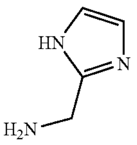 | LCMS m/z 441.12 $[M + H]^{+}$. |

TABLE 16-continued
| Structure and physicochemical data for compounds 350-390 | | | |
|---|---|---|---|
| Cmpound | Product | Amine reagent | $^1$H NMR; LCMS m/z [M + H]$^+$ |
| 374 | 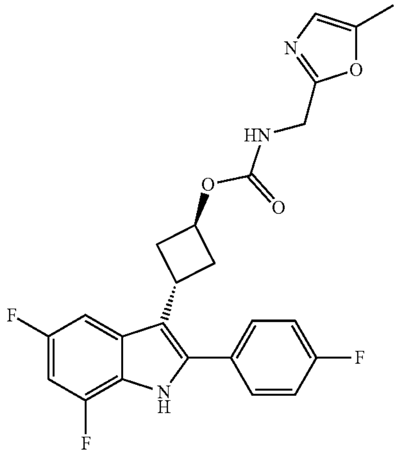 [SMILES: Cc1cnc(CNC(=O)O[C@H]2C[C@H](c3c(-c4ccc(F)cc4)[nH]c4c(F)cc(F)cc43)C2)o1] | 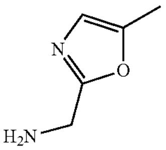 | LCMS m/z 455.97 [M + H]$^+$. |
| 375 | 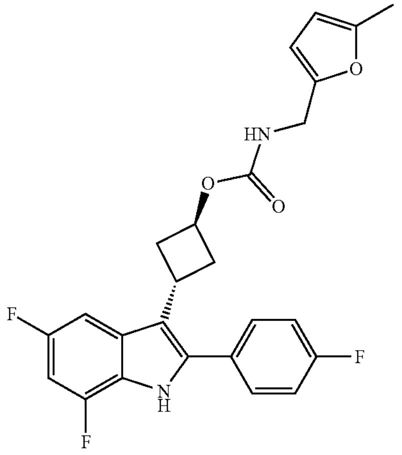 [SMILES: Cc1ccc(CNC(=O)O[C@H]2C[C@H](c3c(-c4ccc(F)cc4)[nH]c4c(F)cc(F)cc43)C2)o1] | 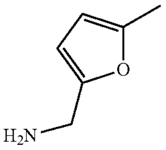 | LCMS m/z 455.32 [M + H]$^+$. |
| 376 | 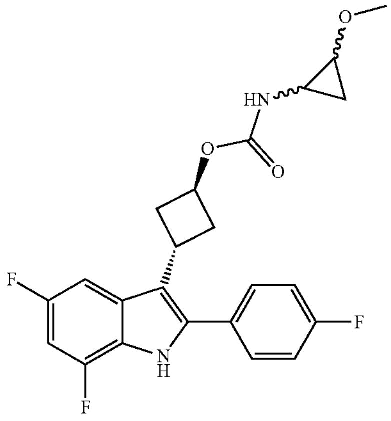 [SMILES: COC1CC1NC(=O)O[C@H]1C[C@H](c2c(-c3ccc(F)cc3)[nH]c3c(F)cc(F)cc32)C1] | 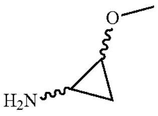 | LCMS m/z 431.18 [M + H]$^+$. |

TABLE 16-continued
Structure and physicochemical data for compounds 350-390
| Cmpound | Product | Amine reagent | $^1$H NMR; LCMS m/z [M + H]$^+$ |
|---|---|---|---|
| 377 | 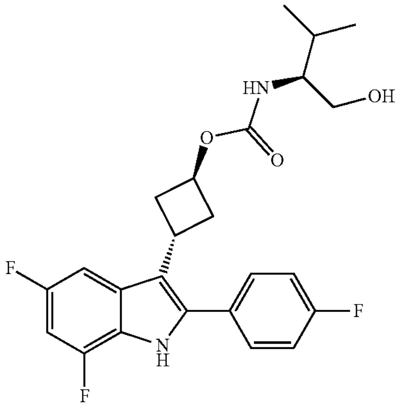 [SMILES: CC(C)[C@@H](CO)NC(=O)O[C@H]1C[C@H](c2c(-c3ccc(F)cc3)[nH]c3c(F)cc(F)cc32)C1] | 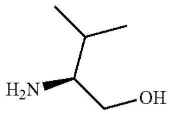 | LCMS m/z 447.31 [M + H]$^+$. |
| 378 | 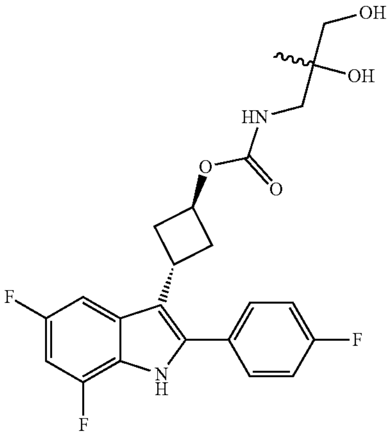 [SMILES: CC(O)(CO)CNC(=O)O[C@H]1C[C@H](c2c(-c3ccc(F)cc3)[nH]c3c(F)cc(F)cc32)C1] | 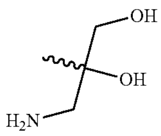 | LCMS m/z 449.39 [M + H]$^+$. |
| 379 | 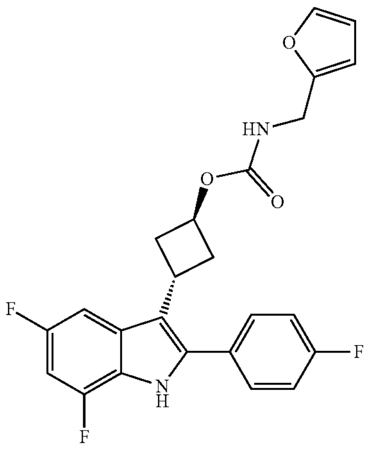 [SMILES: O=C(NCc1ccco1)O[C@H]1C[C@H](c2c(-c3ccc(F)cc3)[nH]c3c(F)cc(F)cc32)C1] | 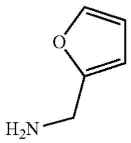 | LCMS m/z 440.99 [M + H]$^+$. |

TABLE 16-continued
| Structure and physicochemical data for compounds 350-390 | | | |
|---|---|---|---|
| Cmpound | Product | Amine reagent | $^1H$ NMR; LCMS m/z $[M + H]^+$ |
| 380 | 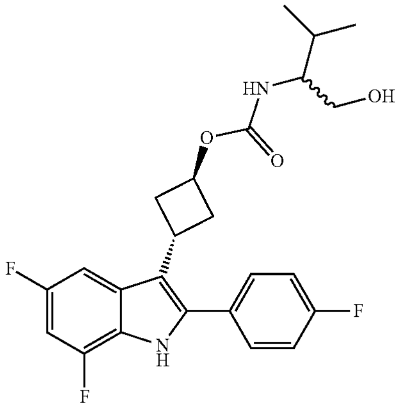 [SMILES: CC(C)C(CO)NC(=O)O[C@H]1C[C@H](c2c(-c3ccc(F)cc3)[nH]c3c(F)cc(F)cc32)C1] | 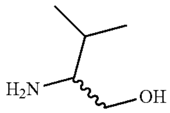 | LCMS m/z 447.18 $[M + H]^+$. |
| 381 | 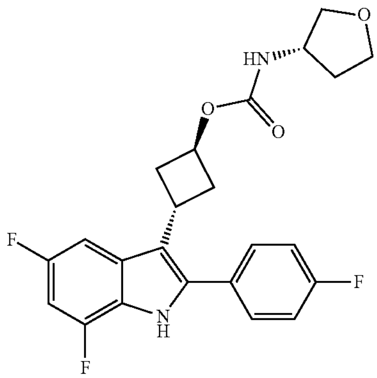 [SMILES: O=C(N[C@H]1CCOC1)O[C@H]1C[C@H](c2c(-c3ccc(F)cc3)[nH]c3c(F)cc(F)cc32)C1] | 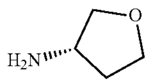 | LCMS m/z 431.28 $[M + H]^+$. |
| 382 | 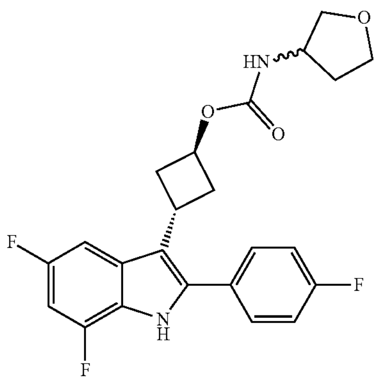 [SMILES: O=C(NC1CCOC1)O[C@H]1C[C@H](c2c(-c3ccc(F)cc3)[nH]c3c(F)cc(F)cc32)C1] | 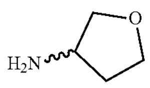 | LCMS m/z 431.35 $[M + H]^+$. |

TABLE 16-continued
Structure and physicochemical data for compounds 350-390
| Cmpound | Product | Amine reagent | $^1$H NMR; LCMS m/z [M + H]$^+$ |
|---|---|---|---|
| 383 | 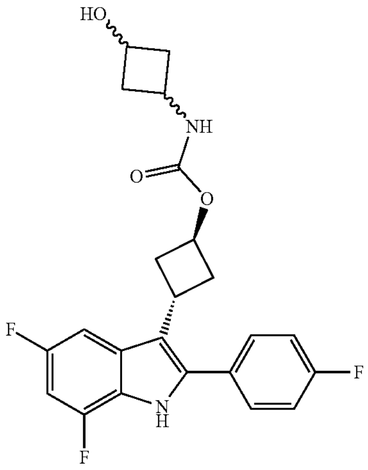 [SMILES: O=C(NC1CC(O)C1)O[C@H]1C[C@H](c2c(-c3ccc(F)cc3)[nH]c3c(F)cc(F)cc32)C1] | 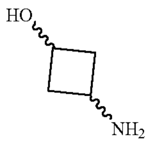 | LCMS m/z 431.28 [M + H]$^+$. |
| 384 | 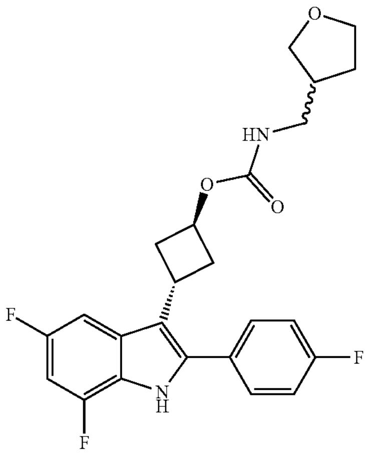 [SMILES: O=C(NCC1CCOC1)O[C@H]1C[C@H](c2c(-c3ccc(F)cc3)[nH]c3c(F)cc(F)cc32)C1] | 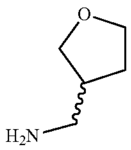 | LCMS m/z 445.32 [M + H]$^+$. |
| 385 | 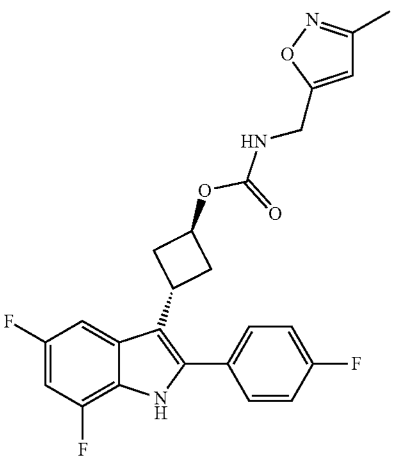 [SMILES: Cc1cc(CNC(=O)O[C@H]2C[C@H](c3c(-c4ccc(F)cc4)[nH]c4c(F)cc(F)cc43)C2)on1] | 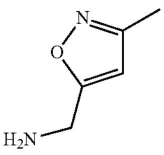 | LCMS m/z 456.14 [M + H]$^+$. |

TABLE 16-continued
| Structure and physicochemical data for compounds 350-390 | | | |
|---|---|---|---|
| Cmpound | Product | Amine reagent | $^1$H NMR; LCMS m/z [M + H]$^+$ |
| 386 | 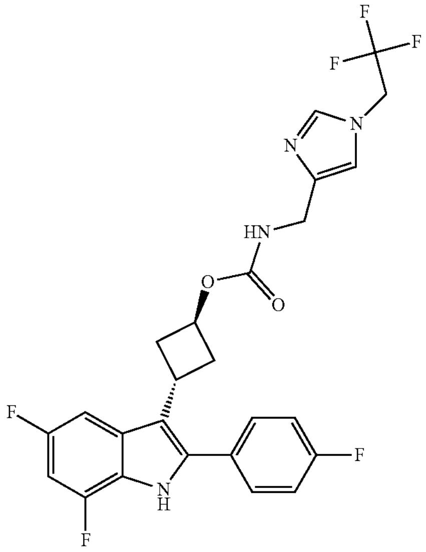 [SMILES: O=C(NCc1cn(CC(F)(F)F)cn1)O[C@H]1C[C@H](c2c(-c3ccc(F)cc3)[nH]c3c(F)cc(F)cc32)C1] | 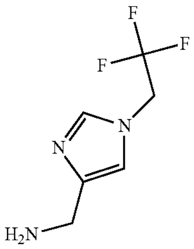 [SMILES: NCc1cn(CC(F)(F)F)cn1] | LCMS m/z 523.14 [M + H]$^+$. |
| 387 | 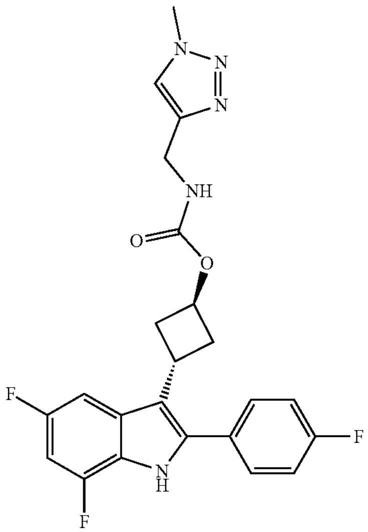 [SMILES: Cn1cc(CNC(=O)O[C@H]2C[C@H](c3c(-c4ccc(F)cc4)[nH]c4c(F)cc(F)cc43)C2)nn1] | 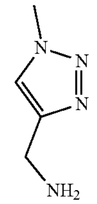 | LCMS m/z 456.27 [M + H]$^+$. |

TABLE 16-continued
| Structure and physicochemical data for compounds 350-390 | | | |
|---|---|---|---|
| Cmpound | Product | Amine reagent | $^1$H NMR; LCMS m/z [M + H]$^+$ |
| 388 | 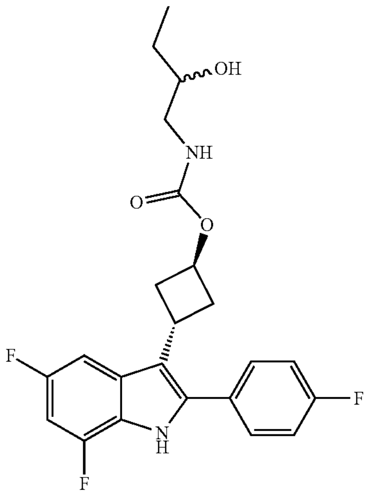 [SMILES: CCC(O)CNC(=O)O[C@H]1C[C@H](c2c(-c3ccc(F)cc3)[nH]c3c(F)cc(F)cc32)C1] | 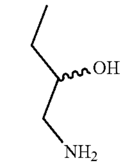 | LCMS m/z 433.2 [M + H]$^+$. |
| 389 | 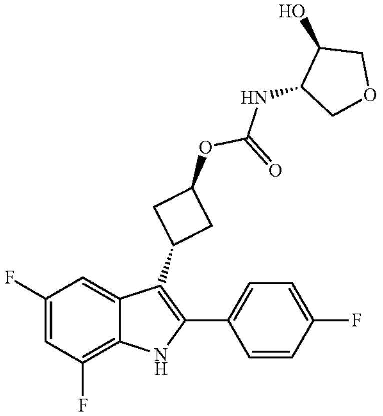 [SMILES: O=C(N[C@H]1COC[C@@H]1O)O[C@H]1C[C@H](c2c(-c3ccc(F)cc3)[nH]c3c(F)cc(F)cc32)C1] | 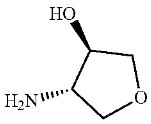 | LCMS m/z 447.15 [M + H]$^+$. |
| 390 | 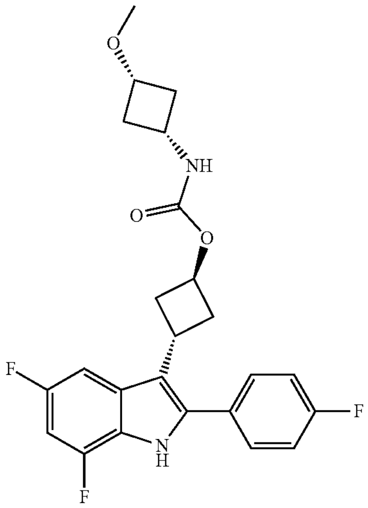 [SMILES: CO[C@H]1C[C@@H](NC(=O)O[C@H]2C[C@H](c3c(-c4ccc(F)cc4)[nH]c4c(F)cc(F)cc43)C2)C1] | 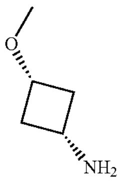 | LCMS m/z 445.29 [M + H]$^+$. |

Compound 391

1-(((1r,3r)-3-(5,7-difluoro-2-(4-fluorophenyl)-1H-indol-3-yl)cyclobutyl)methyl)-3-methylurea (391)

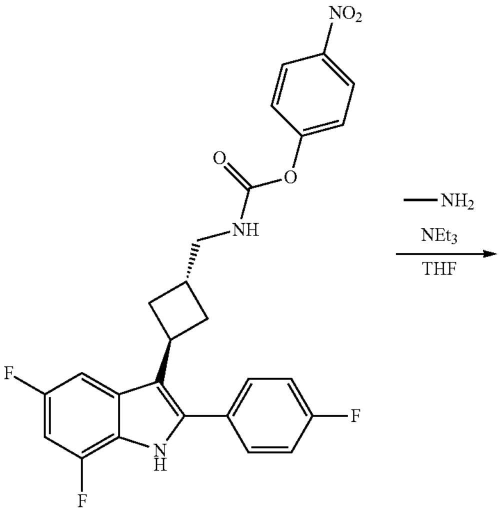

S12

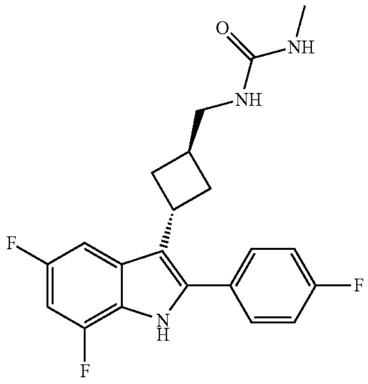

391

Preparation of 1-(((1r,3r)-3-(5,7-difluoro-2-(4-fluorophenyl)-1H-indol-3-yl)cyclobutyl)methyl)-3-methylurea (391)

Standard procedure G: Carbamate Coupling Method

To a solution of 4-nitrophenyl (((1r,3r)-3-(5,7-difluoro-2-(4-fluorophenyl)-1H-indol-3-yl)cyclobutyl)methyl)carbamate S12 (50 mg, 0.1 mmol) and $Et_3N$ (0.03 mL, 0.2 mmol) in THE (2 mL) was added methanamine (0.075 mL, 0.15 mmol, 2 M in THF). The reaction mixture was stirred at 80° C. for 2 h then treated with 1 M aq. HCl and extracted with EtOAc. The organic layer was dried over magnesium sulfate, filtered, concentrated in vacuo, and purified by reversed-phase HPLC (Method: C18 Waters Sunfire column (30×150 mm, 5 micron). Gradient: MeCN in $H_2O$ with 0.1% trifluoroacetic acid) to afford the product. 1-(((1r,3r)-3-(5,7-Difluoro-2-(4-fluorophenyl)-1H-indol-3-yl)cyclobutyl) methyl)-3-methylurea (18 mg, 36%). LCMS m/z 388.15 $[M+H]^+$.

Compounds 392-426

Compounds 392-426 (see Table 17) were prepared in a single step from compound S12 using standard method described for the synthesis of compound 391. Amines were obtained from commercial sources. Any modifications to methods are noted in Table 17 and accompanying footnotes.

TABLE 17

Structure and physicochemical data for compounds 392-426

| Cmpound | Product | Amine | $^1H$ NMR; LCMS m/z $[M + H]^+$ |
|---|---|---|---|
| 392 | 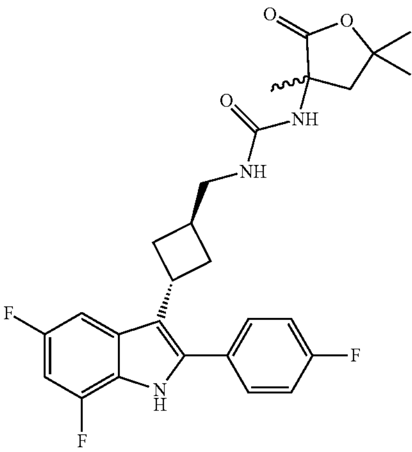 [SMILES: CC1(C)CC(C)(NC(=O)NC[C@H]2C[C@H](c3c(-c4ccc(F)cc4)[nH]c4c(F)cc(F)cc43)C2)C(=O)O1] | 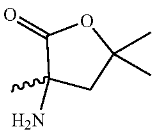 | LCMS m/z 500.18 $[M + H]^+$ |

TABLE 17-continued
| Structure and physicochemical data for compounds 392-426 | | | |
|---|---|---|---|
| Cmpound | Product | Amine | $^1$H NMR; LCMS m/z $[M + H]^+$ |
| 393 | 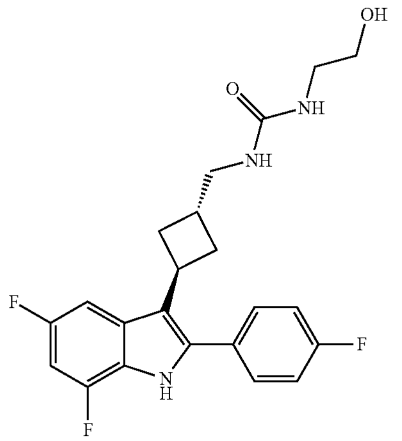 [SMILES: O=C(NCCO)NC[C@H]1C[C@H](c2c(-c3ccc(F)cc3)[nH]c3c(F)cc(F)cc32)C1] | 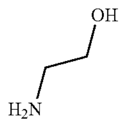 | LCMS m/z 418.15 $[M + H]^+$ |
| 394 | 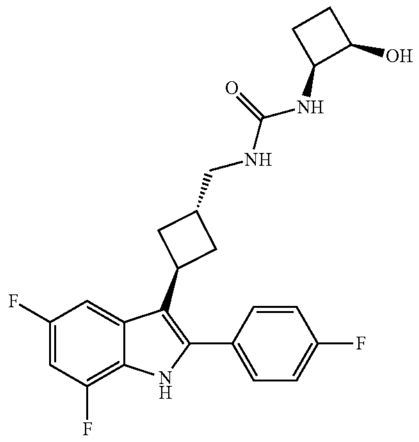 [SMILES: O=C(NC[C@H]1C[C@H](c2c(-c3ccc(F)cc3)[nH]c3c(F)cc(F)cc32)C1)N[C@H]1CC[C@H]1O] | 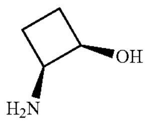 | LCMS m/z 444.02 $[M + H]^+$ |
| 395 | 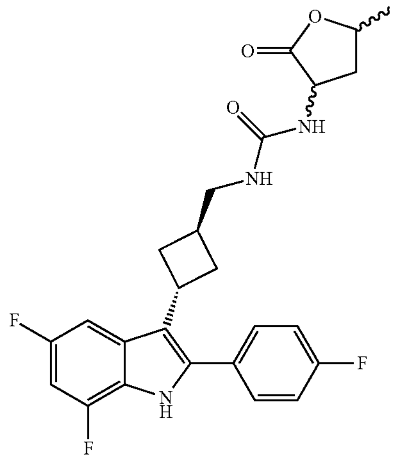 [SMILES: CC1CC(NC(=O)NC[C@H]2C[C@H](c3c(-c4ccc(F)cc4)[nH]c4c(F)cc(F)cc43)C2)C(=O)O1] | 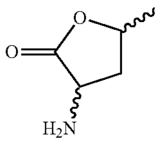 | LCMS m/z 472.16 $[M + H]^+$ |

TABLE 17-continued
| Structure and physicochemical data for compounds 392-426 | | | |
|---|---|---|---|
| Cmpound | Product | Amine | $^1$H NMR; LCMS m/z [M + H]$^+$ |
| 396 | 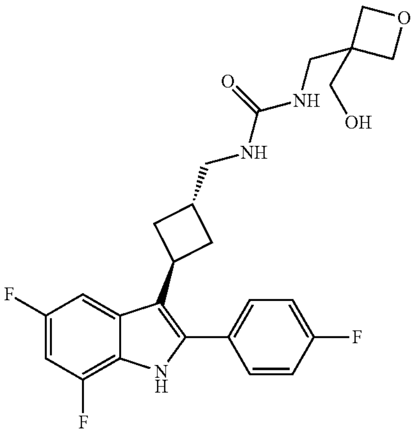 [SMILES: O=C(NCC1(CO)COC1)NC[C@H]1C[C@H](c2c(-c3ccc(F)cc3)[nH]c3c(F)cc(F)cc32)C1] | 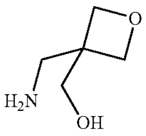 | LCMS m/z 474.18 [M + H]$^+$ |
| 397 | 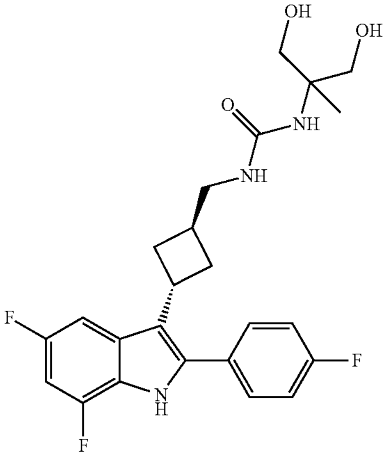 [SMILES: CC(CO)(CO)NC(=O)NC[C@H]1C[C@H](c2c(-c3ccc(F)cc3)[nH]c3c(F)cc(F)cc32)C1] | 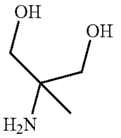 | LCMS m/z 462.33 [M + H]$^+$ |
| 398 | 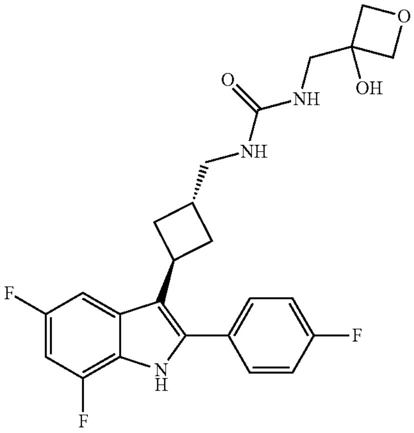 [SMILES: O=C(NCC1(O)COC1)NC[C@H]1C[C@H](c2c(-c3ccc(F)cc3)[nH]c3c(F)cc(F)cc32)C1] | 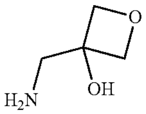 | LCMS m/z 460.3 [M + H]$^+$ |

TABLE 17-continued
| Structure and physicochemical data for compounds 392-426 | | | |
|---|---|---|---|
| Cmpound | Product | Amine | $^1$H NMR; LCMS m/z [M + H]$^+$ |
| 399 | 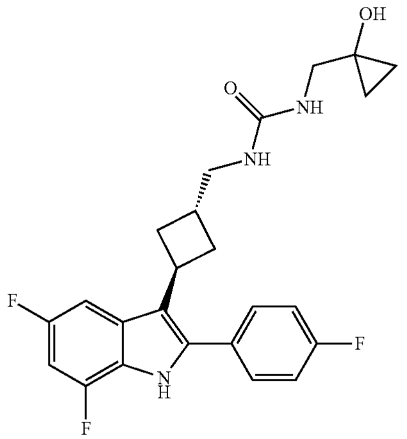 [SMILES: O=C(NCC1(O)CC1)NC[C@H]1C[C@H](c2c(-c3ccc(F)cc3)[nH]c3c(F)cc(F)cc32)C1] | 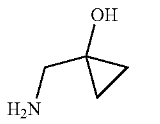 | LCMS m/z 444.15 [M + H]$^+$ |
| 400 | 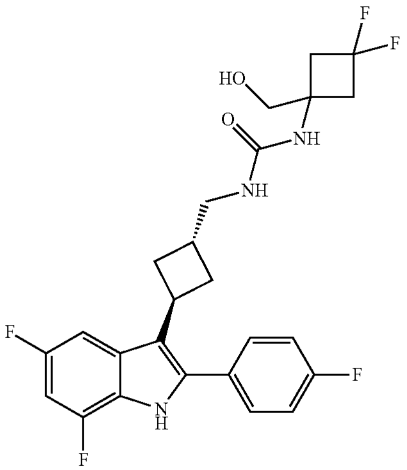 [SMILES: O=C(NC[C@H]1C[C@H](c2c(-c3ccc(F)cc3)[nH]c3c(F)cc(F)cc32)C1)NC1(CO)CC(F)(F)C1] | 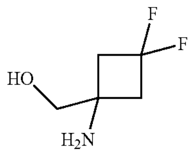 | LCMS m/z 494.15 [M + H]$^+$ |
| 401 | 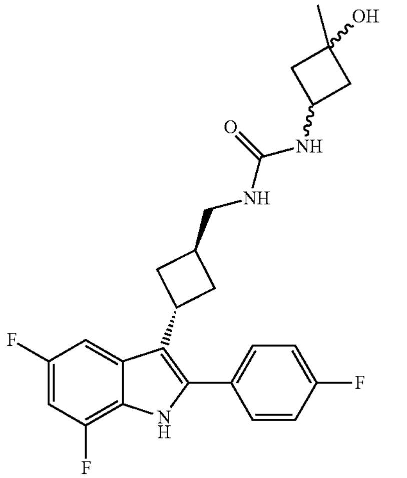 [SMILES: CC1(O)CC(NC(=O)NC[C@H]2C[C@H](c3c(-c4ccc(F)cc4)[nH]c4c(F)cc(F)cc43)C2)C1] | 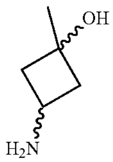 | LCMS m/z 458.32 [M + H]$^+$ |

TABLE 17-continued
Structure and physicochemical data for compounds 392-426
| Cmpound | Product | Amine | $^1$H NMR; LCMS m/z [M + H]$^+$ |
|---|---|---|---|
| 402 | 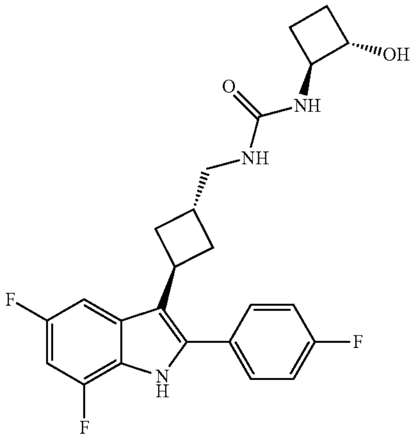 [SMILES: O=C(NC[C@H]1C[C@H](c2c(-c3ccc(F)cc3)[nH]c3c(F)cc(F)cc32)C1)N[C@H]1CC[C@@H]1O] | 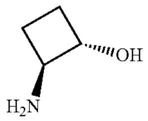 | LCMS m/z 444.15 [M + H]$^+$ |
| 403 | 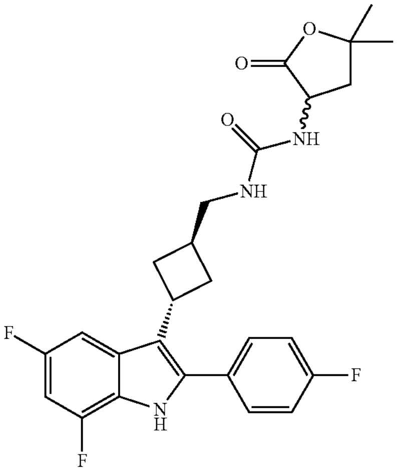 [SMILES: CC1(C)CC(NC(=O)NC[C@H]2C[C@H](c3c(-c4ccc(F)cc4)[nH]c4c(F)cc(F)cc43)C2)C(=O)O1] | 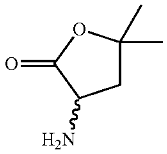 | LCMS m/z 486.14 [M + H]$^+$ |
| 404 | 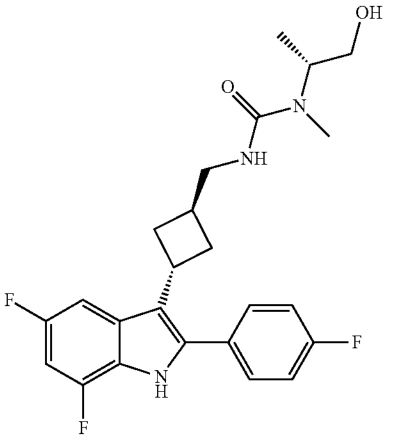 [SMILES: C[C@H](CO)N(C)C(=O)NC[C@H]1C[C@H](c2c(-c3ccc(F)cc3)[nH]c3c(F)cc(F)cc32)C1] | 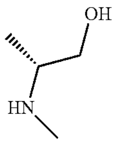 | LCMS m/z 446.17 [M + H]$^+$ |

TABLE 17-continued
| Structure and physicochemical data for compounds 392-426 | | | |
|---|---|---|---|
| Cmpound | Product | Amine | $^1$H NMR; LCMS m/z [M + H]+ |
| 405 | 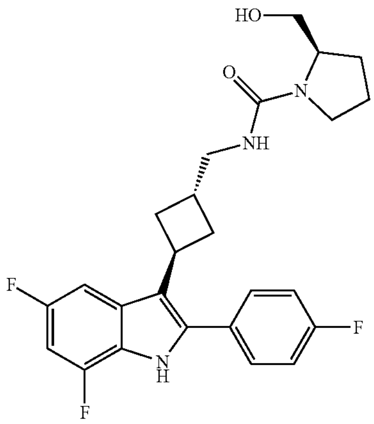 [SMILES: O=C(NC[C@H]1C[C@H](c2c(-c3ccc(F)cc3)[nH]c3c(F)cc(F)cc32)C1)N1CCC[C@@H]1CO] | 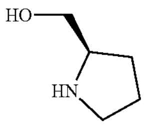 | LCMS m/z 458.16 [M + H]+ |
| 406 | 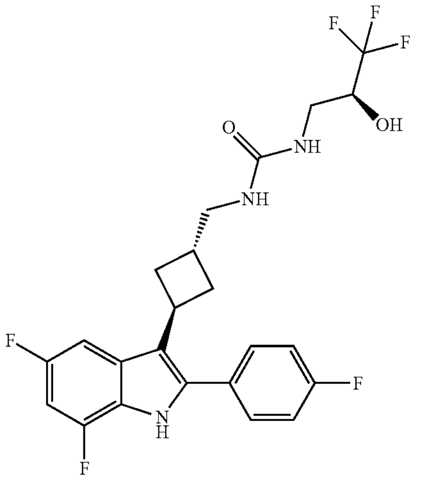 [SMILES: O=C(NC[C@H](O)C(F)(F)F)NC[C@H]1C[C@H](c2c(-c3ccc(F)cc3)[nH]c3c(F)cc(F)cc32)C1] | 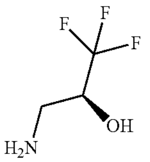 | LCMS m/z 486.14 [M + H]+ |
| 407 | 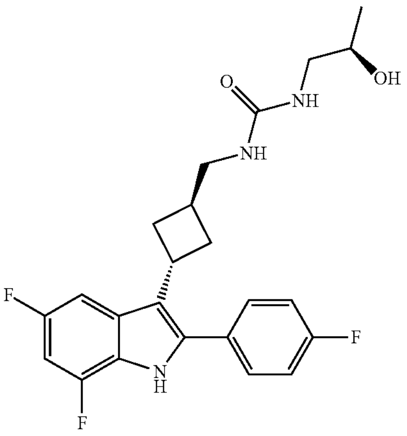 [SMILES: C[C@@H](O)CNC(=O)NC[C@H]1C[C@H](c2c(-c3ccc(F)cc3)[nH]c3c(F)cc(F)cc32)C1] | 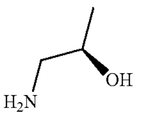 | LCMS m/z 432.4 [M + H]+ |

TABLE 17-continued
| Structure and physicochemical data for compounds 392-426 | | | |
|---|---|---|---|
| Cmpound | Product | Amine | $^1$H NMR; LCMS m/z [M + H]$^+$ |
| 408 | 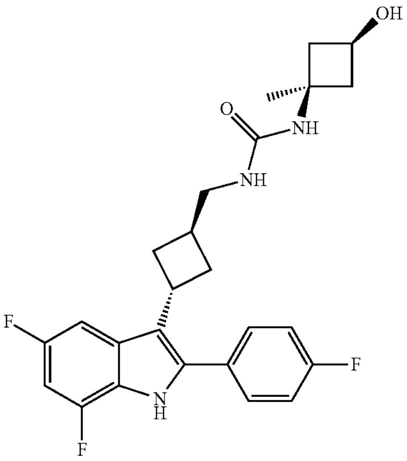 [SMILES: C[C@]1(NC(=O)NC[C@H]2C[C@H](c3c(-c4ccc(F)cc4)[nH]c4c(F)cc(F)cc43)C2)C[C@@H](O)C1] | 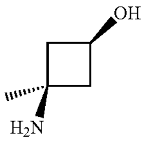 | $^1$H NMR (300 MHz, Chloroform-d) δ 8.12 (s, 1H), 7.53-7.34 (m, 2H), 7.29 (dd, J = 9.5, 2.1 Hz, 1H), 7.25-7.10 (m, 2H), 6.77 (ddd, J = 10.7, 9.4, 2.1 Hz, 1H), 4.94 (s, 3H), 4.29-4.07 (m, 1H), 3.95 (p, J = 9.0 Hz, 1H), 3.40 (d, J = 6.8 Hz, 2H), 2.73-2.47 (m, 5H), 2.47-2.33 (m, 2H), 2.14 (t, J = 9.3 Hz, 2H), 1.38 (s, 3H); LCMS m/z 458.19 |
| 409 | 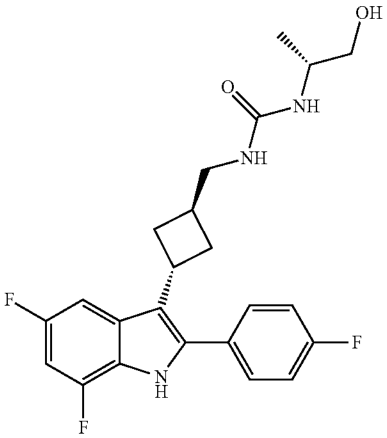 [SMILES: C[C@H](CO)NC(=O)NC[C@H]1C[C@H](c2c(-c3ccc(F)cc3)[nH]c3c(F)cc(F)cc32)C1] | 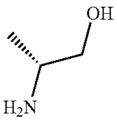 | LCMS m/z 432.16 [M + H]$^+$ |
| 410 | 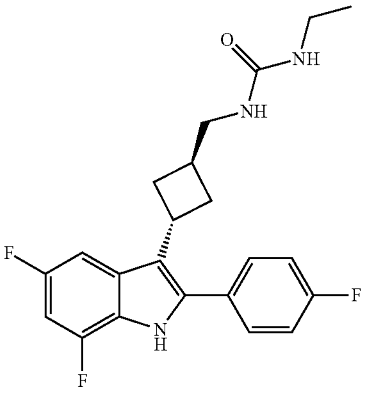 [SMILES: CCNC(=O)NC[C@H]1C[C@H](c2c(-c3ccc(F)cc3)[nH]c3c(F)cc(F)cc32)C1] | 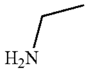 | LCMS m/z 402.16 [M + H]$^+$ |

TABLE 17-continued
| Structure and physicochemical data for compounds 392-426 | | | |
|---|---|---|---|
| Cmpound | Product | Amine | $^1$H NMR; LCMS m/z $[M + H]^+$ |
| 411 | 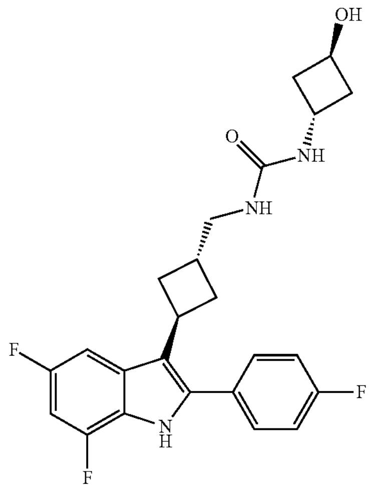 [SMILES: O=C(NC[C@H]1C[C@H](c2c(-c3ccc(F)cc3)[nH]c3c(F)cc(F)cc32)C1)N[C@H]1C[C@H](O)C1] | 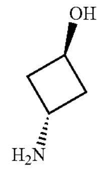 | LCMS m/z 444.02 $[M + H]^+$ |
| 412 | 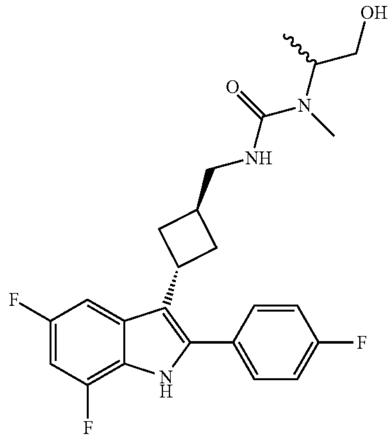 [SMILES: CC(CO)N(C)C(=O)NC[C@H]1C[C@H](c2c(-c3ccc(F)cc3)[nH]c3c(F)cc(F)cc32)C1] | 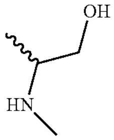 | LCMS m/z 446.17 $[M + H]^+$ |
| 413 | 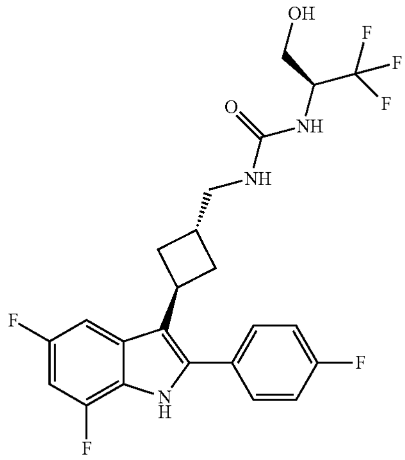 [SMILES: O=C(NC[C@H]1C[C@H](c2c(-c3ccc(F)cc3)[nH]c3c(F)cc(F)cc32)C1)N[C@@H](CO)C(F)(F)F] | 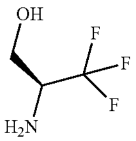 | LCMS m/z 486.04 $[M + H]^+$ |

TABLE 17-continued
Structure and physicochemical data for compounds 392-426
| Cmpound | Product | Amine | $^1$H NMR; LCMS m/z [M + H]$^+$ |
|---|---|---|---|
| 414 | 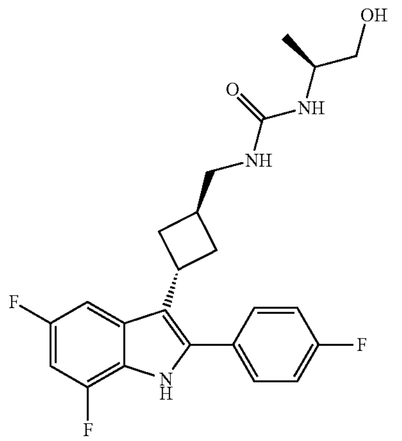 [SMILES: C[C@@H](CO)NC(=O)NC[C@H]1C[C@H](c2c(-c3ccc(F)cc3)[nH]c3c(F)cc(F)cc32)C1] | 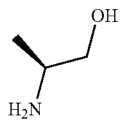 | LCMS m/z 432.4 [M + H]$^+$ |
| 415 | 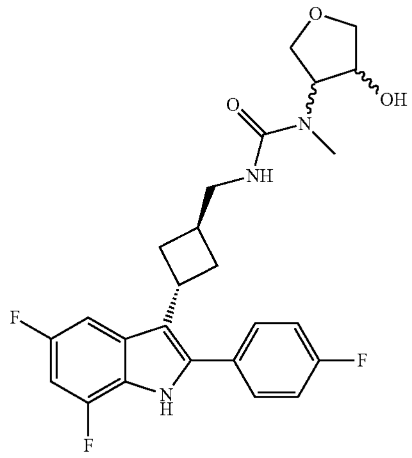 [SMILES: CN(C(=O)NC[C@H]1C[C@H](c2c(-c3ccc(F)cc3)[nH]c3c(F)cc(F)cc32)C1)C1COCC1O] | 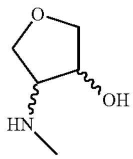 | LCMS m/z 474.18 [M + H]$^+$ |
| 416 | 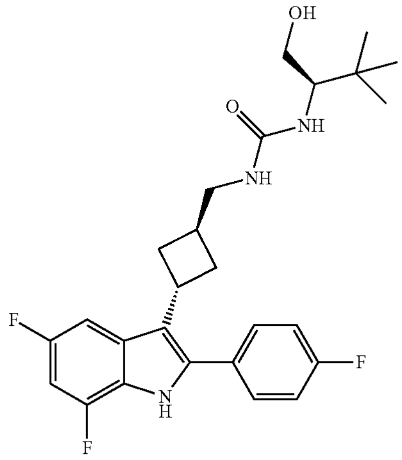 [SMILES: CC(C)(C)[C@H](CO)NC(=O)NC[C@H]1C[C@H](c2c(-c3ccc(F)cc3)[nH]c3c(F)cc(F)cc32)C1] | 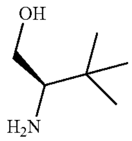 | LCMS m/z 474.08 [M + H]$^+$ |

TABLE 17-continued
| Structure and physicochemical data for compounds 392-426 | | | |
|---|---|---|---|
| Cmpound | Product | Amine | $^1$H NMR; LCMS m/z [M + H]$^+$ |
| 417 | 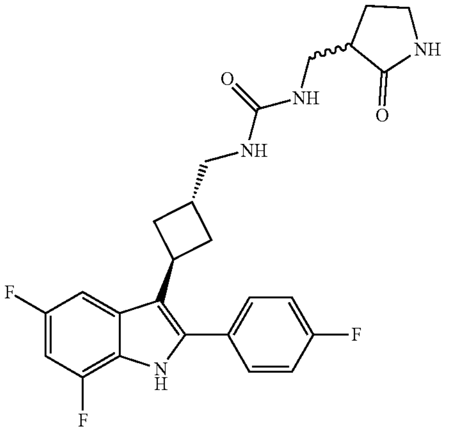 [SMILES: O=C(NCC1CCNC1=O)NC[C@H]1C[C@H](c2c(-c3ccc(F)cc3)[nH]c3c(F)cc(F)cc32)C1] | 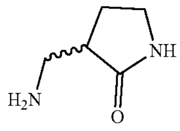 | LCMS m/z 471.15 [M + H]$^+$ |
| 418 | 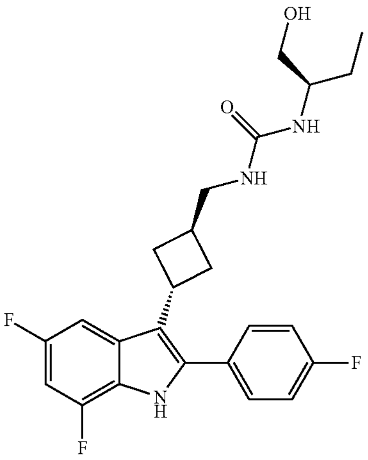 [SMILES: CC[C@H](CO)NC(=O)NC[C@H]1C[C@H](c2c(-c3ccc(F)cc3)[nH]c3c(F)cc(F)cc32)C1] | 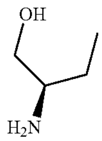 | LCMS m/z 446.33 [M + H]$^+$ |
| 419 | 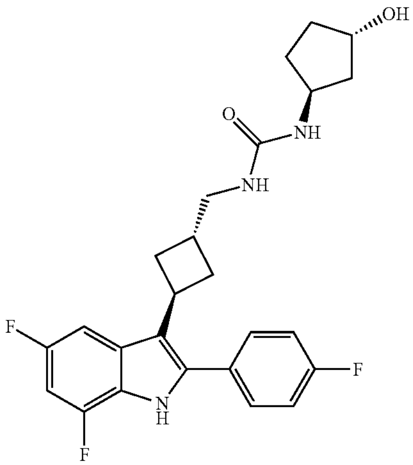 [SMILES: O=C(NC[C@H]1C[C@H](c2c(-c3ccc(F)cc3)[nH]c3c(F)cc(F)cc32)C1)N[C@H]1CC[C@H](O)C1] | 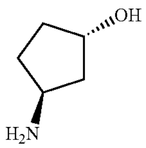 | LCMS m/z 458.16 [M + H]$^+$ |

TABLE 17-continued
| Structure and physicochemical data for compounds 392-426 | | | |
|---|---|---|---|
| Cmpound | Product | Amine | $^1$H NMR; LCMS m/z $[M + H]^+$ |
| 420 | 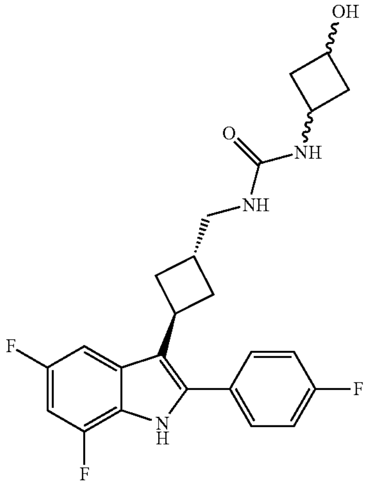 [SMILES: O=C(NC[C@H]1C[C@H](c2c(-c3ccc(F)cc3)[nH]c3c(F)cc(F)cc32)C1)NC1CC(O)C1] | 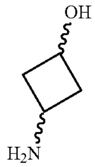 | LCMS m/z 444.15 $[M + H]^+$ |
| 421 | 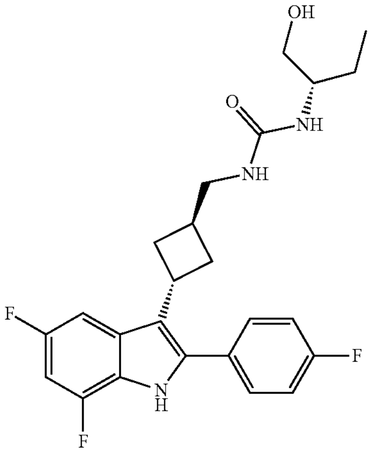 [SMILES: CC[C@@H](CO)NC(=O)NC[C@H]1C[C@H](c2c(-c3ccc(F)cc3)[nH]c3c(F)cc(F)cc32)C1] | 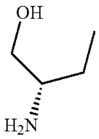 | LCMS m/z 446.17 $[M + H]^+$ |
| 422 | 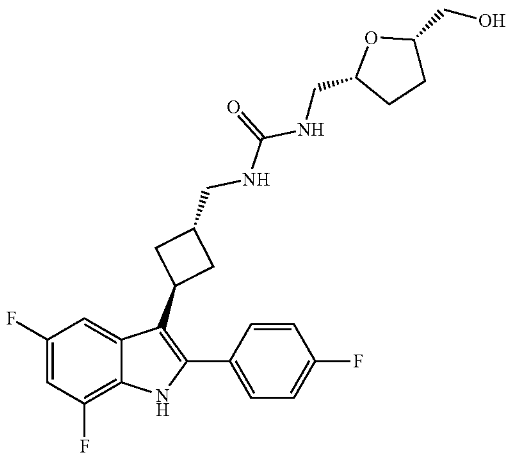 [SMILES: O=C(NC[C@H]1CC[C@@H](CO)O1)NC[C@H]1C[C@H](c2c(-c3ccc(F)cc3)[nH]c3c(F)cc(F)cc32)C1] | 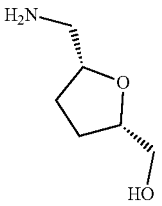 | $^1$H NMR (300 MHz, Chloroform-d) δ 8.05 (s, 1H), 7.43 (dd, J = 8.6, 5.3 Hz, 2H), 7.31 (s, 1H), 7.20 (t, J = 8.6 Hz, 2H), 6.85-6.70 (m, 1H), 4.17-3.88 (m, 3H), 3.84-3.70 (m, 1H), 3.52 (dd, J = 11.8, 4.9 Hz, 1H), 3.43 (d, J = 6.0 Hz, 2H), 3.33 (d, J = 6.4 Hz, 2H), 2.55 (d, J = 7.3 Hz, 3H), 2.23-1.80 (m, 8H), 1.73 (d, J = 17.0 Hz, 2H); LCMS m/z 488.09 |

TABLE 17-continued
| Structure and physicochemical data for compounds 392-426 | | | |
|---|---|---|---|
| Cmpound | Product | Amine | $^1$H NMR; LCMS m/z [M + H]$^+$ |
| 423 | 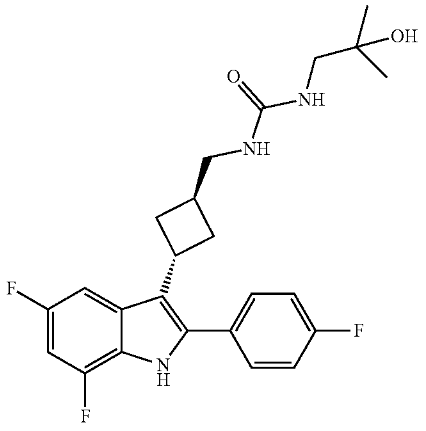 [SMILES: CC(C)(O)CNC(=O)NC[C@H]1C[C@H](c2c(-c3ccc(F)cc3)[nH]c3c(F)cc(F)cc32)C1] | 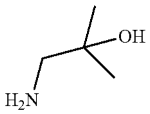 | LCMS m/z 446.35 [M + H]$^+$ |
| 424 | 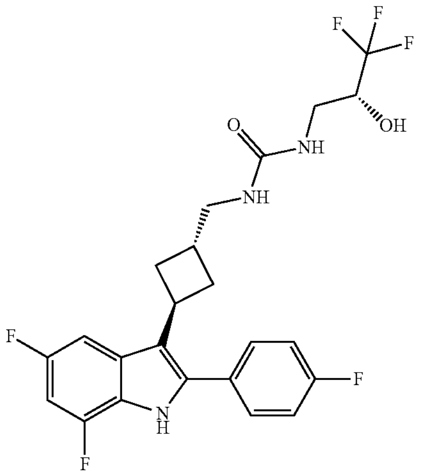 [SMILES: O=C(NC[C@@H](O)C(F)(F)F)NC[C@H]1C[C@H](c2c(-c3ccc(F)cc3)[nH]c3c(F)cc(F)cc32)C1] | 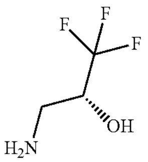 | LCMS m/z 486.27 [M + H]$^+$ |
| 425 | 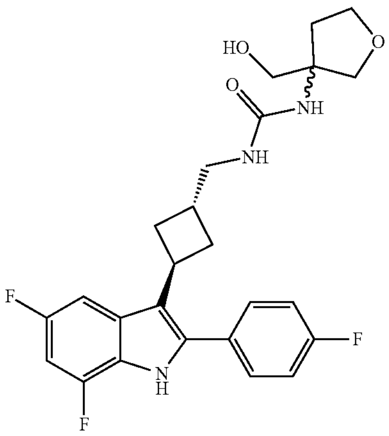 [SMILES: O=C(NC[C@H]1C[C@H](c2c(-c3ccc(F)cc3)[nH]c3c(F)cc(F)cc32)C1)NC1(CO)CCOC1] | 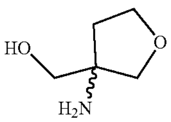 | LCMS m/z 474.18 [M + H]$^+$ |

TABLE 17-continued

Structure and physicochemical data for compounds 392-426

| Cmpound | Product | Amine | $^1$H NMR; LCMS m/z $[M + H]^+$ |
|---|---|---|---|
| 426 | 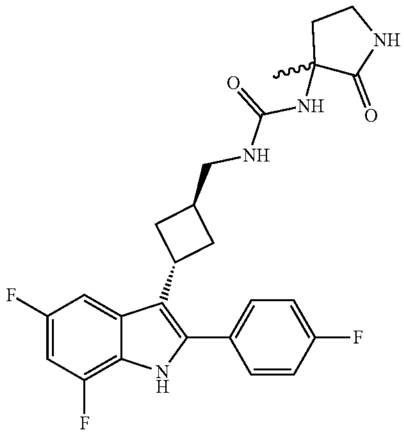 [SMILES: CC1(NC(=O)NC[C@H]2C[C@H](c3c(-c4ccc(F)cc4)[nH]c4c(F)cc(F)cc43)C2)CCNC1=O] | 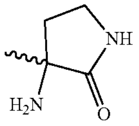 | LCMS m/z 471.15 $[M + H]^+$ |

Compound 427

1-((3-(5,7-difluoro-2-(4fluorophenyl)-1H-indol-3yl) cyclobutyl)methyl)-1-methyl-3-((1-methyl-1H-imidazol-4-yl)methyl)urea (427)

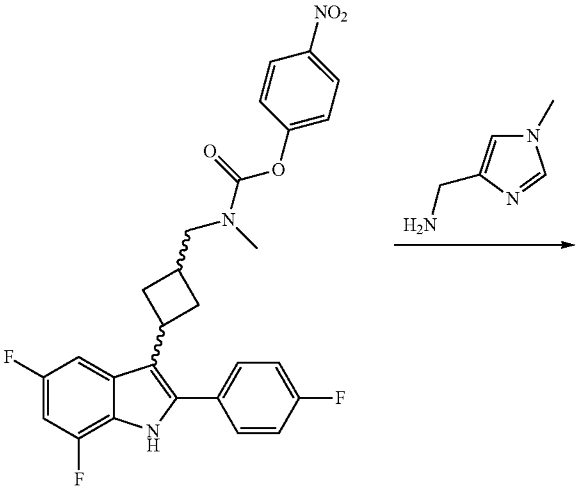

S13

-continued

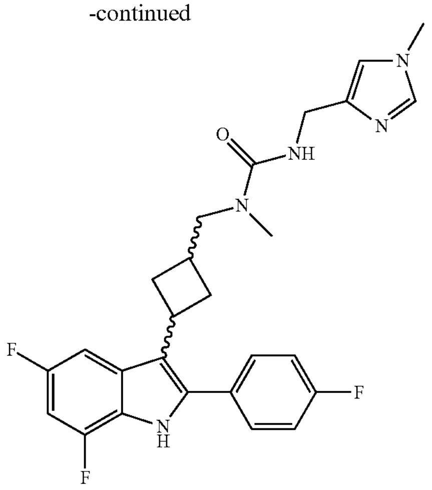

427

Preparation of 1-((3-(5,7-difluoro-2-(4-fluorophenyl)-1H-indol-3-yl)cyclobutyl)methyl)-1-methyl-3-((1-methyl-1H-imidazol-4-yl)methyl)urea (427)

Standard Procedure H: Urea Coupling Method

A solution of 4-nitrophenyl ((3-(5,7-difluoro-2-(4-fluorophenyl)-1H-indol-3-yl)cyclobutyl)methyl)(methyl)carbamate S13 (22 mg, 0.032 mmol), (1-methyl-1H-imidazol-4-yl) methanamine (5 mg, 0.045 mmol), and $Et_3N$ (14 μL, 0.097 mmol) in THF (1 mL) was refluxed for 2 days in a sealed tube, cooled to room temperature and purified by reversed-phase HPLC (Method: C18 Waters Sunfire column (30×150 mm, 5 micron). Gradient: MeCN in $H_2O$ with 0.1% trifluoroacetic acid) to afford the product. 1-((3-(5,7-Difluoro-2-(4-fluorophenyl)-1H-indol-3-yl)cyclobutyl)methyl)-1-methyl-3-((1-methyl-$^1$H-imidazol-4-yl)methyl)urea (5 mg, 26%). LCMS m/z 482.29 $[M+H]^+$.

Compounds 428-432

Compounds 428-432 (see Table 18) were prepared in a single step from compound S13 using standard method described for the synthesis of compound 427. Amines were obtained from commercial sources. Any modifications to methods are noted in Table 18 and accompanying footnotes.

TABLE 18
Structure and physicochemical data for compounds 428-432
| Cmpd | Product | Amine | $^1$H NMR; LCMS mz $[M + H]^+$ |
|---|---|---|---|
| 428 | 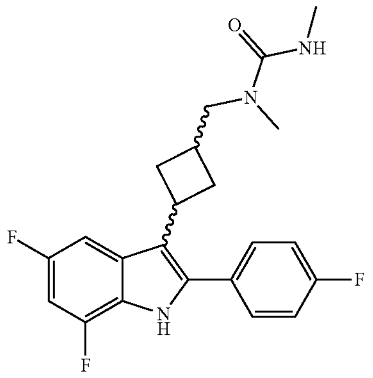 [SMILES: CNC(=O)N(C)CC1CC(c2c(-c3ccc(F)cc3)[nH]c3c(F)cc(F)cc23)C1] | 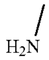 | LCMS m/z 402.16 $[M + H]^+$ |
| 429 | 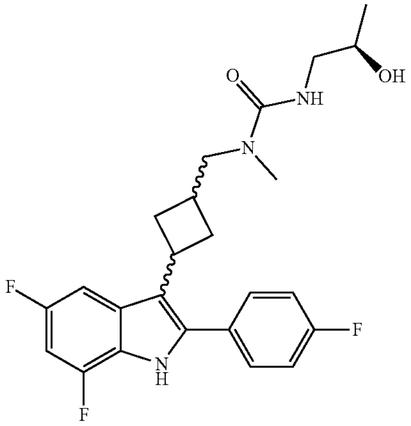 [SMILES: C[C@@H](O)CNC(=O)N(C)CC1CC(c2c(-c3ccc(F)cc3)[nH]c3c(F)cc(F)cc23)C1] | 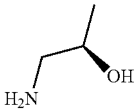 | LCMS m/z 446.27 $[M + H]^+$ |
| 430 | 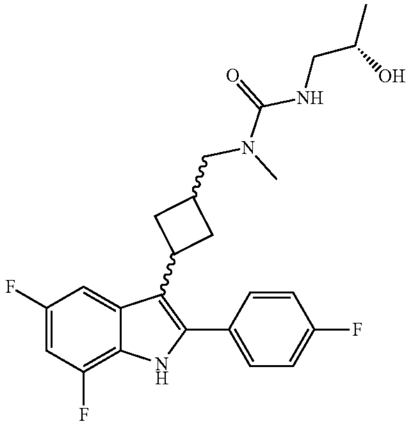 [SMILES: C[C@H](O)CNC(=O)N(C)CC1CC(c2c(-c3ccc(F)cc3)[nH]c3c(F)cc(F)cc23)C1] | 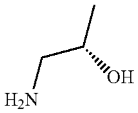 | LCMS m/z 446.17 $[M + H]^+$ |

TABLE 18-continued

| Structure and physicochemical data for compounds 428-432 | | | |
|---|---|---|---|
| Cmpd | Product | Amine | $^1$H NMR; LCMS mz $[M + H]^+$ |
| 431 | 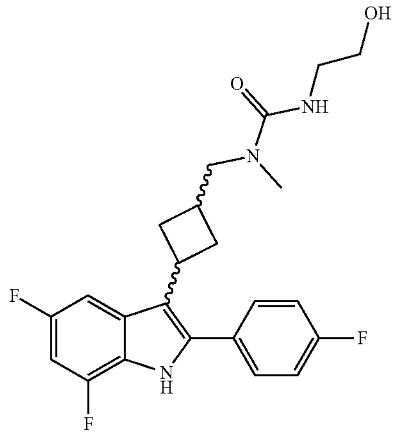 [SMILES: CN(CC1CC(c2c(-c3ccc(F)cc3)[nH]c3c(F)cc(F)cc23)C1)C(=O)NCCO] | 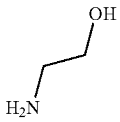 | LCMS m/z 432.19 $[M + H]^+$ |
| 432 | 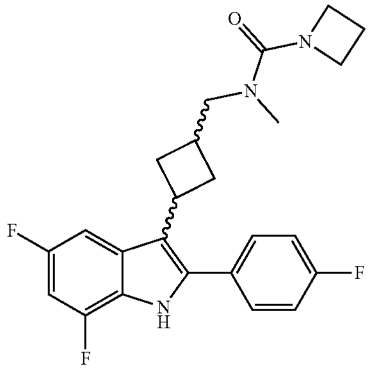 [SMILES: CN(CC1CC(c2c(-c3ccc(F)cc3)[nH]c3c(F)cc(F)cc23)C1)C(=O)N1CCC1] | 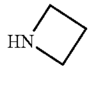 | LCMS m/z 428.19 $[M + H]^+$ |

Compound 433

2-(((3-(5,7-difluoro-2-(4-fluorophenyl)-1H-indol-3-yl)cyclobutyl)methyl)amino)acetamide (433)

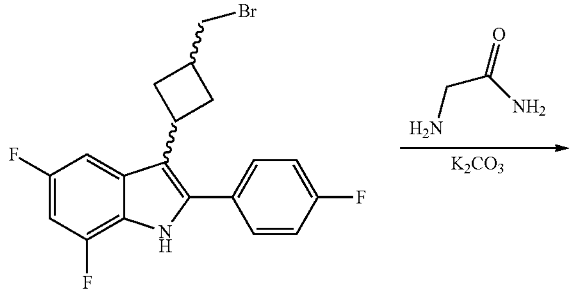

S14

-continued

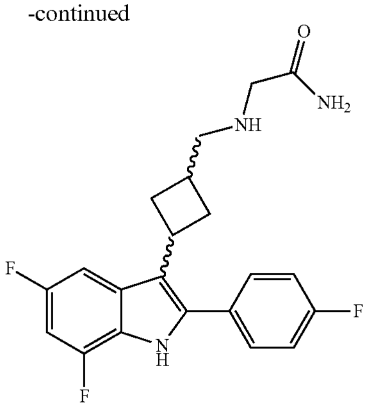

433

Preparation of 2-(((3-(5,7-difluoro-2-(4-fluorophenyl)-1H-indol-3-yl)cyclobutyl)methyl)amino)-acetamide (433)

Standard procedure I: Alkylation Method

A mixture of 3-[3-(bromomethyl)cyclobutyl]-5,7-difluoro-2-(4-fluorophenyl)-1H-indole S14 (25 mg, 0.063 mmol), 2-aminoacetamide (4.7 mg, 0.063 mmol), and $K_2CO3$ (18 mg, 0.13 mmol) in DMF (0.3 mL) was heated to 80° C. for 12 h. The mixture was then diluted with DMSO (~0.5 mL) and purified by reversed-phase HPLC (Method: C18 Waters Sunfire column (30×150 mm, 5 micron). Gradient: MeCN in $H_2O$ with 0.1% trifluoroacetic acid) to afford the product. 2-(((3-(5,7-Difluoro-2-(4-fluorophenyl)-1H-indol-3-yl)cyclobutyl)methyl)amino)acetamide (2 mg, 6%). LCMS m/z 388.19 $[M+H]^+$.

Compounds 434-444

Compounds 434-444 (see Table 19) were prepared in a single step from compound S14 using standard method described for the synthesis of compound 433. Amines were obtained from commercial sources. Any modifications to methods are noted in Table 19 and accompanying footnotes.

TABLE 19

Structure and physicochemical data for compounds 434-444

| Cmpound | Product | Amine | $^1$H NMR; LCMS mz $[M + H]^+$ |
|---|---|---|---|
| 434 | 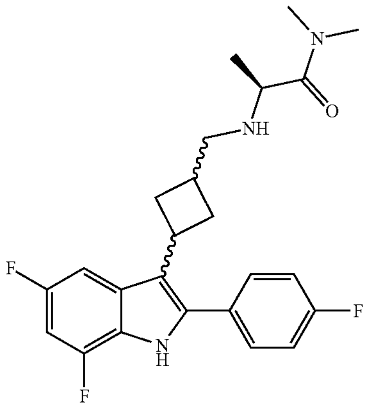 [SMILES: C[C@H](NCC1CC(c2c(-c3ccc(F)cc3)[nH]c3c(F)cc(F)cc23)C1)C(=O)N(C)C] | 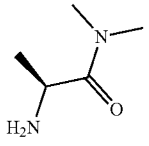 | LCMS m/z 430.21 $[M + H]^+$ |
| 435 | 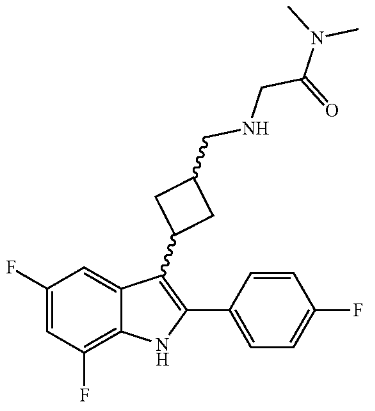 [SMILES: CN(C)C(=O)CNCC1CC(c2c(-c3ccc(F)cc3)[nH]c3c(F)cc(F)cc23)C1] | 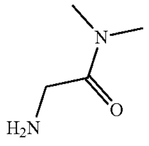 | LCMS m/z 416.2 $[M + H]^+$ |
| 436 | 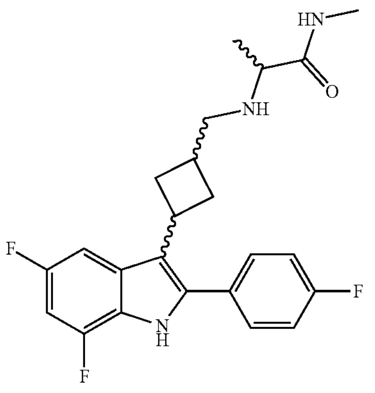 [SMILES: CNC(=O)C(C)NCC1CC(c2c(-c3ccc(F)cc3)[nH]c3c(F)cc(F)cc23)C1] | 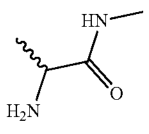 | LCMS m/z 416.21 $[M + H]^+$ |

TABLE 19-continued
| Structure and physicochemical data for compounds 434-444 | | | |
|---|---|---|---|
| Cmpound | Product | Amine | $^1$H NMR; LCMS mz [M + H]$^+$ |
| 437 | 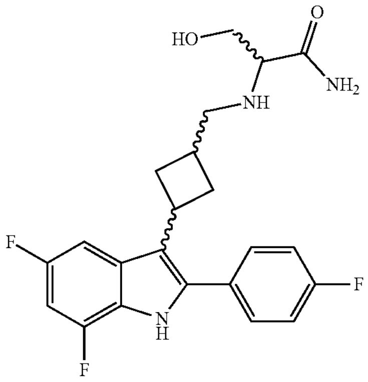 [SMILES: NC(=O)C(CO)NCC1CC(c2c(-c3ccc(F)cc3)[nH]c3c(F)cc(F)cc23)C1] | 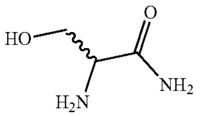 | LCMS m/z 418.19 [M + H]$^+$ |
| 438 | 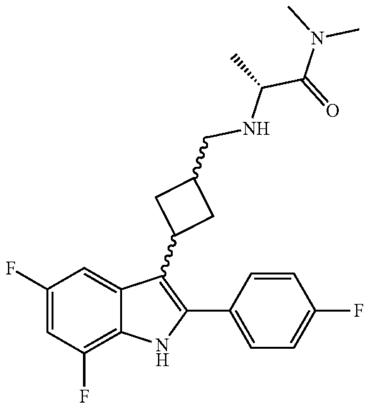 [SMILES: C[C@@H](NCC1CC(c2c(-c3ccc(F)cc3)[nH]c3c(F)cc(F)cc23)C1)C(=O)N(C)C] | 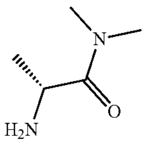 | LCMS m/z 430.21 [M + H]$^+$ |
| 439 | 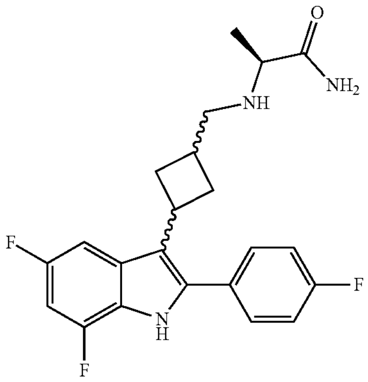 [SMILES: C[C@H](NCC1CC(c2c(-c3ccc(F)cc3)[nH]c3c(F)cc(F)cc23)C1)C(N)=O] | 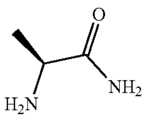 | LCMS m/z 402.2 [M + H]$^+$ |

TABLE 19-continued
| Structure and physicochemical data for compounds 434-444 | | | |
|---|---|---|---|
| Cmpound | Product | Amine | $^{1}$H NMR; LCMS mz [M + H]$^{+}$ |
| 440 | 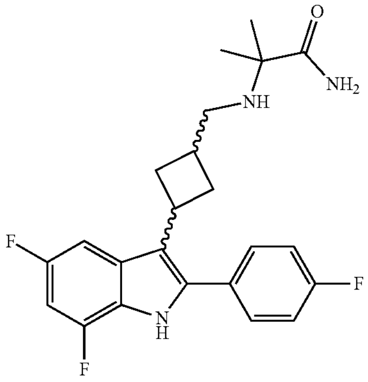 [SMILES: CC(C)(NCC1CC(c2c(-c3ccc(F)cc3)[nH]c3c(F)cc(F)cc23)C1)C(N)=O] | 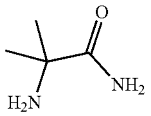 | LCMS m/z 416.21 [M + H]$^{+}$ |
| 441 | 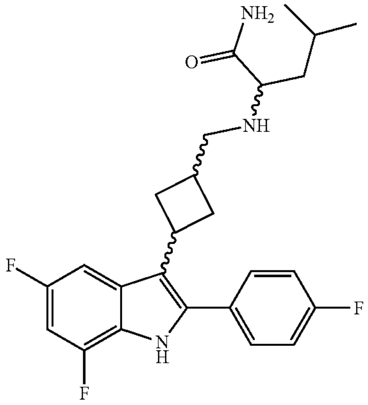 [SMILES: CC(C)CC(NCC1CC(c2c(-c3ccc(F)cc3)[nH]c3c(F)cc(F)cc23)C1)C(N)=O] | 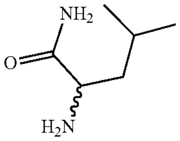 | LCMS m/z 444.46 [M + H]$^{+}$ |
| 442 | 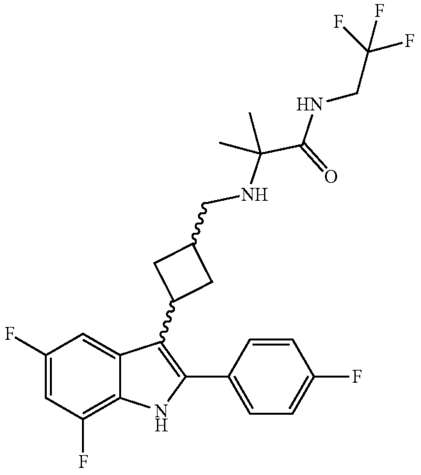 [SMILES: CC(C)(NCC1CC(c2c(-c3ccc(F)cc3)[nH]c3c(F)cc(F)cc23)C1)C(=O)NCC(F)(F)F] | 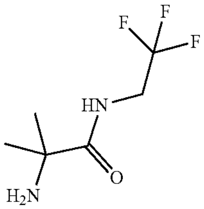 | LCMS m/z 498.19 [M + H]$^{+}$ |

TABLE 19-continued

| Structure and physicochemical data for compounds 434-444 | | | |
|---|---|---|---|
| Cmpound | Product | Amine | $^1$H NMR; LCMS mz $[M + H]^+$ |
| 443 | 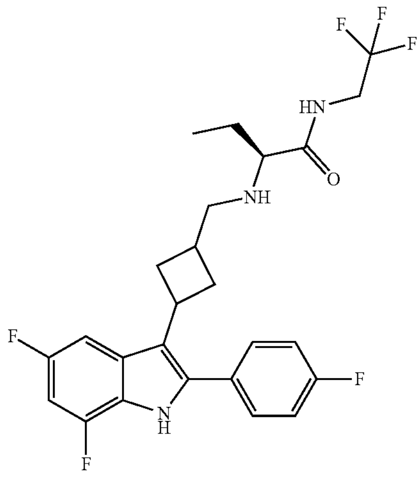 [SMILES: CC[C@H](NCC1CC(c2c(-c3ccc(F)cc3)[nH]c3c(F)cc(F)cc23)C1)C(=O)NCC(F)(F)F] | 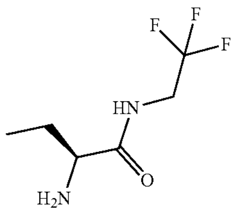 | LCMS m/z 498.19 $[M + H]^+$ |
| 444 | 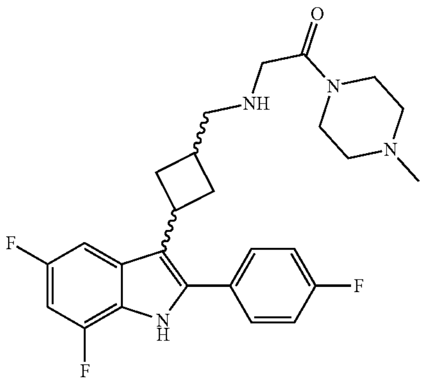 [SMILES: CN1CCN(C(=O)CNCC2CC(c3c(-c4ccc(F)cc4)[nH]c4c(F)cc(F)cc34)C2)CC1] | 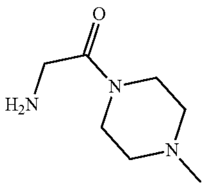 | LCMS m/z 471.22 $[M + H]^+$ |

Compound 445

2-((((1r,3r)-3-(5,7-difluoro-2-(4-fluorophenyl)-1H-indol-3-yl)cyclobutyl)methyl)amino)acetamide (445)

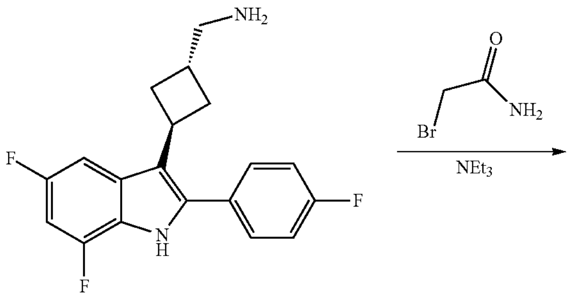

S10

-continued

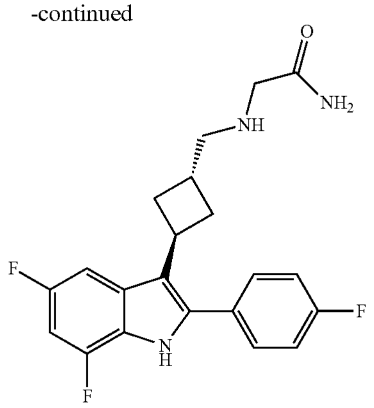

445

Preparation of 2-((((1r,3r)-3-(5,7-difluoro-2-(4-fluorophenyl)-1H-indol-3-yl)cyclobutyl)methyl)-amino) acetamide (445)

Standard procedure J: Alkylation Method

To a solution ((1r,3r)-3-(5,7-difluoro-2-(4-fluorophenyl)-1H-indol-3-yl)cyclobutyl) methanamine S10 (0.050 g, 0.15 mmol) in DMF (4 mL) was added 2-bromoacetamide (22 mg, 0.16 mmol) followed by $Et_3N$ (30 mg, 0.30 mmol). The reaction mixture was stirred at room temperature overnight, filtered and purified by reversed-phase HPLC (Method: C18 Waters Sunfire column (30×150 mm, 5 micron). Gradient: MeCN in $H_2O$ with 0.1% trifluoroacetic acid) to afford the product. 2-((((1r,3r)-3-(5,7-Difluoro-2-(4-fluorophenyl)-1H-indol-3-yl)cyclobutyl)methyl)amino)acetamide (35 mg, 42%). $^1H$ NMR (300 MHz, Acetone-$d_6$) δ 10.70 (s, 1H), 7.61 (ddq, J=8.5, 5.3, 1.7 Hz, 2H), 7.41 (dt, J=9.8, 2.3 Hz, 1H), 7.27 (tdd, J=9.1, 4.1, 2.1 Hz, 2H), 6.84 (ddd, J=11.1, 9.5, 2.0 Hz, 1H), 4.07 (d, J=26.5 Hz, 2H), 3.85 (s, 1H), 3.45 (dd, J=41.3, 7.9 Hz, 2H), 2.95 (s, 1H), 2.78-2.57 (m, 2H), 2.57-2.26 (m, 2H). LCMS m/z 388.16 $[M+H]^+$.

Compounds 446-451

Compounds 446-451 (see Table 20) were prepared in a single step from compound S10 using standard method described for the synthesis of compound 445. Alkyl bromides were obtained from commercial sources. Any modifications to methods are noted in Table 20 and accompanying footnotes.

TABLE 20

Structure and physicochemical data for compounds 446-451

| Cmpd | Product | Alkyl Bromide | $^1H$ NMR; LCMS mz $[M + H]^+$ |
|---|---|---|---|
| 446 | 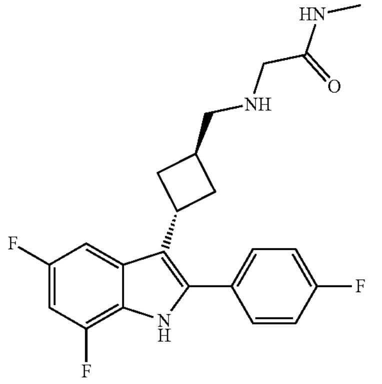 [SMILES: CNC(=O)CNC[C@H]1C[C@H](c2c(-c3ccc(F)cc3)[nH]c3c(F)cc(F)cc32)C1] | 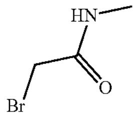 | LCMS m/z 402.07 $[M + H]^+$ |
| 447 | 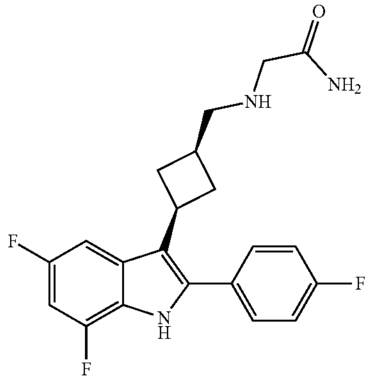 [SMILES: NC(=O)CNC[C@H]1C[C@@H](c2c(-c3ccc(F)cc3)[nH]c3c(F)cc(F)cc32)C1] | 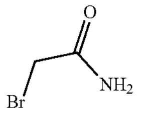 [1] | $^1H$ NMR (300 MHz, Acetone-$d_6$) δ 10.72 (s, 1H), 7.86-7.56 (m, 2H), 7.45-7.19 (m, 3H), 6.84 (tdt, J = 9.5, 3.6, 2.6 Hz, 1H), 4.17-3.91 (m, 3H), 3.83 (ddd, J = 18.1, 10.4, 7.8 Hz, 1H), 3.65-3.42 (m, 1H), 3.36 (d, J = 7.3 Hz, 1H), 2.91-2.54 (m, 3H), 2.50-2.34 (m, 1H), 2.26 (td, J = 11.7, 10.9, 6.4 Hz, 1H); LCMS m/z 388.28 $[M + H]^+$ |
| 448 | 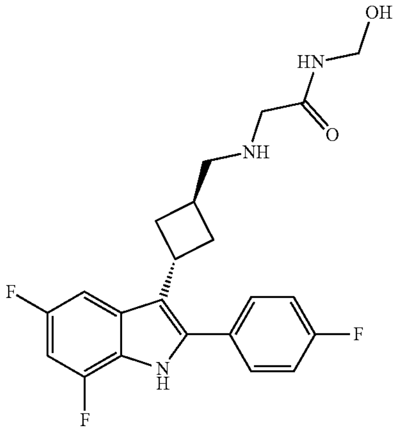 [SMILES: O=C(CNC[C@H]1C[C@H](c2c(-c3ccc(F)cc3)[nH]c3c(F)cc(F)cc32)C1)NCO] | 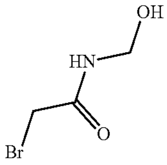 | LCMS m/z 418.19 $[M + H]^+$ |

TABLE 20-continued
| Structure and physicochemical data for compounds 446-451 | | | |
|---|---|---|---|
| Cmpd | Product | Alkyl Bromide | $^1$H NMR; LCMS mz [M + H]$^+$ |
| 449 | 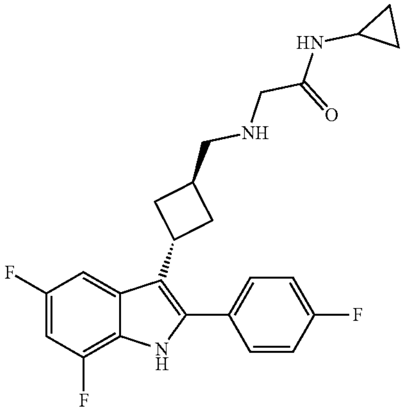 [SMILES: O=C(CNC[C@H]1C[C@H](c2c(-c3ccc(F)cc3)[nH]c3c(F)cc(F)cc32)C1)NC1CC1] | 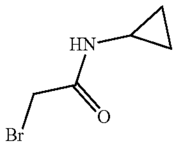 | LCMS m/z 428.19 [M + H]$^+$ |
| 450 | 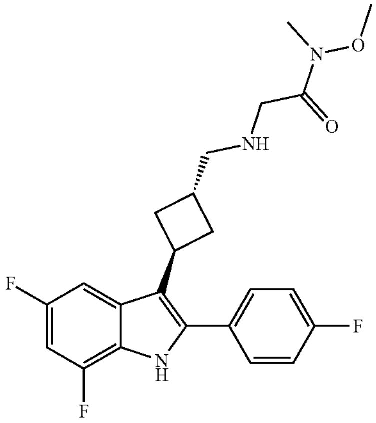 [SMILES: CON(C)C(=O)CNC[C@H]1C[C@H](c2c(-c3ccc(F)cc3)[nH]c3c(F)cc(F)cc32)C1] | 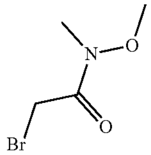 | LCMS m/z 432.2 [M + H]$^+$ |
| 451 | 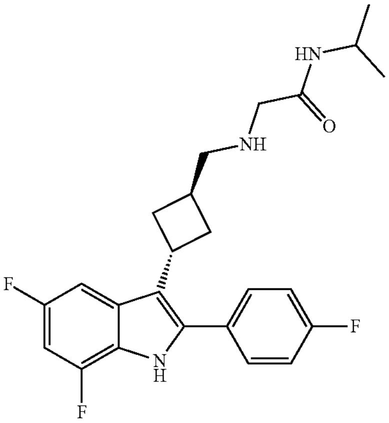 [SMILES: CC(C)NC(=O)CNC[C@H]1C[C@H](c2c(-c3ccc(F)cc3)[nH]c3c(F)cc(F)cc32)C1] | 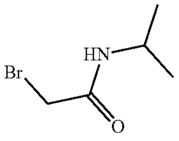 | LCMS m/z 430.21 [M + H]$^+$ |
[1] Compound S11was used as the starting material.

Compound 452

2-[3-[5,7-difluoro-2-(4-fluorophenyl)-1H-indol-3-yl]cyclobutyl]-N-[1-(hydroxymethyl)cyclobutyl]acetamide (452)

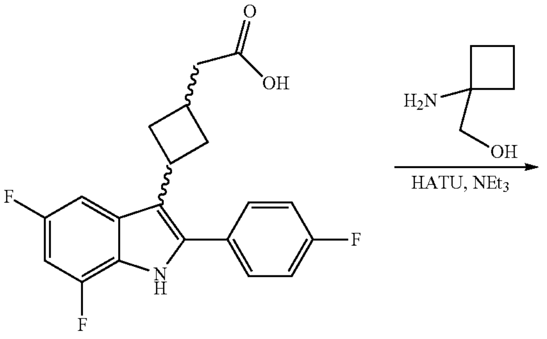

S15

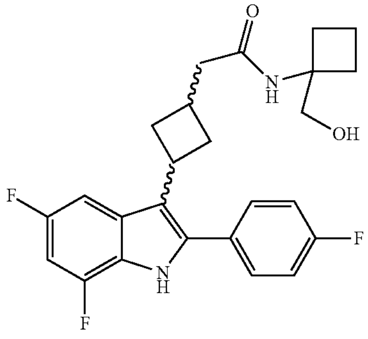

452

Preparation of 2-[3-[5,7-difluoro-2-(4-fluorophenyl)-1H-indol-3-yl]cyclobutyl]-N-[1-(hydroxymethyl)cyclobutyl]acetamide (452)

Standard procedure K: Amide Coupling Method

To a solution of 2-[3-[5,7-difluoro-2-(4-fluorophenyl)-1H-indol-3-yl]cyclobutyl]acetic acid S15 (15 mg, 0.042 mmol) and (1-aminocyclobutyl)methanol (6 mg, 0.06 mmol) in DMSO (1 mL) was added HATU (30 mg, 0.08 mmol) and $Et_3N$ (30 μL, 0.2 mmol). The reaction mixture was allowed to stir for 12 h at ambient temperature. Purification by reversed-phase HPLC (Method: C18 Waters Sunfire column (30×150 mm, 5 micron). Gradient: MeCN in $H_2O$ with 0.1% trifluoroacetic acid) afforded the product. 2-[3-[5,7-Difluoro-2-(4-fluorophenyl)-1H-indol-3-yl]cyclobutyl]-N-[1-(hydroxymethyl)cyclobutyl]acetamide (12.5 mg, 67%). $^1H$ NMR (300 MHz, Chloroform-d) δ 7.51 (ddd, J=8.8, 7.1, 5.3 Hz, 2H), 7.30 (dd, J=9.8, 2.3 Hz, 1H), 7.21 (td, J=9.2, 8.8, 2.2 Hz, 2H), 6.81-6.64 (m, 1H), 3.70 (d, J=6.9 Hz, 3H), 2.63 (d, J=14.2 Hz, 1H), 2.50 (t, J=7.9 Hz, 2H), 2.29 (d, J=7.0 Hz, 2H), 2.27-1.99 (m, 6H), 2.00-1.74 (m, 2H). LCMS m/z 443.18 $[M+H]^+$.

Compounds 453-462

Compounds 453-462 (see Table 21) were prepared in a single step from compound S15 using standard method described for the synthesis of compound 452. Amines were obtained from commercial sources. Any modifications to methods are noted in Table 21 and accompanying footnotes.

TABLE 21

Structure and physicochemical data for compounds 453-462

| Cmpd | Product | Amine | $^1H$ NMR; LCMS m/z $[M + H]^+$ |
|---|---|---|---|
| 453 | 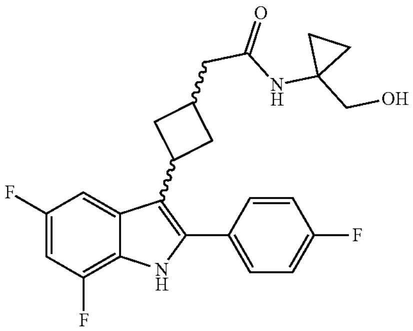 [SMILES: O=C(CC1CC(c2c(-c3ccc(F)cc3)[nH]c3c(F)cc(F)cc23)C1)NC1(CO)CC1] | 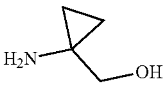 | $^1H$ NMR (300 MHz, Methanol-$d_4$) δ 7.51 (ddd, J = 9.0, 4.6, 2.0 Hz, 2H), 7.34-7.18 (m, 3H), 6.84-6.59 (m, 1H), 4.02-3.66 (m, 1H), 3.55 (s, 1H), 2.59 (t, J = 8.3 Hz, 1H), 2.46 (qd, J = 7.7, 7.2, 2.5 Hz, 2H), 2.28 (d, J = 7.2 Hz, 2H), 2.18-1.89 (m, 3H), 0.84-0.51 (m, 4H); LCMS m/z 429.17 $[M + H]^+$ |

TABLE 21-continued
Structure and physicochemical data for compounds 453-462
| Cmpd | Product | Amine | $^1$H NMR; LCMS m/z $[M + H]^+$ |
|---|---|---|---|
| 454 | 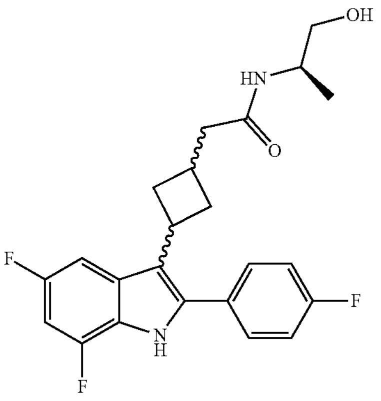 [SMILES: C[C@H](CO)NC(=O)CC1CC(c2c(-c3ccc(F)cc3)[nH]c3c(F)cc(F)cc23)C1] | 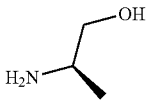 | LCMS m/z 417.75 $[M + H]^+$ |
| 455 | 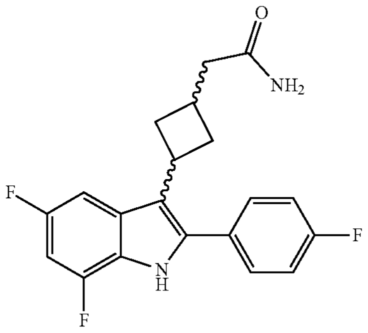 [SMILES: NC(=O)CC1CC(c2c(-c3ccc(F)cc3)[nH]c3c(F)cc(F)cc23)C1] | $NH_3$ | $^1$H NMR (300 MHz, Chloroform-d) δ 7.63-7.45 (m, 2H), 7.40-7.12 (m, 3H), 6.83-6.61 (m, 1H), 4.17-3.45 (m, 1H), 2.75-2.39 (m, 2H), 2.33 (d, J = 7.2 Hz, 2H), 2.24-1.88 (m, 3H); LCMS m/z 359.13 $[M + H]^+$ |
| 456 | 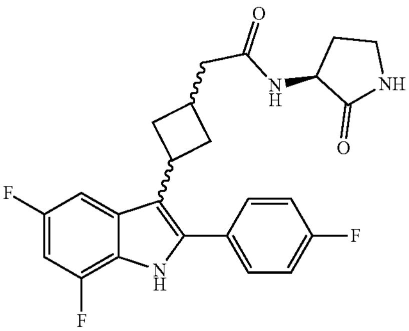 [SMILES: O=C(CC1CC(c2c(-c3ccc(F)cc3)[nH]c3c(F)cc(F)cc23)C1)N[C@H]1CCNC1=O] | 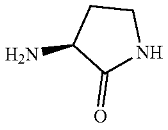 | LCMS m/z 442.13 $[M + H]^+$ |
| 457 | 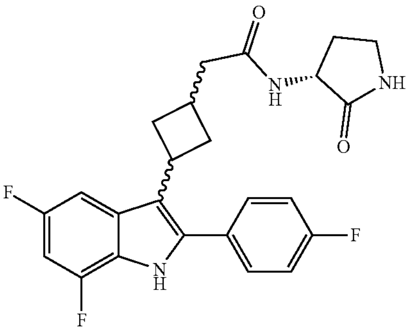 [SMILES: O=C(CC1CC(c2c(-c3ccc(F)cc3)[nH]c3c(F)cc(F)cc23)C1)N[C@@H]1CCNC1=O] | 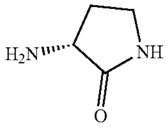 | $^1$H NMR (300 MHz, Chloroform-d) δ 11.58-11.39 (m, 2H), 11.26 (ddd, J = 9.8, 4.1, 2.2 Hz, 1H), 11.20-11.08 (m, 2H), 10.67 (dddd, J = 11.0, 9.6, 3.4, 1.7 Hz, 1H), 8.42 (ddd, J = 10.0, 8.7, 5.1 Hz, 1H), 8.06-7.52 (m, 1H), 7.39-7.27 (m, 4H), 6.58-6.29 (m, 4H), 6.24-5.71 (m, 3H); LCMS m/z 442.13 $[M + H]^+$ |

TABLE 21-continued

| Cmpd | Product | Amine | $^1H$ NMR; LCMS m/z $[M + H]^+$ |
|---|---|---|---|
| Structure and physicochemical data for compounds 453-462 | | | |
| 458 | 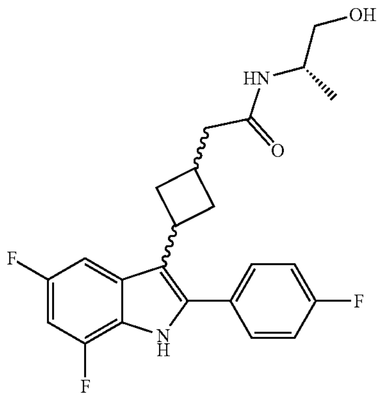 [SMILES: C[C@@H](CO)NC(=O)CC1CC(c2c(-c3ccc(F)cc3)[nH]c3c(F)cc(F)cc23)C1] | 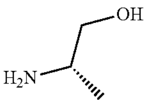 | $^1H$ NMR (300 MHz, Chloroform-d) δ 7.60-7.41 (m, 2H), 7.30 (dt, J = 9.8, 2.5 Hz, 1H), 7.24-7.10 (m, 2H), 6.71 (tdd, J = 9.6, 3.3, 1.6 Hz, 1H), 4.06-3.85 (m, 1H), 3.68 (ddd, J = 18.3, 10.4, 7.7 Hz, 1H), 3.45 (td, J = 10.1, 9.6, 5.2 Hz, 2H), 2.73-2.38 (m, 3H), 2.32 (d, J = 7.0 Hz, 2H), 2.20-1.88 (m, 2H), 1.12 (td, J = 7.2, 1.1 Hz, 3H); LCMS m/z 417.18 $[M + H]^+$ |
| 459 | 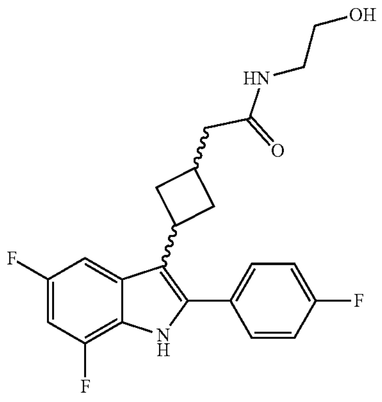 [SMILES: O=C(CC1CC(c2c(-c3ccc(F)cc3)[nH]c3c(F)cc(F)cc23)C1)NCCO] | 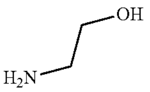 | $^1H$ NMR (300 MHz, Chloroform-d) δ 7.57-7.45 (m, 2H), 7.35-7.14 (m, 3H), 6.72 (ddt, J = 11.0, 9.6, 2.7 Hz, 1H), 4.04-3.64 (m, 1H), 3.56 (h, J = 5.9 Hz, 2H), 3.30-3.23 (m, 2H), 2.77-2.41 (m, 3H), 2.34 (d, J = 7.2 Hz, 2H), 2.22-1.94 (m, 3H); LCMS m/z 403.13 $[M + H]^+$ |
| 460 | 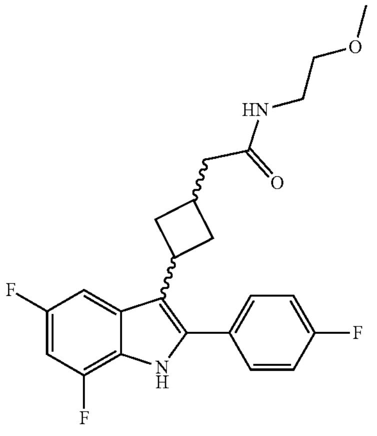 [SMILES: COCCNC(=O)CC1CC(c2c(-c3ccc(F)cc3)[nH]c3c(F)cc(F)cc23)C1] | 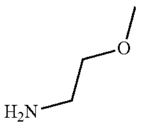 | $^1H$ NMR (300 MHz, Chloroform-d) δ 7.59-7.41 (m, 2H), 7.35-7.17 (m, 3H), 7.10-6.64 (m, 1H), 4.06-3.59 (m, 1H), 3.45-3.37 (m, 2H), 3.30 (d, J = 1.8 Hz, 5H), 2.65-2.43 (m, 2H), 2.32 (d, J = 7.1 Hz, 2H), 2.19-1.87 (m, 3H); LCMS m/z 417.18 $[M + H]^+$ |

TABLE 21-continued

| Structure and physicochemical data for compounds 453-462 | | | |
|---|---|---|---|
| Cmpd | Product | Amine | $^1H$ NMR; LCMS m/z $[M + H]^+$ |
| 461 | 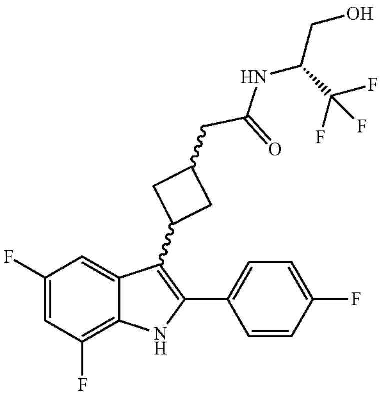 [SMILES: O=C(CC1CC(c2c(-c3ccc(F)cc3)[nH]c3c(F)cc(F)cc23)C1)N[C@H](CO)C(F)(F)F] | 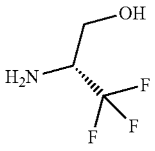 | $^1H$ NMR (300 MHz, Chloroform-d) δ 7.58-7.43 (m, 2H), 7.39-7.28 (m, 1H), 7.27-7.14 (m, 2H), 6.72 (ddd, J = 11.5, 9.6, 2.7 Hz, 1H), 3.79 (dd, J = 11.8, 4.6 Hz, 1H), 3.76-3.58 (m, 1H), 2.70-2.57 (m, 1H), 2.53-2.37 (m, 4H), 2.13 (dd, J = 18.8, 8.9 Hz, 3H); LCMS m/z 471.12 $[M + H]^+$ |
| 462 | 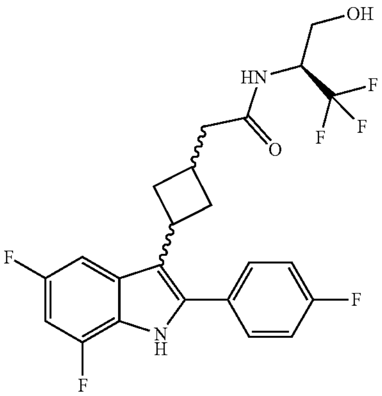 [SMILES: O=C(CC1CC(c2c(-c3ccc(F)cc3)[nH]c3c(F)cc(F)cc23)C1)N[C@@H](CO)C(F)(F)F] | 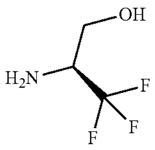 | $^1H$ NMR (300 MHz, Chloroform-d) δ 7.59-7.45 (m, 2H), 7.29 (dd, J = 9.9, 2.2 Hz, 1H), 7.25-7.17 (m, 2H), 6.71 (ddd, J = 11.0, 9.6, 2.1 Hz, 1H), 4.61 (dd, J = 13.7, 6.9 Hz, 1H), 3.79 (dd, J = 11.9, 4.7 Hz, 1H), 3.73-3.59 (m, 1H), 2.73-2.56 (m, 1H), 2.56-2.38 (m, 4H), 2.13 (dd, J = 19.3, 9.5 Hz, 3H); LCMS m/z 471.22 $[M + H]^+$ |

Compound 463

3-[5,7-difluoro-2-(4-fluorophenyl)-1H-indol-3-yl]-N-[(1R)-2-hydroxy-1-methyl-ethyl]cyclopentanecarboxamide (463)

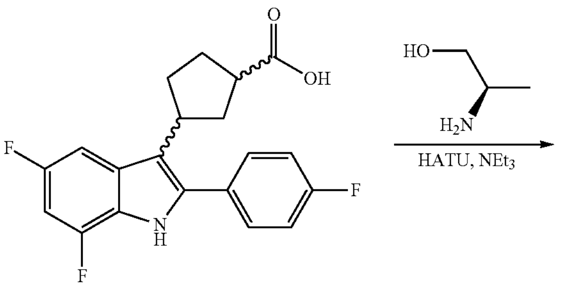

S16

-continued

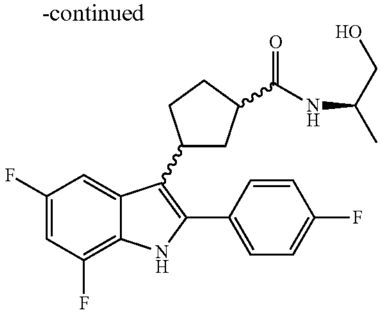

463

Preparation of 3-[5,7-difluoro-2-(4-fluorophenyl)-1H-indol-3-yl]-N-[(1R)-2-hydroxy-1-methyl-ethyl] cyclopentanecarboxamide (463)

To a solution of 3-[5,7-difluoro-2-(4-fluorophenyl)-1H-indol-3-yl]cyclopentanecarboxylic acid S16 (22 mg, 0.061 mmol), (2R)-2-aminopropan-1-ol (7 mg, 0.09 mmol), and HATU (45 mg, 0.12 mmol) in DMSO (1 mL) was added triethylamine (40 μL, 0.3 mmol). The mixture was stirred at room temperature for 12 h. The mixture was purified by reversed-phase HPLC (Method: C18 Waters Sunfire column (30×150 mm, 5 micron). Gradient: MeCN in $H_2O$ with 0.1% trifluoroacetic acid) to afford the product. 3-[5,7-Difluoro-2-(4-fluorophenyl)-1H-indol-3-yl]-N-[(1R)-2-hydroxy-1-methyl-ethyl]cyclopentanecarboxamide (15.8 mg, 62%). LCMS m/z 417.18 $[M+H]^+$.

Compound 464

3-[5,7-difluoro-2-(4-fluorophenyl)-1H-indol-3-yl]-N-ethyl-azetidine-1-carboxamide (464)

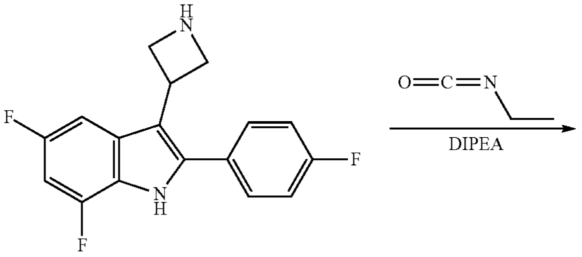

S17

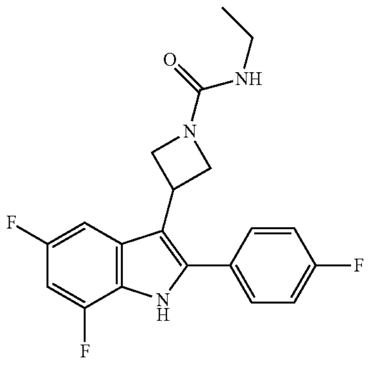

464

Preparation of 3-[5,7-difluoro-2-(4-fluorophenyl)-1H-indol-3-yl]-N-ethyl-azetidine-1-carboxamide (464)

To a solution of 3-(azetidin-3-yl)-5,7-difluoro-2-(4-fluorophenyl)-1H-indole (Trifluoroacetate salt) S17 (12 mg, 0.029 mmol) and isocyanatoethane (10 mg, 0.1 mmol) in DMSO (1 mL) was added DIPEA (20 μL, 0.1 mmol). The mixture was stirred at room temperature for 1 h and purified by reversed-phase HPLC (Method: C18 Waters Sunfire column (30×150 mm, 5 micron). Gradient: MeCN in $H_2O$ with 0.1% trifluoroacetic acid) to afford the product. 3-[5,7-Difluoro-2-(4-fluorophenyl)-1H-indol-3-yl]-N-ethyl-azetidine-1-carboxamide (7 mg, 64%). LCMS m/z 374.14 $[M+H]^+$.

Compound 465

3-(5,7-difluoro-2-(4-fluorophenyl)-1H-indol-3-yl)-N-(2,2-difluoroethyl)azetidine-1-carboxamide (465)

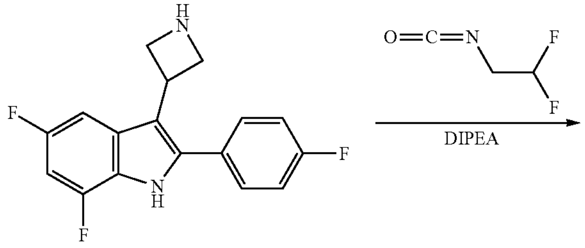

S17

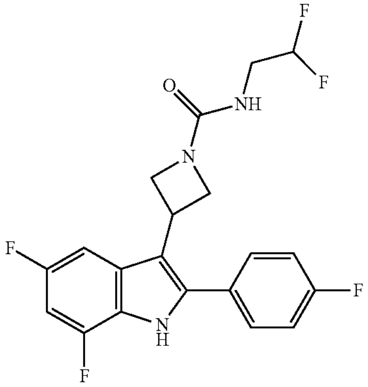

465

Preparation of 3-(5,7-difluoro-2-(4-fluorophenyl)-1H-indol-3-yl)-N-(2,2-difluoroethyl)azetidine-1-carboxamide (465)

To a solution of 3-(azetidin-3-yl)-5,7-difluoro-2-(4-fluorophenyl)-1H-indole (trifluoroacetate salt) S17 (20 mg, 0.05 mmol) and 1,1-difluoro-2-isocyanato-ethane (9 mg, 0.08 mmol) in DMSO (1 mL) was added DIPEA (40 μL, 0.2 mmol). The reaction mixture was allowed to stir for 1 h at ambient temperature and purified by reversed-phase HPLC (Method: C18 Waters Sunfire column (30×150 mm, 5 micron). Gradient: MeCN in $H_2O$ with 0.1% trifluoroacetic acid) to afford the product. 3-(5,7-Difluoro-2-(4-fluorophenyl)-1H-indol-3-yl)-N-(2,2-difluoroethyl)azetidine-1-carboxamide (20.5 mg, 99%). $^1H$ NMR (300 MHz, Methanol-$d_4$) δ 7.60-7.42 (m, 2H), 7.35-7.16 (m, 3H), 6.80 (ddd, J=11.0, 9.6, 2.2 Hz, 1H), 5.88 (tt, J=56.5, 4.2 Hz, 1H), 4.39 (td, J=7.7, 2.2 Hz, 2H), 4.29-3.99 (m, 3H), 3.52 (td, J=14.8, 4.2 Hz, 2H). LCMS m/z 410.07 $[M+H]^+$.

Example 2. Assays for Detecting and Measuring APOL1 Inhibitor Properties of Compounds Acute APOL1 Thallium Assay with Inducible Stable Clones of HEK 293 Cells Apolipoprotein L1 (APOL1) proteins form potassium-permeable cation pores in the plasma membrane. APOL1 risk variants (G1 and G2) induce greater potassium flux than G0 in HEK293 cells. This assay exploits the permeability of thallium (Tl+) through ligand-gated potassium channels. The dye produces a bright fluorescent signal upon binding to Tl+ conducted through potassium channels. The intensity of the Tl+ signal is proportional to the number of potassium channels in the open state. Therefore, it provides a functional indication of the potassium channel activities. During the initial dye-loading step, the Tl+ indicator dye as an acetoxymethyl (AM) ester enters the cells through passive diffusion. Cytoplasm esterases cleave the AM ester and relieve its active thallium-sensitive form. The cells are then stimulated with Tl+. The increase of fluorescence in the assay represents the influx of Tl+ into the cell specifically through the potassium channel (i.e. through APOL1 pores), providing a functional measurement of potassium channel/pore activity. The Thallium assay is conducted with cells expressing G1 APOL1.

Reagents and Materials

APOL1 Cell Line (HEK T-Rex Stable Inducible Cell Line)

HEK T-Rex System

Tetracycline (Tet) inducible mammalian expression system.

Stably express the Tet repressor to regulate transcription.

Expression under the full-length CMV promoter.

APOL1 stable inducible cell line Clone used: G1 DC3.25

Tissue Culture Media

Cell Culture Medium

DMEM+10% FBS+P/S+5 μg/mL blasticidin+1 μg/mL puromycin.

500 mL DMEM+55 mL FBS+5 mL P/S+280 μL blasticidin S HCl (10 mg/mL)+56 μL puromycin (10 mg/mL).

Cell Assay Medium

DMEM with 2% FBS+pen strep.

Reagents:

| | | |
|---|---|---|
| PBS | 7.4 pH<br>no phenol red<br>no sodium pyruvate<br>Concentration: 1X | Gibco Cat. No. 10-010-49 |
| Trypsin | 0.25%/EDTA 2.21 mM in HBSS | Wisent, Cat. No. 325-043-EL |
| DMEM | High Glucose, no sodium pyruvate, with phenol red, with glutamine | GIBCO, Cat. No. 11960-051 |
| FBS | Tet System Approved FBS US Sourced | TakaraCat. No. 631101 |
| HEPES Buffer | 1M | Invitrogen, Cat. No. 15630-080 |
| HBSS | calcium<br>magnesium<br>no phenol red | Life Technologies, Cat. No. 14025-126 |
| DMSO | | |
| Penicillin Streptomycin (P/S) | Sterile filtered for cell culture<br>Concentration: 100X | Wisent, Cat. No. 450-201-EL |
| Puromycin Dihydrochloride | Concentration: 10 mg/mL | Gibco, Cat. No. A11138-03 |
| Blasticidin S HCl | Concentration: 10 mg/mL | Gibco, Cat. No. A11139-03 |
| Ouabain | Prepare 100 mM stock in DMSO<br>aliquot and store at −20° C. | Tocris, Cat. No. 1076 |
| Probenicid | Resuspend in 1 mL HBSS 20 mM HEPES | Invitrogen, Cat. No. P36400 |
| Tetracyclin | Prepare 1 mg/mL stock in $H_2O$<br>aliquot and store at −20° C. | Sigma-Aldrich, Cat. No. T7660 |

Materials

| | |
|---|---|
| Corning ® BioCoat ™ Poly-D-Lysine 384-well black, transparent, flat bottom tissue culture plates | Cat. No. 354663, Lot No. 31616006 |
| Corning ® 384-well microplate, clear polypropylene, round bottom, sterile | Costar Cat. No.: 3656 |
| FLIPR pipette tips, 384-well | Molecular Devices, Cat. No. 9000-0764 |
| FLIPR Potassium Assay Kit | Molecular Devices, Cat. No. R8223 |

Instruments and Equipment

Nuaire cell culture hood, Cat. No. 540-600

37° C./5% CO incubator link to robotic arm, Liconic: STX110

Molecular Devices FLIPR$^{Tetra}$ High throughput cellular screening system, Cat. No. FT0324, Molecular Devices ThermoFisher MultiDrop 384, Cat. No. 5840300

Biotek Microfill, Cat. No. ASF1000A-4145

BioRad TC10 cell counter, Cat. No. 145-0010

Assay Procedures

Cells Scaled Up from Frozen Vials

APOL1 G1 3.25 (HEK293 T-Rex) frozen vials: 5 million cells per vial

Step 1, Day 1: Defrost frozen vial into T-225.

Step 2, Day 5: (when 85% confluent): Split one T-225 at $3\times10^6$ cells per flask.

Step 3, Day 8: Splits cells to set up for the assay plates as described below.

Cell Culture

T-Rex APOL1 HEK cells are split twice per week to keep the confluence state below 85% of the culture flask surface area. Cells can be kept until passage 25.

Cell Culture Medium

DMEM high glucose+10% FBS, +P/S, +5 μg/mL blasticidin, +1 μg/mL puromycin.

500 mL DMEM, +55 mL FBS, +5 mL P/S, +280 μL blasicidin 10 mg/mL, +56 μL Puromycin 10 mg/mL.

Assay Media

Opti-MEM reduced serum medium from Invitrogen.

Day 1

Preparation of Cell Assay Plates

Culture medium is removed from the x $cm^2$ T-flask by aspiration.

The cell monolayer is rinsed with PBS 1× at room temperature. PBS is removed by aspiration.

Cells are trypsinized using Trypsin.

The flasks are incubated at room temperature for 2-3 minutes.

Complete DMEM medium is then added. Cell suspension is then transferred to a 50 mL Falcon polypropylene tube.

Cells are then counted using a Biorad TC10 cell counter and the required amount of cells are centrifuged at 1200 RPM for 5 minutes. Required amount is $1.3\times10^6$ cells/mL APOL1 T-Rex HEK cells.

The pellet is suspended in the assay medium.

Using the MultiDrop, add 20 μL to each well (corresponds to 26000 cells total per well) of a 384-well black, transparent, flat bottom Poly-D coated plate.

Tetracycline as prepared in the following section is added to the cells before plating to induce APOL1 expression.

Plates are left at room temperature for 20 to 30 minutes before incubation at 37° C. and 5% $CO_2$.

Preparation of Tetracyclin

Tetracyclin stock is prepared at 1 mg/mL in $H_2O$, aliquoted and stored at −20° C.

On the day the cells are plated for the assay, the tetracycline working concentration is prepared as follows:

Predilute tetracyclin stock at 100× by transferring 50 μL stock in 5 mL assay media to give 10 μg/mL intermediate stock.

Prepare tetracycline at 4× if added with Biomek to the cell plates or added directly on cells to give a 1× tetracycline concentration according to Table 22 below.

TABLE 22

Concentration of Tetracycline for cell plate.

| Clones | 1X Tet ng/mL | 5X Tet ng/mL | mL predilution | mL diluted cell suspension |
|---|---|---|---|---|
| G1 DC3.25 | 15 | 75 | 0.3 | 39.7 |

Day 2

Preparation of Thallium Loading Dye and Cells Loading FLIPR® Potassium Assay Kit R8223

Preparation of the Loading Buffer:

1. Remove one vial each of Component A (Dye) and Component C (Pluronic) from the freezer, and then equilibrate to room temperature.
2. For the Bulk Kit, prepare 200 mL of 20 mM HEPES plus 1×HBSS, pH 7.4 as Component B.
3. Dissolve the contents of the Component C vial in DMSO, and the mix thoroughly by vortexing.
4. Combine the vial of Component A (dye) with 10 mL of the Component B buffer (HBSS 20 mM HEPES).
5. Combine the Component C solution from step 3 to the Component A solution from step 4, and then mix by vortexing for 1 to 2 minutes until the contents of the vial are dissolved. Note: It is important that the contents are completely dissolved to ensure reproducibility between experiments.
6. For the Bulk Kit only, combine the solution from step 5 with the remaining 190 mL of the prepared Component B buffer, and then mix thoroughly.

For each 10 mL of prepared dye add: 200 μL Probenicid (equals 2.5 mM final in assay plate) and 20 μL of 100 mM ouabain (equals 100 μM in assay plate).

Add 25 μL loading dye to each well of assay plate containing 25 μL. Link to robotic arm (with multidrop or microfill).

Incubate for 30 minutes at room temperature.

Preparation of Drug Plates and Transfer of Compounds to Assay Plates

The compounds are plated in assay ready plates (ARP). The plate layout in FIG. 1 shows the plate map for ARPs for dose response.

The compounds are hydrated with 20 μL HBSS with 20 mM HEPES.

The compounds are transferred to the assay plates 30 minutes after loading thalium sensitive dye as described in Preparation of Thallium Loading Dye described above.

The compounds are diluted by a 1:500 ratio for the final concentration.

The compound transfer is done using FLIPR. Mix: 3 strokes, 10 μl with speed @ 5 μl/sec, Height 20 μl. Aspirate: 10 μl with speed @ 5 μl/sec, Height 5 μl; Tip up speed of 20 mm/sec. Dispense: 10 μl with speed @ 5 l/sec, Height 10 μl; liquid removal speed of 20 mm/sec.

Incubate for 30 minutes at room temperature.

Preparation of the Thallium Sulfate Source Plate

Prepare a 5× thallium sulfate solution in 1× chloride buffer.

For 5 mL of 5× thallium source plate: 1 mL of Chloride Free 5×, 0.5 mL $Tl_2SO_4$ 50 mM (2 mM equivalent final), 3.5 mL $H_2O$.

Dispense in 384-well Corning PP round-bottom plates (Costar, Cat. No. 3656).

Need 12.5 μL per well for each assay plate+dead volume.

Spin briefly.

Start Assay on FLIPR 384-Head

Parameters

Excitation: 470-495 nm; Emission: 515-575 nm.

Addition volume: 12.5 μL.

Aspirate: 12.5 μl with speed @ 20 μl/sec, Height 5 μl; Tip up speed of 20 mm/sec Dispense: 12.5 μl with speed @ 20 μl/sec, Height 40 μl; liquid removal speed of 20 mm/sec.

Read baseline for 10 seconds; transfer 12.5 μL to assay plate.

Read every second for 60 seconds.

Keep tips on head for thallium addition.

Data Analysis

Stat file: Export slope (rate) between 17 and 32 seconds.

Analyze using (No Tet DMSO) and (Tet DMSO) controls (set up Stimulation and neutral controls, respectively).

Calculate percent inhibition thallium rate versus controls.

Data is reported as $IC_{50}$ (half maximum inhibitory concentration) and maximum percent inhibition.

*Trypanosoma brucei brucei* Lysis Assay Using APOL1 Recombinant Protein

*Trypanosoma brucei brucei* is a blood stream parasite to which human, gorillas and baboon are immune due to the presence of the APOL1 protein in their HDL particles. The protein is uptaken by the parasite via the TbHpHb receptor located in its flagellar pocket and is bonded by the Hpr protein contained in the HDL particles which triggers the receptor endocytosis by the parasite.

Following endocytosis, the formed vesicle containing the HDL particle matures from early to late endosome, and subsequently to lysosome. The concomitant pH change in the lumen of the vesicle triggers the insertion of the APOL1 protein into the membrane of the late endosome/lysosome and hereby triggers lysosomal membrane premeabilisation and as a further downstream event, trypanosome lysis. *Trypanosoma brucei brucei* is sensitive to lysis by all three APOL1 variants (G0, G1, and G2).

The *Trypanosoma brucei brucei* lysis assay is a lysis assay of the parasite using recombinant APOL1 protein variant followed by a fluorescent detection method of viability by the addition of AlamarBlue reagent to the assay well, a general metabolic redox indicator (AlamarBlue assay).

Briefly, the AlamarBlue active compound, the resazurin, a blue, water soluble, non-toxic and cell permeable molecule, which can be followed by absorbance, is reduced by various metabolic pathways into resorufin, a red compound which can be followed by either absorbance or fluorescence. The assay allows the calculation of the percent viability (percent of living Trypanosomes remaining in each well) at the end of a lysis relative to the untreated condition by interpolation of fluorescent values (FLU) on a standard curve with a known amount of seeded trypanosome/well.

Reagents and Materials

*Trypanosoma brucei brucei* (ATCC, Cat. No. PRA-382) Lister 427 VSG 221 bloodstream form.

Thaw/Expansion Media (ATCC Medium 2834 Modified HMI-9 Medium)

| | | |
|---|---|---|
| IMDM | 250 mL | 76.3% |
| FBS | 25 mL | 7.63% |
| Serum Plus | 25 mL | 7.63% |
| HMI-9 | 25 mL | 7.63% |
| Hypoxanthine | 2.5 mL | 0.763% |
| | 327.5 mL total | |

Assay Media (No Phenol Red/No FBS): Make on Day of Use

| | | |
|---|---|---|
| IMDM No Phenol Red | 250 mL | 82.6% |
| Serum Plus | 25 mL | 8.26% |
| HMI-9 | 25 mL | 8.26% |
| Hypoxanthine | 2.5 mL | 0.826% |
| | 302.5 mL total | |

HMI-9 (10×)

| | |
|---|---|
| Bathocuproine disulfonic acid | 280 mg |
| Cysteine | 1820 mg |
| Sodium pyruvate (100x) | 100 mL |
| Uracil | 100 mg |
| Cytosine | 100 mg |
| 2-mercaptoethanol | 140 µL |
| Water | 900 mL |
| | 1000 mL total |

Hypoxanthine Stock (100×)-9 (10×)

| | |
|---|---|
| Sodium Hydroxide | 0.8 g |
| Hypoxanthine | 2.72 g |
| Water | 200 mL |
| | 200 mL total |

Media Reagents

| | | |
|---|---|---|
| IMDM | Phenol Red<br>sodium pyruvate<br>L-glutamine<br>25 mM HEPES | Life Technologies, Cat. No. 12440 |
| IMDM | NO Phenol Red<br>sodium pyruvate<br>L-glutamine<br>25 mM HEPES | Life Technologies, Cat. No. 21056 |
| FBS | Heat inactivated | Sigma-Aldrich, Cat. No. F8317-500 mL |
| Serum Plus | medium supplement | Sigma-Aldrich, Cat. No. 14008C |
| Bathocuproine disulfonic acid | | Sigma-Aldrich, Cat. No. B1125-1G |
| Cysteine | | Sigma-Aldrich, Cat. No. C7352-25G |
| Sodium Pyruvate Solution | 100x | Sigma-Aldrich, Cat. No. S8636-100ml |
| Uracil | | Sigma-Aldrich, Cat. No. U1128-25G |
| Cytosine | | Sigma-Aldrich, Cat. No. C3506-1G |
| 2-mercaptoethanol | | Sigma-Aldrich, Cat. No. M3148-25ml |
| Hypoxanthine | | Sigma, Cat. No. H9636 |

-continued

| | |
|---|---|
| Sodium hydroxide | Sigma-Aldrich, Cat. No. S8045-500G |

Materials

| | | |
|---|---|---|
| T75/T175 | Nunc ™ Non-Treated flask<br>Non-TC treated<br>Vented/White lids with filter | T75 Thermo-Fisher Cat. No. 156800<br>T175 Thermo-Fisher Cat. No. 159926 |
| Assay Plates | 384 well black clear bottom<br>Non-sterile<br>Non-TC treated | Corning ® Cat. No. 3762 |
| Polypropylene storage plates | | Corning ® Cat. No. 3656 |
| Plate Lids | Clear universal sterile lids | Thermo-Fisher Cat. No. 250002 |
| Bravo Tips | 30 µL tips for 384 well | Axygen Cat. No. VT-384-31UL-R-S |
| E1-Clip Tip pipette 12 channel adjustable 2-125 µL | | Thermo-Fisher Cat. No. 4672070BT |
| Tips | 125 µL E1-Clip steril filter | Thermo-Fisher Cat. No. 94420153 |
| Tips | 125 µL E1-Clip steril (non-filter) | Thermo-Fisher Cat. No. 94410153 |

Equipment

El-Clip Tip pipette 12 channel adjustable 2-125 µL, Cat. No. 4672070BT

ThermoFisher MultiDrop 384, Cat. No. 5840300

Multidrop

Agilent Bravo, Cat. No. G5409A

Bravo

SpectraMax M5

Assay Ready Plates (ARPs)

ARPs comes in two formats:

10 mM final top concentration with a 2.5 fold dilution down.

5 mM final top concentration with a 3 fold dilution down.

Both have a 10 point Dose response.

0.1% DMSO final in the Black Assay Plate.

Compounds are diluted 1000 fold in the Black Assay Plate.

Each plate is designed for 14 compounds in duplicate.

In the final Black Assay Plate:

| | | |
|---|---|---|
| Column 1: | Media only (no APOL1) | (100% viable) |
| Column 2-23: | 0.05 µg/mL APOL1 (~$EC_{90}$) | (10% viable with APOL1) |
| Column 24: | 0.1 µg/mL APOL1 ($EC_{100}$) | (Approx. 0% viable) |

Assay Procedures

*Trypanosoma brucei brucei* Culture

Protocol A

Step 1, Day 1

That the cells at 35° C. for no more than 2 minutes.

Resuspend one vial gently in 20 mL pre-warmed media and incubate in a T75 flask at 37° C. and 5% $CO_2$.

Do not remove the cryoprotective agent.

Step 2, Day 4

Centrifuge at 800×g for 5 minutes at room temperature.

Resuspend in 1 mL media.

Make a 1:25 fold dilution (10 μL/240 μL media).

Count on a hemocytometer (after adding parasites).

Let sit for 1-2 minutes for the parasites to settle.

Count should be approximately 100 viable motile parasites/16 grid or approximately $25\times10^6$ parasites/flask.

Passage the parasites by adding $1\times10^6$ parasites/T75 flask in 20 mL media.

Passage the parasites by adding $2.33\times10^6$ parasites/T175 flask in 46.6 mL media.

For every T75 flask should make enough for approximately 1.5×384 well assay plates.

For every T175 flask should make enough for approximately 3.8×384 well assay plates.

Step 3, Day 6

Centrifuge at 800×g for 5 minutes.

Resuspend in 3 mL assay media (No phenol red, no FBS) per 75 starting flask.

Resuspend in 7 mL assay media (No phenol red, no FBS) per 175 flask

Make a 1:25 fold dilution.

Count by hemocytometer.

Every T75 flask set up should have approximately $75\times10^6$ parasites/flask (verify doubling time=8.7 hrs±1 hr).

Every T175 flask set up should have approximately $175\times10^6$ parasites/flask (verify doubling time=8.7 hrs±1 hr).

Require $46\times10^6$ parasites per 384 well plate (at 120,000 parasites per well).

Protocol B

Step 1, Day 1

Thaw the cells at 35° C. for not more than 2 minutes.

Resuspend one vial gently in 20 mL of pre-warmed mediate and incubate in a T75 flask at 37° C. and 5% CO2.

Do not remove the cryoprotective agent.

Step 2, Day 2

Centrifuge at 800×g for 5 minutes at room temperature.

Resuspend in 1 mL media.

Make a 1:25 fold dilution (10 μL/240 μL media).

Let sit for 1-2 minutes for the parasites to settle.

Count should be approximately 100 viable motile parasites/16 grid or approximately $8\times10^6$ parasites per flask.

Passage the parasites by adding $1.25\times10^6$ parasites per T75 flask in 20 mL media.

For every T75 flask set up should have approximately 1.5×384 well assay plates.

For every T175 flask setup should have approximately 3.8×384 well assay plates.

Step 3, Day 5

Centrifuge at 800×g for 5 minutes.

Resuspend in 3 mL assay media (No phenol red, no FBS) per T75 starting flask.

Resuspend in 7 mL assay media (No phenol red, no FBS) per T175 starting flask.

Make a 1:25 fold dilution.

Count by hemocytometer.

Every T75 flask should have approximately $75\times10^6$ parasites per flask (verify doubling time: 7.7 hrs±1 hr).

Every T175 flask should have approximately $175\times10^6$ parasites per flask (verify doubling time: 7.7 hrs±1 hr).

Lysis Assay Setup

APOL1 G1 Protein

Remove an aliquot of the 1.2 mg/mL APOL1 protein stock from −70° C.

Determine amount required for the experiment:

Need 11.5 mL of 0.1 μg/mL APOL1 per 384 well plate.

Need 0.5 mL of 0.2 μg/mL APOL1 per 384 well plate for control.

Make initial 1:10 dilution (10 μL/90 μL) into Assay media (now at 120 μg/mL).

Using APOL1 at a final concentration of 0.05 μg/mL for an ~$EC_{50}$. Need to determine this value for each new lot of protein used.

Adding 30 mL/well of 2× APOL1 concentration of 0.1 μg/mL.

Solution A: Measure 8.33 μL (120 μg/mL) in 10 mL for a 0.1 μg/mL 2× stock.

Solution B: Measure 16.67 μL (120 μg/mL) in 10 mL for a 0.2 μg/mL 2× stock control.

Multidrop

Black Assay Plate (384 well black well clear bottom, Cat. No. 3762).

Column 1: Dispense 30 μL/well of Assay media (no APOL1).

Column 2-23: Dispense 30 μL/well of Solution A (0.1 μg/mL APOL1).

Column 24: Dispense 30 μL/well of Solution B (0.2 μg/mL APOL1).

Storage Plate (Polypropylene storage plate, Corning© Cat. No. 3656).

Column 1-24: Dispense 80 μL Assay media (no APOL1) per well (30 mL media/plate).

Bravo: Compound Transfer

Place the storage plate, the Assay Ready Plate (ARP), and Black Assay Plate on the deck.

Transfer 20 μL from the storage plate to the ARP and mix.

Transfer 6 μL from the ARP to the Black Assay Plate and mix.

Black Assay Plates are now ready for Trypanosome addition.

Trypanosome Addition:

Once the Black Assay Plates have compounds added, begin harvesting the Trypanosomes as described in Step 3 of the *Trypanosoma brucei brucei* Culture section.

Count the Trypanosomes and prepare at $5\times10^6$/mL in Assay media (No Phenol red and no FBS).

Requires 9.2 mL of $5\times10^6$ trypanosomes/mL for each 384 well plate ($46\times10^6$/plate).

Add 24 μL of $5\times10^6$ trypanosomes mix to each well of a 384 well plate using the E1-Clip multichannel 12 channel 2-125 μL adjustable pipette.

Once addition is complete, tap plate on the surface to ensure liquid is within each well.

Place plates on the plate shaker for approximately 10 seconds and shake to ensure even distribution and that no drops are left on any edges.

Place in incubator overnight (16 hrs) at 37° C. and 5% $CO_2$.

Each well should include 60 μL:

30 μL 2× APOL1 media, 6 μL of 10× compounds, and 24 μL of trypanosome solution.

AlamarBlue Addition

After 16 hr overnight in incubator, remove required amount of AlamarBlue (2.3 mL/plate) from the bottle stored in refrigerator, and warm up briefly in a 37° C. water bath.

Add 6 μL/well using the E1-Clip Multichannel 12 channel 2-125 μL adjustable pipette.

Protect from light and incubate the plate at 37° C. and 5% $CO_2$ for 2.5 hrs.

Read on SpectraMax (Softmax Pro 6.4 software, excitation: 555 nm, emission: 585 nm)

Potency Data for Compounds 1 to 286

The compounds of Formulae (I), (II), (IIIa), (IIIb), and (IVa) are useful as inhibitors of APOL1 activity. Table 23 below illustrates the $IC_{50}$ of the compounds 1 to 286 using procedures described above (assays described above in Example 2A and 2B). In Table 23 below, the following meanings apply. For $IC_{50}$: "+++" means <0.25 μM; "++" means 0.25 μM to 1.0 μM; "+" means greater than 1.0 μM. N.D.=Not determined.

TABLE 23

Potency data for Compounds 1 to 286

| Compound No. | Thallium Assay ($IC_{50}$) | Trypanosoma Assay ($IC_{50}$) |
|---|---|---|
| 1 | +++ | +++ |
| 2 | +++ | +++ |
| 3 | ++ | ++ |
| 4 | ++ | +++ |
| 5 | ++ | ++ |
| 6 | +++ | +++ |
| 7 | ++ | ++ |
| 8 | +++ | +++ |
| 9 | ++ | ++ |
| 10 | + | + |
| 11 | ++ | +++ |
| 12 | + | ++ |
| 13 | +++ | +++ |
| 14 | ++ | ++ |
| 15 | + | ++ |
| 16 | +++ | +++ |
| 17 | ++ | ++ |
| 18 | + | + |
| 19 | ++ | ++ |
| 20 | + | ++ |
| 21 | ++ | ++ |
| 22 | + | ++ |
| 23 | ++ | ++ |
| 24 | + | + |
| 25 | ++ | +++ |
| 26 | ++ | ++ |
| 27 | +++ | +++ |
| 28 | ++ | + |
| 29 | + | ++ |
| 30 | + | + |
| 31 | +++ | ++ |
| 32 | +++ | +++ |
| 33 | ++ | + |
| 34 | + | ++ |
| 35 | + | ++ |
| 36 | +++ | +++ |
| 37 | + | ++ |
| 38 | + | ++ |
| 39 | + | + |
| 40 | ++ | + |
| 41 | + | + |
| 42 | + | + |
| 43 | N.D. | N.D. |
| 44 | + | + |
| 45 | ++ | +++ |
| 46 | +++ | +++ |
| 47 | ++ | +++ |
| 48 | +++ | +++ |
| 49 | + | + |

TABLE 23-continued

Potency data for Compounds 1 to 286

| Compound No. | Thallium Assay ($IC_{50}$) | Trypanosoma Assay ($IC_{50}$) |
|---|---|---|
| 50 | + | + |
| 51 | ++ | ++ |
| 52 | ++ | ++ |
| 53 | + | + |
| 54 | +++ | +++ |
| 55 | + | + |
| 56 | ++ | ++ |
| 57 | + | + |
| 58 | ++ | ++ |
| 59 | ++ | ++ |
| 60 | + | ++ |
| 61 | + | + |
| 62 | ++ | + |
| 63 | + | + |
| 64 | + | + |
| 65 | ++ | ++ |
| 66 | + | + |
| 67 | + | + |
| 68 | ++ | ++ |
| 69 | + | + |
| 70 | + | + |
| 71 | ++ | +++ |
| 72 | + | + |
| 73 | + | ++ |
| 74 | ++ | ++ |
| 75 | ++ | +++ |
| 76 | + | + |
| 77 | + | + |
| 78 | +++ | +++ |
| 79 | +++ | +++ |
| 80 | + | + |
| 81 | ++ | ++ |
| 82 | ++ | ++ |
| 83 | + | + |
| 84 | + | ++ |
| 85 | ++ | +++ |
| 86 | + | + |
| 87 | + | + |
| 88 | + | + |
| 89 | + | + |
| 90 | + | ++ |
| 91 | + | + |
| 92 | + | ++ |
| 93 | + | + |
| 94 | + | + |
| 95 | + | + |
| 96 | + | + |
| 97 | + | + |
| 98 | + | + |
| 99 | + | + |
| 100 | + | + |
| 101 | + | ++ |
| 102 | + | + |
| 103 | + | + |
| 104 | ++ | +++ |
| 105 | + | ++ |
| 106 | + | + |
| 107 | + | ++ |
| 108 | + | + |
| 109 | + | + |
| 110 | + | ++ |
| 111 | + | ++ |
| 112 | + | + |
| 113 | + | + |
| 114 | + | + |
| 115 | ++ | +++ |
| 116 | + | + |
| 117 | + | ++ |
| 118 | + | + |
| 119 | + | + |
| 120 | + | + |
| 121 | + | + |
| 122 | + | + |
| 123 | + | ++ |
| 124 | ++ | ++ |

TABLE 23-continued

| Potency data for Compounds 1 to 286 | | |
|---|---|---|
| Compound No. | Thallium Assay ($IC_{50}$) | Trypanosoma Assay ($IC_{50}$) |
| 125 | +++ | +++ |
| 126 | + | + |
| 127 | + | ++ |
| 128 | + | + |
| 129 | ++ | +++ |
| 130 | + | + |
| 131 | + | + |
| 132 | + | + |
| 133 | + | + |
| 134 | + | + |
| 135 | + | + |
| 136 | + | + |
| 137 | + | + |
| 138 | + | ++ |
| 139 | ++ | ++ |
| 140 | + | + |
| 141 | + | ++ |
| 142 | ++ | +++ |
| 143 | + | + |
| 144 | ++ | ++ |
| 145 | + | ++ |
| 146 | + | ++ |
| 147 | + | + |
| 148 | + | + |
| 149 | ++ | +++ |
| 150 | + | ++ |
| 151 | + | + |
| 152 | + | + |
| 153 | ++ | +++ |
| 154 | + | + |
| 155 | + | ++ |
| 156 | + | + |
| 157 | + | + |
| 158 | + | ++ |
| 159 | + | + |
| 160 | ++ | +++ |
| 161 | + | ++ |
| 162 | ++ | ++ |
| 163 | ++ | +++ |
| 164 | ++ | +++ |
| 165 | +++ | +++ |
| 166 | +++ | +++ |
| 167 | ++ | ++ |
| 168 | ++ | +++ |
| 169 | ++ | +++ |
| 170 | ++ | +++ |
| 171 | ++ | +++ |
| 172 | ++ | +++ |
| 173 | +++ | +++ |
| 174 | + | ++ |
| 175 | ++ | ++ |
| 176 | ++ | +++ |
| 177 | ++ | ++ |
| 178 | + | ++ |
| 179 | + | ++ |
| 180 | + | + |
| 181 | ++ | ++ |
| 182 | + | + |
| 183 | ++ | ++ |
| 184 | ++ | ++ |
| 185 | ++ | ++ |
| 186 | +++ | +++ |
| 187 | + | + |
| 188 | ++ | ++ |
| 189 | + | + |
| 190 | ++ | +++ |
| 191 | ++ | +++ |
| 192 | + | +++ |
| 193 | ++ | ++ |
| 194 | +++ | +++ |
| 195 | +++ | +++ |
| 196 | ++ | +++ |
| 197 | ++ | +++ |
| 198 | ++ | +++ |
| 199 | ++ | ++ |

TABLE 23-continued

| Potency data for Compounds 1 to 286 | | |
|---|---|---|
| Compound No. | Thallium Assay ($IC_{50}$) | Trypanosoma Assay ($IC_{50}$) |
| 200 | +++ | +++ |
| 201 | +++ | +++ |
| 202 | ++ | +++ |
| 203 | ++ | ++ |
| 204 | ++ | +++ |
| 205 | + | + |
| 206 | ++ | +++ |
| 207 | + | + |
| 208 | + | + |
| 209 | + | + |
| 210 | + | ++ |
| 211 | ++ | ++ |
| 212 | + | ++ |
| 213 | + | + |
| 214 | ++ | ++ |
| 215 | + | + |
| 216 | + | + |
| 217 | + | ++ |
| 218 | ++ | +++ |
| 219 | ++ | +++ |
| 220 | + | ++ |
| 221 | +++ | +++ |
| 222 | ++ | +++ |
| 223 | + | +++ |
| 224 | + | + |
| 225 | + | ++ |
| 226 | +++ | N.D. |
| 227 | + | ++ |
| 228 | + | + |
| 229 | +++ | N.D. |
| 230 | +++ | N.D. |
| 231 | + | N.D. |
| 232 | + | N.D. |
| 233 | + | N.D. |
| 234 | + | N.D. |
| 235 | N.D. | N.D. |
| 236 | + | N.D. |
| 237 | ++ | N.D. |
| 238 | ++ | N.D. |
| 239 | + | N.D. |
| 240 | ++ | N.D. |
| 241 | + | N.D. |
| 242 | + | N.D. |
| 243 | + | N.D. |
| 244 | + | N.D. |
| 245 | + | N.D. |
| 246 | + | N.D. |
| 247 | + | N.D. |
| 248 | + | N.D. |
| 249 | + | N.D. |
| 250 | + | N.D. |
| 251 | ++ | N.D. |
| 252 | + | N.D. |
| 253 | + | N.D. |
| 254 | + | N.D. |
| 255 | + | N.D. |
| 256 | ++ | N.D. |
| 257 | + | N.D. |
| 258 | + | N.D. |
| 259 | + | N.D. |
| 260 | ++ | N.D. |
| 261 | + | N.D. |
| 262 | + | N.D. |
| 263 | ++ | N.D. |
| 264 | + | N.D. |
| 265 | + | N.D. |
| 266 | + | N.D. |
| 267 | + | N.D. |
| 268 | + | N.D. |
| 269 | + | N.D. |
| 270 | + | N.D. |
| 271 | ++ | N.D. |
| 272 | + | N.D. |
| 273 | ++ | N.D. |
| 274 | + | N.D. |

TABLE 23-continued

| Potency data for Compounds 1 to 286 | | |
|---|---|---|
| Compound No. | Thallium Assay ($IC_{50}$) | Trypanosoma Assay ($IC_{50}$) |
| 275 | + | N.D. |
| 276 | ++ | N.D. |
| 277 | + | N.D. |
| 278 | ++ | ++ |
| 279 | ++ | N.D. |
| 280 | +++ | N.D. |
| 281 | +++ | N.D. |
| 282 | ++ | N.D. |
| 283 | ++ | N.D. |
| 284 | ++ | N.D. |
| 285 | +++ | N.D. |
| 286 | +++ | N.D. |

Potency Data for Compounds 287 to 465

The compounds of Formulae (I), (Ia), (II), (IIIa), (IIIb), (IV), (Va), and (Vb) are useful as inhibitors of APOL1 activity. Table 24 below illustrates the $IC_{50}$ of Compounds 287 to 465 using procedures described above (assays described above in Example 2A and 2B). In Table 24 below, the following meanings apply. For $IC_{50}$: "+++" means <0.25 μM; "++" means between 0.25 M and 1.0 μM; "+" means greater than 1.0 μM. N.D.=Not determined.

TABLE 24

| Potency data for Compounds 287 to 465 | | |
|---|---|---|
| Compound No. | Thallium Assay ($IC_{50}$) | Trypanosoma Assay ($IC_{50}$) |
| 287 | + | N.D. |
| 288 | + | N.D. |
| 289 | ++ | N.D. |
| 290 | + | N.D. |
| 291 | ++ | N.D. |
| 292 | + | N.D. |
| 293 | + | N.D. |
| 294 | + | N.D. |
| 295 | ++ | N.D. |
| 296 | + | N.D. |
| 297 | + | N.D. |
| 298 | + | N.D. |
| 299 | ++ | N.D. |
| 300 | + | N.D. |
| 301 | + | N.D. |
| 302 | + | N.D. |
| 303 | + | N.D. |
| 304 | + | N.D. |
| 305 | + | N.D. |
| 306 | + | N.D. |
| 307 | + | N.D. |
| 308 | + | N.D. |
| 309 | + | N.D. |
| 310 | + | N.D. |
| 311 | + | N.D. |
| 312 | + | N.D. |
| 313 | + | N.D. |
| 314 | + | N.D. |
| 315 | + | N.D. |
| 316 | + | N.D. |
| 317 | + | N.D. |
| 318 | + | N.D. |
| 319 | + | N.D. |
| 320 | + | N.D. |
| 321 | + | N.D. |
| 322 | + | N.D. |
| 323 | + | N.D. |
| 324 | + | N.D. |
| 325 | + | N.D. |
| 326 | + | N.D. |
| 327 | + | N.D. |
| 328 | + | N.D. |

TABLE 24-continued

| Potency data for Compounds 287 to 465 | | |
|---|---|---|
| Compound No. | Thallium Assay ($IC_{50}$) | Trypanosoma Assay ($IC_{50}$) |
| 329 | + | N.D. |
| 330 | + | N.D. |
| 331 | + | N.D. |
| 332 | + | N.D. |
| 333 | + | N.D. |
| 334 | + | N.D. |
| 335 | + | N.D. |
| 336 | + | N.D. |
| 337 | + | N.D. |
| 338 | + | N.D. |
| 339 | + | N.D. |
| 340 | + | N.D. |
| 341 | + | N.D. |
| 342 | + | N.D. |
| 343 | + | N.D. |
| 344 | + | N.D. |
| 345 | + | N.D. |
| 346 | + | N.D. |
| 347 | + | N.D. |
| 348 | N.D. | N.D. |
| 349 | +++ | N.D. |
| 350 | ++ | N.D. |
| 351 | ++ | N.D. |
| 352 | ++ | N.D. |
| 353 | ++ | N.D. |
| 354 | ++ | N.D. |
| 355 | ++ | N.D. |
| 356 | ++ | N.D. |
| 357 | ++ | N.D. |
| 358 | ++ | N.D. |
| 359 | ++ | N.D. |
| 360 | ++ | N.D. |
| 361 | + | N.D. |
| 362 | + | N.D. |
| 363 | + | N.D. |
| 364 | + | N.D. |
| 365 | + | N.D. |
| 366 | + | N.D. |
| 367 | + | N.D. |
| 368 | + | N.D. |
| 369 | + | N.D. |
| 370 | + | N.D. |
| 371 | + | N.D. |
| 372 | + | N.D. |
| 373 | + | N.D. |
| 374 | + | N.D. |
| 375 | + | N.D. |
| 376 | + | N.D. |
| 377 | + | N.D. |
| 378 | + | N.D. |
| 379 | + | N.D. |
| 380 | + | N.D. |
| 381 | + | N.D. |
| 382 | + | N.D. |
| 383 | + | N.D. |
| 384 | + | N.D. |
| 385 | + | N.D. |
| 386 | + | N.D. |
| 387 | + | N.D. |
| 388 | + | N.D. |
| 389 | + | N.D. |
| 390 | + | N.D. |
| 391 | ++ | N.D. |
| 392 | + | N.D. |
| 393 | + | N.D. |
| 394 | + | N.D. |
| 395 | + | N.D. |
| 396 | + | N.D. |
| 397 | + | N.D. |
| 398 | + | N.D. |
| 399 | + | N.D. |
| 400 | + | N.D. |
| 401 | + | N.D. |
| 402 | + | N.D. |
| 403 | + | N.D. |

TABLE 24-continued

| Potency data for Compounds 287 to 465 | | |
|---|---|---|
| Compound No. | Thallium Assay ($IC_{50}$) | Trypanosoma Assay ($IC_{50}$) |
| 404 | + | N.D. |
| 405 | + | N.D. |
| 406 | + | N.D. |
| 407 | + | N.D. |
| 408 | + | N.D. |
| 409 | + | N.D. |
| 410 | + | N.D. |
| 411 | + | N.D. |
| 412 | + | N.D. |
| 413 | + | N.D. |
| 414 | + | N.D. |
| 415 | + | N.D. |
| 416 | + | N.D. |
| 417 | + | N.D. |
| 418 | + | N.D. |
| 419 | + | N.D. |
| 420 | + | N.D. |
| 421 | + | N.D. |
| 422 | + | N.D. |
| 423 | + | N.D. |
| 424 | + | N.D. |
| 425 | + | N.D. |
| 426 | + | N.D. |
| 427 | + | N.D. |
| 428 | + | N.D. |
| 429 | + | N.D. |
| 430 | + | N.D. |
| 431 | + | N.D. |
| 432 | + | N.D. |
| 433 | +++ | +++ |
| 434 | ++ | N.D. |
| 435 | ++ | N.D. |
| 436 | ++ | N.D. |
| 437 | ++ | N.D. |
| 438 | + | N.D. |
| 439 | + | N.D. |
| 440 | + | N.D. |
| 441 | + | N.D. |
| 442 | + | N.D. |
| 443 | + | N.D. |
| 444 | + | N.D. |
| 445 | +++ | +++ |
| 446 | +++ | N.D. |
| 447 | +++ | +++ |
| 448 | +++ | N.D. |
| 449 | ++ | N.D. |
| 450 | ++ | N.D. |
| 451 | + | N.D. |
| 452 | + | N.D. |
| 453 | ++ | N.D. |
| 454 | + | N.D. |
| 455 | +++ | +++ |
| 456 | + | N.D. |
| 457 | + | N.D. |
| 458 | + | N.D. |
| 459 | + | N.D. |
| 460 | + | N.D. |
| 461 | + | N.D. |
| 462 | + | N.D. |
| 463 | + | N.D. |
| 464 | ++ | N.D. |
| 465 | ++ | N.D. |

Other Embodiments

This disclosure provides merely exemplary embodiments of the disclosure. One skilled in the art will readily recognize from the disclosure and claims, that various changes, modifications and variations can be made therein without departing from the spirit and scope of the disclosure as defined in the following claims.

The invention claimed is:

1. A compound chosen from compounds of Formula (I):

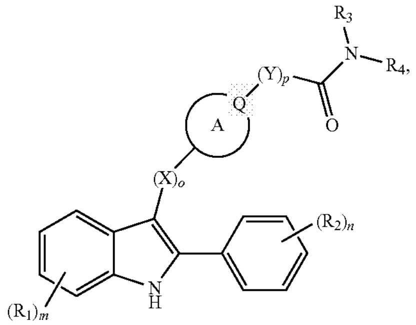

(I)

pharmaceutically acceptable salts thereof, solvates of any of the foregoing, and deuterated derivatives of any of the foregoing, wherein:

(i) Ring A is a 3- to 7-membered ring wherein the ring is a cyclic alkyl or a heterocycle;

(ii) Q is N or $CR^5$;

(iii) each $R_1$ is independently chosen from halogen groups, hydroxy, thiol, amino, cyano, —$OC(O)C_1$-$C_6$ linear, branched, and cyclic alkyl groups, —$C(O)OC_1$-$C_6$ linear, branched, and cyclic alkyl groups, —$NHC(O)C_1$-$C_6$ linear, branched, and cyclic alkyl groups, —$C(O)NHC_1$-$C_6$ linear, branched, and cyclic alkyl groups, —NHC(O)aryl groups, —C(O)NHaryl groups, —NHC(O)heteroaryl groups, —C(O)NHheteroaryl groups, —$NHS(O)_2C_1$-$C_6$ linear, branched, and cyclic alkyl groups, —$S(O)_2NHC_1$-$C_6$ linear, branched, and cyclic alkyl groups, —$NHS(O)_2$aryl groups, —$S(O)_2$NHaryl groups, —$NHS(O)_2$heteroaryl groups, —$S(O)_2$NHheteroaryl groups, —$NHC(O)NHC_1$-$C_6$ linear, branched, and cyclic alkyl groups, —NHC(O)NHaryl groups, —NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups, $C_1$-$C_6$ linear, branched, and cyclic halothioalkyl groups, $C_1$-$C_6$ linear, branched, and cyclic haloalkoxy groups, benzyloxy, benzylamino, or benzylthio groups, 3- to 6-membered heterocycloalkenyl groups,
3- to 6-membered heterocycloalkyl groups, and
5- and 6-membered heteroaryl groups; or two $R_1$ groups, together with the carbon atoms to which they are attached, form a $C_4$-$C_8$ cycloalkyl group, an aryl group, or a heteroaryl group;

(iv) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(v) m is chosen from 1, 2, 3, and 4;

(vi) n is chosen from 1, 2, 3, 4, and 5;

(vii) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with one to four groups independently chosen from:
$C_1$-$C_6$ alkyl groups,
aryl groups,
heteroaryl groups,
halogen groups,
hydroxy, and
amino;

(viii) Y is chosen from divalent amino, divalent oxygen, divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with one to three groups independently chosen from
$C_1$-$C_6$ alkyl groups optionally substituted with hydroxy,
$C_3$-$C_6$ cyclic alkyl,
aryl groups,
heteroaryl groups,
halogen groups,
hydroxy, and
amino, or wherein the divalent alkyl groups, divalent alkoxy groups, divalent aminoalkyl groups, and divalent thioalkyl groups are optionally fused to a $C_3$-$C_6$ cyclic alkyl;

(ix) o is chosen from 0, 1, 2, 3, and 4;

(x) p is chosen from 0, 1, 2, 3, and 4;

(xi) $R_3$ is chosen from:
hydrogen,
$C_1$-$C_6$ linear and branched alkylsulfonyl groups,
$C_1$-$C_6$ linear and branched alkoxy groups optionally substituted with a $C_3$-$C_6$ cyclic alkyl group or a 3- to 6-membered heterocycle,
$C_1$-$C_6$ cyclic alkyl groups optionally substituted with one to four groups independently chosen from:
halogen groups,
hydroxy,
oxo,
$C_1$-$C_6$ linear and branched alkoxy groups,
$C_1$-$C_6$ linear and branched alkyl groups optionally substituted with one or two groups independently chosen from hydroxy and $C_1$-$C_6$ linear and branched alkoxy groups, and
amido groups,
heterocyclic groups optionally substituted with one to four groups independently chosen from:
halogen groups,
oxo,
hydroxy, and
$C_1$-$C_6$ linear and branched alkyl groups optionally substituted with one or two groups independently chosen from hydroxy and $C_1$-$C_6$ linear and branched alkoxy groups,
aryl groups optionally substituted with one to four groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups,
heteroaryl groups optionally substituted with one to four groups independently chosen from hydroxy and $C_1$-$C_6$ linear alkyl groups, and
$C_1$-$C_7$ linear and branched alkyl groups, wherein the alkyl groups are optionally substituted with one to five groups independently chosen from:
amino groups,
hydroxy,
oxo,
cyano,
carboxylic acid,
halogen groups,
amido groups optionally substituted with one or two groups independently chosen from $C_1$-$C_6$ linear, branched, and cyclic alkyl groups and $C_1$-$C_6$ linear, branched, and cyclic hydroxyalkyl groups,
$C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, $C_1$-$C_6$ linear and branched alkylsulfonyl groups, aryl groups optionally substituted with one or two groups independently chosen from halogen groups, hydroxy, $C_1$-$C_6$ linear and branched alkyl groups optionally substituted with one or two groups independently chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups, (xii) $R_4$ is chosen from:

hydrogen, $C_1$-$C_6$ linear and branched alkylsulfonyl groups, $C_1$-$C_6$ linear and branched alkoxy groups optionally substituted with a $C_3$-$C_6$ cyclic alkyl group or a 3- to 6-membered heterocycle, $C_1$-$C_6$ cyclic alkyl groups optionally substituted with one to four groups independently chosen from:

halogen groups, hydroxy, oxo, $C_1$-$C_6$ linear and branched alkoxy groups, $C_1$-$C_6$ linear and branched alkyl groups optionally substituted with one or two groups independently chosen from hydroxy and $C_1$-$C_6$ linear and branched alkoxy groups, and amido groups, heterocyclic groups optionally substituted with one to four groups independently chosen from:

halogen groups, oxo, hydroxy, and $C_1$-$C_6$ linear and branched alkyl groups optionally substituted with one or two groups independently chosen from hydroxy and $C_1$-$C_6$ linear and branched alkoxy groups, aryl groups optionally substituted with one to four groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, heteroaryl groups optionally substituted with one to four groups independently chosen from hydroxy and $C_1$-$C_6$ linear alkyl groups, and $C_1$-$C_7$ linear and branched alkyl groups, wherein the alkyl groups are substituted with one to five groups independently chosen from:

amino groups, hydroxy, oxo, cyano, carboxylic acid, halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, $C_1$-$C_6$ linear and branched alkylsulfonyl groups, aryl groups optionally substituted with one or two groups independently chosen from halogen groups, hydroxy, $C_1$-$C_6$ linear and branched alkyl groups optionally substituted with one or two groups independently chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups, or $R_3$ and $R_4$, together with the nitrogen atom to which they are attached, form a 4- to 10-membered heterocyclyl group optionally substituted with one to four groups independently chosen from hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups; and or $R_3$ and $R_4$, together with the nitrogen atom to which they are attached, form a 4- to 10-membered heterocyclyl group optionally substituted with one to four groups independently chosen from hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups; and (xiii) $R_5$ is absent or is chosen from:

hydrogen, halogen groups, hydroxy, thiol, amino, and $C_1$-$C_6$ linear and branched alkyl groups, wherein when $R_5$ is absent, Q is a bridgehead atom.

2. A compound chosen from compounds of Formula (I):

(I)

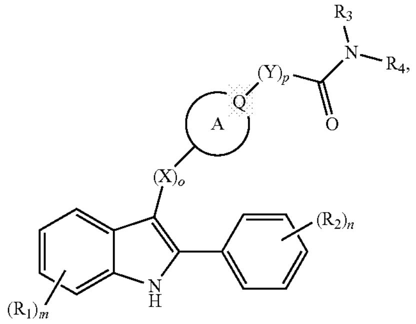

pharmaceutically acceptable salts thereof, solvates of any of the foregoing, and deuterated derivatives of any of the foregoing, wherein:

(i) Ring A is chosen from:

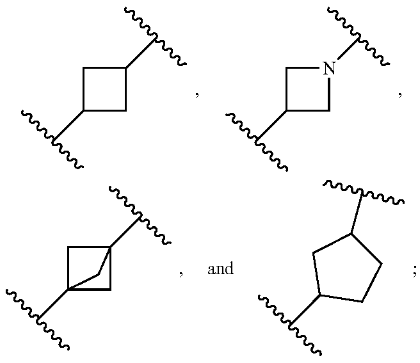

(ii) Q is N or $CR^5$;

(iii) each $R_1$ is independently chosen from halogen groups, hydroxy, thiol, amino, cyano, —$OC(O)C_1$-$C_6$ linear, branched, and cyclic alkyl groups, —$C(O)OC_1$-$C_6$ linear, branched, and cyclic alkyl groups, —$NHC(O)C_1$-$C_6$ linear, branched, and cyclic alkyl groups, —$C(O)NHC_1$-$C_6$ linear, branched, and cyclic alkyl groups, —NHC(O)aryl groups, —C(O)NHaryl groups, —NHC(O)heteroaryl groups, —C(O)NHheteroaryl groups, —$NHS(O)_2C_1$-$C_6$ linear, branched, and cyclic alkyl groups, —$S(O)_2NHC_1$-$C_6$ linear, branched, and cyclic alkyl groups, —$NHS(O)_2$aryl groups, —$S(O)_2$NHaryl groups, —$NHS(O)_2$heteroaryl groups, —$S(O)_2$NHheteroaryl groups, —$NHC(O)NHC_1$-$C_6$ linear, branched, and cyclic alkyl groups, —NHC(O)NHaryl groups,
—NHC(O)NHheteroaryl groups,
$C_1$-$C_6$ linear, branched, and cyclic alkyl groups,
$C_2$-$C_6$ linear, branched, and cyclic alkenyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3- to 6-membered heterocycloalkenyl groups,
3- to 6-membered heterocycloalkyl groups, and
5- and 6-membered heteroaryl groups; or two $R_1$ groups, together with the carbon atoms to which they are attached, form a $C_4$-$C_8$ cycloalkyl group, an aryl group, or a heteroaryl group;

(iv) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(v) m is chosen from 0, 1, 2, 3, and 4;

(vi) n is chosen from 0, 1, 2, 3, 4, and 5;

(vii) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with one to four groups independently chosen from:
$C_1$-$C_6$ alkyl groups,
aryl groups,
heteroaryl groups,
halogen groups,
hydroxy, and
amino;

(viii) Y is chosen from divalent amino, divalent oxygen, divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with one to three groups independently chosen from
$C_1$-$C_6$ alkyl groups optionally substituted with hydroxy,
$C_3$-$C_6$ cyclic alkyl,
aryl groups,
heteroaryl groups,
halogen groups,
hydroxy, and
amino, or wherein the divalent alkyl groups, divalent alkoxy groups, divalent aminoalkyl groups, and divalent thioalkyl groups are optionally fused to a $C_3$-$C_6$ cyclic alkyl;

(ix) o is chosen from 0, 1, 2, 3, and 4;

(x) p is chosen from 0, 1, 2, 3, and 4;

(xi) $R_3$ and $R_4$ are independently chosen from:
hydrogen,
$C_1$-$C_6$ linear and branched alkylsulfonyl groups,
$C_1$-$C_6$ linear and branched alkoxy groups optionally substituted with a $C_3$-$C_6$ cyclic alkyl group or a 3- to 6-membered heterocycle,
$C_1$-$C_6$ cyclic alkyl groups optionally substituted with one to four groups independently chosen from:
halogen groups,
hydroxy,
oxo,
$C_1$-$C_6$ linear and branched alkoxy groups,
$C_1$-$C_6$ linear and branched alkyl groups optionally substituted with one or two groups independently chosen from hydroxy and $C_1$-$C_6$ linear and branched alkoxy groups, and
amido groups,
heterocyclic groups optionally substituted with one to four groups independently chosen from:
halogen groups,
oxo,
hydroxy, and
$C_1$-$C_6$ linear and branched alkyl groups optionally substituted with one or two groups independently chosen from hydroxy and $C_1$-$C_6$ linear and branched alkoxy groups,
aryl groups optionally substituted with one to four groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups,
heteroaryl groups optionally substituted with one to four groups independently chosen from hydroxy and $C_1$-$C_6$ linear alkyl groups, and $C_1$-$C_7$ linear and branched alkyl groups, wherein the alkyl groups are optionally substituted with one to five groups independently chosen from:

amino groups, hydroxy, oxo, cyano, carboxylic acid, halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, $C_1$-$C_6$ linear and branched alkylsulfonyl groups, aryl groups optionally substituted with one or two groups independently chosen from halogen groups, hydroxy, $C_1$-$C_6$ linear and branched alkyl groups optionally substituted with one or two groups independently chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups, or $R_3$ and $R_4$, together with the nitrogen atom to which they are attached, form a 4- to 10-membered heterocyclyl group optionally substituted with one to four groups independently chosen from hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups independently chosen from $C_1$-$C_6$ linear, branched, and cyclic alkyl groups, carboxamide groups optionally substituted with one to four groups independently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups; and (xii) $R_5$ is hydrogen.

3. The compound, deuterated derivative, or pharmaceutically acceptable salt according to claim 1, wherein Q is $CR^5$.

4. The compound, deuterated derivative, or pharmaceutically acceptable salt according to claim 1, wherein each $R_1$ is independently chosen from halogen groups and $C_1$-$C_6$ linear, branched, and cyclic haloalkyl groups.

5. The compound, deuterated derivative, or pharmaceutically acceptable salt according to claim 1, wherein each $R_1$ is independently chosen from fluoro and $CF_3$.

6. The compound, deuterated derivative, or pharmaceutically acceptable salt according to claim 1, wherein each $R_2$ is independently chosen from halogen groups.

7. The compound, salt, or deuterated derivative according to claim 1, wherein each $R_2$ is fluoro.

8. The compound, salt, or deuterated derivative according to claim 1, wherein m is 2.

9. The compound, salt, or deuterated derivative according to claim 1, wherein n is 1.

10. The compound, salt, or deuterated derivative according to claim 1, wherein X is chosen from divalent $C_1$-$C_8$ linear, branched, and cyclic alkyl groups, wherein the divalent alkyl groups are optionally substituted with one to four groups chosen from:

$C_1$-$C_6$ alkyl groups, aryl groups, heteroaryl groups, halogen groups, hydroxy, and amino.

11. The compound, salt, or deuterated derivative according to claim 1, wherein X is chosen from $-CH_2-$ and $-CH_2-CH_2-$.

12. The compound, salt, or deuterated derivative according to claim 1, wherein Y is chosen from divalent amino, divalent oxygen, divalent $C_1$-$C_8$ linear, branched, and cyclic alkyl groups, and divalent $C_1$-$C_8$ linear, branched, and cyclic aminoalkyl groups, wherein the divalent alkyl groups and divalent aminoalkyl groups are optionally substituted with one to three groups independently chosen from $C_1$-$C_6$ alkyl groups optionally substituted with hydroxy, $C_3$-$C_6$ cyclic alkyl, oxo, and hydroxy, or wherein the divalent alkyl groups, divalent alkoxy groups, divalent aminoalkyl groups, and divalent thioalkyl groups are optionally fused to a $C_3$-$C_6$ cyclic alkyl.

13. The compound, salt, or deuterated derivative according to claim 1, wherein Y is chosen from

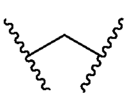 , 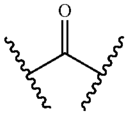 , 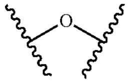 ,

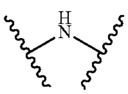 , 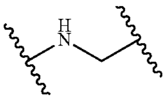 , 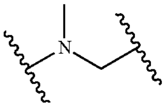 ,

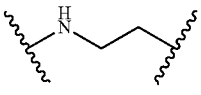 , 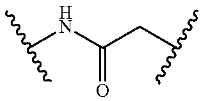 ,

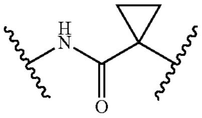 , 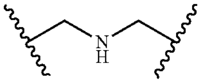 ,

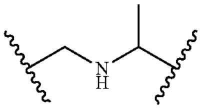 , 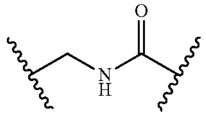 ,

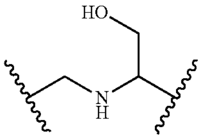 , 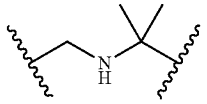 ,

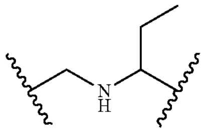 , 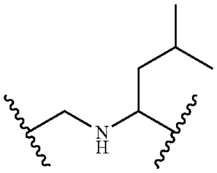 ,

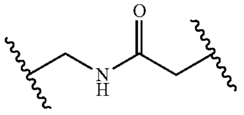 , 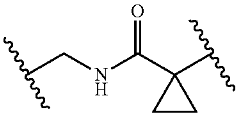 , and

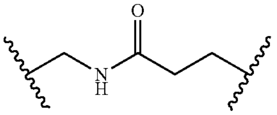 .

14. The compound, salt, or deuterated derivative according to claim 1, wherein o is 0 or 1.

15. The compound, salt, or deuterated derivative according to claim 1, wherein p is 0 or 1.

16. The compound, salt, or deuterated derivative according to claim 1, wherein $R_3$ is hydrogen, and $R_4$ is chosen from:

hydrogen, $C_1$-$C_6$ linear and branched alkylsulfonyl groups, $C_1$-$C_6$ linear and branched alkoxy groups optionally substituted with a $C_3$-$C_6$ cyclic alkyl group or a 3- to 6-membered heterocycle, $C_1$-$C_6$ cyclic alkyl groups optionally substituted with one to four groups independently chosen from:

halogen groups, hydroxy, oxo, $C_1$-$C_6$ linear and branched alkoxy groups, $C_1$-$C_6$ linear and branched alkyl groups optionally substituted with one or two groups independently chosen from hydroxy and $C_1$-$C_6$ linear and branched alkoxy groups, and amido groups, heterocyclic groups optionally substituted with one to four groups independently chosen from:

halogen groups, oxo, hydroxy, and $C_1$-$C_6$ linear and branched alkyl groups optionally substituted with one or two groups independently chosen from hydroxy and $C_1$-$C_6$ linear and branched alkoxy groups, heteroaryl groups optionally substituted with one to four groups independently chosen from hydroxy and $C_1$-$C_6$ linear alkyl groups, and $C_1$-$C_7$ linear and branched alkyl groups, wherein the alkyl groups are optionally substituted with one to five groups independently chosen from:

amino groups, hydroxy, oxo, cyano, carboxylic acid, halogen groups, amido groups optionally substituted with one or two groups independently chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups independently chosen from halogen groups, $C_1$-$C_6$ linear and branched alkoxy groups, $C_1$-$C_6$ linear and branched alkyl groups optionally substituted with one or two hydroxy groups, and hydroxy, $C_2$-$C_6$ linear and branched alkynyl groups, $C_2$-$C_6$ linear and branched alkoxy groups optionally substituted with at least one hydroxy, carbonyl-(4-methylpiperazin-1-yl), carbonyl-(N-morpholino), 4- to 10-membered heterocyclyl groups optionally substituted with one or two groups independently chosen from halogen groups, oxo, hydroxy, $C_1$-$C_6$ linear and branched alkoxy groups, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one to three groups independently chosen from halogen groups, hydroxy, and $C_1$-$C_6$ linear and branched alkyl groups optionally substituted with one to three groups independently from hydroxy, halogen groups, and $C_1$-$C_6$ linear and branched alkoxy groups.

17. The compound, salt, or deuterated derivative according to claim 1, wherein $R_3$ and $R_4$, together with the nitrogen atom to which they are attached, form a 4- to 10-membered heterocyclyl group optionally substituted with one to four groups independently chosen from:

hydroxy, oxo, $C_1$-$C_6$ linear, branched, and cyclic alkyl groups optionally substituted with one to four groups independently chosen from hydroxy, amino groups, $C_1$-$C_6$ linear, branched, and cyclic alkoxy groups, oxo, and $C_3$-$C_6$ cyclic alkyl groups optionally substituted with one or two groups independently chosen from hydroxy and $C_1$-$C_6$ linear and branched alkyl groups, amide groups optionally substituted with one to four groups indepedently chosen from $C_1$-$C_6$ linear, branched, and cyclic alkyl groups, carboxamide groups optionally substituted with one to four groups indepedently chosen from $C_1$-$C_6$ linear, branched, and cyclic alkyl groups, $C_1$-$C_6$ linear, branched, and cyclic alkoxy groups optionally substituted with one to four groups independently chosen from oxo, $C_1$-$C_6$ linear, branched, and cyclic alkyl groups, and heterocyclic groups, 4- to 10-membered heterocyclyl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups, and 4- to 10-membered heteroaryl groups optionally substituted with one or two groups independently chosen from halogen groups, hydroxy, and $C_1$-$C_6$ linear and branched alkyl groups optionally substituted with one or two groups independently chosen from hydroxy and $C_1$-$C_6$ linear and branched alkoxy groups.

18. The compound, salt, or deuterated derivative according to claim 1, wherein $R_5$ is independently chosen from hydrogen, fluoro, and methyl.

19. The compound, salt, or deuterated derivative according to claim 2, wherein the compound is selected from compounds of Formula (V-a) and (V-b):

(V-a)

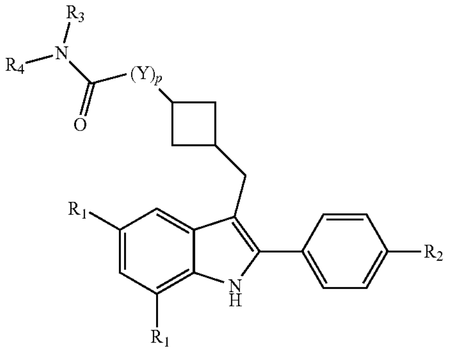

and (V-b)

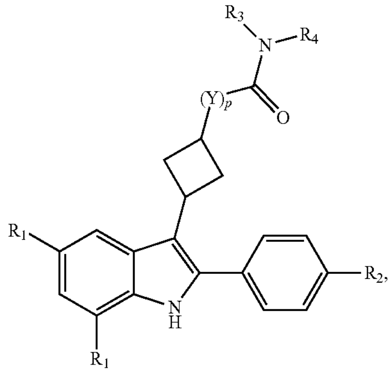

pharmaceutically acceptable salts thereof, solvates of any of the foregoing, and deuterated derivatives of any of the foregoing, wherein $R^1$, $R^2$, $R^3$, $R^4$, Y, and p are as defined in claim 2.

20. A compound chosen from compounds of Formula (Ia):

(Ia)

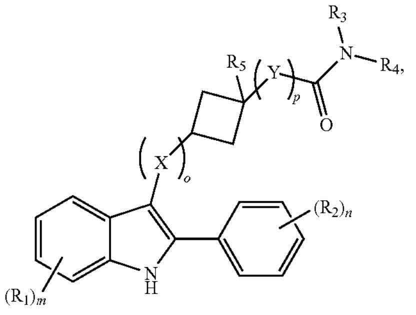

pharmaceutically acceptable salts thereof, solvates of any of the foregoing, and deuterated derivatives of any of the foregoing, wherein:

(i) each $R_1$ is independently chosen from halogen groups, hydroxy, thiol, amino, cyano, —$OC(O)C_1$-$C_6$ linear, branched, and cyclic alkyl groups, —$C(O)OC_1$-$C_6$ linear, branched, and cyclic alkyl groups, —$NHC(O)C_1$-$C_6$ linear, branched, and cyclic alkyl groups, —$C(O)NHC_1$-$C_6$ linear, branched, and cyclic alkyl groups, —NHC(O)aryl groups, —C(O)NHaryl groups, —NHC(O)heteroaryl groups, —C(O)NHheteroaryl groups, —$NHS(O)_2C_1$-$C_6$ linear, branched, and cyclic alkyl groups, —$S(O)_2NHC_1$-$C_6$ linear, branched, and cyclic alkyl groups, —$NHS(O)_2$aryl groups, —$S(O)_2$NHaryl groups, —$NHS(O)_2$heteroaryl groups, —$S(O)_2$NHheteroaryl groups, —$NHC(O)NHC_1$-$C_6$ linear, branched, and cyclic alkyl groups, —NHC(O)NHaryl groups, —NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups, $C_1$-$C_6$ linear, branched, and cyclic halothioalkyl groups, $C_1$-$C_6$ linear, branched, and cyclic haloalkoxy groups, benzyloxy, benzylamino, or benzylthio groups, 3- to 6-membered heterocycloalkenyl groups, 3- to 6-membered heterocycloalkyl groups, and 5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(iii) m is chosen from 0, 1, 2, 3, and 4;

(iv) n is chosen from 0, 1, 2,3 4, and 5;

(v) X is chosen from divalent $C_1$-$C_8$ linear, branched, and cyclic alkyl groups and divalent $C_1$-$C_8$ linear, branched, and cyclic thioalkyl groups, wherein the divalent alkyl groups and divalent thioalkyl groups are optionally substituted with at least one group chosen from
$C_1$-$C_6$ alkyl groups,
aryl groups,
heteroaryl groups,
halogen groups,
hydroxy, and
amino;

(vi) Y is chosen from divalent $C_1$-$C_8$ linear, branched, and cyclic alkyl groups, divalent $C_1$-$C_8$ linear, branched, and cyclic alkoxy groups, divalent $C_1$-$C_8$ linear, branched, and cyclic aminoalkyl groups, and divalent $C_1$-$C_8$ linear, branched, and cyclic thioalkyl groups, wherein the divalent alkyl groups, divalent alkoxy groups, divalent aminoalkyl groups, and divalent thioalkyl groups are optionally substituted with at least one group chosen from
$C_1$-$C_6$ alkyl groups,
aryl groups,
heteroaryl groups,
halogen groups,
hydroxy, and
amino;

(vii) o is chosen from 0, 1, 2, 3, and 4;

(viii) p is chosen from 0, 1, 2, 3, and 4;

(ix) $R_3$ and $R_4$ are independently chosen from
hydrogen,
$C_1$-$C_6$ linear and branched alkylsulfonyl groups,
$C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups,
heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups,
heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:
amino groups,
hydroxy,
cyano,
carboxylic acid,
halogen groups,
amido groups optionally substituted with one or two groups chosen from $C_1$-$C_6$ linear, branched, and cyclic alkyl groups and $C_1$-$C_6$ linear, branched, and cyclic hydroxyalkyl groups,
$C_3$-$C_6$ cyclic alkyl groups optionally substituted with one or two groups chosen from halogen groups and hydroxy,
$C_1$-$C_6$ linear and branched alkynyl groups,
$C_1$-$C_6$ linear and branched alkoxy groups optionally substituted with at least one hydroxy,
$C_1$-$C_6$ linear and branched alkylsulfonyl groups,
aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups,
carbonyl-(4-methylpiperazin-1-yl),
carbonyl-(N-morpholino),
4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and
4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each $R_5$ is independently chosen from hydrogen, halogen groups, hydroxy, thiol, amino, and $C_1$-$C_6$ linear and branched alkyl groups.

21. A compound chosen from compounds of Formula (II):

(II)

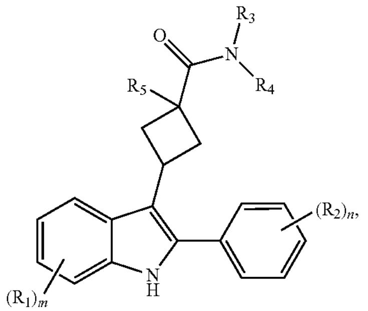

pharmaceutically acceptable salts thereof, solvates of any of the foregoing, and deuterated derivatives of any of the foregoing, wherein:

(i) each $R_1$ is independently chosen from halogen groups, hydroxy, thiol, amino, cyano, —$OC(O)C_1$-$C_6$ linear, branched, and cyclic alkyl groups, —$C(O)OC_1$-$C_6$ linear, branched, and cyclic alkyl groups, —$NHC(O)C_1$-$C_6$ linear, branched, and cyclic alkyl groups, —$C(O)NHC_1$-$C_6$ linear, branched, and cyclic alkyl groups, —NHC(O)aryl groups, —C(O)NHaryl groups, —NHC(O)heteroaryl groups, —C(O)NHheteroaryl groups, —$NHS(O)_2C_1$-$C_6$ linear, branched, and cyclic alkyl groups, —$S(O)_2NHC_1$-$C_6$ linear, branched, and cyclic alkyl groups, —$NHS(O)_2$aryl groups, —$S(O)_2$NHaryl groups, —$NHS(O)_2$heteroaryl groups, —$S(O)_2$NHheteroaryl groups, —$NHC(O)NHC_1$-$C_6$ linear, branched, and cyclic alkyl groups, —NHC(O)NHaryl groups, —NHC(O)NHheteroaryl groups, $C_1$-$C_6$ linear, branched, and cyclic alkyl groups, $C_2$-$C_6$ linear, branched, and cyclic alkenyl groups, $C_1$-$C_6$ linear, branched, and cyclic hydroxyalkyl groups, $C_1$-$C_6$ linear, branched, and cyclic alkoxy groups, $C_1$-$C_6$ linear, branched, and cyclic thioalkyl groups, $C_1$-$C_6$ linear, branched, and cyclic haloalkyl groups, $C_1$-$C_6$ linear, branched, and cyclic haloaminoalkyl groups, $C_1$-$C_6$ linear, branched, and cyclic halothioalkyl groups, $C_1$-$C_6$ linear, branched, and cyclic haloalkoxy groups, benzyloxy, benzylamino, or benzylthio groups, 3- to 6-membered heterocycloalkenyl groups, 3- to 6-membered heterocycloalkyl groups, and 5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from halogen groups, hydroxy, thiol, amino, cyano, —$NHC(O)C_1$-$C_6$ linear, branched, and cyclic alkyl groups, —$C(O)NHC_1$-$C_6$ linear, branched, and cyclic alkyl groups, —NHC(O)aryl groups, —C(O)NHaryl groups, —NHC(O)heteroaryl groups, —C(O)NHheteroaryl groups, —$NHS(O)_2C_1$-$C_6$ linear, branched, and cyclic alkyl groups, —$S(O)_2NHC_1$-$C_6$ linear, branched, and cyclic alkyl groups, —$NHS(O)_2$aryl groups, —$S(O)_2$NHaryl groups, —$NHS(O)_2$heteroaryl groups, —$S(O)_2$NHheteroaryl groups, —$NHC(O)NHC_1$-$C_4$ linear, branched, and cyclic alkyl groups, —NHC(O)NHaryl groups, —NHC(O)NHheteroaryl groups, $C_1$-$C_4$ linear, branched, and cyclic alkyl groups, $C_2$-$C_4$ linear, branched, and cyclic alkenyl groups, $C_1$-$C_4$ linear, branched, and cyclic hydroxyalkyl groups, $C_1$-$C_4$ linear, branched, and cyclic alkoxy groups, $C_1$-$C_4$ linear, branched, and cyclic thioalkyl groups, $C_1$-$C_4$ linear, branched, and cyclic haloalkyl groups, $C_1$-$C_4$ linear, branched, and cyclic haloaminoalkyl groups, $C_1$-$C_4$ linear, branched, and cyclic halothioalkyl groups, and $C_1$-$C_4$ linear, branched, and cyclic haloalkoxy groups;

(iii) m is chosen from 0, 1, 2, 3, and 4;

(iv) n is chosen from 0, 1, 2, 3, 4, and 5;

(v) $R_3$ and $R_4$ are independently chosen from hydrogen, $C_1$-$C_6$ linear and branched alkylsulfonyl groups, $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each $R_5$ is independently chosen from hydrogen, halogen groups, hydroxy, thiol, amino, and $C_1$-$C_6$ linear and branched alkyl groups, halogen groups, and methyl;

(iii) m is 0, 1 or 2; and (iv) n is 1 or 2.

22. A compound chosen from compounds of Formula (IIIa)

(IIIa)

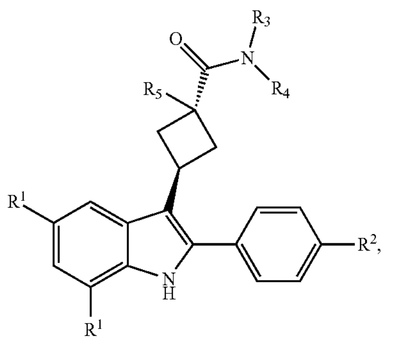

compounds of Formula (IIIb):

(IIIb)

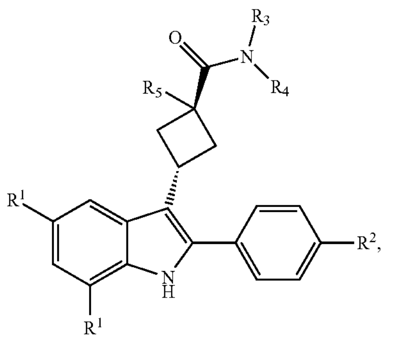

pharmaceutically acceptable salts of any of the foregoing, solvates of any of the foregoing, and deuterated derivatives of any of the foregoing, wherein:

(i) each $R_1$ is independently chosen from:
halogen groups,
hydroxy,
thiol,
amino,
cyano,
—OC(O)$C_1$-$C_6$ linear, branched, and cyclic alkyl groups,
—C(O)O$C_1$-$C_6$ linear, branched, and cyclic alkyl groups,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_6$ linear, branched, and cyclic alkyl groups,
—NHC(O)NHaryl groups,
—NHC(O)NHheteroaryl groups,
$C_1$-$C_6$ linear, branched, and cyclic alkyl groups,
$C_2$-$C_6$ linear, branched, and cyclic alkenyl groups,
$C_1$-$C_6$ linear, branched, and cyclic hydroxyalkyl groups,
$C_1$-$C_6$ linear, branched, and cyclic alkoxy groups,
$C_1$-$C_6$ linear, branched, and cyclic thioalkyl groups,
$C_1$-$C_6$ linear, branched, and cyclic haloalkyl groups,
$C_1$-$C_6$ linear, branched, and cyclic haloaminoalkyl groups,
$C_1$-$C_6$ linear, branched, and cyclic halothioalkyl groups,
$C_1$-$C_6$ linear, branched, and cyclic haloalkoxy groups,
benzyloxy, benzylamino, or benzylthio groups,
3- to 6-membered heterocycloalkenyl groups,
3- to 6-membered heterocycloalkyl groups, and
5- and 6-membered heteroaryl groups; or two $R_1$ groups, together with the carbon atoms to which they are attached, form a $C_4$-$C_8$ cycloalkyl group, an aryl group, or a heteroaryl group;

(ii) each $R_2$ is independently chosen from:
halogen groups,
hydroxy,
thiol,
amino,
cyano,
—NHC(O)$C_1$-$C_6$ linear, branched, and cyclic alkyl groups,
—C(O)NH$C_1$-$C_6$ linear, branched, and cyclic alkyl groups,
—NHC(O)aryl groups,
—C(O)NHaryl groups,
—NHC(O)heteroaryl groups,
—C(O)NHheteroaryl groups,
—NHS$(O)_2C_1$-$C_6$ linear, branched, and cyclic alkyl groups,
—S$(O)_2$NH$C_1$-$C_6$ linear, branched, and cyclic alkyl groups,
—NHS$(O)_2$aryl groups,
—S$(O)_2$NHaryl groups,
—NHS$(O)_2$heteroaryl groups,
—S$(O)_2$NHheteroaryl groups,
—NHC(O)NH$C_1$-$C_4$ linear, branched, and cyclic alkyl groups,
—NHC(O)NHaryl groups,
—NHC(O)NHheteroaryl groups,
$C_1$-$C_4$ linear, branched, and cyclic alkyl groups,
$C_2$-$C_4$ linear, branched, and cyclic alkenyl groups,
$C_1$-$C_4$ linear, branched, and cyclic hydroxyalkyl groups,
$C_1$-$C_4$ linear, branched, and cyclic alkoxy groups,
$C_1$-$C_4$ linear, branched, and cyclic thioalkyl groups,
$C_1$-$C_4$ linear, branched, and cyclic haloalkyl groups,
$C_1$-$C_4$ linear, branched, and cyclic haloaminoalkyl groups,
$C_1$-$C_4$ linear, branched, and cyclic halothioalkyl groups, and
$C_1$-$C_4$ linear, branched, and cyclic haloalkoxy groups;

(iii) m is chosen from 0, 1, 2, 3, and 4;

(iv) n is chosen from 0, 1, 2, 3, 4, and 5;

(v) $R_3$ and $R_4$ are independently chosen from:
hydrogen,
$C_1$-$C_6$ linear and branched alkylsulfonyl groups,
$C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from:

hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (vi) each $R_5$ is independently chosen from hydrogen, halogen groups, hydroxy, thiol, amino, and $C_1$-$C_6$ linear and branched alkyl groups.

23. A compound chosen from compounds of Formula (IV):

(IV)

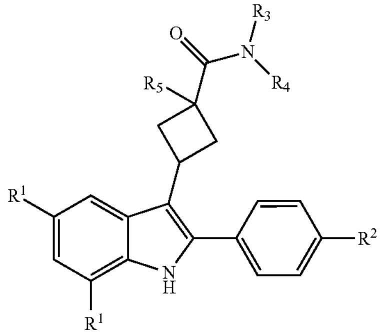

pharmaceutically acceptable salts thereof, solvates of any of the foregoing, and deuterated derivatives of any of the foregoing, wherein:

(i) each $R_1$ and $R_2$ is independently chosen from:

fluoro, chloro, bromo, cyano, methyl, cyclopropyl, ethyl, hydroxypropyl, isopropyl, propen-2-yl, dihydrofuran, furan, and methoxy;

(ii) $R_3$ and $R_4$ are independently chosen from:

hydrogen, $C_1$-$C_6$ linear and branched alkylsulfonyl groups, $C_1$-$C_6$ cyclic alkyl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, and amido groups, heterocyclic groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, aryl groups optionally substituted with at least one group chosen from halogen groups, hydroxy, $C_1$-$C_6$ linear and branched alkyl groups optionally substituted with one or two groups chosen from hydroxy and $C_1$-$C_6$ linear and branched alkoxy groups, heteroaryl groups optionally substituted with at least one group chosen from $C_1$-$C_6$ linear alkyl groups, and $C_1$-$C_6$ linear and branched alkyl groups, wherein the alkyl groups are optionally substituted with at least one group chosen from:

amino groups, hydroxy, cyano, carboxylic acid, halogen groups, amido groups optionally substituted with one or two groups chosen from $C_1$-$C_6$ linear, branched, and cyclic alkyl groups and $C_1$-$C_6$ linear, branched, and cyclic hydroxyalkyl groups, $C_3$-$C_6$ cyclic alkyl groups optionally substituted with one or two groups chosen from halogen groups and hydroxy, $C_1$-$C_6$ linear and branched alkynyl groups, $C_1$-$C_6$ linear and branched alkoxy groups optionally substituted with at least one hydroxy, $C_1$-$C_6$ linear and branched alkylsulfonyl groups, aryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, carbonyl-(4-methylpiperazin-1-yl), carbonyl-(N-morpholino), 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, or $R_3$ and $R_4$, together with the nitrogen atom to which they are attached, form a 4- to 10-membered heterocyclyl group optionally substituted with at least one group chosen from hydroxy, oxo, $C_1$-$C_6$ linear, branched, and cyclic alkyl groups optionally substituted with at least one groups chosen from hydroxy, amino groups, $C_1$-$C_6$ linear, branched, and cyclic alkoxy groups, amide groups optionally substituted with at least one group chosen from $C_1$-$C_6$ linear, branched, and cyclic alkyl groups, carboxamide groups optionally substituted with at least one group chosen from $C_1$-$C_6$ linear, branched, and cyclic alkyl groups, $C_1$-$C_6$ linear, branched, and cyclic alkoxy groups optionally substituted with at least one group chosen from $C_1$-$C_6$ linear, branched, and cyclic alkyl groups and heterocyclic groups, 4- to 10-membered heterocyclyl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups, and 4- to 10-membered heteroaryl groups optionally substituted with one or two groups chosen from halogen groups, hydroxy, $C_1$-$C_6$ linear and branched alkyl groups optionally substituted with one or two groups chosen from hydroxy and $C_1$-$C_6$ linear and branched alkoxy groups; and (iii) each $R_5$ is independently chosen from:

hydrogen, halogen groups, hydroxy, thiol, amino, and $C_1$-$C_6$ linear and branched alkyl groups.

24. A compound chosen from

1

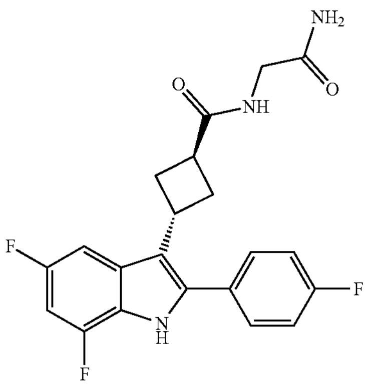

-continued
2
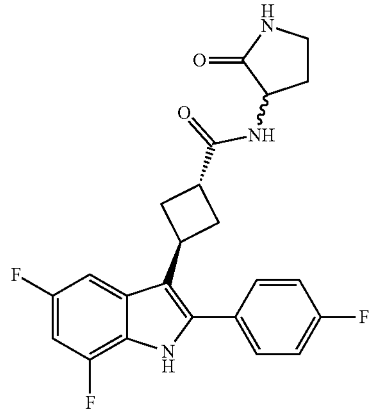
3
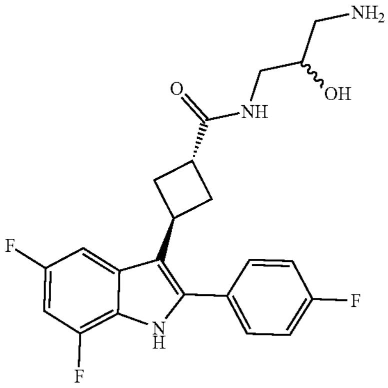
4
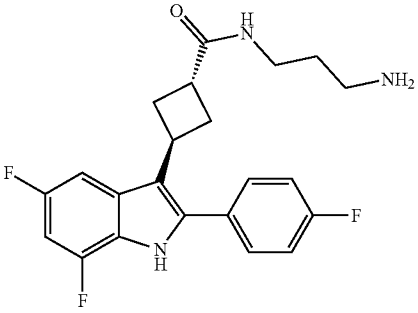
5
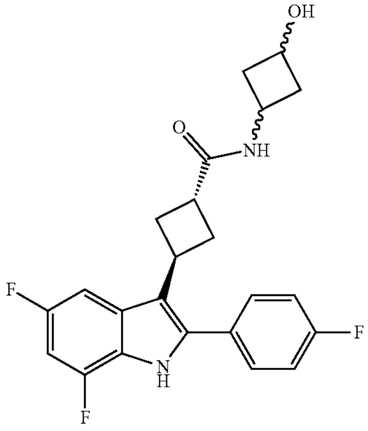
-continued
6
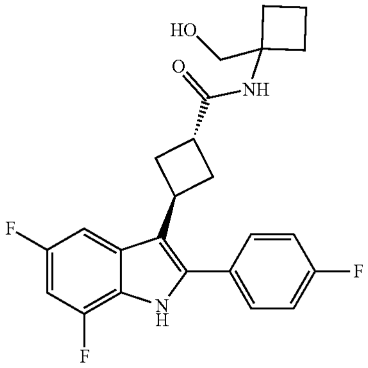
7
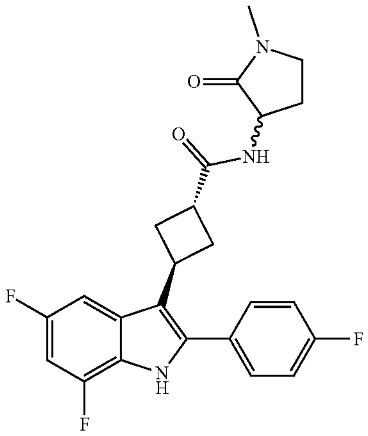
8
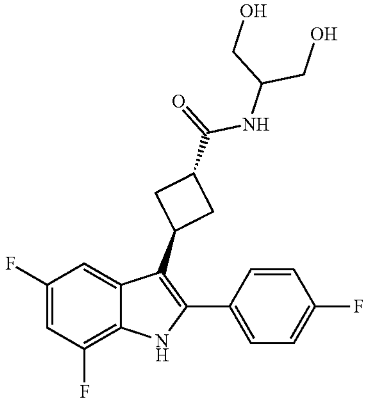
9
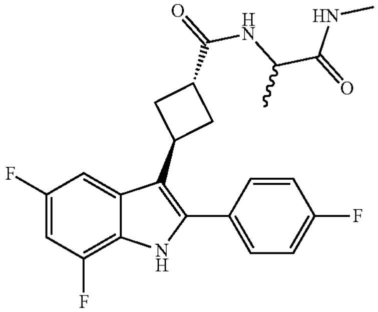

-continued
10
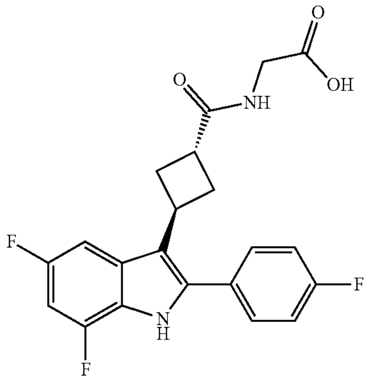
11
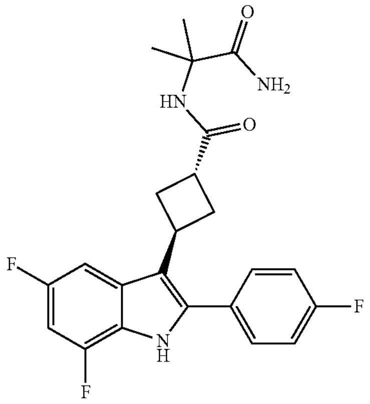
12
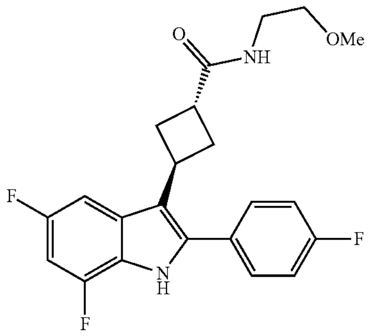
13
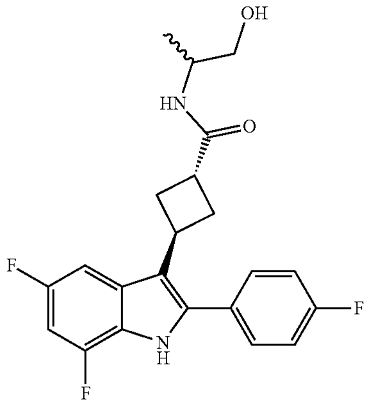
-continued
14
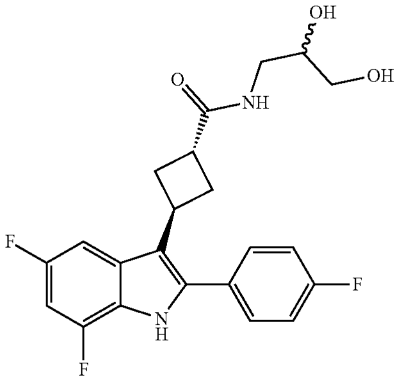
15
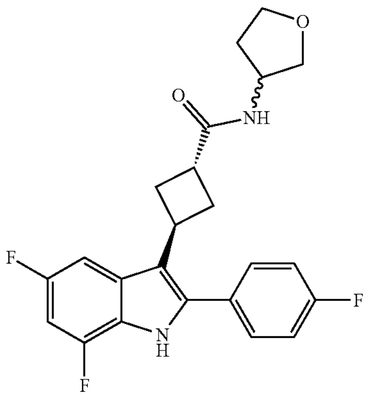
16
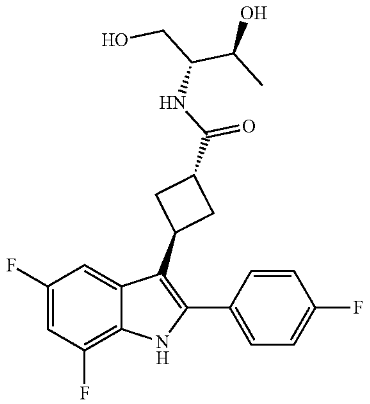
17
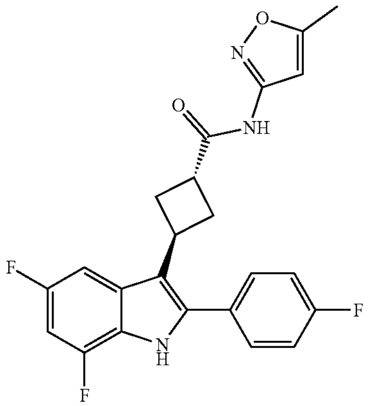

-continued
18
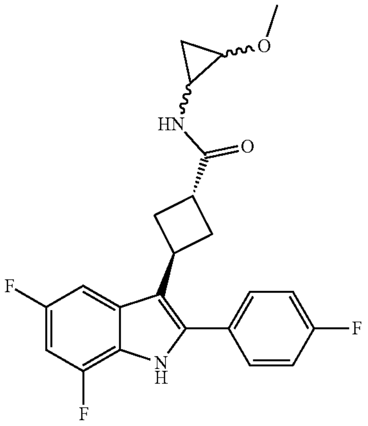
19
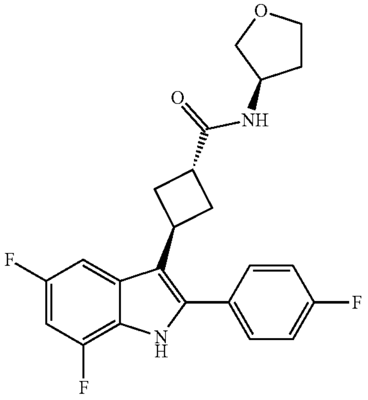
20
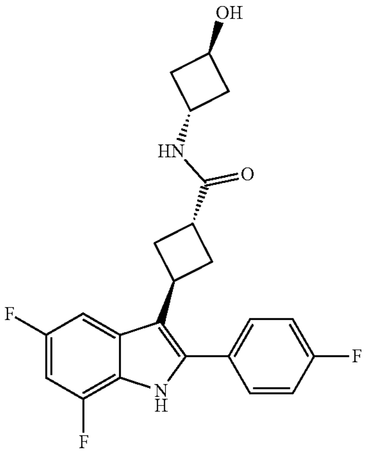
-continued
21
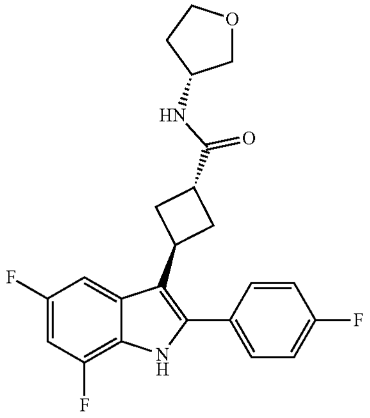
22
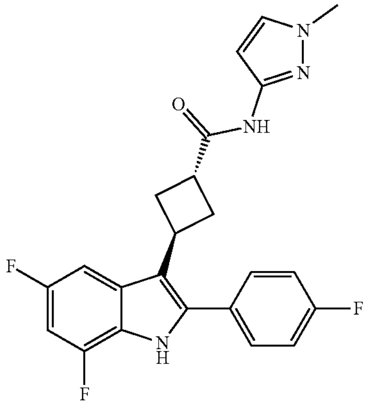
23
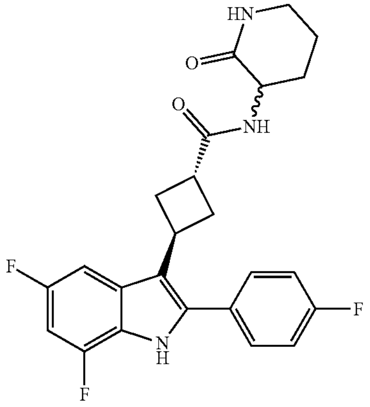
24
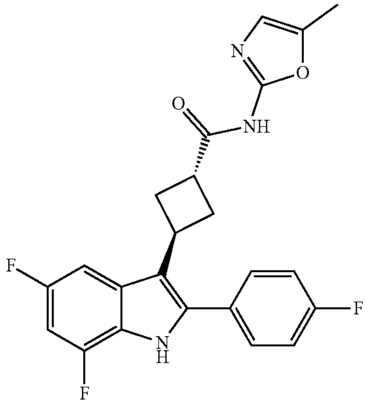

-continued
25
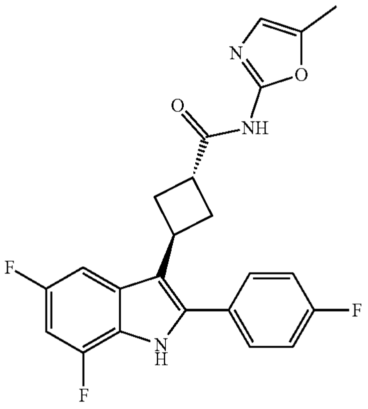
26
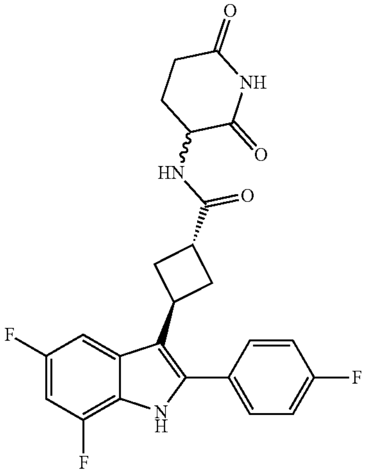
27
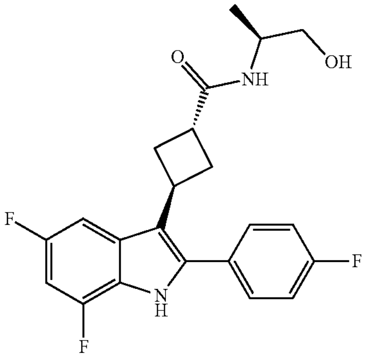
28
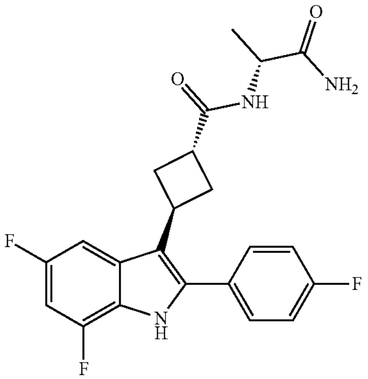
-continued
29
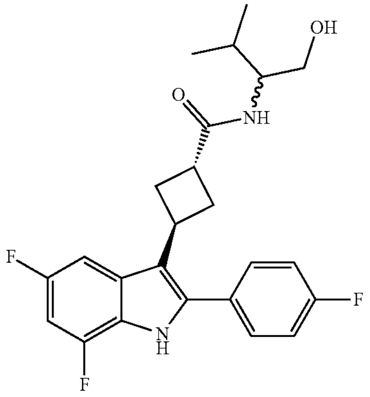
30
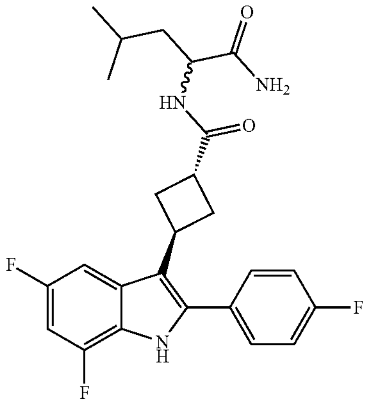
31
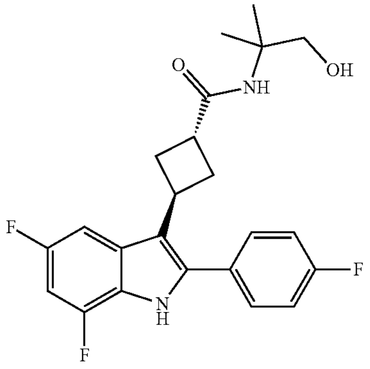
32
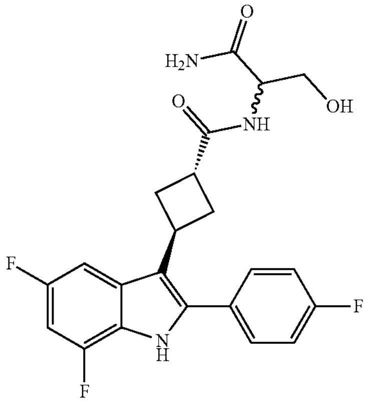

-continued
33
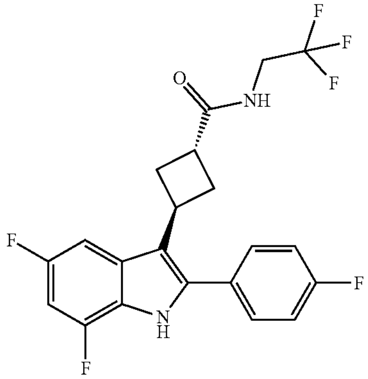
34
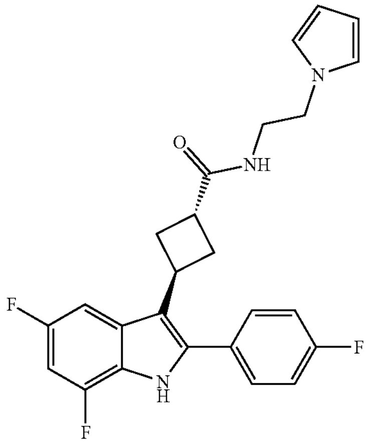
35
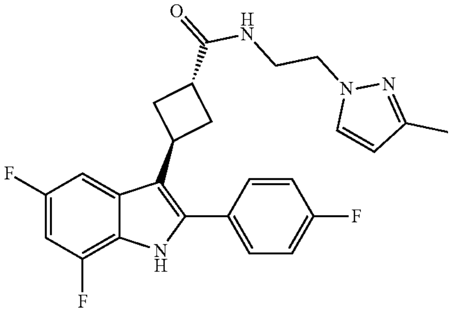
36
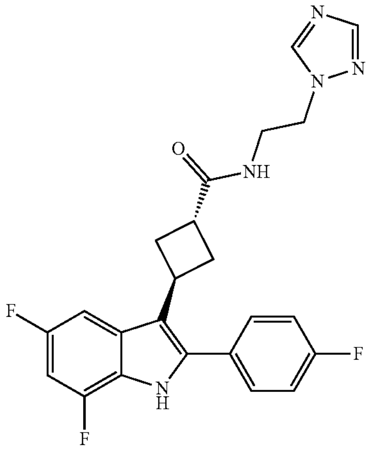
-continued
37
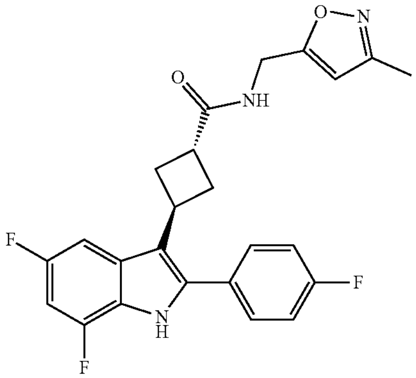
38
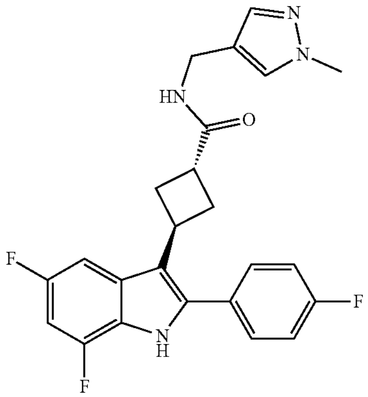
39
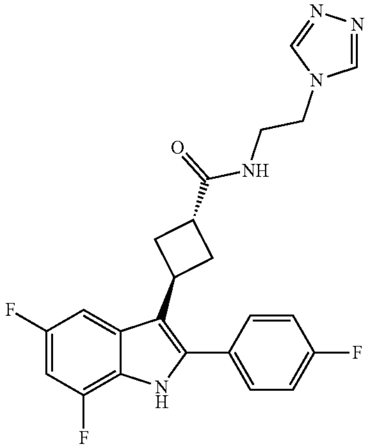
40
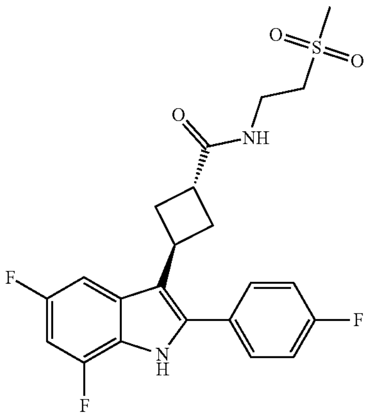

41
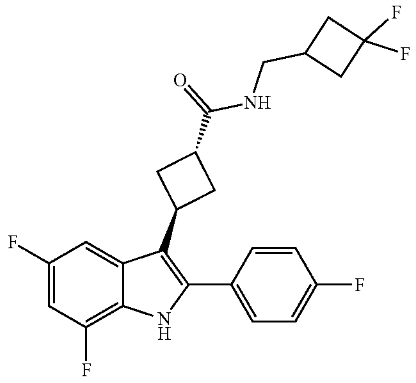
42
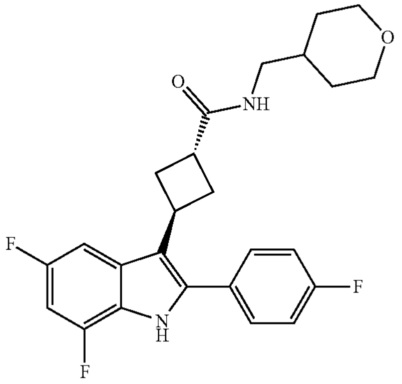
43
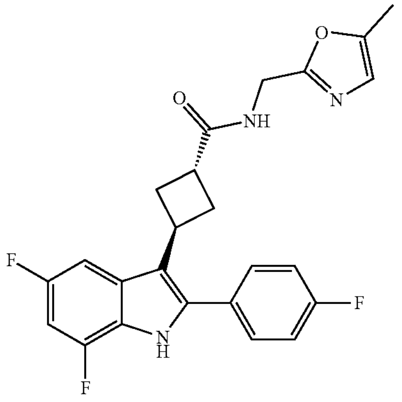
44
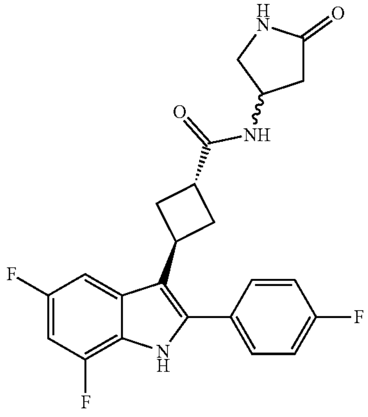
45
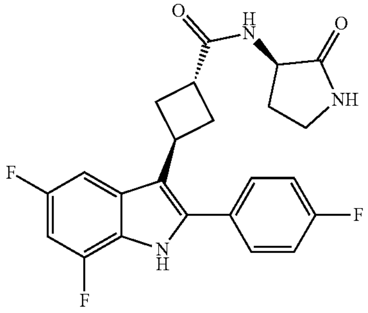
46
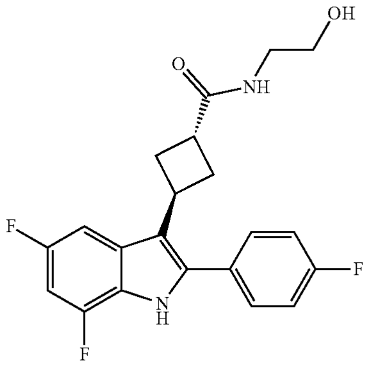
47
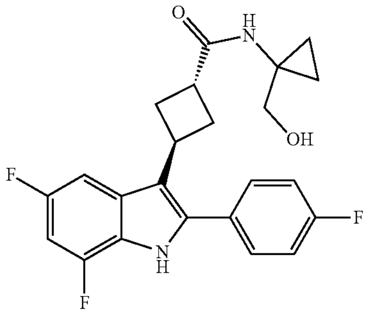
48
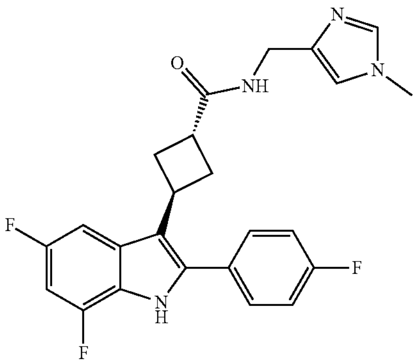

-continued
49
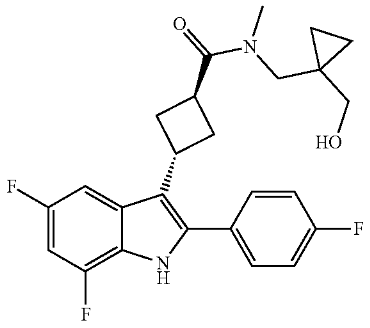
50
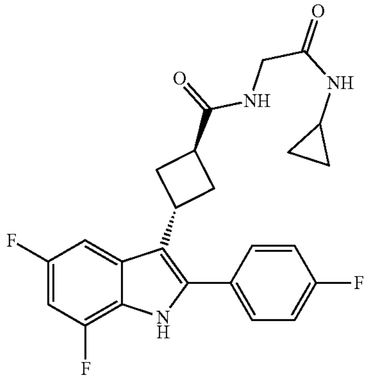
51
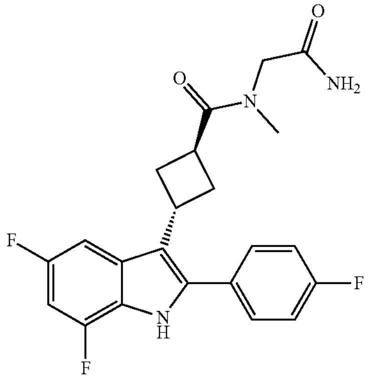
52
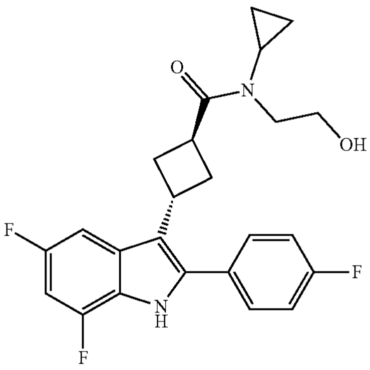
-continued
53
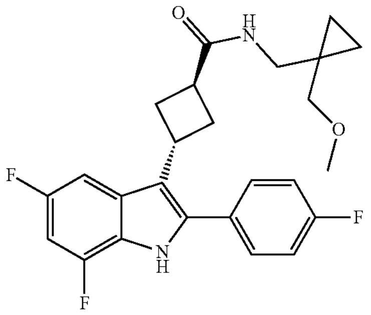
54
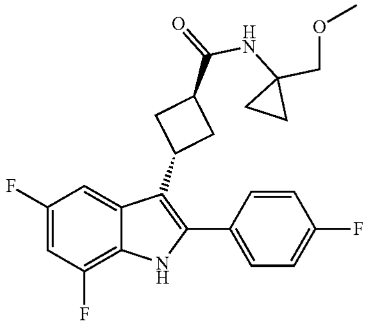
55
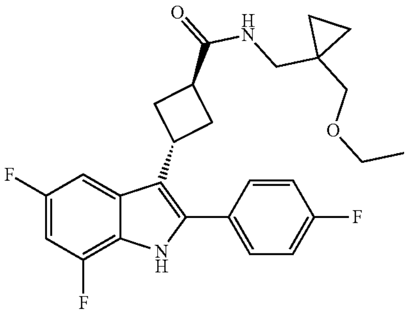
56
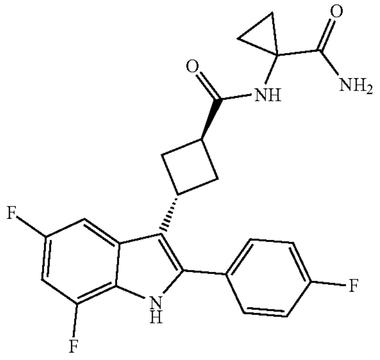

-continued
57
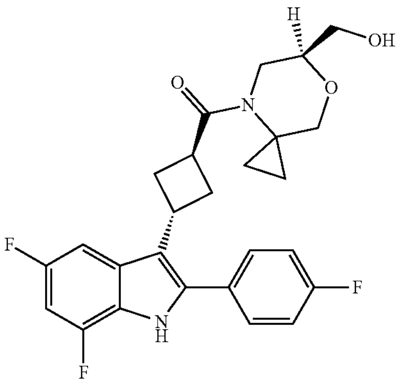
58
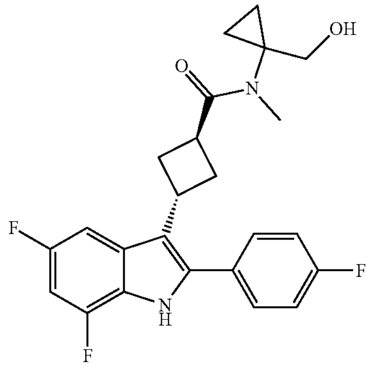
59
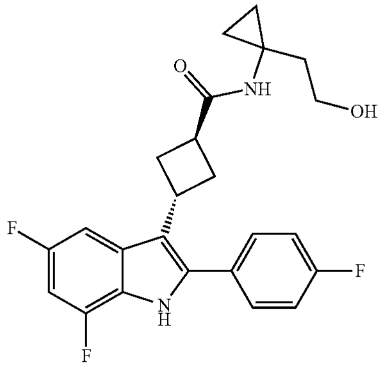
60
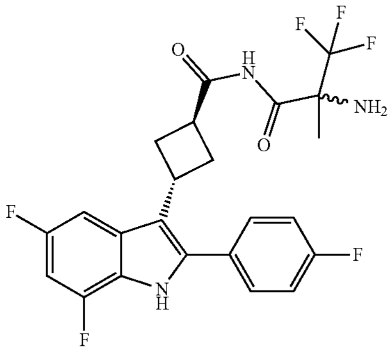
-continued
61
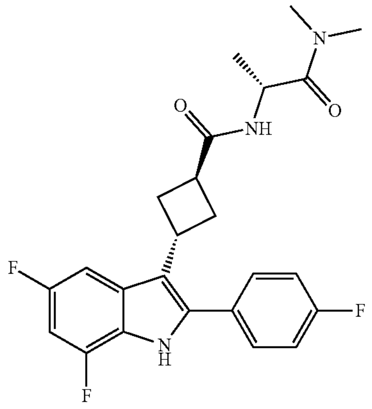
62
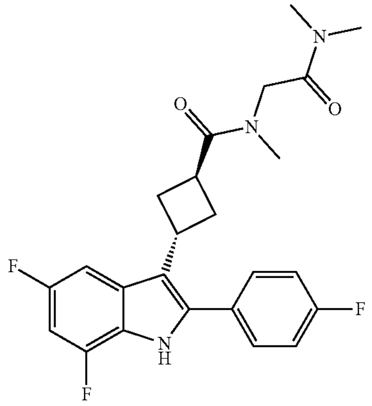
63
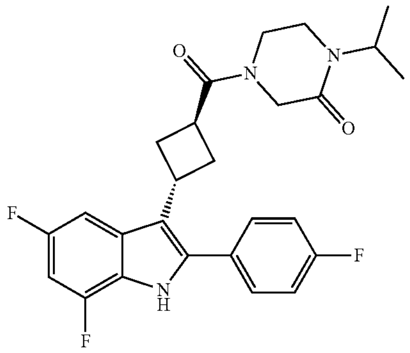
64
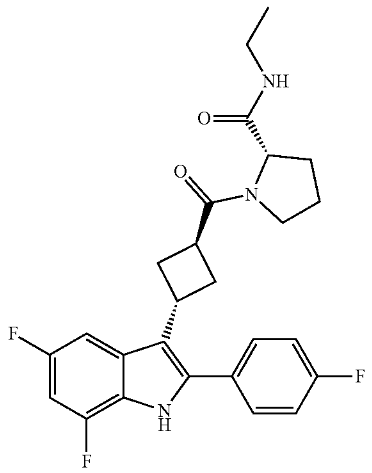

-continued
65
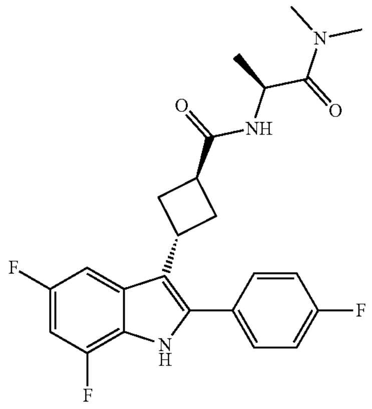
66
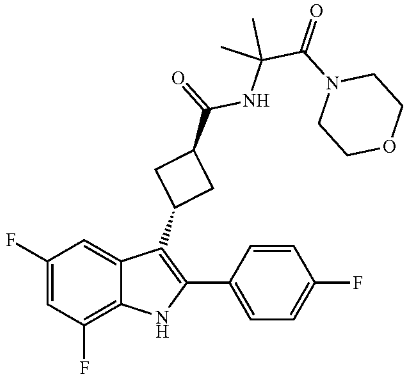
67
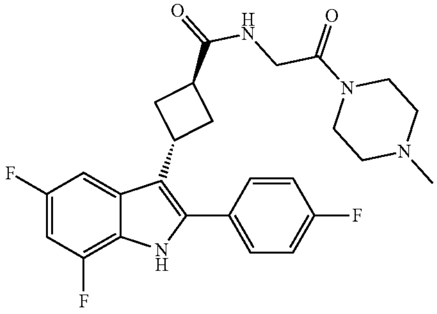
68
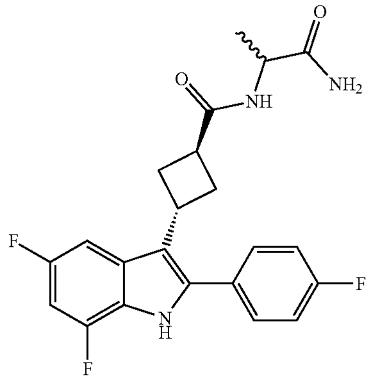
-continued
69
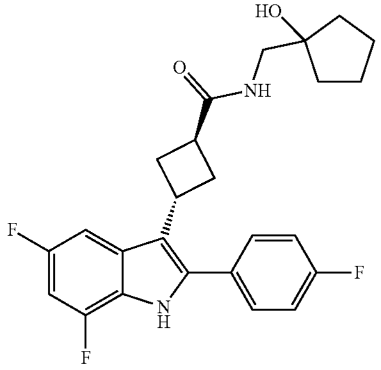
70
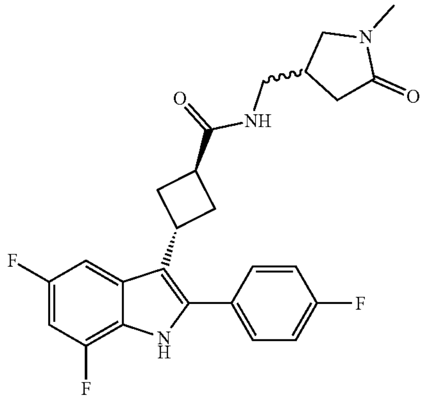
71
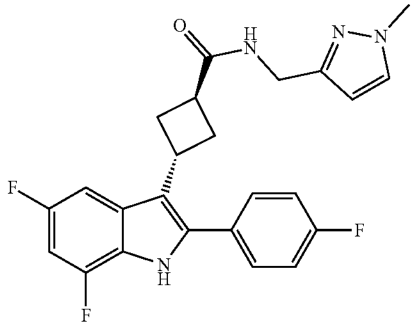
72
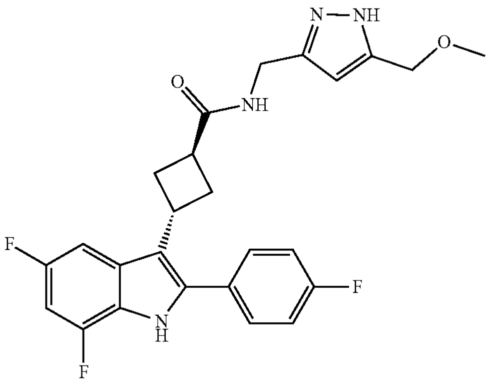

-continued
73
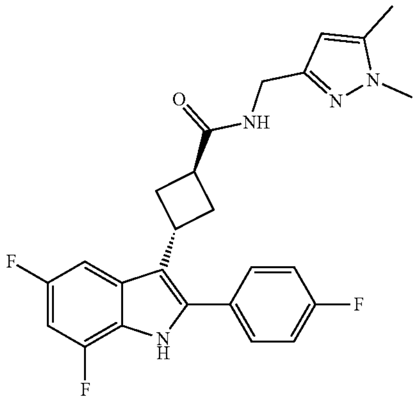
74
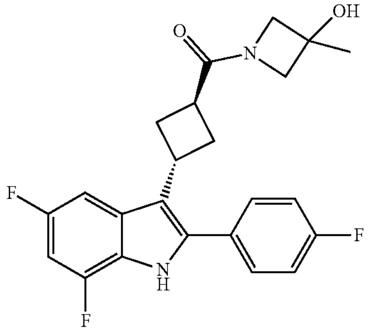
75
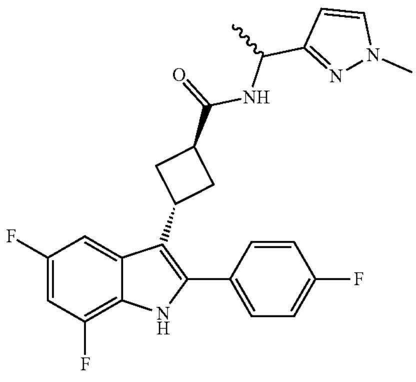
76
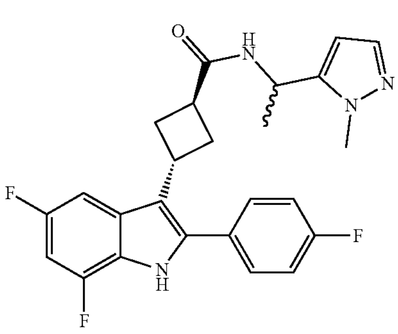
-continued
77
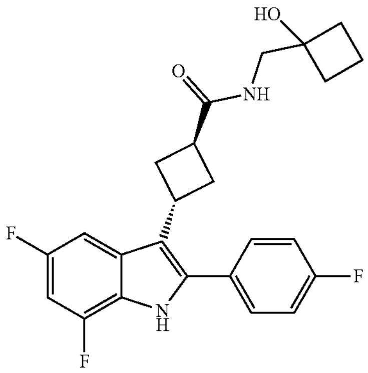
78
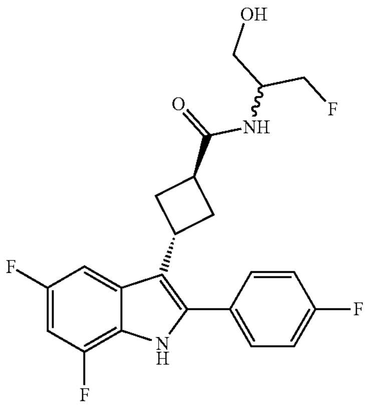
79
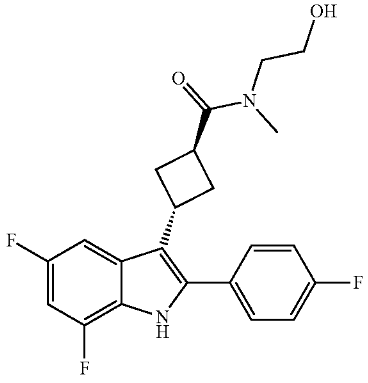
80
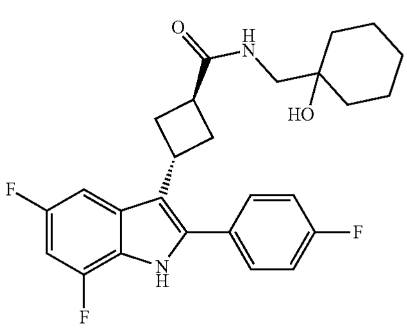

81
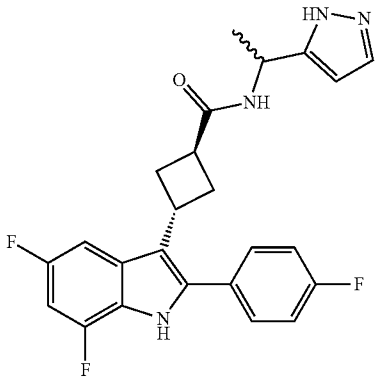
82
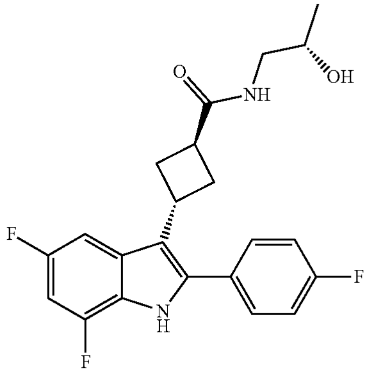
83
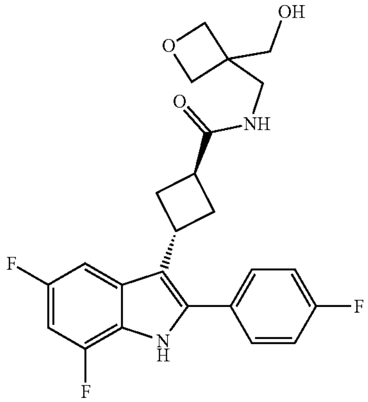
84
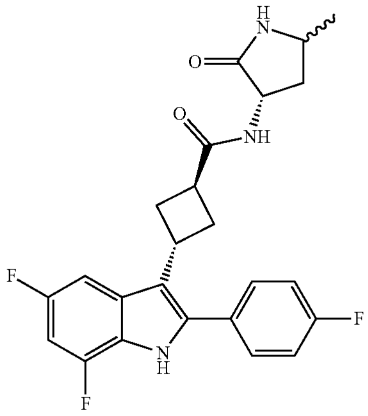
85
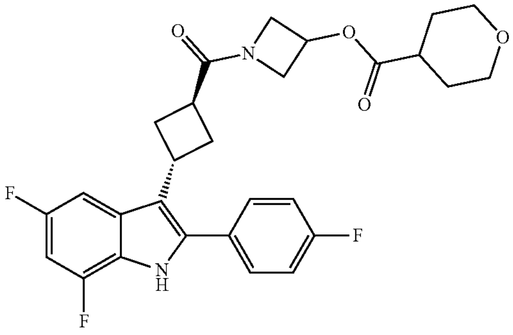
86
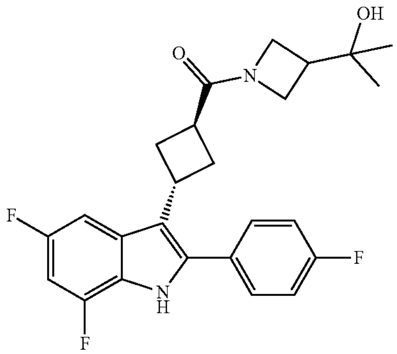
87
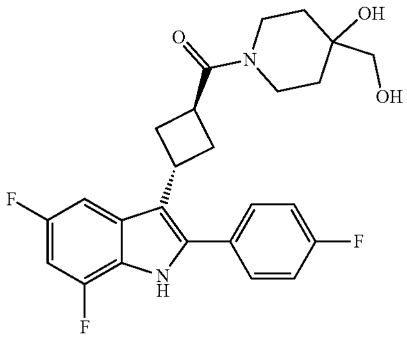
88
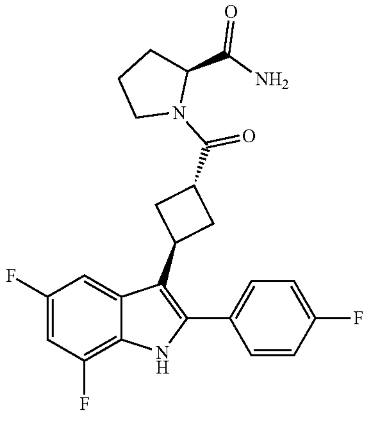

-continued
89
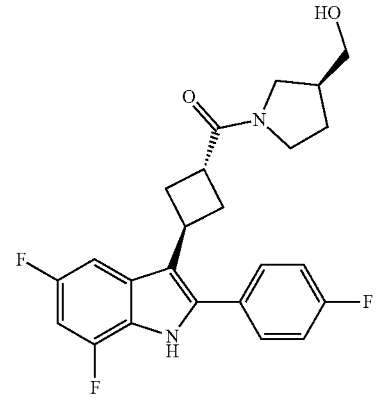
90
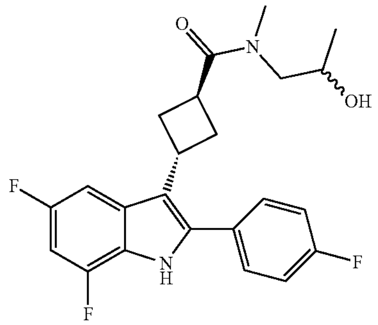
91
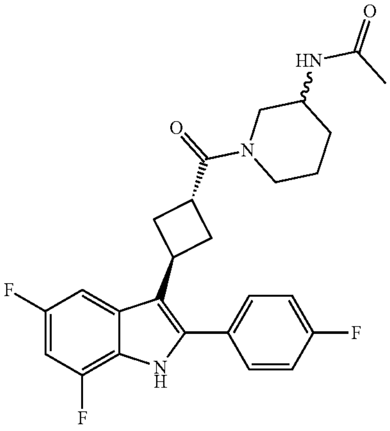
92
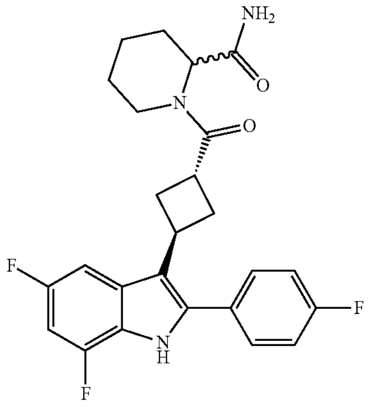
-continued
93
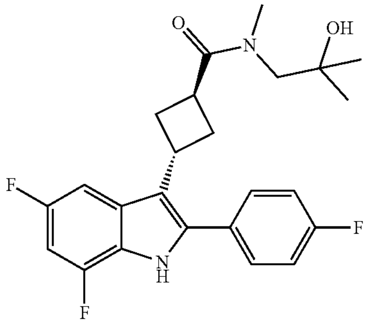
94
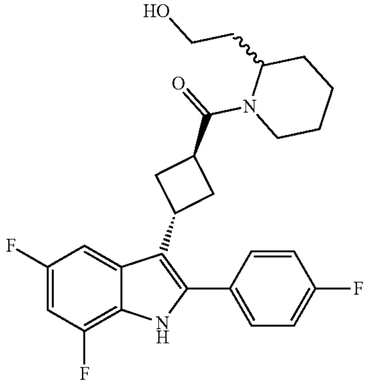
95
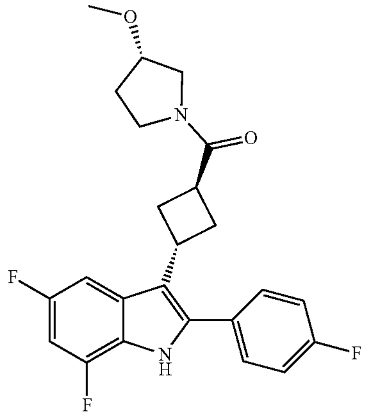
96
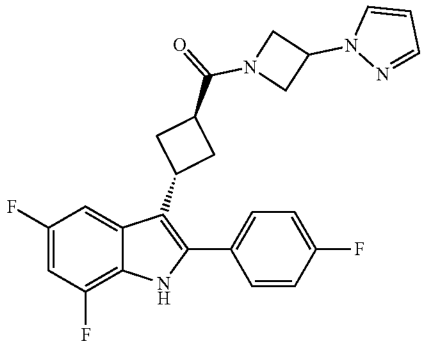

-continued
97
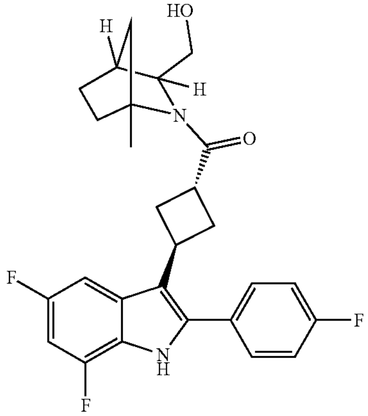
98
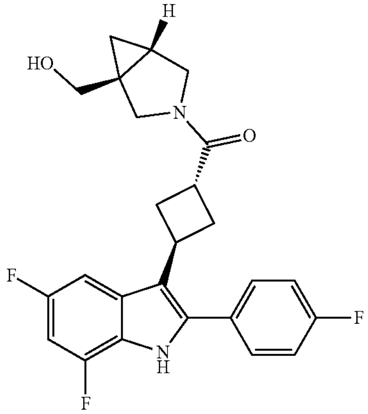
99
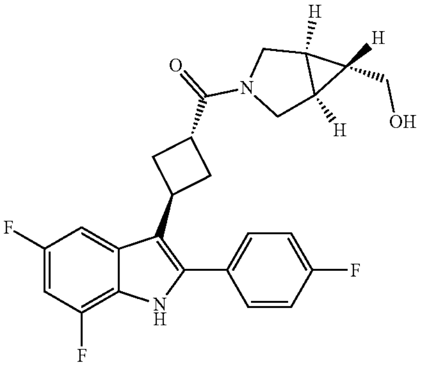
100
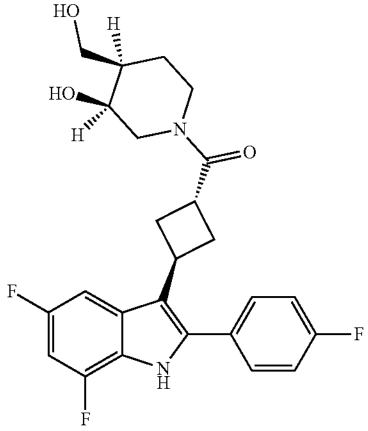
-continued
101
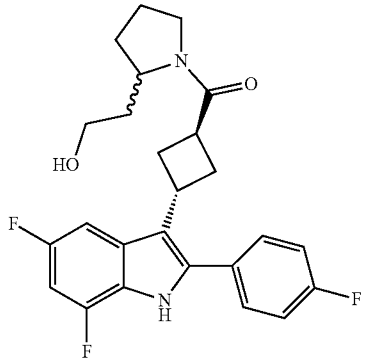
102
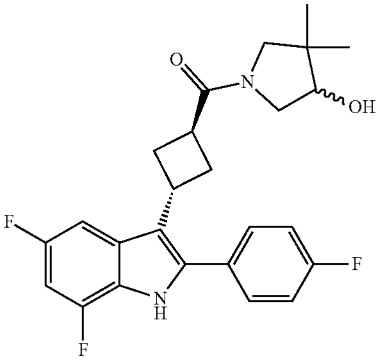
103
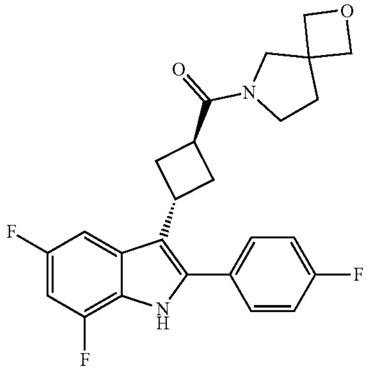
104
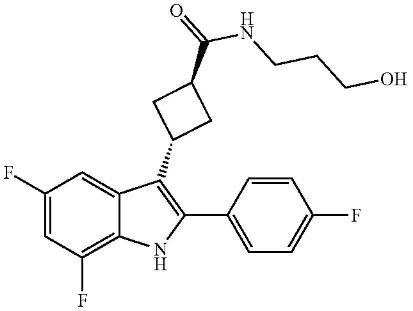

-continued
105
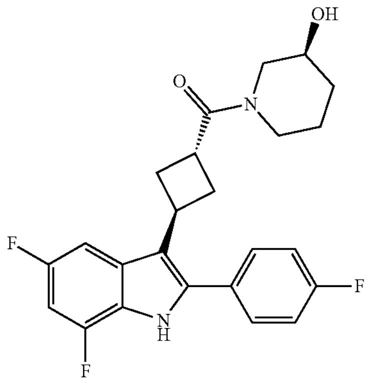
106
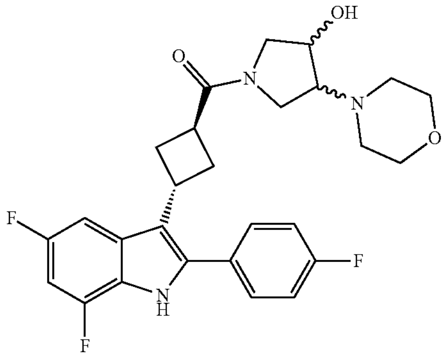
107
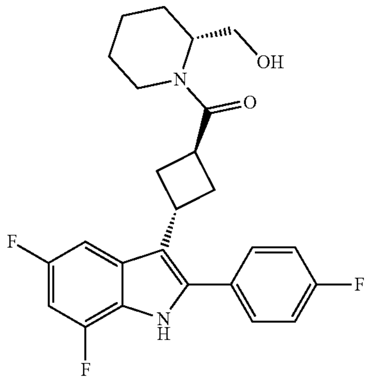
108
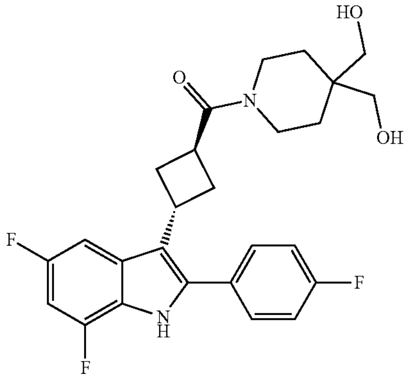
-continued
109
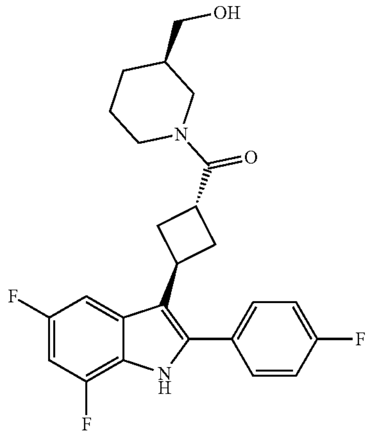
110
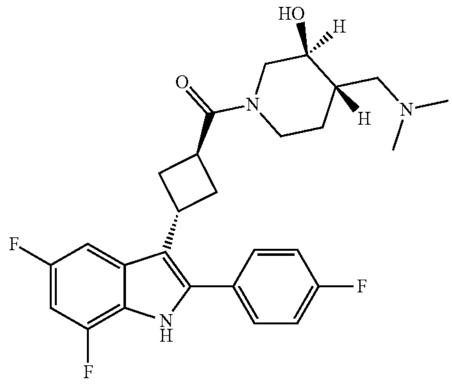
111
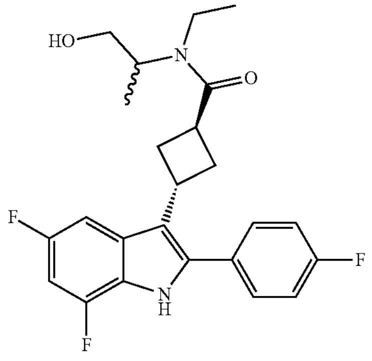
112
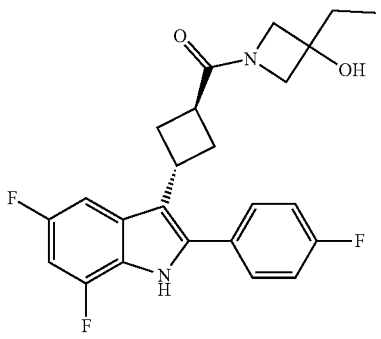

-continued
113
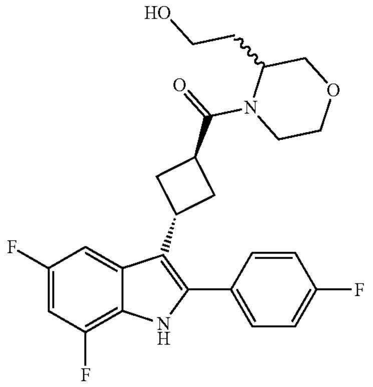
114
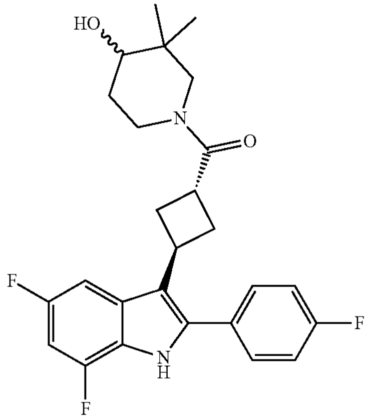
115
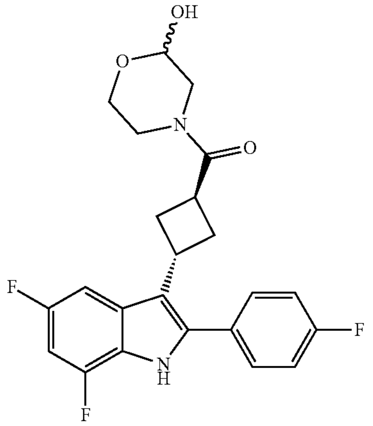
116
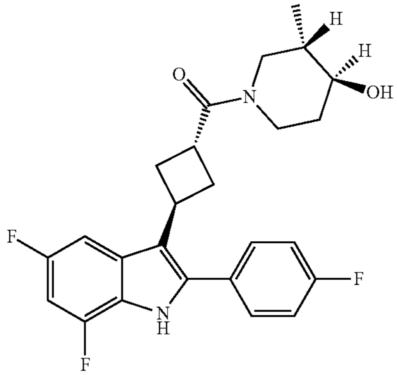
-continued
117
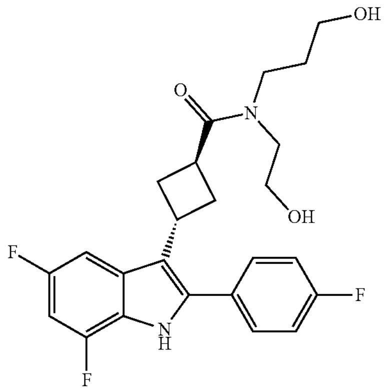
118
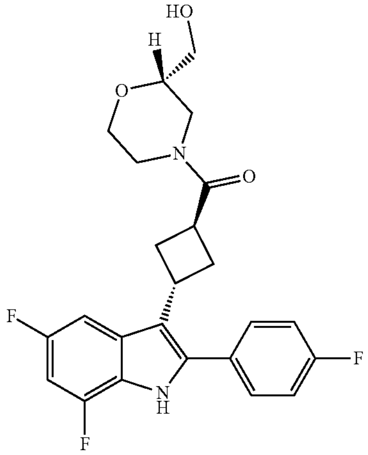
119
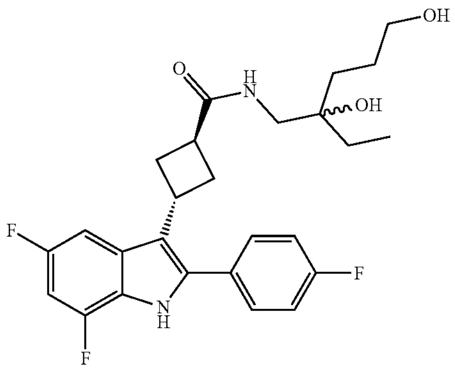
120
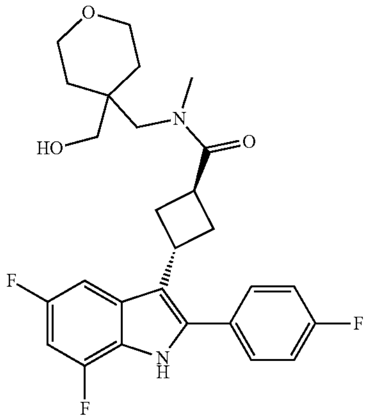

-continued
121
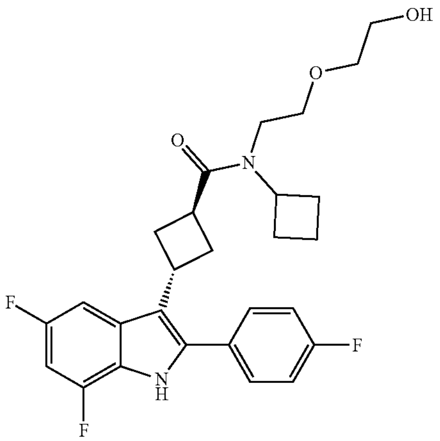
122
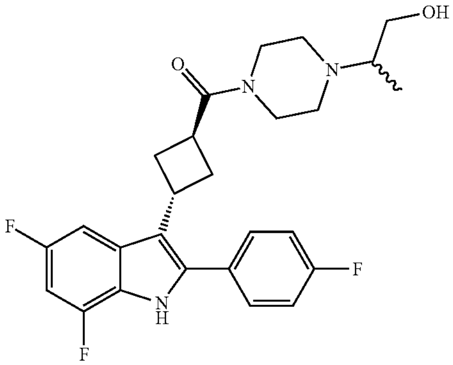
123
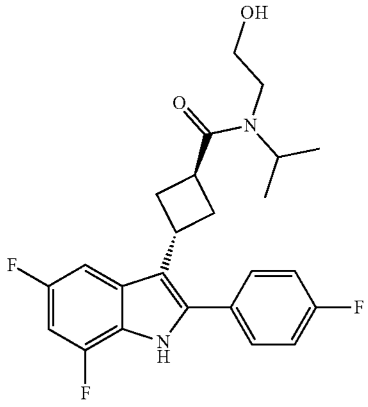
124
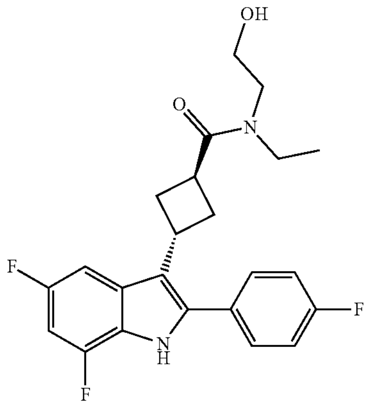
-continued
125
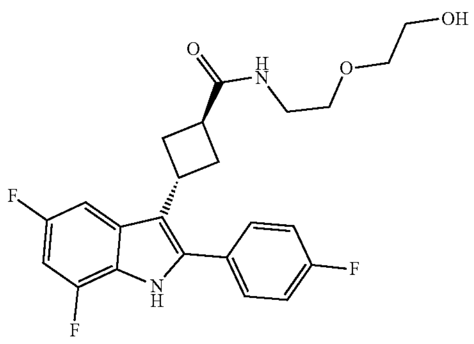
126
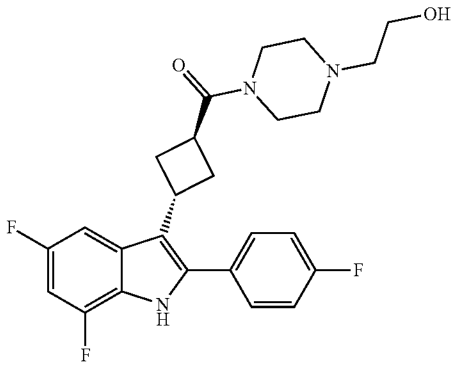
127
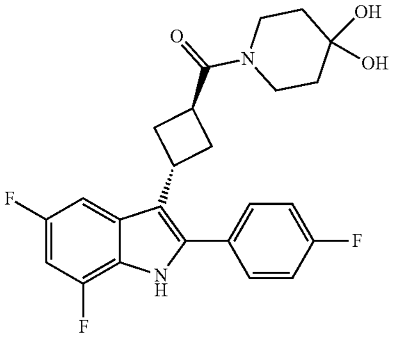
128
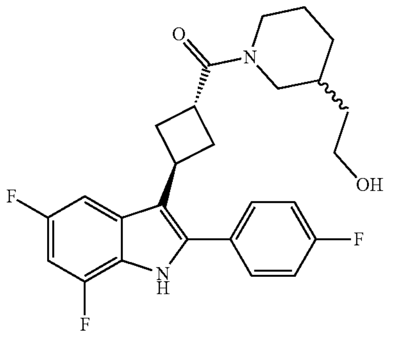

129
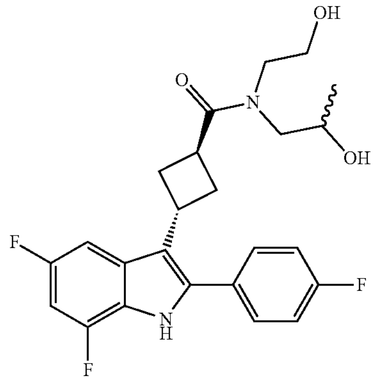
130
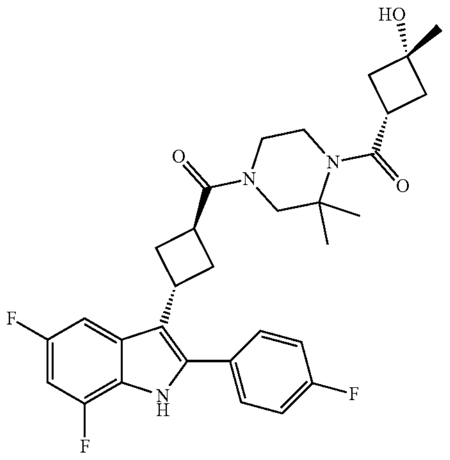
131
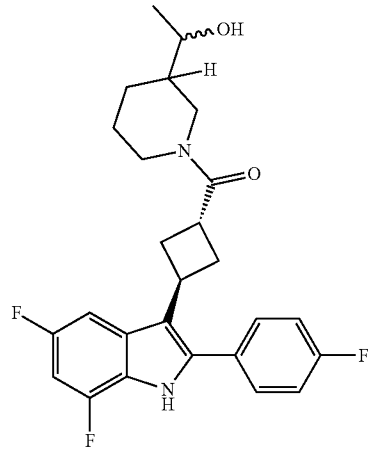
132
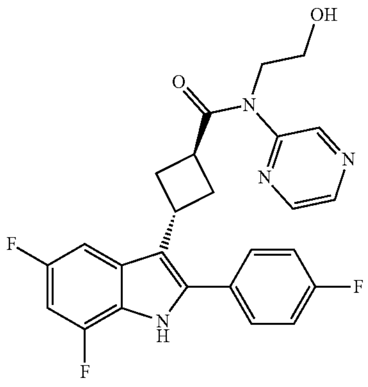
133
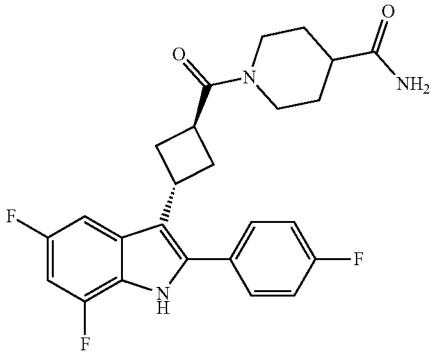
134
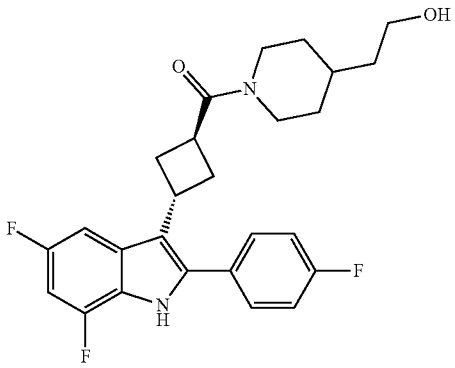
135
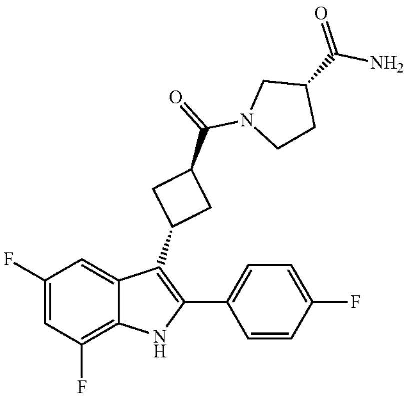

-continued
136
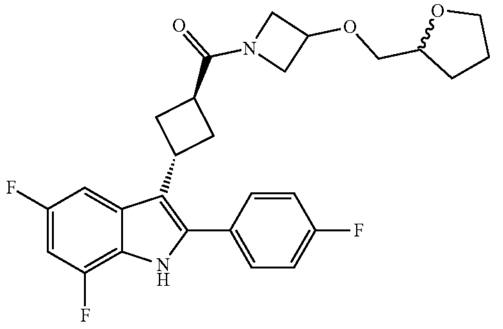
137
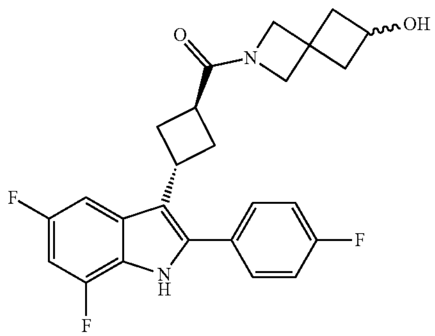
138
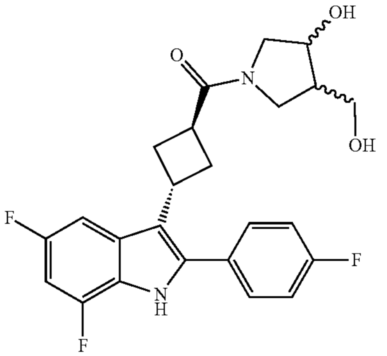
139
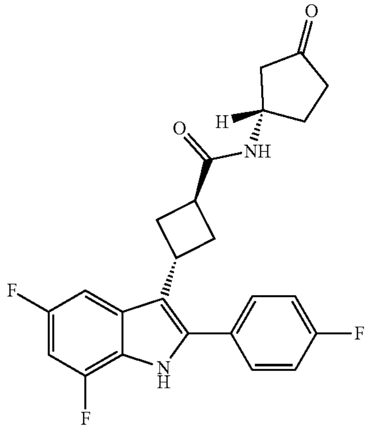
-continued
140
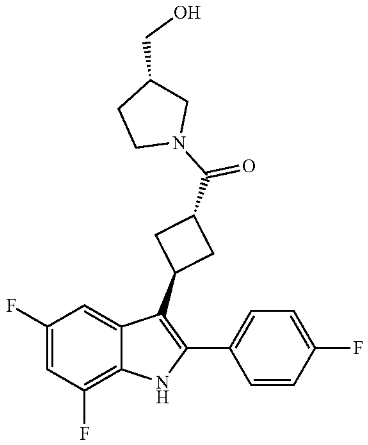
141
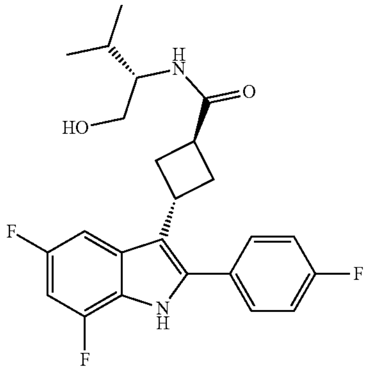
142
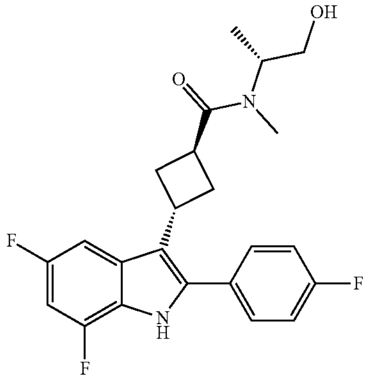
143
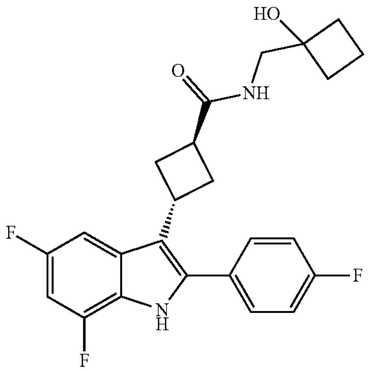

-continued
144
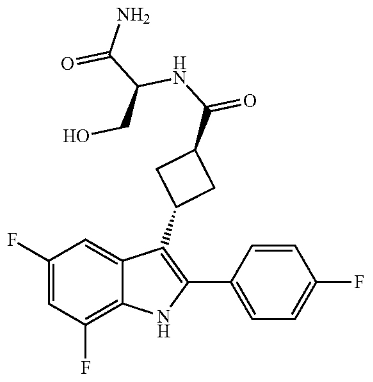
145
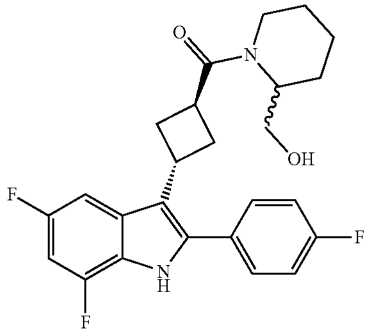
146
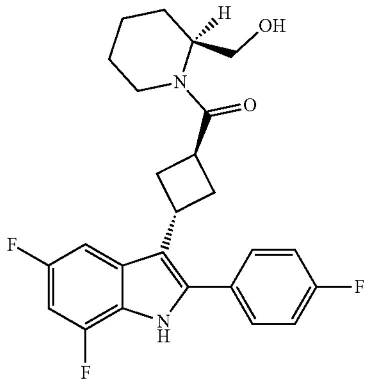
147
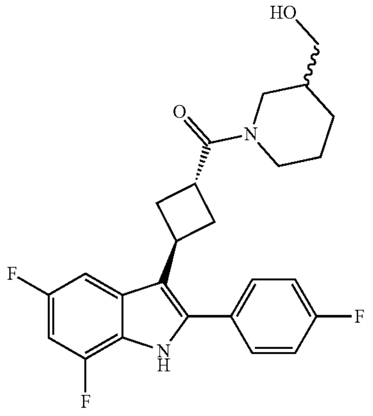
-continued
148
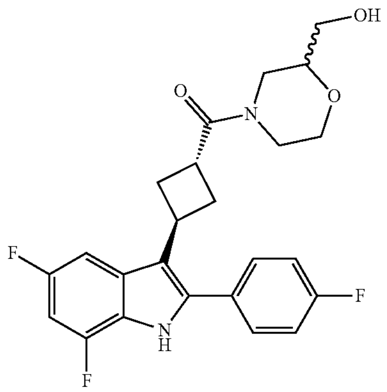
149
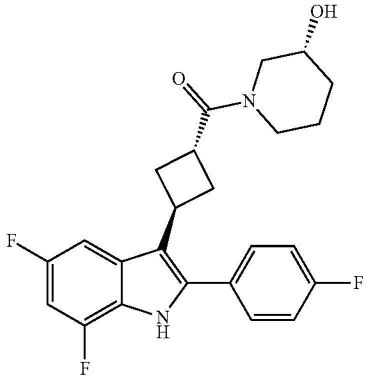
150
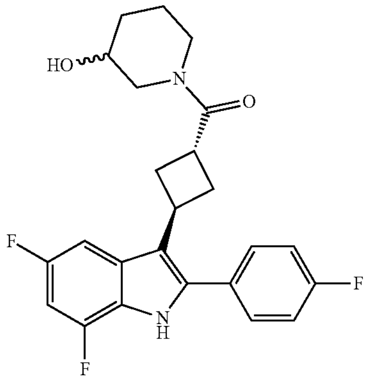
151
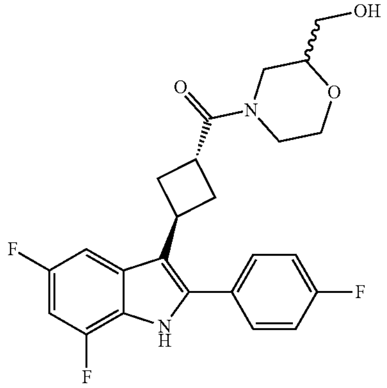

-continued
152
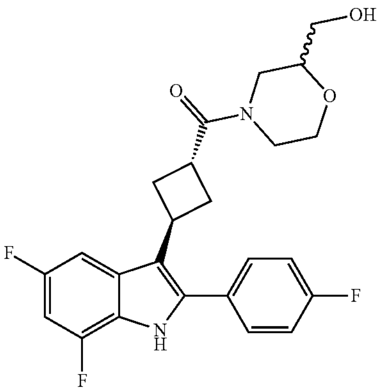
153
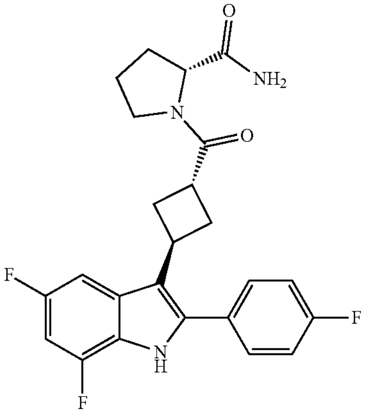
154
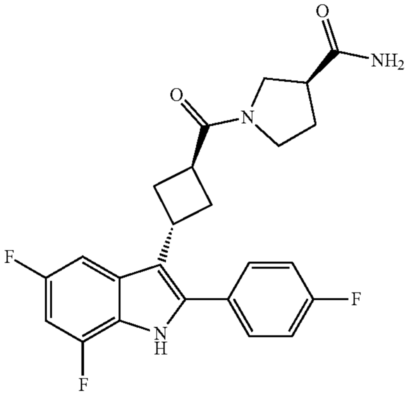
155
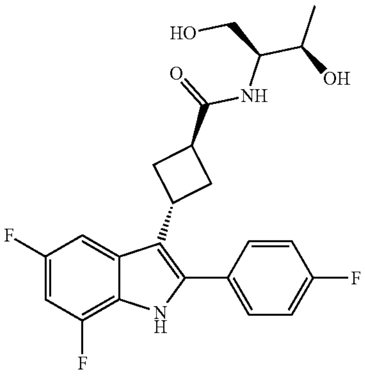
-continued
156
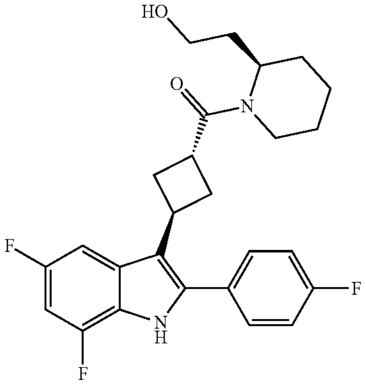
157
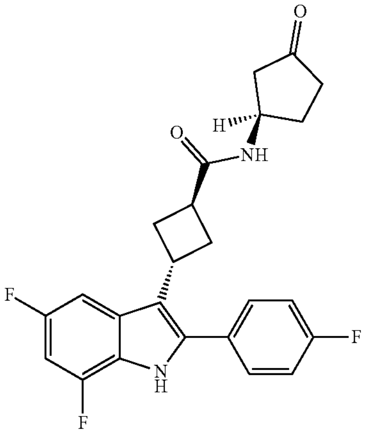
158
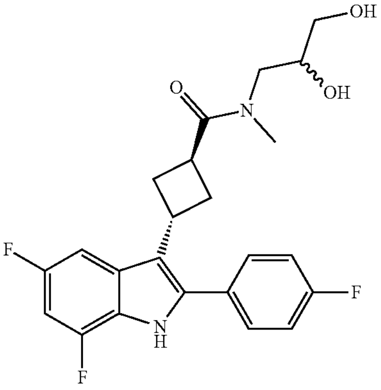
159
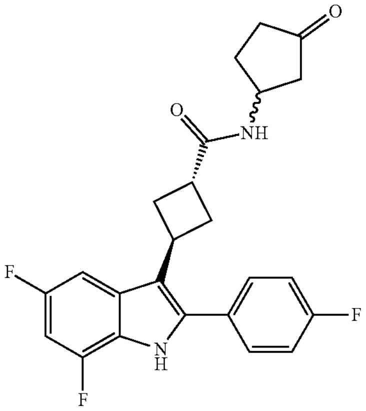

-continued
160
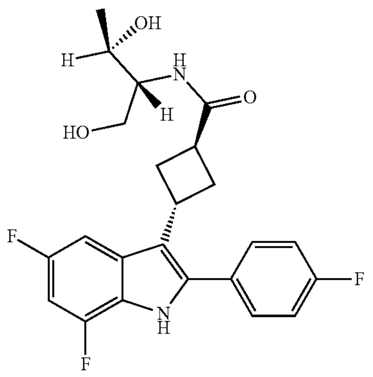
161
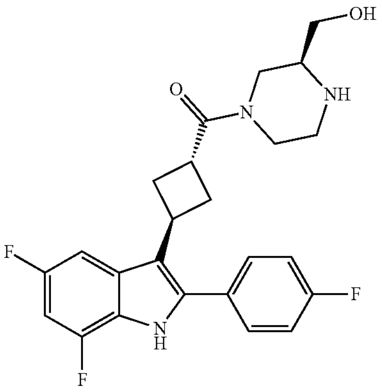
162
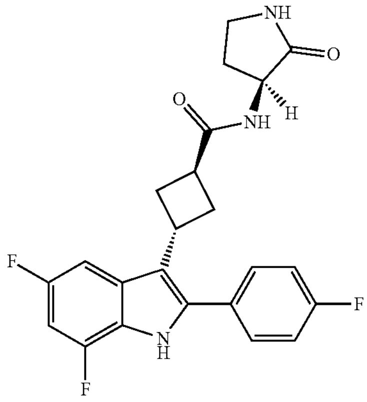
163
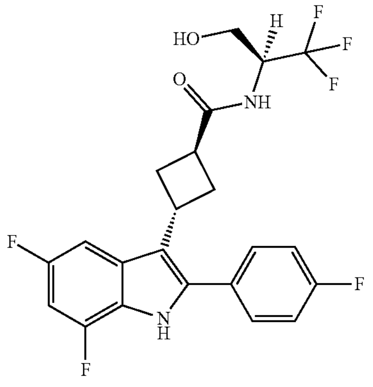
-continued
164
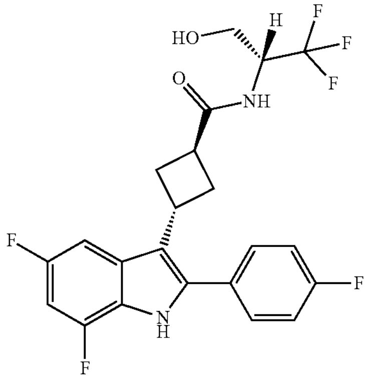
165
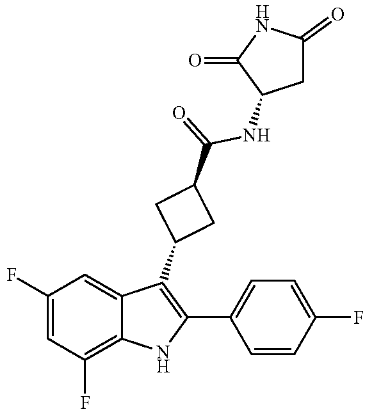
166
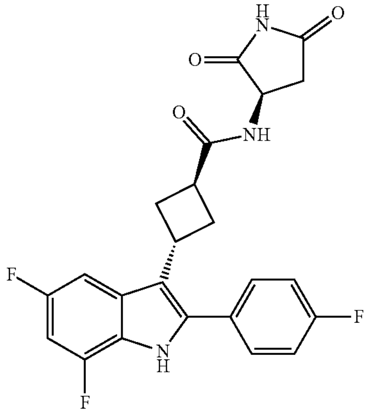
167
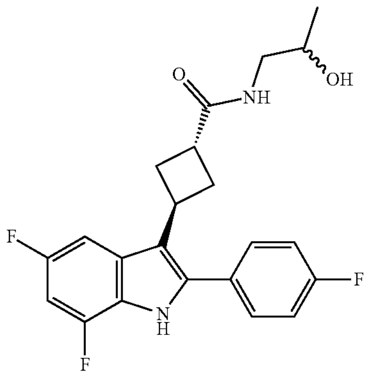

-continued
168
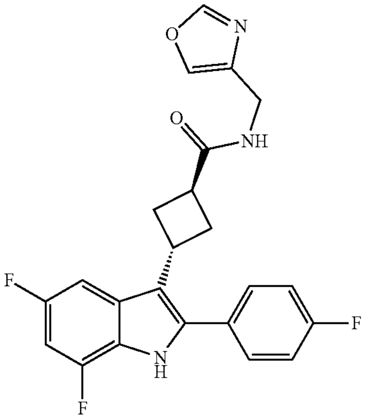
169
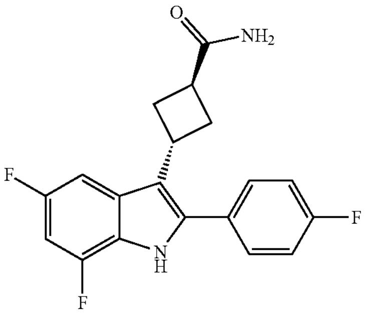
170
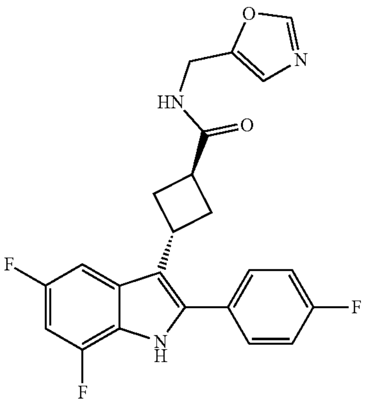
171
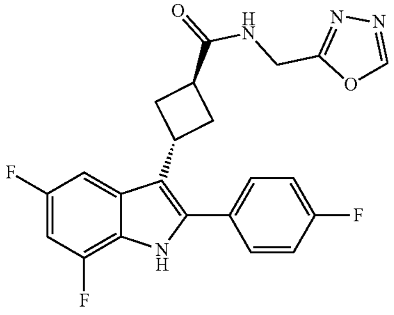
-continued
172
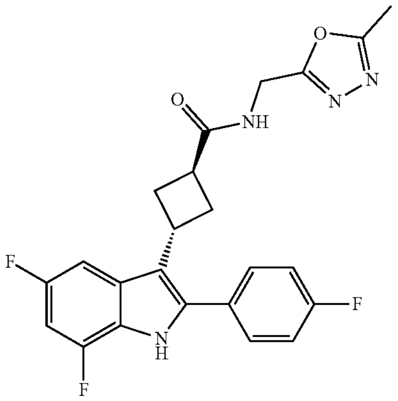
173
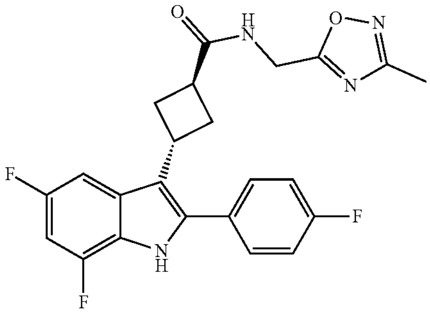
174
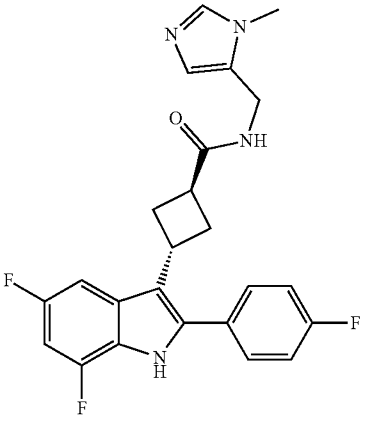
175
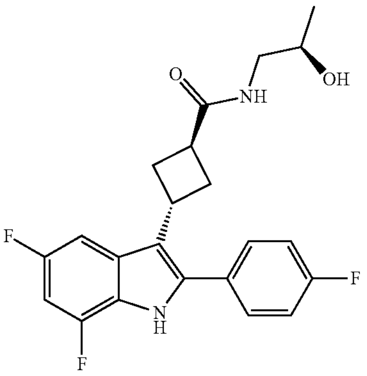

-continued
176
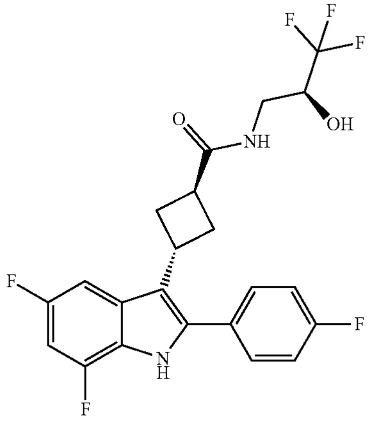
177
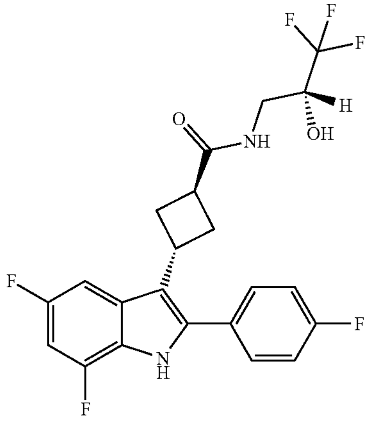
178
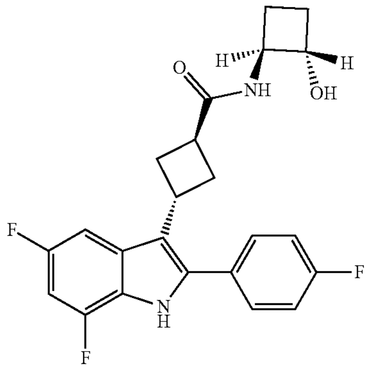
179
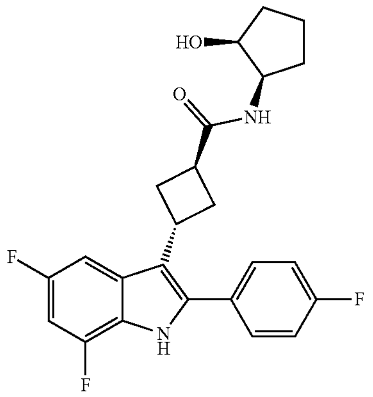
-continued
180
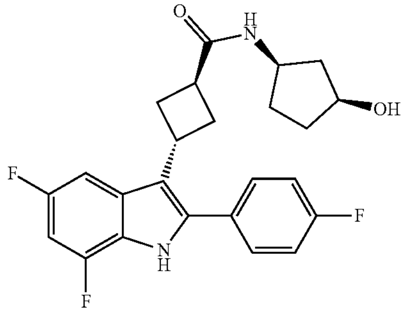
181
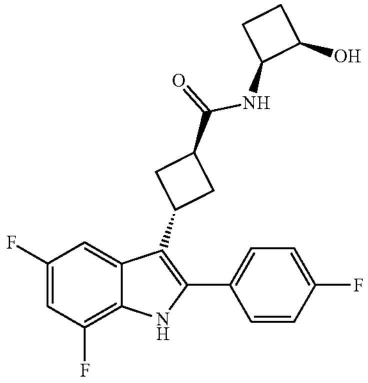
182
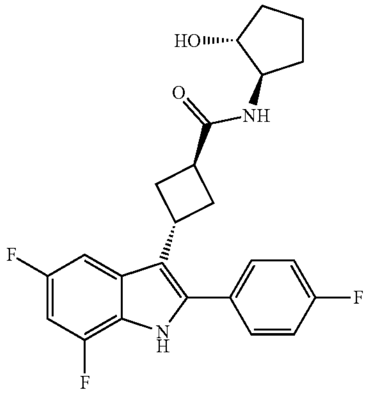
183
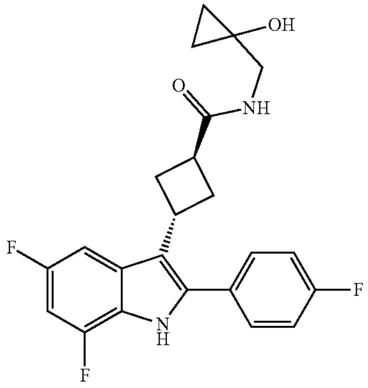

-continued
184
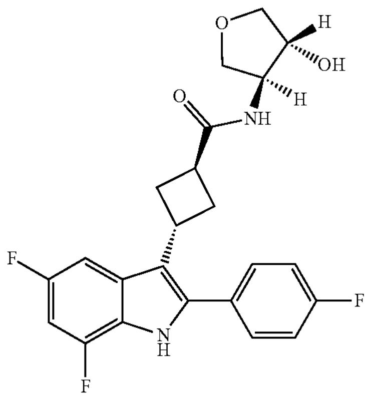
185
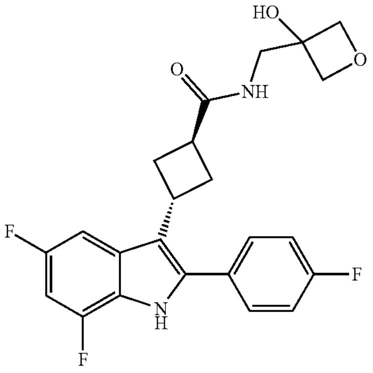
186
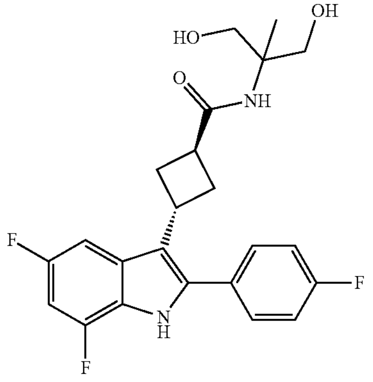
187
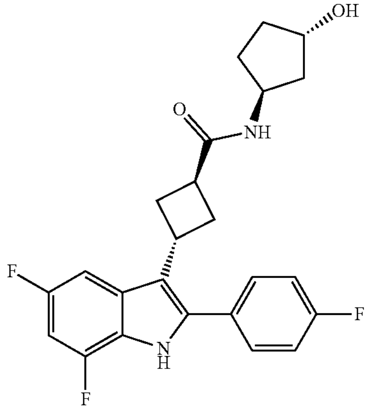
-continued
188
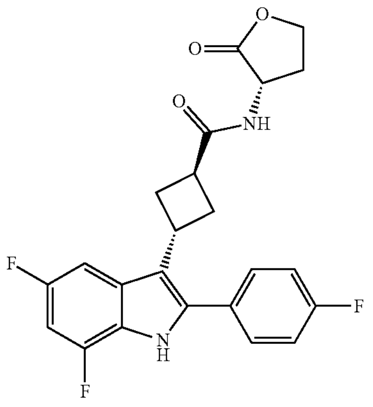
189
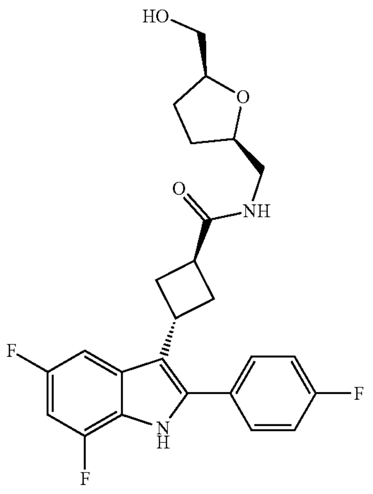
190
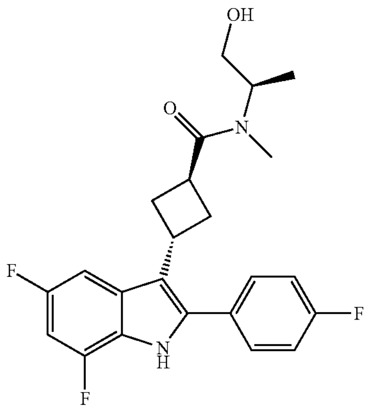

-continued
191
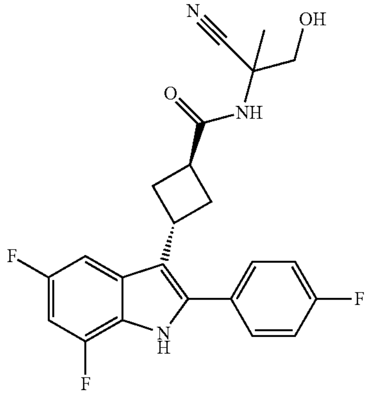
192
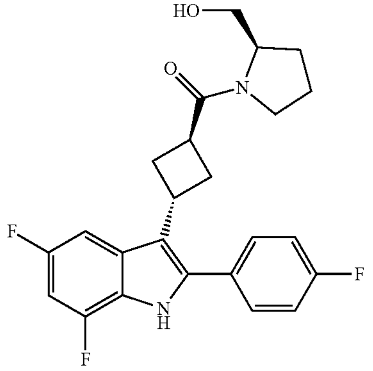
193
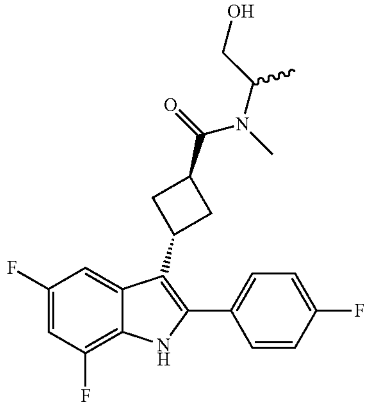
194
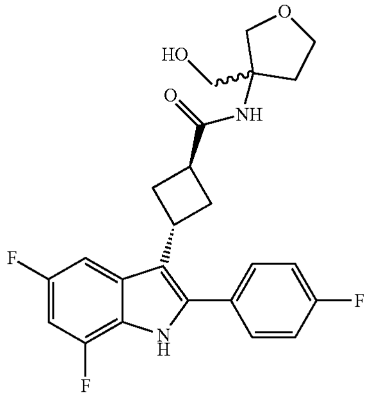
-continued
195
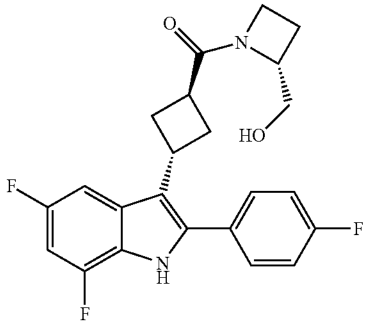
196
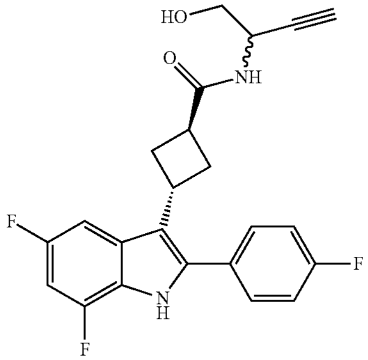
197
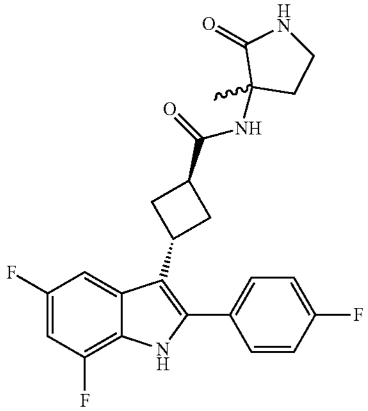
198
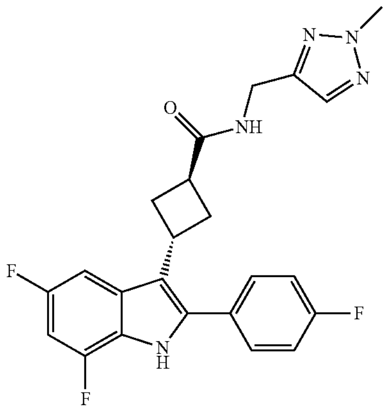

-continued
199
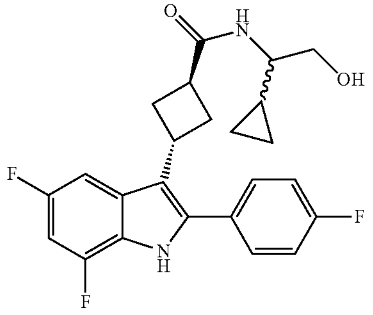
200
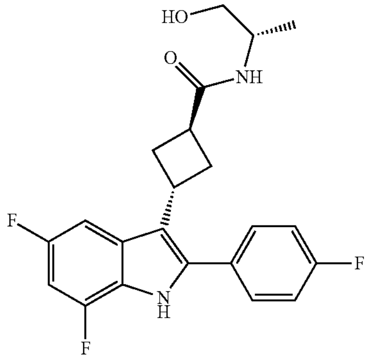
201
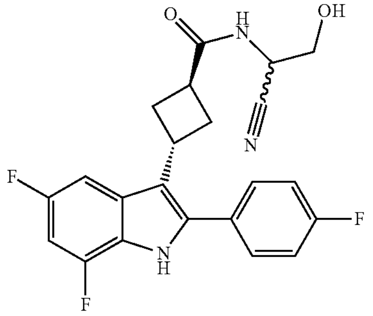
202
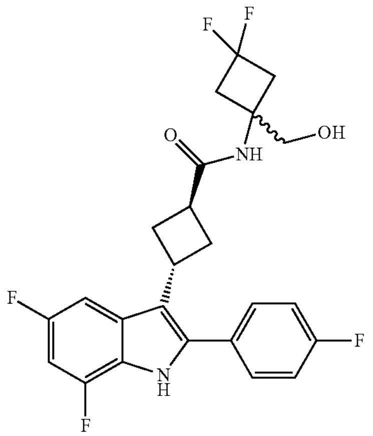
-continued
203
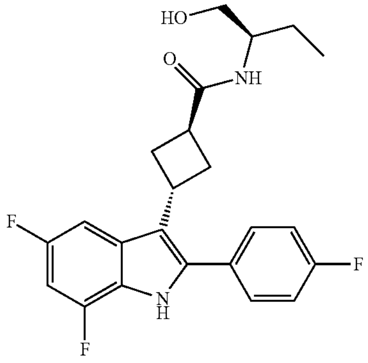
204
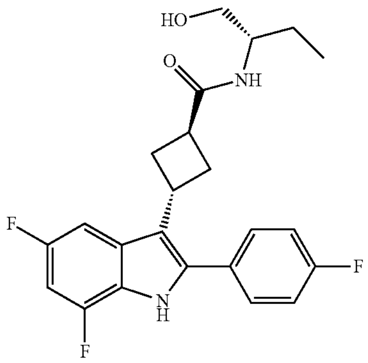
205
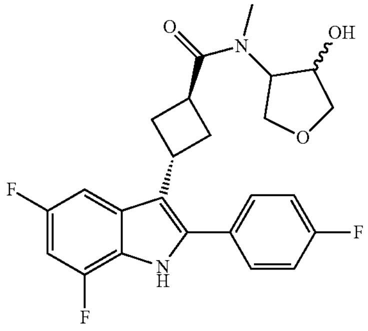
206
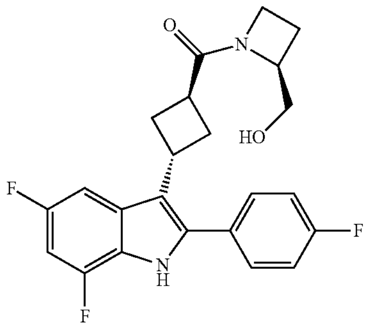

-continued
207
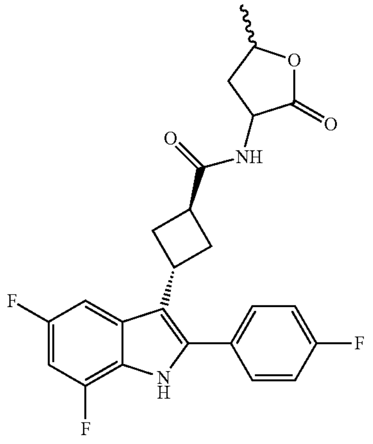
208
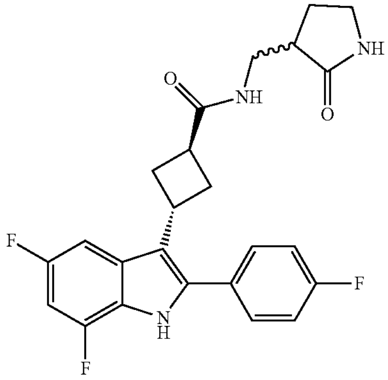
209
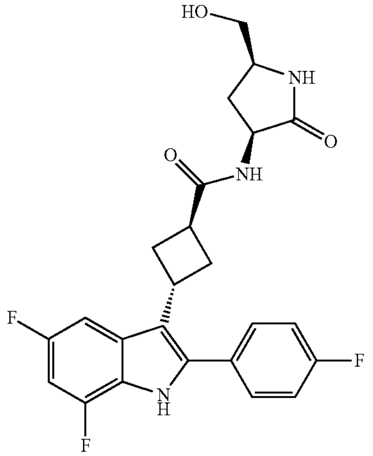
210
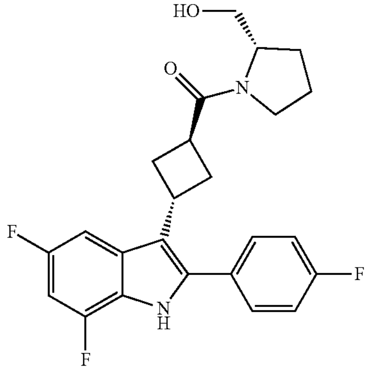
-continued
211
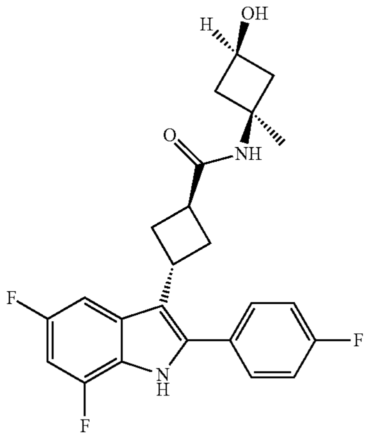
212
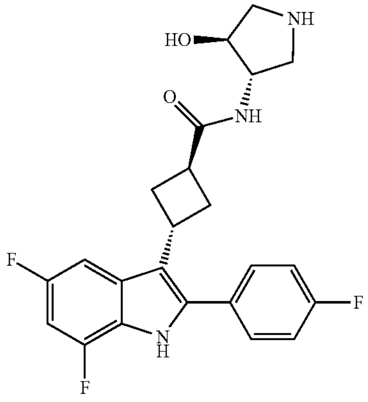
213
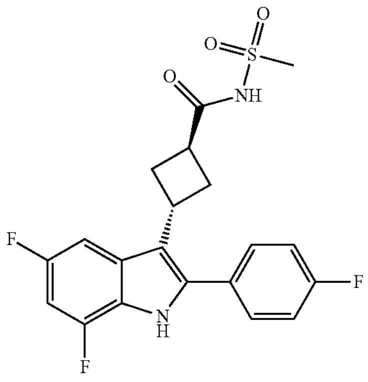
214
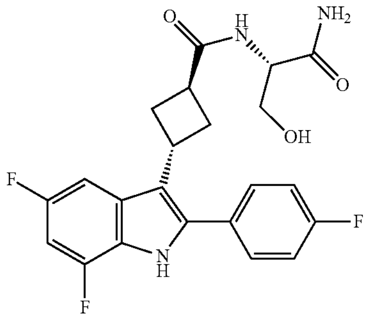

-continued
215
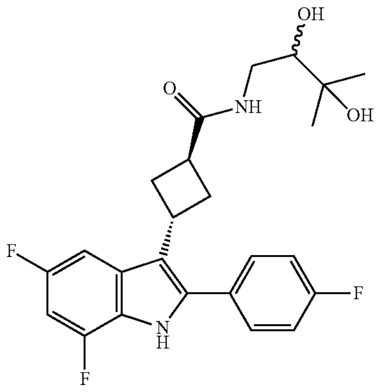
216
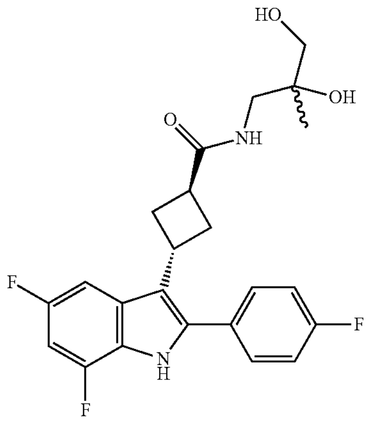
217
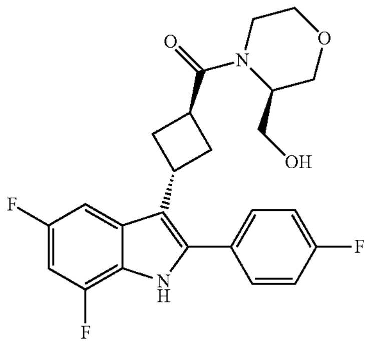
218
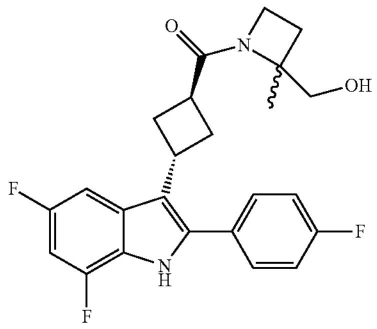
-continued
219
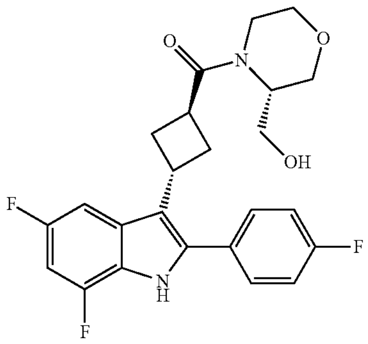
220
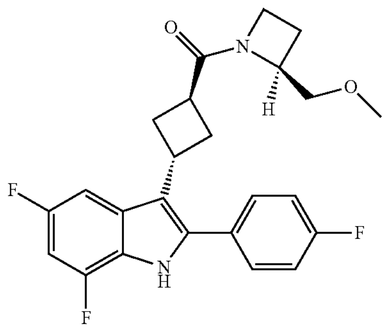
221
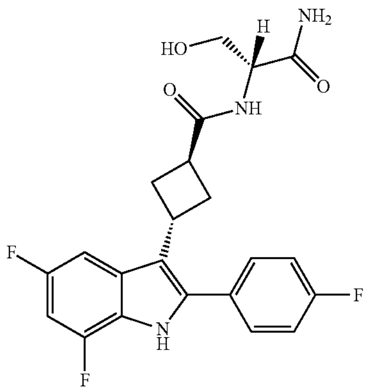
222
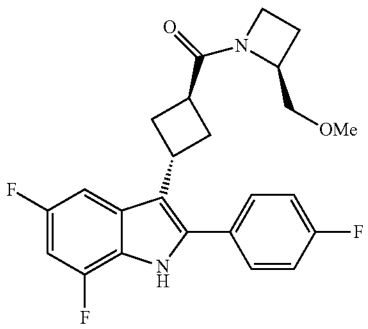

-continued
223
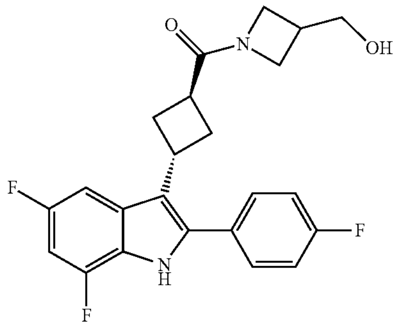
224
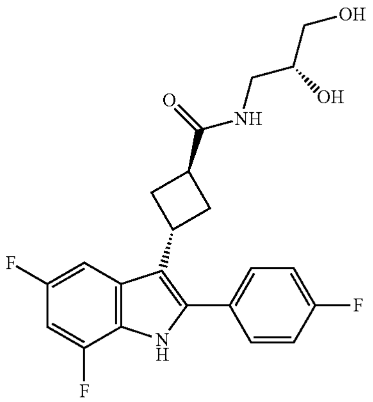
225
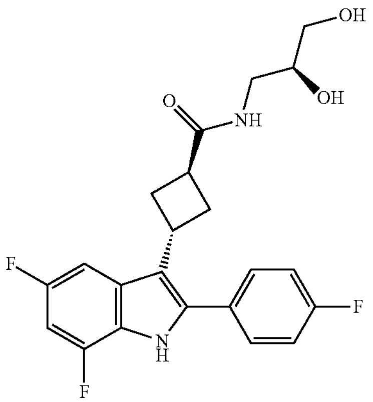
226
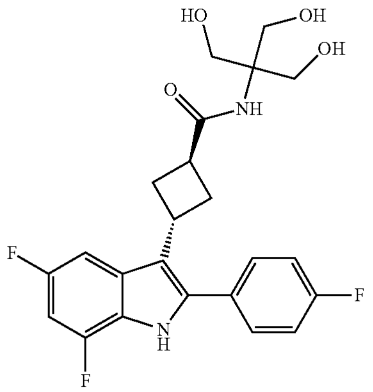
-continued
227
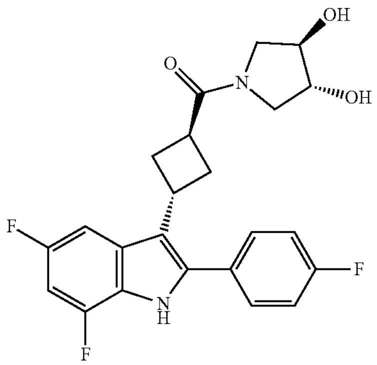
228
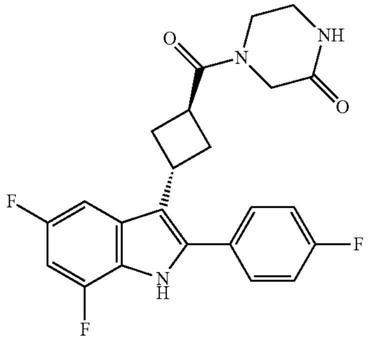
229
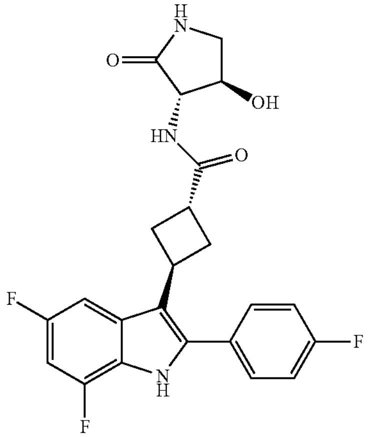
230
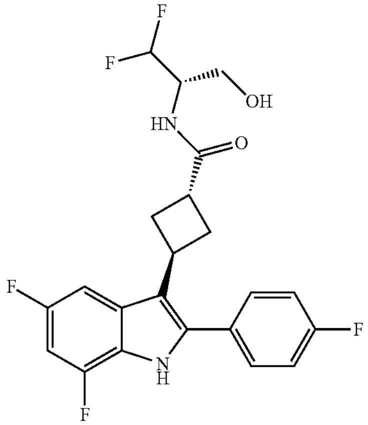

231
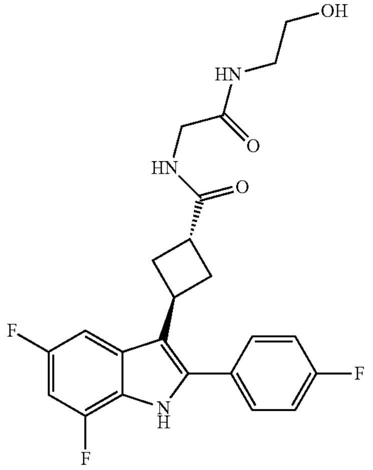
232
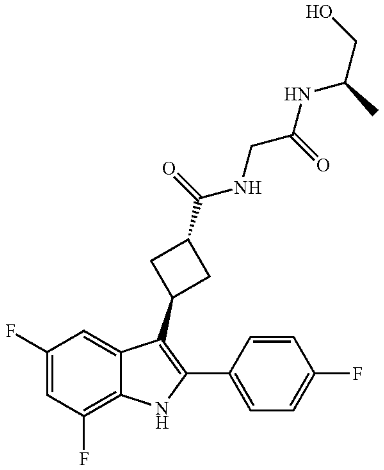
233
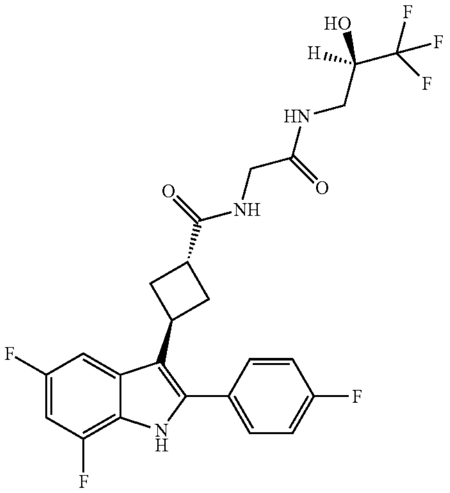
234
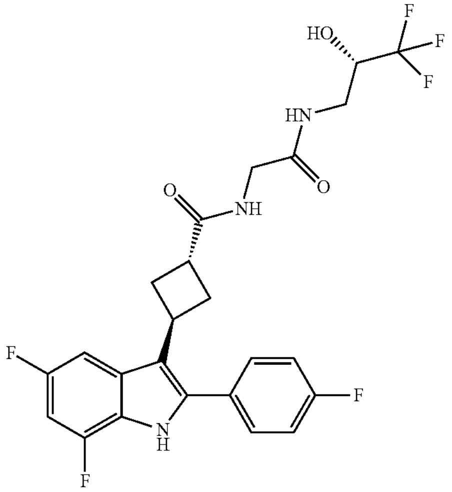
235
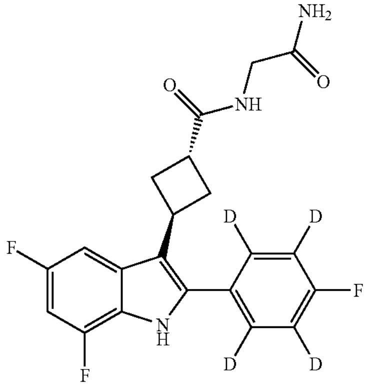
236
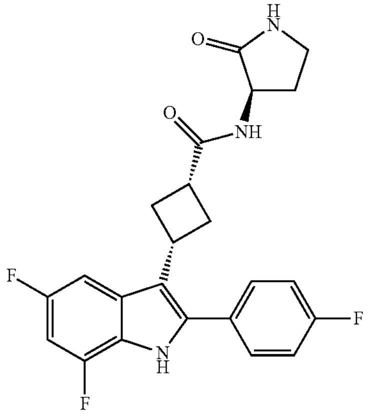
237
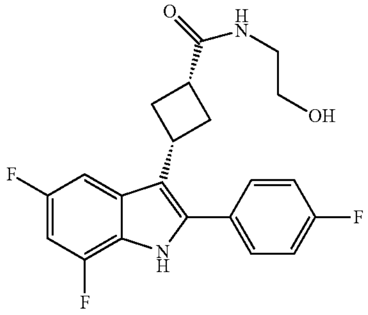

-continued
238
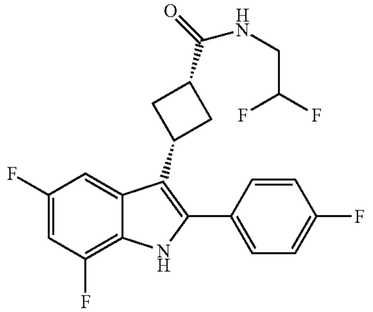
239
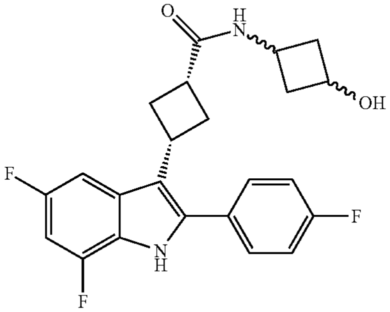
240
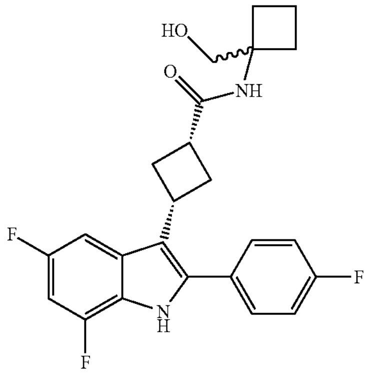
241
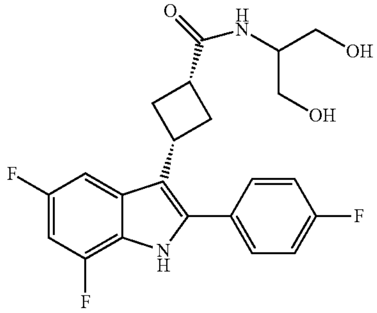
242
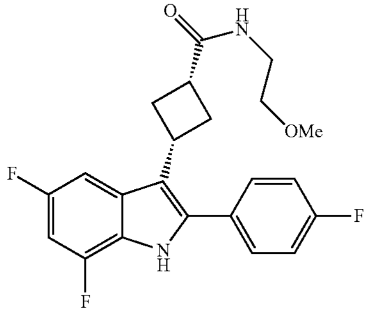
-continued
243
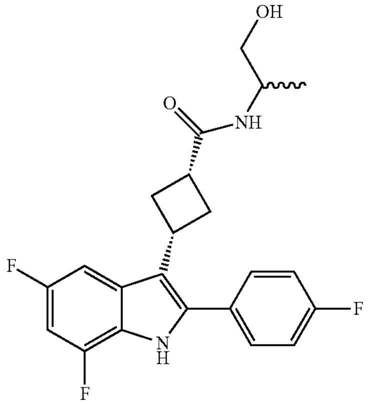
244
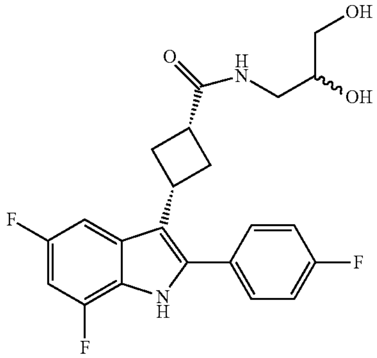
245
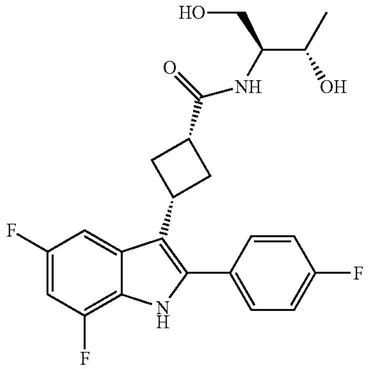
246
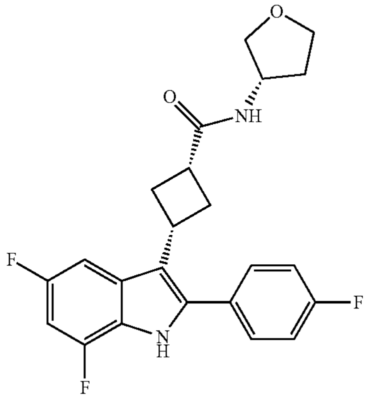

-continued
247
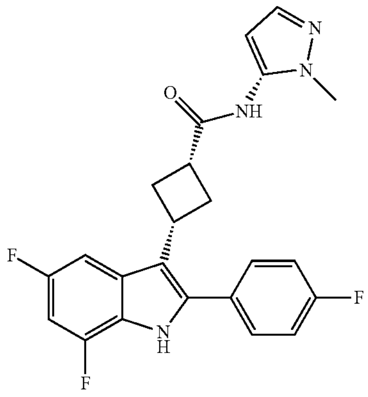
248
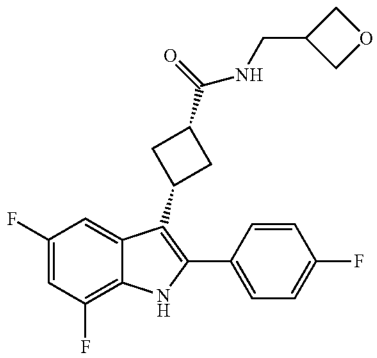
249
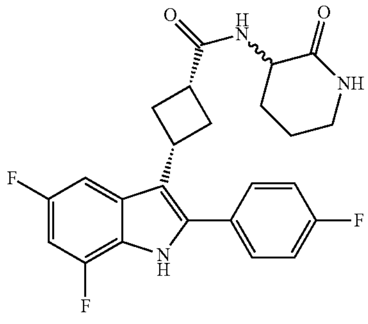
250
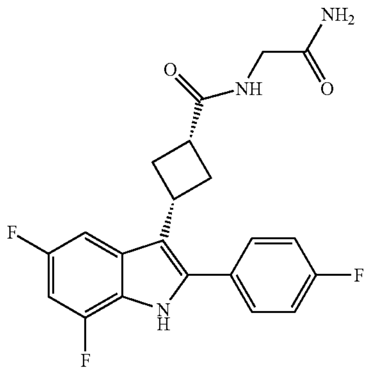
-continued
251
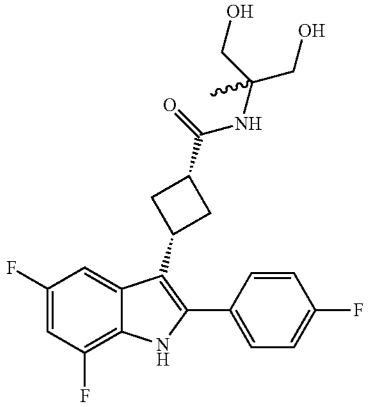
252
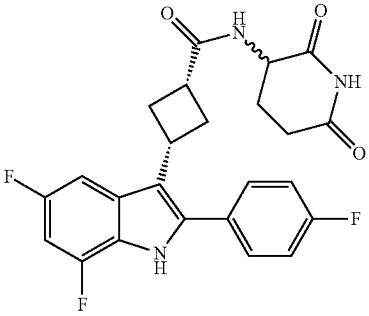
253
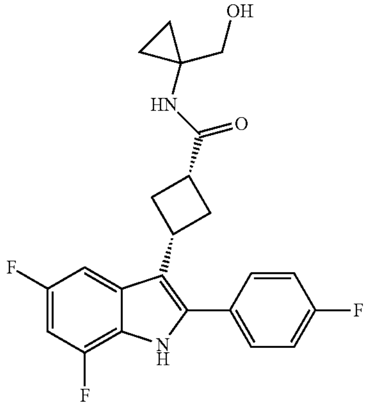
254
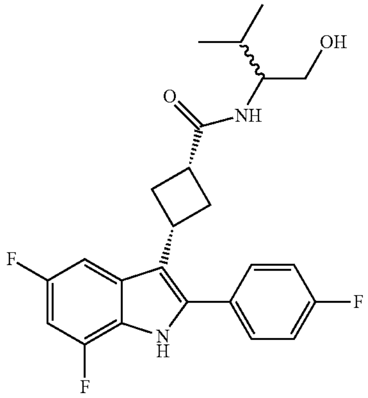

-continued
255
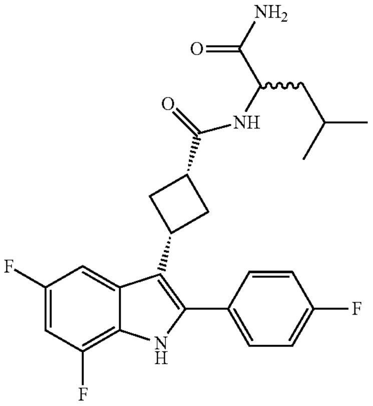
256
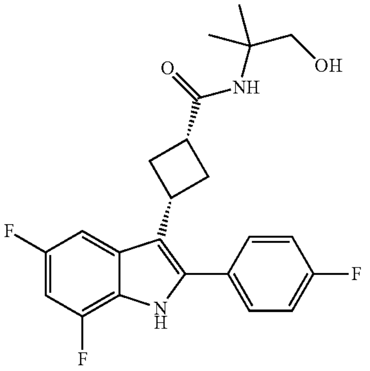
257
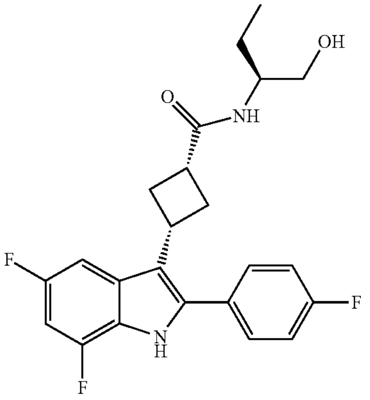
258
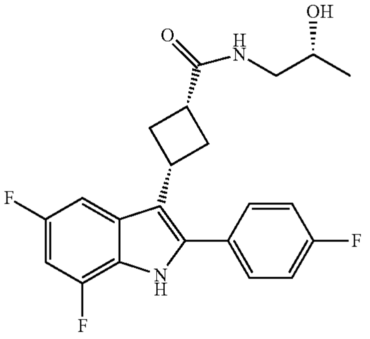
-continued
259
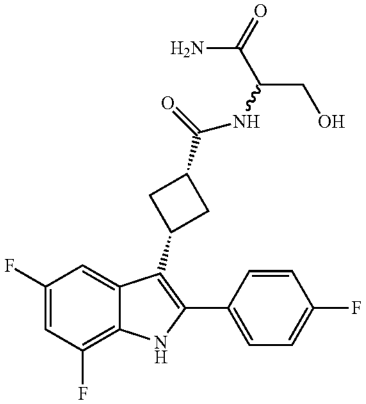
260
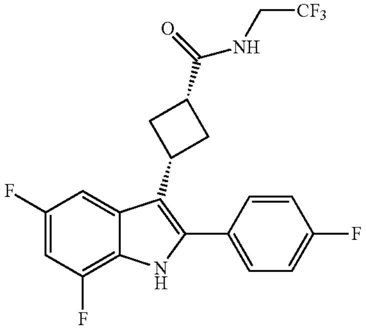
261
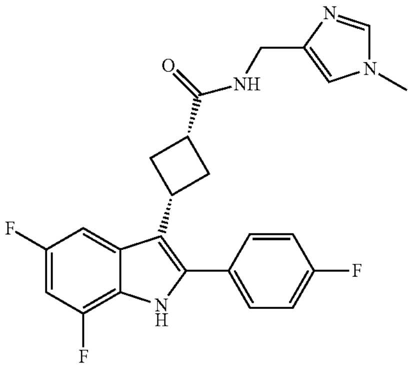
262
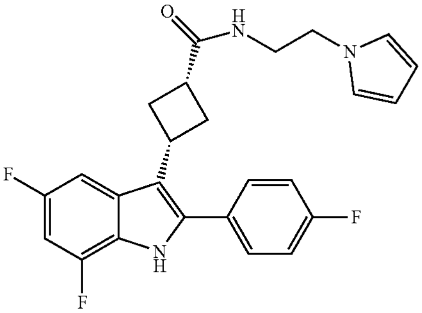

-continued
263
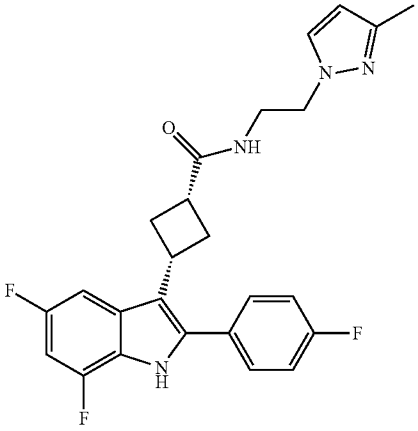
264
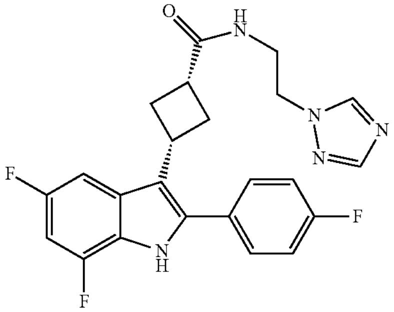
265
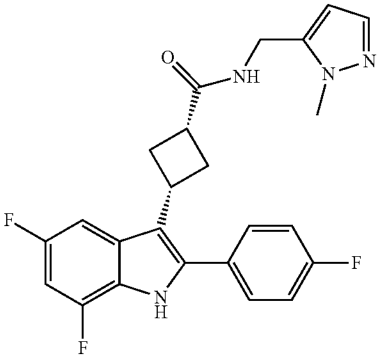
266
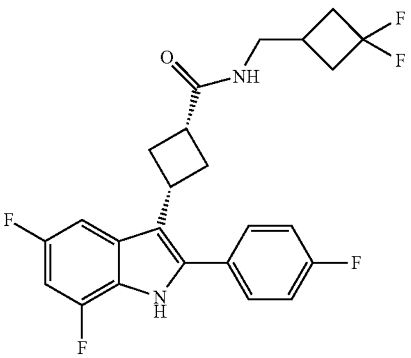
-continued
267
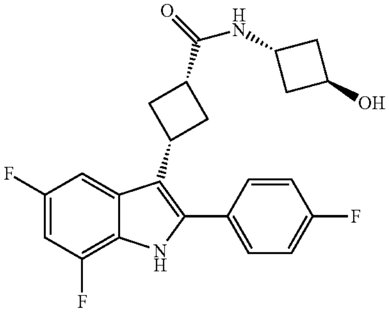
268
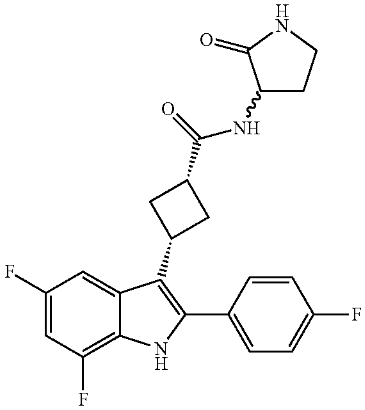
269
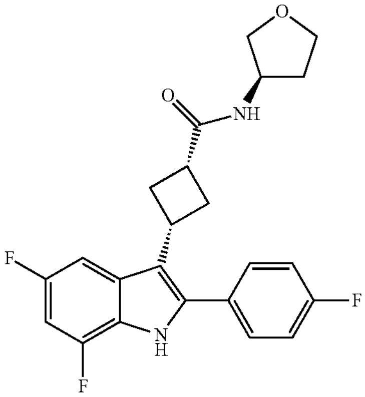
270
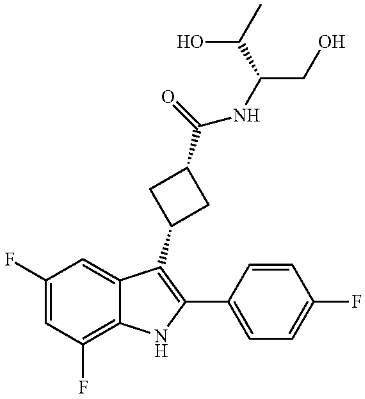

-continued
271
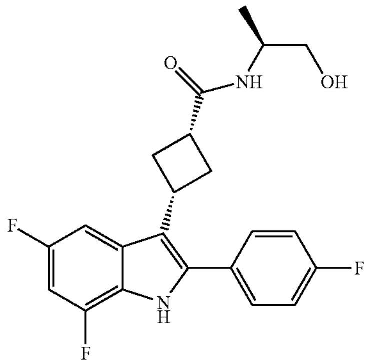
272
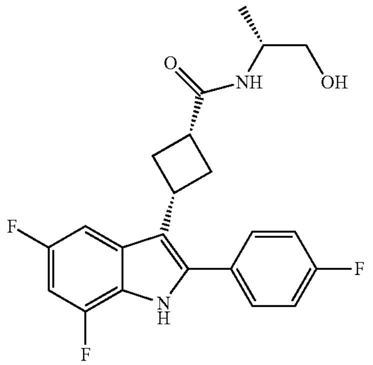
273
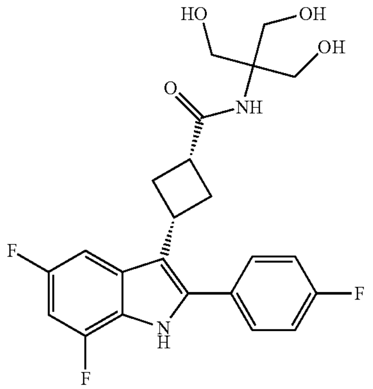
274
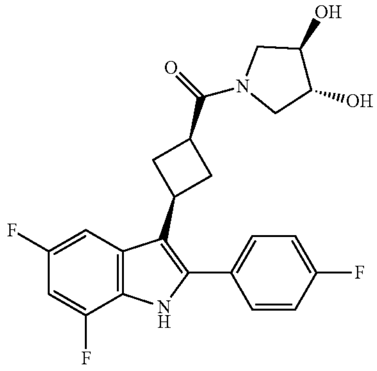
-continued
275
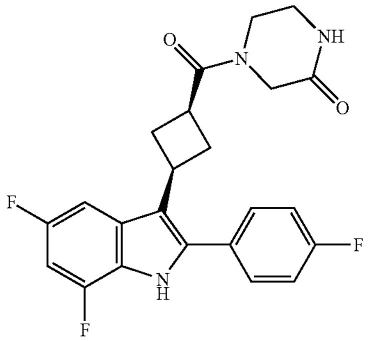
276
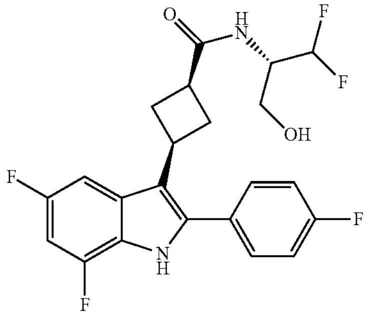
277
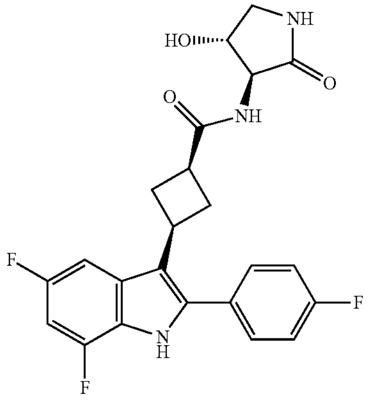
278
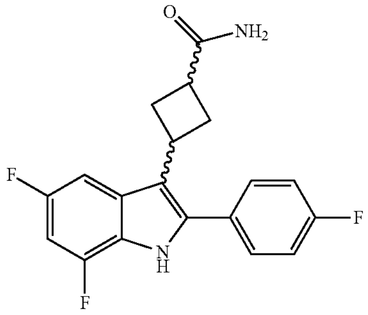

-continued
279
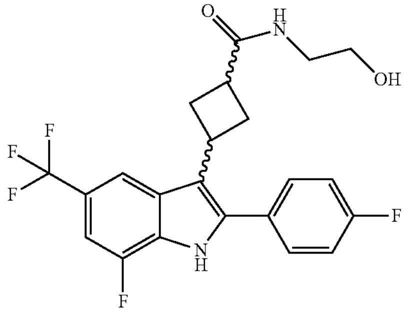
280
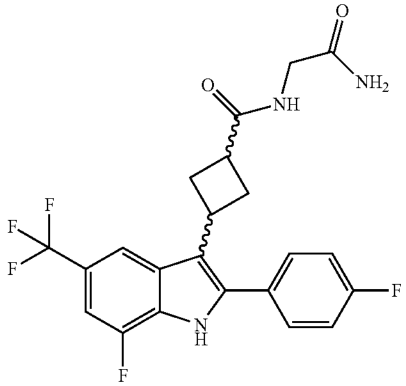
281
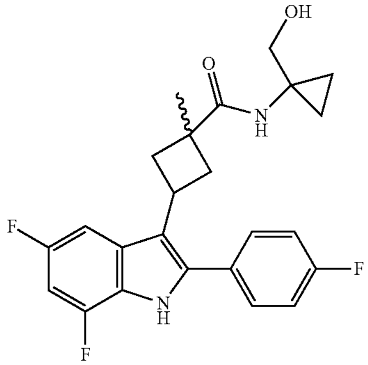
282
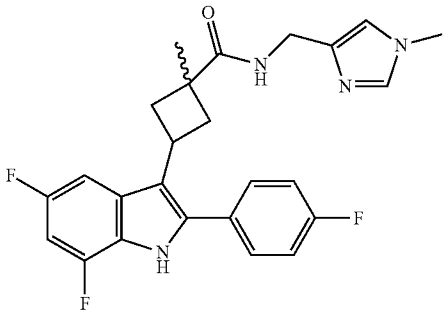
-continued
283
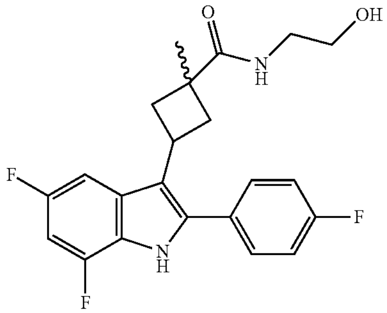
284
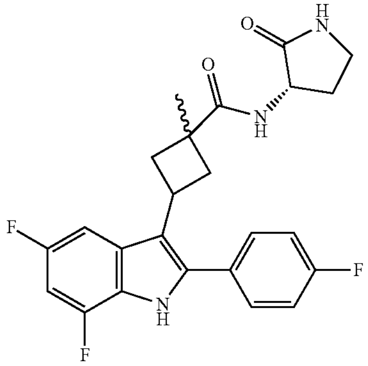
285
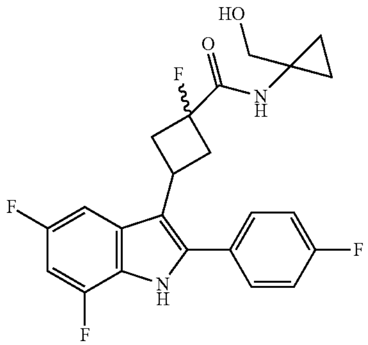
286
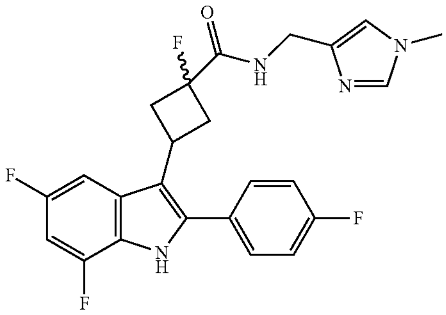
pharmaceutically acceptable salts thereof, solvates of any of the foregoing, and deuterated derivatives of any of the foregoing.

25. A compound chosen from
287
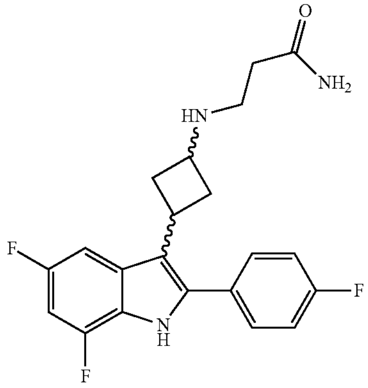
288
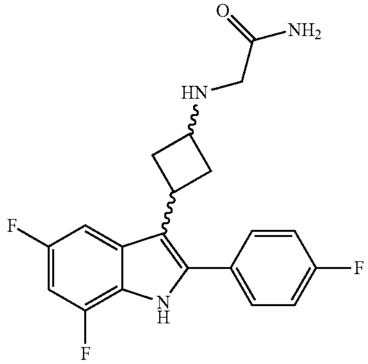
289
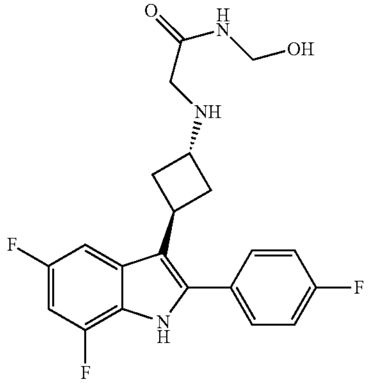
290
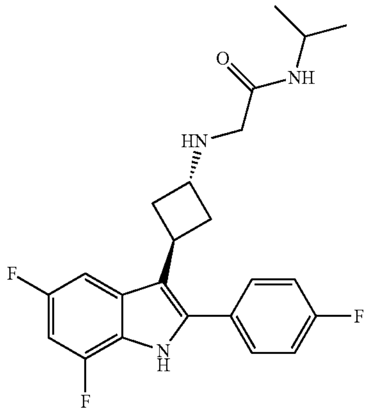
-continued
291
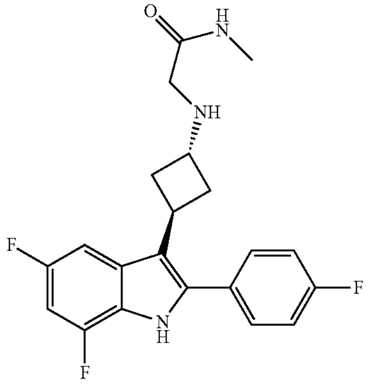
292
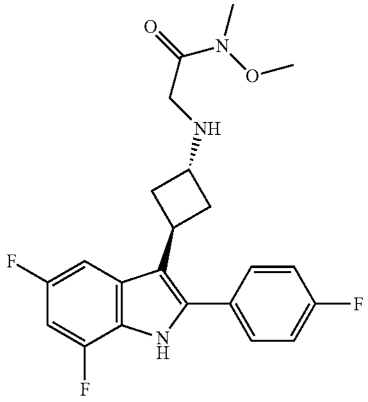
293
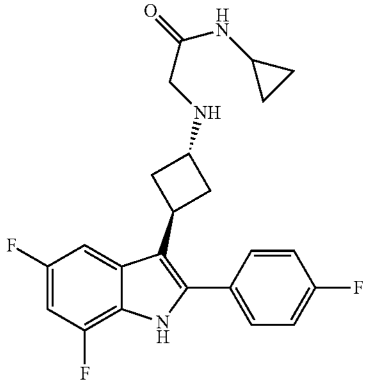
294
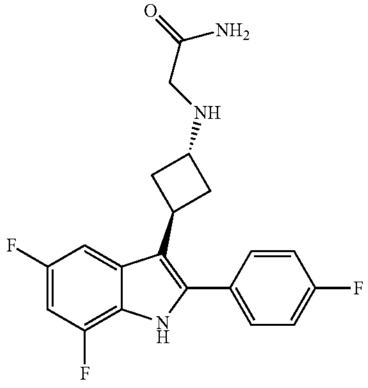

-continued
295
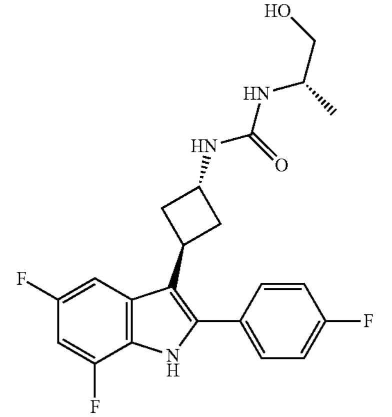
296
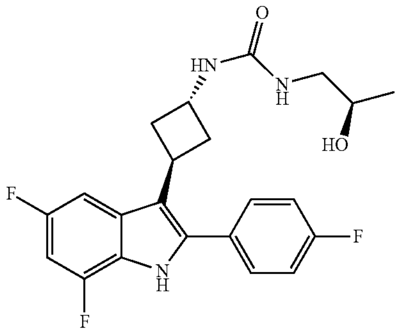
297
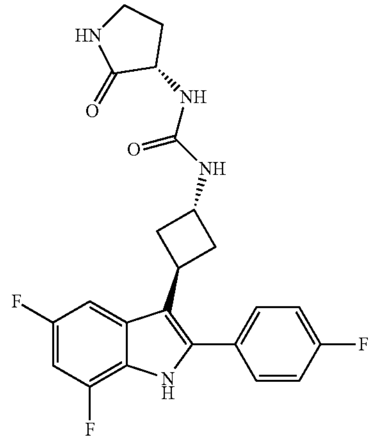
298
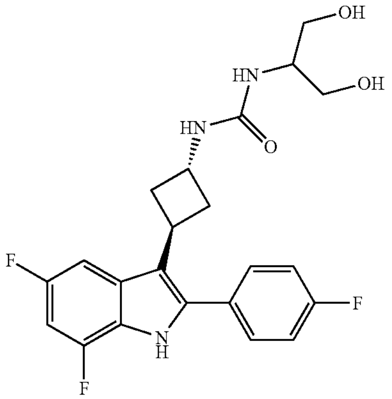
-continued
299
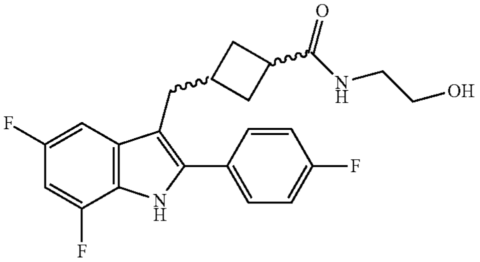
300
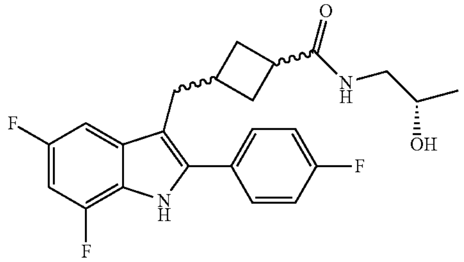
301
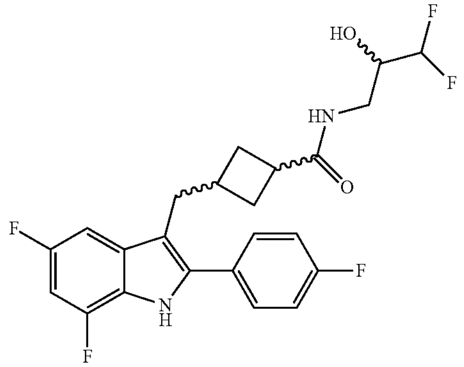
302
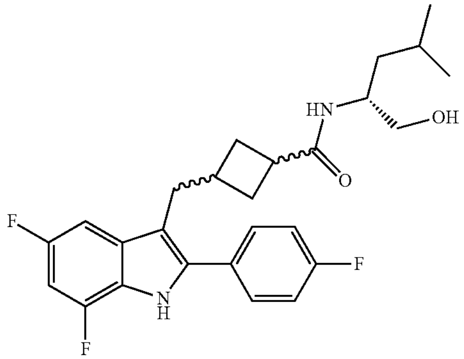
303
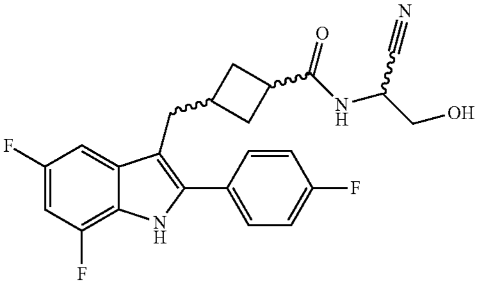

-continued
304
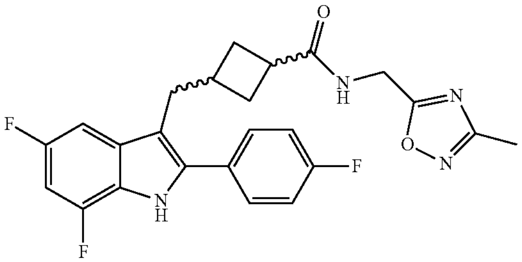
305
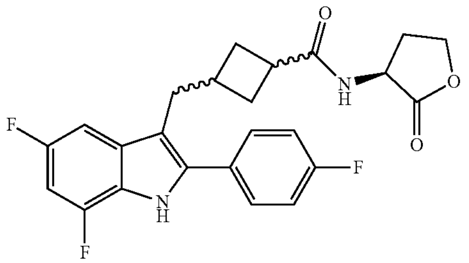
306
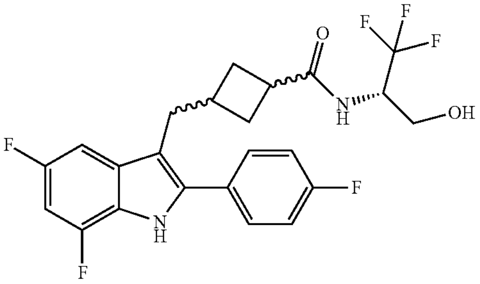
307
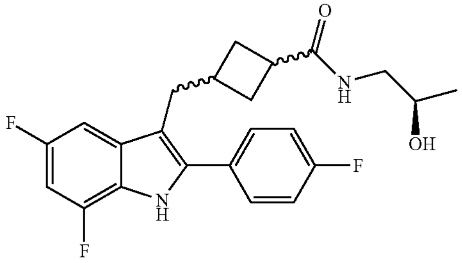
308
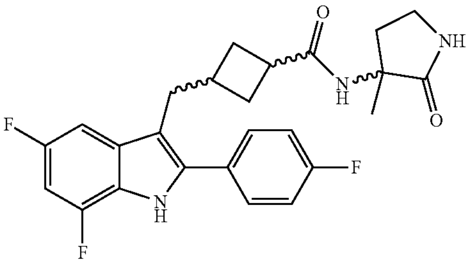
-continued
309
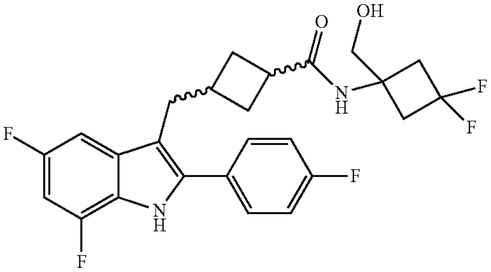
310
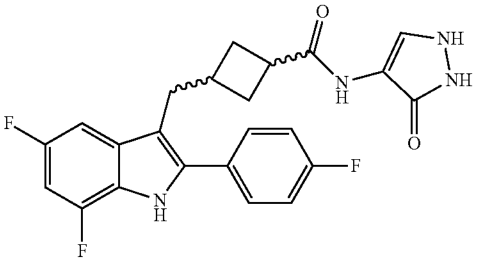
311
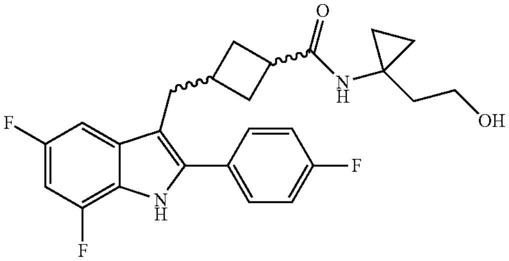
312
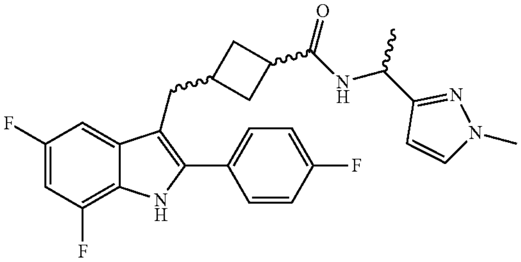
313
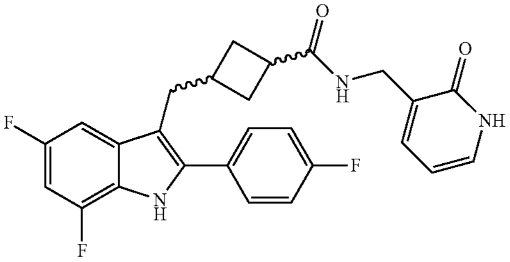

-continued
314
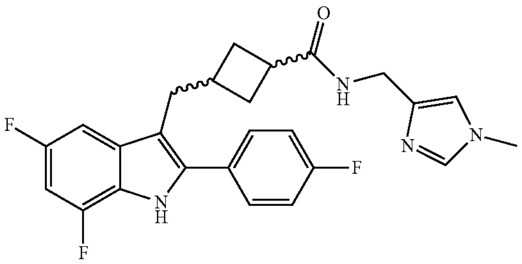
315
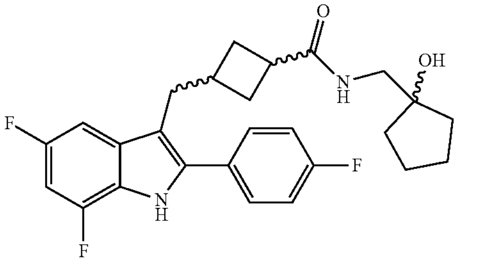
316
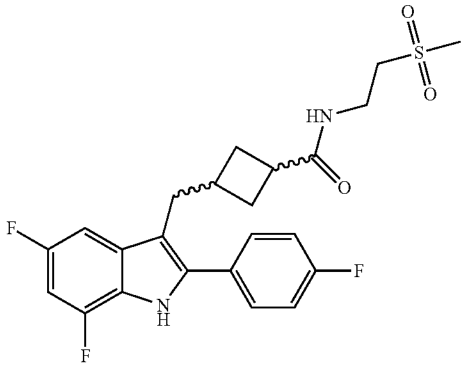
317
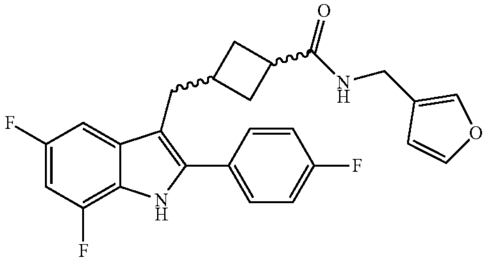
318
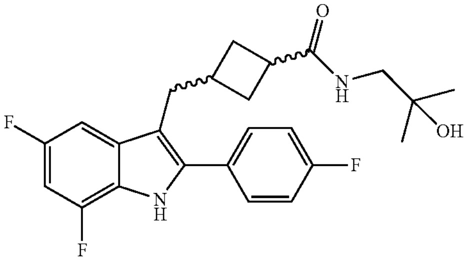
-continued
319
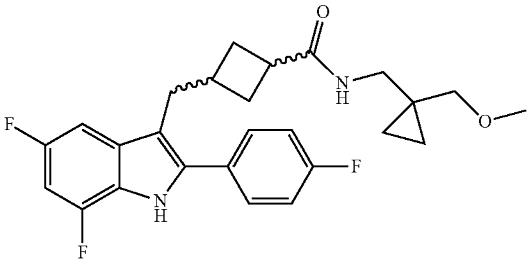
320
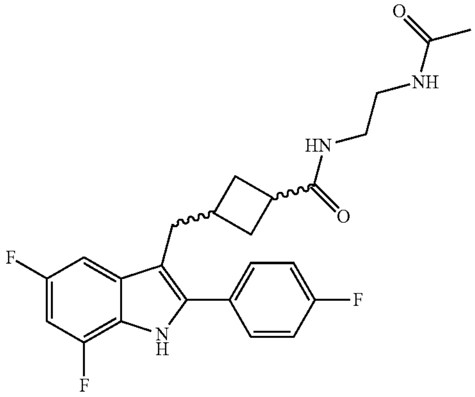
321
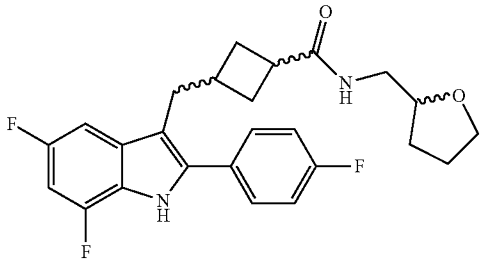
322
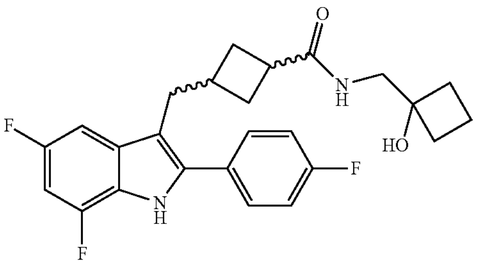
323
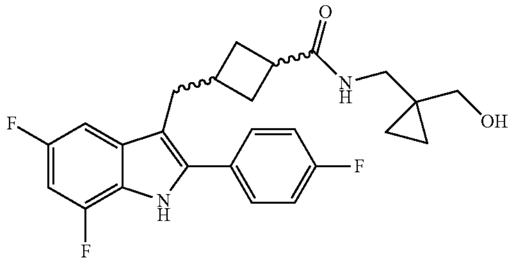

-continued
324
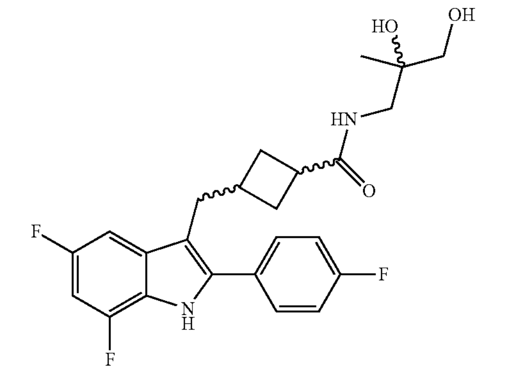
325
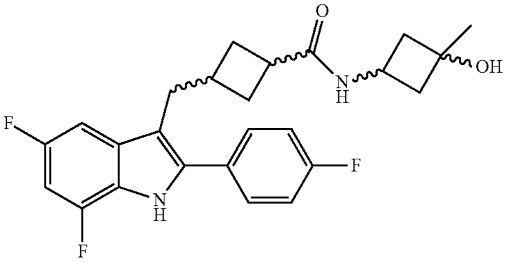
326
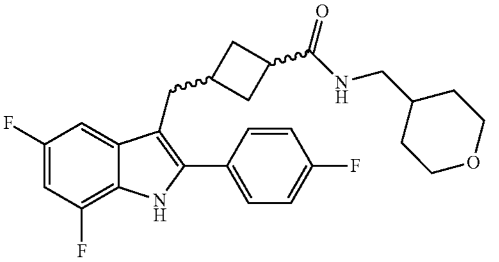
327
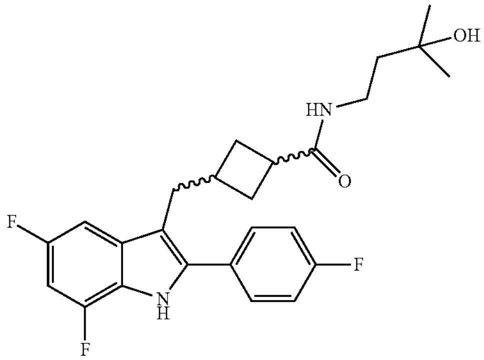
328
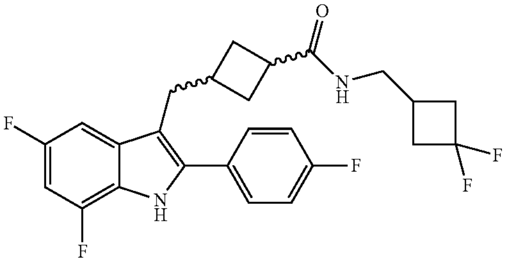
-continued
329
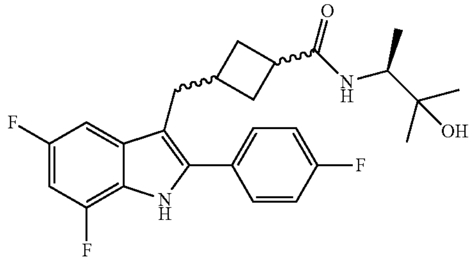
330
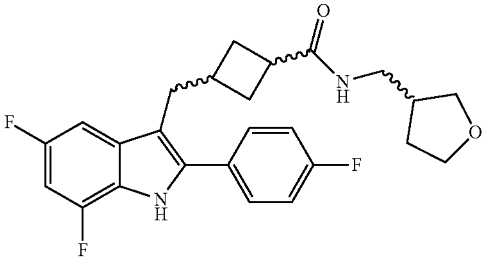
331
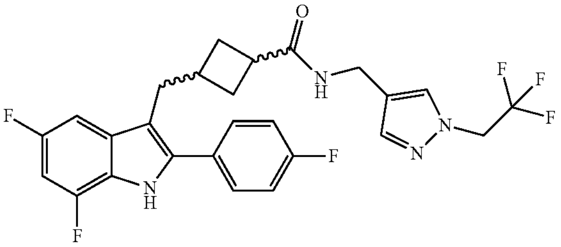
332
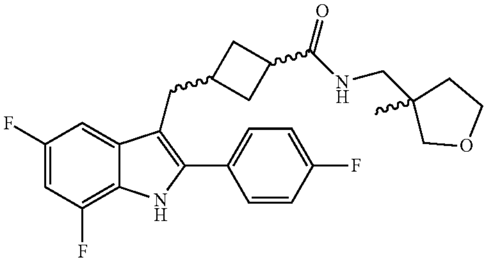
333
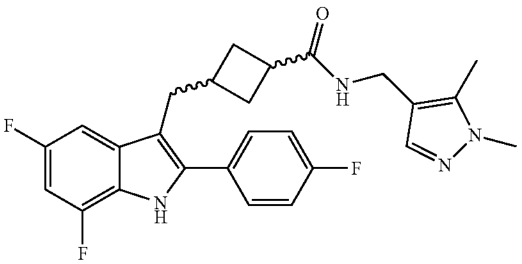
334
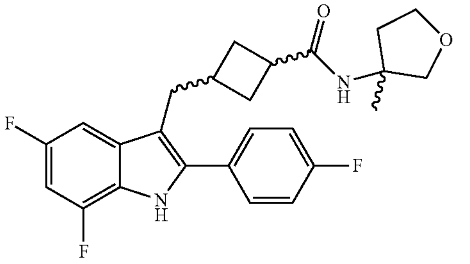

-continued
335
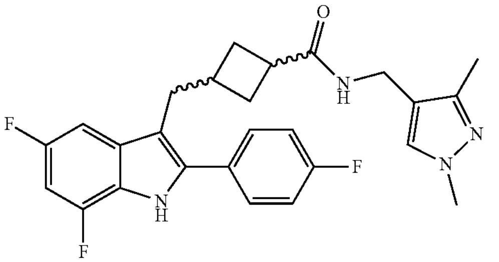
336
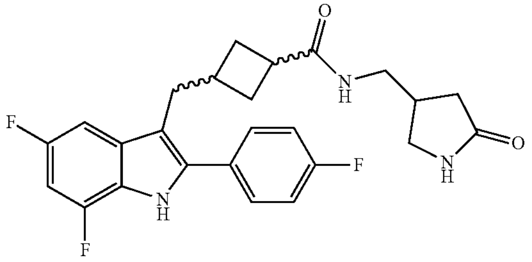
337
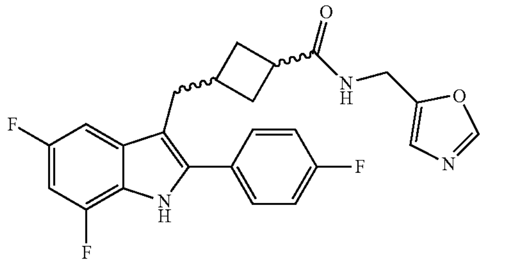
338
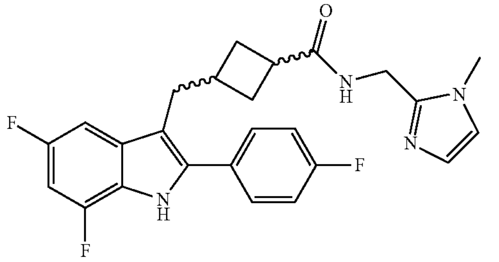
339
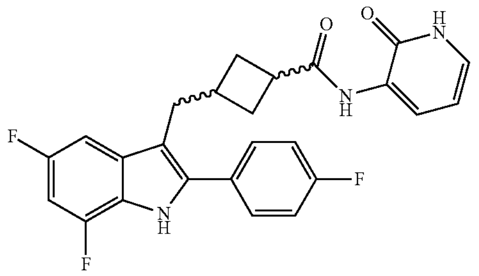
-continued
340
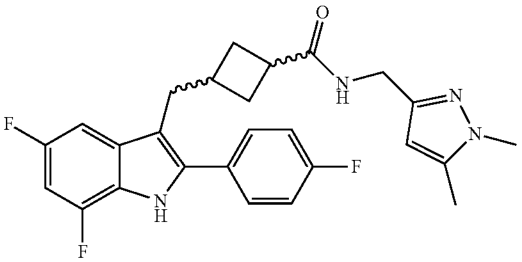
341
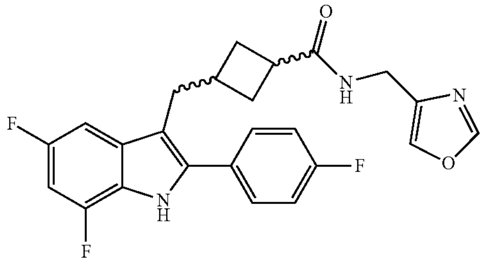
342
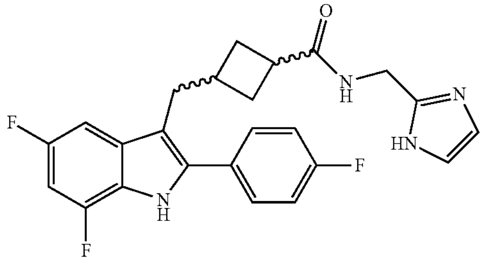
343
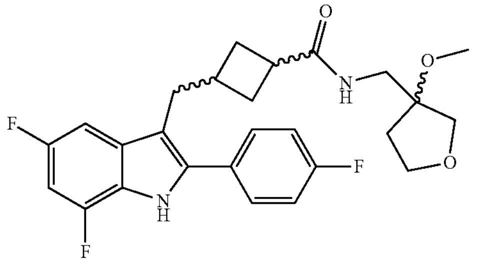
344
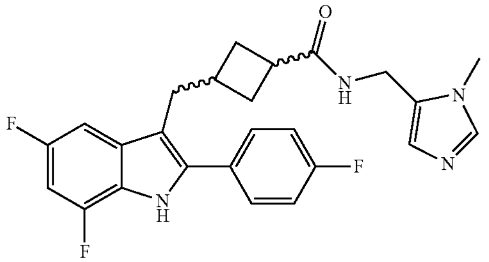
345
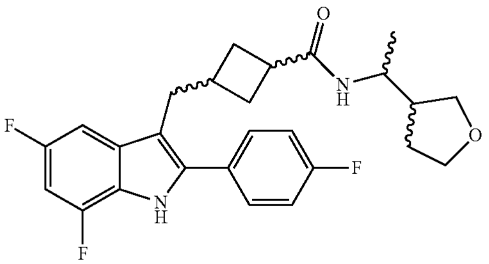

-continued
346
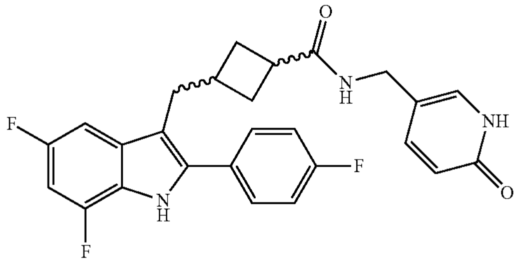
347
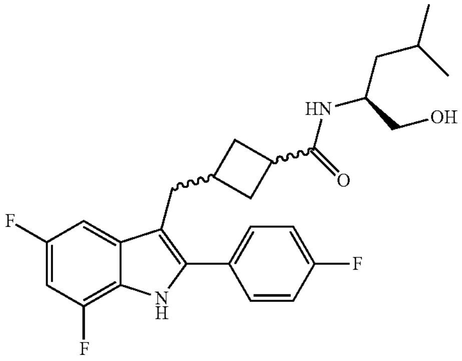
348
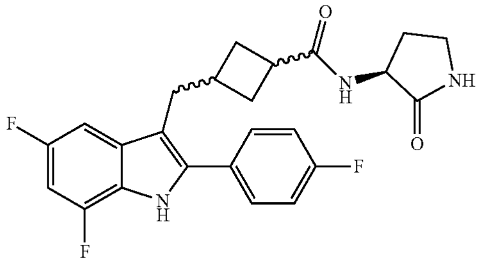
349
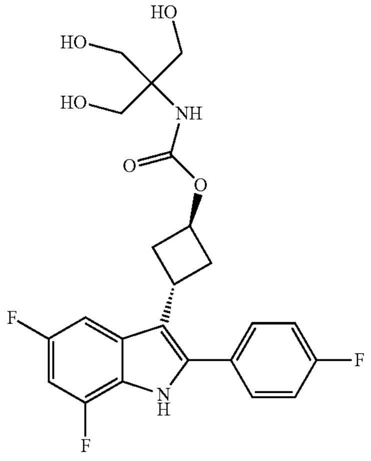
-continued
350
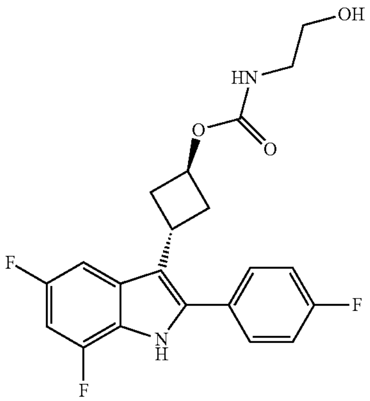
351
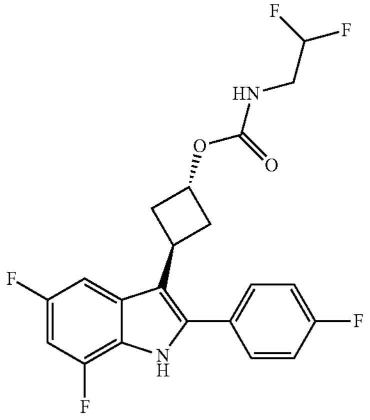
352
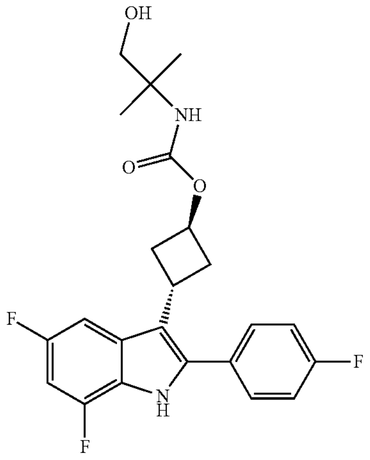

-continued
353
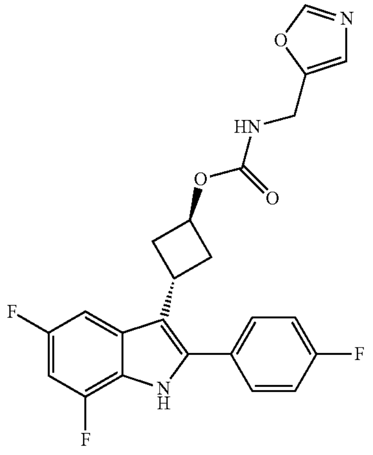
354
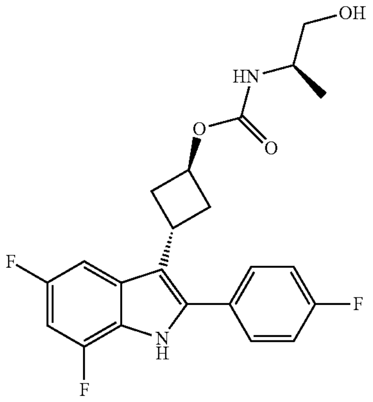
355
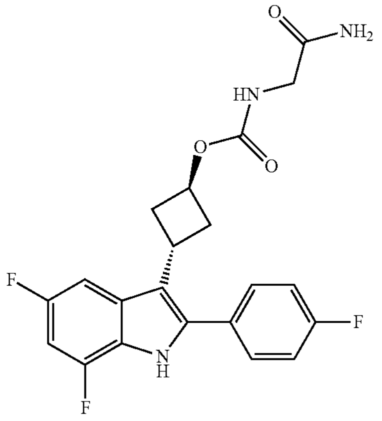
-continued
356
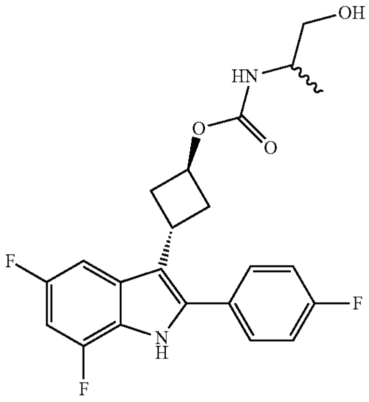
357
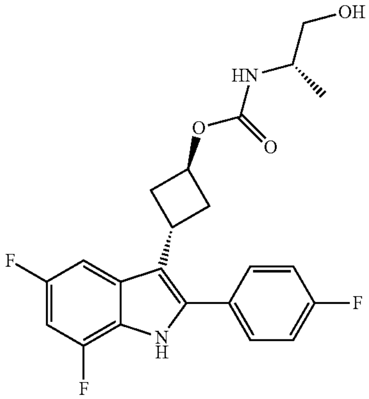
358
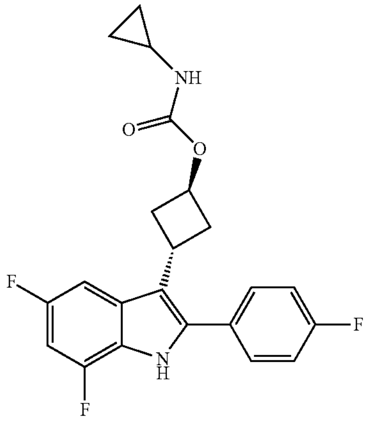

359
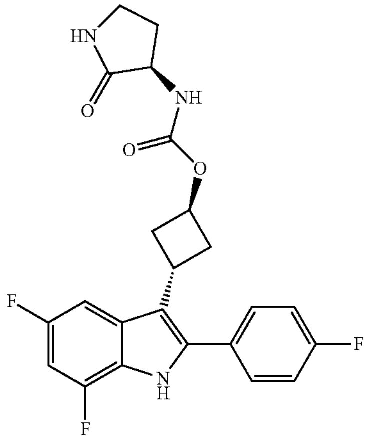
360
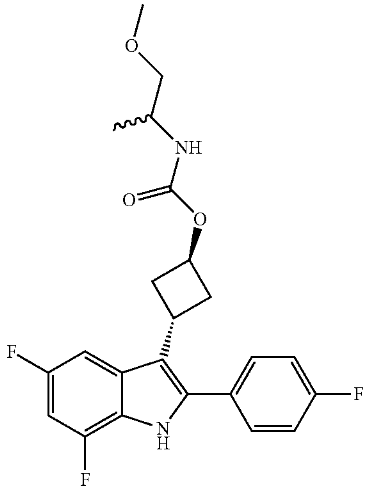
361
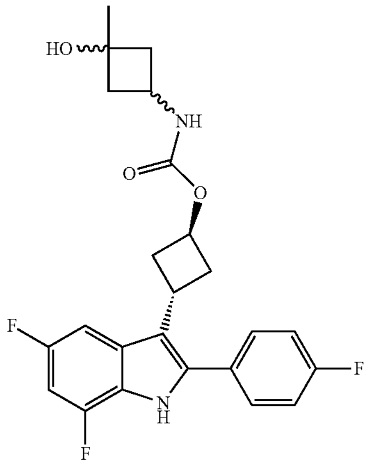
362
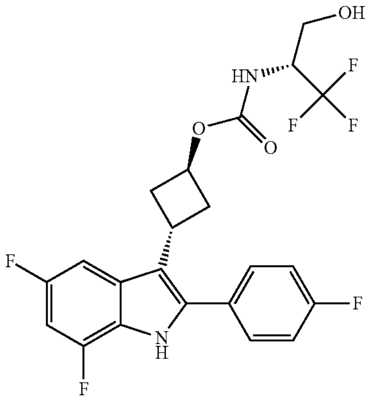
363
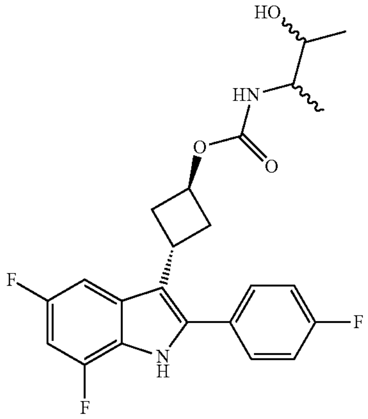
364
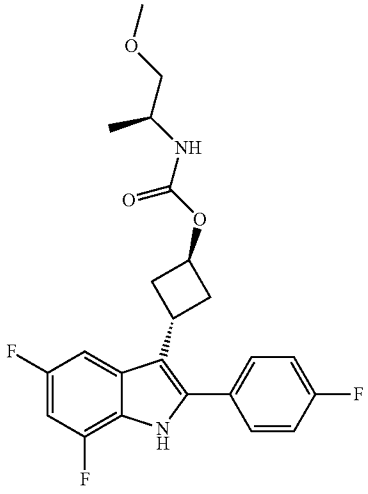

-continued
365
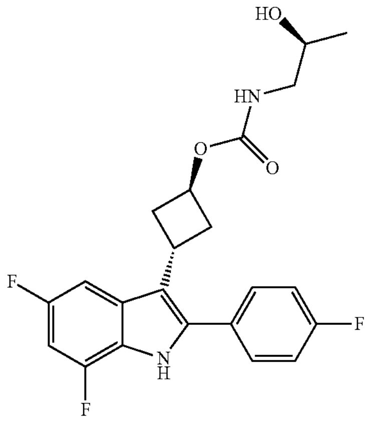
366
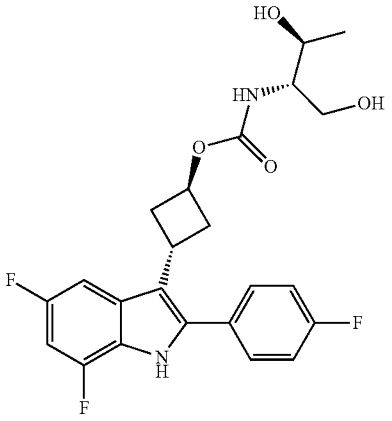
367
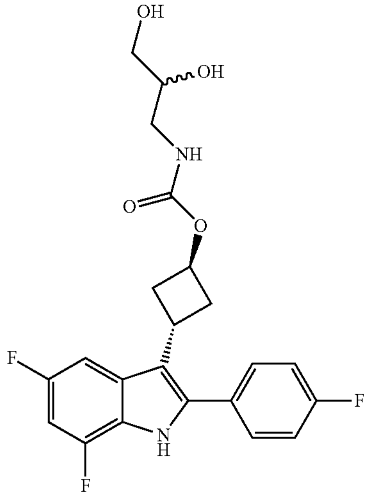
-continued
368
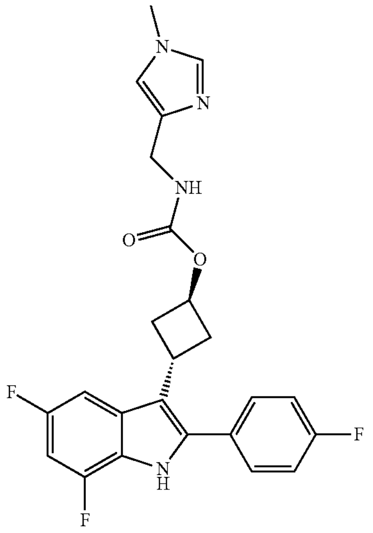
369
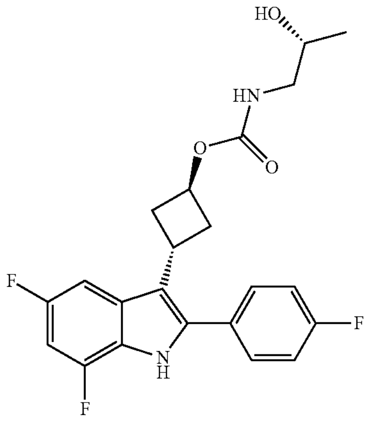
370
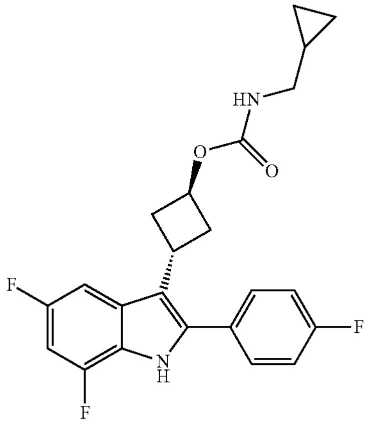

-continued
371
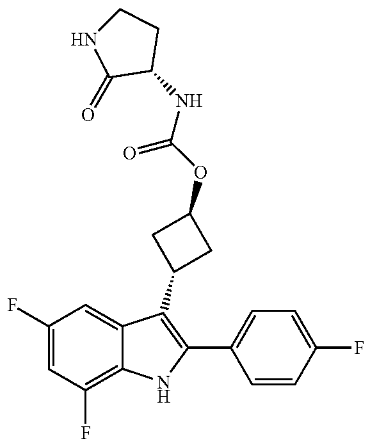
372
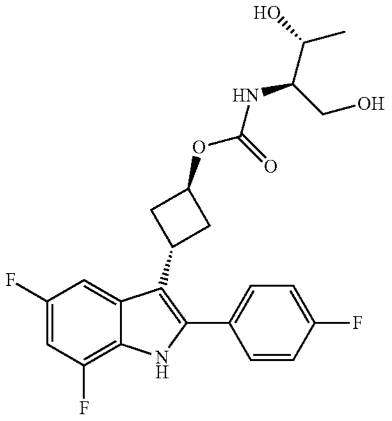
373
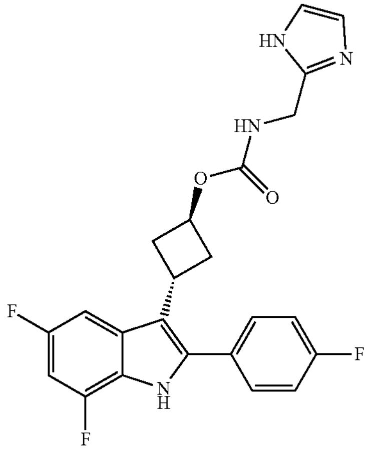
-continued
374
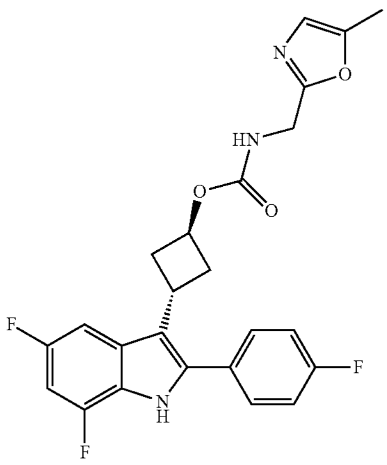
375
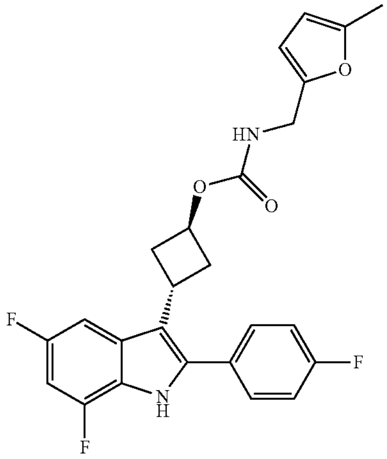
376
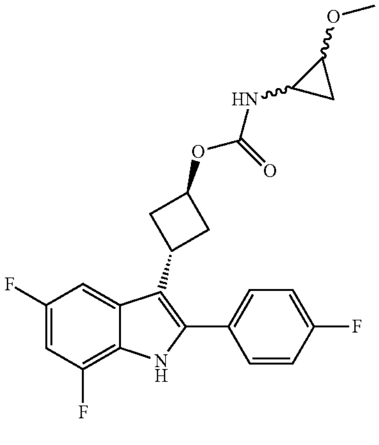

377
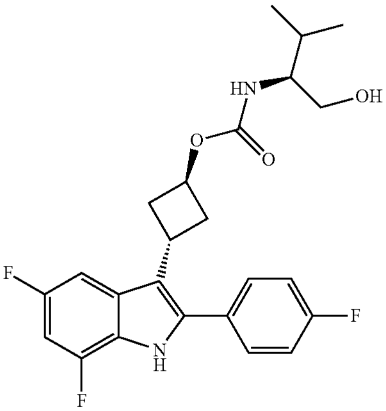
378
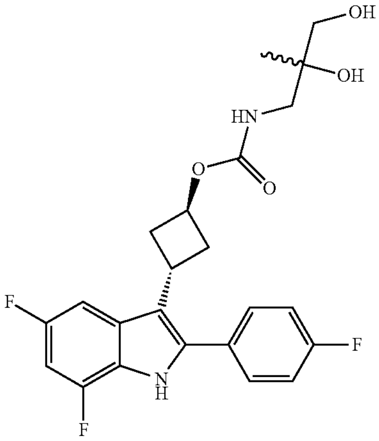
379
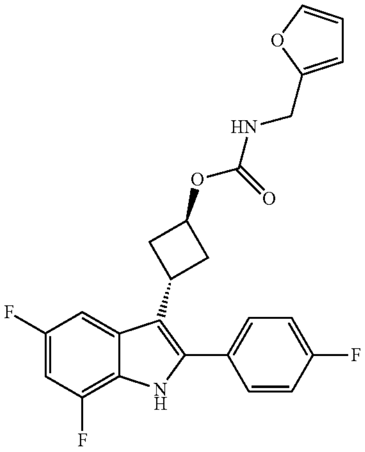
380
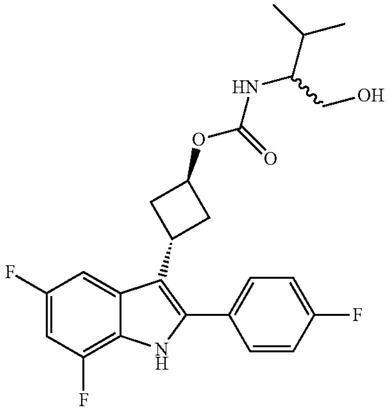
381
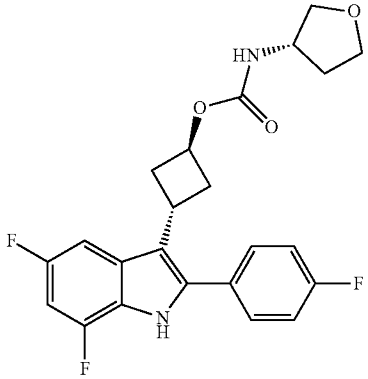
382
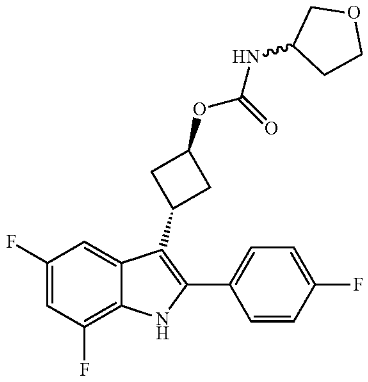
383
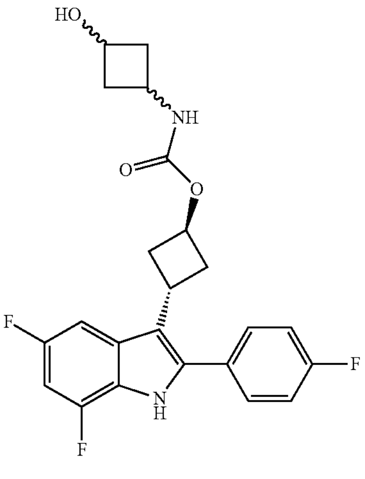

-continued
384
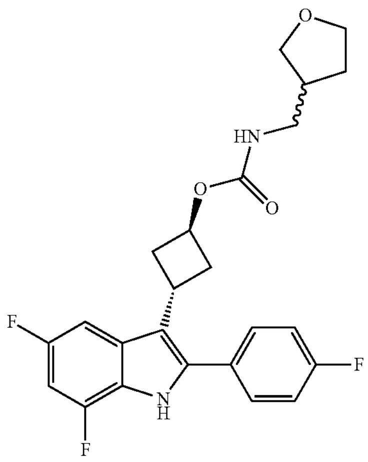
385
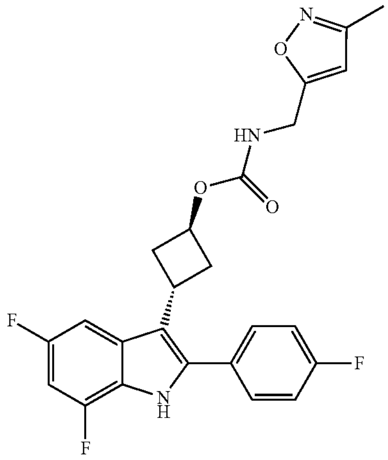
386
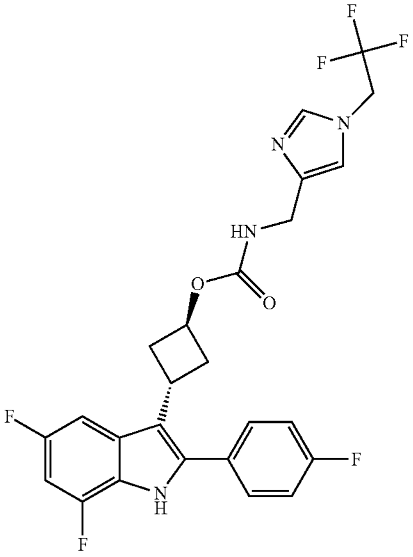
-continued
387
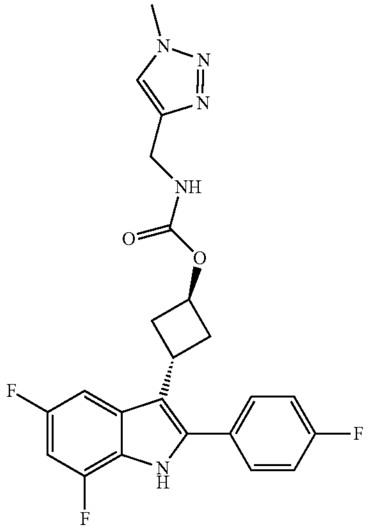
388
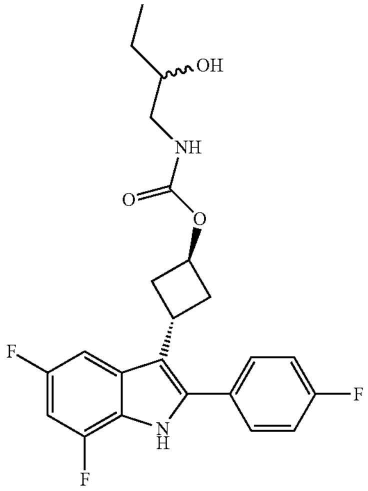
389
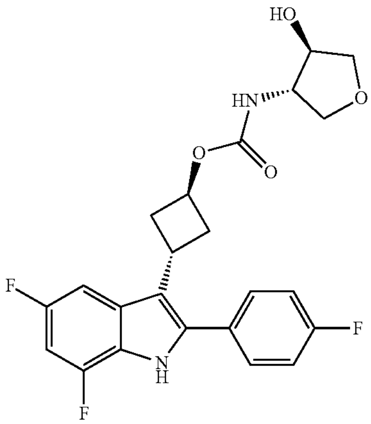

-continued
390
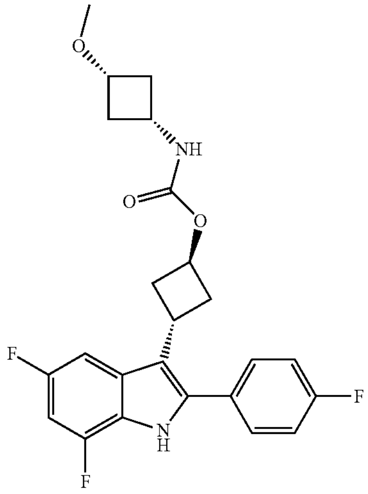
391
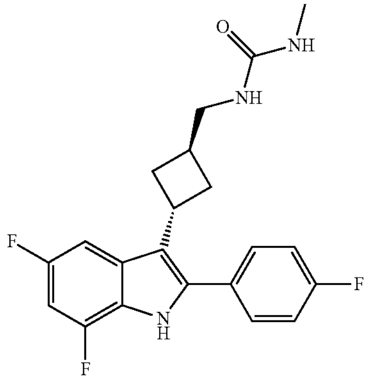
392
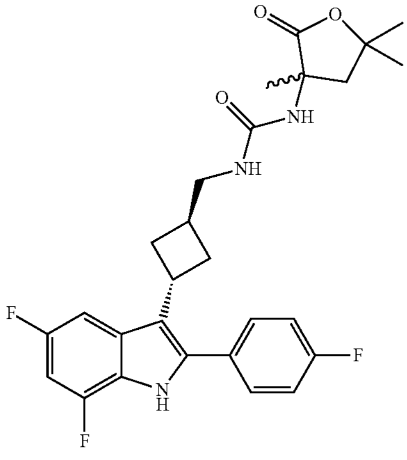
-continued
393
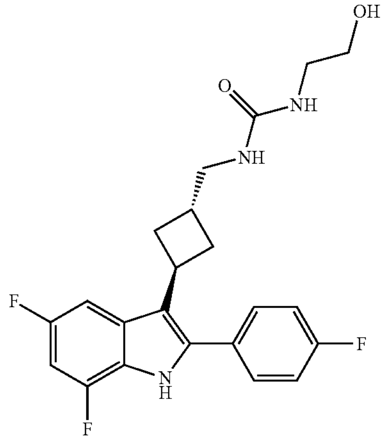
394
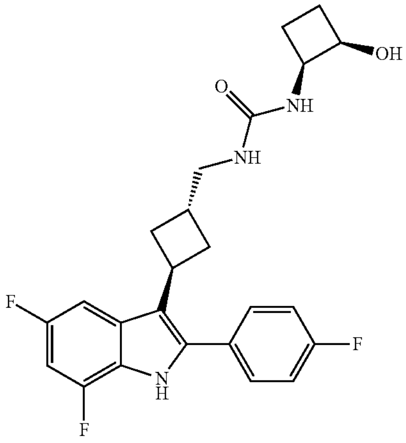
395
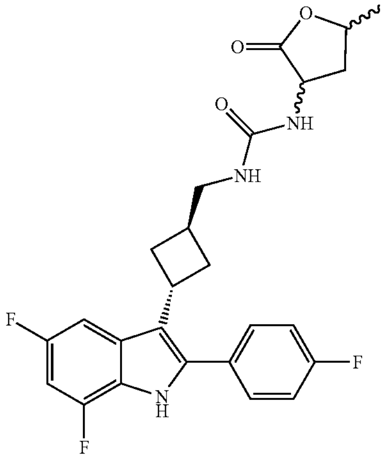

-continued
396
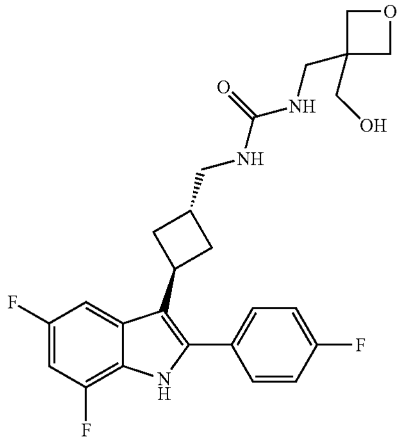
397
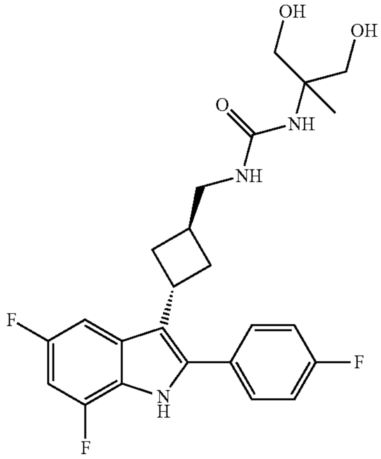
398
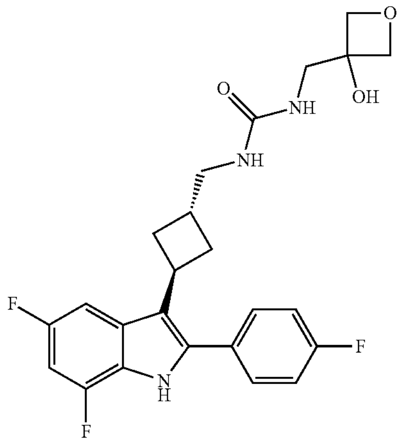
-continued
399
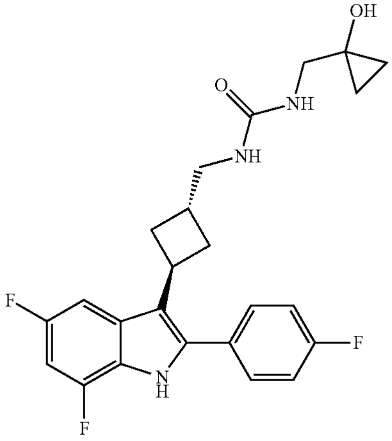
400
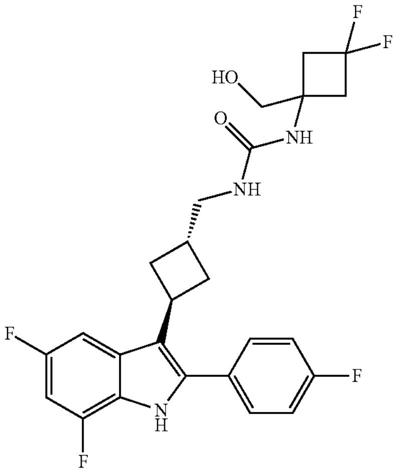
401
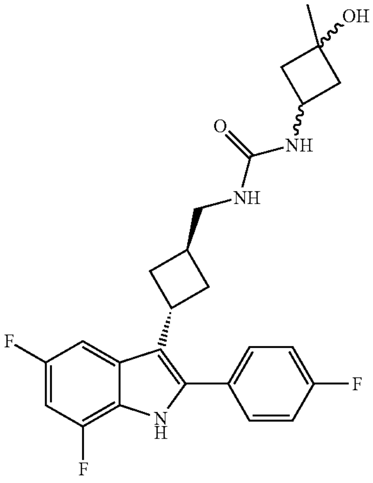

-continued
402
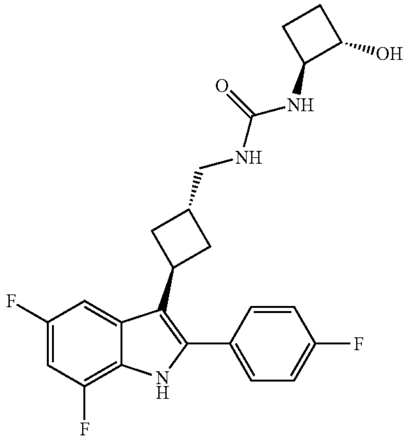
403
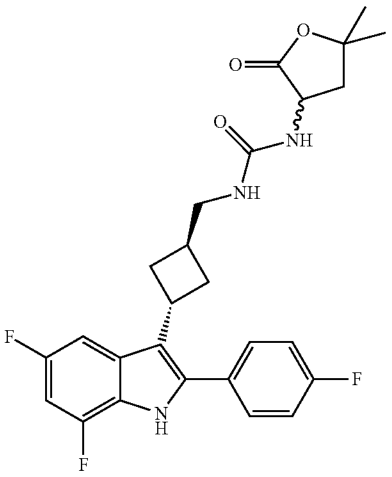
404
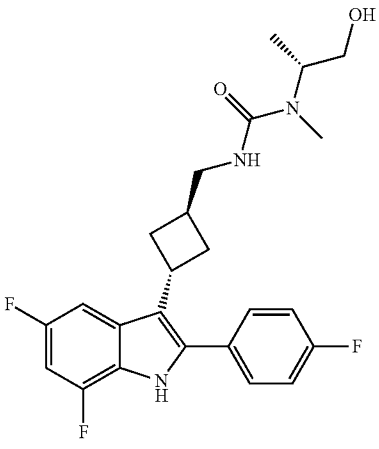
-continued
405
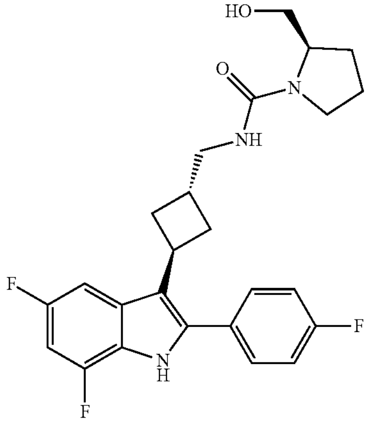
406
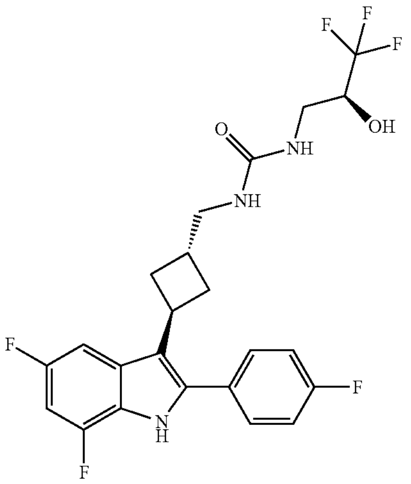
407
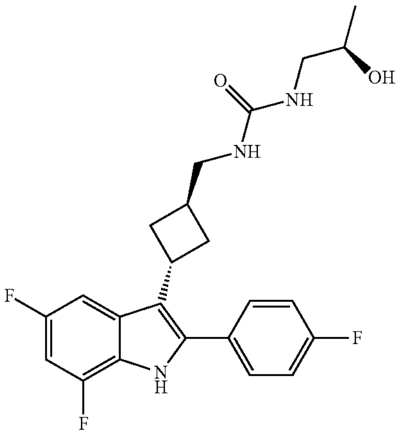

408
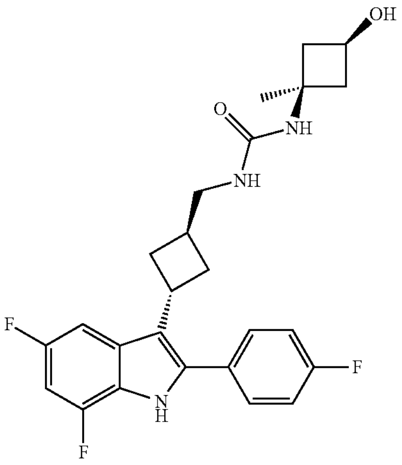
409
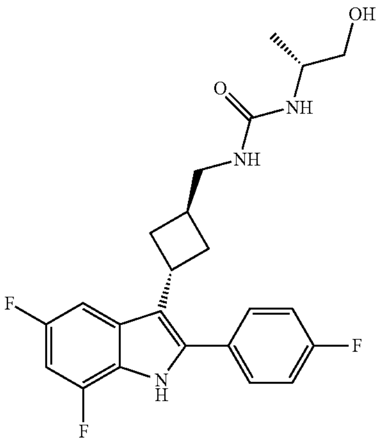
410
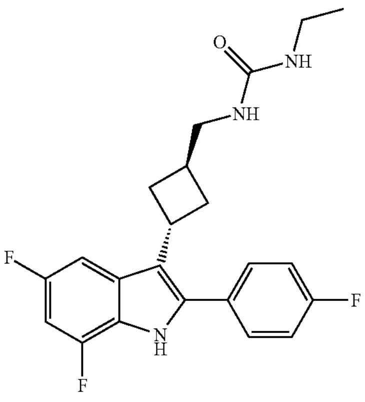
411
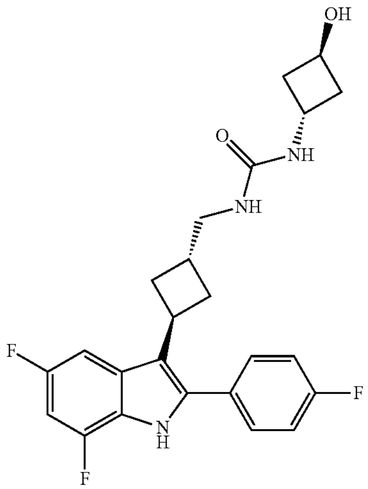
412
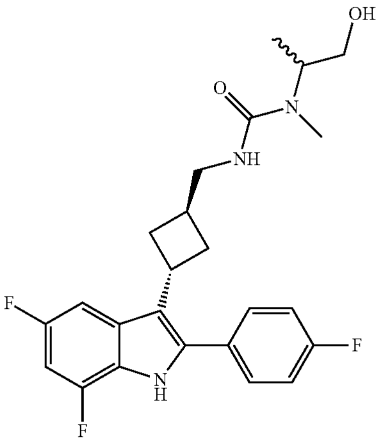
413
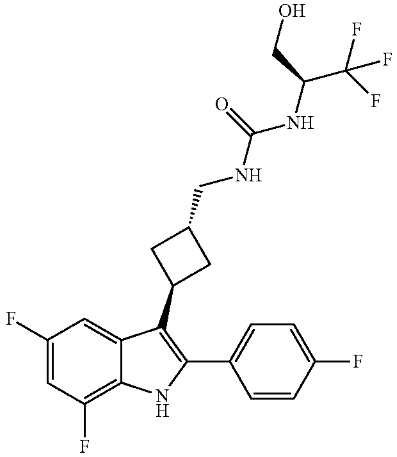

-continued
414
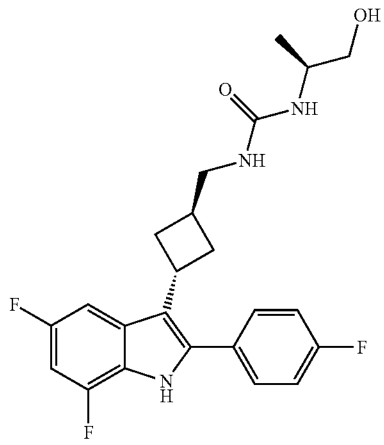
415
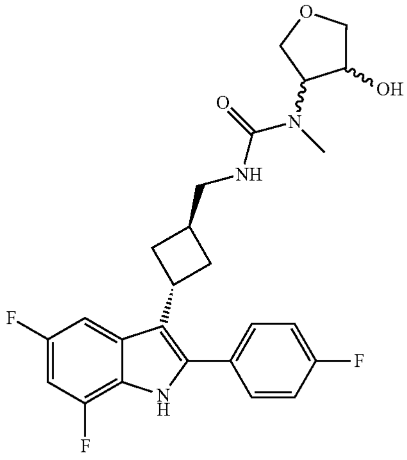
416
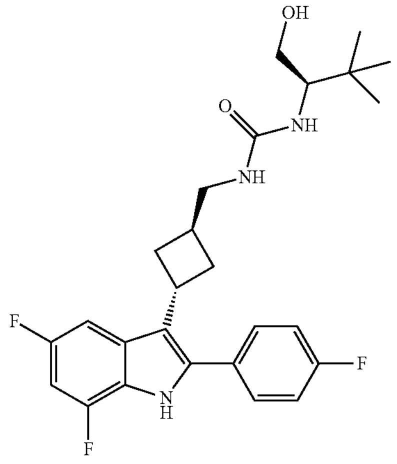
-continued
417
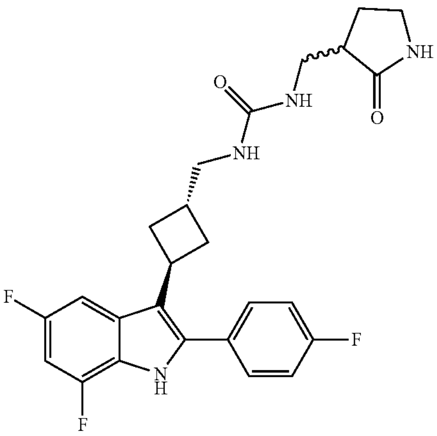
418
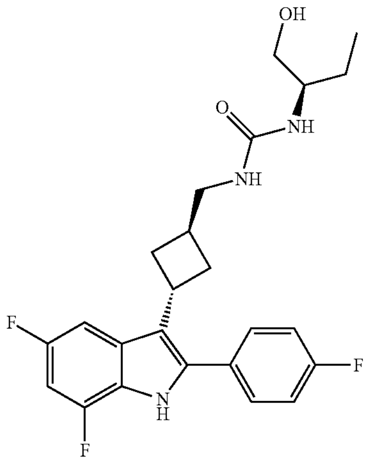
419
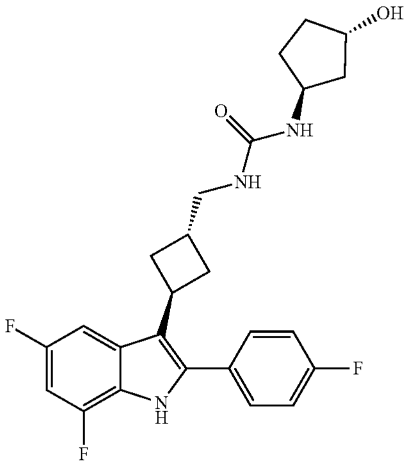

-continued
420
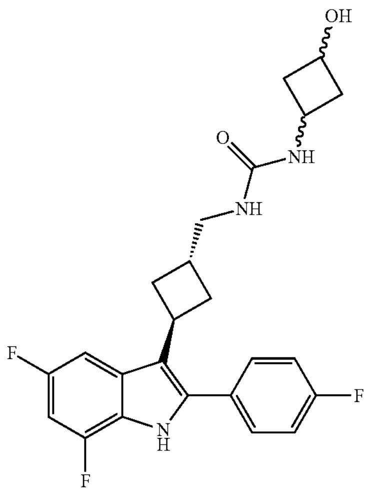
421
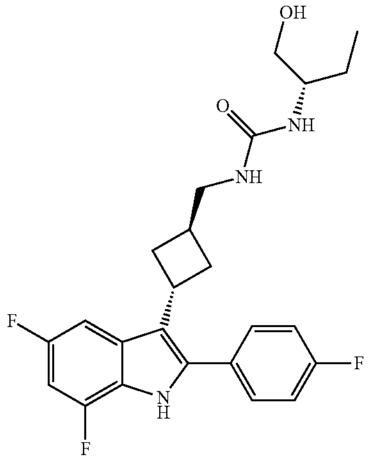
422
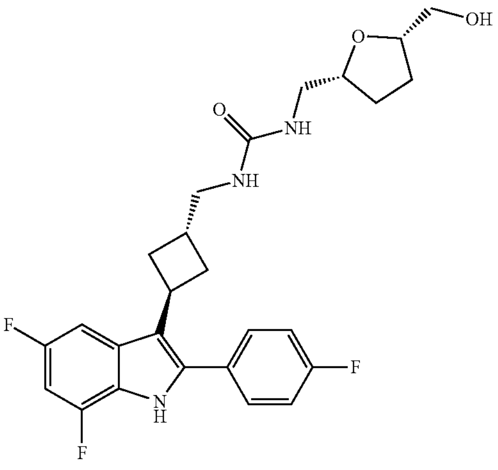
-continued
423
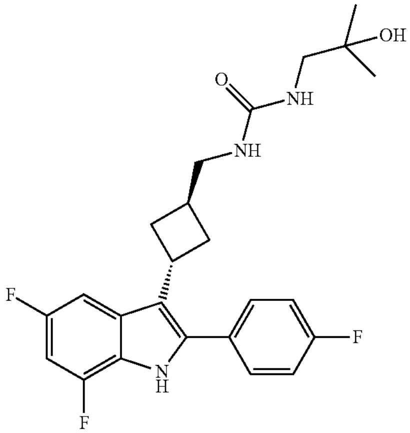
424
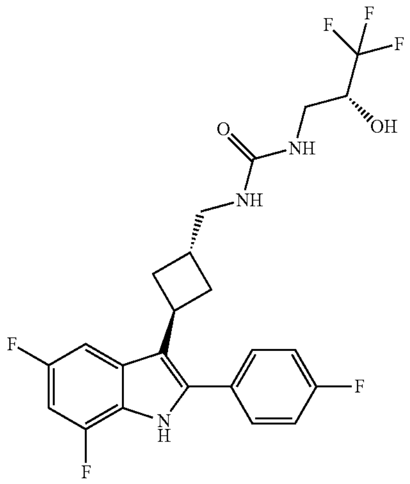
425
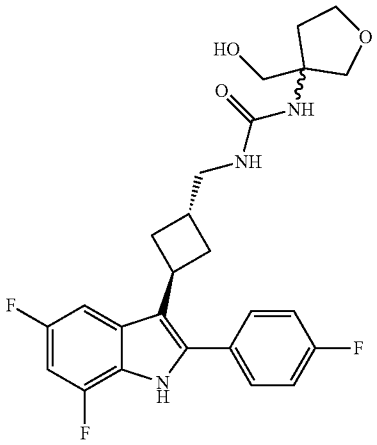

-continued
426
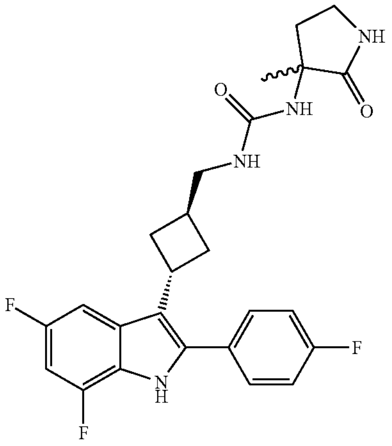
427
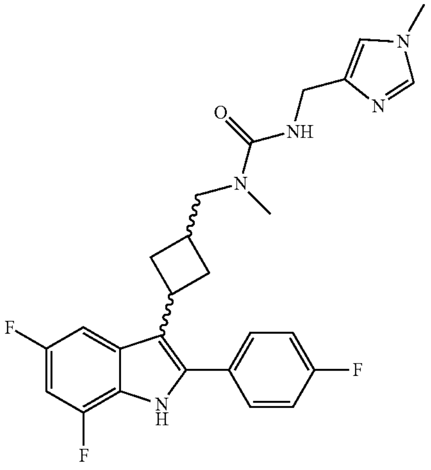
428
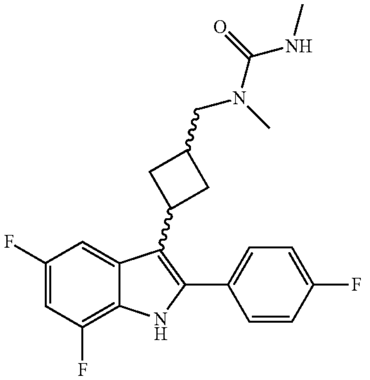
-continued
429
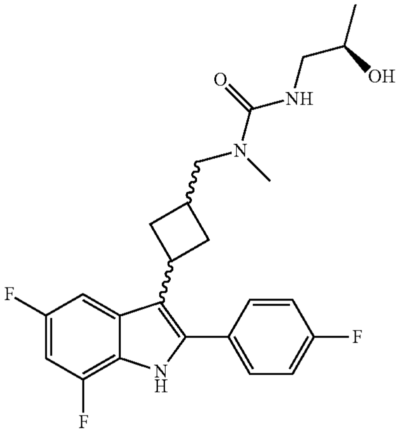
430
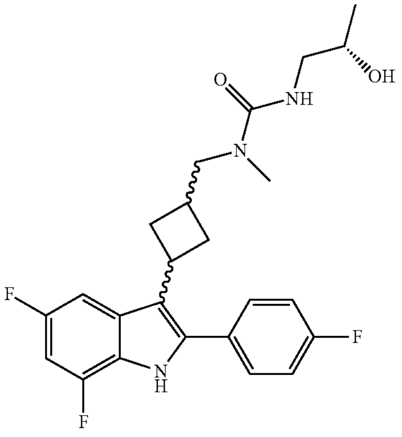
431
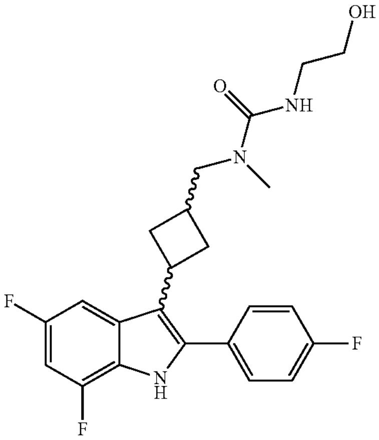

-continued
432
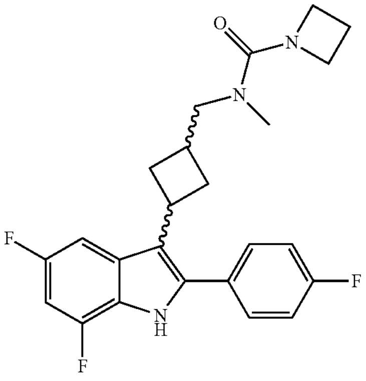
433
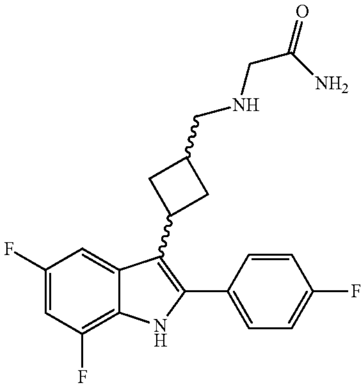
434
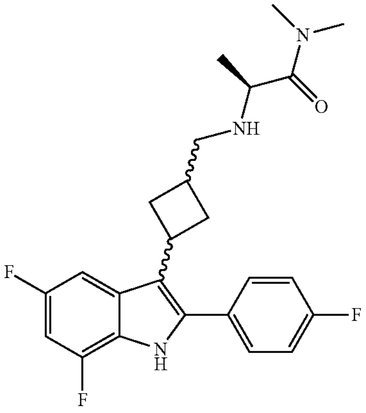
435
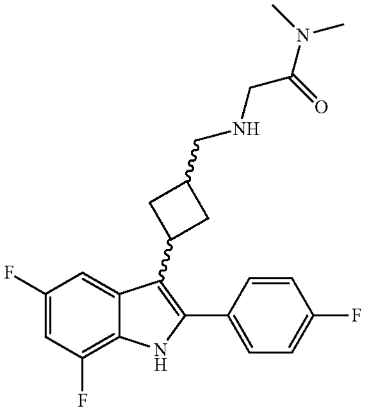
-continued
436
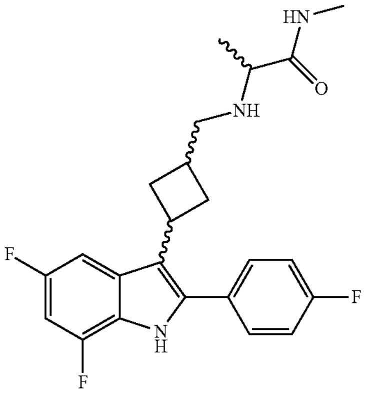
437
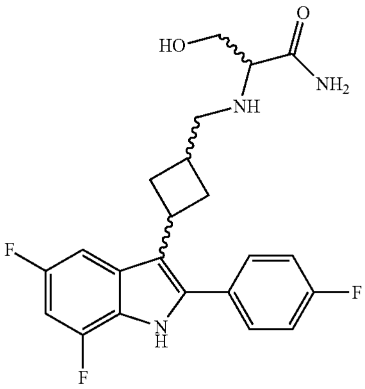
438
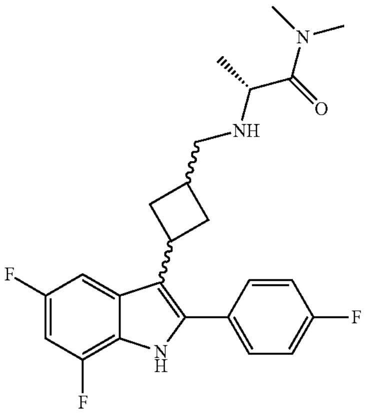
439
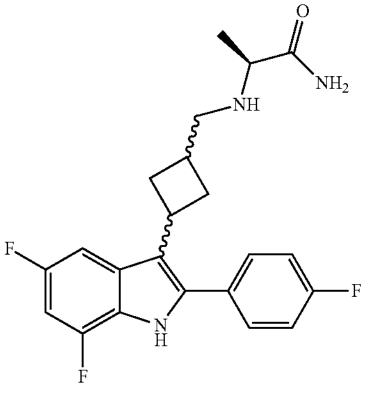

-continued
440
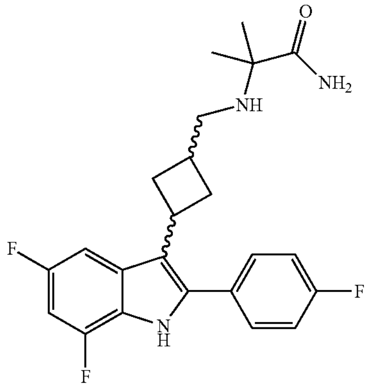
441
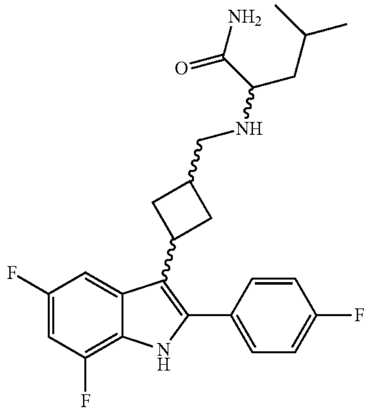
442
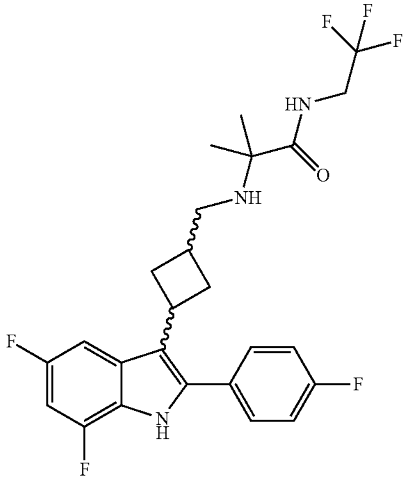
-continued
443
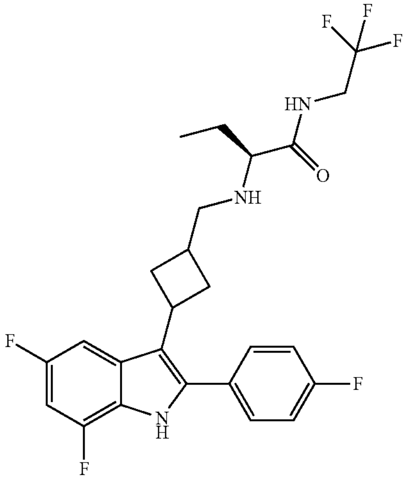
444
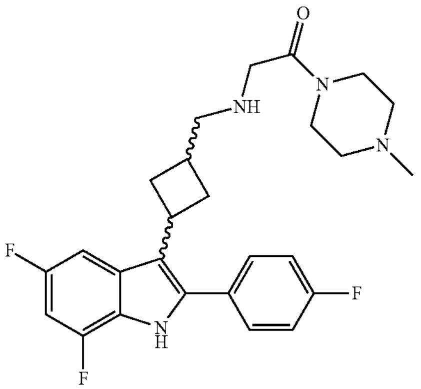
445
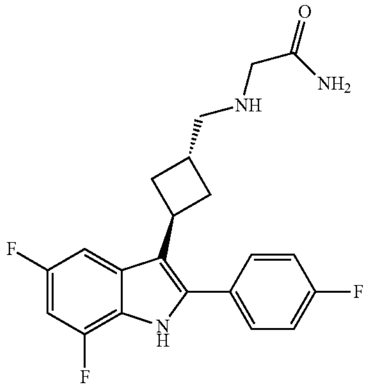
446
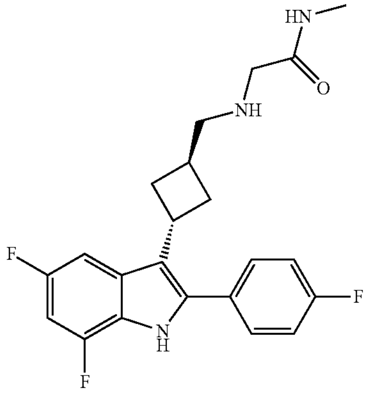

-continued
447
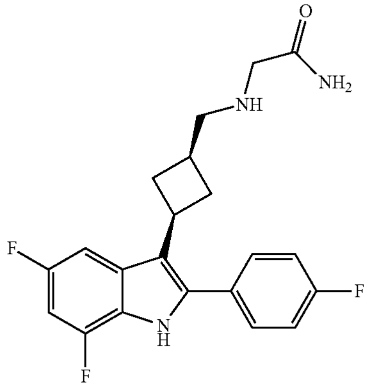
448
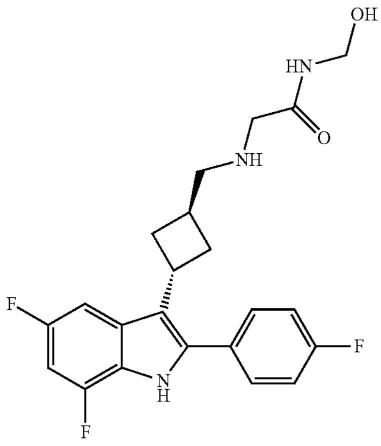
449
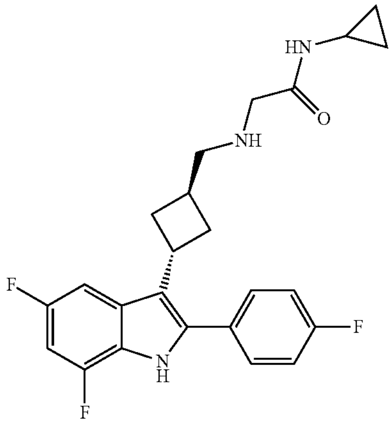
-continued
450
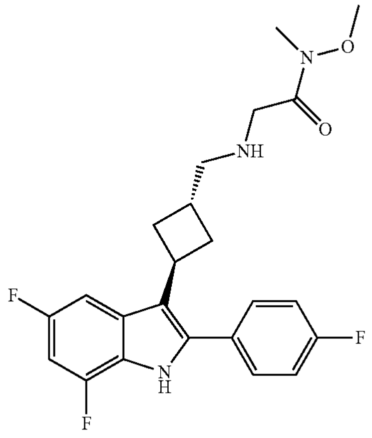
451
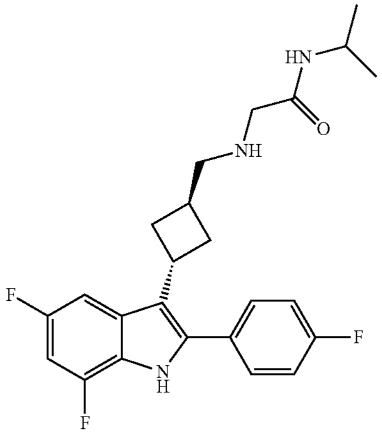
452
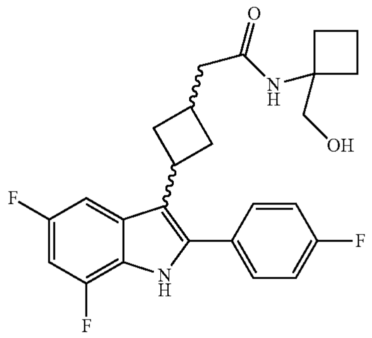
453
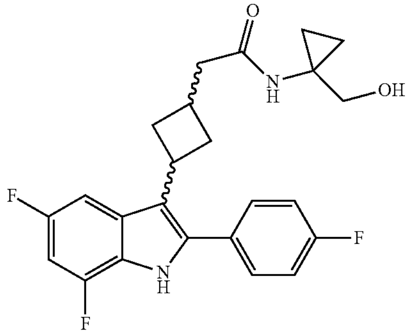

-continued
454
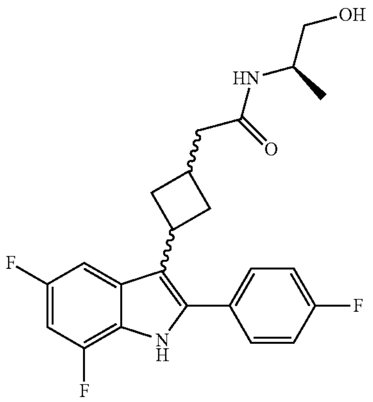
455
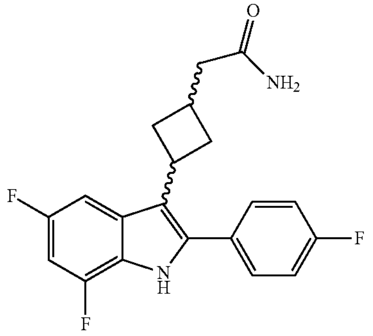
456
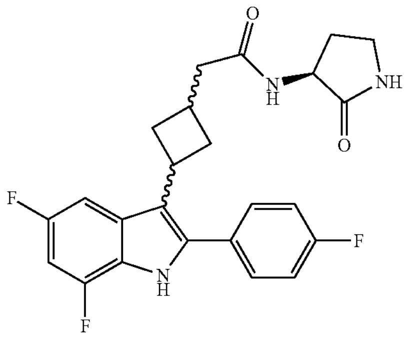
457
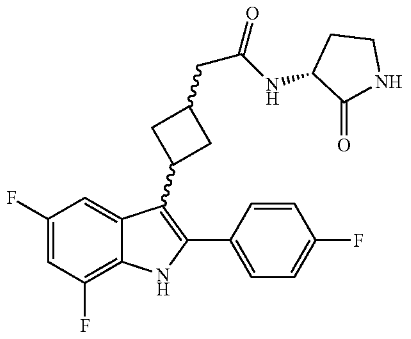
-continued
458
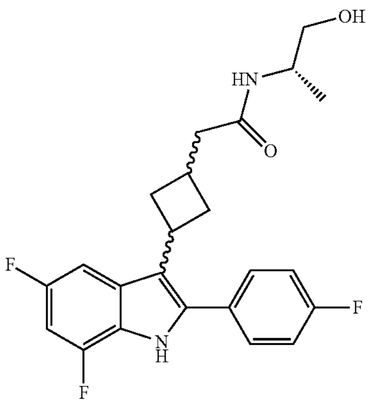
459
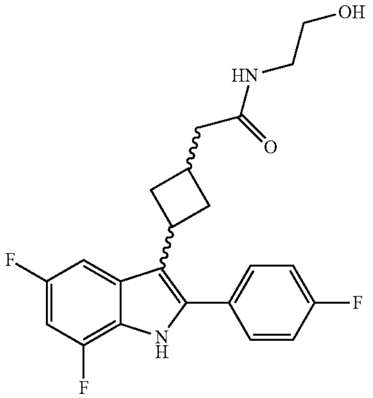
460
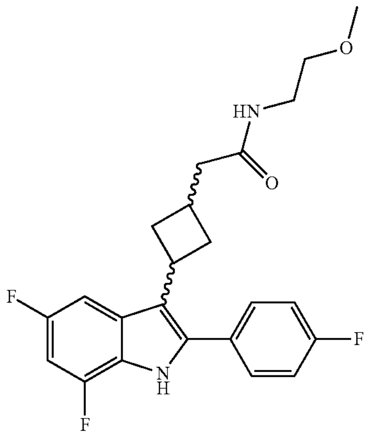
461
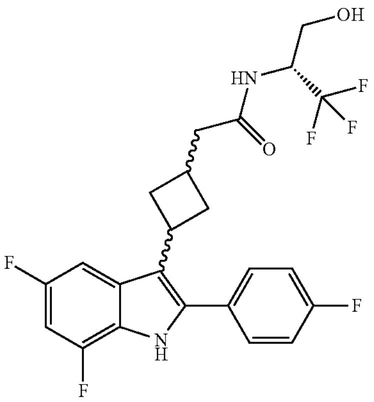

-continued

462

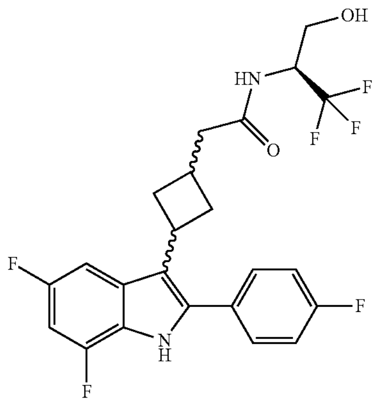

463

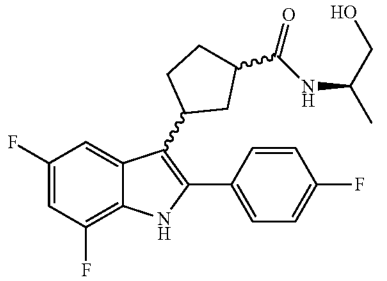

464

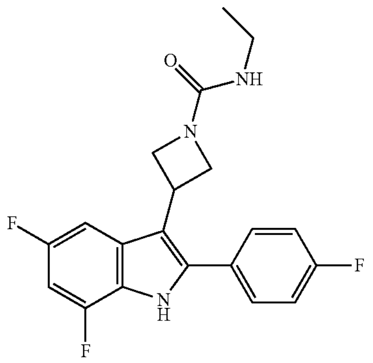

-continued

465

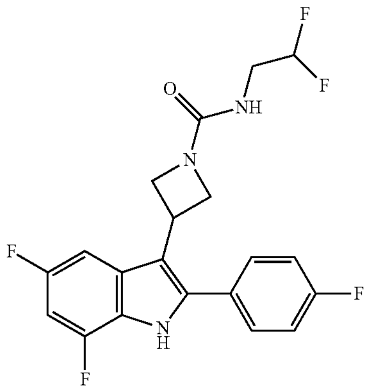

pharmaceutically acceptable salts thereof, solvates of any of the foregoing, and deuterated derivatives of any of the foregoing.

26. A pharmaceutical composition comprising the compound, salt, or deuterated derivative according to claim 1 and a pharmaceutically acceptable carrier.

27. A method of treating APOL1 mediated kidney disease comprising administering to a patient in need thereof the compound, salt, or deuterated derivative according to claim 1 or a pharmaceutical composition according to claim 26.

28. The method according to claim 27, wherein the APOL1 mediated kidney disease is selected from ESKD, NDKD, FSGS, HIV-associated nephropathy, arterionephrosclerosis, lupus nephritis, microalbuminuria, and chronic kidney disease.

29. The method according to claim 27, wherein the APOL1 mediated kidney disease is associated with APOL1 genetic alleles chosen from homozygous G1: S342G:I384M and homozygous G2:N388del:Y389del.

30. The method according to claim 27, wherein the APOL1 mediated kidney disease is associated with compound heterozygous G1: S342G:I384M and G2: N388del:Y389del APOL1 genetic alleles.

31. A method of inhibiting APOL1 activity comprising contacting said APOL1 with the compound, salt, or deuterated derivative according to claim 1 or a pharmaceutical composition according to claim 26.

32. The method according to claim 31, wherein the APOL1 is associated with APOL1 genetic alleles chosen from homozygous G1: S342G:I384M and homozygous G2: N388del:Y389del.

33. The method according to claim 31, wherein the APOL1 is associated with compound heterozygous G1: S342G:I384M and G2: N388del:Y389del APOL1 genetic alleles.

* * * * *

UNITED STATES PATENT AND TRADEMARK OFFICE
CERTIFICATE OF CORRECTION

PATENT NO. : 12,116,343 B2
APPLICATION NO. : 17/161474
DATED : October 15, 2024
INVENTOR(S) : Leslie A. Dakin et al.

It is certified that error appears in the above-identified patent and that said Letters Patent is hereby corrected as shown below:

In the Claims

Claim 24, Column 623, Lines 1-15, Compound 247:

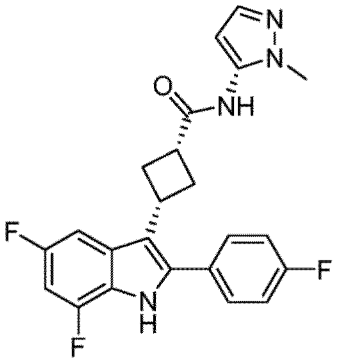

Should be replaced with:

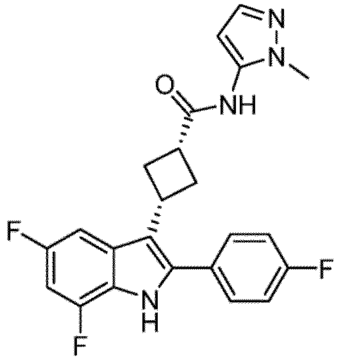

Signed and Sealed this
Twenty-second Day of April, 2025

Coke Morgan Stewart
*Acting Director of the United States Patent and Trademark Office*